(12) United States Patent
Menkedick et al.

(10) Patent No.: US 7,520,006 B2
(45) Date of Patent: Apr. 21, 2009

(54) HOSPITAL BED INCLUDING MOVEABLE FOOT PORTION

(75) Inventors: Douglas J. Menkedick, Guilford, IN (US); Eugene E. Osborne, Hebron, KY (US); Robert M. Zerhusen, Cincinnati, OH (US); David A. Albersmeyer, Batesville, IN (US); Roger S. Philbeck, Lawrenceburg, IN (US); Aziz Ali Bhai, Batesville, IN (US); Nicholas C. Batta, Batesville, IN (US); Terry L. Richter, Cincinnati, OH (US); Tom Riggs, Milan, IN (US); Kenith W. Chambers, Batesville, IN (US); Steven J. Schwartz, Cincinnati, OH (US); Matthew R. Knue, Moores Hill, IN (US); Steve A. Dixon, Cincinnati, OH (US); Joshua W. Shenk, Batesville, IN (US); Brent Goodwin, Batesville, IN (US); Andrew F. Skinner, Batesville, IN (US);

(Continued)

(73) Assignee: Hill-Rom Services, Inc., Wilmington, DE (US)

( * ) Notice: Subject to any disclaimer, the term of this patent is extended or adjusted under 35 U.S.C. 154(b) by 0 days.

(21) Appl. No.: 11/393,631

(22) Filed: Mar. 30, 2006

(65) Prior Publication Data

US 2006/0162079 A1 Jul. 27, 2006

Related U.S. Application Data

(63) Continuation of application No. 10/657,696, filed on Sep. 8, 2003, now Pat. No. 7,296,312.

(60) Provisional application No. 60/408,698, filed on Sep. 6, 2002, provisional application No. 60/409,748, filed on Sep. 11, 2002, provisional application No. 60/489,171, filed on Jul. 22, 2003, provisional application No. 60/490,467, filed on Jul. 28, 2003.

(51) Int. Cl.
*A61G 7/015* (2006.01)
*A61G 7/018* (2006.01)

(52) U.S. Cl. .................................. 5/618; 5/624; 5/600

(58) Field of Classification Search ............. 5/616–618, 5/613, 624, 621, 600, 740, 953, 655.9, 730
See application file for complete search history.

(56) References Cited

U.S. PATENT DOCUMENTS 585,834 A 7/1897 Ruth (Continued)

FOREIGN PATENT DOCUMENTS

DE 2310603 9/1974
DE 199 00 602 C1 7/2000

(Continued)

OTHER PUBLICATIONS

The NI Developer Zone website (http://zone.ni.com/devzone/cda/tut/p/id/2732), published May 14, 2008.*

(Continued)

*Primary Examiner*—Robert G Santos
(74) *Attorney, Agent, or Firm*—Barnes & Thornburg LLP

(57) ABSTRACT

A patient support including a frame and a mattress supported by the frame. The frame includes a deck support and a deck supporting the mattress.

25 Claims, 138 Drawing Sheets

(75) Inventors: Gregory J. Figel, Mason, OH (US); James R. Stolpmann, Lawrenceburg, IN (US); James K. Findlay, Fishers, IN (US); Glenn C. Suttman, Batesville, IN (US); Brian J. Hoffman, Lawrenceburg, IN (US); Irvin J. Vanderpohl, III, Greensburg, IN (US); David W. Hornbach, Brookville, IN (US); Paul R. Weil, Lawrenceburg, IN (US); Kenneth L. Kramer, Greensburg, IN (US); Jeffrey R. Welling, Batesville, IN (US); Eric R. Meyer, Greensburg, IN (US); Jack Wilker, Jr., Shelbyville, IN (US); David P. Lubbers, Cincinnati, OH (US); Roberta M. Murnyack, Cincinnati, OH (US); Cami S. Scheele, Batesville, IN (US)

U.S. PATENT DOCUMENTS

| Patent | | Date | Inventor |
|---|---|---|---|
| 595,734 | A | 12/1897 | Rand et al. |
| 598,054 | A | 1/1898 | Meany |
| 1,017,153 | A | 2/1912 | Kampe |
| 1,043,370 | A | 11/1912 | Stubbs |
| 1,261,040 | A | 4/1918 | Lanes |
| 1,398,203 | A | 11/1921 | Schmidt |
| 1,440,783 | A | 1/1923 | Kiley |
| 2,245,909 | A | 6/1941 | Enfiajian |
| 2,281,209 | A | 4/1942 | Smith |
| 2,452,366 | A | 10/1948 | Freund |
| 2,477,400 | A | 7/1949 | Beem et al. |
| 2,500,742 | A | 3/1950 | Taylor |
| 2,556,591 | A | 6/1951 | Loxley |
| 2,564,083 | A | 8/1951 | Stachert |
| 2,605,151 | A | 7/1952 | Shampaine |
| 2,687,536 | A | 8/1954 | Miller |
| 2,719,769 | A | 10/1955 | Murphy |
| 2,722,017 | A | 11/1955 | Burst et al. |
| 2,734,104 | A | 2/1956 | Gollhofer |
| 2,766,463 | A | 10/1956 | Bendersky |
| 2,869,614 | A | 1/1959 | Wamsky |
| 3,003,160 | A | 10/1961 | Goodman |
| 3,010,121 | A | 11/1961 | Breach |
| 3,036,314 | A | 5/1962 | Wetzler |
| 3,053,568 | A | 9/1962 | Miller |
| 3,099,440 | A | 7/1963 | Burzlaff |
| 3,112,500 | A | 12/1963 | MacDonald |
| 3,138,805 | A | 6/1964 | Piazza |
| 3,195,151 | A | 7/1965 | Boyer |
| 3,210,779 | A | 10/1965 | Herbold |
| 3,220,021 | A | 11/1965 | Nelson |
| 3,220,022 | A | 11/1965 | Nelson |
| 3,233,255 | A | 2/1966 | Propst |
| 3,239,853 | A | 3/1966 | MacDonald |
| 3,309,717 | A | 3/1967 | Black |
| 3,317,931 | A | 5/1967 | Benoit et al. |
| 3,393,004 | A | 7/1968 | Williams |
| 3,406,772 | A | 10/1968 | Ahrent et al. |
| 3,456,269 | A | 7/1969 | Goodman |
| 3,506,989 | A | 4/1970 | Ross et al. |
| 3,526,008 | A | 9/1970 | Pruim |
| 3,585,659 | A | 6/1971 | Burst et al. |
| 3,593,350 | A | 7/1971 | Knight et al. |
| 3,598,947 | A | 8/1971 | Osborne |
| 3,640,566 | A | 2/1972 | Hodge |
| 3,663,772 | A | 5/1972 | Grabel et al. |
| 3,665,528 | A | 5/1972 | Kjelberg et al. |
| 3,724,003 | A | 4/1973 | Ellwanger et al. |
| 3,814,414 | A | 6/1974 | Chapa |
| 3,822,425 | A | 7/1974 | Scalar |
| 3,845,947 | A | 11/1974 | Lee |
| 3,893,197 | A | 7/1975 | Ricke |
| 3,897,973 | A | 8/1975 | Long et al. |
| 3,902,204 | A | 9/1975 | Lee |
| 3,905,591 | A | 9/1975 | Schorr et al. |
| 3,916,461 | A | 11/1975 | Kerstholt |
| 3,932,903 | A | 1/1976 | Adams et al. |
| 3,977,664 | A | 8/1976 | Mitchell et al. |
| 3,993,051 | A | 11/1976 | Maruyama |
| 4,016,613 | A | 4/1977 | Benoit et al. |
| 4,038,709 | A | 8/1977 | Kerwit |
| 4,062,075 | A | 12/1977 | Stern et al. |
| 4,078,269 | A | 3/1978 | Weipert |
| 4,103,376 | A | 8/1978 | Benoit et al. |
| 4,127,906 | A | 12/1978 | Zur |
| 4,139,917 | A | 2/1979 | Fenwick |
| 4,150,269 | A | 4/1979 | Henkel |
| 4,168,099 | A | 9/1979 | Jacobs et al. |
| 4,183,109 | A | 1/1980 | Howell |
| 4,193,149 | A | 3/1980 | Welch |
| 4,195,829 | A | 4/1980 | Reser |
| 4,205,665 | A | 6/1980 | Burton |
| 4,225,989 | A | 10/1980 | Corbett et al. |
| 4,231,030 | A | 10/1980 | Weiss |
| 4,231,124 | A | 11/1980 | Croxton |
| 4,240,169 | A | 12/1980 | Roos |
| 4,258,445 | A | 3/1981 | Zur |
| 4,259,762 | A | 4/1981 | Civitelli |
| 4,293,746 | A | 10/1981 | Braaten |
| 4,312,500 | A | 1/1982 | Janssen |
| 4,336,621 | A | 6/1982 | Schwartz et al. |
| 4,345,344 | A | 8/1982 | Gadoury et al. |
| 4,354,838 | A | 10/1982 | Hoyer et al. |
| 4,369,535 | A | 1/1983 | Ekkerink |
| 4,386,254 | A | 5/1983 | Eberhardt et al. |
| 4,409,695 | A | 10/1983 | Johnston et al. |
| 4,411,035 | A | 10/1983 | Fenwick |
| 4,425,673 | A | 1/1984 | Werner |
| 4,453,732 | A | 6/1984 | Assanah et al. |
| 4,472,845 | A | 9/1984 | Chivetta et al. |
| 4,494,259 | A | 1/1985 | Miller et al. |
| 4,539,560 | A | 9/1985 | Fleck et al. |
| 4,542,547 | A | 9/1985 | Sato |
| 4,545,084 | A | 10/1985 | Peterson |
| 4,557,471 | A | 12/1985 | Pazzini |
| 4,612,679 | A | 9/1986 | Mitchell |
| 4,625,345 | A | 12/1986 | Wood |
| 4,638,516 | A | 1/1987 | Vrzalik |
| 4,653,129 | A | 3/1987 | Kuck et al. |
| 4,654,903 | A | 4/1987 | Chubb et al. |
| 4,675,926 | A | 6/1987 | Lindblom et al. |
| 4,680,790 | A | 7/1987 | Packard et al. |
| 4,685,159 | A | 8/1987 | Oetiker |
| 4,724,555 | A | 2/1988 | Poehner et al. |
| 4,745,647 | A | 5/1988 | Goodwin |
| 4,751,754 | A | 6/1988 | Bailey et al. |
| 4,768,249 | A | 9/1988 | Goodwin |
| 4,769,584 | A | 9/1988 | Irigoyen et al. |
| 4,797,962 | A | 1/1989 | Goode |
| 4,811,435 | A | 3/1989 | Foster et al. |
| 4,821,470 | A | 4/1989 | Kappers et al. |
| 4,847,929 | A | 7/1989 | Pupovic |
| 4,851,625 | A | 7/1989 | Liebich |
| 4,856,123 | A | 8/1989 | Henderson et al. |
| 4,858,260 | A | 8/1989 | Failor et al. |
| 4,858,481 | A | 8/1989 | Abraham |
| 4,862,529 | A | 9/1989 | Peck |
| 4,862,530 | A | 9/1989 | Chen |
| 4,894,876 | A | 1/1990 | Fenwick |
| 4,912,787 | A | 4/1990 | Bradcovich |
| 4,944,055 | A | 7/1990 | Shainfeld |
| 4,949,410 | A | 8/1990 | Failor et al. |
| 4,951,032 | A | 8/1990 | Langsam |
| 4,953,243 | A | 9/1990 | Birkmann |

| | | | | | | |
|---|---|---|---|---|---|---|
| 4,974,905 A | 12/1990 | Davis | 5,873,137 A | 2/1999 | Yavets-Chen | |
| 4,985,946 A | 1/1991 | Foster et al. | 5,878,452 A | 3/1999 | Brooke et al. | |
| 5,035,014 A | 7/1991 | Blanchard | 5,883,615 A | 3/1999 | Fago et al. | |
| 5,040,253 A | 8/1991 | Cheng | 5,890,765 A | 4/1999 | LaPointe et al. | |
| 5,054,141 A | 10/1991 | Foster et al. | 5,906,016 A | 5/1999 | Ferrand et al. | |
| 5,060,425 A | 10/1991 | Kappers et al. | 5,906,017 A | 5/1999 | Ferrand et al. | |
| 5,063,624 A | 11/1991 | Smith et al. | 5,918,505 A | 7/1999 | Jensen | |
| 5,072,463 A | 12/1991 | Willis | 5,934,280 A | 8/1999 | Viard et al. | |
| 5,074,000 A | 12/1991 | Soltani et al. | 5,939,803 A | 8/1999 | Frost | |
| 5,077,843 A | 1/1992 | Dale et al. | 5,987,671 A | 11/1999 | Heimbrock et al. | |
| 5,083,332 A | 1/1992 | Foster et al. | 6,006,379 A | 12/1999 | Hensley | |
| 5,083,334 A | 1/1992 | Huck et al. | 6,008,598 A | 12/1999 | Luff et al. | |
| 5,095,561 A | 3/1992 | Green et al. | 6,016,580 A | 1/2000 | Heimbrock et al. | |
| 5,103,519 A | 4/1992 | Hasty | 6,021,533 A | 2/2000 | Ellis et al. | |
| 5,105,486 A | 4/1992 | Peterson | 6,067,019 A | 5/2000 | Scott | |
| 5,109,554 A | 5/1992 | Borders et al. | 6,076,208 A | 6/2000 | Heimbrock et al. | |
| 5,117,521 A | 6/1992 | Foster et al. | 6,089,593 A | 7/2000 | Hanson et al. | |
| 5,127,034 A | 6/1992 | Wright | 6,131,868 A | 10/2000 | Welling et al. | |
| 5,129,117 A | 7/1992 | Celestina et al. | 6,158,295 A | 12/2000 | Nielsen | |
| 5,148,562 A | 9/1992 | Borders et al. | 6,163,903 A | 12/2000 | Weismiller et al. | |
| 5,157,787 A | 10/1992 | Donnellan et al. | 6,178,576 B1 | 1/2001 | Newell | |
| 5,157,800 A | 10/1992 | Borders | 6,182,310 B1 | 2/2001 | Weismiller et al. | |
| 5,179,744 A | 1/1993 | Foster et al. | 6,185,767 B1 | 2/2001 | Brooke et al. | |
| 5,193,633 A | 3/1993 | Ezenwa | 6,208,250 B1 | 3/2001 | Dixon et al. | |
| 5,205,004 A | 4/1993 | Hayes et al. | 6,212,714 B1 | 4/2001 | Allen et al. | |
| D336,577 S | 6/1993 | Celestina et al. | 6,223,369 B1 | 5/2001 | Maier et al. | |
| 5,216,769 A | 6/1993 | Eakin | 6,226,821 B1 | 5/2001 | Heimbrock et al. | |
| 5,230,113 A | 7/1993 | Foster et al. | 6,240,583 B1 | 6/2001 | Brooke et al. | |
| 5,235,258 A | 8/1993 | Schuerch | 6,260,221 B1 | 7/2001 | Grabell et al. | |
| 5,235,713 A | 8/1993 | Guthrie et al. | 6,282,738 B1 | 9/2001 | Heimbrock et al. | |
| 5,267,364 A | 12/1993 | Volk | 6,290,194 B1 | 9/2001 | Chaconas et al. | |
| 5,269,388 A | 12/1993 | Reichow et al. | 6,295,675 B1 | 10/2001 | Ellis et al. | |
| 5,279,010 A | 1/1994 | Ferrand et al. | 6,321,878 B1 | 11/2001 | Mobley et al. | |
| 5,283,096 A | 2/1994 | Greenberg et al. | 6,336,235 B1 | 1/2002 | Ruehl | |
| 5,317,769 A | 6/1994 | Weismiller et al. | 6,351,678 B1 | 2/2002 | Borders | |
| 5,323,565 A | 6/1994 | Kappers et al. | 6,353,950 B1 | 3/2002 | Bartlett et al. | |
| 5,324,900 A | 6/1994 | Gonser et al. | 6,438,776 B2 | 8/2002 | Ferrand et al. | |
| 5,348,326 A | 9/1994 | Fullenkamp et al. | 6,473,921 B2 | 11/2002 | Brooke et al. | |
| 5,367,728 A | 11/1994 | Chang | 6,484,221 B1 * | 11/2002 | Lorinser et al. | 710/200 |
| 5,370,111 A | 12/1994 | Reeder et al. | 6,496,993 B2 * | 12/2002 | Allen et al. | 5/624 |
| 5,394,580 A | 3/1995 | Foster et al. | 6,539,566 B1 | 4/2003 | Hayes | |
| 5,398,354 A | 3/1995 | Balonick et al. | 6,559,783 B1 * | 5/2003 | Stoneking | 341/141 |
| 5,422,521 A | 6/1995 | Neer et al. | 6,606,670 B1 * | 8/2003 | Stoneking et al. | 710/14 |
| 5,423,231 A | 6/1995 | Helfrich et al. | 6,611,979 B2 | 9/2003 | Welling et al. | |
| 5,444,880 A | 8/1995 | Weismiller et al. | 6,658,680 B2 | 12/2003 | Osborne et al. | |
| 5,450,639 A | 9/1995 | Weismiller et al. | 6,684,427 B2 * | 2/2004 | Allen et al. | 5/624 |
| 5,454,126 A | 10/1995 | Foster et al. | 6,691,346 B2 * | 2/2004 | Osborne et al. | 5/600 |
| 5,479,666 A | 1/1996 | Foster et al. | 6,880,189 B2 * | 4/2005 | Welling et al. | 5/624 |
| 5,527,097 A | 6/1996 | Martin | 6,910,236 B2 * | 6/2005 | Rene | 5/624 |
| 5,537,701 A | 7/1996 | Elliott | 6,957,461 B2 | 10/2005 | Osborne et al. | |
| 5,542,136 A | 8/1996 | Tappel | 6,978,500 B2 * | 12/2005 | Osborne et al. | 5/600 |
| 5,542,138 A | 8/1996 | Williams et al. | 7,000,272 B2 * | 2/2006 | Allen et al. | 5/624 |
| 5,577,279 A | 11/1996 | Foster et al. | 7,171,708 B2 * | 2/2007 | Osborne et al. | 5/618 |
| 5,579,550 A | 12/1996 | Bathrick et al. | 7,216,384 B2 * | 5/2007 | Allen et al. | 5/618 |
| 5,611,094 A | 3/1997 | D'Entremont | 7,296,312 B2 * | 11/2007 | Menkedick et al. | 5/611 |
| 5,636,394 A | 6/1997 | Bartley | 7,406,731 B2 * | 8/2008 | Menkedick et al. | 5/618 |
| 5,653,064 A | 8/1997 | Kappers et al. | 7,454,805 B2 * | 11/2008 | Osborne et al. | 5/618 |
| 5,666,681 A | 9/1997 | Meyer et al. | 2001/0001163 A1 * | 5/2001 | Allen et al. | 5/624 |
| 5,687,437 A | 11/1997 | Goldsmith | 2001/0011393 A1 | 8/2001 | Brooke et al. | |
| 5,689,839 A | 11/1997 | Laganiere et al. | 2001/0011394 A1 | 8/2001 | Heimbrock et al. | |
| 5,701,618 A | 12/1997 | Brugger | 2001/0029628 A1 | 10/2001 | Ferrand et al. | |
| 5,715,548 A | 2/1998 | Weismiller et al. | 2001/0032362 A1 | 10/2001 | Welling et al. | |
| 5,720,059 A | 2/1998 | Allevato et al. | 2002/0002742 A1 | 1/2002 | Osborne et al. | |
| 5,732,423 A | 3/1998 | Weismiller et al. | 2002/0013965 A1 | 2/2002 | Wilson | |
| 5,737,781 A | 4/1998 | Votel | 2002/0014951 A1 | 2/2002 | Kramer et al. | |
| 5,745,937 A | 5/1998 | Weismiller et al. | 2002/0059679 A1 | 5/2002 | Weismiller et al. | |
| 5,749,123 A | 5/1998 | Warren et al. | 2002/0066142 A1 | 6/2002 | Osborne et al. | |
| 5,771,511 A | 6/1998 | Kummer et al. | 2002/0080037 A1 | 6/2002 | Dixon et al. | |
| 5,781,949 A | 7/1998 | Weismiller et al. | 2002/0092096 A1 | 7/2002 | Heimbrock et al. | |
| 5,802,636 A | 9/1998 | Corbin et al. | 2003/0051291 A1 | 3/2003 | Brooke et al. | |
| 5,802,640 A | 9/1998 | Ferrand et al. | 2003/0051292 A1 | 3/2003 | Ferrand et al. | |
| 5,806,111 A | 9/1998 | Heimbrock et al. | 2003/0088920 A1 * | 5/2003 | Allen et al. | 5/624 |
| 5,808,552 A | 9/1998 | Wiley et al. | 2003/0093860 A1 | 5/2003 | Kramer | |

| | | | |
|---|---|---|---|
| 2004/0034936 A1* | 2/2004 | Welling et al. ............... | 5/624 |
| 2004/0128765 A1* | 7/2004 | Osborne et al. ............... | 5/600 |
| 2004/0177445 A1* | 9/2004 | Osborne et al. ............... | 5/600 |
| 2004/0221391 A1* | 11/2004 | Allen et al. .................... | 5/624 |
| 2005/0172405 A1 | 8/2005 | Menkedick et al. | |
| 2005/0273940 A1* | 12/2005 | Petrosenko et al. ............ | 5/722 |
| 2006/0075559 A1* | 4/2006 | Skinner et al. ................. | 5/615 |
| 2006/0075560 A1* | 4/2006 | Osborne et al. ............... | 5/618 |
| 2006/0096029 A1* | 5/2006 | Osborne et al. ............... | 5/618 |
| 2006/0096030 A1* | 5/2006 | Allen et al. .................... | 5/624 |
| 2006/0162079 A1* | 7/2006 | Menkedick et al. ........... | 5/624 |
| 2006/0168730 A1* | 8/2006 | Menkedick et al. ........... | 5/618 |
| 2006/0168731 A1* | 8/2006 | Menkedick et al. ........... | 5/618 |
| 2007/0010719 A1* | 1/2007 | Huster et al. ................ | 600/300 |
| 2007/0169271 A1* | 7/2007 | Allen et al. .................... | 5/624 |
| 2008/0010748 A1* | 1/2008 | Menkedick et al. ........... | 5/600 |
| 2008/0052831 A1* | 3/2008 | Weismiller et al. ........... | 5/616 |
| 2008/0078030 A1* | 4/2008 | Lee et al. ....................... | 5/616 |
| 2008/0201847 A1* | 8/2008 | Menkedick et al. ........... | 5/600 |
| 2008/0201851 A1* | 8/2008 | Menkedick et al. ........... | 5/611 |
| 2008/0209635 A1* | 9/2008 | Gonzalez et al. .............. | 5/600 |
| 2008/0289108 A1 | 11/2008 | Menkedick et al. ........... | 5/610 |
| 2009/0013470 A1* | 1/2009 | Richards et al. ............... | 5/613 |

FOREIGN PATENT DOCUMENTS

| | | |
|---|---|---|
| EP | 0 037 063 A2 | 10/1981 |
| EP | 0 218 301 A2 | 4/1987 |
| EP | 0 341 570 A3 | 11/1989 |
| EP | 0 349 067 A1 | 1/1990 |
| EP | 0 485 362 A3 | 5/1992 |
| EP | 0 558 108 A2 | 9/1993 |
| GB | 7095 | 9/1913 |
| GB | 1 466 080 | 3/1977 |
| GB | 2 015 872 A | 9/1979 |
| GB | 2 169 195 A | 7/1986 |
| GB | 2 313 303 | 11/1997 |
| JP | 53-37515 | 9/1978 |
| JP | 02-109563 | 4/1990 |
| JP | 02-154760 | 6/1990 |
| JP | 02-156950 | 6/1990 |
| JP | 02-200262 | 8/1990 |
| JP | 03-155862 | 7/1991 |
| JP | 3-186212 | 8/1991 |
| JP | 3-193005 | 8/1991 |
| JP | 3-237976 | 10/1991 |
| JP | 07-124201 | 5/1995 |
| JP | 08-280747 | 10/1996 |
| JP | 10-005284 | 1/1998 |
| WO | WO 98/17153 | 4/1998 |
| WO | WO 99/15126 | 4/1999 |
| WO | WO 00/07537 | 2/2000 |
| WO | WO 00/69386 | 11/2000 |
| WO | WO 01/47340 | 7/2001 |
| WO | WO 01/62151 | 8/2001 |
| WO | WO 03/79953 | 10/2003 |
| WO | WO 03/88885 | 10/2003 |

OTHER PUBLICATIONS

Akrotech 4000 Brochure, LUMEX, 1992.
"Impression™" Brochure, Kinetic Concepts, Inc., Aug. 1996.
Stryker Medical Go Bed™ brochure, 2 pgs., 2001.
Hill-Rom Med Surg Bed Accessories brochure, 1998 (6 pgs.).
Office Action for U.S. Appl. No. 11/864,442 dated Mar. 17, 2008, 8 pages.
Claims as they stand in U.S. Appl. No. 11/864,442, 5 pages.
Office Action for U.S. Appl. No. 11/393,645 dated Apr. 14, 2008, 8 pages.
Preliminary Amendment for U.S. Appl. No. 11/393,645 dated Jul. 9, 2007 showing the claims as they stand, 7 pages.
International Standard ISO 11898-1 Road Vehicles - Controller area network (CAN)-Part. 1: Data link layer and physical signaling, 52 pages, Dec. 1, 2003.
International Standard ISO 11898-1 Road Vehicles - Controller area network (CAN)-Part. 2: High-speed medium access unit, 20 pages, Dec. 1, 2003.
Official Action in U.S. Appl. No. 11/393,645, mailed Aug. 12, 2008, 5 pages.
Response to Official Action in U.S. Appl. No. 11/393,645, mailed Dec. 12, 2008, 8 pages.

* cited by examiner

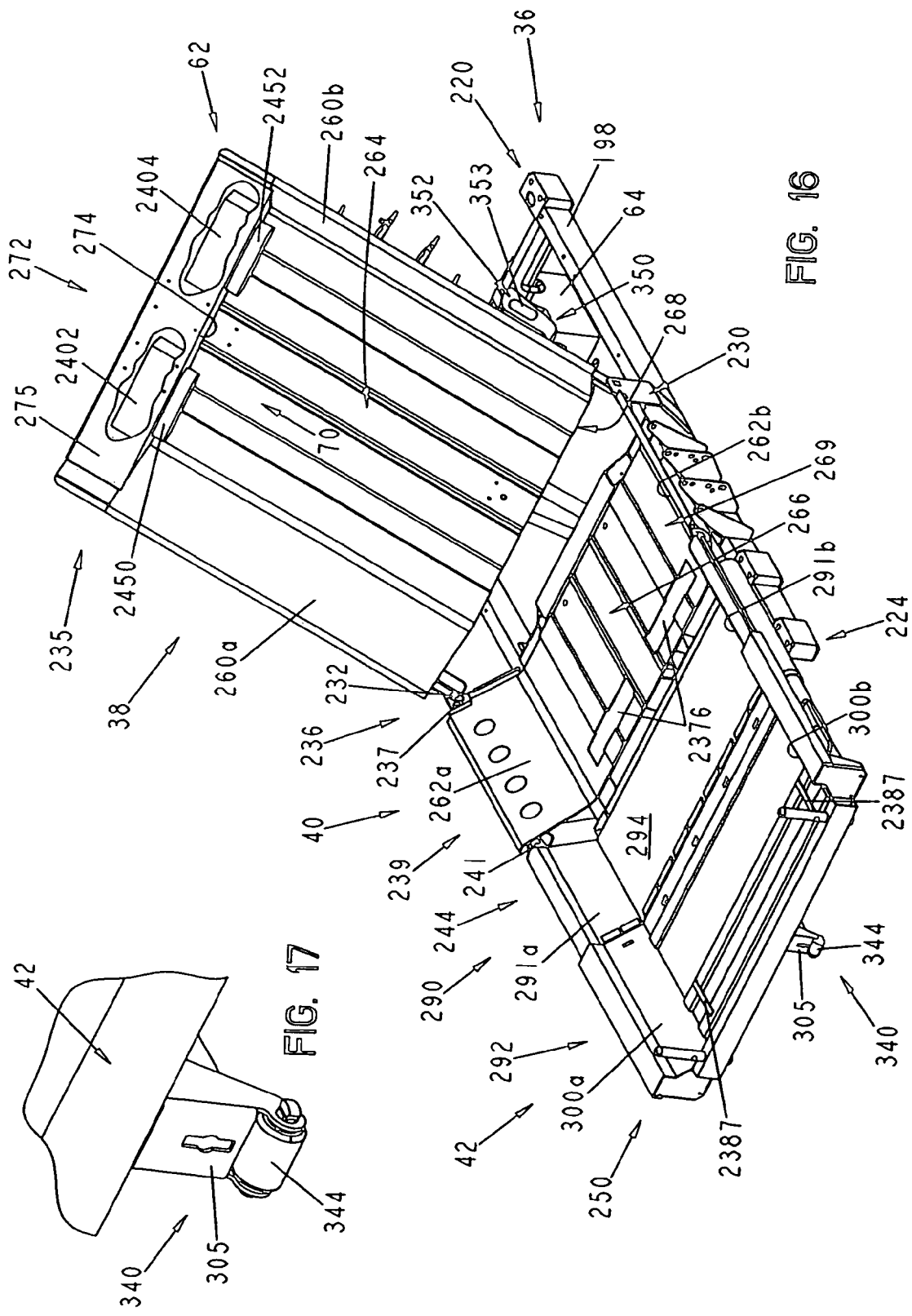

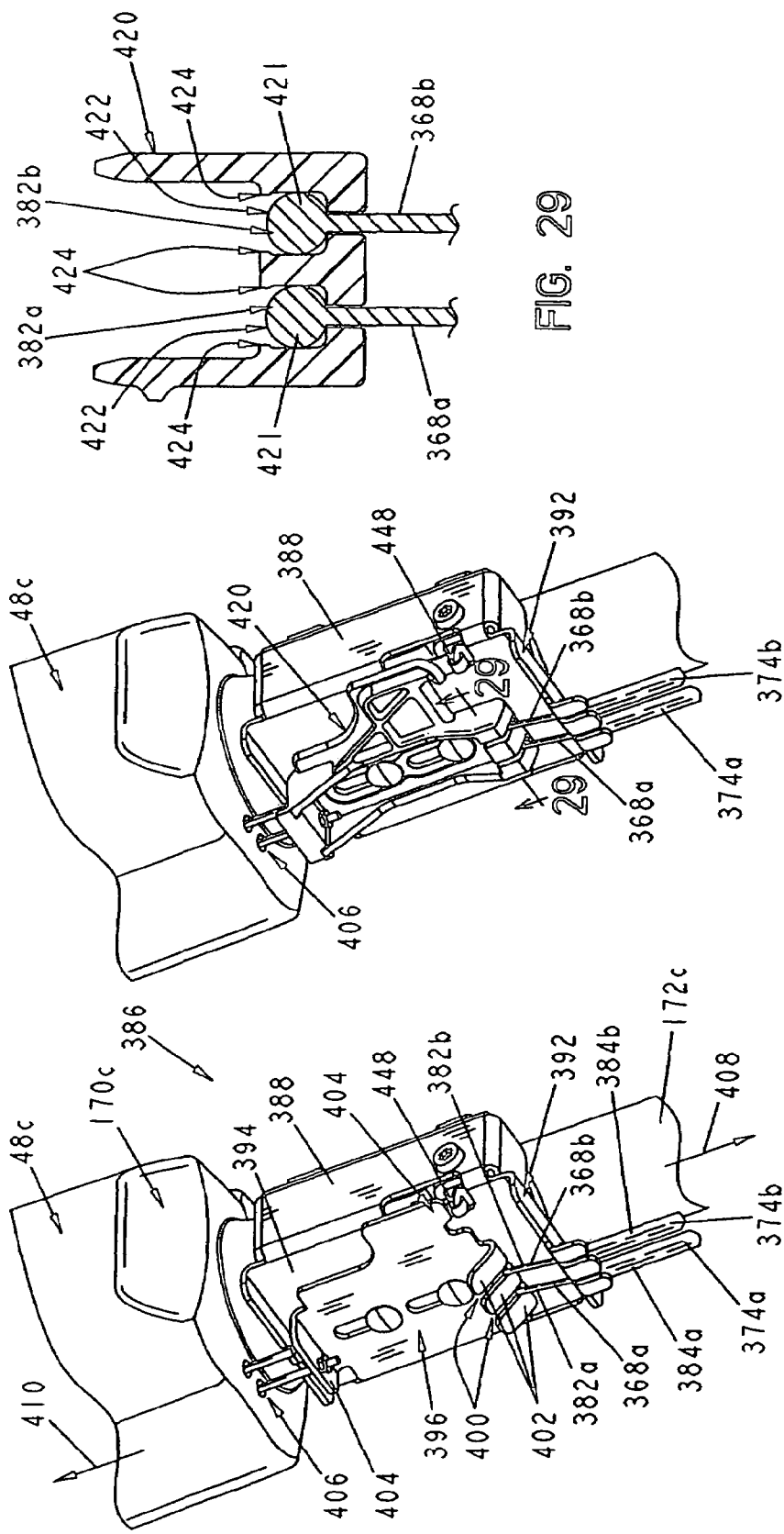

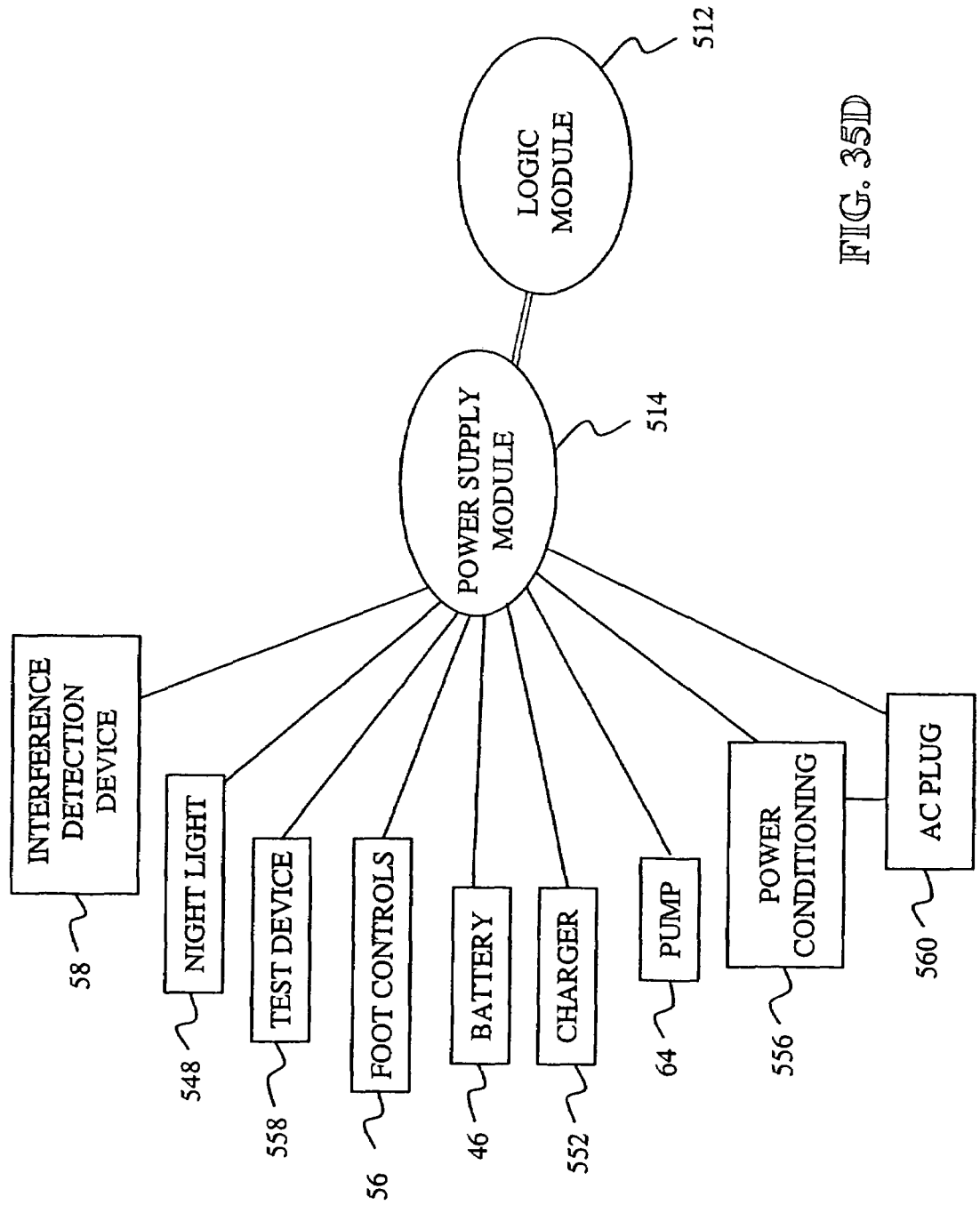

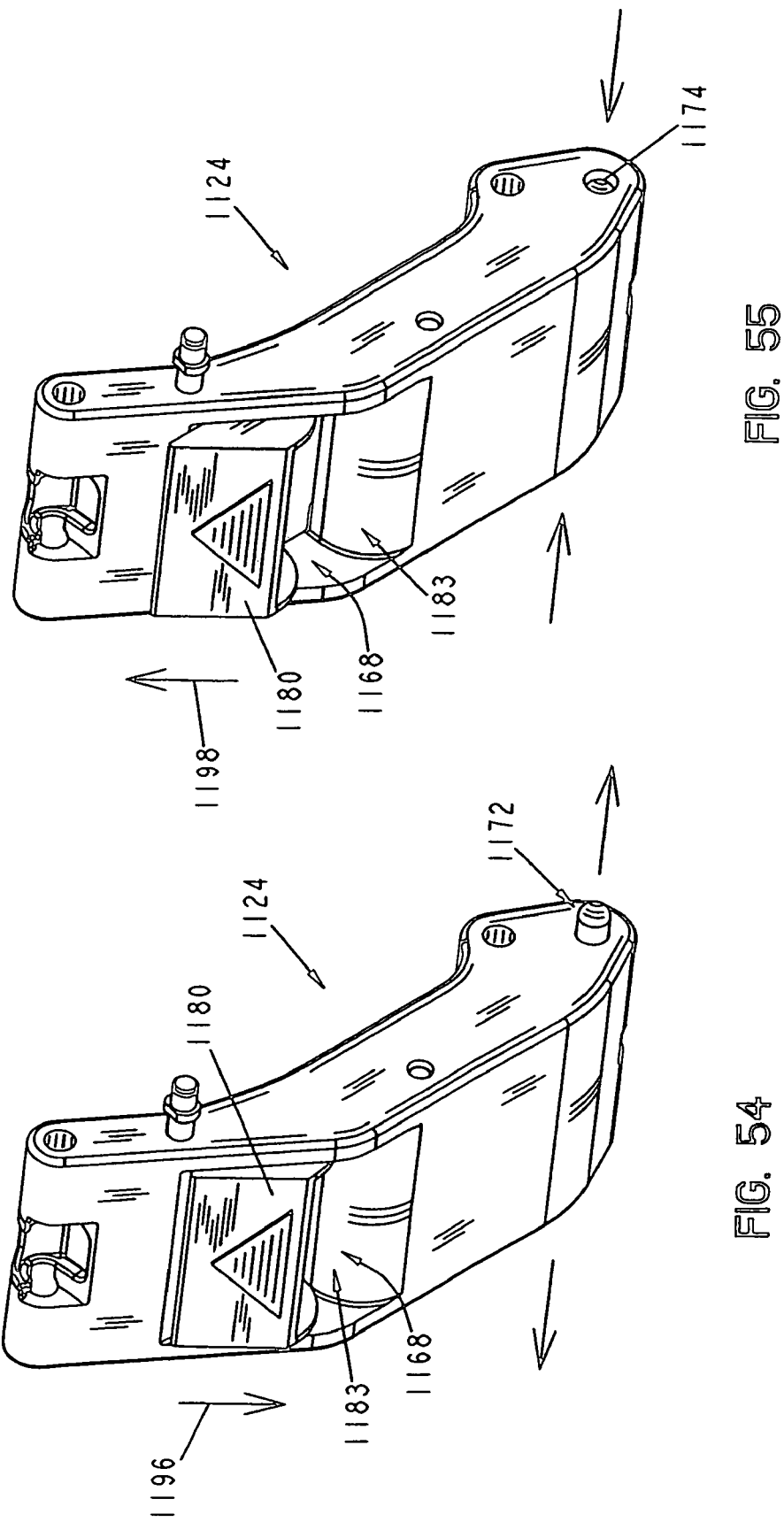

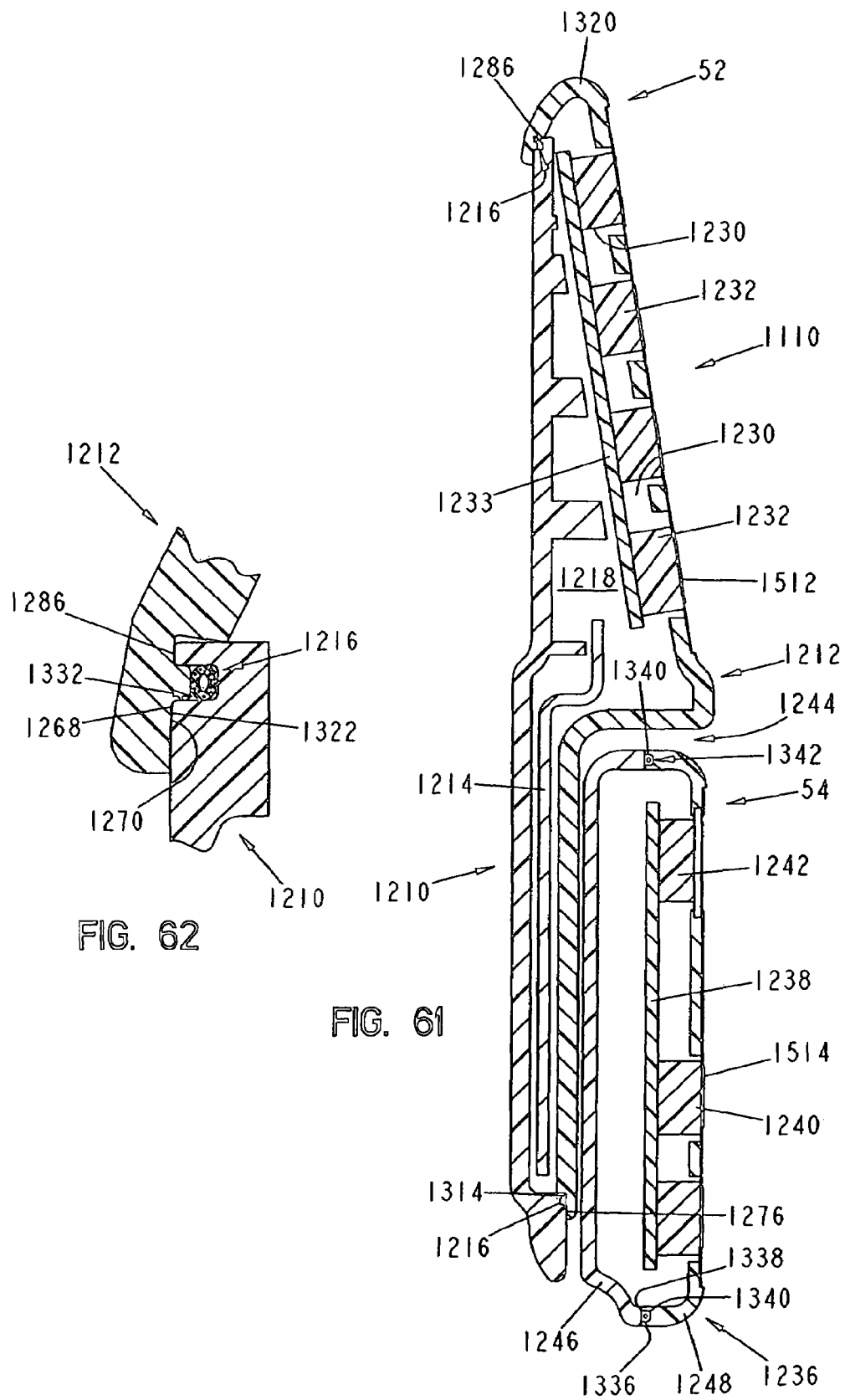

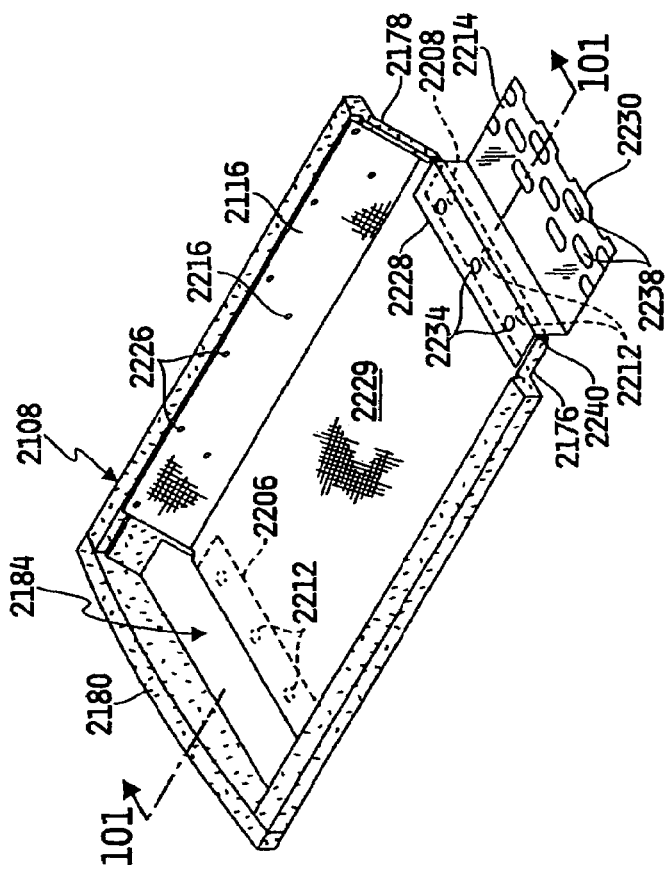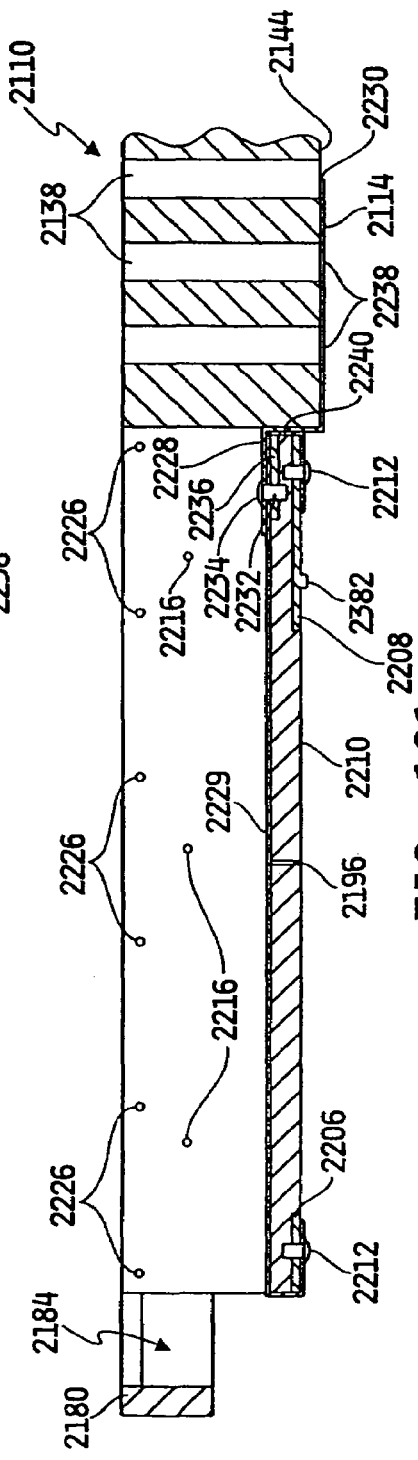
FIG. 100
FIG. 101

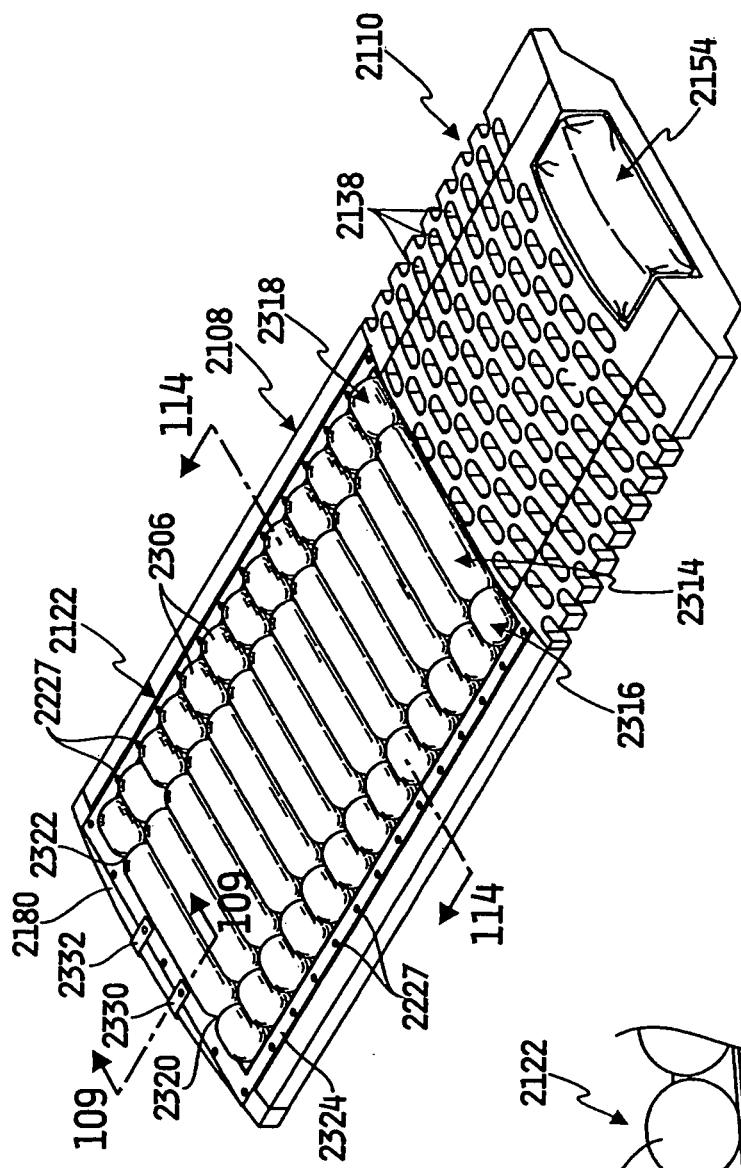
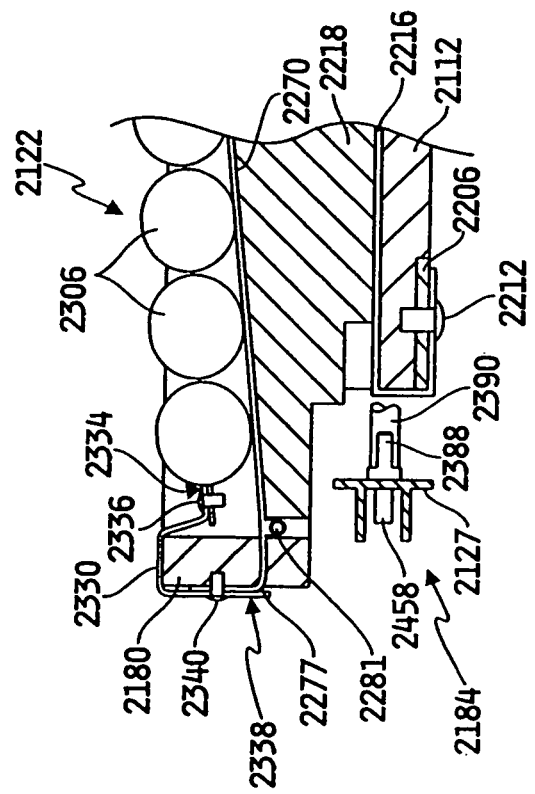
FIG. 108
FIG. 109

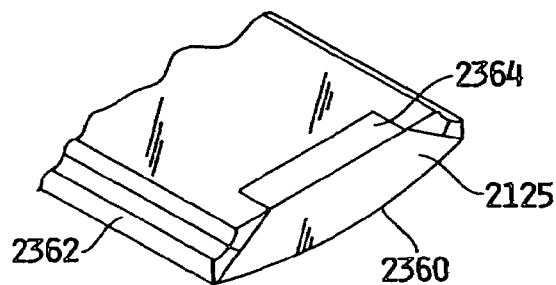
FIG. 110
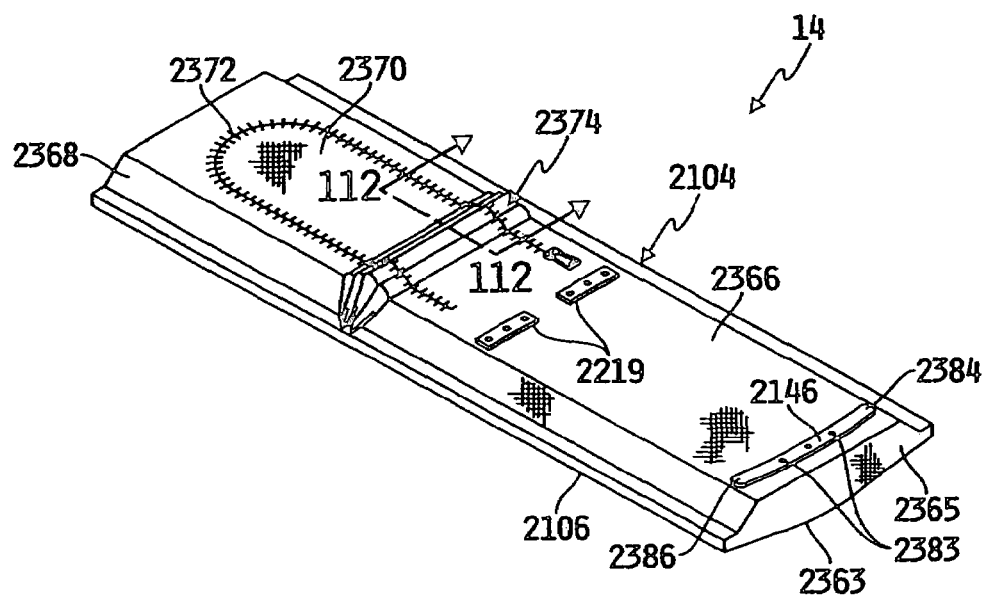
FIG. 111
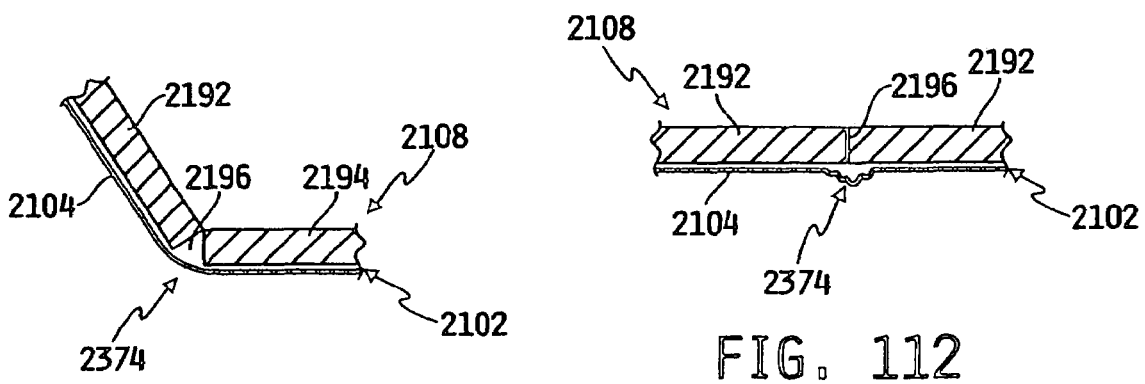
FIG. 113
FIG. 112

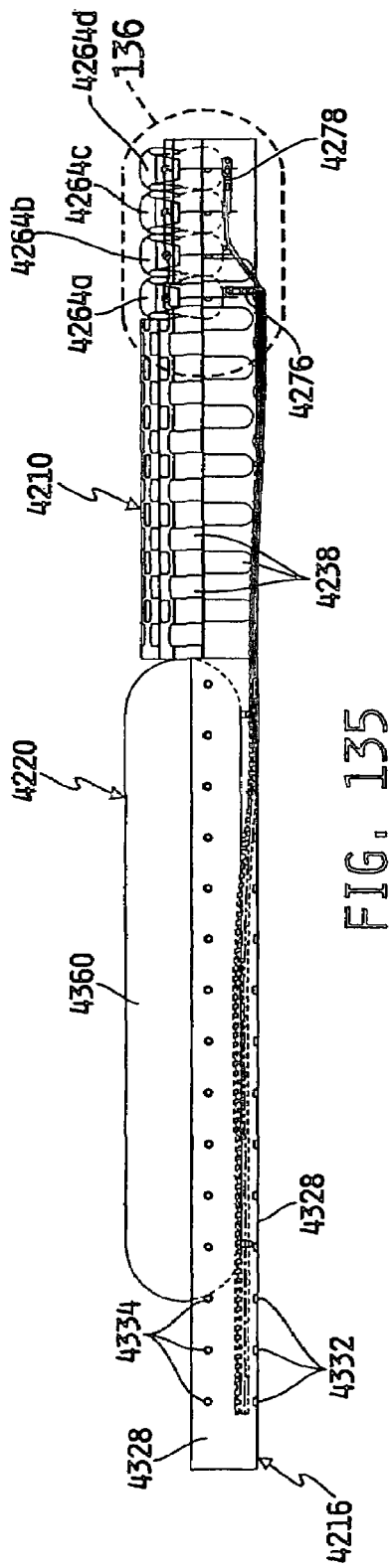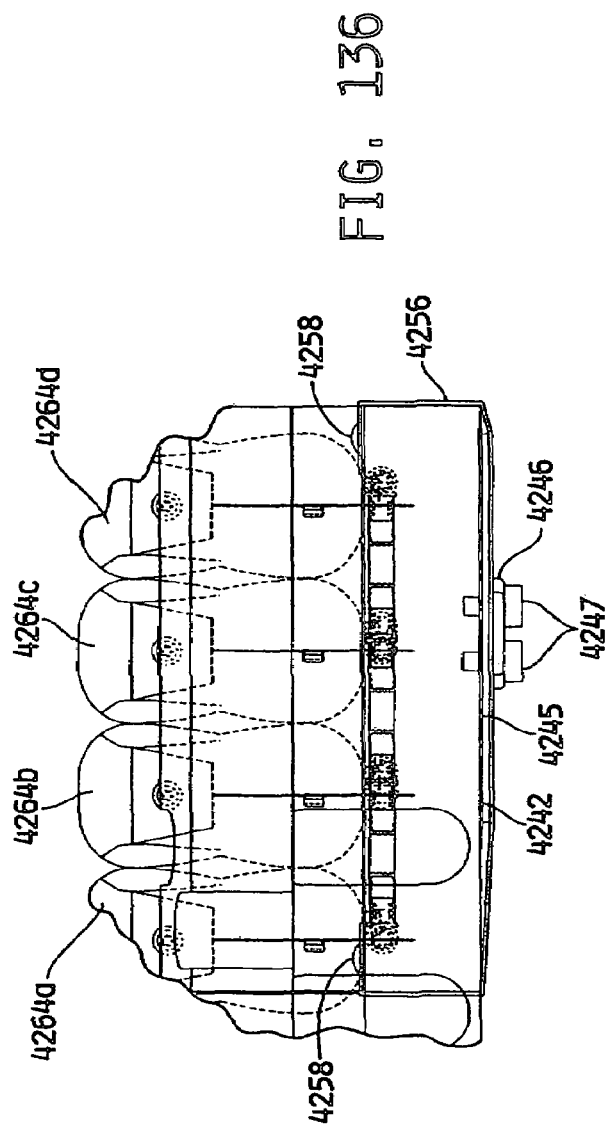

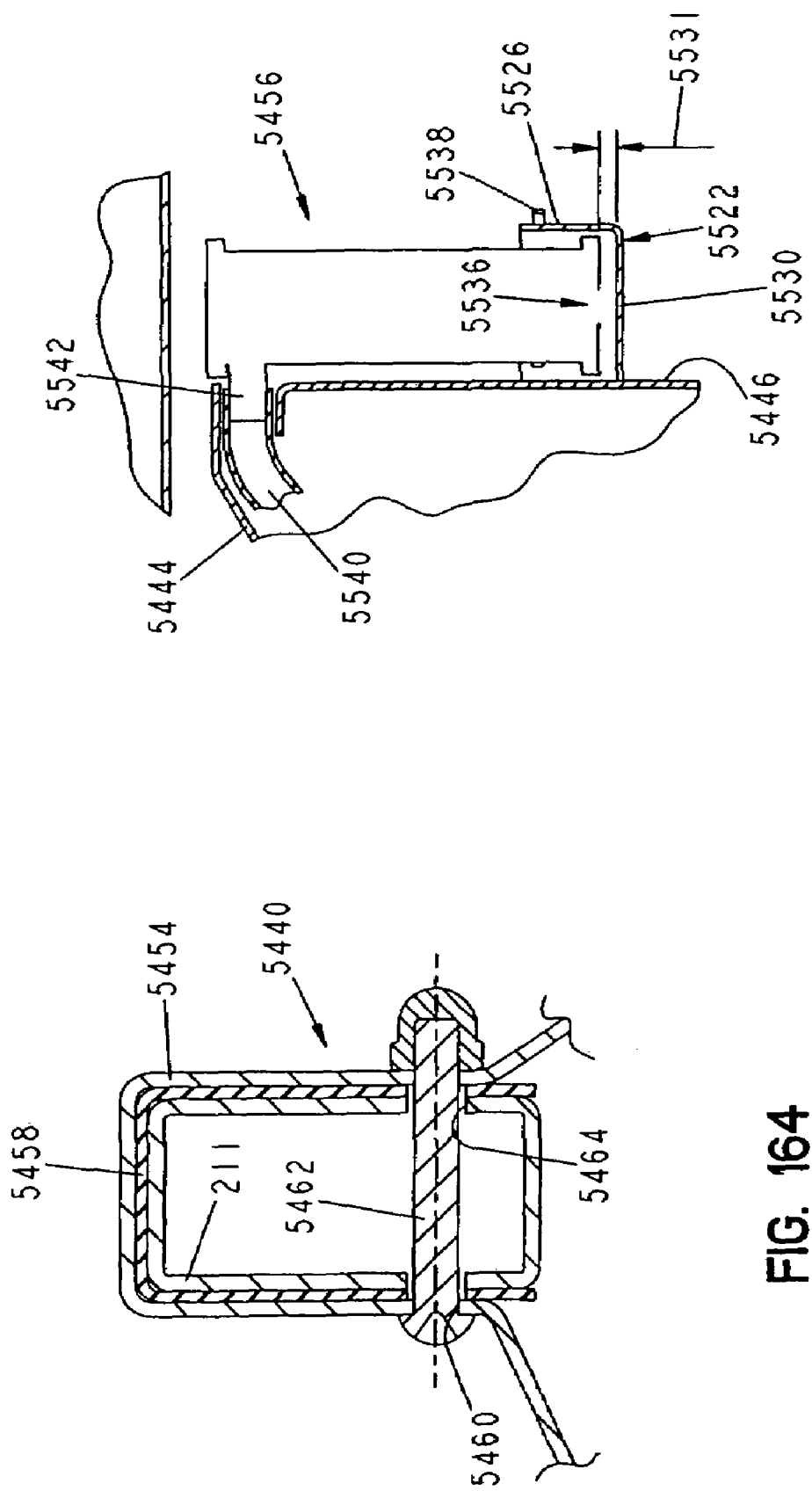

HOSPITAL BED INCLUDING MOVEABLE FOOT PORTION

CROSS-REFERENCE TO RELATED APPLICATIONS

This application is a continuation of U.S. patent application Ser. No. 10/657,696, filed Sep. 8, 2003, now U.S. Pat. No. 7,296,312, which claims the benefit of U.S. Provisional Patent Application Ser. No. 60/408,698, filed Sep. 6, 2002, titled Hospital Bed; U.S. Provisional Patent Application Ser. No. 60/409,748, filed Sep. 11, 2002, titled Bed Siderail; U.S. Provisional Patent Application Ser. No. 60/489,171, filed Jul. 22, 2003, titled Hospital Bed; and U.S. Provisional Patent Application Ser. No. 60/490,467, filed Jul. 28, 2003, titled Hospital Bed, the disclosures of all of which are expressly incorporated by reference herein.

This application relates to U.S. patent application Ser. No. 09/750,741, filed Dec. 29, 2000, titled Hospital Bed, which claims the benefit of U.S. Provisional Patent Application Ser. No. 60/173,428, filed Dec. 29, 1999, titled Hospital Bed; U.S. patent application Ser. No. 09/751,031, filed Dec. 29, 2000, titled Foot Controls for a Bed, which claims the benefit of U.S. Provisional Patent Application Ser. No. 60/173,428, filed Dec. 29, 1999, titled Hospital Bed; U.S. patent application Ser. No. 09/750,859, filed Dec. 29, 2000, titled Mattress Having a Retractable Foot Section, which claims the benefit of U.S. Provisional Patent Application Ser. No. 60/173,428, filed Dec. 29, 1999, titled Hospital Bed; and U.S. patent application Ser. No. 10/225,780, filed Aug. 22, 2002, titled Apparatus and Method for Closing Hospital Bed Gaps, which claims the benefit of U.S. Provisional Patent Application Ser. No. 60/397,342, filed Jul. 19, 2002, titled Apparatus and Method for Closing Hospital Bed Gaps and U.S. Provisional Patent Application Ser. No. 60/314,276, filed Aug. 22, 2001, titled Apparatus and Method for Closing Hospital Bed Gaps. This application further relates to PCT Patent Application No. PCT/US00/35656, filed Dec. 29, 2000, titled Hospital Bed. The disclosures of all the above-mentioned patent applications are expressly incorporated by reference herein.

BACKGROUND AND SUMMARY OF THE INVENTION

The present invention relates to a hospital bed. More particularly, the present invention relates to a hospital bed illustratively having siderails, an articulating deck, and a mattress.

Hospital bed and other patient supports are known. Typically, such patient supports are used to provide a support surface for patients or other individuals for treatment, recuperation, or rest. Many such patient supports include a frame, a deck supported by the frame, a mattress, siderails configured to block egress of a patient from the mattress, and a controller configured to control one or more features of the bed.

BRIEF DESCRIPTION OF THE DRAWINGS

The detailed description particularly refers to the accompanying figures in which:

FIG. 16 is an upper perspective view of the deck and weigh frame of the patient support of FIG. 1, showing the foot section in an extended position, the head section elevated relative to the seat section and a partition of the head section showing the manifold assembly on a first side of the partition and first and second manifold receiving connectors on a second side of the partition;

FIG. 17 is a perspective view of the roller coupled to the end of the foot section shown in FIG. 16;

FIG. 27 is a perspective view of a actuator assembly of the CPR system of the patient support showing a housing coupled to the cylinder rod of the actuator, a first embodiment of a slide bracket slidably coupled to the housing and coupled to the cable which is further coupled to the handle of FIG. 23 and a release pin of the actuator, and a switch located on the housing;

FIG. 28 is a perspective view of the actuator assembly of FIG. 27 showing a second embodiment of the slide bracket, the slide bracket having detents positively couple the ends of the cable;

FIG. 29 is a cross sectional view of the coupling of the second embodiment of the slide bracket and the ends of the cable taken along lines 29-29 of FIG. 28;

FIG. 35D is a block diagram detailing a portion of the control system of FIG. 35 by illustrating the interconnection between various control components and the power supply module;

FIG. 54 is a perspective view of the link of FIG. 49, showing pins of the latch extending out from the link;

FIG. 55 is a view similar to FIG. 54, showing the pins withdrawn into the link;

FIG. 61 is a cross sectional view taken along line 61-61 of FIG. 46;

FIG. 62 is an enlarged view of a portion of FIG. 61, showing an O-ring seal positioned between a main body of head end siderail and a cover of head end siderail;

FIG. 100 is a perspective view similar to that of FIG. 98, illustrating the mounting substrate and the foot section securing substrate coupled the receiving base;

FIG. 101 is a cross-sectional view taken along line 101-101 of FIG. 100 illustrating the mounting substrate and the foot section securing substrate coupled to the base, and further illustrating a portion of the foot section;

FIG. 108 is a perspective view of the mattress assembly of FIG. 92 with the outer cover, the sheer liner, and the fire barrier removed for clarity;

FIG. 109 is a cross-sectional view taken along line 109-109 of FIG. 108;

FIG. 110 is a detail perspective of the sheer liner applied to the head end of the mattress assembly of FIG. 92;

FIG. 111 is a bottom perspective view of the mattress assembly of FIG. 92, illustrating the mattress anchors and the access port;

FIG. 112 is a side cross-sectional view, in partial schematic, illustrating the body section of the receiving base in a substantially planar position;

FIG. 113 is a side cross-sectional view similar to FIG. 112, illustrating the body section of the receiving base with the base section elevated relative to the seat section;

FIG. 115 is a end elevational view similar to that of FIG. 114, illustrating the right turn assist bladder inflated for assisting in the turning of a patient supported on the mattress assembly;

FIG. 116 is a block diagram illustrating various pneumatic connections between the mattress and the air control system of the present invention;

FIG. 117 is a front elevational view of a manifold assembly of the present invention configured to supply a fluid to the air mattress assembly of FIG. 92 and supported by the articulating deck of the patient support of FIG. 1;

FIG. 118 is a bottom elevational view of the manifold assembly of FIG. 117;

FIG. 119 is a cross-sectional view taken along line 119-119 of FIG. 117, illustrating a normally-closed spring biased valve and a normally-open spring biased valve;

FIG. 120 is a detailed perspective view illustrating the manifold receiving fluid connector and the mating mattress fluid connector of the present invention;

FIG. 121 is a front elevational view of the mattress fluid connector of FIG. 120;

FIG. 122 is a perspective view of a sealing gasket of the present invention for use with the manifold receiving fluid connector of FIG. 120;

FIG. 123 is a cross-sectional view illustrating the sealing gasket of FIG. 122 coupled intermediate the partition and the manifold receiving connector;

FIG. 124 is a block diagram of an illustrative embodiment pressure control system for controlling inflation of air bladders in accordance with the present invention;

FIG. 125 is a flow diagram of an illustrative embodiment process for controlling inflation of air bladders in accordance with the present invention;

FIG. 126 is a flow diagram of an illustrative embodiment process for controlling operation of turn assist bladders in accordance with the present invention;

Figure 1:
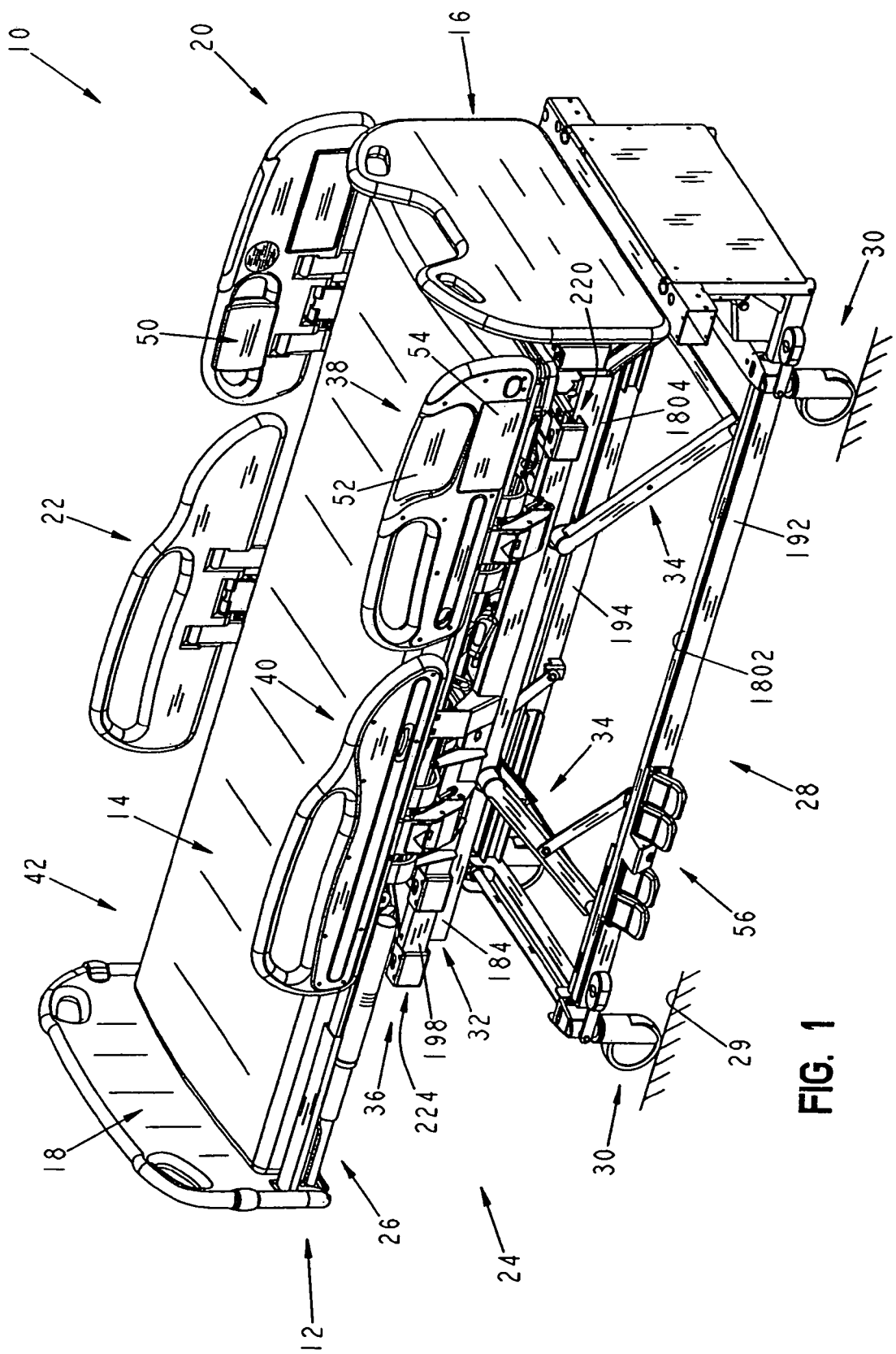
FIG. 1 is a perspective view of a patient support showing the patient support including a deck support, a deck having a plurality of sections coupled to and positioned above the deck support, a mattress supported by the deck, a headboard coupled to the deck support, a first pair of siderails coupled to the deck, a second pair of siderails coupled to the deck support, and foot pedal controls coupled to the deck support.
Figure 57:
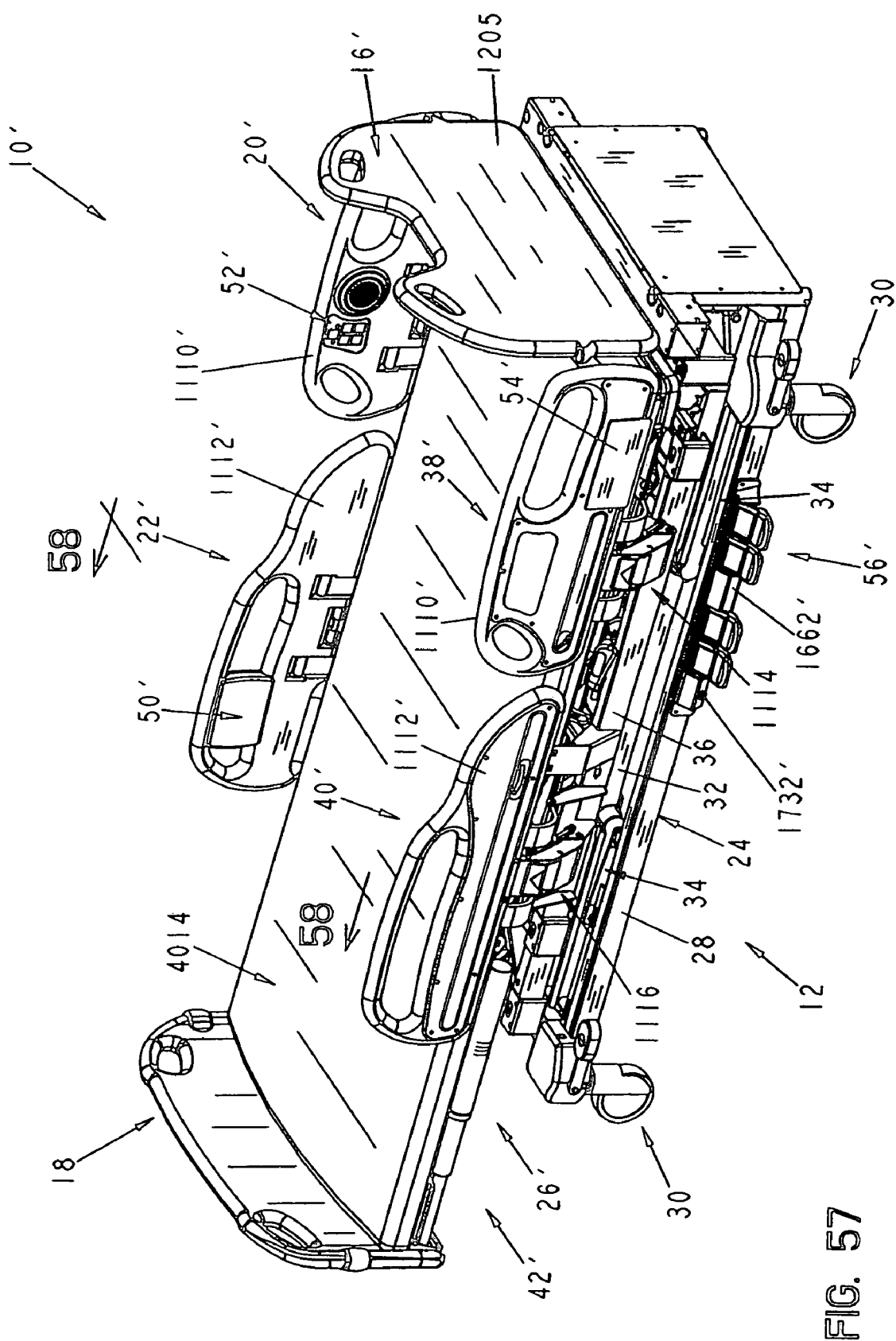
FIG. 57 is a perspective view similar to FIG. 1, illustrating an alternative embodiment patient support including alternative embodiments of headboard, head end siderails, and foot pedal controls coupled to the deck support.
Figure 127:
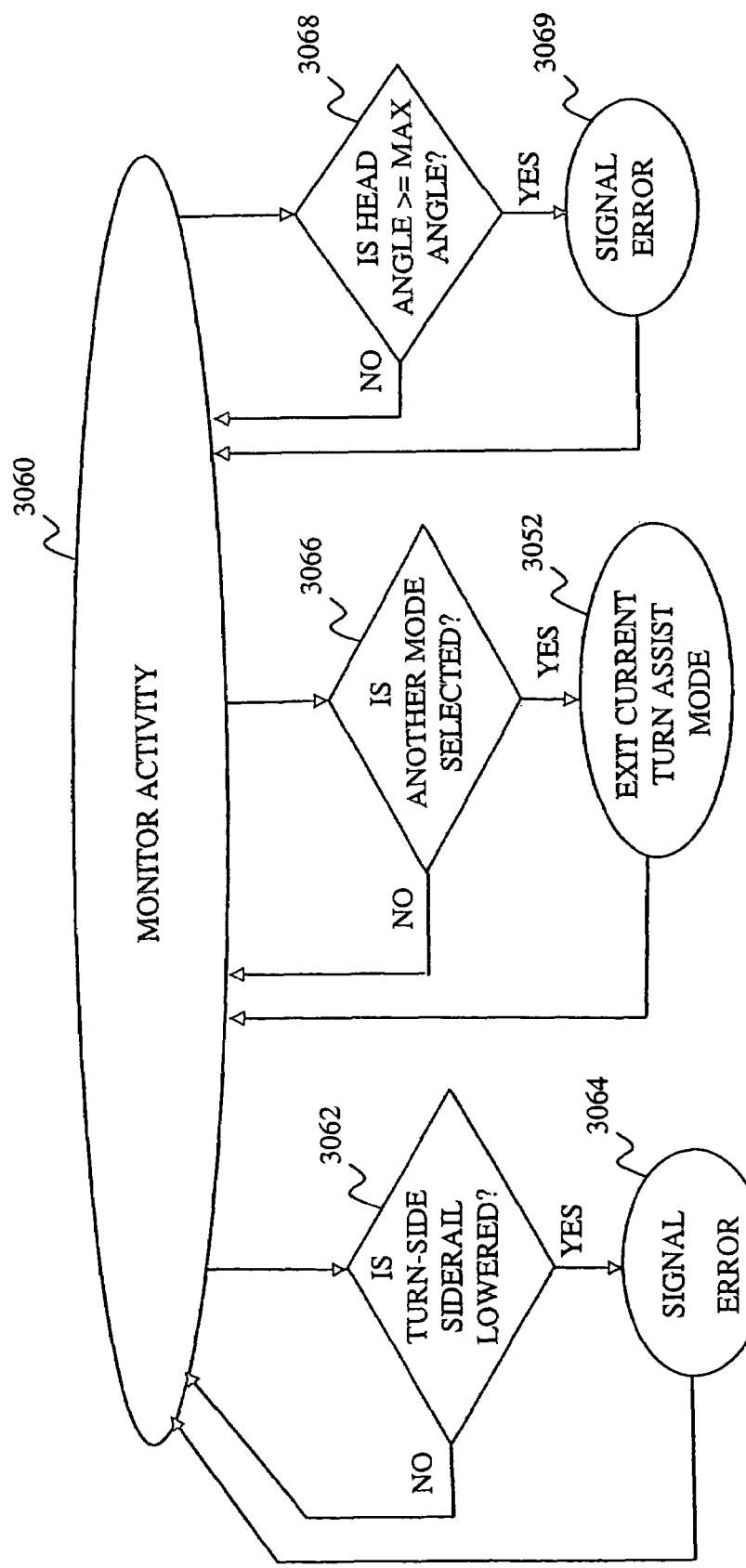
Figure 128:
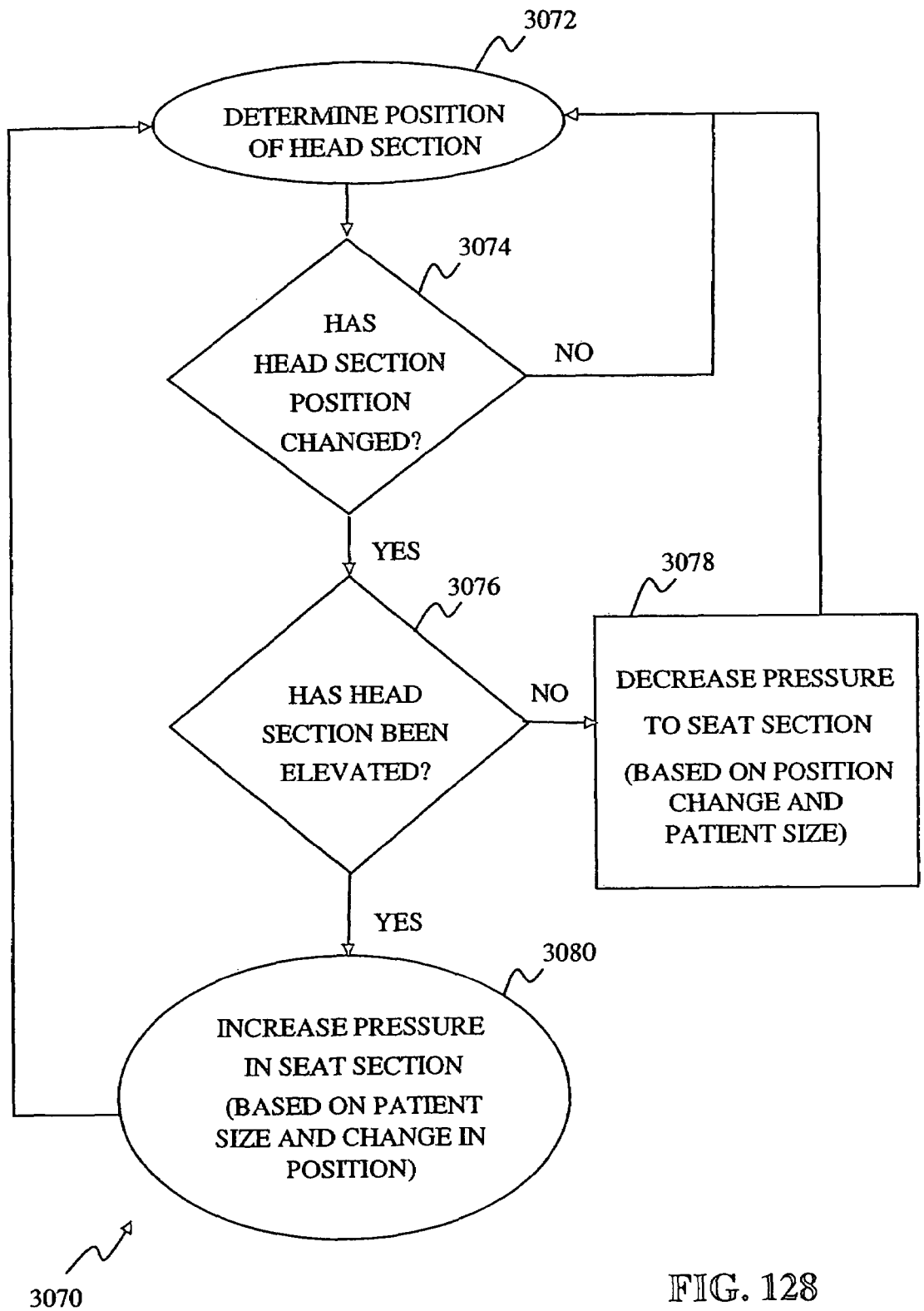
Figure 129:
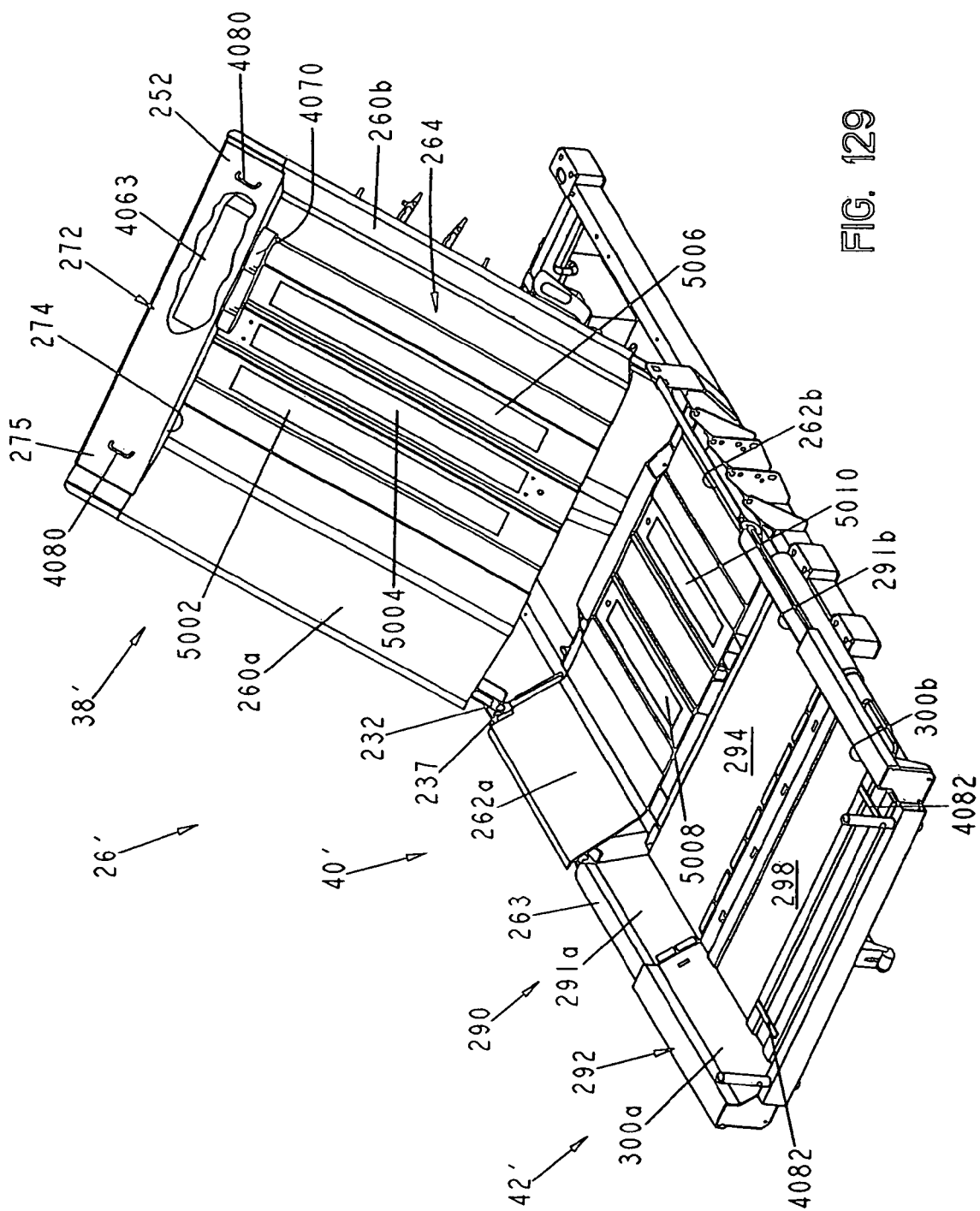
Figure 130:
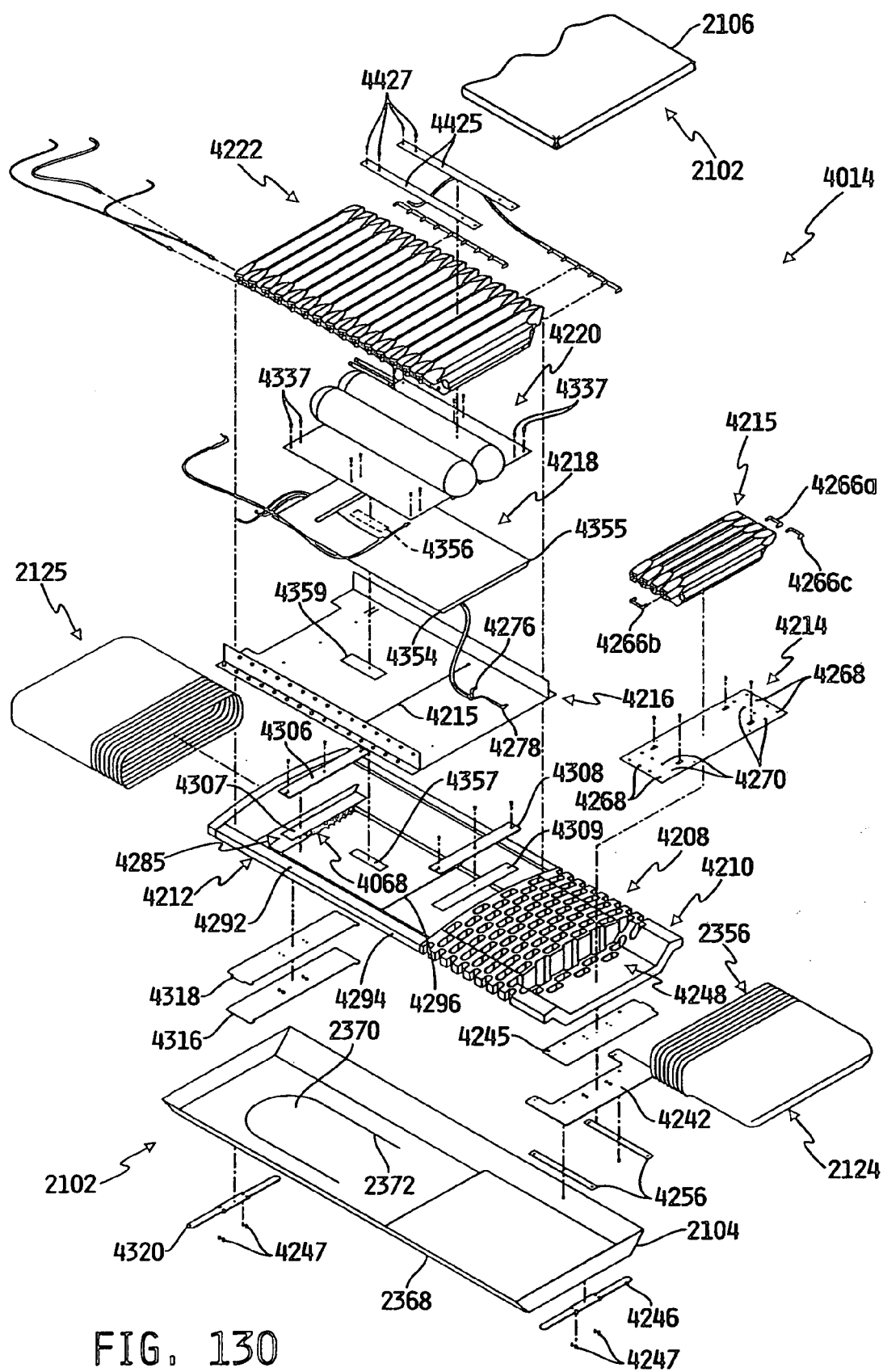
Figure 131:
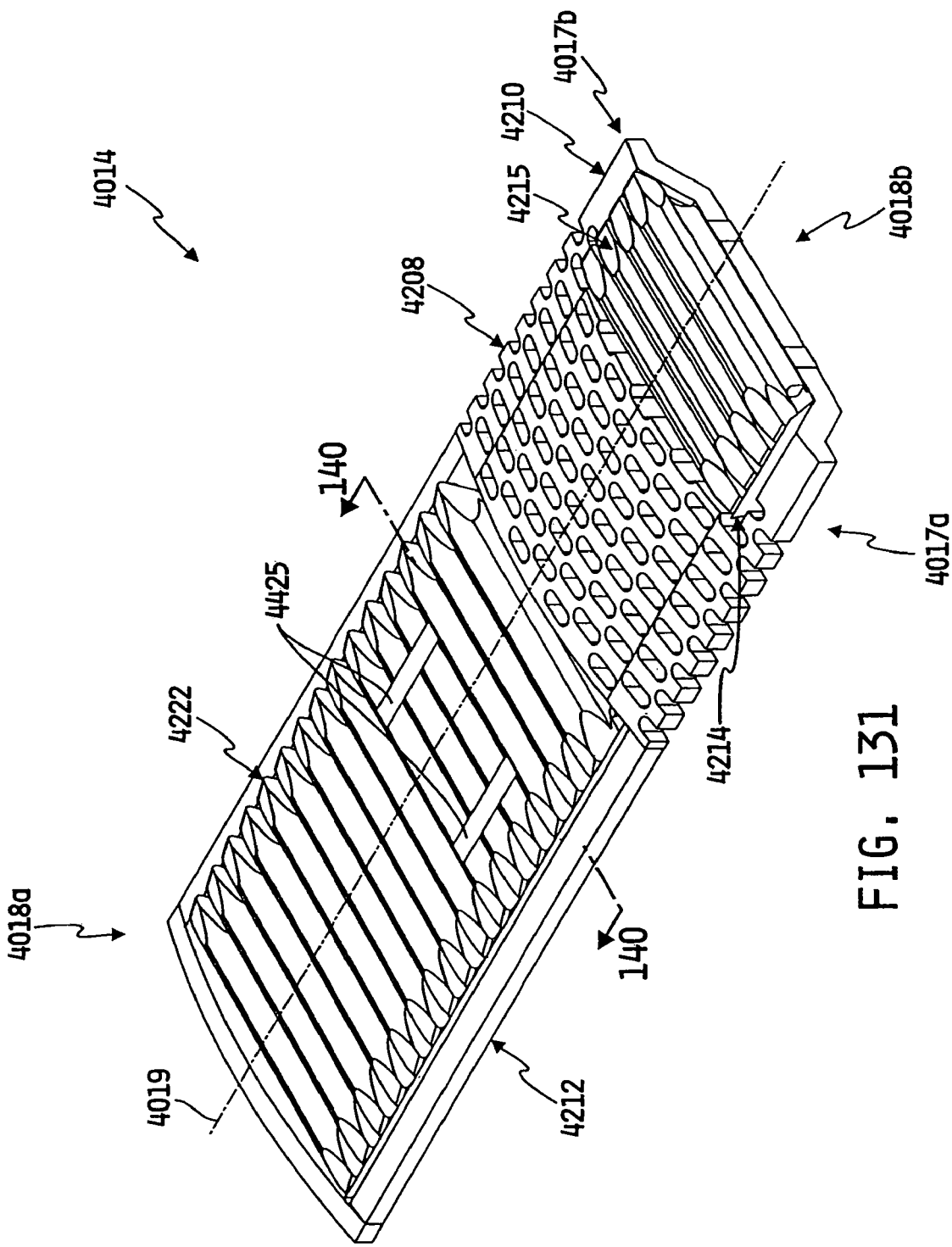
Figure 132:
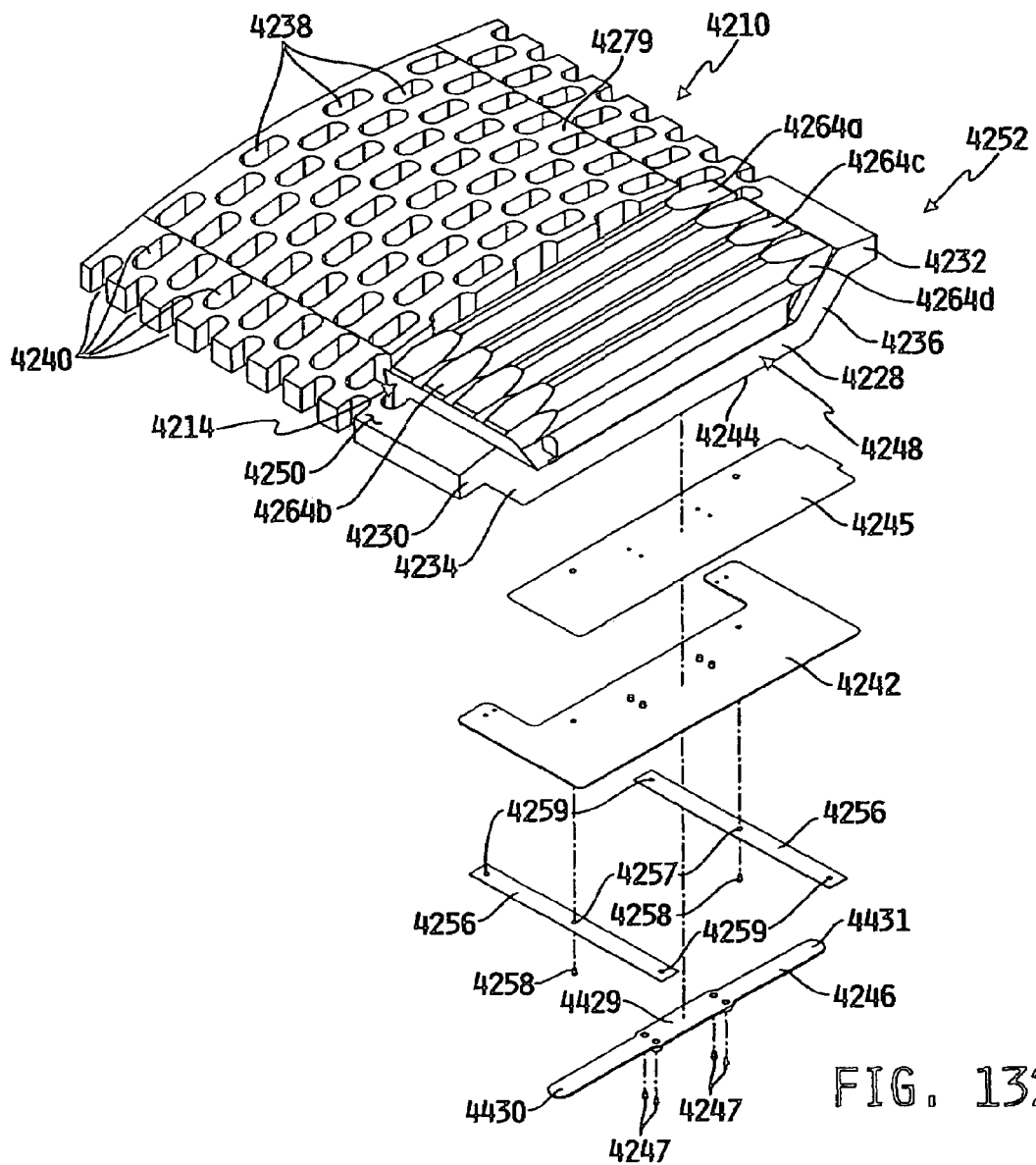
Figure 133:
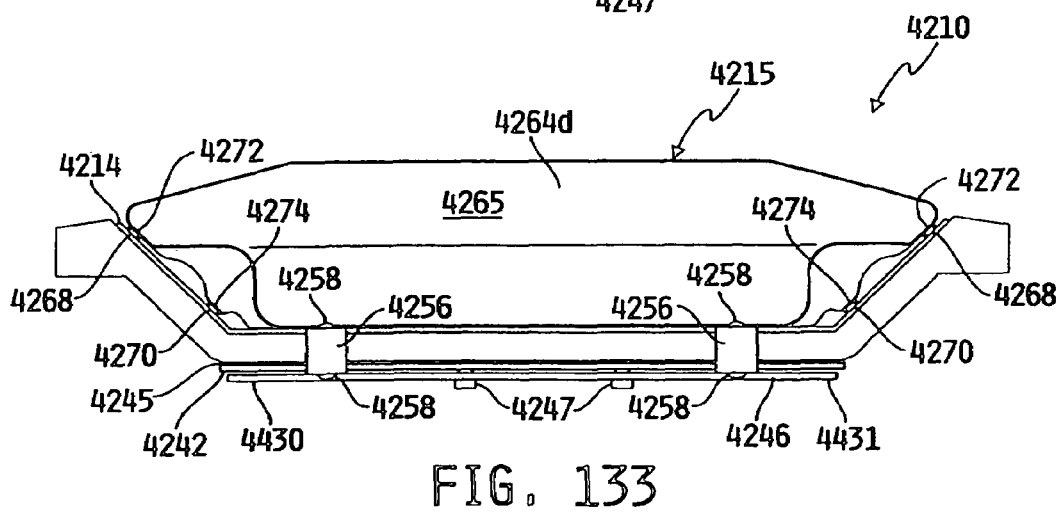
Figure 134:
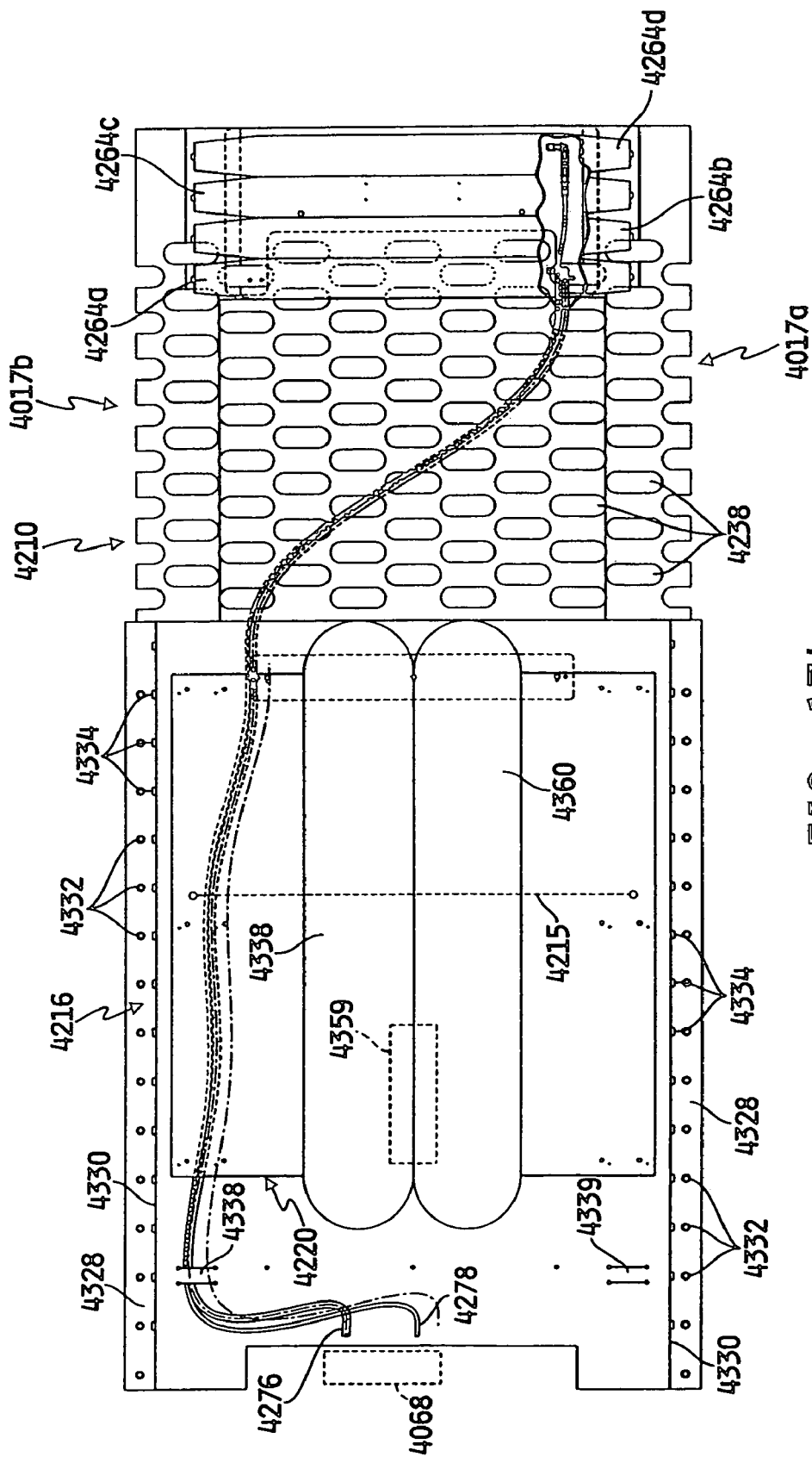
Figure 137:
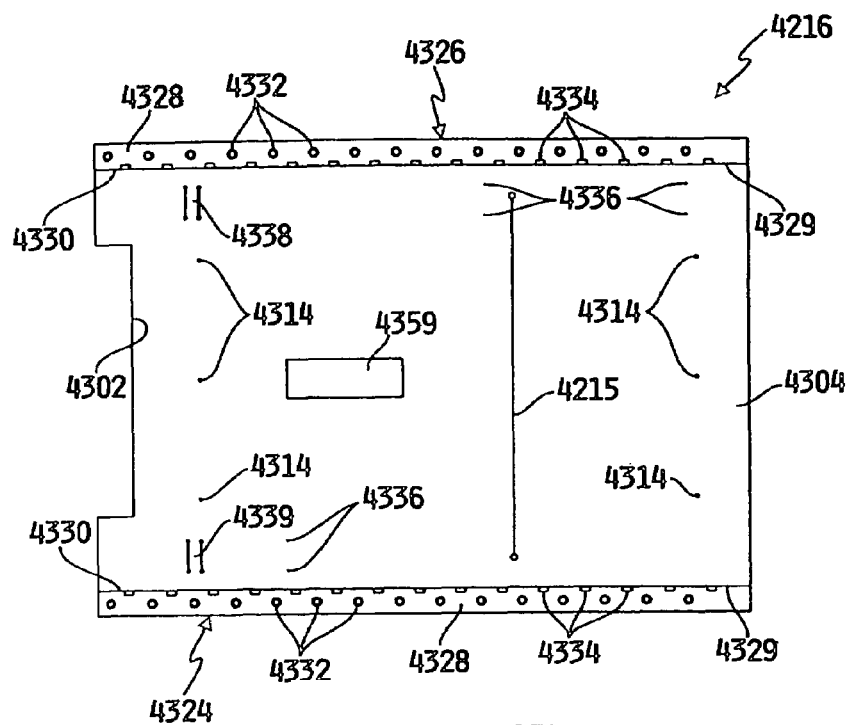
Figure 138:
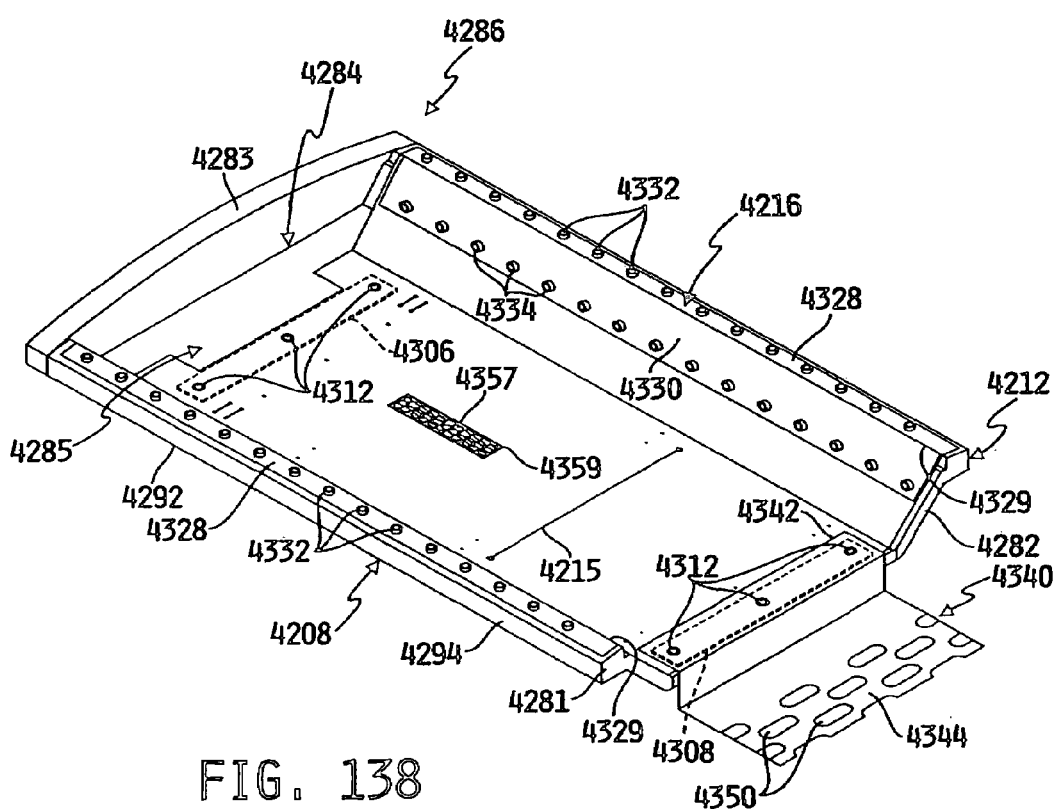
Figure 139:
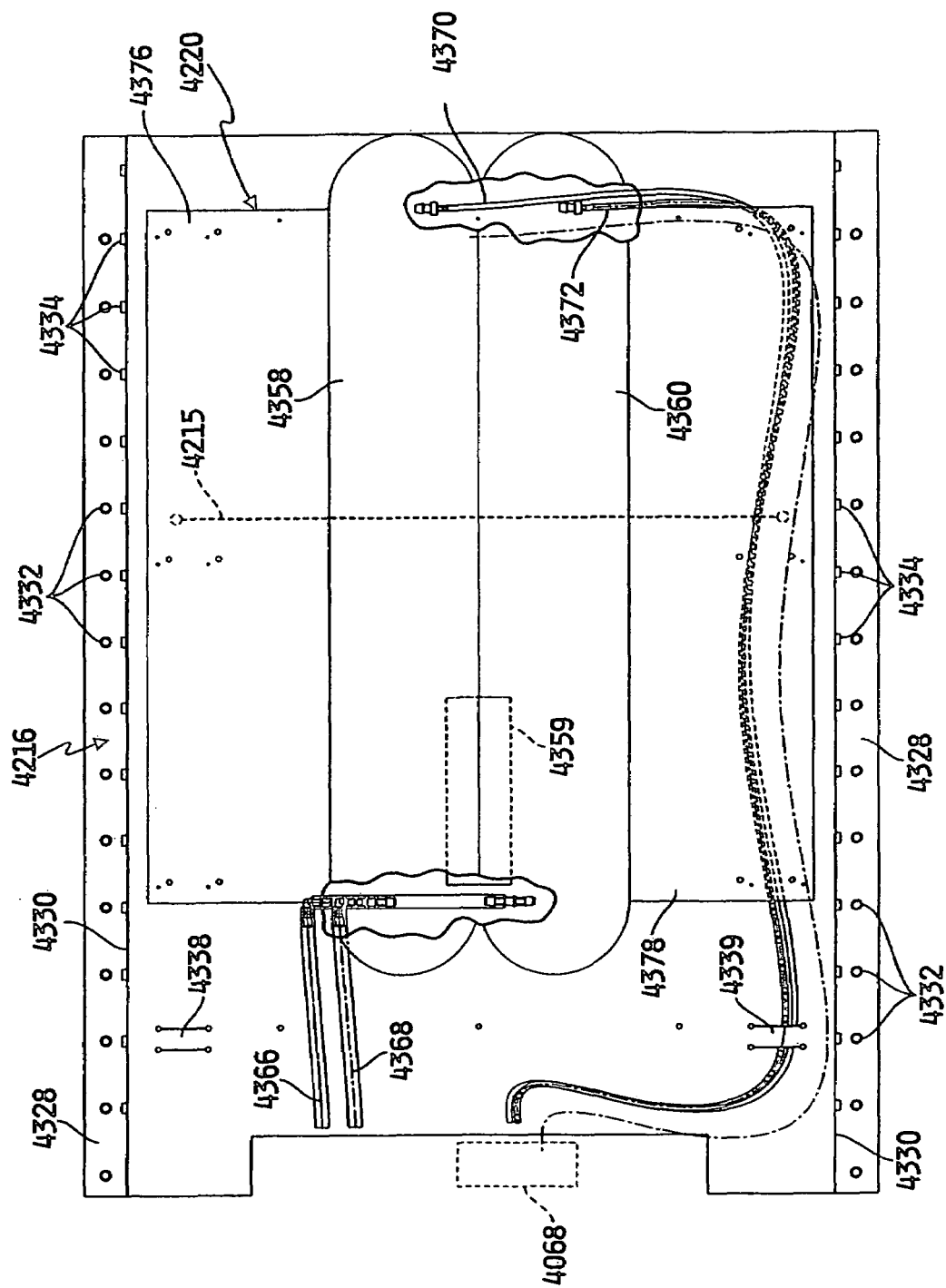
Figure 140:
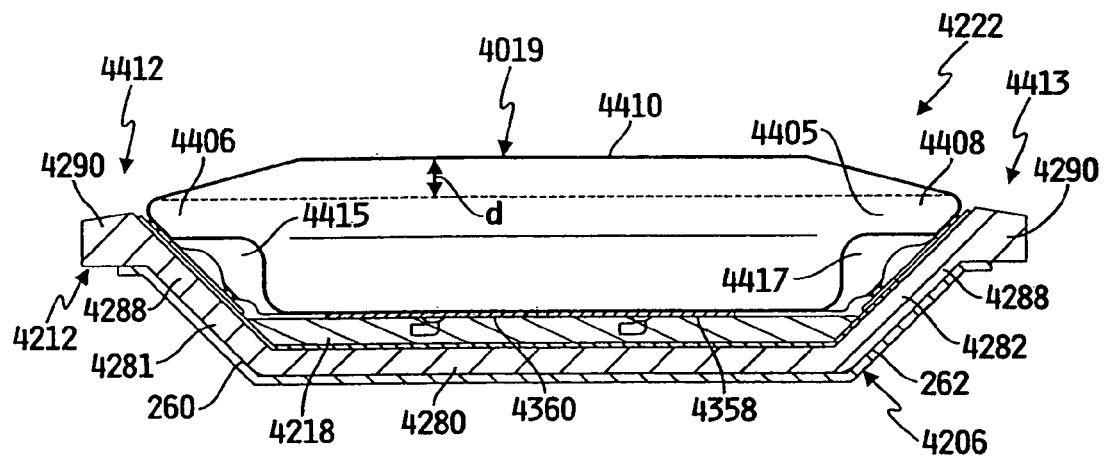
Figure 141:
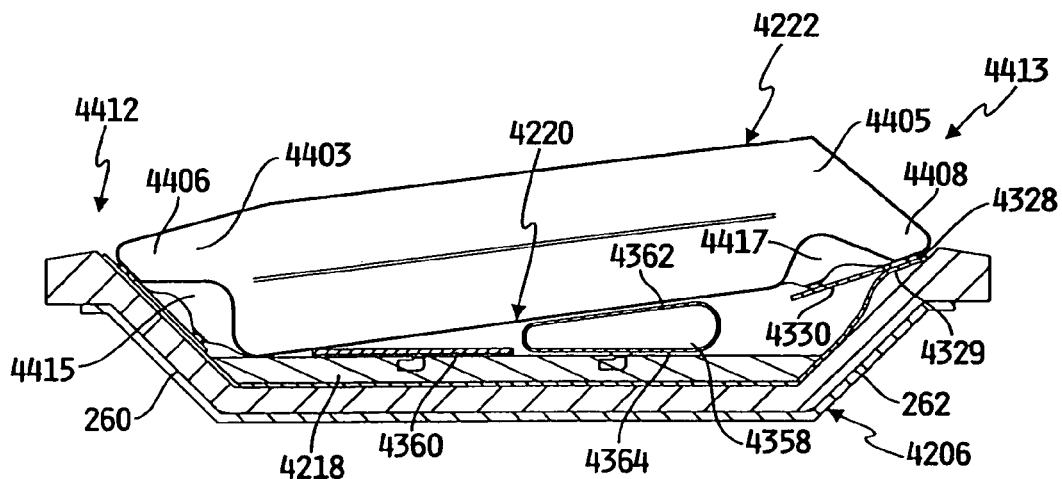
Figure 142:
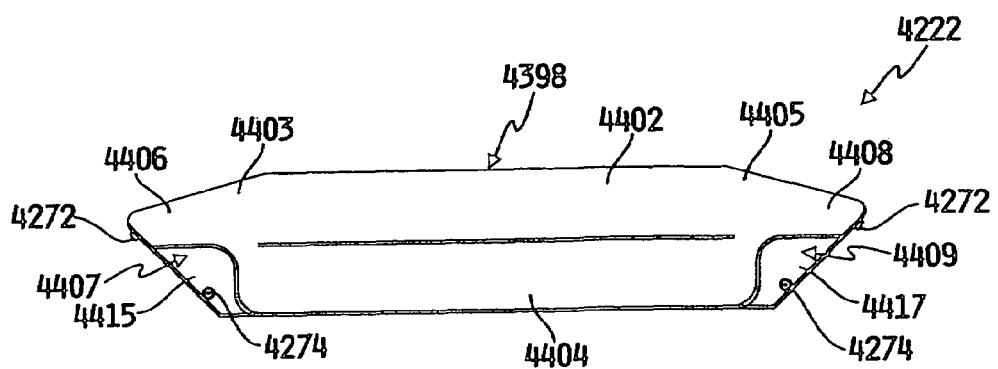
Figure 143:
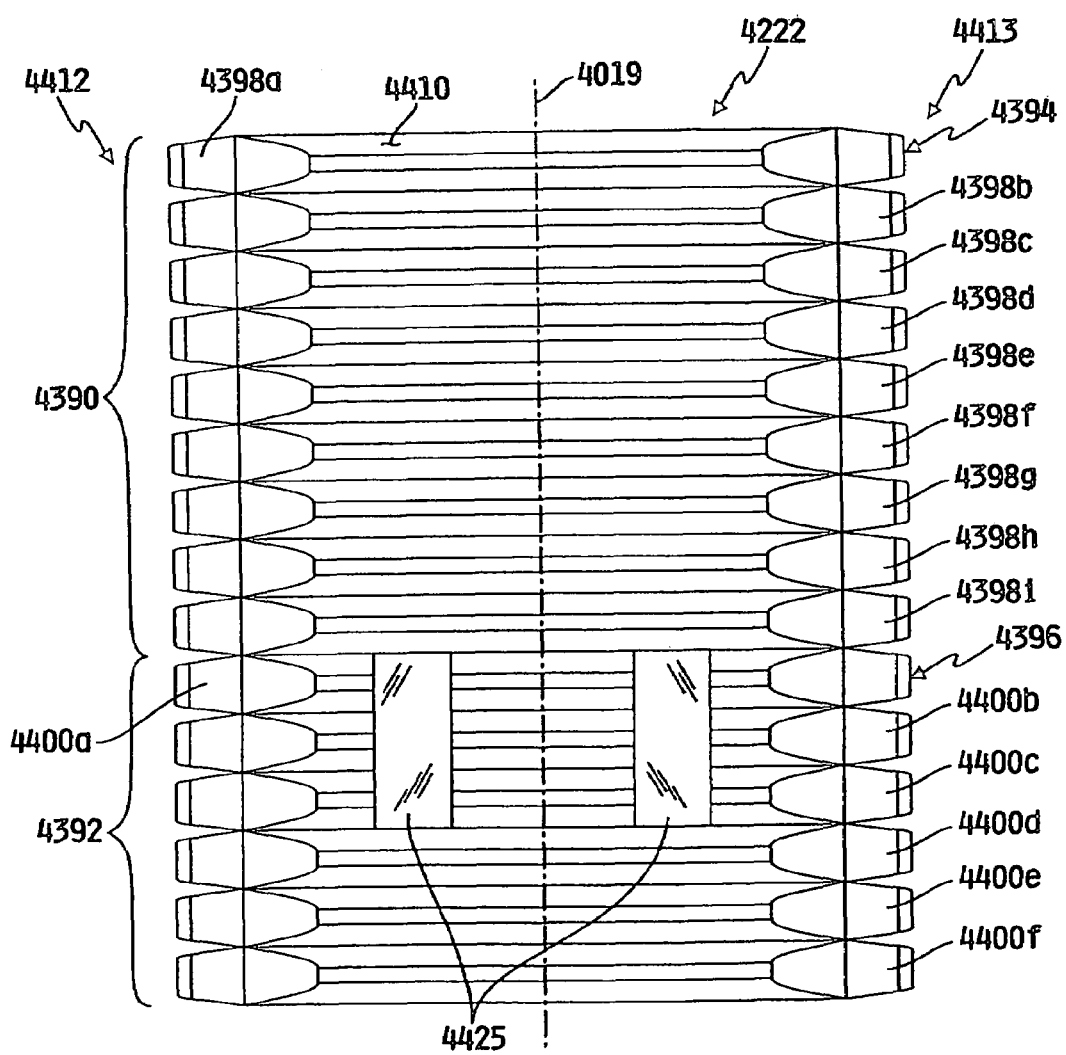
Figure 144:
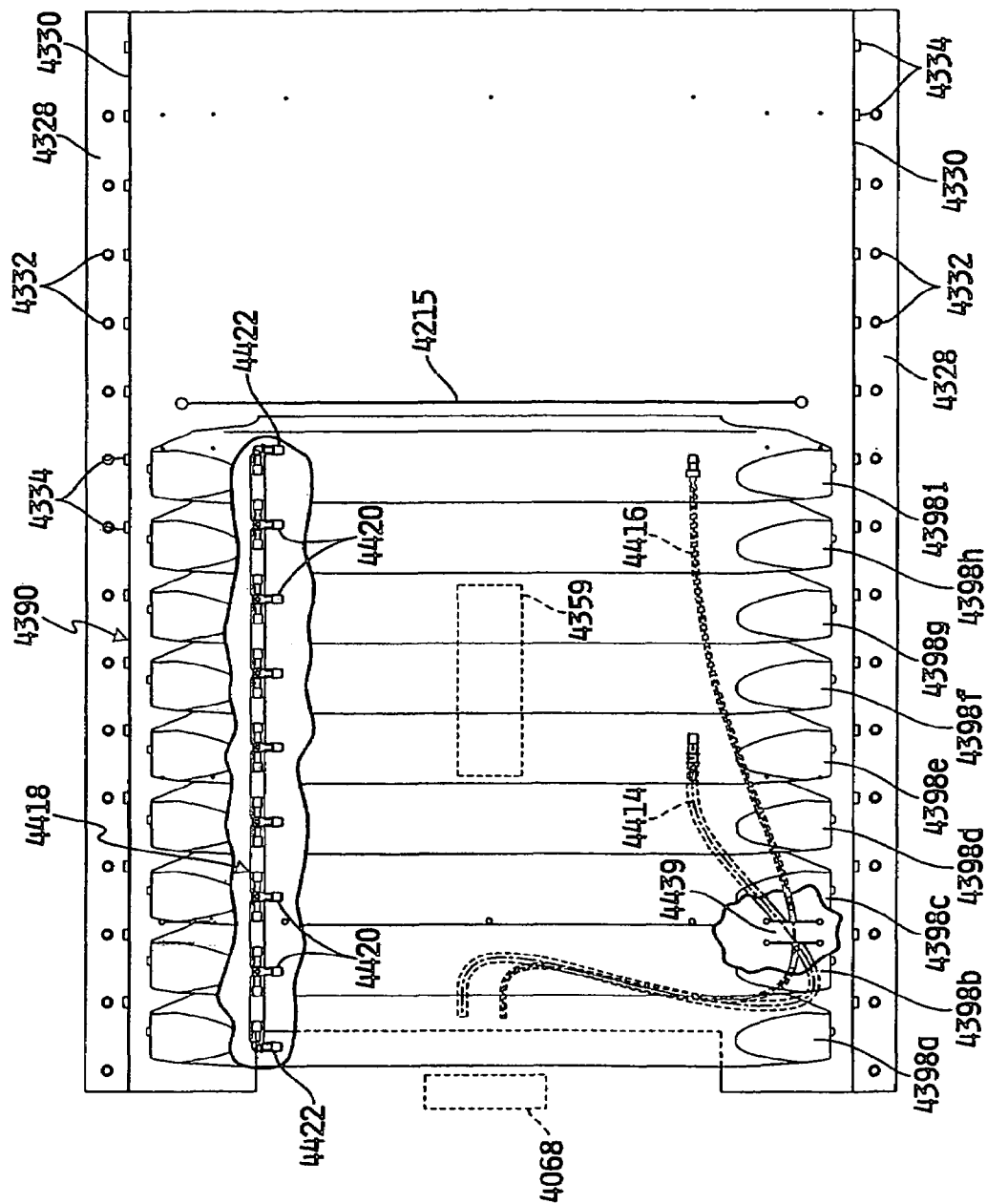
Figure 145:
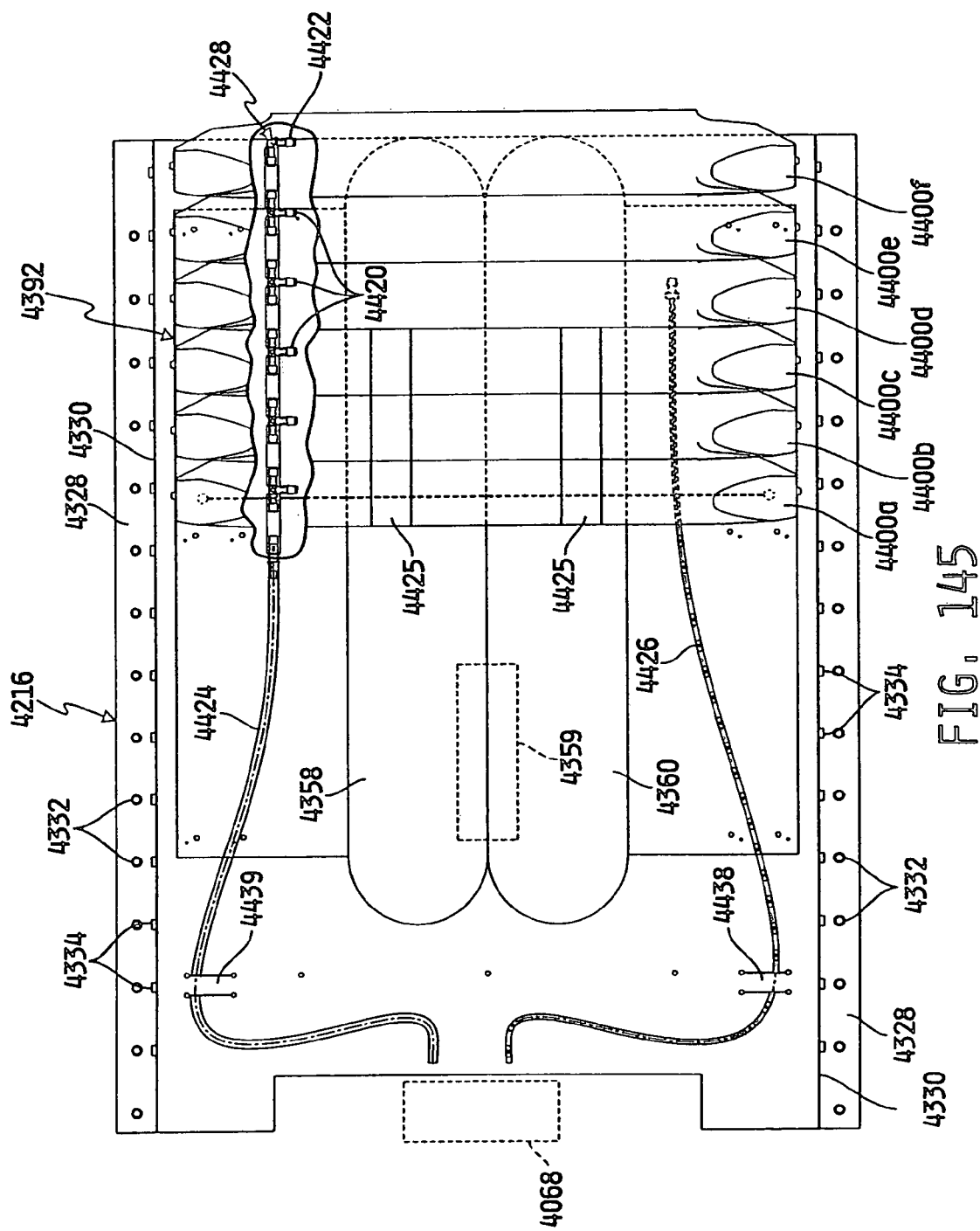
Figure 146:
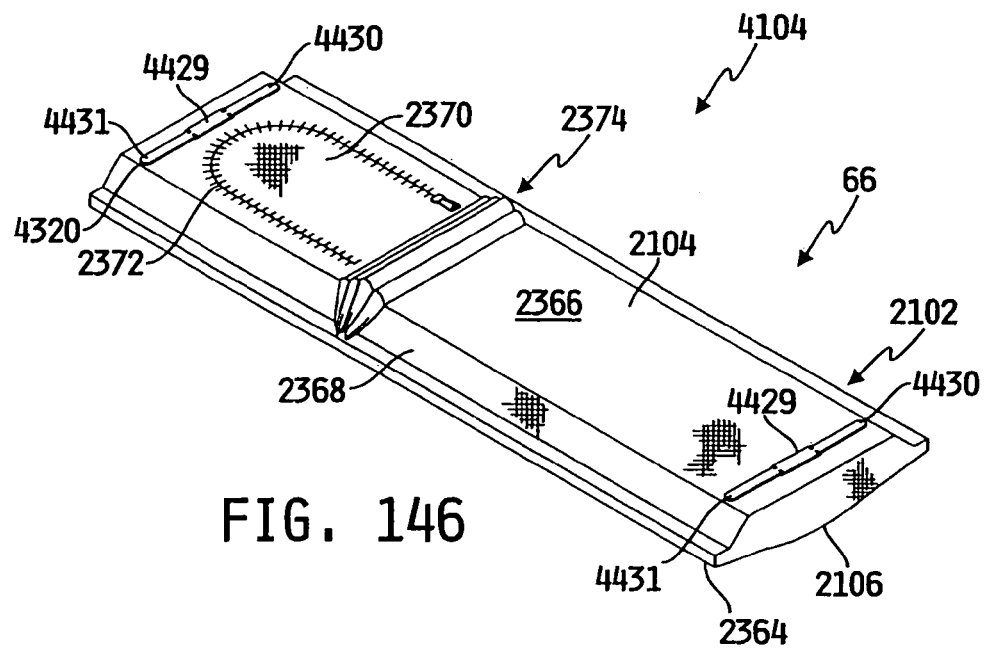
Figure 149:
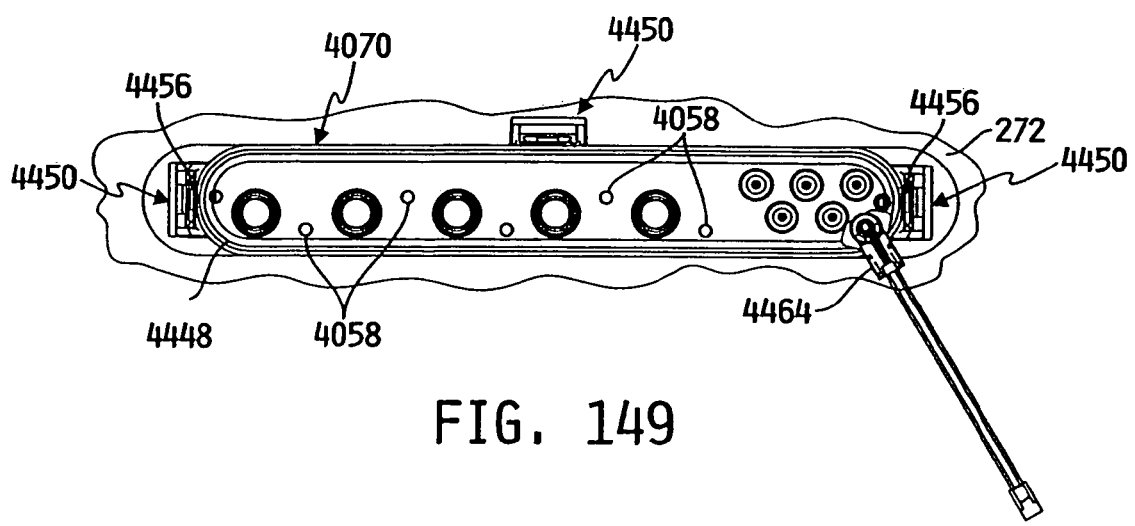
Figure 147:
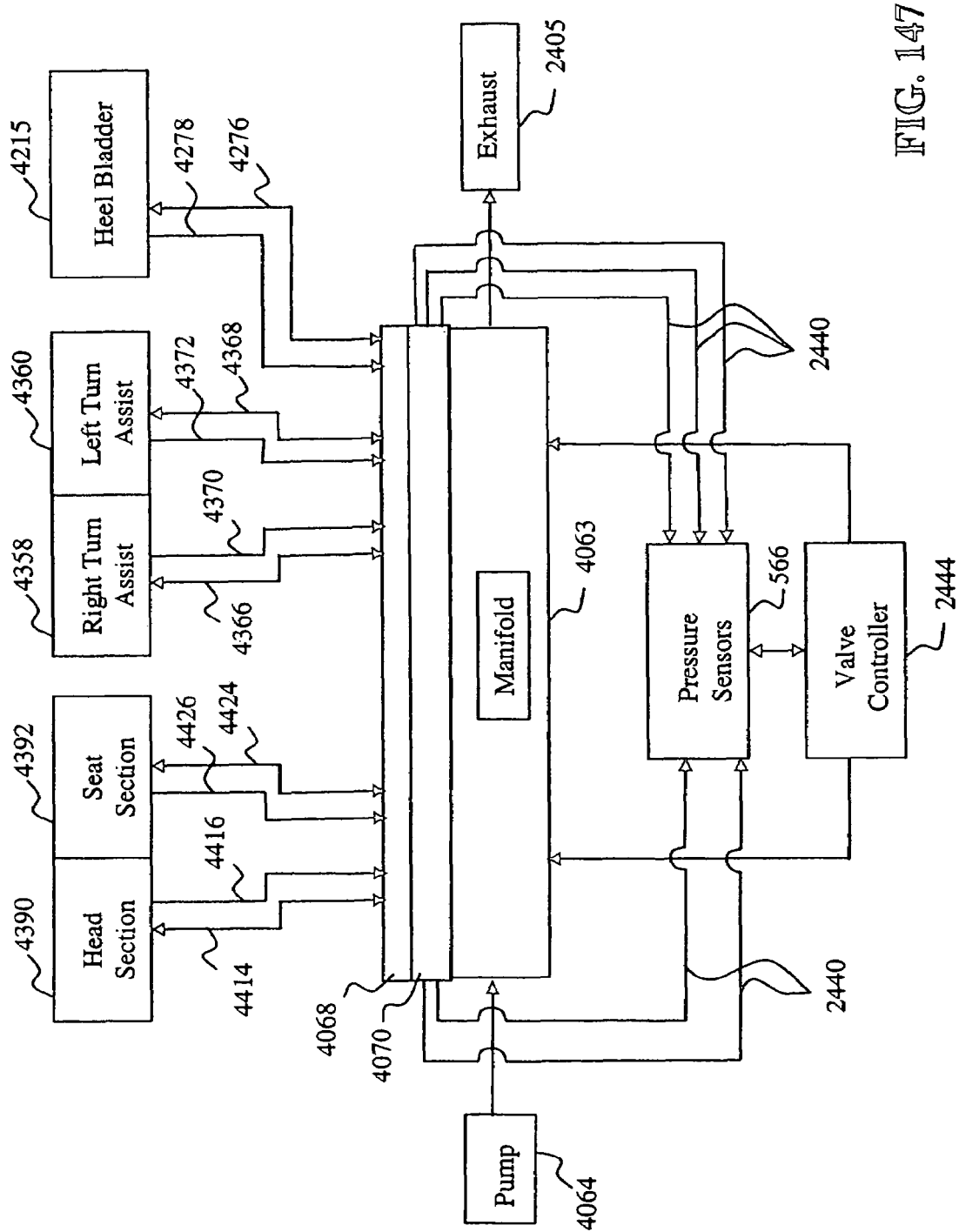
Figure 148:
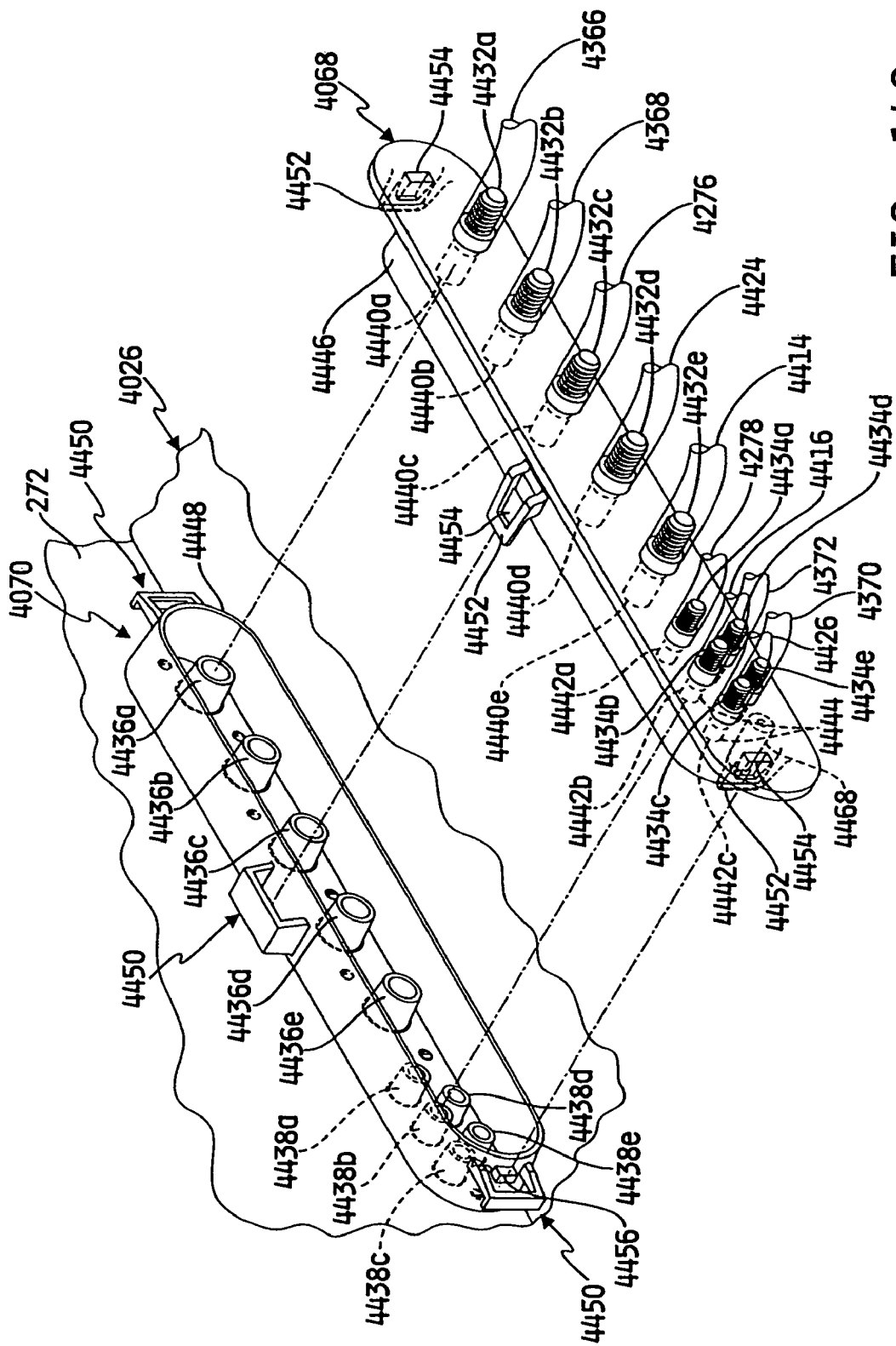
Figure 150:
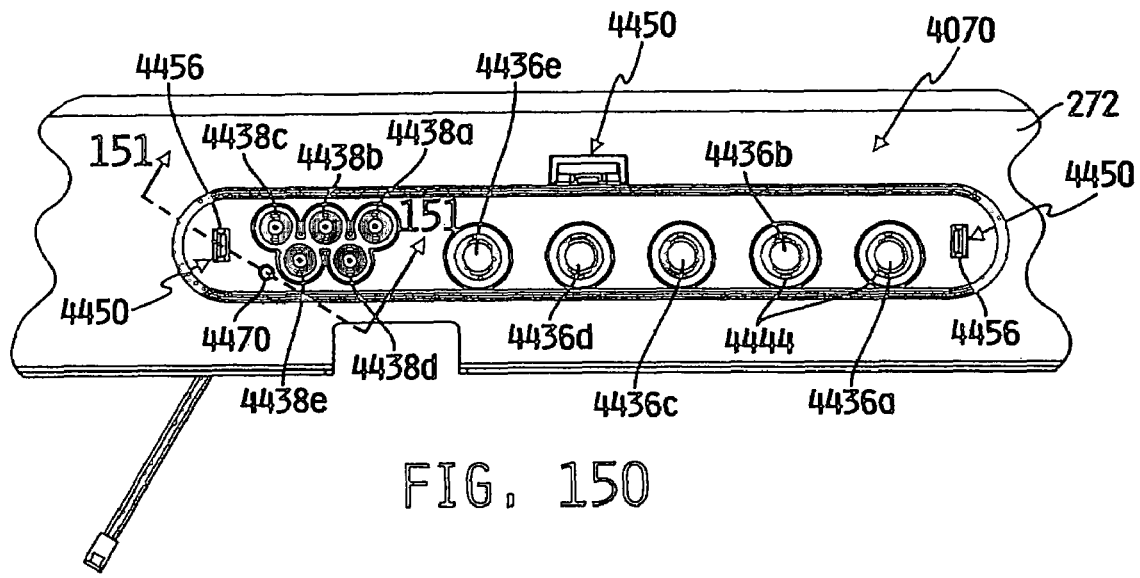
Figure 151:
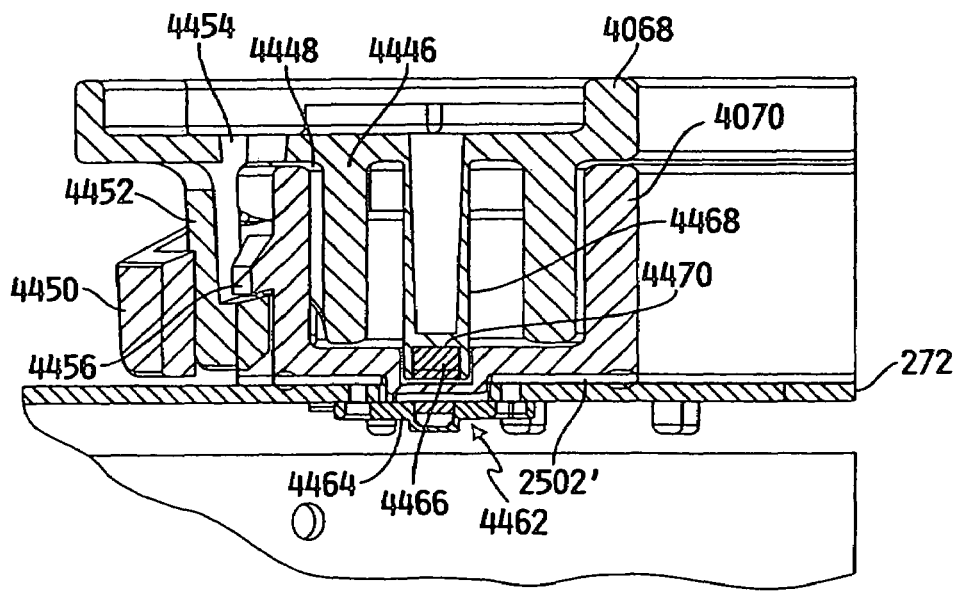
Figure 152:
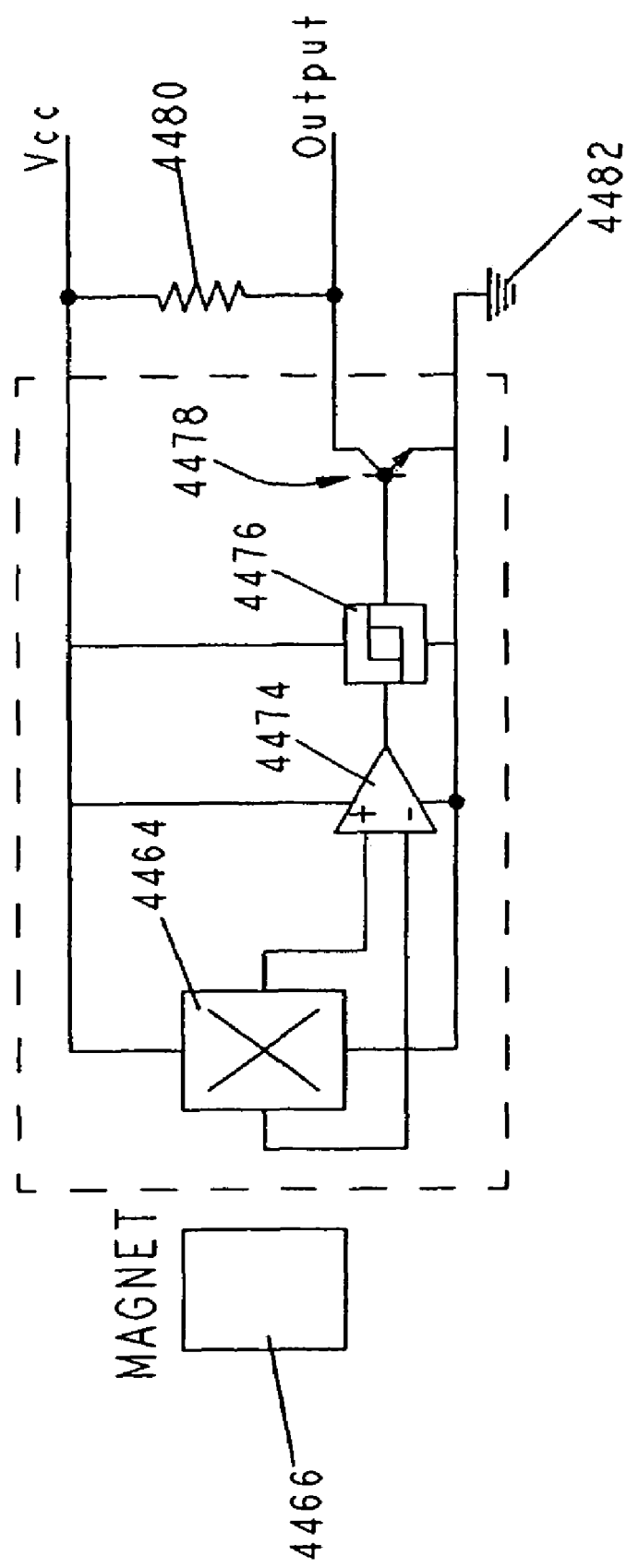
Figure 153:
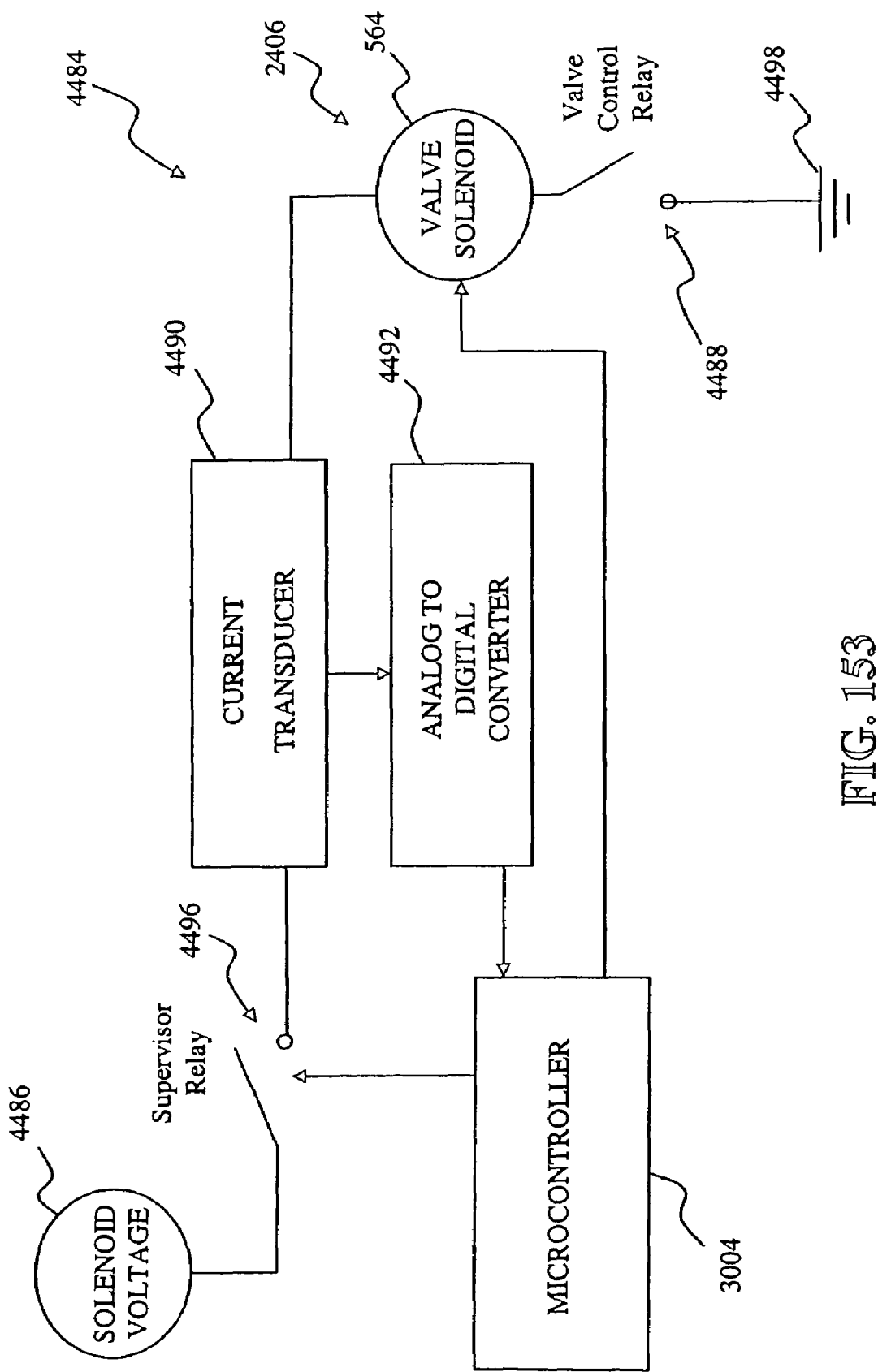
Figure 154:
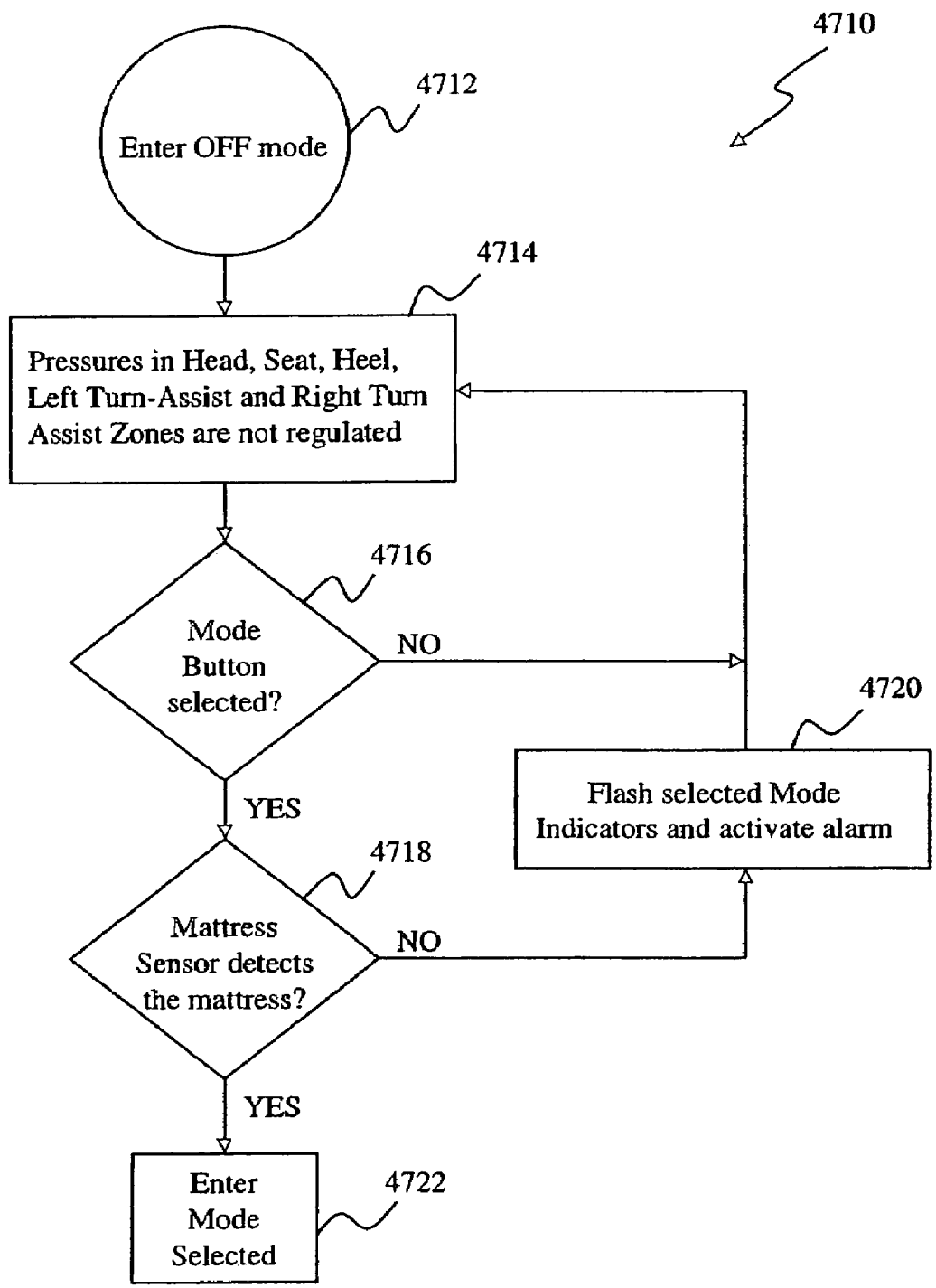
Figure 155:
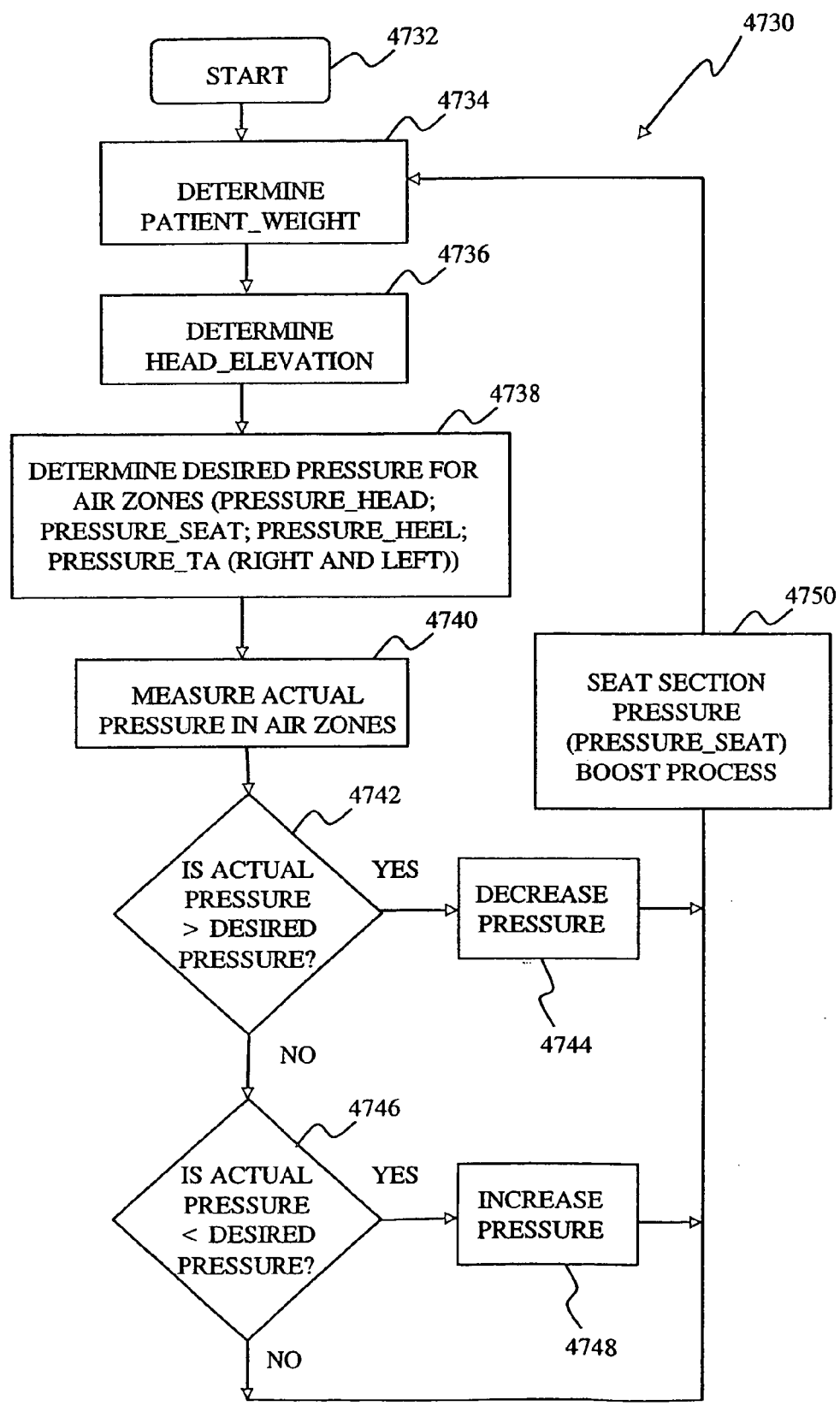
Figure 156:
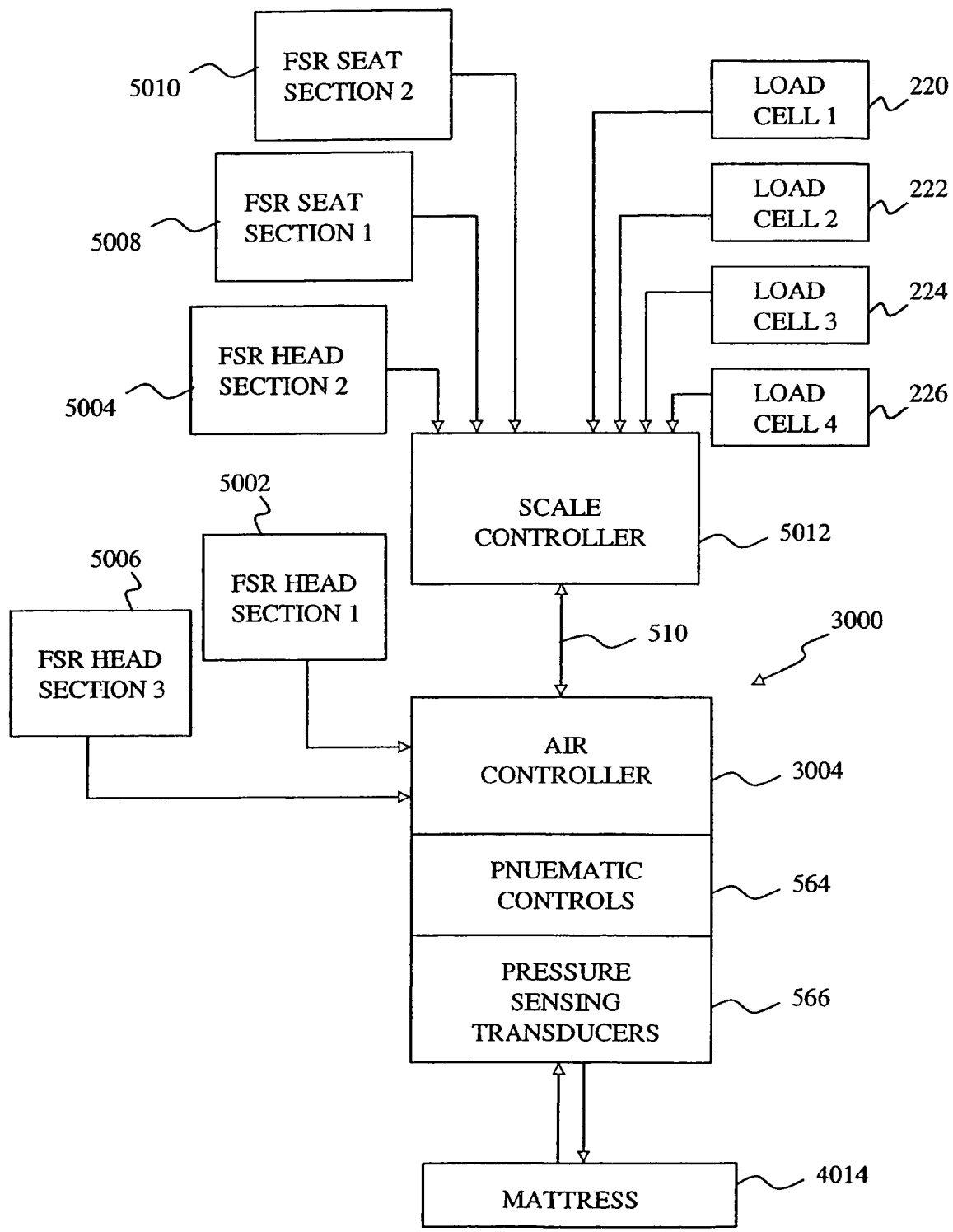
Figure 157:
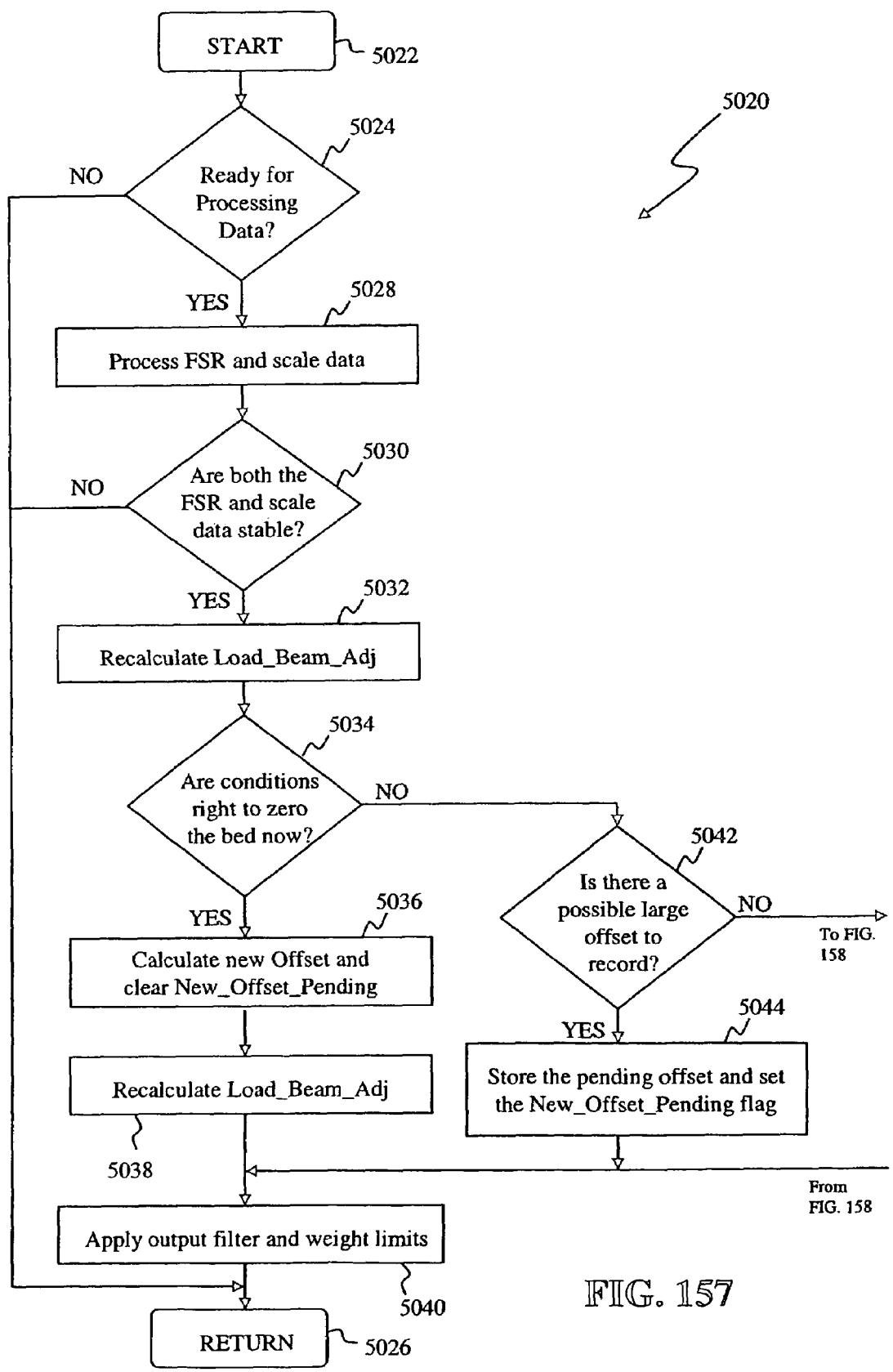
Figure 158:
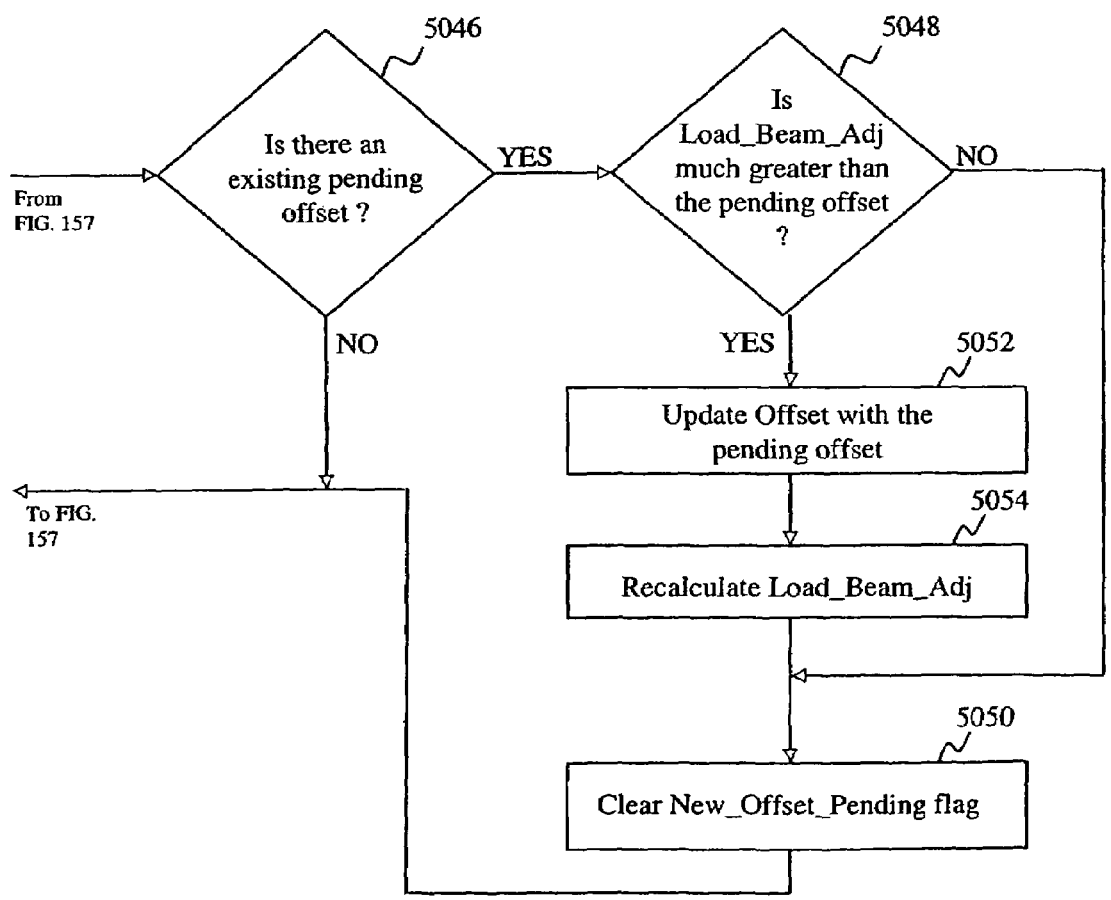
Figure 159:
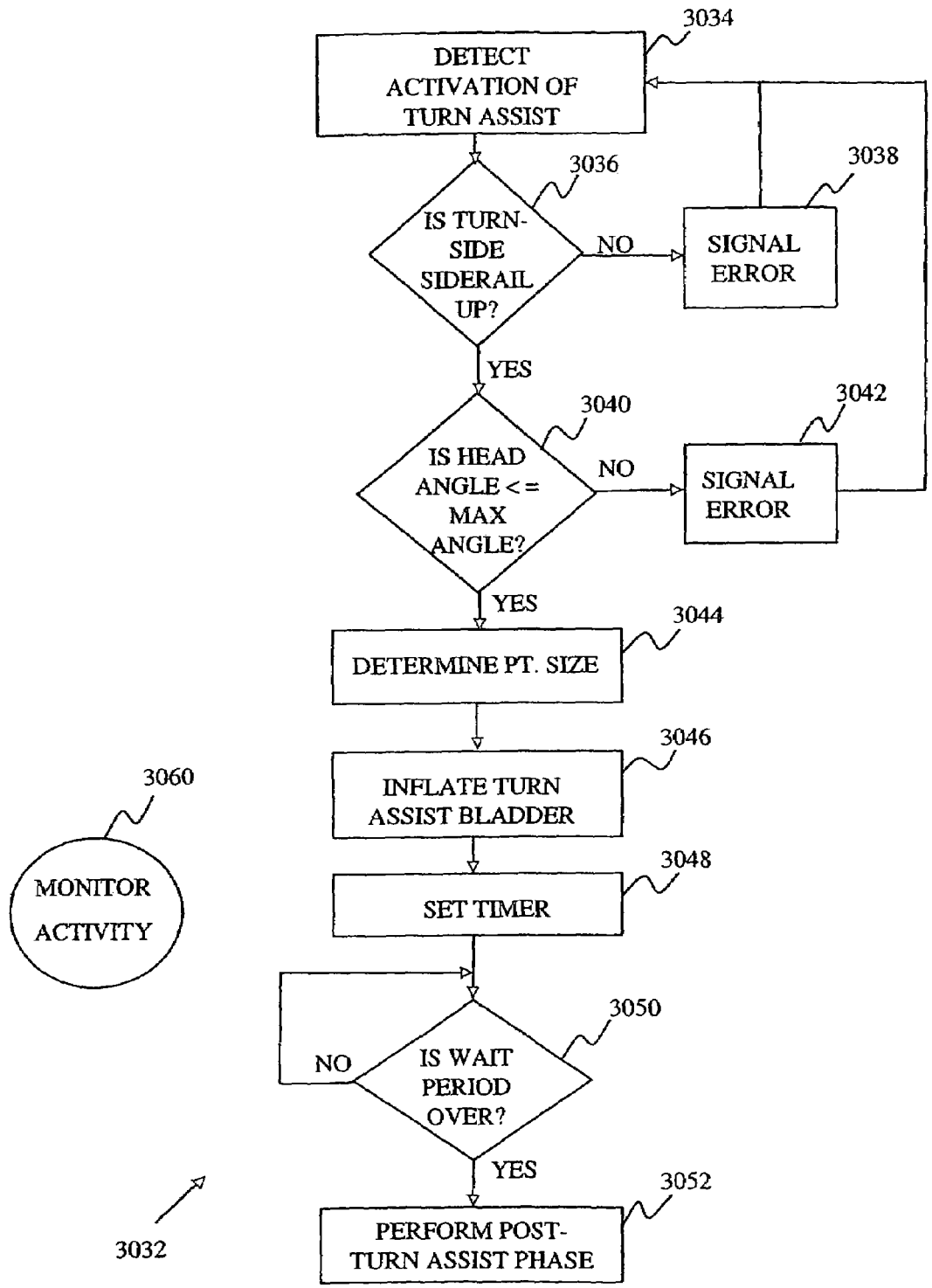
Figure 160:
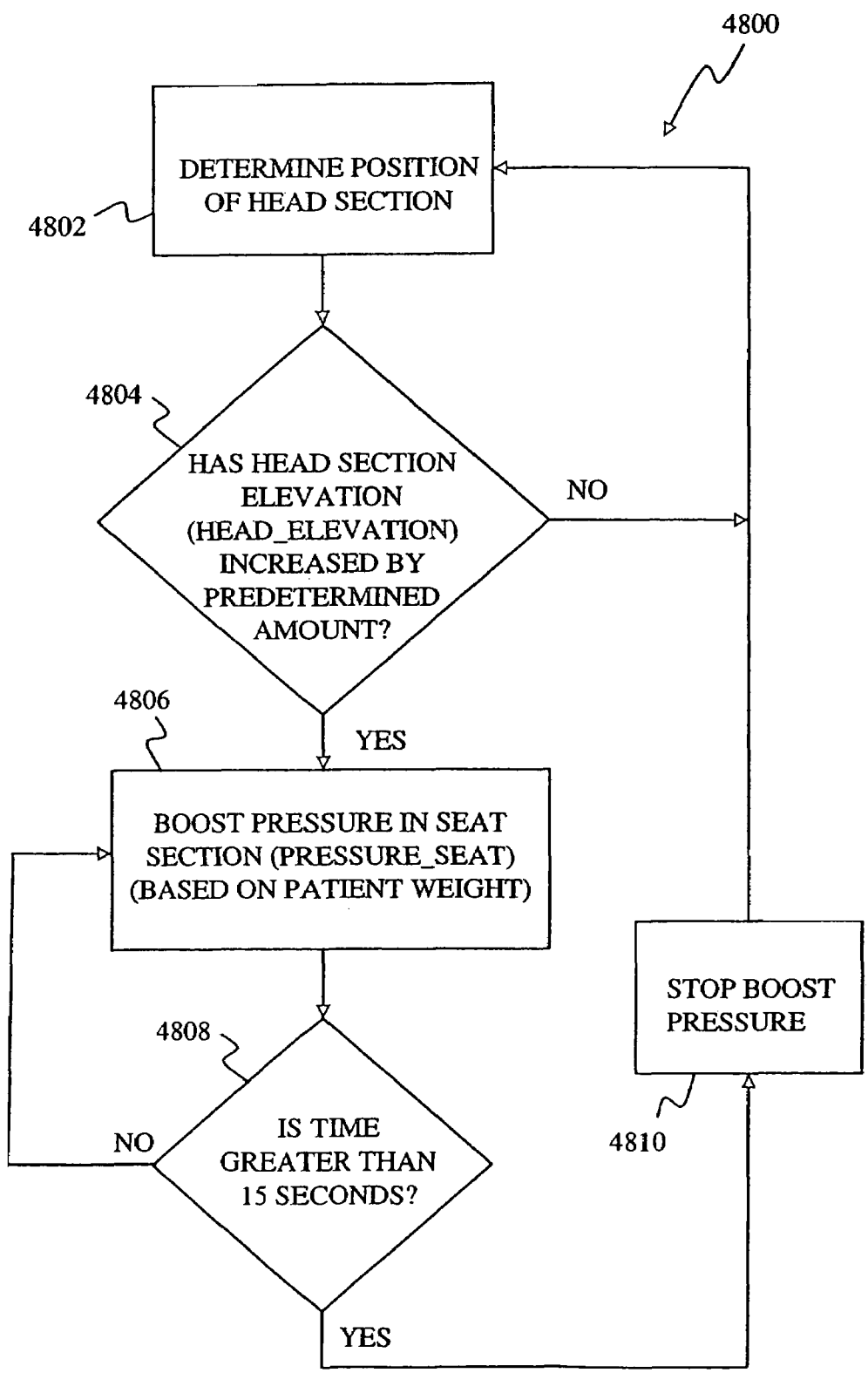
Figure 161:
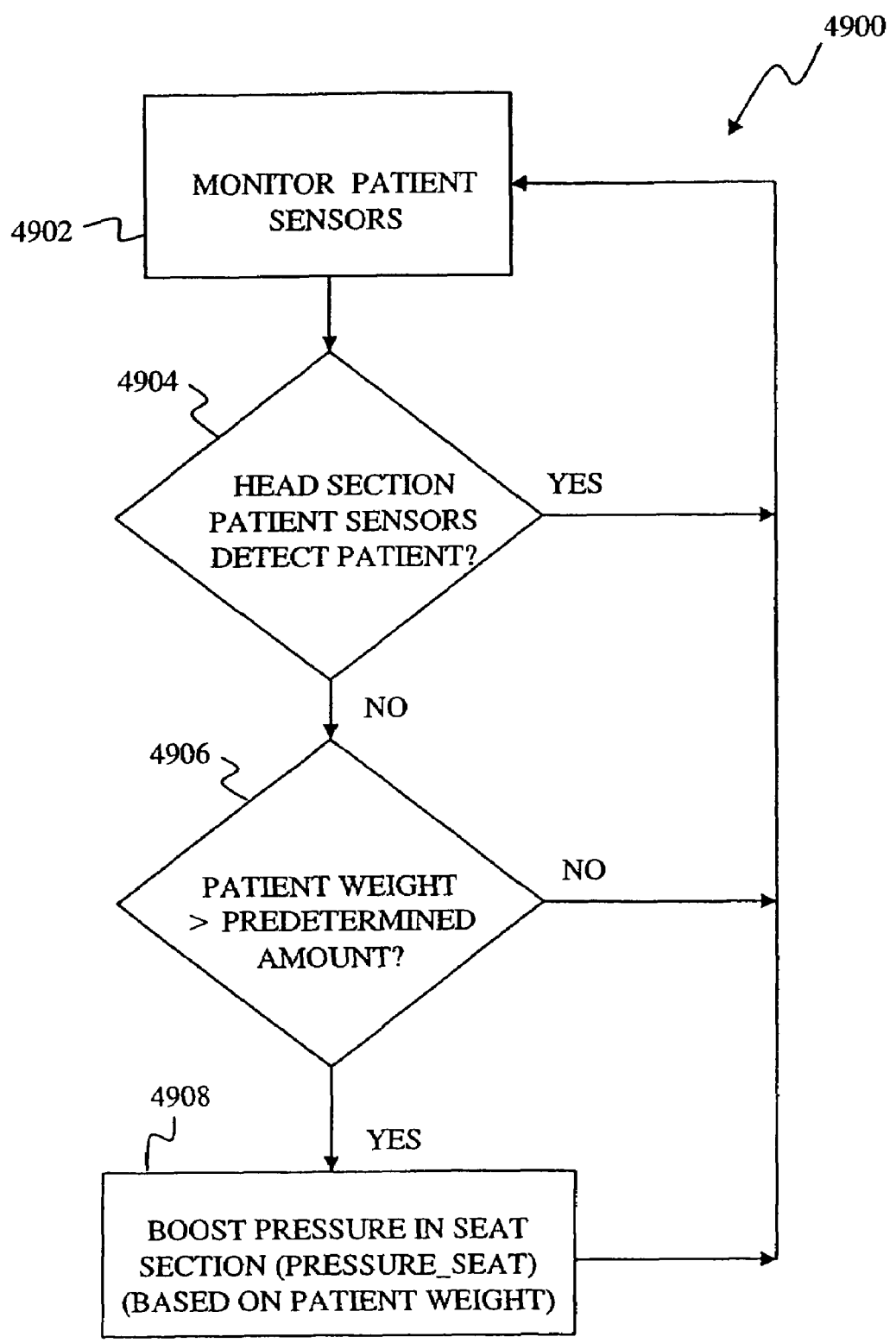
Figure 162:
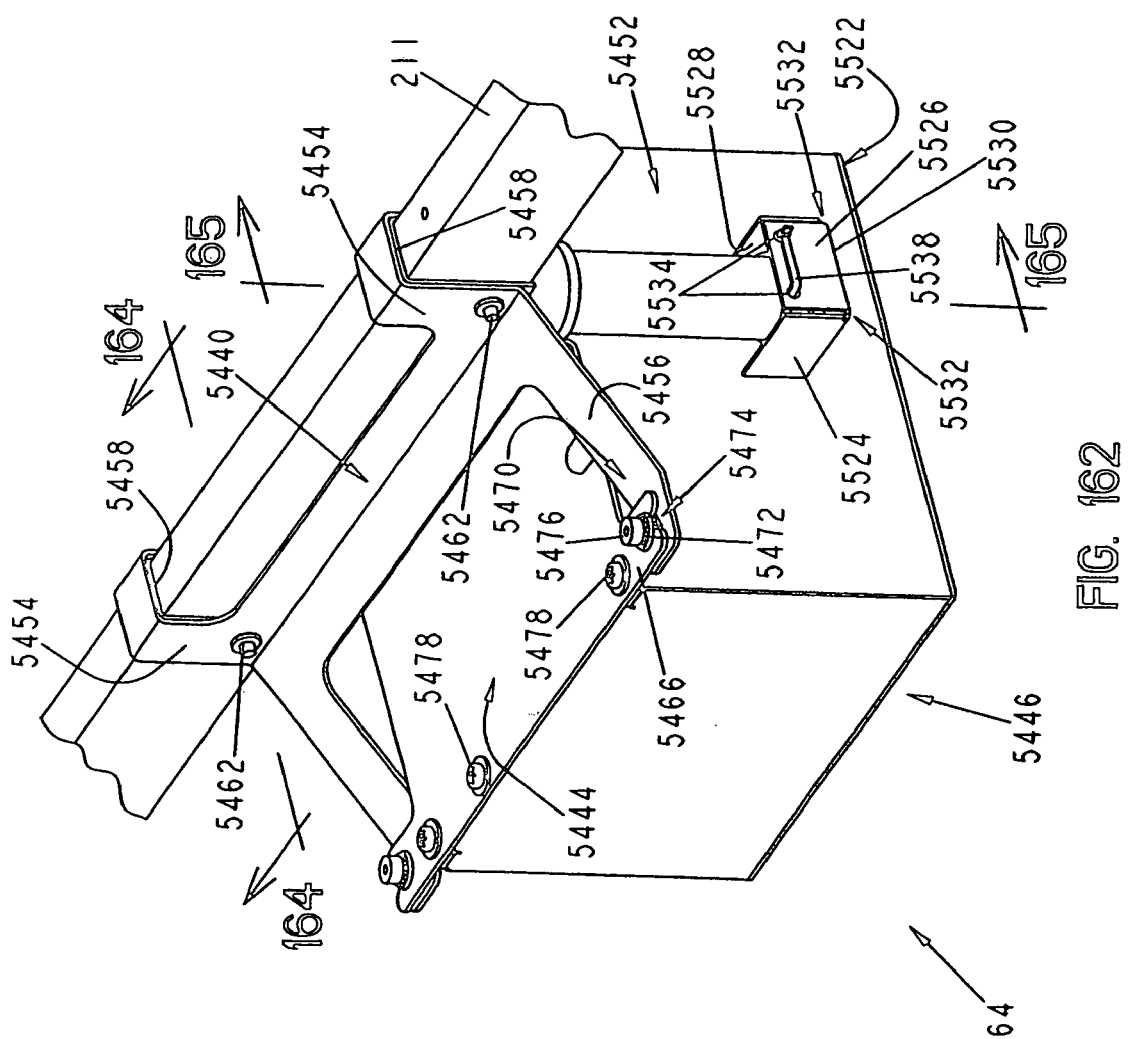
Figure 163:
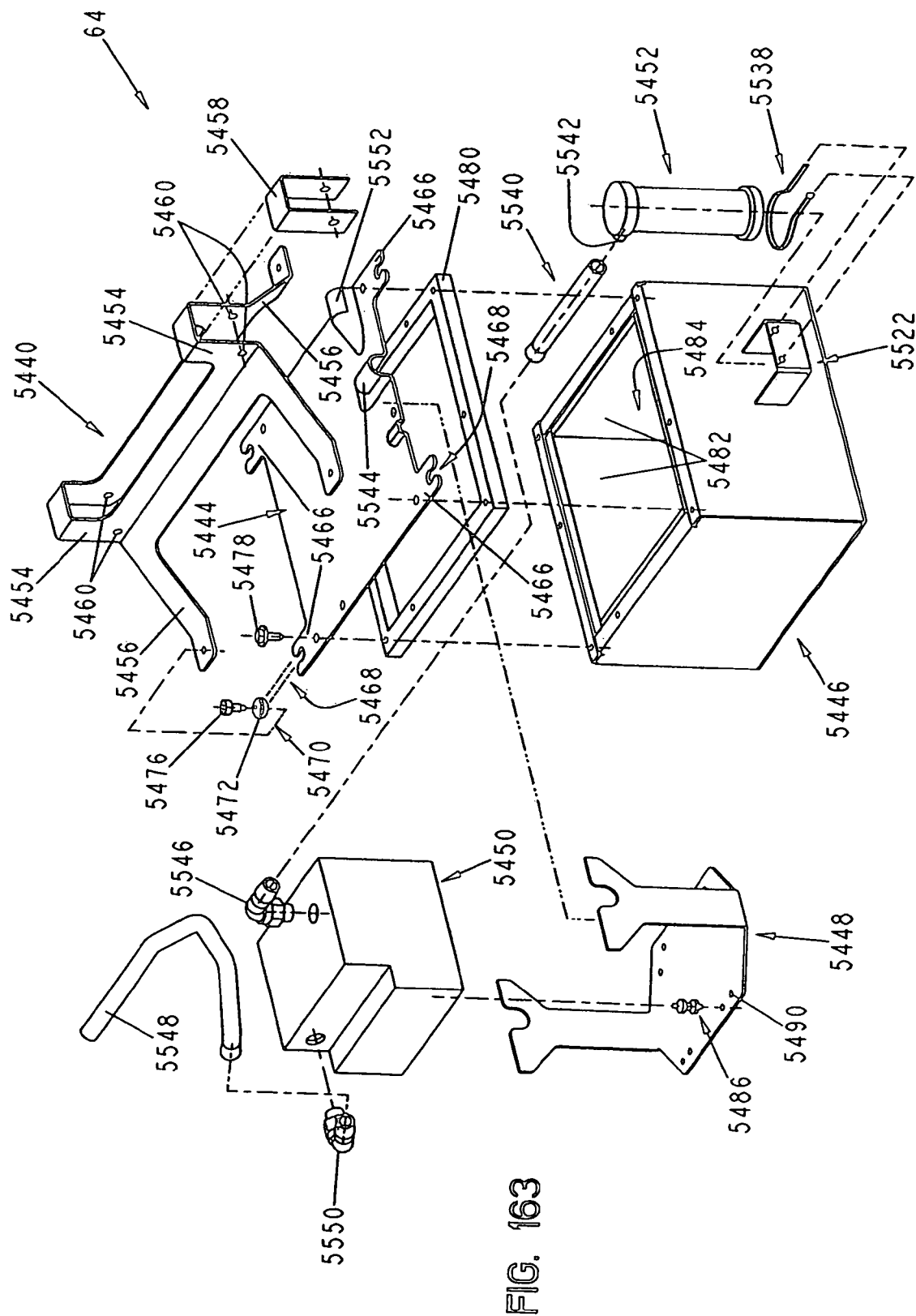
Figure 167:
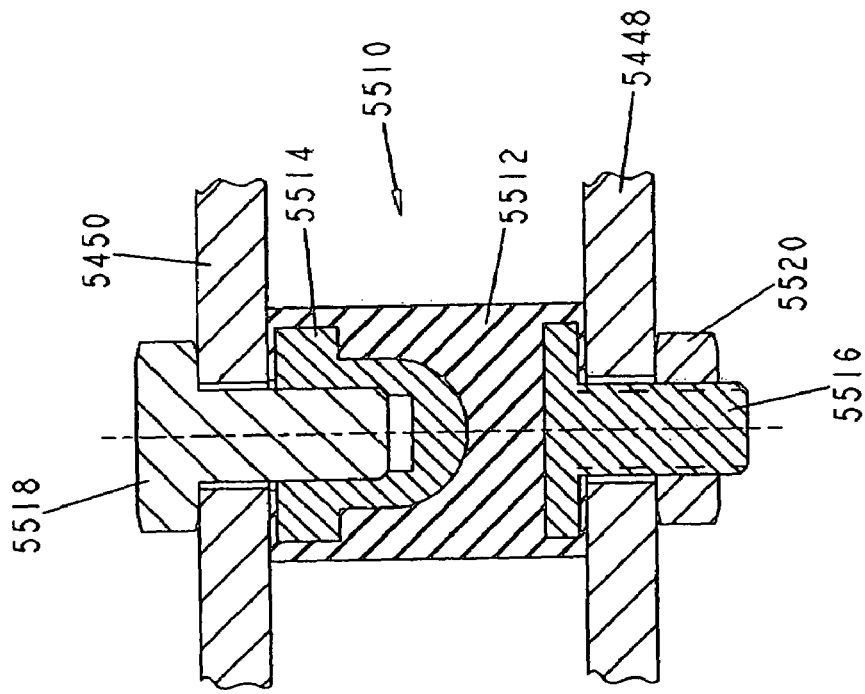
Figure 166:
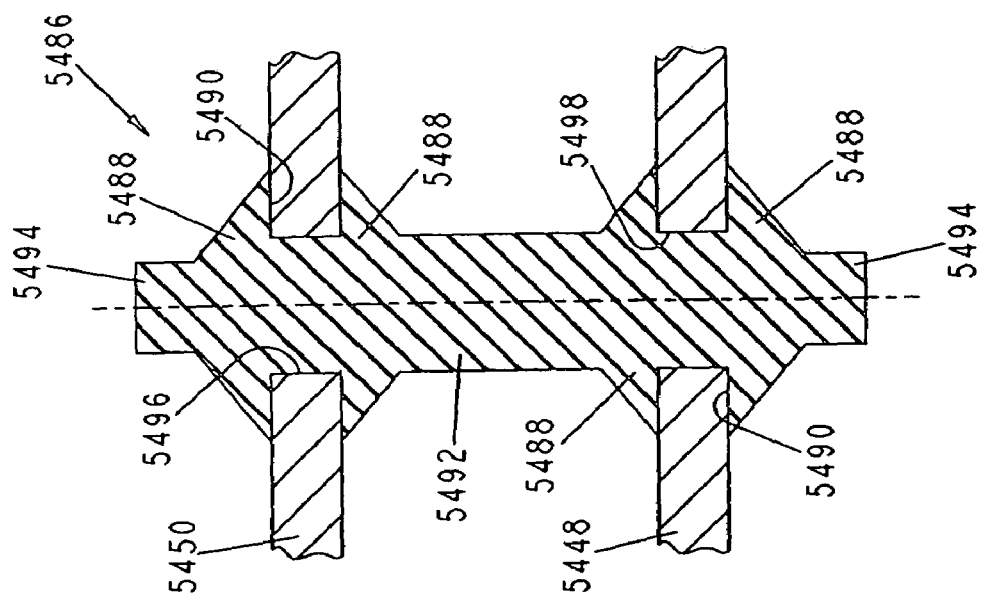
Figure 168:
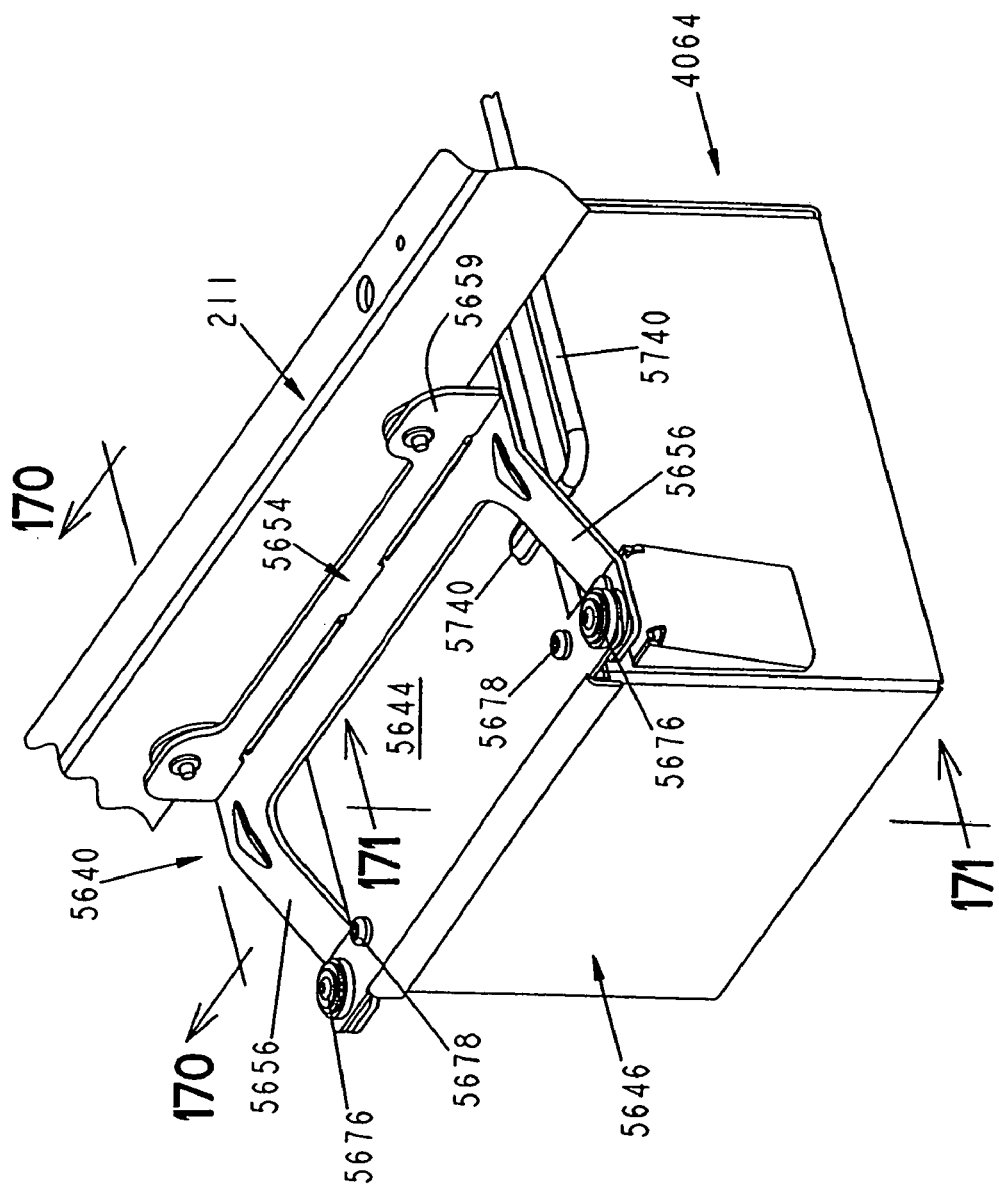
Figure 169:
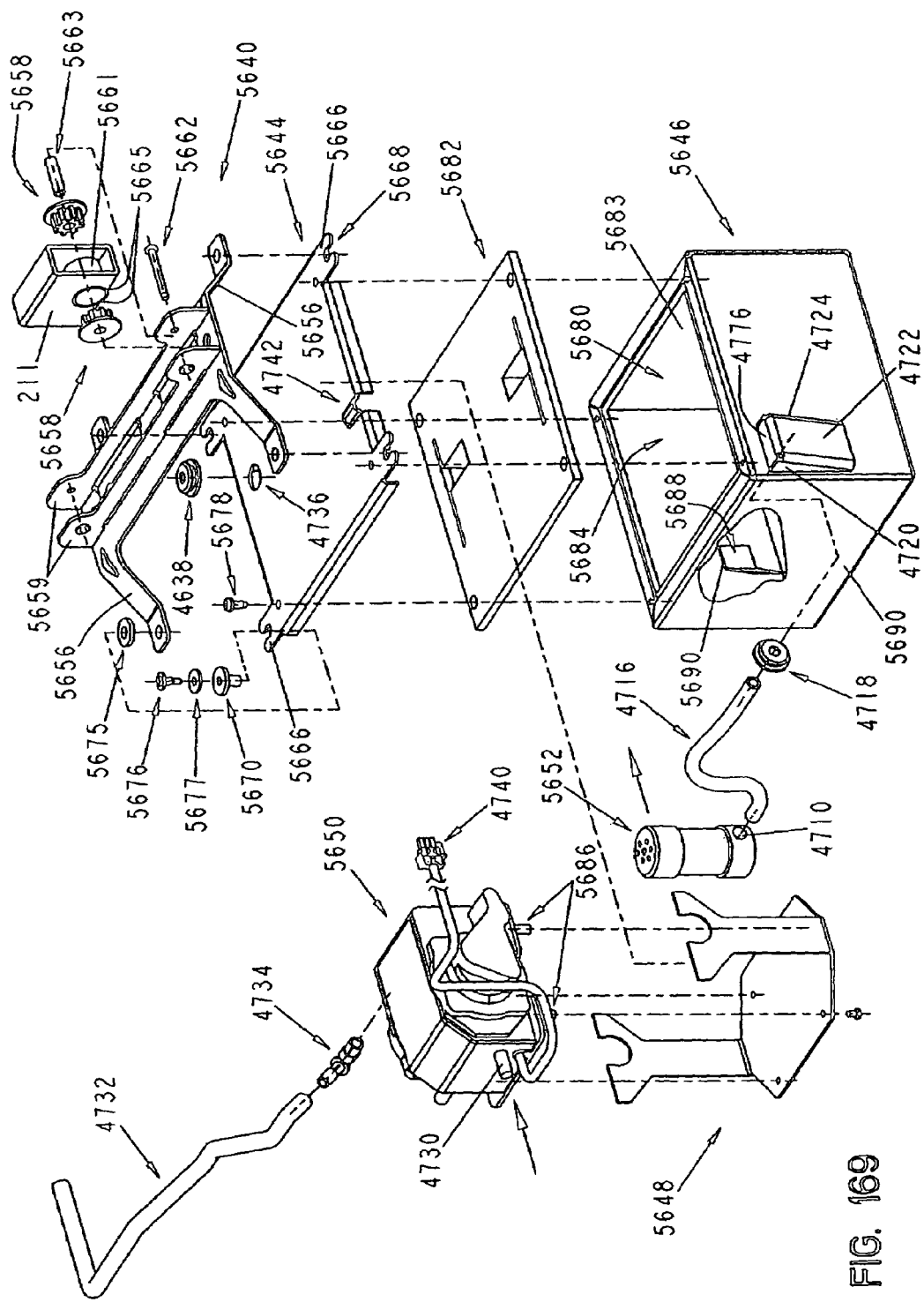
Figure 170:
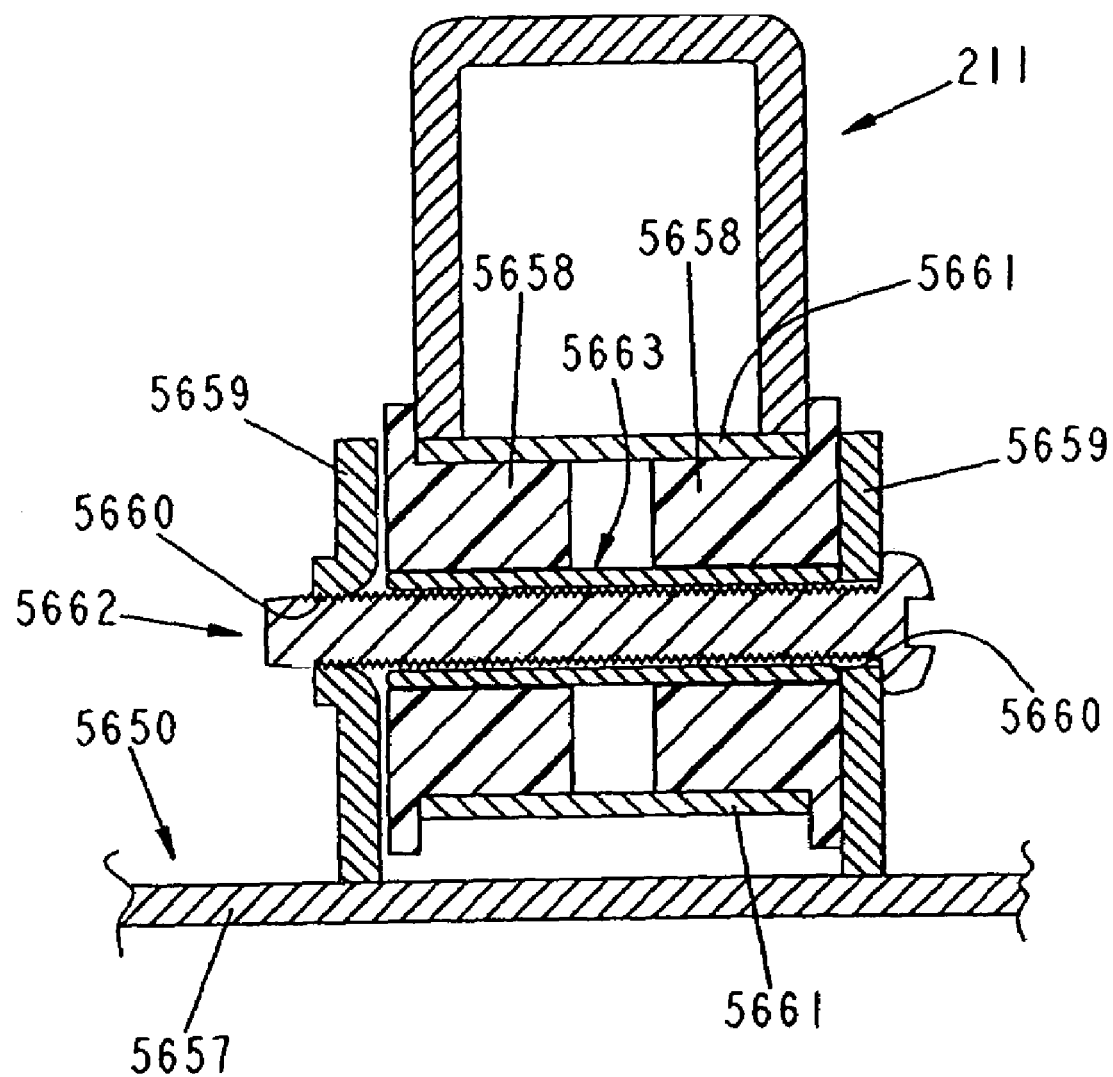
Figure 171:
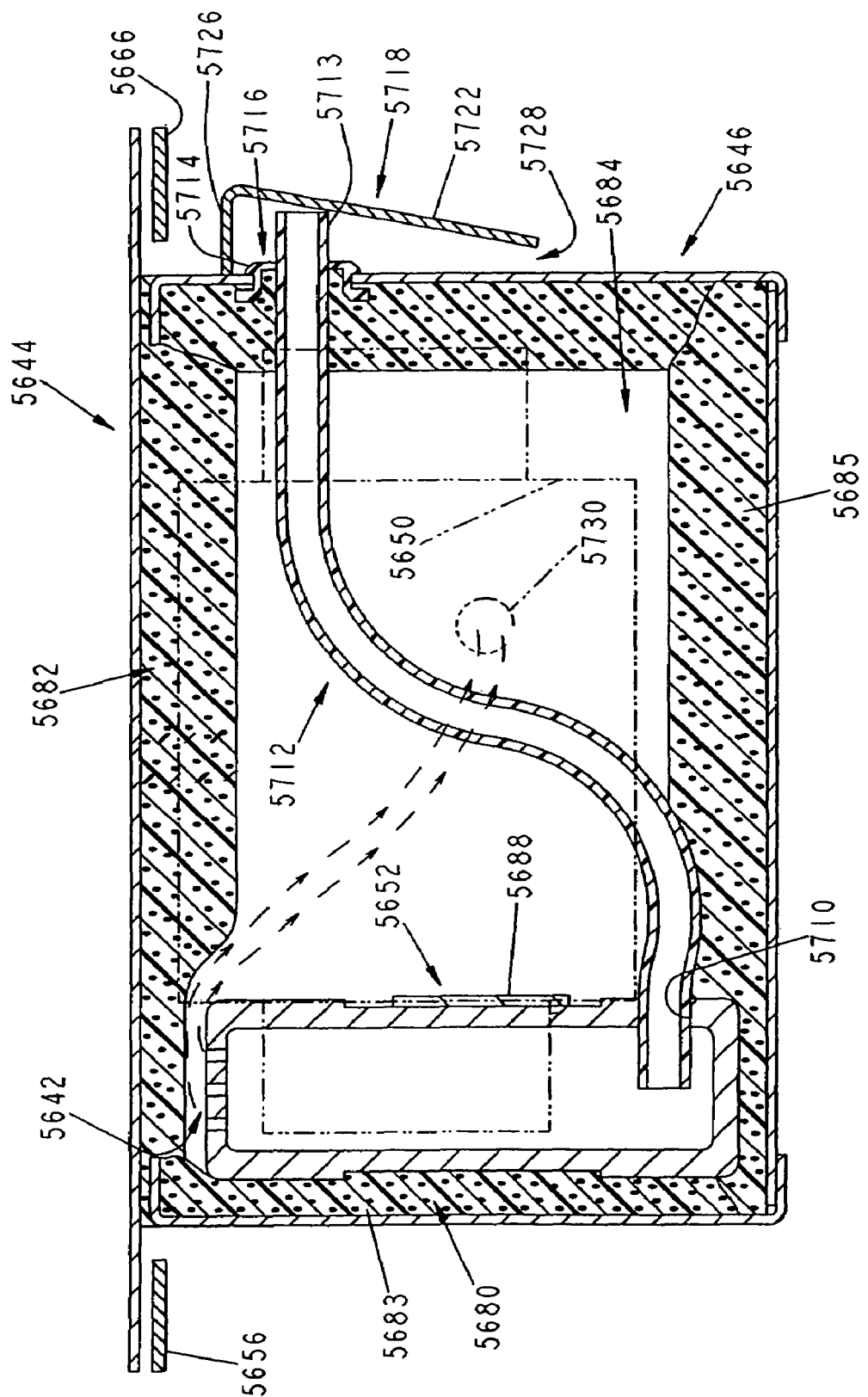
Figure 172:
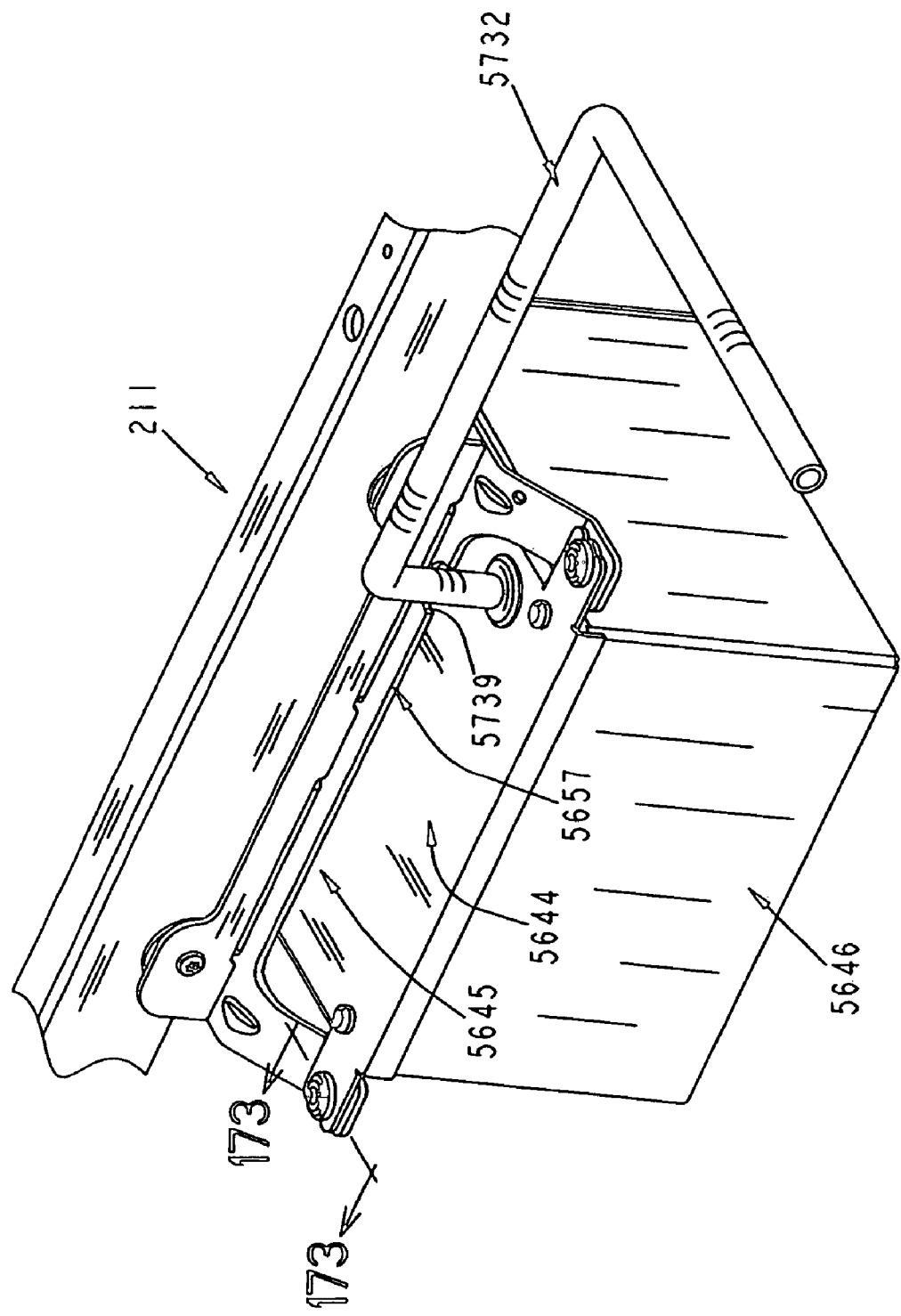

FIG. 127 is a flow diagram of an illustrative embodiment process for monitoring activity during the operation of turn assist bladders in accordance with the present invention;

FIG. 128 is a flow diagram of an illustrative embodiment process for controlling inflation of air bladders in accordance with the present invention;

FIG. 129 is an upper perspective view of the deck and weigh frame of the alternative embodiment patient support of FIG. 57 showing the foot section in an extended position, the head section elevated relative to the seat section, a partition of the head section with portions cutaway showing a manifold assembly on a first side of the partition and a manifold connector on a second side of the partition, and patient sensors supported by the head section and the seat section;

FIG. 130 is an exploded perspective view of an illustrative embodiment of the modular mattress assembly of the present invention, with the top cover removed for clarity;

FIG. 131 is a perspective view of the modular mattress assembly of FIG. 130, with the outer cover, the shear liner, and the fire barrier removed for clarity;

FIG. 132 is a partially exploded perspective view of a foot section of the mattress assembly of FIG. 130, illustrating a heel pressure relief bladder assembly received within a heel zone cavity, and with the outer cover, the shear liner, and the fire barrier removed for clarity;

FIG. 133 is an end elevational view of the foot section of FIG. 132;

FIG. 134 is a top plan view of the foot section, the turn assist bladder assembly, and the mounting substrate of the mattress assembly of FIG. 130, illustrating the routing of the fill tube and the sensor tube from proximate a head end of the mattress assembly to the air bladders of the heel pressure relief bladder assembly;

FIG. 135 is a side elevational view of the partial mattress assembly of FIG. 134;

FIG. 136 is a fragmentary view of the partial mattress assembly shown in FIG. 135;

FIG. 137 is a top plan view of the mounting substrate of the mattress assembly of FIG. 130;

FIG. 138 is a perspective view of the mounting substrate and the foot section securing substrate coupled the receiving base of the mattress assembly of FIG. 130;

FIG. 139 is a top plan view of the turn assist bladder assembly and the mounting substrate of the mattress assembly of FIG. 130, illustrating the routing of the fill tubes and the sensor tubes from proximate a head end of the mattress assembly to the air bladders of the turn assist bladder assembly;

FIG. 140 is a cross-sectional view taken along line 140-140 of FIG. 131, illustrating the left turn assist bladder and the right turn assist bladder in inactive, deflated modes of operation;

FIG. 141 is a cross-sectional view similar to that of FIG. 140 illustrating the right turn assist bladder in an active, inflated mode of operation, and the left turn assist bladder in an inactive, deflated mode of operation;

FIG. 142 is an end elevation view of an air bladder of the upper bladder assembly of the mattress assembly of FIG. 130;

FIG. 143 is a top plan view of the upper bladder assembly of the mattress assembly of FIG. 130;

FIG. 144 is a top plan view of the head zone of the upper bladder assembly and the mounting substrate of the mattress assembly of FIG. 130, illustrating the routing of the fill tube and the sensor tube from proximate a head end of the mattress assembly to the air bladders of the head zone, with the mounting substrate disconnected from the air bladders for illustrative purposes;

FIG. 145 is a top plan view of the seat zone of the upper bladder assembly and the mounting substrate of the mattress assembly of FIG. 130, illustrating the routing of the fill tube and the sensor tube from proximate a head end of the mattress assembly to the air bladders of the seat zone, with the mounting substrate disconnected from the air bladders for illustrative purposes;

FIG. 146 is a bottom perspective view of the mattress assembly of FIG. 130, illustrating the mattress anchors and the access port;

FIG. 147 is a block diagram illustrating various pneumatic connections between the mattress air zones and the air control system of the present invention;

FIG. 148 is a detailed perspective view of illustrative embodiment manifold fluid connector and mattress fluid connector of the present invention;

FIG. 149 is a rear elevational view of the manifold fluid connector of FIG. 148, with the manifold and portions of the partition removed for clarity, illustrating a mattress sensor of the present invention;

FIG. 150 is a front elevational view of the manifold fluid connector of FIG. 149;

FIG. 151 is a cross-sectional view taken along line 151-151 of FIG. 150, illustrating the connection between the manifold fluid connector and the mattress fluid connector of the present invention;

FIG. 152 is an electrical diagram of the mattress sensor and associated circuitry for the manifold fluid connector of FIG. 148;

FIG. 153 is a block diagram of an illustrative embodiment valve sensor configured to detect the type of valve for controlling inflation of air zones of the mattress assembly of FIG. 130;

FIG. 154 is a flow diagram of an illustrative embodiment process for operating the mattress sensor of FIG. 149;

FIG. 155 is a flow diagram of an illustrative embodiment process for controlling inflation of air zones of the mattress assembly of FIG. 130;

FIG. 156 is a block diagram of an illustrative embodiment system for determining the weight of a patient supported by the deck of the patient support of FIG. 57;

FIG. 157 is a flow diagram of an illustrative process for determining the weight of a patient supported by the deck of the patient support of FIG. 57;

FIG. 158 is a continuation of the flow diagram of FIG. 157;

FIG. 159 is a flow diagram of an illustrative embodiment process for controlling operation of turn assist bladders of the mattress assembly of FIG. 130;

FIG. 160 is a flow diagram of an illustrative embodiment process for boosting pressure of seat air zone in response to elevation of the head air zone of the air mattress;

FIG. 161 is a flow diagram of an illustrative embodiment process for boosting pressure of seat air zone in response to a patient sitting up;

FIG. 162 is a perspective view of an illustrative pump of the patient support of FIG. 1, showing the pump supported by a strut of the intermediate frame;

FIG. 163 is a exploded perspective view of the pump of FIG. 162;

FIG. 164 is a cross-sectional view taken along line 164-164 of FIG. 162, showing the pump coupled to the strut;

FIG. 165 is a cross-sectional view taken along line 165-165 of FIG. 162, showing a filter and muffler unit of the pump;

FIG. 166 is a cross-sectional view of a resilient foot of the pump of FIG. 162;

FIG. 167 is a view similar to FIG. 166, showing an alternative embodiment resilient foot;

FIG. 168 is a perspective view of an alternative embodiment air pump, showing the air pump supported by the strut of the weigh frame;

FIG. 169 is an exploded perspective view of the air pump of FIG. 168;

FIG. 170 is a cross-sectional view taken along line 170-170 of FIG. 168 showing the air pump coupled to the strut;

FIG. 171 is a cross-sectional view taken along line 171-171 of FIG. 168 showing a filter and muffler unit of the air pump;

FIG. 172 is another perspective view of the air pump of FIG. 168; and

Figure 173:
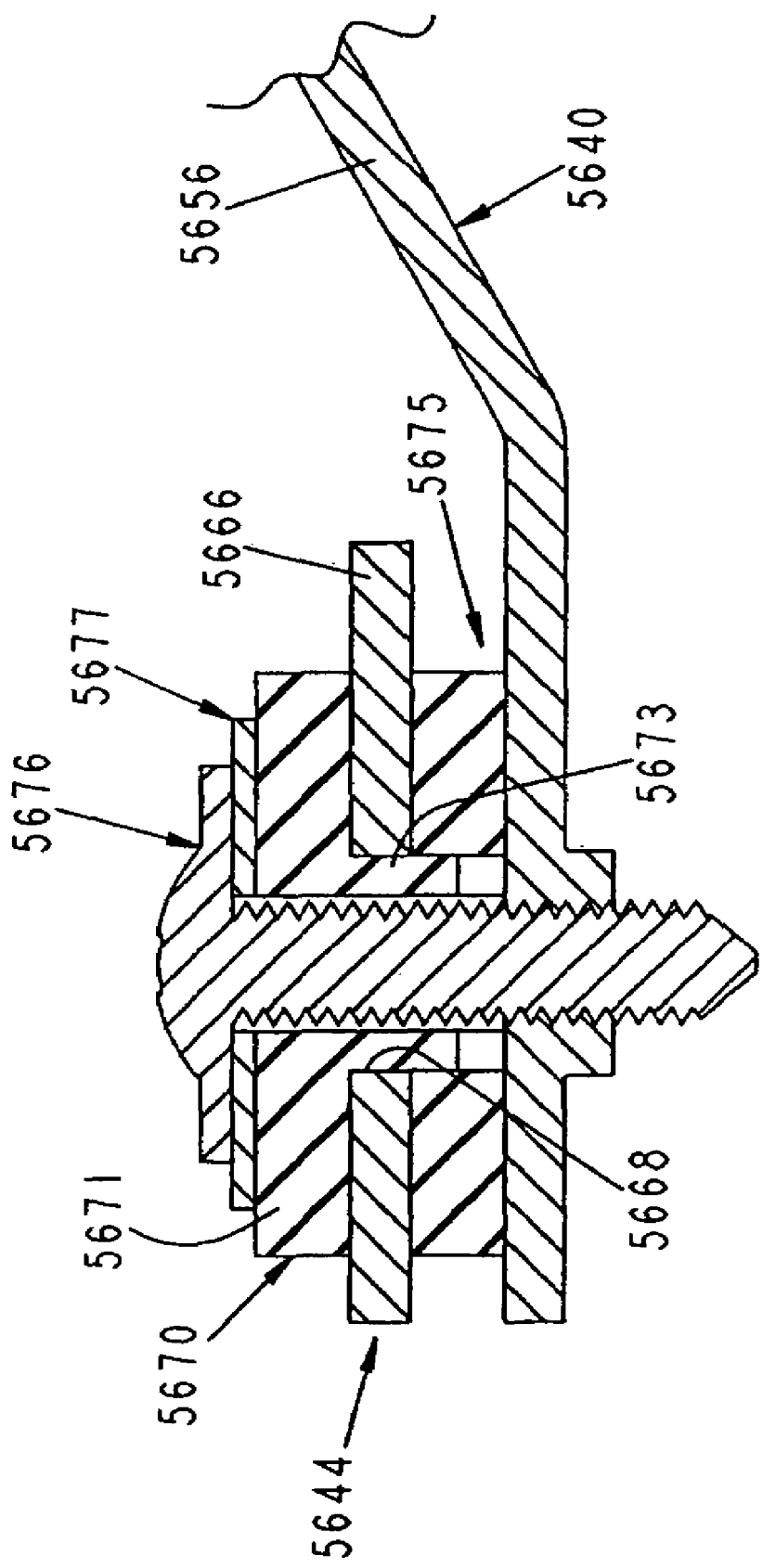

FIG. 173 is a cross-sectional view taken along line 173-173 of FIG. 172.

DETAILED DESCRIPTION OF THE DRAWINGS

A patient support 10 according to the present disclosure is shown in FIG. 1. Patient support 10 includes a frame 12, a mattress 14 supported by frame 12, a headboard 16, a footboard 18, a pair of head end siderails 20, and a pair of foot end siderails 22. Frame 12 includes a deck support 24 and a deck 26 supporting mattress 14 and extending between opposing head and foot ends 25 and 27. Deck support 24 includes a base frame 28 supported on the floor 29 by a plurality of caster wheels 30, an intermediate frame 32, a pair of lift arms 34 configured to raise and lower intermediate frame 32 relative to base frame 28, and a weigh frame 36 supported by intermediate frame 32. Deck 26 is supported by weigh frame 36 and is configured to articulate between a plurality of positions. As illustrated in FIGS. 1 and 3-7, deck 26 includes a head section 38 pivotably coupled to weigh frame 32, a seat section 40 pivotably coupled to weigh frame 32, and an adjustable length leg or foot section 42 pivotably coupled to seat section 40.

Head end siderails 20 are coupled to head section 38 and may be moved between raised and lowered positions. Foot end siderails 22 are coupled to weigh frame 32 and may also be moved between raised and lowered positions.

A control system 44 is provided to control various functions of patient support 10. Control system 44 and the remainder of patient support 10 are powered by an AC plug connection 45 to a building outlet or a battery 46 supported by frame 12.

Control system 44 operates and monitors a plurality of linear actuators 48 provided to extend and retract adjustable length leg section 42, to move intermediate frame 32 relative to base frame 28, to move head section 38 relative to weigh frame 32, to move seat section 40 relative to weigh frame 32, and to move leg section 42 relative to seat section 40.

Control system 44 includes a plurality of input devices including a detachable siderail controller 50 configured to removably couple to any of head and foot end siderails 20, 22, a first pair of permanent siderail controllers 52 coupled to head end siderails 20, a second pair of permanent siderail controllers 54 pivotably coupled to head end siderails 20, and a pair of foot pedal controls 56 coupled to base frame 28.

Control system 44 also includes an obstacle detection device 58 illustratively coupled to base frame 28 to detect possible clearance issues between intermediate frame 32 and base frame 28. Control system 44 further includes a plurality of actuator position detectors or motor sensor (as discussed below) provided with each of the plurality of actuators 48. A plurality of load cells (discussed below) are also provided between weigh frame 36 and intermediate frame 32 to provide signals that indicate of the weight supported by intermediate frame 32. Control system 44 uses these signals to determine the weight of a patient positioned on mattress 14. Additionally, control system 44 includes a plurality of siderail position detectors or sensors 60 configured to provide signals indicative of the position of siderails 20, 22.

Control system 44 is configured to control a pump 64 in fluid communication with a manifold 62 supported on head section 38 of deck 26. Manifold 62 is in fluid communication with mattress 14 to regulate the flow of air to and from mattress 14. Mattress 14 includes an outer cover 66 and a first pair of connectors 68 coupled to outer cover 66. A second pair of connectors 70 is provided on head section 38 of deck 26 that align and couple with first pair of connectors 68.

Deck Support

As previously mentioned and as shown in FIG. 1, deck support 24 includes a base frame 28 supported on the floor 29 by a plurality of caster wheels or caster devices 30, an intermediate frame 32, a pair of lift arms 34 configured to raise and lower intermediate frame 32 relative to base frame 28, and a weigh frame 36 supported by intermediate frame 32. Linear actuators 48a and 48b, shown in FIG. 2, provide power to actuate lift arms 34 and in turn to raise and lower intermediate frame 32 relative to base frame 28.

Figure 8:
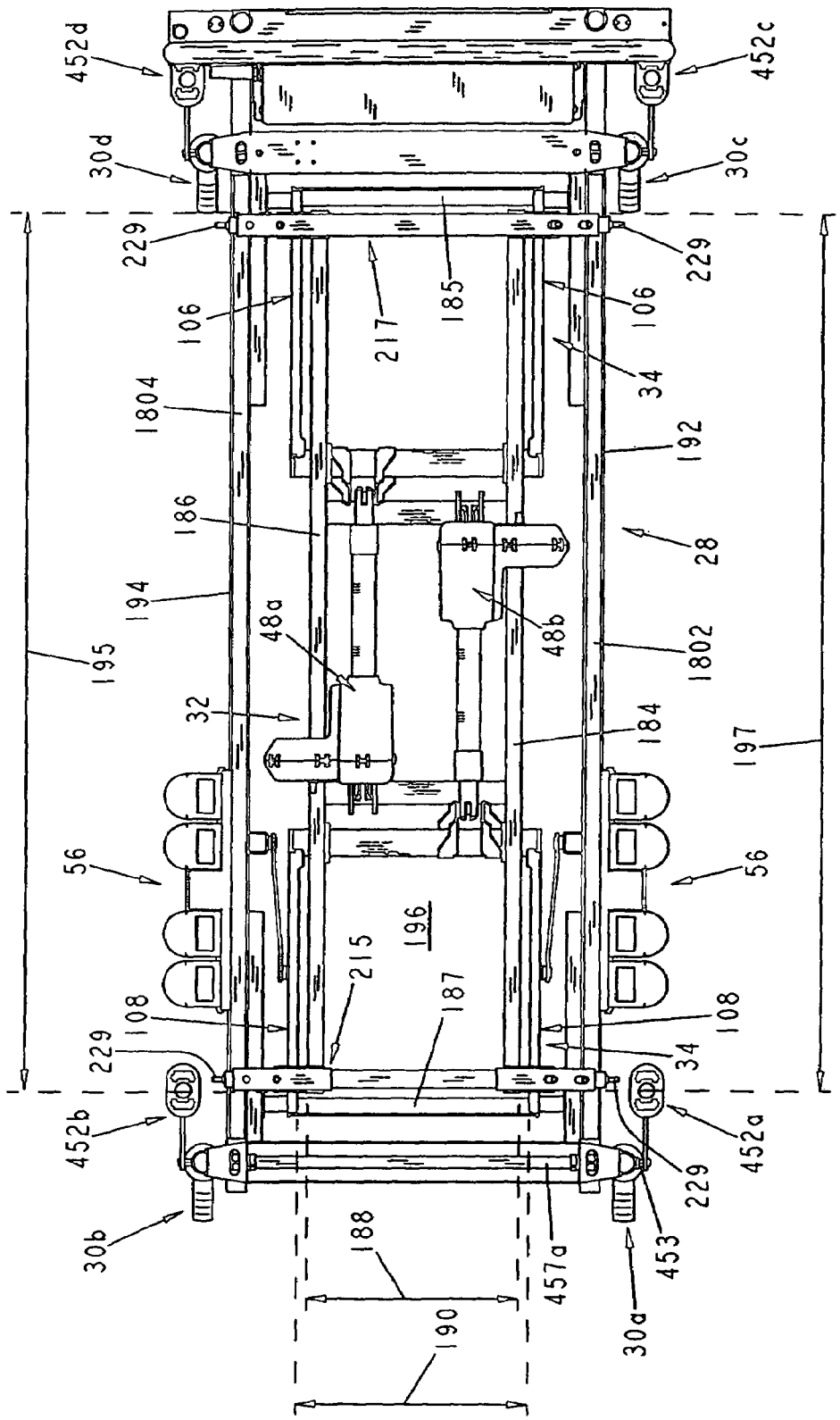
FIG. 8 is a top plan view of the patient support of FIG. 7, showing the nesting of the intermediate frame within the base frame.
Figure 9:
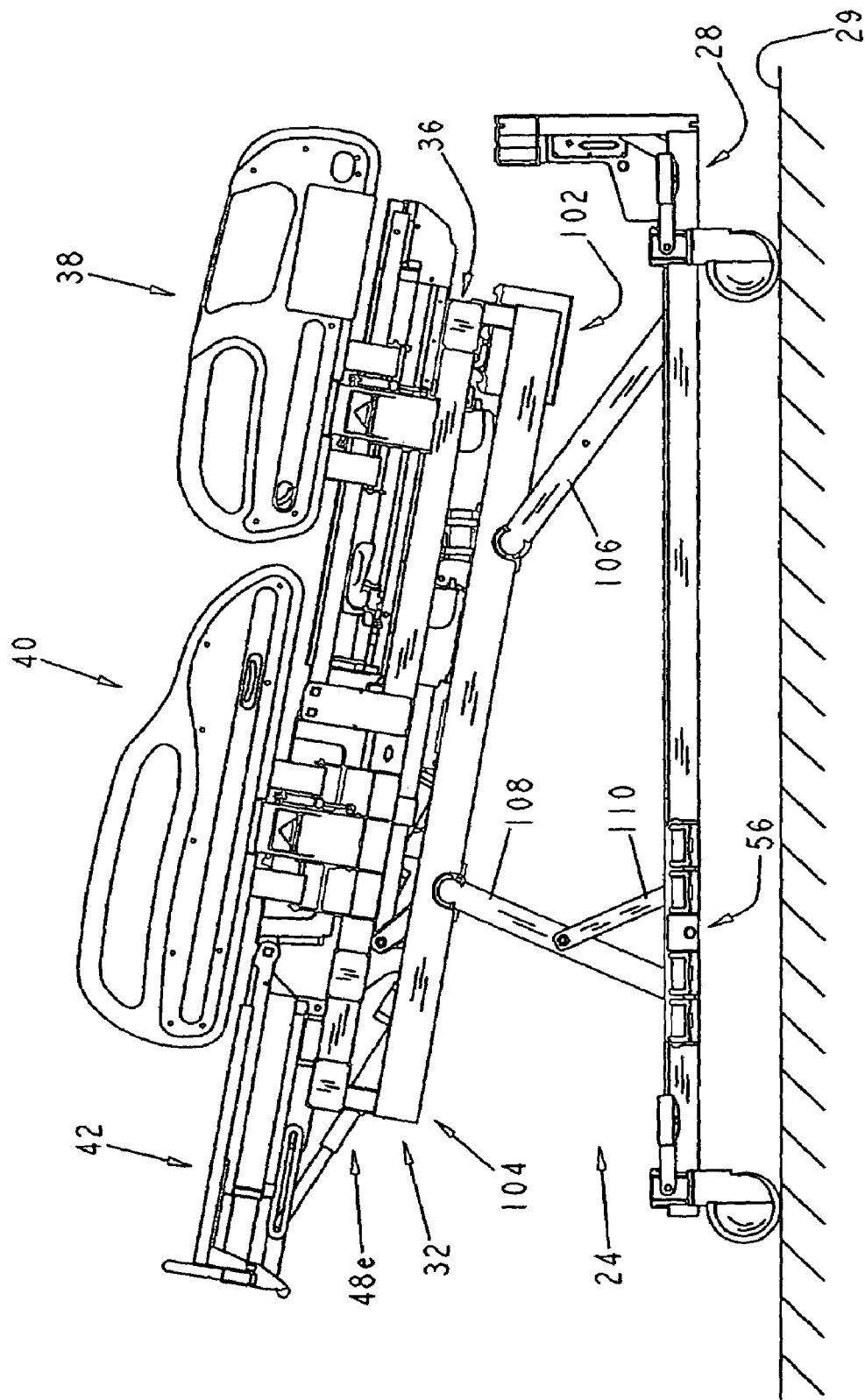
FIG. 9 is a side elevation view of the patient support of FIG. 1, showing the deck support in a Trendelenburg position and the deck in a linear relationship.
Figure 10:
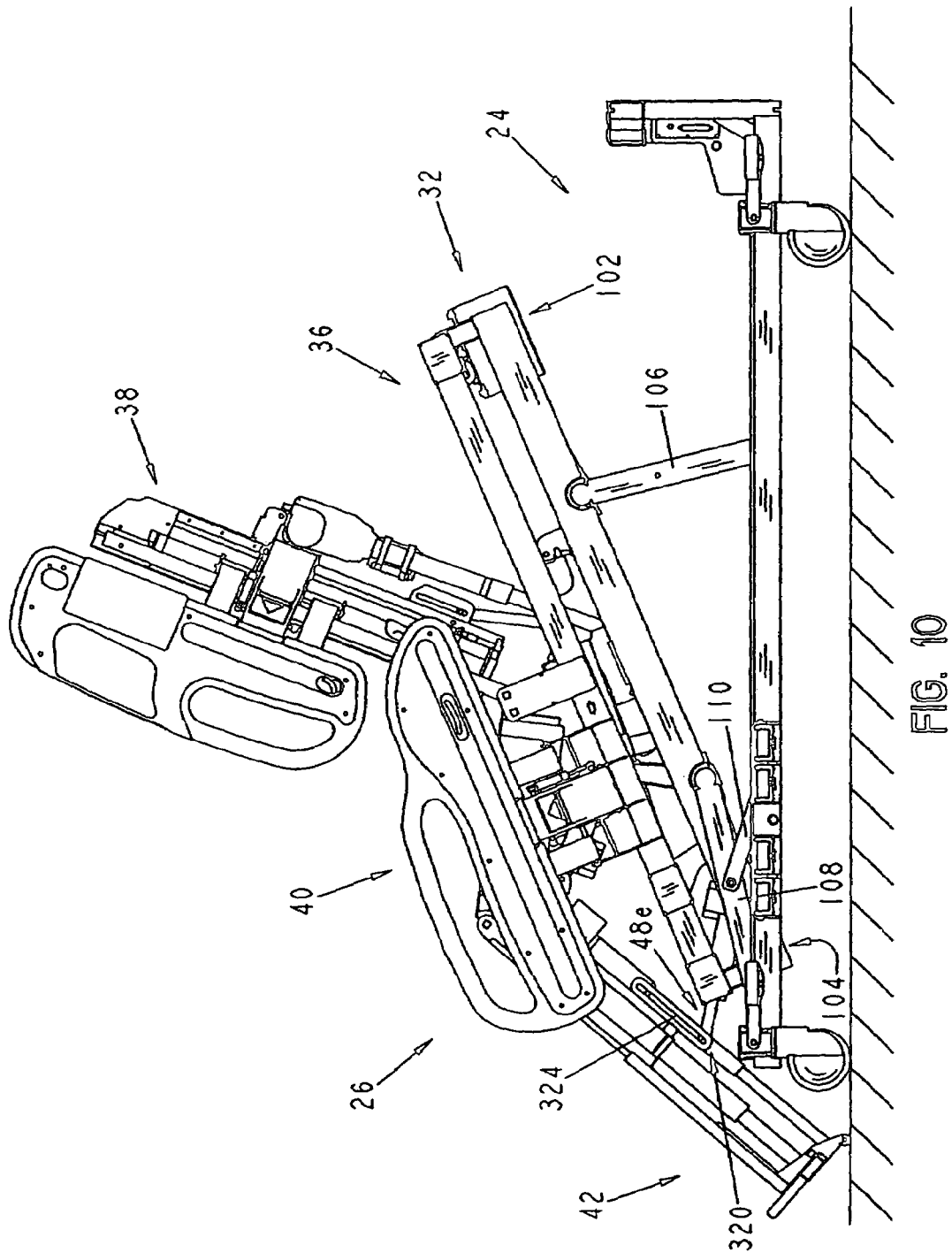
FIG. 10 is a side elevation view of the patient support of FIG. 1, showing the patient support in a second chair-like position with the deck support in a Reverse Trendelenburg position, the head section raised by the head actuator, the seat section elevated by the seat actuator, the leg section lowered by the leg actuator and the leg section optionally shown in the extended position.
Figure 11:
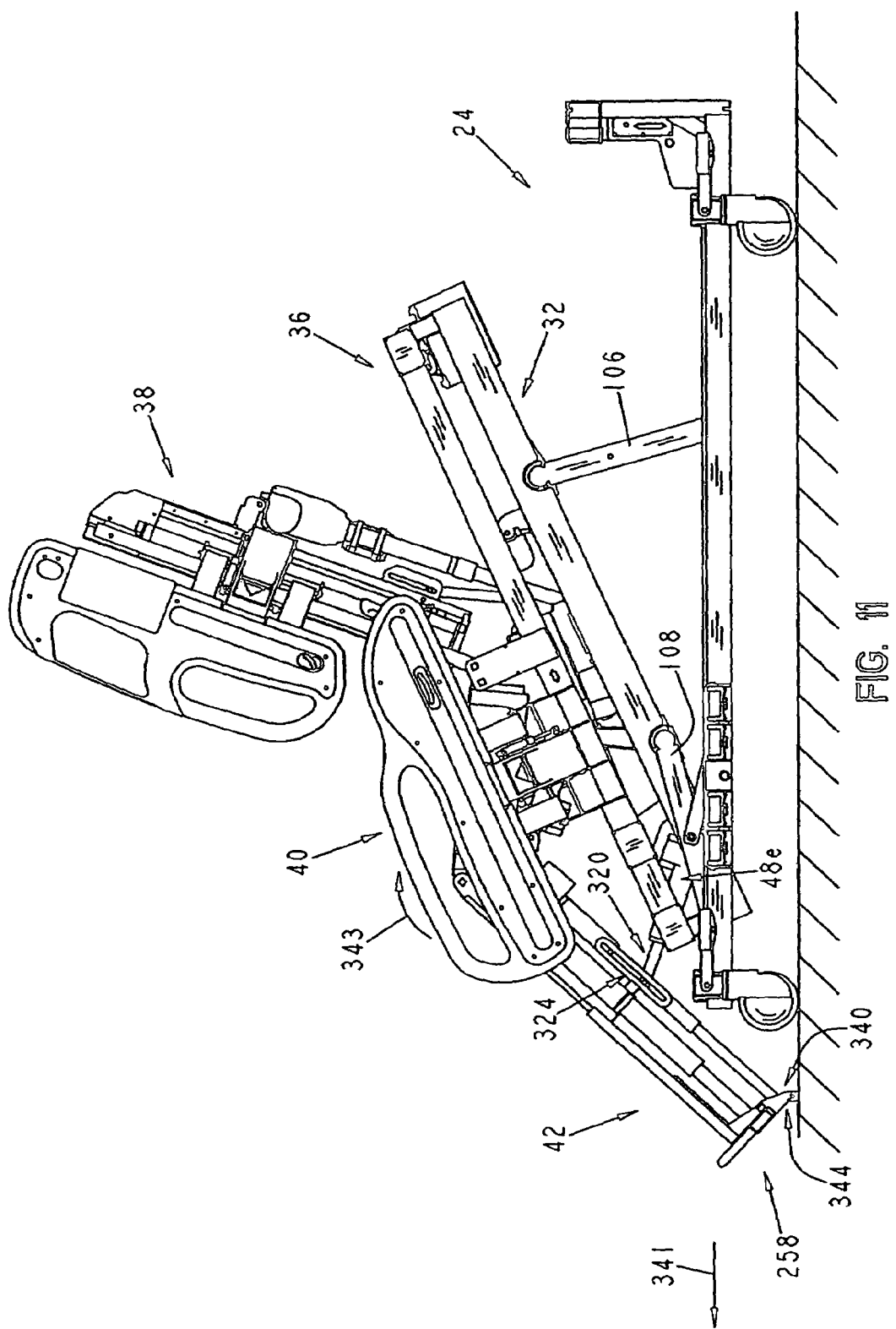
FIG. 11 is a side elevation view generally similar to FIG. 10, showing the leg section of the deck is in an extended position and the leg section being lowered by the leg actuator, the leg section not being fully lowered due to contact with an obstruction, the floor, by a roller coupled to the leg section and the leg section and the obstruction prevented from damage by the roller translating the leg section along the floor, the leg section rotating relative to the seat section and by the leg section actuator traveling up the elongated slot provided in the coupling bracket between the leg section and the leg actuator.

As explained in more detail below, lift arms 34 and linear actuators 48a and 48b, commonly referred to as a hi/low mechanism, are configured to position deck support 24 in at least the following positions: a raised or upper position wherein intermediate frame 32 and weigh frame 36 are above base frame 28 (FIGS. 1-6); a first lowered position wherein at least a portion of intermediate frame 32 and/or weigh frame 36 is nested within base frame 28 (FIG. 7); a Trendelenburg position wherein a head end 102 of intermediate frame 32 is lower than a foot end 104 of intermediate frame 32 (FIG. 8); and a Reverse Trendelenburg position wherein foot end 104 of intermediate frame 32 is lower than head end 102 of intermediate frame 32 (FIGS. 9, 10 and 11). One skilled in the art will appreciate that the positions shown in FIGS. 1-11 are exemplary positions and that intermediate frame 32 is positionable in a wide variety of positions relative to base frame 28.

Lift Arms

Figure 2:
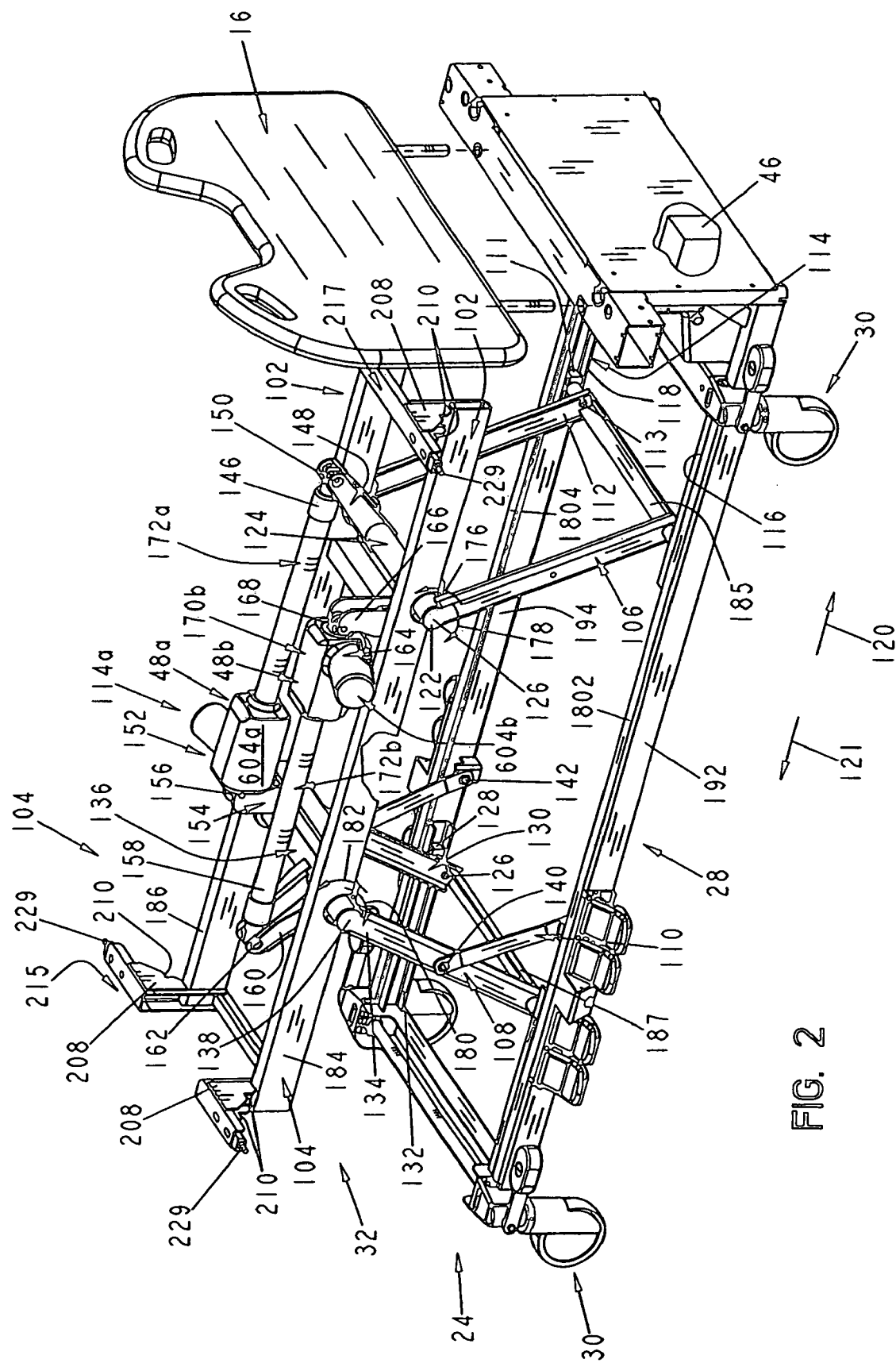
FIG. 2 is a perspective view of the patient support of FIG. 1 with the deck, mattress, first pair of siderails and second pair of siderails removed and the headboard spaced apart from the deck support, the deck support being in a raised position and comprising a base frame, an intermediate frame spaced apart from the base frame, a first pair of lifting arms configured to raise and lower a head end of the intermediate frame, and a second pair of lifting arms configured to raise and lower a foot end of the intermediate frame.

Referring to FIG. 2, lift arms 34 include a pair of head links 106 pivotably coupled to head end 102 of intermediate frame 32 and slidably and pivotably coupled to base frame 28, a pair of foot links 108 pivotably coupled to foot end 104 of intermediate frame 32 and slidably and pivotably coupled to base frame 28, and a pair of guide links 110 pivotably coupled to respective foot links 108 and pivotably coupled to base frame 28 at a fixed pivot point. Alternatively, the guide links 110 are pivotably coupled to the respective foot links 108, and the intermediate frame 32, or pivotably coupled to the respective head links 106 and the base frame 28, or pivotably coupled to the respective head links 106 and the intermediate frame 32. In further alternative embodiments, two sets of guide links 110 are provided, one set pivotably coupled to the foot links 108 and either the base frame 28 or the intermediate frame 32 and one set coupled to the head links 106 and either the base frame 28 or the intermediate frame 32.

Each head link 106 is slidably coupled to base frame 28 and pivotably coupled to intermediate frame 32. Alternatively, each of the head links 106 is slidably coupled to either the base frame 28 or the intermediate frame 32. As illustratively shown in FIG. 2, each head link 106 is slidably and pivotably coupled to base frame 28 at pivot 113 by a slide block 111. Slide block 111 is pivotably coupled to a lower portion 112 of head link 106 and slidably received in a guide 114 coupled to base frame 28. In one embodiment, the material used for the slide blocks 111 and the guides 114 and the surface characteristics of the slide blocks 111 and the guides 114 are chosen to reduce the coefficient of friction between the slide blocks 111 and the guides 114.

Guide 114 includes an upper channel 116 and a lower channel 118 which define two directions of travel 120 and 121 for slide block 111. Upper channel 116 and lower channel 118 are further configured to restrict the movement of slide block 111 in any direction other than directions of travel 120 and 121. Slide blocks 111 are preferred because they are capable of spreading the load of intermediate frame 32, deck 26 and other patient support components over a larger surface area than other types of couplers. Alternative methods of coupling the head links 106 to the base frame 28 can be used provided that the lower portion of the head links 106 can pivot relative to the base frame 28 and can move along the directions of travel 120, 121. Examples include a roller, a plurality of rollers, or interlocking members.

Illustratively, an upper end 122 of each head link 106 is pivotably coupled to intermediate frame 32 through a cross link 124. Alternatively, the head links 106 are directly pivotably coupled to the intermediate frame 32. In a further alternative, the head links 106 are pivotably coupled to the base frame 28 and slidably and pivotably coupled to the intermediate frame 32.

Cross link 124 extends between each head link 106 and is rigidly coupled to, each head link 106. As such, cross link 124 coordinates the simultaneous movement of head links 106. Cross link 124 is received through openings (not shown) formed in intermediate frame 32 and is pivotable relative to intermediate frame 32. In one embodiment, a bearing or other means is used to increase the ease by which cross link 124 pivots relative to intermediate frame 32.

Each foot link 108, is slidably and pivotably coupled to base frame 28. Illustratively each foot link 108 is coupled to base frame 28 at pivot 126 by slide block 128 which is pivotably coupled to a lower portion 130 of foot link 108 and slidably received in a guide 132 coupled to base frame 28. Guide 132 and slide block 128 are generally identical to guide 114 and slide block 111 discussed in conjunction with head links 106. As such, guide 132 is configured to restrict the movement of slide block 128 in any direction other than directions of travel 120 and 121. Alternative methods of coupling the foot links 108 to the base frame 28 can be used provided that the lower portion of the foot links 108 can pivot relative to the base frame 28 and can move along the directions of travel 120, 121. Examples include a roller, a plurality of rollers, or interlocking members.

An upper end 134 of each foot link 108 is pivotably coupled to intermediate frame 32 through a cross link 136. Alternatively, the foot links 108 are directly pivotably coupled to the intermediate frame 32. Cross link 136 is generally identical to cross link 124 and cooperates with intermediate frame 32 and foot links 108 in the same manner as cross link 124 with intermediate frame 32 and head links 106. Alternatively, the upper end 134 of each foot link 108 is slidably and pivotably coupled to the intermediate frame 32 and pivotably coupled to the base frame 28.

Guide links 110 restrict the motion of foot links 108 such that the pivot point 138 between foot links 108 and intermediate frame 32 is restrained to move vertically without moving horizontally. This restriction prevents horizontal movement of intermediate frame 32 relative to base frame 28 during the raising and lowering of intermediate frame 32. This restrained movement prevents intermediate frame 32 from moving through an arc while moving between the upper position of FIG. 2 and the lower position of FIG. 7 so that intermediate frame 32 can be raised and lowered without requiring additional hospital room for clearance.

It will be appreciated that, in order for guide links 110 to perform the restriction function, the distance between pivots 140 (pivot between guide link 110 and foot link 108) and 142 (pivot between guide links 110 and base frame 28) of guide links 110 is one half the distance between pivot 126 (pivot between slide blocks 128 and base frame 28) and pivot 138 (pivot between upper ends 134 of foot links 108 and intermediate frame 32). Further, each guide link 110 is pivotably coupled to the respective foot link 108 at pivot 140 that is one half the distance between pivot 126 of the associated slide block 128 and pivot 138 of the upper end of the respective foot link 108. Thus, the distance between upper pivot 140 of each guide link 110 and the lower pivot 142 of each guide link 110 is equal to the distance between upper pivot 140 of each guide link 110 and upper pivot 138 of each foot link 108. As a result of this link geometry, upper pivots 138 of foot links 108 are maintained in vertical alignment with lower pivot 142 of guide links 110 during the raising and lowering of intermediate frame 32 relative to base frame 28.

Linear Actuators

As stated earlier, linear actuators 48a and 48b provide power to actuate lift arms 34 and in turn to raise and lower intermediate frame 32 relative to base frame 28. Linear actuator 48a is coupled to and actuates head links 106 and linear actuator 48b is coupled to and actuates foot links 108. As such, foot end 104 and head end 102 of intermediate frame 32 can be raised and lowered independent of one another. Alternatively, head links 106 and foot links 108 of the decking system are coupled together such that a single actuator raises and lowers the head end 102 and the foot end 104 of the intermediate frame 32 at the same time.

Illustratively, a first end 146 of linear actuator 48a is coupled to head links 106 through an extension link 148 that is rigidly coupled to cross link 124 which, in turn, is rigidly coupled to head links 106. As shown in FIG. 2, first end 146 is pivotably coupled to extension link 148 through a fastener or pivot pin 150. A second end 152 of linear actuator 48a is coupled to a first bracket 154 which is rigidly coupled to intermediate frame 32. As shown in FIG. 2, second end 152 is pivotably coupled to first bracket 154 through a fastener or pivot pin 156.

Similarly, a first end 158 of linear actuator 48b is coupled to foot links 108 through an extension link 160 that is rigidly coupled to cross link 136 which, in turn, is rigidly coupled to foot links 108. As shown in FIG. 2, first end 158 is pivotably coupled to extension link 160 through a fastener or pivot pin 162. A second end 164 of linear actuator 48b is coupled to a second bracket 166 which is rigidly coupled to intermediate frame 32. Second end 164 is pivotably coupled to second bracket 166 through a fastener or pivot pin 168.

Each actuator 48a and 48b is preferably an electric linear actuator having respective cylinder bodies 170, cylinder rods 172, and motors 604 that operate to extend and retract cylinder rods 172 relative to cylinder bodies 170. As such, actuators 48a and 48b have variable lengths and therefore adjust the distance between pivot pins 150 and 156 and pivot pins 162 and 168, respectively. In one illustrative embodiment, actuators 48a and 48b are Linak actuators, Model No. LA34, available from LINAK U.S. Inc. located at 2200 Stanley Gault Parkway, Louisville Ky. 40223. Further, actuators 48c, 48d, 48e and 48f are also illustratively electric linear actuators, and in one embodiment are also Linak actuators. More particularly, actuator 48c is illustratively a Linak actuator, Model No. LA34 and actuators 48d-48f are illustratively Linak actuators, Model No. LA31. In alternative embodiments, all of the actuators 48 or any one or more of the actuators are other types of electric actuators, pneumatic actuators, hydraulic actuators, mechanical actuators, link systems or other components known to those of ordinary skill in the art for coordinating movement of components relative to one another.

The actuation of either actuator 48a or 48b alone causes either the respective head end 102 of intermediate frame 32 or the respective foot end 104 of intermediate frame 32 to be raised or lowered relative to base frame 28. Referring to FIG. 2, head end 102 of intermediate frame 32 is lowered relative to base frame by the retraction of cylinder rod 172a of actuator 48a. As cylinder rod 172a of actuator 48a is retracted, the distance between pivot pins 150 and 156 is reduced. This reduction in pivot spacing causes extension link 148 to move toward first bracket 154 which in turn causes cross link 124 and head links 106 to rotate in direction 176 about pivot 126. Since lower portions 112 of head links 106 are restrained to move only in directions of travel 120 and 121 of guide 114, the rotation of head links 106 in direction 176 causes lower portions 112 of head links 106 to travel in direction 120. As a result upper ends 122 of head links 106 are lowered relative to base frame 28 and therefore head end 102 of intermediate frame 32 is lowered relative to base frame 28.

Head end 102 of intermediate frame 32 is raised relative to base frame 28 by the extension of cylinder rod 172 of actuator 48a. As cylinder rod 172 of actuator 48a is extended the distance between pivot pins 150 and 156 is increased. This increase in pivot spacing causes extension link 148 to move away from first bracket 154 which, in turn, causes cross link 124 and head links 106 to rotate in a direction 178 counter to direction 176 about pivot 126. The rotation of head links 106 in direction 178 counter to direction 176 causes lower portions 112 of head links 106 to travel in direction 121. As a result, upper ends 122 of head links 106 are raised relative to base frame 28 and therefore, head end 102 of intermediate frame 32 is raised relative to base frame 28.

Foot end 104 of intermediate frame 32 is lowered relative to base frame 28 by the retraction of cylinder rod 172b of actuator 48b. As cylinder rod 172b of actuator 48b is retracted the distance between pivot pins 162 and 168 is reduced. This reduction in pivot spacing causes extension link 160 to move toward second bracket 166 which, in turn, causes cross link 136 and foot links 108 to rotate in direction 180 about pivot 138. Since lower portions 130 of foot links 108 are restrained to move only in directions of travel 120 and 121 of guide 132, the rotation of foot links 108 in direction 180 causes lower portions 130 of foot links 108 to travel in direction 121. As a result, upper ends 134 of foot links 108 are lowered relative to base frame 28 and therefore, foot end 104 of intermediate frame 32 is lowered relative to base frame 28.

Foot end 104 of intermediate frame 32 is raised relative to base frame 28 by the extension of cylinder rod 172*b* of actuator 48*b*. As cylinder rod 172*b* of actuator 48*b* is extended, the distance between pivots 162 and 168 is increased. This increase in pivot spacing causes extension link 160 to move away from second bracket 166 which, in turn, causes cross link 136 and foot links 108 to rotate in a direction 182 counter to direction 180 about pivot 138. The rotation of foot links 108 in direction 182 counter to direction 180 causes lower portions 130 of foot links 108 to travel in direction 120. As a result, upper ends 134 of foot links 108 are raised relative to base frame 28 and therefore, foot end 104 of intermediate frame 32 is raised relative to base frame 28.

The simultaneous actuation of actuators 48*a* and 48*b* causes both head end 102 and foot end 104 of intermediate frame 32 to raise or lower relative to base frame 28. As shown in FIG. 2, the simultaneous extension of both actuators 48*a* and 48*b* causes both head end 102 and foot end 104 of intermediate frame 32 to raise relative to base frame 28 and intermediate frame 32 to be spaced apart from base frame 28. The simultaneous retraction of both actuators 48*a* and 48*b* causes both head end 102 and foot end 104 of intermediate frame 32 to lower relative to base frame 28. It should be appreciated that actuator 48*a* can be extended while actuator 48*b* is retracted, resulting in head end 102 being raised while foot end 104 is lowered, or that actuator 48*a* can be retracted while actuator 48*b* is extended, resulting in head end 102 being lowered while foot end 104 is raised.

Further, in an alternative embodiment the direction of one of the actuators 48*a*, 48*b* is reversed such that to raise the intermediate frame 32 relative to the base frame 28 a first of the two actuators 48*a*, 48*b* is extended and the second actuator 48*b*, 48*a* is retracted. Further, to lower the intermediate frame 32 relative to the base frame 28 the second actuator 48*b*, 48*a* is extended and the first actuator 48*a*, 48*b* is retracted.

Referring further to FIG. 2, deck support 24 is in an upper position when actuators 48*a* and 48*b* are both extended. Deck support 24 is moved from the upper position of FIG. 2 to the Trendelenburg position of FIG. 8 by retracting actuator 48*a* and thus lowering head end 102 of intermediate frame 32. Deck support 24 is returned to the upper position of FIG. 2 by extending actuator 48*a* back to its prior length. Deck support 24 is moved from the upper position of FIG. 2 to the Reverse Trendelenburg position of FIGS. 9 and 10 by retracting actuator 48*b* and thus lowering foot end 104. Deck support 24 is returned to the upper position of FIG. 2 by extending actuator 48*b* back to its prior length.

Figure 7:
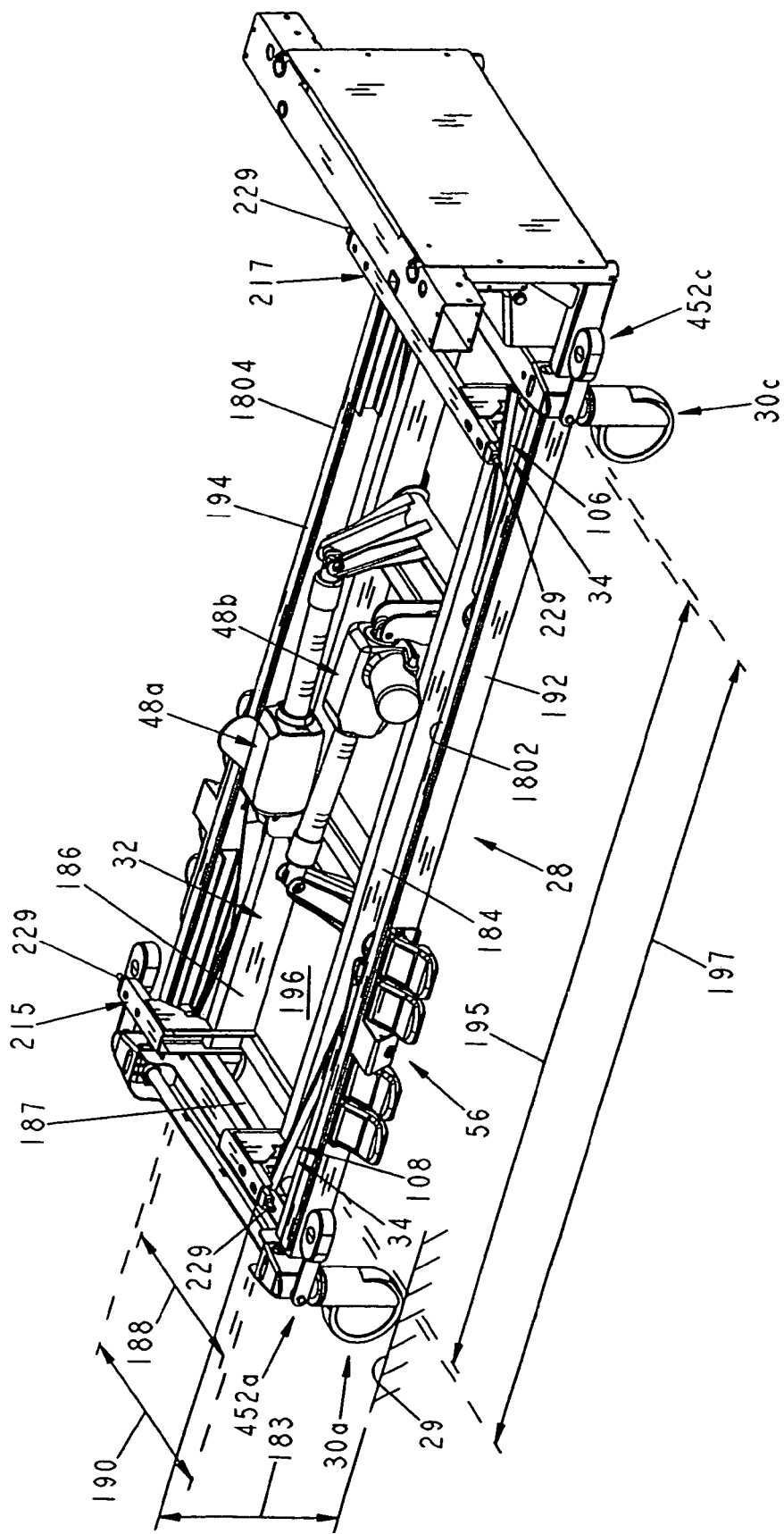
FIG. 7 is a partial perspective view of the patient support of FIG. 2, showing the deck support in a lowered position wherein the intermediate frame nests within the base frame.

Deck support 24 is moved from the upper position of FIG. 2 to the lowered position of FIG. 7 by simultaneously retracting actuators 48*a* and 48*b* and thus lowering both head end 102 and foot end 104 of intermediate frame 32. Deck support 24 is moved back to the upper position of FIG. 2 from the lowered position of FIG. 7 by simultaneously extending actuators 48*a* and 48*b*. It should be appreciated that actuators 48*a* and 48*b* can place the patient support 10 in a variety of positions from any starting position and that the upper position shown in FIG. 2 is simply a reference starting position used to explain the operation of the deck support.

Since actuators 48*a* and 48*b* retract and extend at substantially the same rates, the simultaneous retraction of actuators 48*a* and 48*b* causes intermediate frame 32 to be maintained in a generally horizontal position as it is vertically transitioned from the upper position of FIG. 2 to the lowered position of FIG. 7 and then raised back again to the upper position of FIG. 2. Further, control system 44 is configured to control each actuator 48*a-f* and therefore can independently control the speed of each actuator 48*a-f*. Also, as discussed above, guide links 110 are configured to generally maintain the vertical alignment of intermediate frame 32 and base frame 28 such that intermediate frame 32 does not "swing" outwardly or inwardly relative to base frame 28 as intermediate frame 32 is transitioned between various positions.

One of the purposes of intermediate frame 32 being configured to raise and lower relative to base frame 28 is to aid in the ingress of a patient to and egress of a patient from patient support 10. To allow intermediate frame 32 to lower further and thus provide additional assistance in the ingress to and egress of the patient from patient support 10, patient support 10 is configured to provide a lowered position, as shown in FIG. 7, wherein portions of deck support 24 nest within other portions of deck support 24. Thus, an overall height 183 of deck support 24 and, in turn, an overall height of mattress 14 is reduced. Further, by placing patient support 10 in the lowered position of FIG. 7, the possibility of patient injury due to accidental egress from patient support 10 is reduced due to the fact that the patient is closer to the floor 29 than in conventional patient supports.

Nesting Frames

As shown in FIGS. 7 and 8, portions of intermediate frame 32 are configured to nest within base frame 28 and/or extend below base frame 28 when intermediate frame is in the lowered position. Alternatively, the base frame 28 can be configured to nest within the intermediate frame 32 when the intermediate frame 32 is in the lowered position. As shown in FIGS. 2, 7 and 8, longitudinally-extending members 184, 186 of intermediate frame 32 define a first outer width 188 of intermediate frame 32 that is less than an inner width 190 defined by longitudinally extending members 192, 194 of base frame 28 and lifting arms 34. Further, an outer length 195 of intermediate frame 32 is less than an inner length 197 of base frame 28 and lifting arms 34, illustratively shown as the separation between cross link 185, shown in FIGS. 2 and 8, of head links 106 and cross link 187 of foot links 108. As such, as intermediate frame 32 is lowered to the lowered position, portions of intermediate frame 32 are received within an interior region 196 defined by base frame 28 and lifting arms 34, thereby reducing overall height 183 of deck support 24.

It should be noted that when deck support 24 is in the lowered position, head links 106, foot links 108 and guide links 110 are rotated beyond horizontal, such that pivots 126, 138, 140 are generally lower than pivots 142, 143, 144. In one embodiment, head links 106, foot links 108 and guide links 110 are generally rotated from approximately 80° above horizontal in the upper position of FIG. 2 to approximately 10° below horizontal in the lowered position of FIG. 7. As shown in FIG. 2, intermediate frame 32 includes a plurality of gussets 208 which each include a stop surface 210. Stop surface 210 is configured to contact and rest upon foot links 104 and head links 106, respectively, when intermediate frame 32 is fully lowered. Stop surfaces 210 are configured to prevent other portions of patient support 10, such as siderails 20, 22, from contacting base frame 28. Alternatively, the stop surface 210 is configured to contact and rest upon the base frame 28.

It is further contemplated that portions of weigh frame 36 are configured to nest within base frame 28 when intermediate frame 32 is in the lowered position. Longitudinally extending members 198, 200, shown in FIGS. 3, 4 and 13, of weigh frame 36 define an outer width 202 of weigh frame 36 that may be less than inner width 190 of base frame 28 and lifting arms 34 (FIG. 7). Further, an outer length 204 of weigh frame 36 may be less than inner length 197 of base frame 28 and lifting arms 34. As such, as intermediate frame 32 is lowered to the lowered position, portions of weigh frame 36 as well as intermediate frame 32 may nest within or extend below base frame 28 thereby further reducing overall height 183 of deck support 24.

Weigh Frame

Figure 13:
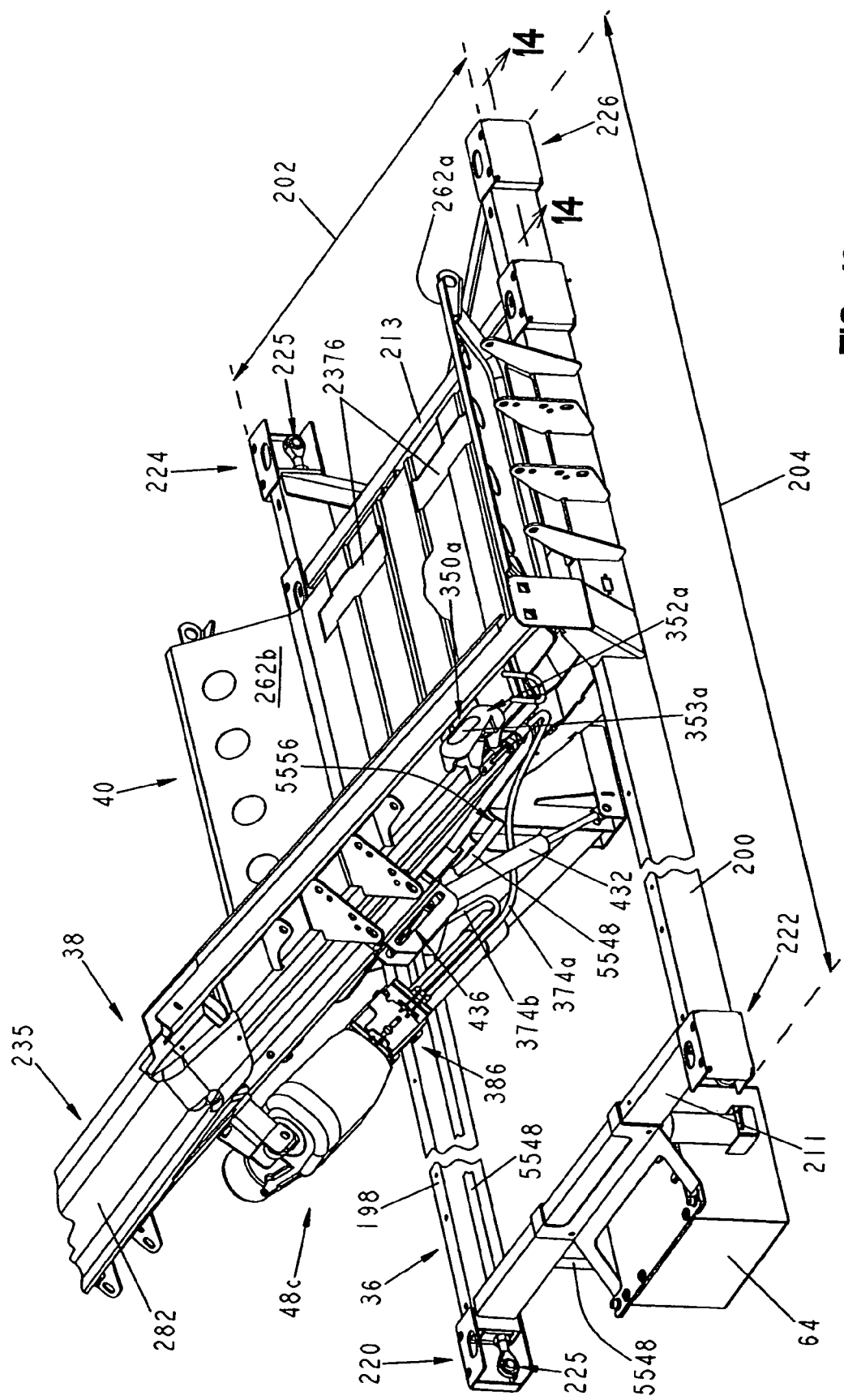
FIG. 13 is a perspective view of the deck and weigh frame of the patient support of FIG. 1 with the leg section removed and showing the head section elevated.
Figure 14:
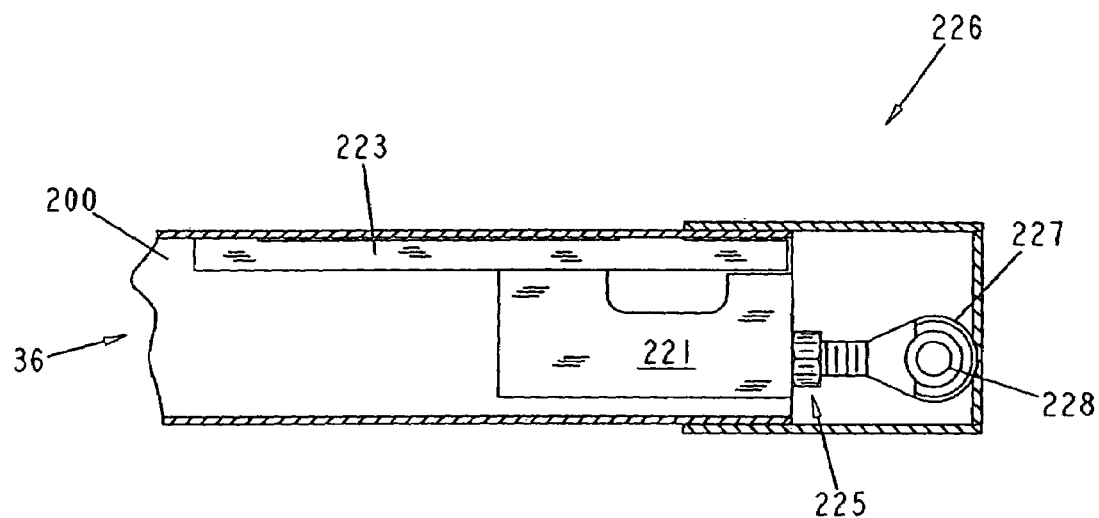
FIG. 14 is a side view of one of the load cells which couple together the intermediate frame and the weigh frame taken along lines 14-14 in FIG. 13.

As noted above, intermediate frame 32 is coupled to weigh frame 36. As shown in FIGS. 13 and 14, weigh frame 36 includes longitudinally extending members 198, 200 and transversely extending members 211, 213. Load cells 220, 222, 224, 226 are coupled to a respective end of longitudinally extending members 198, 200.

Referring further to FIG. 14, load cell 226 is shown. The description below of load cell 226 is descriptive of all of load cells 220, 222, 224, 226 unless specifically noted otherwise. Load cell 226 includes a load member, load beam, or cell block (hereinafter "cell block 221") that is mounted at one of the four corners of the weigh frame 36. Conventional strain gages (not shown) are included in load cell 226 and are coupled to cell block 221. The strain gages operate in a conventional manner to provide an indication of the load supported by load cell 226. That is, a known input voltage is applied to input leads (not shown) coupled to the strain gages and, as cell blocks 221 deflect due to the application of a load, the resistance of the strain gages changes resulting in a change in an output signal generated on output leads (not shown) coupled to the strain gages. In the illustrative embodiment, the input and output leads are bundled together in a cable (not shown) that is routed between load cell 226 and conventional signal conditioning circuitry (not shown).

Block 221 is coupled to a mounting bar 223 of weigh frame 36 by suitable fasteners, such as bolts (not shown). Mounting bar 223 and block 221 are received in the interior region of weigh frame members 198, 200 as shown best in FIG. 14. A stud 225 is coupled to block 221 and includes a socket portion 227 and a ball portion 228. Socket portion 227 is configured to capture ball portion 228 and to allow ball portion 228 to rotate relative to socket portion 227.

Figure 3:
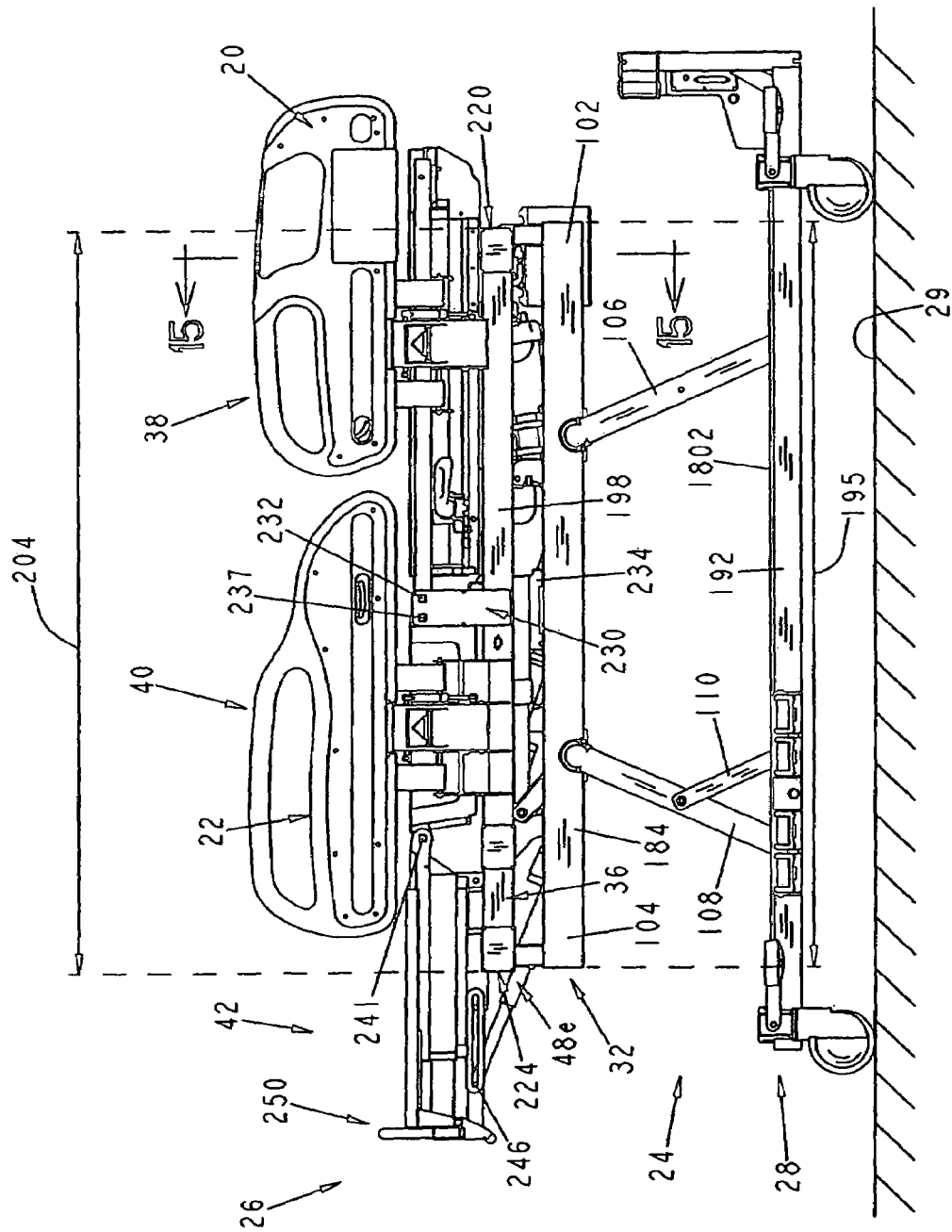
FIG. 3 is a side elevation view of the patient support of FIG. 1, showing the deck support in an upper position and the deck sections in a linear relationship or bed configuration.
Figure 15:
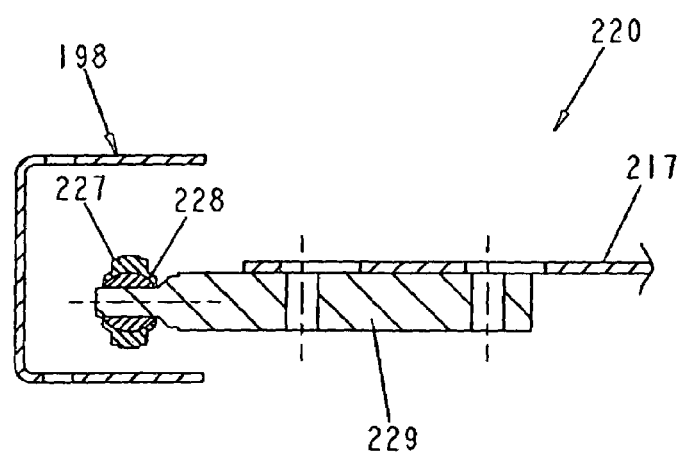
FIG. 15 is a cross sectional view taken along lines 15-15 in FIG. 3, showing the coupling of the intermediate frame and the weigh frame with a load cell.

Load cells 220, 222, 224, 226 are further configured to be coupled to transversely extending members 215, 217 of intermediate frame 32, shown in FIG. 2. As such weigh frame 36 is coupled to intermediate frame 32 and supported by load cells 220, 222, 224, 226. Referring to FIGS. 2, 3 and 15, a stud 229 is fastened to each opposing end of transversely extending members 215 and 217 of intermediate frame 32 and is configured to be received by ball portion 228 respective of load cells 220, 222, 224, 226. As such, studs 229 and ball portions 228 couple weigh frame 36 to intermediate frame 32.

The weight of weigh frame 36 and anything supported by weigh frame 36, such as deck 26, mattress 14, and a patient, is transmitted to load cells 220, 222, 224, 226. This weight deflects or otherwise changes a characteristic of load cells 220, 222, 224, 226 that is detected to determine the total weight supported thereby. By subtracting a known weight of weigh frame 36, deck 26, mattress 14 and any other bed components supported on weigh frame 36, the weight of the patient positioned on patient support 10 can be determined. Additional description of illustrative load cells and methods for determining a patient's weight, position in the bed, and other indications provided by load cells is provided in U.S. patent application Ser. No. 09/669,707, filed Sep. 26, 2000, titled Load Cell Apparatus, to Mobley et al., the disclosure of which is expressly incorporated by reference herein. According to alternative illustrative embodiments of the present disclosure, other configurations and methods of using load cells or other devices to determine a patient's weight or other information related to the patient known to those of ordinary skill in the art are provided herein.

Mattress Deck

Figure 4:
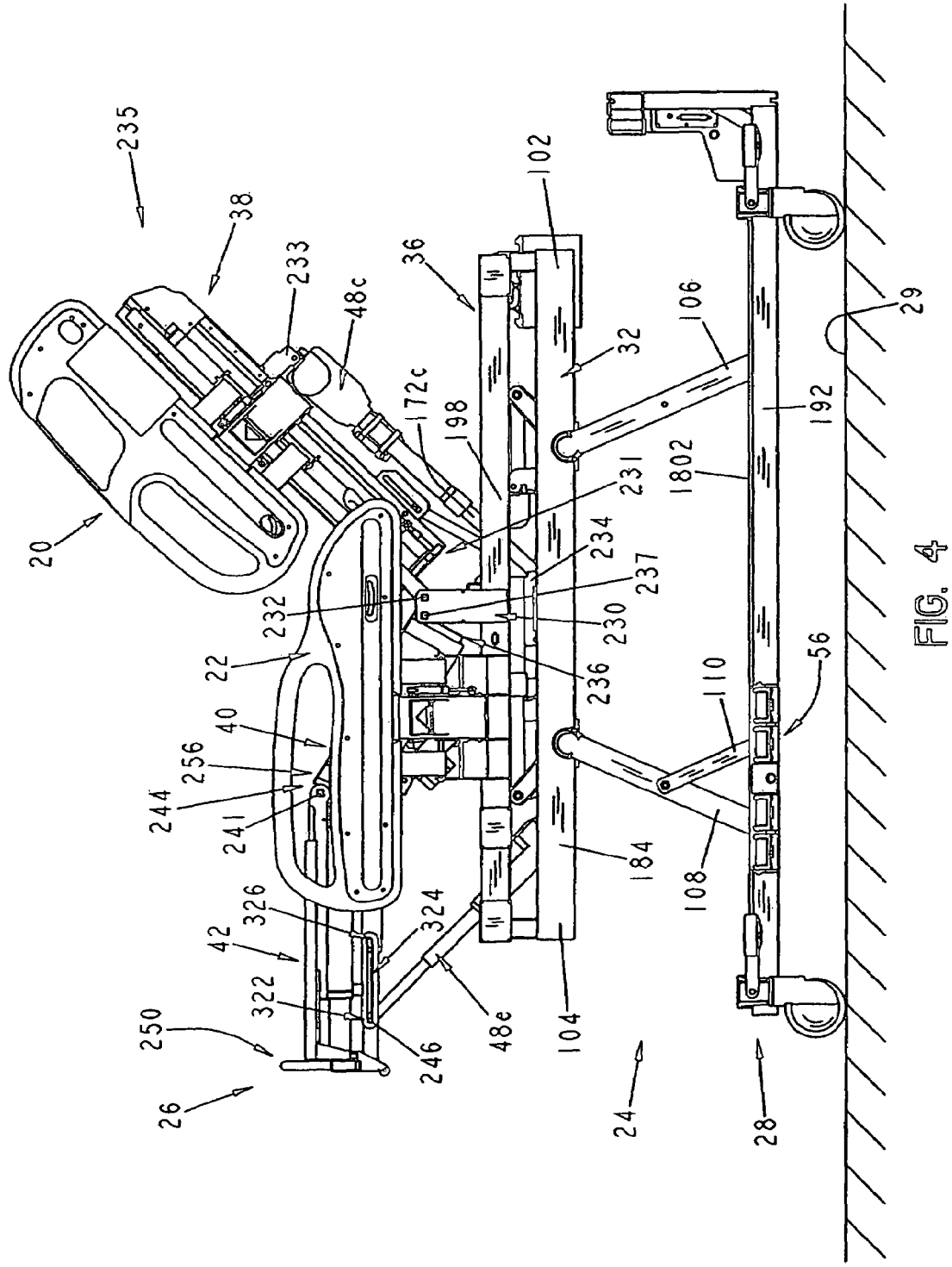
FIG. 4 is a side elevation view of the patient support of FIG. 1, showing the deck support in the upper position of FIG. 3 and a head section of the deck elevated by a head section actuator and a seat section of the deck elevated by a seat section actuator.
Figure 5:
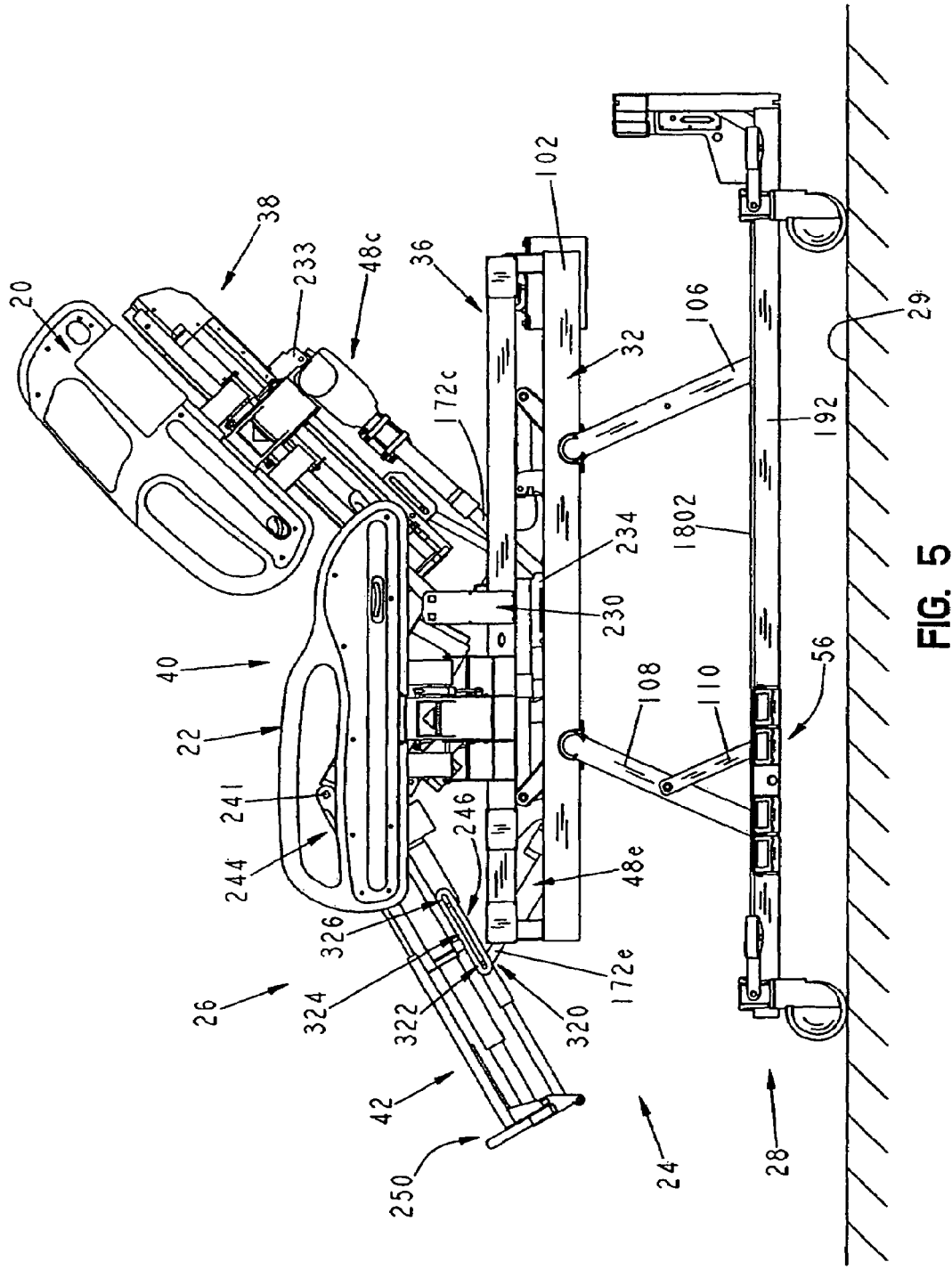
FIG. 5 is a side elevation view of the patient support of FIG. 1, showing a first chair-like configuration of the patient support with the deck support, the head section of the deck and the seat section of the deck in generally the same positions as shown in FIG. 4 and a retractable leg section of the deck in the extended position and lowered by a leg section actuator.
Figure 18:
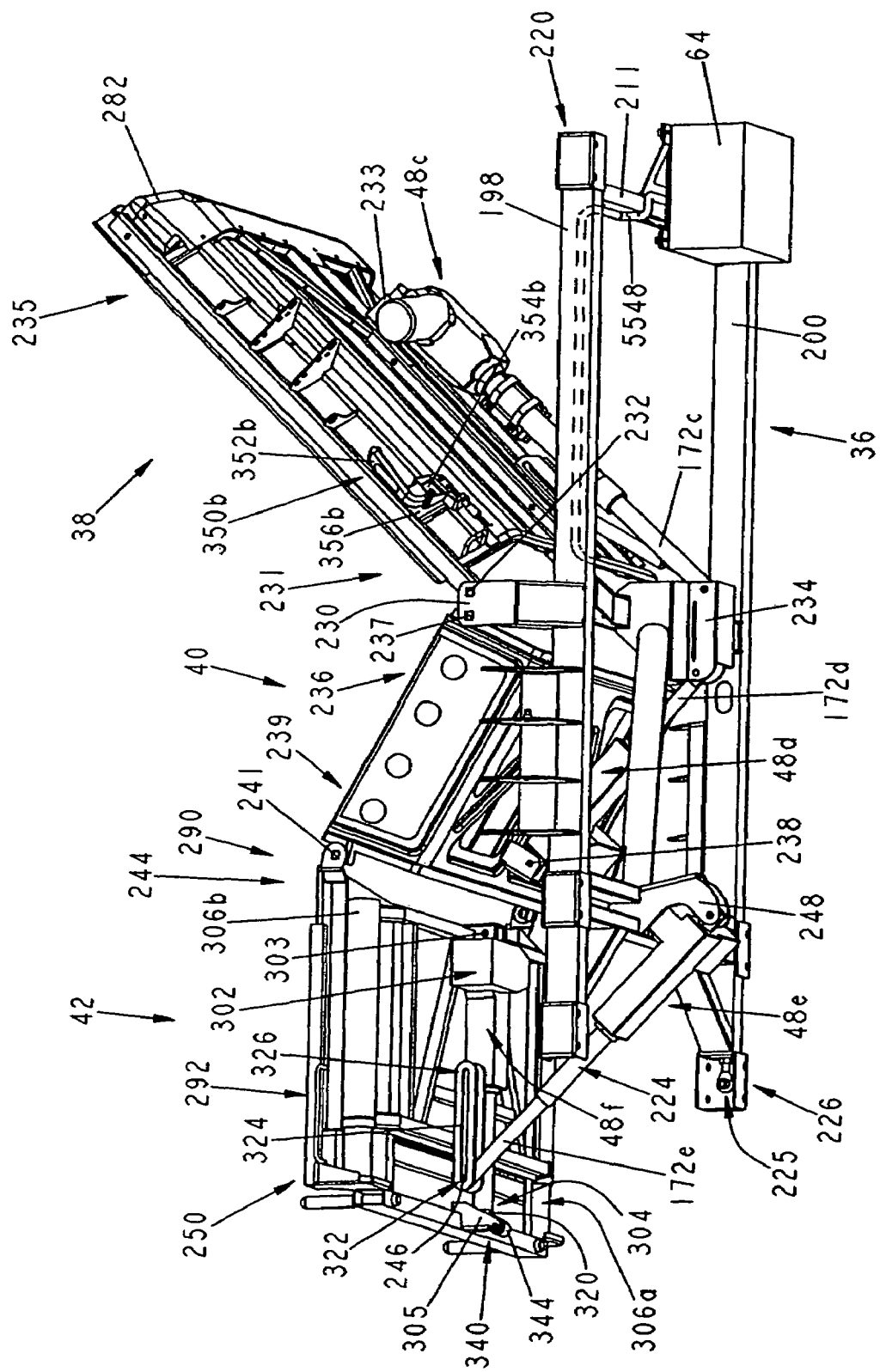
FIG. 18 is a lower perspective view of the deck and the weigh frame of the patient support of FIG. 1, showing the foot section in a retracted position, the seat section upwardly angled and the head section upwardly angled.

As shown in FIGS. 3-5 and as previously mentioned, deck 26 is coupled to weigh frame 36 and includes several sections 38, 40, 42 that are configured to articulate between a plurality of positions. Head section 38 is positioned adjacent headboard 16 (FIG. 1) and is pivotably coupled to weigh frame 36. In the illustrated embodiment as shown in FIGS. 16 and 18, a first end 231 of head section 38 is pivotably coupled to upwardly extending flanges 230 of weigh frame 36 such that head section 38 is rotatable about a pivot 232. Head section 38 is further coupled to actuator 48c. In the illustrated embodiment actuator 48c is pivotably coupled to a downwardly extending bracket 233 of head section 38 and to a bracket 234 of weigh frame 36. Actuator 48c is configured to raise a second end 235 of head section 38. As such, second end 235 of head section 38 can be raised or lowered relative to first end 231, by the extension or retraction of the length of cylinder 172c of actuator 48c.

Seat section 40 is positioned adjacent head section 38 and is pivotably coupled to weigh frame 36. In the illustrated embodiment as shown in FIGS. 16 and 18, a first end 236 of seat section 40 is pivotably coupled to flanges 230 of weigh frame 36 such that seat section 40 is rotatable about a pivot 237. Seat section 40 is further coupled to actuator 48d. In the illustrated embodiment, actuator 48d is pivotably coupled to a downwardly extending bracket 238 of seat section 40 and to bracket 234 of weigh frame 36. Actuator 48d is configured to raise a second end 256 of seat section 40. As such, second end 239 of seat section 40 may be raised or lowered relative to first end 236, by the extension or retraction of the length of cylinder 172d of actuator 48d.

Leg or foot section 42 is positioned adjacent seat section 40 and is pivotably coupled to seat section 40. In the illustrated embodiment as shown in FIGS. 16 and 18, second end 239 of seat section 40 is pivotably coupled to a first end 244 of leg section 42 such that leg section 42 is rotatable about a pivot 241. Leg section 42 is further coupled to actuator 48e. In the illustrated embodiment, actuator 48e is slidably coupled to a bracket 246 of leg section 42 and is pivotably coupled to a bracket 248 of weigh frame 36. Actuator 48e is configured to raise a second end 250 of leg section 42. As such, second end 250 of leg section 42 can be raised or lowered relative to first end 244, by the extension or retraction of the length of cylinder 172e of actuator 48e.

Deck 26 is configured to support mattress 14. As shown in FIG. 16, head section 38 and seat section 40 each includes angled side walls 260a, 260b and 262a, 262b, respectively. Further, head section 38 and seat section 40 each includes substantially flat lower deck portions, floors or walls 264 and 266 connected to side walls 260a, 260b and 262a, 262b, respectively. Angled side walls 260a, 260b and floor 264 and angled side walls 262a, 262b and floor 266 each cooperate to define a support surface for a portion of mattress 14. As shown in FIG. 16, the angled walls 260a, 260b and 262a, 262b are oriented to form obtuse angles with their respective floors 264 and 266. In one illustrative embodiment, the angle formed is approximately 135 degrees. According to alternative embodiments of the present disclosure, the obtuse angles between the side walls and the floor may range from slightly more than 90 degrees to slightly less than 180 degrees. According to other alternative embodiments of the present disclosure, the angles are right angles or acute angles.

The lowered central portion, generally corresponding to floors 264 and 266 of head section 38 and seat section 40, respectively, provides ample space for mattress 14 to be positioned. By having a lowered central portion, the pivot of a patient's hip when the patient is positioned on mattress 14 is more in line with pivots 232, 237 of head section 38 and seat section 40 and provides ample space to provide a mattress 14 that provides adequate support for the patient. In one illustrative embodiment, the position of the pivot of the hip of the patient is about two inches above the pivots 232, 237 of the head and seat sections 38 and 40 of the deck 26. In another illustrative embodiment, the position of the pivot of the hip of the patient is generally in line with the pivots 232, 237 of the head and seat sections 38 and 40 of the deck 26. By minimizing the distance between the pivot of the patient's hip and the pivots 232, 237 of the head and seat sections 38 and 40, the amount of shear exerted against the patient is reduced as either the head or seat 38, 40 section is raised or lowered. By reducing the amount of shear exerted against the patient, the possibility of the patient experiencing skin breakdown is reduced.

As further shown in FIG. 16, head section 38 and seat section 40 further have tapered adjacent end portions 268, 269 providing clearance therebetween during titling of head section 38 or during tilting of seat section 40.

Figure 19:
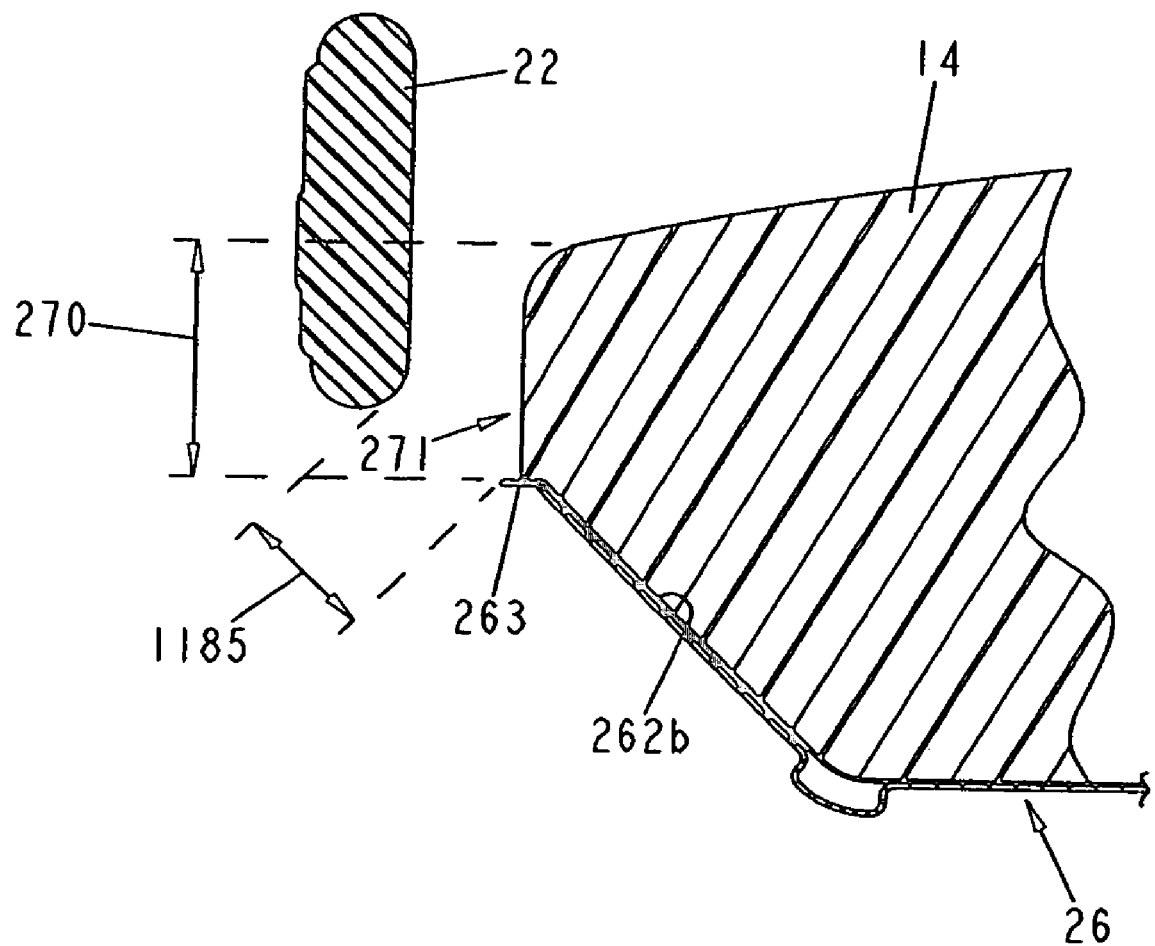
FIG. 19 is a cross sectional view taken along lines 19-19 in FIG. 3, showing the gap between the deck and one of the foot end siderails.

In one illustrative embodiment, as previously described, the distance between the pivot of a patient's hip and pivots 232, 237 is about two inches. Referring to FIG. 19, this translates into about a two inch thick section 270 of mattress 14 at the edge of the deck 26. The thickness of the mattress 14 at the edge of the deck 26, illustratively about two inches, provides needed support for the lateral transfer of the patient into and out of patient support 10. Further, the thickness of the mattress 14 at the edge of the deck 26 provides a grip 271 for the patient to grasp to aid in the egress from patient support 10. In one embodiment the thickness of grip 271 is about two inches.

Head Section

Referring again to FIG. 16, head section 38 further includes a partition 272 located proximate to second end 235. A generally vertical wall 274 and a generally horizontal wall 275 form partition 272. In alternative embodiments, vertical wall 274 may be contoured or sloped at any angle relative to horizontal wall 275. On a mattress side of partition 272, first and second manifold receiving connectors 70 are coupled to wall 272.

On the side opposite the mattress side, or manifold side of partition 272, manifold 62 is coupled to partition 272. Referring to FIGS. 16 and 18, a cover 282 is provided to enclose the manifold side of partition 272. Cover 282 is coupled to the remainder of head section 38 by fasteners, such as snaps, screws, hook and loop fasteners, hinges, magnets, or other suitable fasteners. In one embodiment, a noise barrier (not shown) is positioned between the cover 282 and the remainder of the deck 26. An illustrative noise barrier is formed from conventional foam.

As explained in more detail herein, first and second manifold receiving connectors 70 are configured to be coupled to mattress connectors 68, which are in fluid communication with mattress 14. Manifold 62 is configured to be in fluid communication with pump 64. As such, mattress 14 may be easily assembled to patient support 10 by simply coupling first and second manifold receiving connectors 70 with connectors 68. In alternate embodiments, a single or three or more manifold receiving connectors are coupled to the partition.

In one embodiment, at least vertical wall 274 of partition 272 is removably coupled to head section 38. Vertical wall 274 is assembled with manifold 62 and first and second manifold receiving connectors 70 to form a sub-assembly. The sub-assembly is then coupled to head section 38 by any suitable fastening means including screws, bolts, snaps, clasps, latches, or other suitable fastening means. As such, the sub-assembly may be configured for a variety of mattress configurations and assembled into the remainder of patient support 10.

Foot Section

Referring further to FIG. 16, leg or foot section 42 is transversely contoured similar to head section 38 and seat section 40. However, leg section 42 further includes a first leg section member 290 and a second leg section member 292 which are movable relative to each other and thereby allow leg section 42 to be positioned in a retracted position, shown best in FIG. 18, and in an extended position shown best in FIG. 20. In alternative embodiments, one or more of the head section 38, seat section 40 and leg section 42 are comprised of multiple section members that are movable relative to each other to allow the respective section to lengthen or retract.

Figure 20:
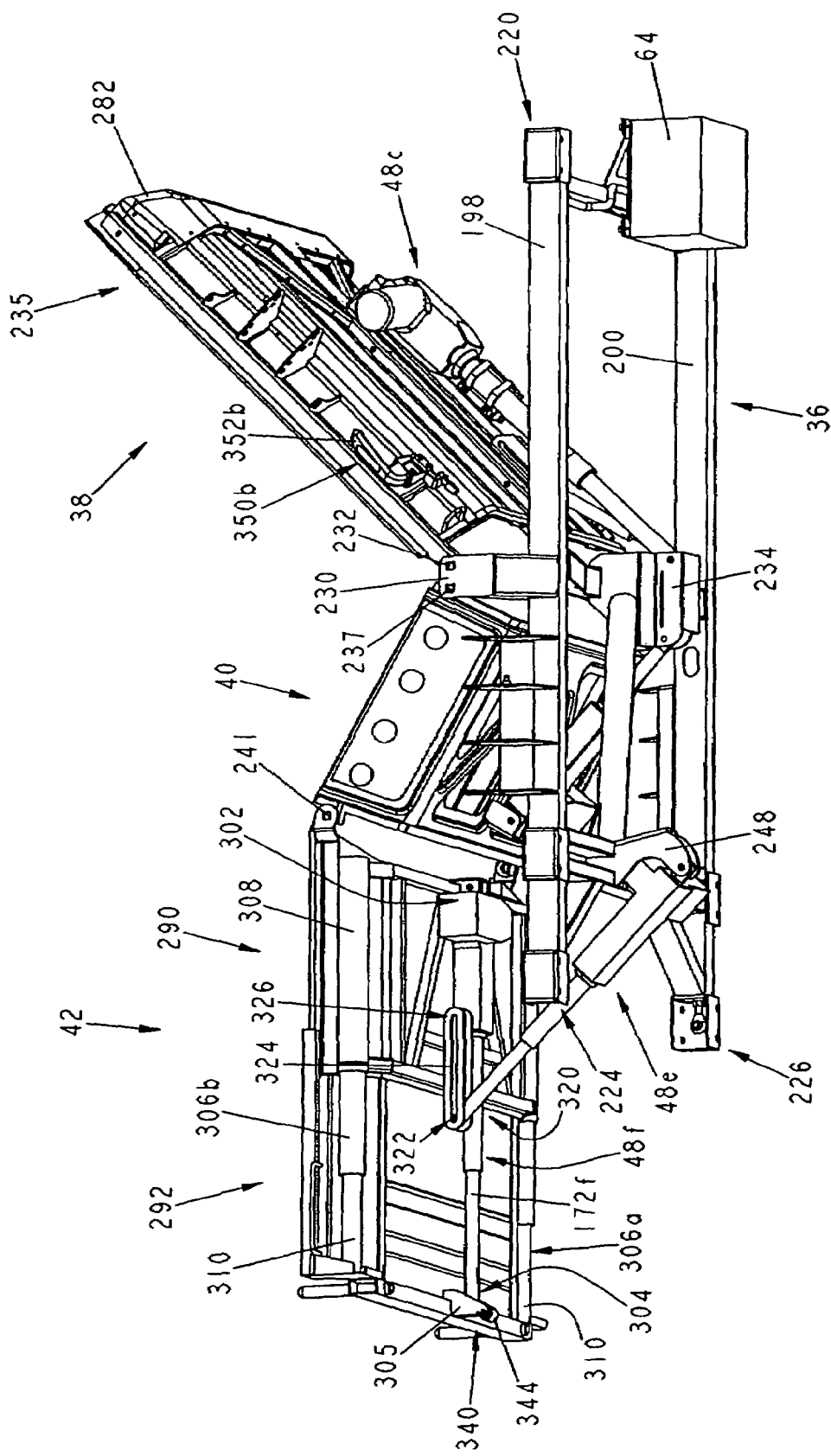
FIG. 20 is generally similar to FIG. 18 showing the foot section of the patient support in an extended position.
Figure 21:
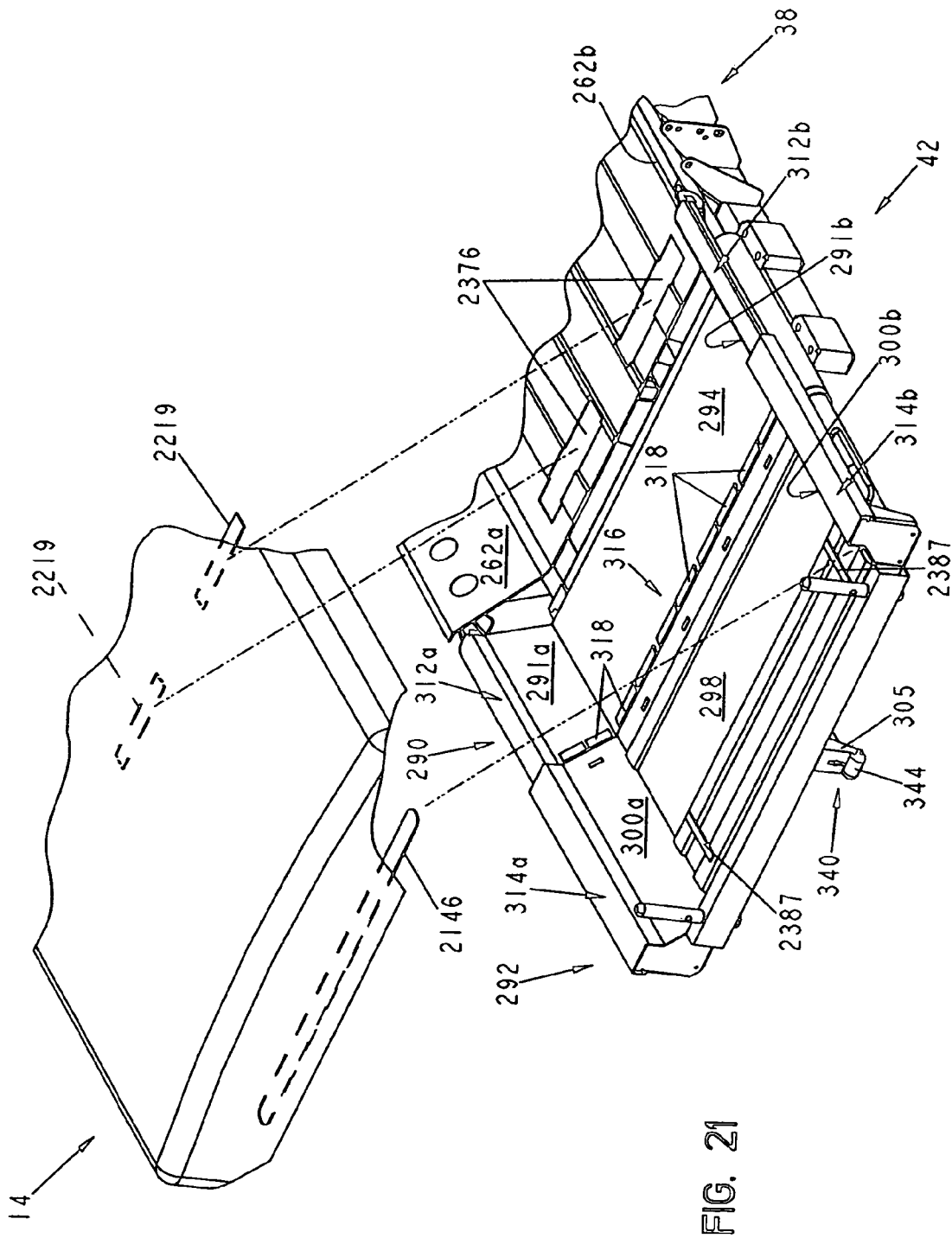
FIG. 21 is a perspective view of the leg section and a portion of the seat section of the deck and the mattress of FIG. 1, the leg section including a transverse recess positioned below retaining arms and the seat section including a pair of transverse recesses, the mattress being shown spaced apart from the deck and configured to be coupled to the retaining arms of the leg section with a leg section anchor and to the recesses of the seat section with seat section anchors.

Referring to FIGS. 16 and 21, first leg section member 290 includes a generally flat floor or wall 294 and angled side walls 291a, 291b. Second leg section member 292 includes a generally flat floor or wall 298 and angled side walls 300a, 300b. Floor 298 and side walls 300a, 300b of second leg section member 292 are configured to overlay floor 294 and side walls 291a, 291b of first leg section member 290. As such, second leg section member 292 is configured to slide over first leg section member 290 as leg section 42 is translated between an extended position (FIG. 20) and a retracted position (FIG. 18), or between a retracted position (FIG. 18) and an extended position (FIG. 20). Alternatively, the first leg section member 290 is configured to slide over the second leg section member 292 as the leg section 42 is translated between an extended position and a retracted position, or between a retracted position and an extended position.

Referring further to FIGS. 18 and 20, second leg section member 292 is translated relative to first leg section member 290 by actuator 48f. A first end 302 of actuator 48f is coupled to first leg section member 290 and a second end 304 of actuator 48f is coupled to second leg section member 292. In the illustrated embodiment, first end 302 of actuator 48f is coupled to a bracket 303 of first leg section member 290. Similarly, second end 304 of actuator 48f is coupled to a bracket 305 of second leg section member 292. To extend second leg section member 292 relative to first leg section member 290, cylinder rod 172f of actuator 48f is extended. To retract second leg section member 292 relative to first leg section member 290, cylinder rod 172f of actuator 48f is retracted. In the preferred embodiment, actuator 48f is an electric actuator, such as a Linak actuator, and is controlled by control system 44 as described herein. In alternative embodiments the actuator 48f is a mechanical actuator, a pneumatic actuator, a hydraulic actuator, a link system or other suitable means to move the second leg section member 292 relative to the first leg section member 290.

First leg section member 290 and second leg section member 292 are maintained in longitudinal alignment at least in part by guide members 306a, 306b. Illustratively, guide member 306a, 306b are telescoping tubes that extend and retract in a linear fashion as the first and second leg section members 290 and 292 move relative to each other. As shown in FIG. 20, a first end 308 of guide members 306 are coupled to first leg section member 290 and a second end 310 of guide members 306 are coupled to second leg section member 292. As such as actuator 48f extends or retracts, guide members 306 are configured to extend or retract opposite sides of second leg section member 292 at the same rate, thereby preventing the second leg section 292 and the first leg section 290 from binding. In alternative embodiments, the guide members may comprise slide blocks and guide channels, interlocking members, rollers and associated races, or other suitable guiding means.

Referring to FIGS. 16 and 21, second leg section member 292 is further guided relative to first leg section member 290 by operably coupled interlocking portions 312a and 314a of angled walls 291 and 300a, respectively, and by operably coupled interlocking portions 312b and 314b of angled walls 293 and 300b, respectively.

Referring further to FIGS. 16 and 21, floor 294 of first leg section member 290 and floor 298 of second leg section member 292 are separated by a separator 316. Separator 316 is made of a material, such as plastic, that assists in the movement of second leg section member 292 relative to first leg section member 290. In the illustrated embodiment, separator 316 includes a plurality of flexible finger members 318 which are coupled to second leg section member 292 and contact first leg section member 290. Fingers 318 are connected to second leg section member 292 to maintain the position of fingers 318 at the interface between first leg section member 290 and second leg section member 292. In alternative embodiments, separator 316 may comprise a strip attached to the end of the second leg section member 292, a series of rollers, or other means to facilitate the sliding of the second leg section member 292 relative to the first leg section member 290.

In alternative embodiments other suitable extendable foot sections 42 may be used. Illustrative suitable foot sections include the patient supports and corresponding foot sections described in U.S. Pat. No. 6,212,714 issued Apr. 10, 2001 to Allen et al., the disclosure of which is expressly incorporated by reference herein, and U.S. Pat. No. 6,163,903 issued Dec. 26, 2000 to Weismiller et al., the disclosure of which is expressly incorporated by reference herein.

As previously mentioned, leg section 42 of deck 26 is adjustable in length so that it can be moved from a retracted position to an extended position. Preferably, the length of leg section 42 is adjusted depending upon the height of the patient positioned on mattress 14 so that the patient's foot is positioned adjacent to footboard 18, shown in FIG. 1. For example, leg section 42 is extended to position the heels of a tall patient adjacent to footboard 18. Leg section 42 is retracted to position the heels of a shorter patient adjacent to footboard 18.

Also illustratively, mattress 14 is configured to be extended and retracted with leg section 42 as discussed in more detail herein. As such, the heel of the patient may be maintained over a given section of mattress 14, such as heel pressure relief member 2154 (FIGS. 93-95) which is configured to provide heel-pressure relief.

According one embodiment of the present disclosure, the length of leg section 42 corresponds to the position of head section 38. For example, if head section 38 is raised to the titled position as shown in FIG. 21, leg section 42 of deck 26 is controlled by control system 44 to automatically extend by a given distance. If head section 38 is lowered, leg section 42 is controlled by control system 44 to automatically retract to its pre-extended position. More particularly, control system 44 coordinates movement of head section 38 and leg section 42 by simultaneously controlling actuators 48c and 48f. By corresponding the extension and retraction of leg section 42 with the movement of head section 38, the patient's foot is maintained above heel pressure relief member 2154 of mattress 14. Furthermore, if footboard 18 is used as a foot prop, the patient's foot is maintained at a steady distance relative to footboard 18 during raising and lowering of head section 38.

Preferably, the degree of automatic extension of leg section 42 is a function of the angle of head section 38. The further up head section 38 is raised from a generally linear relationship with seat section 40, the more leg section 42 is extended so that heel pressure relief member 2154 is continuously positioned under the patient's heel throughout the range of motion of head section 38.

Mattress Deck Articulation

Figure 22:
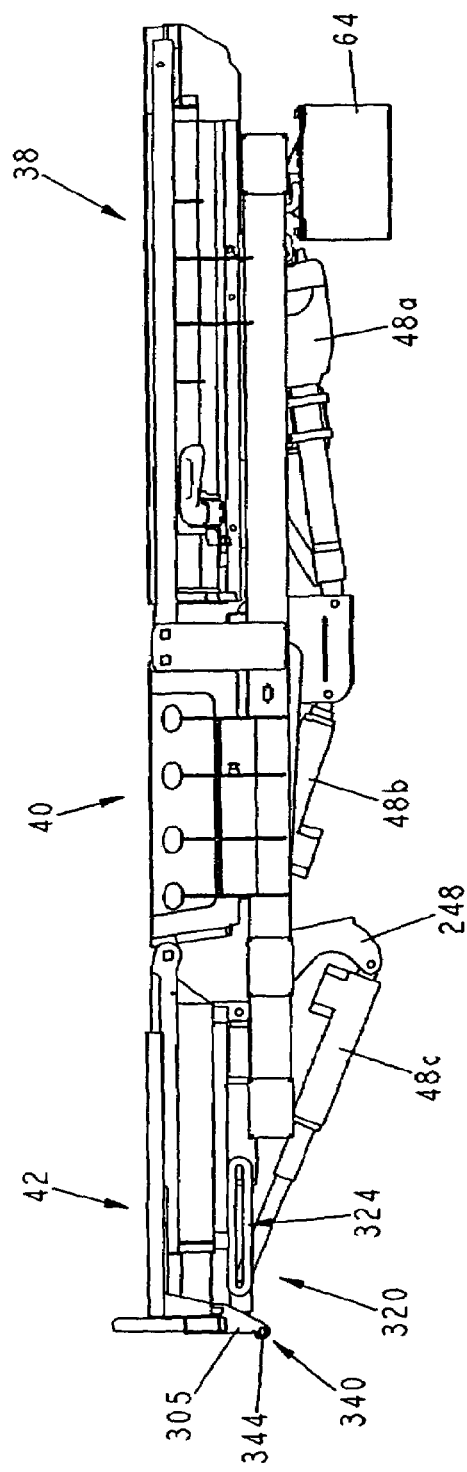
FIG. 22 is a side view of the deck and the weigh frame of the patient support of FIG. 1, showing the head, seat and leg sections of the deck in a linear relationship or bed configuration.

As stated previously, patient support 10 is positionable in a plurality of positions. Referring to FIGS. 1 and 3 and 22, head section 38, seat section 40 and leg section 42 are in a linear relationship relative to each other. In one illustrative embodiment, head section 38, seat section 40 and leg section 42 are placed in the linear relationship by control system 44 in response to a single button being depressed on one of controllers 50, 52, 54.

Referring to FIG. 4, head section 38 is rotated about pivot 232 such that second end 235 is raised relative to first end 231. Second end 235 is raised by control system 44 controlling actuator 48c to further extend cylinder 172 of actuator 48c. In one illustrative embodiment, head section 38 is raised by control system 44 in response a first button being depressed on one of controllers 50, 52, 54 and lowered by control system 44 in response to a second button being depressed on same controller 50, 52, 54.

Also, shown in FIG. 4, seat section 40 is rotated about pivot 237 such that second end 239 is raised relative to first end. Second end 239 is raised by control system 44 controlling actuator 48d to further extend cylinder 172d of actuator 48d. Leg section 42, in FIG. 4, is raised due to the rotation of seat section 40 and the coupling of leg section 42 to seat section 40, but leg section 42 remains in a generally horizontal position due to the rotation of actuator 48e. In one illustrative embodiment, seat section 40 is raised by control system 44 in response to a first button being depressed on same and lowered by control system 44 in response to a second button being depressed on the same controller 50, 52, 54.

Referring to FIG. 5, head section 38 and seat section 40 are in generally the same position as in FIG. 4. However, second end 250 of leg section 42 has been lowered such that second end 250 is lower relative to first end 244. Second end 250 is lowered relative to first end 244 by control system 44 controlling actuator 48e to further retract cylinder 172e of actuator 48e. In one illustrative embodiment, head section 38, seat section 40 and leg section 42 are placed in the configuration shown in FIG. 5 by control system 44 in response to a chair button on one of controllers 50, 52, 54 being depressed. In an alternate embodiment, the leg section 42 is raised by control system 44 in response to a leg section up button being depressed on one of the controllers 50, 52, 54, and lowered by control system 44 in response to a leg section down button being depressed on the same controller 50, 52, 54.

Referring further to FIGS. 4, 5, 18 and 20, the weight of actuator 48e and leg section 42 maintains a first end 320 of actuator 48e adjacent a first end 322 of slot 324 in bracket 246 as cylinder 172e of actuator 48e is retracted, as opposed to first end 320 of actuator 48e traveling towards a second end 326 of slot 324. The configuration of deck in FIG. 5 is an illustrative first chair-like position.

Further, leg section actuator 48e is lengthened by control system 44 when seat section 40 is lowered from the elevated position shown in FIG. 5. Leg section actuator 48e is lengthened to prevent any interference between leg section 42 and seat section 40.

Figure 6:
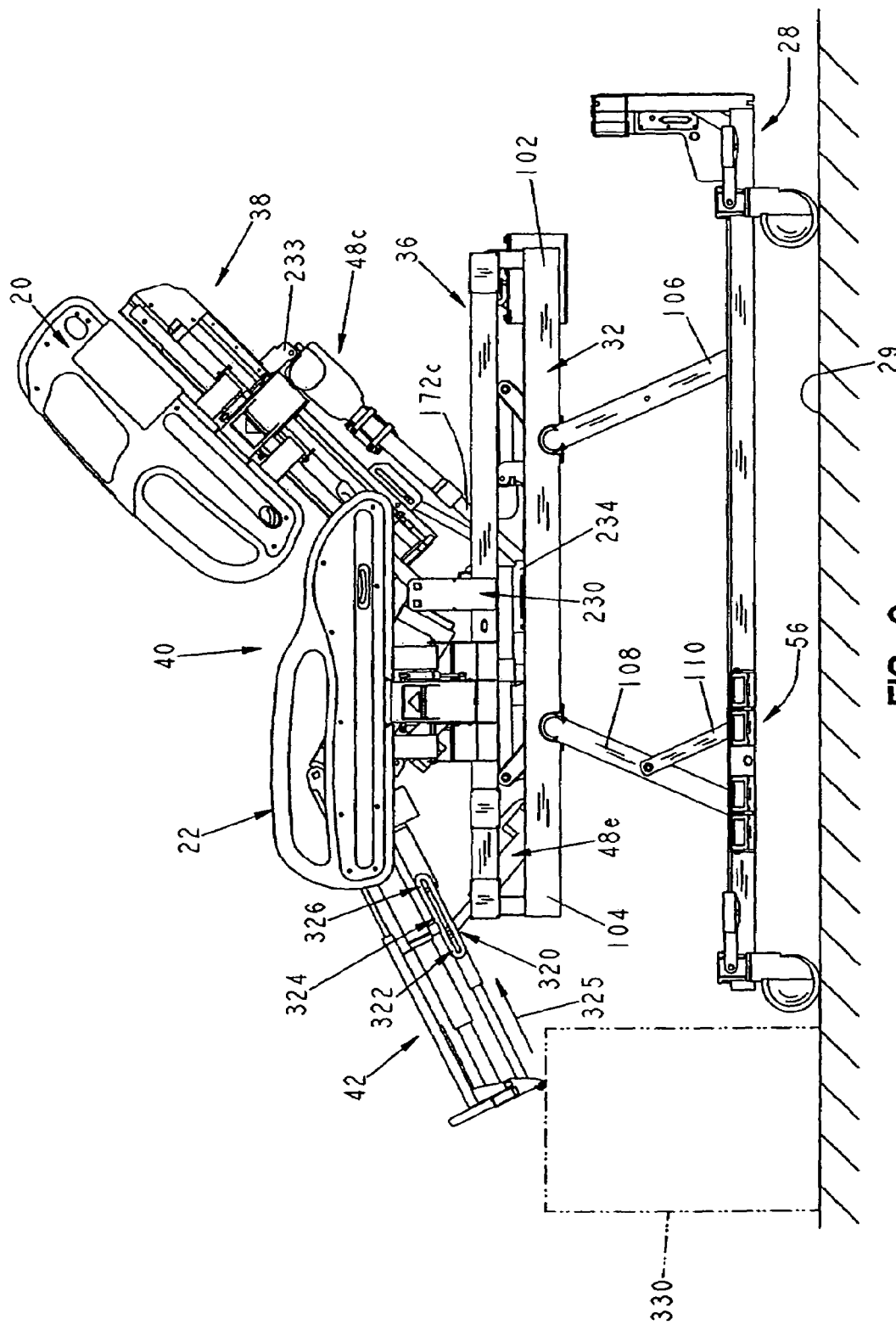
FIG. 6 is a side elevation view generally similar to FIG. 5, showing the leg section of the deck in an extended position and the leg section being lowered by the leg actuator, the leg section not being fully lowered due to contact with an obstruction and the leg section and the obstruction prevented from damage by the leg section actuator traveling up an elongated slot provided in a coupling bracket between the leg section and the leg actuator.

FIG. 6 illustrates leg section 42 not being movable between the position of leg section 42 in FIG. 4 and the position of leg section in FIG. 5, due to an obstruction 330 impeding the movement of leg section 42. Example obstructions include a cart, a wheelchair, a table, a trashcan or any other item. As shown in FIG. 6, when leg section 42 encounters obstruction 330 first end 320 of actuator 48e travels along elongated slot 324 in the direction of arrow 325 toward second end 326 of slot 324. As such, slot 324 serves as a safety device to avoid crushing obstruction 330 and to avoid destruction of actuator 48e and damage to patient support 10.

The length of slot 324 is selected to allow actuator 48e to move from a fully extended position to a fully retracted position while first end 320 of actuator 48e travels in slot 324. As such, actuator 48e will encounter the end of its range of motion or travel (fully retracted) before or coincident with first end 320 of actuator 48e reaching second end 326 of slot 324. Therefore, leg section 42 will not crush or otherwise damage obstruction 330 due to the continued pressure applied by actuator 48e, actuator 48e will not be damaged due to a larger than expected load being placed on actuator 48e, and patient support 10 will not be damaged.

Alternative methods may be used to keep the leg section 42 from damaging the obstruction and to keep from damaging the actuator 48e. A first example is to monitor the load placed on the actuator 48e with the control system 44 and to disengage or reverse the motion of the actuator 48e in response to a larger than expected load for retracting the actuator 48e. A second example is to place a pressure sensor along the bottom of the leg section 42 and to disengage the actuator 48e when a higher than expected pressure is detected. An illustrative sensor may be the obstacle detection system of the present invention disclosed herein. Other known safety systems may also be used.

In alternative embodiments, the elongated slot 324 is located on the bracket 248 attached to the weigh frame 36 and the actuator 48e is pivotably coupled to the leg section 42 and slidably and pivotably coupled to the weigh frame 36. In a further alternative embodiment, the elongated slot 324 is located on the joint between the leg section 42 and the seat section 40 such that the leg section 42 and the seat section 40 are pivotably and slidably coupled, the leg section 42 and the actuator 48e are pivotably coupled and the actuator 48e and the weigh frame 36 are pivotably coupled. In still further alternative embodiments, the elongated slot 324 feature is incorporated into the configuration for the head section 38, is incorporated into the configuration for the seat section 40, or is incorporated into the lifting arms 34 configuration.

Referring to FIG. 10, a second chair-like configuration of patient support 10 is shown. Head section 38, seat section 40 and leg section 42 of deck 26 are generally oriented relative to intermediate frame 32 as shown in FIG. 5. However, deck support 24 is positioned generally in a Reverse Trendelenburg position, wherein foot end 104 of intermediate frame 32 is lower than head end 102 of intermediate frame 32. Deck support 24 is placed in the second chair-like position by retracting actuator 48b, shown in FIG. 2, and thus lowering foot links 108. In one illustrative embodiment, patient support 10 is placed in the configuration shown in FIG. 10 by control system 44 in response to a first button being depressed on one of controllers 50, 52, 54 and in response to a second button being depressed on one of controllers 50, 52, 54. In an alternative embodiment, the patient support is placed in the configuration shown in FIG. 10 in response to a button being depressed on the controllers. In a further alternate embodiment, the patient support 10 is placed in the configuration of FIG. 5 in response to a first chair button on one of controllers 50, 52, 54 being depressed and is placed in the configuration of FIG. 10 in response to a second chair button on the same controller 50, 52, 54 being depressed.

A further safety device 340 is shown in FIG. 17 and is coupled to leg section 42. Safety device 340 includes bracket 305 rigidly coupled to leg section 42 and a roller 344 rotatably coupled to bracket 305. Safety device 340 similar to slot 324 protects patient support 10 from damage and also protects an obstruction, such as obstruction 330 or the floor 29 (FIG. 6), from damage. Alternatively, the roller 344 of the safety device 340 is directly coupled to or integrated with the leg section 42, thereby eliminating the bracket 305.

In FIG. 11, patient support 10 is transitioned to the second-chair like configuration, however either due to the fact that leg section 42 is extended, discussed in more detail herein, or that deck support 24 is somewhat lowered, second end 250 of leg section 42 contacts the floor and could potentially be damaged prior to patient support 10 fully transitioning to the second chair like position. As shown in FIG. 11, safety device 340 is configured to translate second end 250 of leg section 42 in a direction 341 while leg section 42 rotates in a direction 343 to avoid damage to leg section 42.

As second end 250 of leg section 42 is translated in direction 341 and leg section 42 is rotated in direction 343 relative to seat section, first end 320 of actuator 48e is traveling within slot 324. As discussed earlier in connection with FIG. 6, slot 324 allows the actuator 48e to continue to retract without further lowering leg section 42. However, in the current case, wherein patient support 10 is transitioning from the first chair-like configuration of FIG. 5 to the second chair-like configuration of FIG. 10, actuator 48e is not retracting. In the current case of FIGS. 10 and 11, first end 320 of actuator 48e, a fixed link (since not retracting or extending), travels within slot 324 and thus leg section 42 rotates to avoid crushing the obstruction or causing damage to the patient support 10. As such, safety device 340 functions in concert with slot 324. It should be appreciated that roller 344 reduces the friction between the floor 29 and leg section 42, thereby allowing leg section 42 to more easily rotate and translate.

Figure 12:
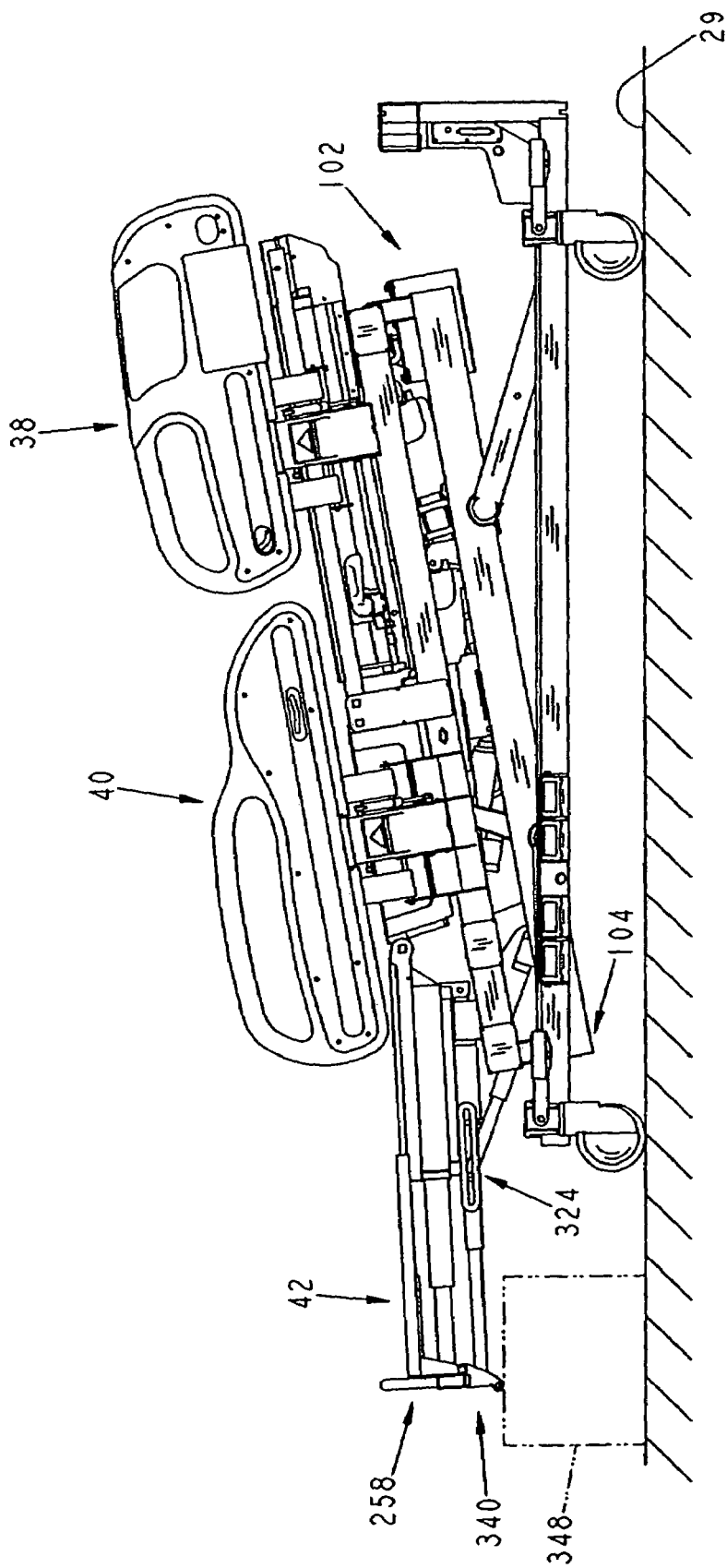
FIG. 12 is a side elevation view of the patient support of FIG. 1, showing the deck support in a Reverse Trendelenburg position, the head and seat sections of the deck in a generally linear relationship with the leg section in an extended position and slightly angled relative to the head and seat sections due to contact with an obstruction by the roller coupled to the leg section and the leg section and the obstruction prevented from damage by the roller translating the leg section relative to the obstruction, the leg section rotating relative to the seat section and by the leg section actuator traveling up the elongated slot provided in the coupling bracket between the leg section and the leg actuator.

A further instance wherein safety device 340 protects both leg section 42 and an obstruction from damage is when deck 26 is in a linear configuration with leg section 42 in an extended position and the patient support 10 is moved to a Reverse Trendelenburg position from a low position. As shown in FIG. 12, patient support 10 is transitioning from a low position, wherein both actuators 48a and 48b, shown in FIG. 2, are generally retracted, to a Reverse Trendelenburg position, wherein actuator 48b remains generally retracted and actuator 48a is generally extended to raise head end 102 of intermediate frame 32 relative to foot end 104. In such a configuration, the second end 250 of leg section 42 could either contact the floor 29 or an obstruction 348, such as a foot. In either case, safety device 340 and safety device 324 cooperate to rotate leg section 42 relative to seat section 40 and thereby reduce the likelihood of damage to both leg section 42 and the obstruction 348.

CPR Configuration

Often it is required to configure patient support 10 in a CPR configuration which is tailored to assist a caregiver in providing CPR to the patient supported on patient support 10. In one illustrative example, a CPR configuration is defined by placing the head, seat and leg sections 38, 40, 42 in a generally linear relationship and to inflate an upper bladder assembly 2122 to an elevated or a maximum pressure in the manner further described herein. In a further illustrative CPR configuration, the head, seat and leg sections 38, 40, 42 are placed in a generally linear relationship, the upper bladder assembly 2122 is inflated to an elevated or a maximum pressure and decking support 24 is oriented such that head end 102 is lower relative to foot end 104, generally a Trendelenburg position as shown in FIG. 9.

Patient support 10 may be placed in the preferred CPR configuration by providing an indication to control system 44 which in turn controls actuators 48c, 48d, 48e to place head, seat, and leg sections 38, 40, 42 in a generally linear relationship, controls pump 64 to inflate upper bladder assembly 2122 to the desired pressure, and controls actuators 48a and 48b of deck support 24 to lower head end 102 relative to foot end 104. The details of control system 44 and how control system 44 controls actuators 48a-f and pump 64 are further described herein.

Illustratively, patient support 10 is placed in the preferred CPR configuration by manually lowering head section 38 to a lowered position and providing an indication to control system 44 which, in turn, controls actuators 48d and 48e to place head, seat and leg sections 38, 40, 42 in a linear relationship, controls pump 64 to inflate upper bladder assembly 2122 to the desired pressure, and controls actuators 48a and 48b of deck support 24 to lower head end 102 relative to foot end 104. Referring to FIG. 18, both the manual lowering of head section 38 and the providing of an indication to control system 44 are initiated by the actuation of a first or user input 350 from a first state corresponding to an off or inactive condition to a second state corresponding to an on or active condition and are continued as long as first input 350 remains in the on or active condition.

Figure 23:
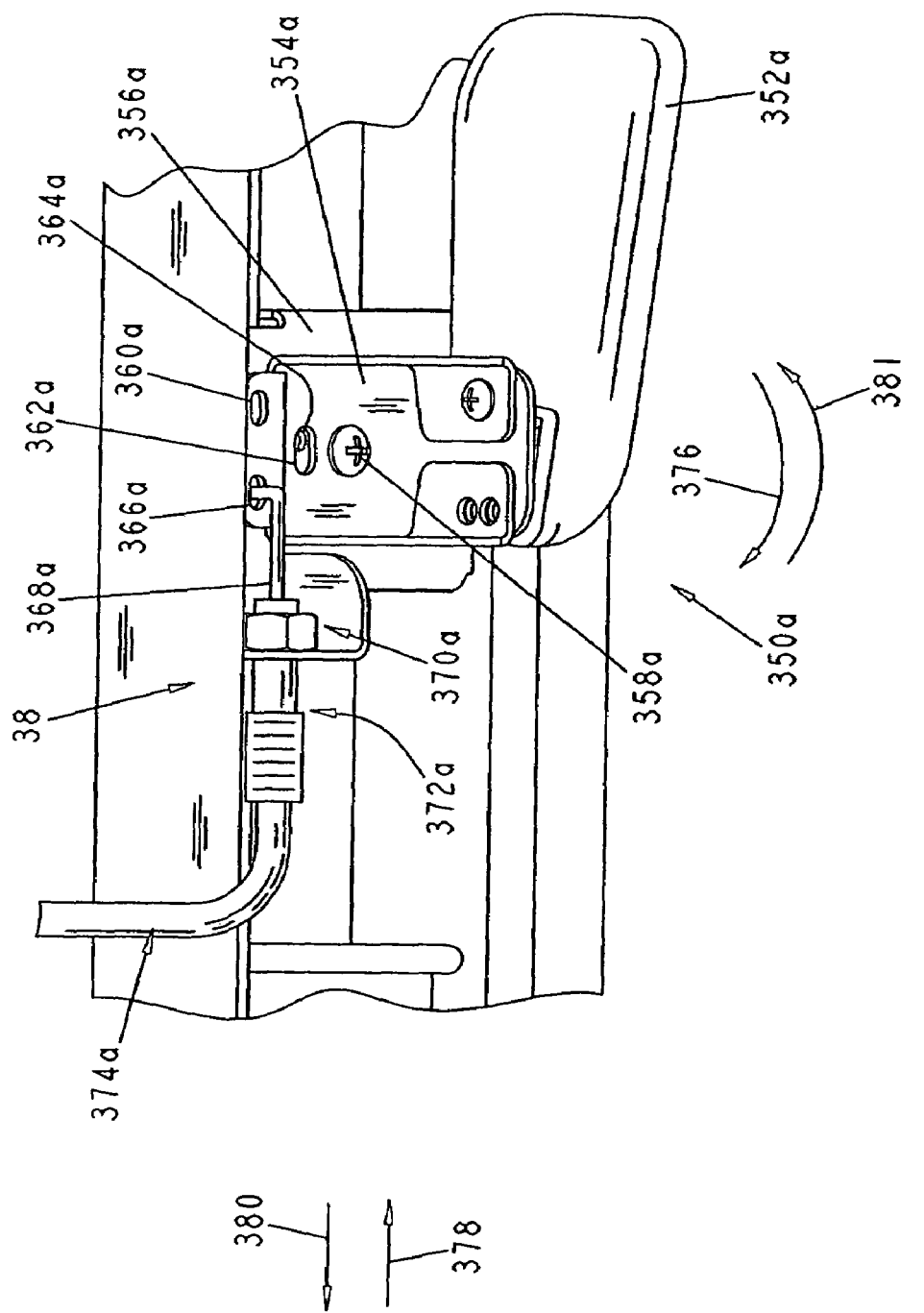
FIG. 23 is a detail view of a portion of the head section of the deck of the patient support of FIG. 1 showing a portion of a CPR system comprising a handle and handle bracket rotatably coupled to the deck and further coupled to a cable which is coupled to the actuator assembly of FIGS. 27 and 28.
Figure 24:
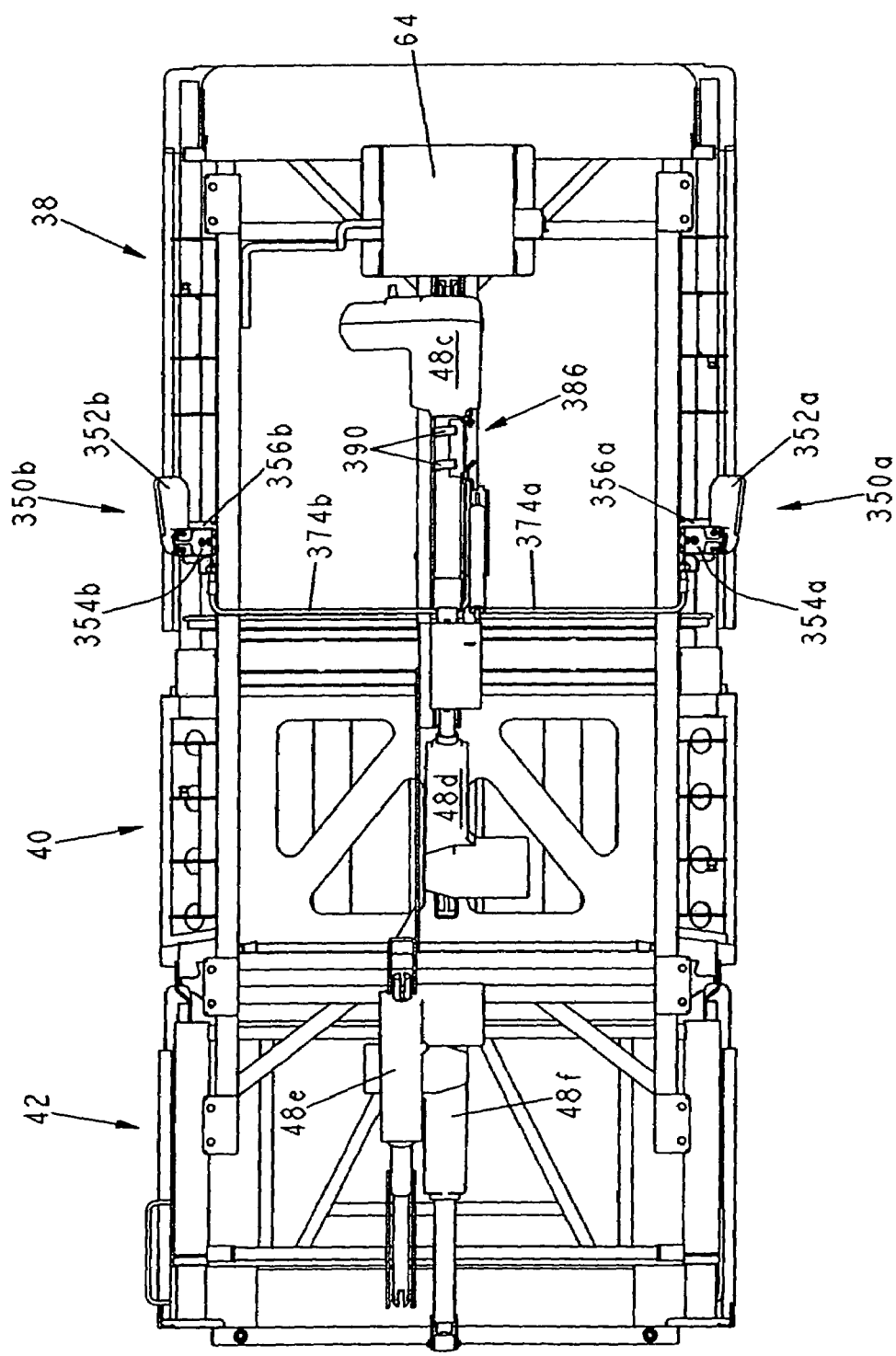
FIG. 24 is a bottom view of the deck and the weigh frame of FIG. 22.

Referring to FIGS. 13, 16, 18, 23 and 24, first input 350 includes a handle 352 positioned adjacent a longitudinal side of head section 38. As shown in FIG. 24, a pair of first inputs 350 are provided, each first input member 350 being supported adjacent opposing right or left longitudinal sides of the head section 38. In the following description, the first inputs 350 and related components adjacent the left and right sides will be specifically identified by the respective reference number followed by reference letter "a" or "b". It should be appreciated that both first inputs 350a and 350b have identical components and are mirror images of each other. Further, each first input 350a and 350b is configured to function independently of the other first input 350a and 350b. Each handle 352 is coupled to a handle bracket 354 which is rotatably coupled to a bracket 356 which is rigidly coupled to head section 38. Handle bracket 354 is rotatably coupled to bracket 356 by a first fastener 358. The degree of rotation of handle bracket 354 relative to bracket 356 is limited by a stop, illustratively fastener 360 (FIG. 23), which is received in an elongated slot 362 in handle bracket 354.

In one illustrative embodiment, handle 352 includes an indicia 353, shown in FIG. 16, that indicates that the handle corresponds to a CPR condition. Illustrative indicia includes wording such as "CPR" or other text, color-coding, embossed characters or combinations thereof. In alternative embodiments, the indicia is a part of a pedal, a button, a switch, a lever arm, or other suitable actuatable members Referring further to FIG. 23, each handle bracket 354 includes a flange 364 that is configured to couple a first end 366 of a cable 368. Bracket 356 includes a flange 370 configured to couple a first end 372 of a cable housing 374. Cable 368 is free to translate or move within cable housing 374. As such, as handle bracket 354 is rotated in direction 376 relative to bracket 356, cable 368 is extended from cable housing 374 generally in direction 378. As explained later, cable 368 biases in direction 380, in the absence of an external force applied to handle 352, thereby causing handle bracket 354 and handle 352 to rotate in direction 381, opposite direction 376.

Referring to FIGS. 24-28, a second end 382 of each cable 368 and a second end 384 of each cable housing 374 are coupled to an actuator assembly 386 which, in turn, is coupled to actuator 48c. Actuator assembly 386 includes a housing 388 coupled to cylinder rod 172 of actuator 48c by retainers 390, shown in FIGS. 24 and 25. Flange 392 extends from a top portion 394 of housing 388 and is configured to couple to second end 384 of each cable housing 374. A slide bracket 396 is slidably coupled to top portion 394 of housing 388. Slide bracket 396 receives second end 382 of each cable 368 in one of the plurality of slots 400 defined by a plurality of upwardly extending flanges 402 of slide bracket 396. A further flange 404 of slide bracket 396 is coupled to a release pin 406 of actuator 48c. As known in the art, release pin 406 of actuator 48c is configured to allow cylinder rod 172c of actuator 48c to freely move relative to cylinder body 170c, such that rod 172c can be freely extended from or retracted within cylinder body 170c.

Figure 26:
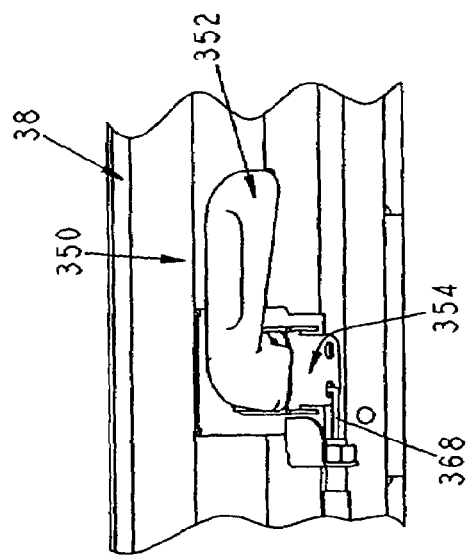
FIG. 26 is detail view generally similar to FIG. 23 with the fasteners which couple the handle bracket to the deck not shown.

Slide bracket 396 is coupled to each handle bracket 354 through cables 368. As such, the rotation of either handle 352a, 352b by a caregiver rotates respective handle bracket 354a, 354b which, in turn, translates first end 366a, 366b of cable 368a, 368b away from first end 372a, 372b of cable housing 374a, 374b, which translates second end 382a, 382b of cable 368a, 368b toward second end 384a, 384b of cable housing 374a, 374b in a direction 408 (FIG. 26). The translation of either cable 368a, 368b in direction 408 translates both slide bracket 396 and release pin 406 in direction 408. As such, while the caregiver keeps either handle 352a, 352b in its rotated position, cylinder rod 172c of actuator 48c is freely moveable relative to cylinder body 170c of actuator 48c and head section 38 may be manually lowered or raised.

As known in the art, release pin 406 is biased in direction 410 counter to direction 408. As release pin 406 moves in direction 410, cylinder rod 172c of actuator 48c is no longer freely movable relative to cylinder body 170 of actuator 48c. Therefore, when the caregiver releases both handles 352a, 352b release pin 406 due to its bias translates slide bracket 396 in direction 410 which in turn through respective cables 368a, 368b rotates handle bracket 354a, 354b and handle 352a, 352b in direction 381 (FIG. 23). As such, actuator 48c is once again actuatable by control system 44 instead of manually.

Figure 25:
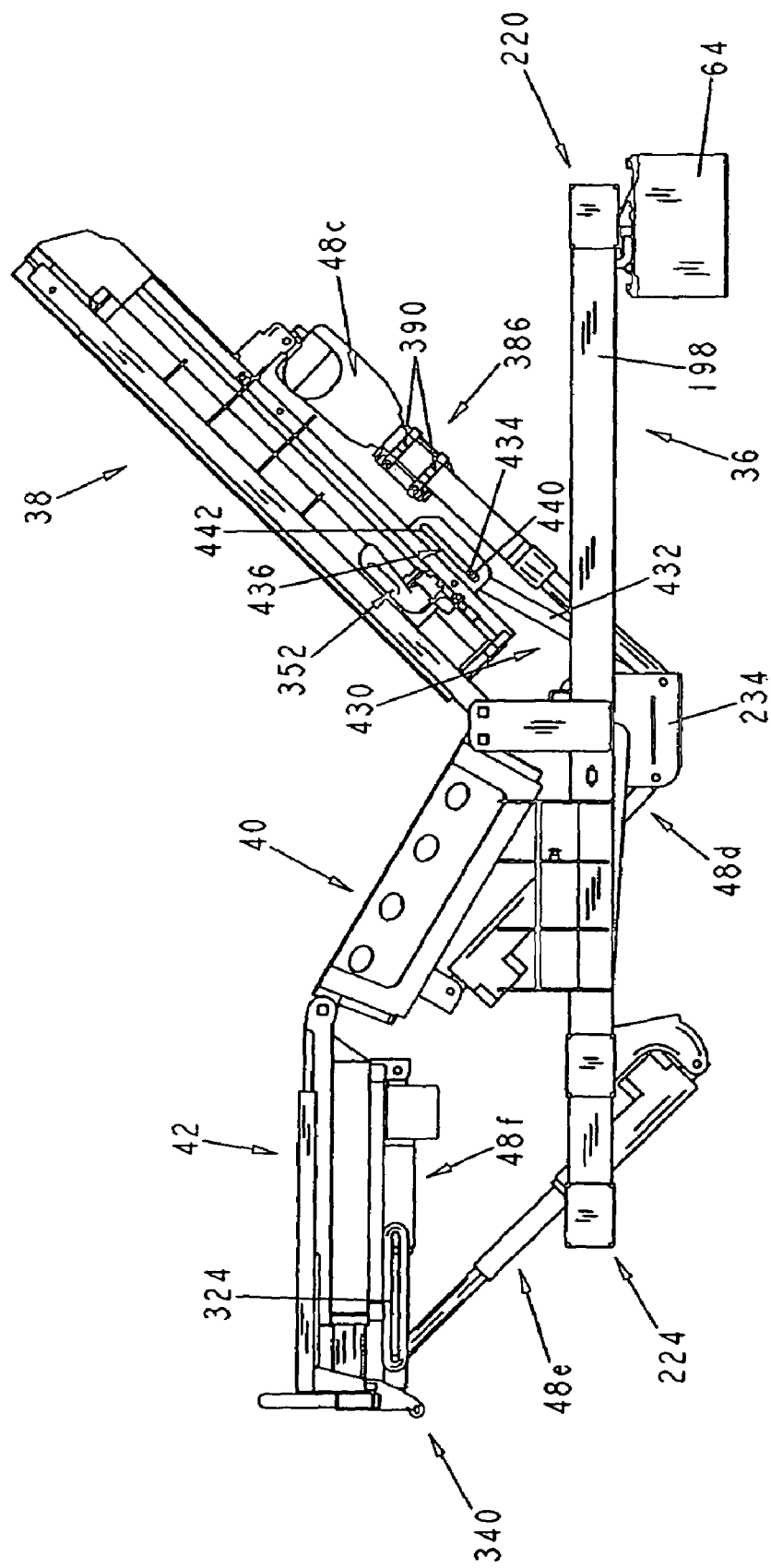
FIG. 25 is a side view of the deck and the weigh frame of the patient support of FIG. 1, showing the head section elevated, the seat section elevated and the leg section elevated and generally horizontal.

Referring to FIG. 25, as the caregiver manually lowers head section 38, a damper 430 is provided to reduce the rate at which head section 38 is lowered thereby ensuring that head section 38 does not abruptly move to the lowered position. Illustratively, damper 430 is a gas spring 432 which is pivotably coupled to weigh frame 36 and slidably and pivotably coupled to head section 38. A first end 434 of gas spring 432 is received in an elongated slot 436 of a bracket 438 which is rigidly coupled to head section 38. As head section 38 is lowered from the elevated position to an intermediate position, first end 434 of damper 430 travels from a first end 440 of slot 436, generally corresponding to the elevated position, towards a second end 442 of slot 436, generally corresponding to the intermediate position. In an illustrative embodiment, the intermediate position corresponds to a position approximately two-thirds of the travel distance from the elevated position to the lowered position.

Gas spring 432 has an uncompressed state generally corresponding to head section 38 being positioned between the intermediate position and the elevated position and a compressed state generally corresponding to head section 38 being positioned between the intermediate position and the lowered position. As head section 38 moves from the intermediate position to the lowered position, first end 434 of gas spring 432 stays proximate to second end 442 of slot 436 and a rod 444 of gas spring 432 is forced to slidably move into a housing 446 of gas spring 432 against the biasing force exerted by gas spring 432. In general, gas spring 432 prefers to be in the uncompressed state and resists movement to the compressed state. As such, gas spring 432 resists the movement of head section 38 from the intermediate position to the lowered position and thereby slows the rate of travel of head section 38 to the lowered position.

Gas spring 432 is of conventional design. In alternative embodiments, other types of dampers may be used. Example dampers include compressible foam, air bladders, compressible springs, and other suitable damping means.

Referring to FIG. 26, housing 388 further includes a second input or control 448 that is connected to control system 44. Illustratively, second input/CPR release 448 is a switch which is engaged by slide bracket 396. When switch 448 is closed, control system 44 receives an indication that switch 4148s been closed. Control system 44 proceeds to place the other portions of patient support 10 in the preferred CPR configuration. First, control system 44, if needed, actuates actuators 48d and 48e to place seat section 40 and leg section 42 in a linear relationship with head section 38 corresponding to head section 38 being in a lowered position. Second, control system 44, if needed, inflates upper bladder assembly 2122 to the desired pressure. Third, control system 44, if needed, actuates actuators 48a and 48b to lower head end 102 of decking support 24 relative to foot end 104 of decking support 24. If switch 448 remains closed, control system 44 preferably lowers head end 102 about 12° to about 15° relative to foot end 104.

If switch 448 is opened as a result of the caregiver releasing handle 352 before control system 44 completes the aforementioned tasks, control system 44 aborts the uncompleted tasks. For example, if the caregiver could release handle 352 when head end 102 is approximately 5° lower than foot end 104. It is understood that switch 448 may be located in a variety of locations and activated in a variety of ways. For instance, switch 448 may be placed on handle 352 or handle bracket 354. In alternate embodiments, the handle 352 is replaced by a foot pedal, a button, a switch, a lever arm or other suitable actuatable members.

Referring to FIG. 28, a second embodiment slide bracket 420 is shown. Slide bracket 420 is made from a plastic material and generally functions similar to slide bracket 396. Slide bracket 420 is slidably coupled to housing 388, is coupled to release pin 406, and is configured to engage switch 448. Slide bracket 420 is further coupled to second ends 3822, 382b of cable 368a, 368b.

Figure 30:
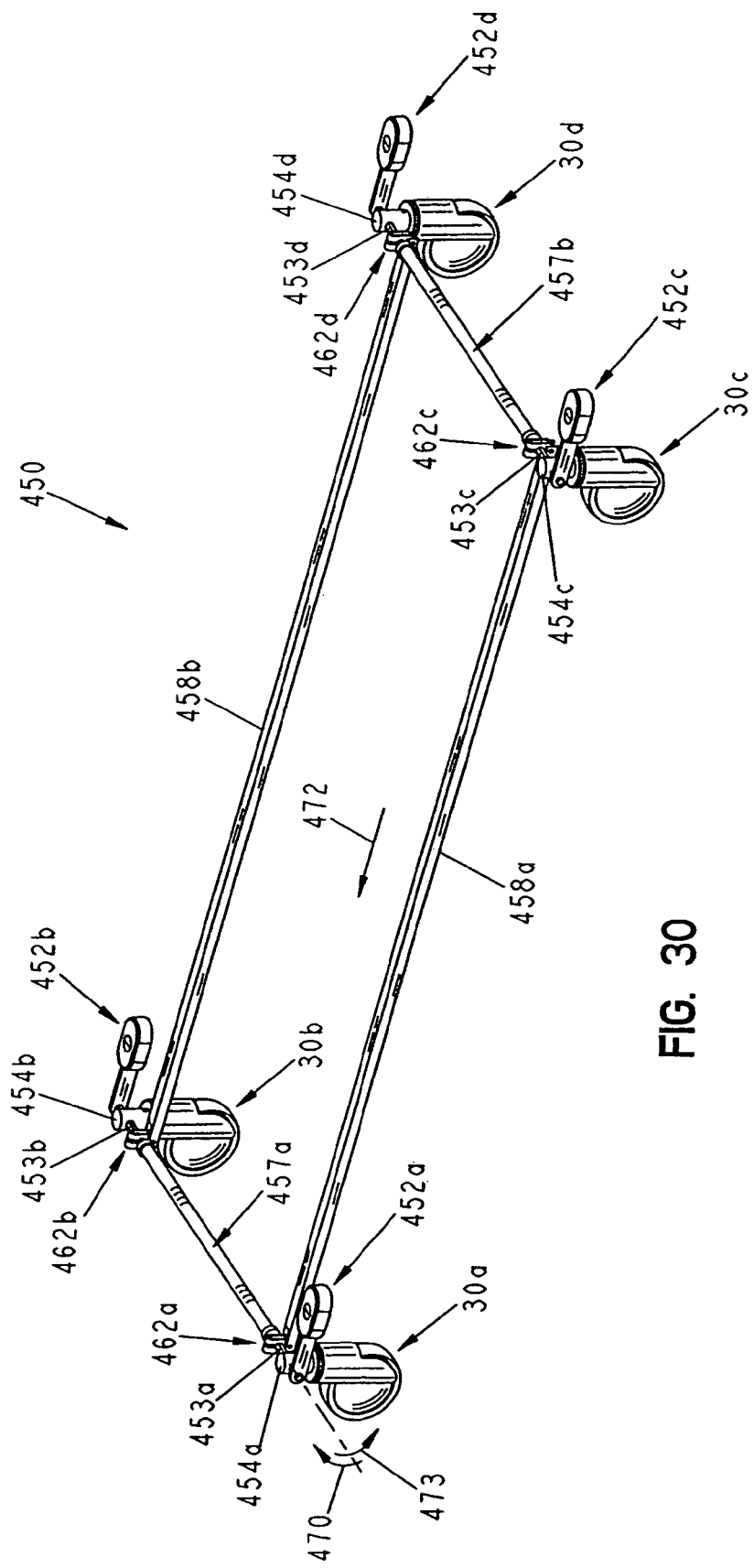
FIG. 30 is a perspective view of the caster braking system of the patient support of FIG. 1 showing four caster devices, a first pair of caster devices being interconnected by a first transverse rod, a second pair of caster devices being interconnected by a second transverse rod and the first and second pairs of caster devices being interconnected by a pair of longitudinal brake links.

Referring to FIG. 30, second end 382 of each cable 368 includes a retainer 421 which is received within a recess 422 on slide bracket 420. Illustratively, the retainer 421 may comprise a spherical member or a disk crimped on the second end 382 of cable 368. In order to enter recess 422, retainer 421 on second end 382 must pass by detent 424 which is configured to retain second end 382 in recess 422.

Caster Braking System

Referring to FIGS. 29-33, patient support 10 further includes a caster braking system 450. The caster braking system 450 interconnects each caster device 30a, 30b, 30c, 30d to provide simultaneous braking of casters devices 30a, 30b, 30c, 30d. Each caster device 30a, 30b, 30c, 30d is associated with a foot brake pedal 452a, 452b, 452c, 452d. To simultaneously brake all caster devices 30a, 30b, 30c, 30d, the caregiver steps on one of foot brake pedals 452 and caster braking system 450 locks all four caster devices 30a, 30b, 30c, 30d against rolling. In alternative embodiments the caster devices 30 are brake/steer caster devices opposed to simply brake caster devices.

Figure 32:
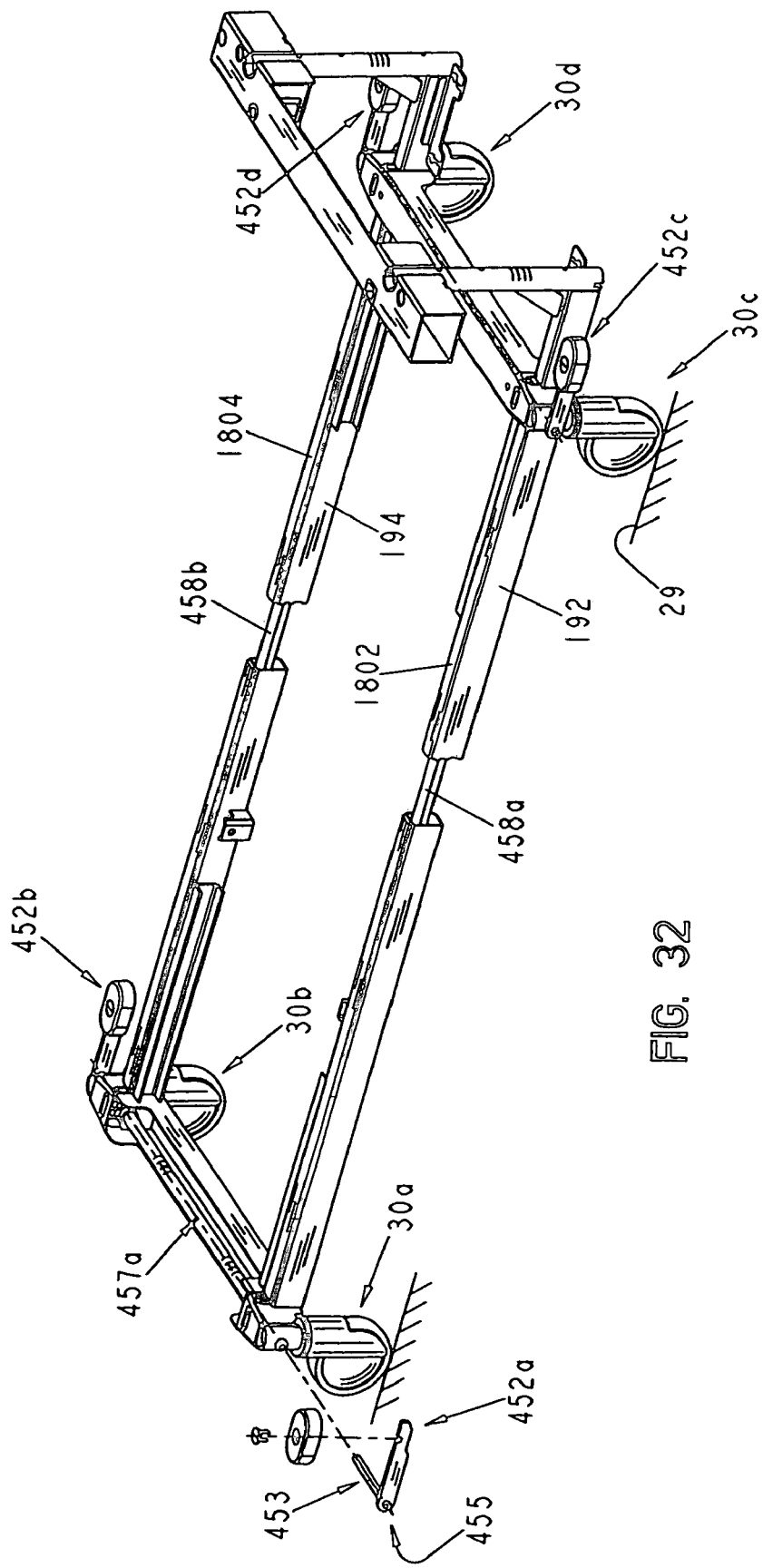
FIG. 32 is a perspective view of the base frame of the deck support of FIG. 2, showing a pedal and hexagonal rod of the caster braking system spaced apart from the corresponding caster device and showing first and second brake links which interconnect a first pair of caster devices and a second pair of caster devices, the first and second brake links being received within an interior of first and second longitudinal members of the base frame.

Each caster device 30 includes a braking mechanism (not shown) that is coupled to a caster-brake link, illustratively a faceted shaft such as hexagonal shaft 453, such that rotation of hexagonal shaft 453 engages the braking mechanism. As shown in FIG. 32, each hexagonal shaft 453 is received within a sleeve 454 of caster device 30 wherein shaft 453 is coupled to the braking mechanism. Additional description of a caster braking system similar to the caster braking system 450 of the present disclosure including the illustrative braking mechanism is provided in U.S. patent application Ser. No. 09/263, 039, filed Mar. 5, 1999, to Mobley et al., entitled Caster and Braking System, and issued as U.S. Pat. No. 6,321,878 on Nov. 27, 2001, the disclosure of which is expressly incorporated by reference herein. According to alternative embodiments of the present disclosure other configurations of caster braking and/or steering systems with or without simultaneous locking functions are provided for use with the foot brake pedal 452 and caster-brake link of the present disclosure.

Figure 31:
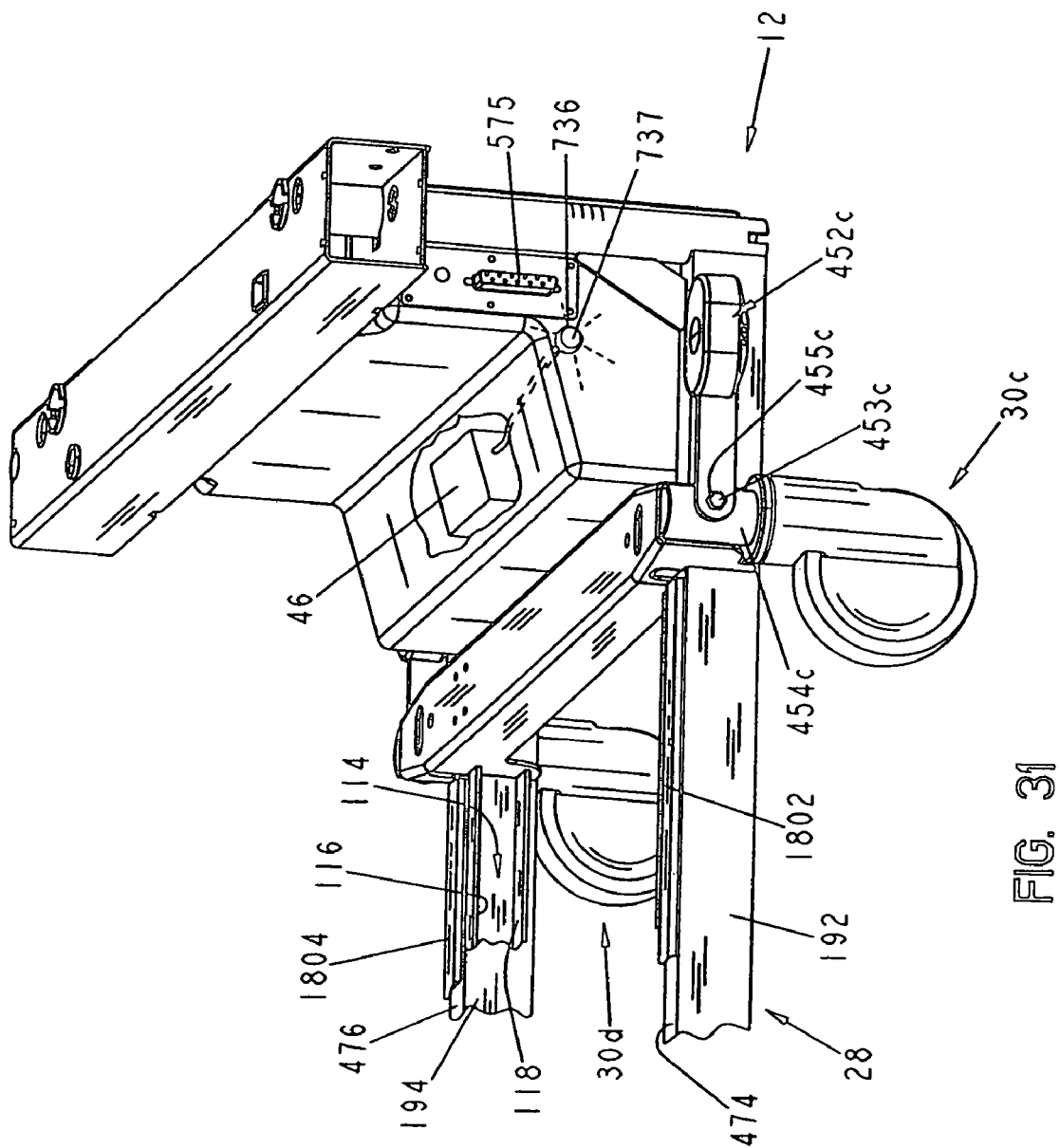
FIG. 31 is a perspective view of a portion of the deck support of FIG. 2 showing a first pair of caster devices, a battery housing, a battery enable switch coupled to the battery housing and a communication link coupled to the battery housing.

As shown in FIGS. 29 and 31, a first end 455 of hexagonal shaft 453 is coupled to foot pedal 452. A second end 456 of hexagonal shaft 453 is coupled to a rod 457. Rods 457a, 457b interconnect transversely spaced caster pairs 30a, 30b and 30c, 30d, respectively. Rod 457a is coupled to hexagonal shafts 453a and 453b and rod 457 is coupled to hexagonal shafts 453c and 453d. As such, the braking of either caster device 30a or caster device 30b results in the braking of the other caster device of caster device 30a and caster device 30b. Similarly, the braking of either caster device 30c or caster device 30d results in the braking of the other caster device 30c or caster device 30d.

Further, transversely spaced caster device pairs 30a, 30b and 30c, 30d are interconnected by a longitudinally extending brake links 458a, 458b, respectively. Brake links 458a, 458b are configured to interact with the caster device pairs 30a, 30b, 30c, 30d such that the braking of any one caster device 30a, 30b, 30c, 30d simultaneously brakes the remaining caster devices 30a, 30b, 30c, 30d.

As shown in FIGS. 29 and 32, a first end 460 of brake link 458a is pivotably coupled to a bracket 462a by a fastener 464. Illustratively bracket 462 is a U-shaped bracket having a first leg 466 and a second leg 468. The lower portions of legs 466, 468 are configured to pivotably couple to brake link 458. Bracket 462 further includes a generally hexagonal opening for coupling bracket 462 to hexagonal shaft 453.

In operation, a caregiver depresses one of the foot pedals 452, such as foot pedal 452a, to simultaneously brake all four caster devices 30a, 30b, 30c, 30d. Illustratively, foot pedals 452 are shown on a first side of each caster device 30. Alternatively, the foot pedals 452 may be located on the other side of the caster devices 30 or each caster device 30 could have more than a single foot pedal 452 associated with the caster device 30. The depressed foot pedal 452a causes the rotation of hexagonal shaft 453a in direction 470 as illustrated in FIG. 29.

The rotating of hexagonal shaft 453a in turn engages the braking mechanism (not shown) of caster device 30a, rotates rod 457a in direction 470 and rotates bracket 462a in direction 470. The rotation of rod 457a further rotates hexagonal shaft 453a in direction 470 thereby engaging the brake mechanism of caster device 30b. The rotation of bracket 462a translates brake link 458a in a direction 472. The translation of brake link 458a in direction 472 results in the rotation of bracket 462c in direction 470 which, in turn, rotates hexagonal shaft 453c in direction 470, thereby engaging the brake mechanism of caster device 30c. The braking mechanism of caster device 30d is engaged by the rotation of hexagonal shaft 453d either through the translation of brake link 458b similar to the translation of brake link 458a and/or through the rotation of rod 457b similar to the rotation of rod 457a. In alternative embodiments, the caster braking system 450 includes only two transverse rods 457 and a single brake link 458 or two brake links 458 and a single transverse rod 457.

In order to unlock the caster braking system 450 of the present invention, one of the four pedals 452, such as pedal 452a is rotated in a direction 473 counter to the direction 470, thereby disengaging the braking mechanism of caster device 30a. The braking devices of casters 30b, 30c, 30d are disengaged in a manner similar to how they are engaged through rods 457a, 457b and brake links 458a, 458b.

Figure 33:
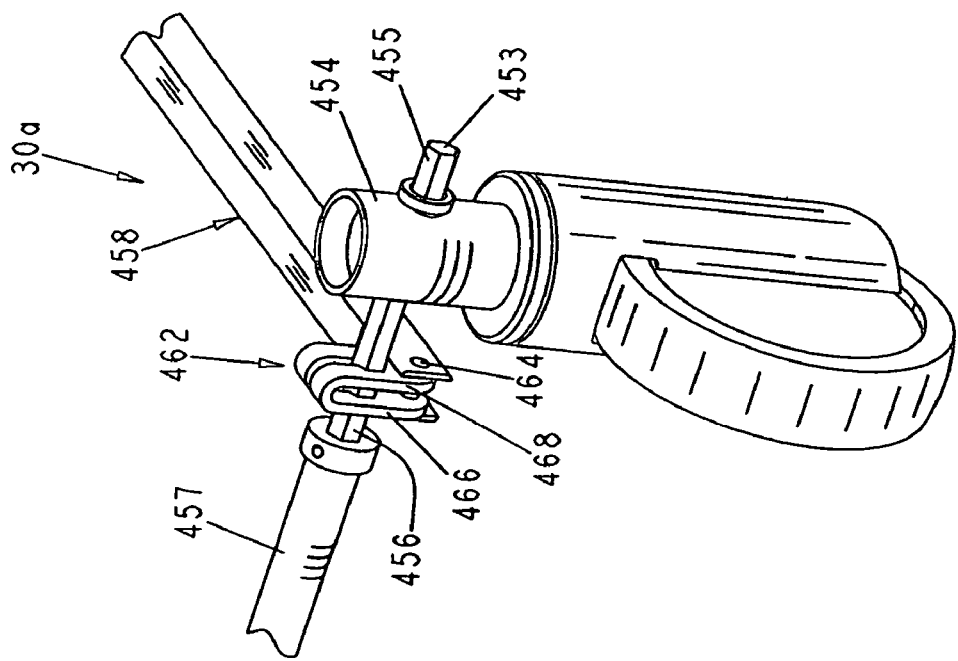
FIG. 33 is a perspective view of one of the caster devices of FIG. 32 coupled to a first transverse rod and the first longitudinal brake link.

As stated previously, it is advantageous to lower intermediate frame 32 as low as possible to the floor to aid egress from and ingress to patient support 10 and to prevent injury in case of accidental fall from patient support 10. The configuration of caster braking system 450 has a low profile which provides additional clearance for deck 26, siderails 20, 22 and other patient support components as deck support 24 is lowered. As such, intermediate frame 32 can be further lowered. As shown in FIG. 31, brake links 458a, 458b of caster brake system 450 extends through longitudinal frame member 192 and brake link 458b extends through longitudinal frame member 194. As shown in FIG. 33, brake links 458 are positioned lower than hexagonal rods 453 such that a top surface 474, 476 of longitudinal frame members 192, 194 can be lower to the floor 29. Therefore, greater clearance is provided and intermediate frame 32 can be further lowered relative to base frame 28.

Control System

Figure 35:
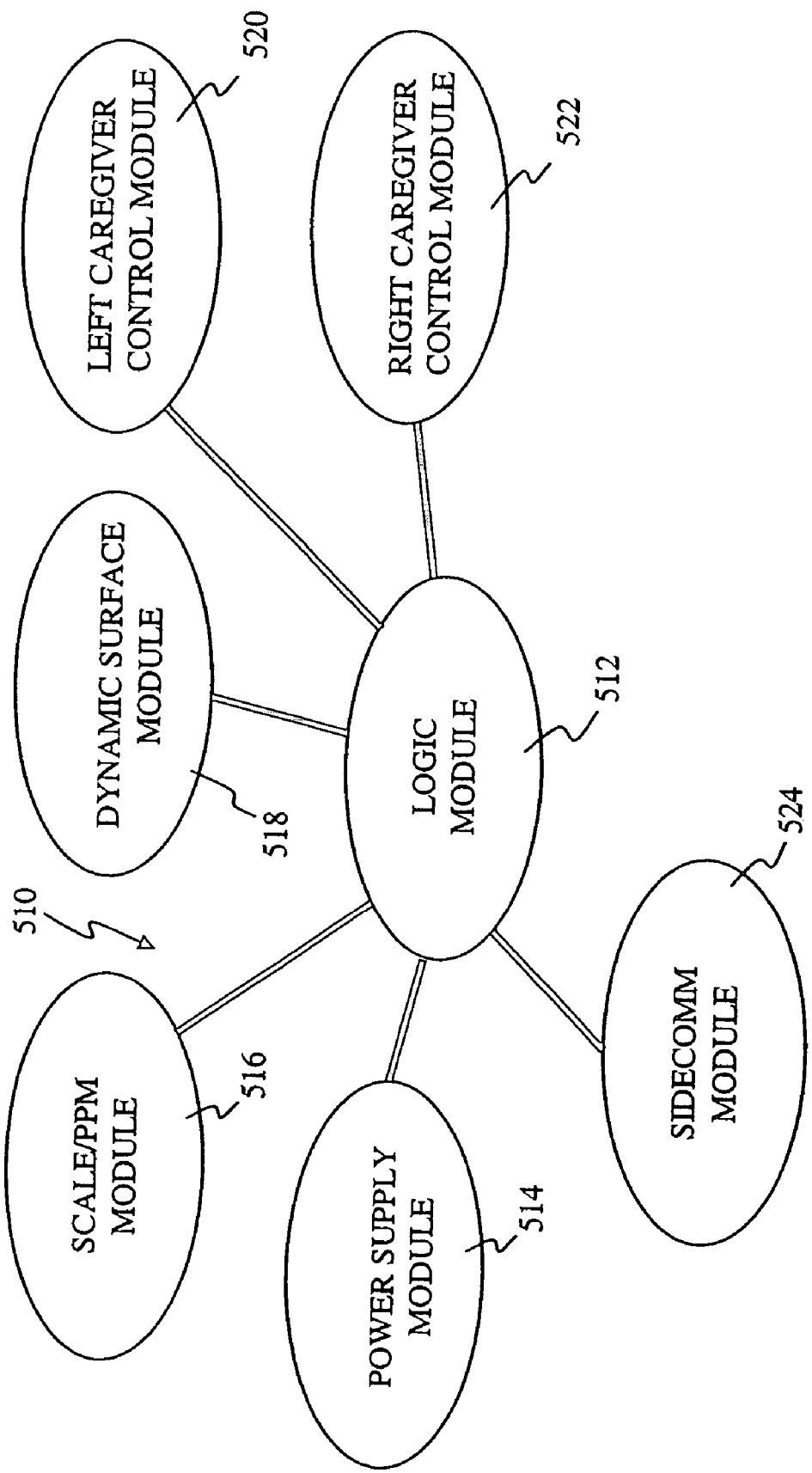
FIG. 35 is a block diagram illustrating the interconnection of various modules of an illustrative embodiment control system of a patient support of the present invention.

Referring now to FIG. 35, control system 44 includes various controls, interfaces, sensors, and actuators that communicate via a plurality of control modules (described below) connected together by a network 510. A control system having certain characteristics in common with control system 44 is described in U.S. Pat. No. 5,771,511 (hereinafter "the '511 patent"), which is hereby expressly incorporated herein by reference. Unlike the peer-to-peer network described in the '511 patent, network 510 is a controller area network (CAN) having a serial bus connecting the modules, each of which includes a controller, a transceiver and associated electronics. In one embodiment, the bus includes a twisted pair of wire conductors. In general, each module is capable of transmitting data on the bus (when the bus is idle), and multiple modules can simultaneously access the bus. Information transmissions (or messages) are not addressed for receipt by a specific module. Instead, as will be further described below, each message is broadcast on the bus to all modules, and includes an identifier that each module uses to determine whether to process the message. If the message is relevant to a particular module, it is processed. Otherwise, it is ignored.

Figure 35A:
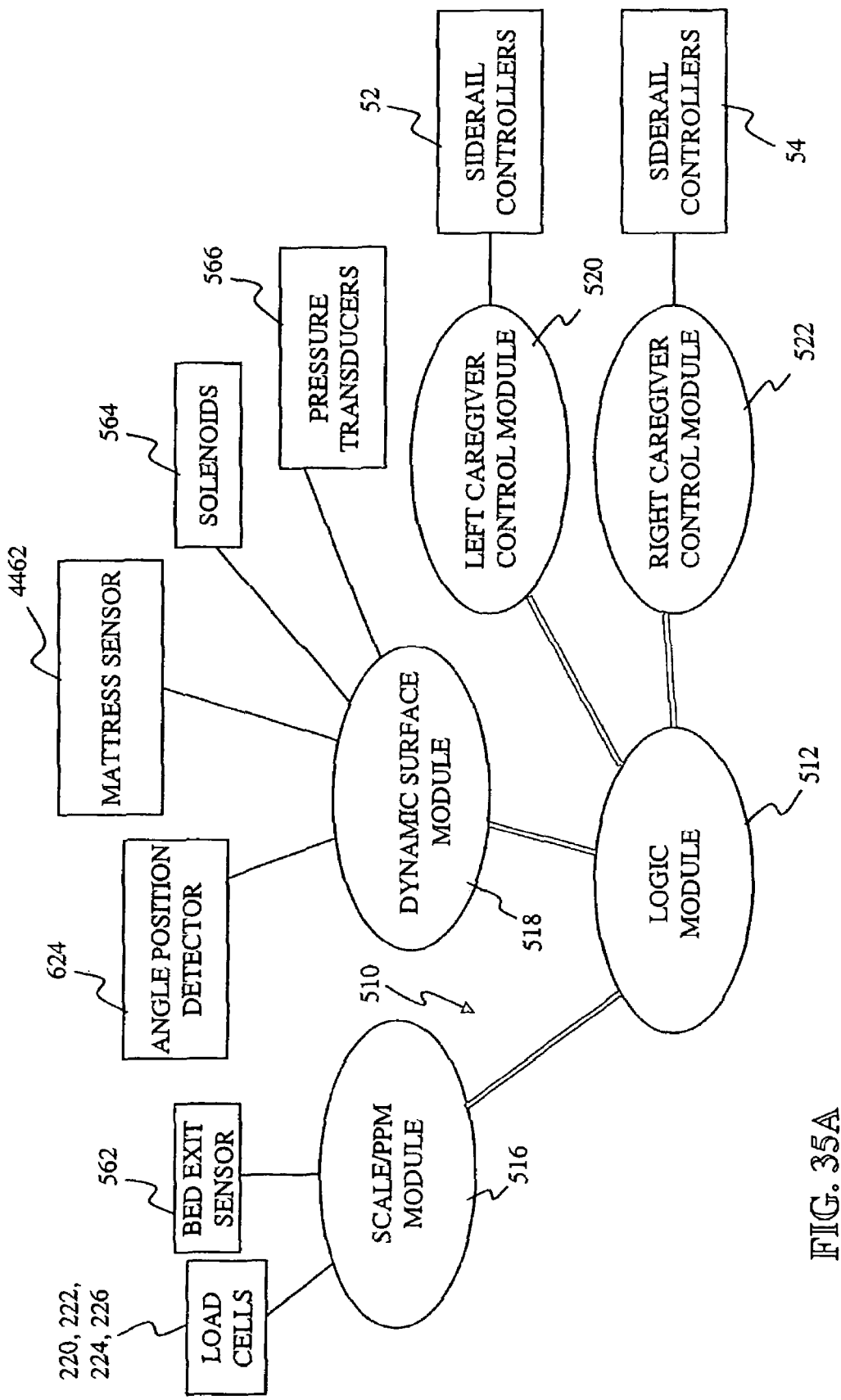
FIG. 35A is a block diagram detailing a portion of the control system of FIG. 35 by illustrating the interconnection between various control components and the scale/ppm module, the dynamic surface module, the left caregiver control module, and the right caregiver control module.
Figure 35B:
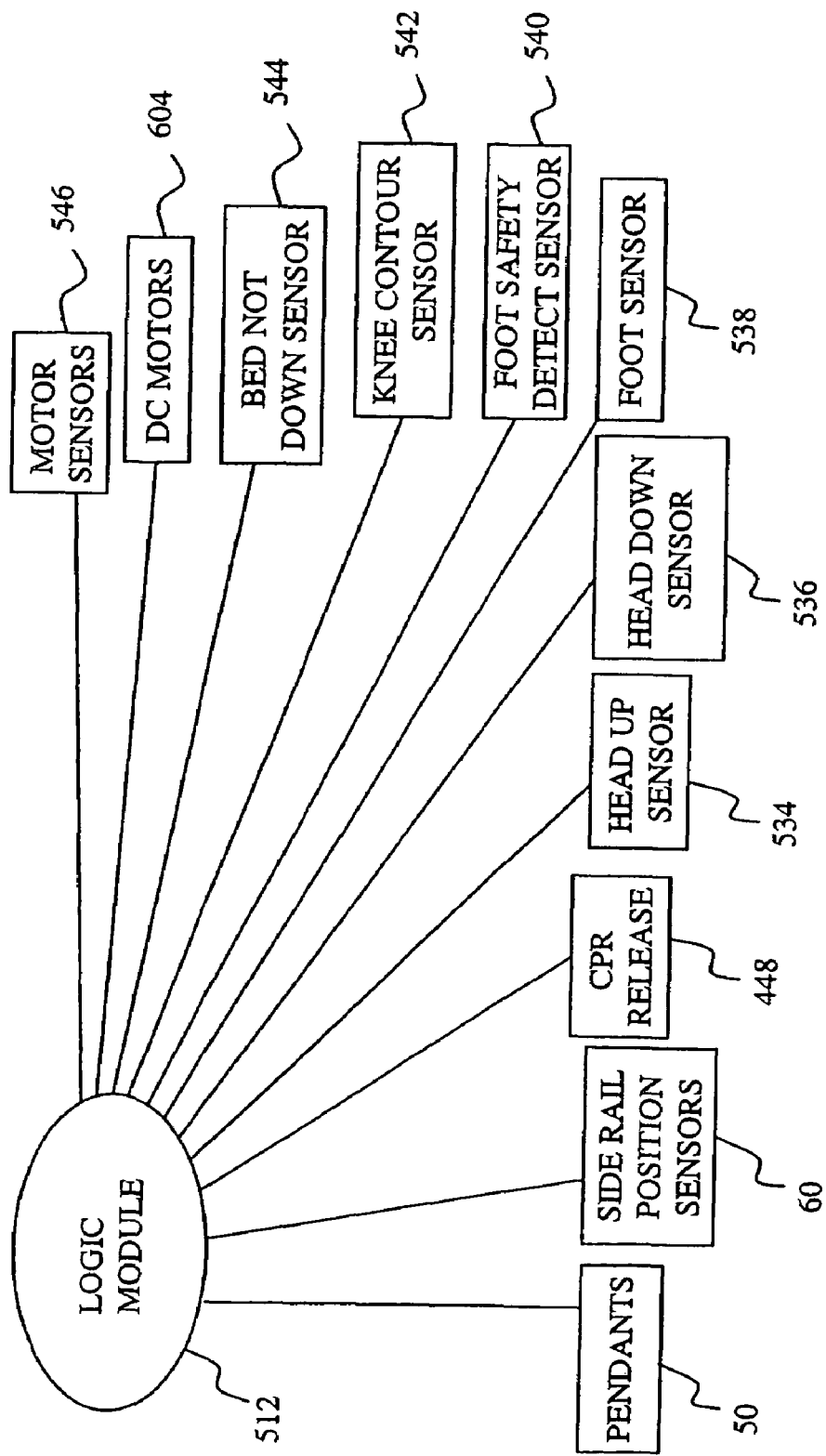
FIG. 35B is a block diagram detailing a portion of the control system of FIG. 35 by illustrating the interconnection between various control components and the logic module.

As shown in FIG. 35, seven modules are connected to network 510 for controlling the operation of patient support 10. The modules include a logic module 512, a power supply module 514, a scale/ppm module 516, a dynamic surface module 518, a left caregiver module 520, a right caregiver module 522, and a sidecomm module 524. With reference to FIG. 35B, logic module 512 is electrically coupled to detachable siderail controller 50 (or patient pendant(s)), CPR release switch 448, DC motors 604 of linear actuators 48, and a plurality of sensors including side rail position sensors 60, a head up sensor 534, a head down sensor 536, a foot sensor 538, a foot safety detect sensor 540, a knee contour sensor 542, a bed-not-down sensor 544, and motor sensors 546.

As illustrated in FIG. 35D, power supply module 514 is electrically coupled to obstacle detection device 58, a night light 548, foot pedal controls 56, battery 46, a battery charger 552, pneumatic pump 64, and power conditioning circuitry 556. Power supply module 514 further includes a connector (not shown) for receiving a test device 558 for performing various diagnostic and test functions. Power conditioning circuitry 556 is connected to a conventional AC plug 45. With reference to FIG. 35A, scale/ppm module 516 is electrically coupled to the load cells 220, 222, 224, 226 connected to weigh frame 36, and to a bed exit sensor 562.

Figure 35C:
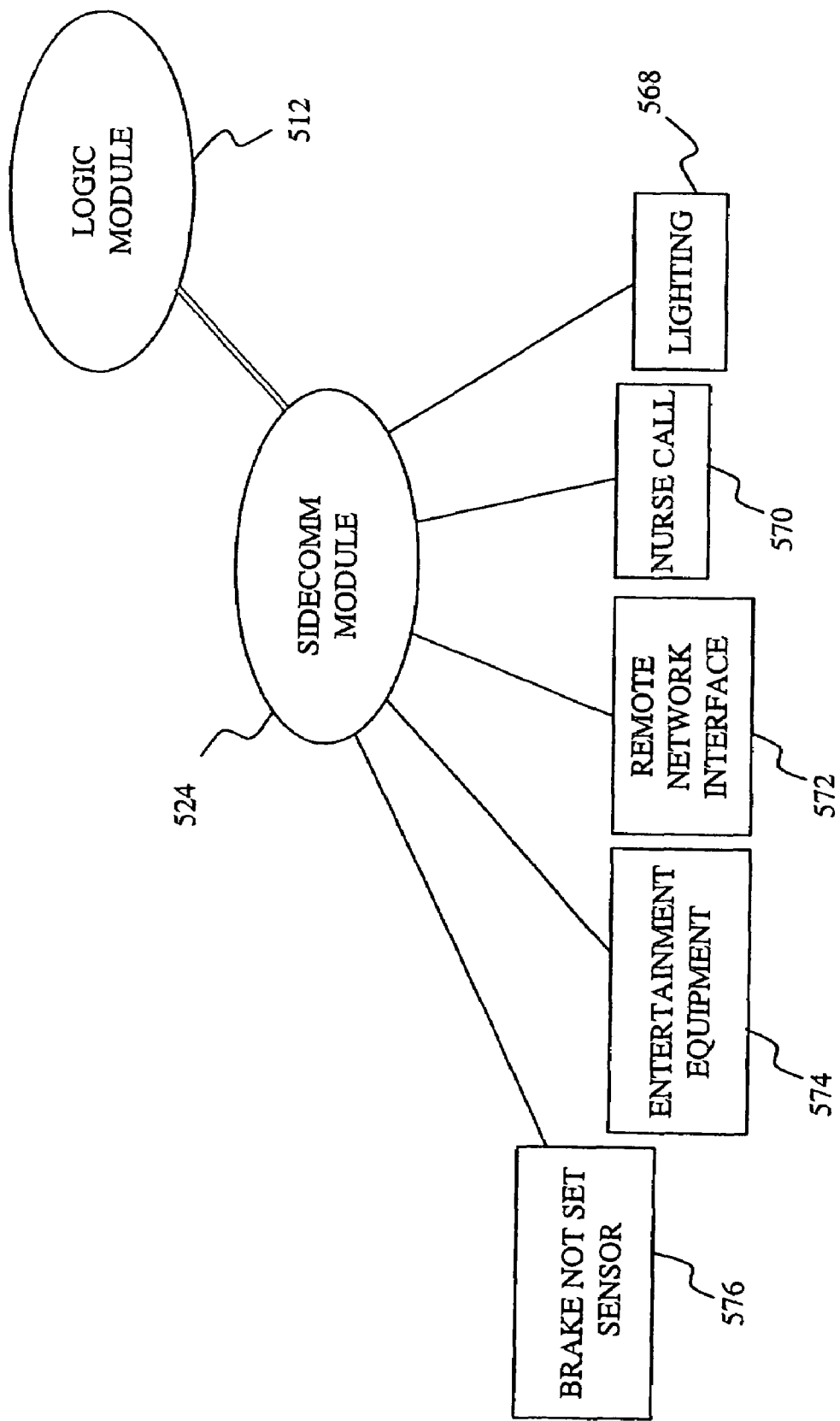
FIG. 35C is a block diagram detailing a portion of the control system of FIG. 35 by illustrating the interconnection between various control components and the sidecomm module.

With reference to FIG. 35A, dynamic surface module 518 is electrically coupled to a plurality of solenoids 564 for controlling characteristics of mattress 14, and a plurality of pressure transducers 566 associated with mattress 14 for sensing air pressures of various components of mattress 14. Left caregiver control module 520 is electrically coupled to first pair of permanent siderail controllers 52 mounted to left head end siderail 20. Right caregiver control module 522 is similarly electrically coupled to first pair of permanent siderail controllers 54 mounted to right head end siderail 20. The configuration and operation of first and second pair of permanent siderail controllers 52, 54 are further described elsewhere herein. Finally, with reference to FIG. 35C, sidecomm module 524 is electrically coupled to room lighting controls 568, a nurse call control 570, a remote network interface 572, entertainment equipment 574 (e.g., radio and television), and a brake-not-set sensor 576.

It should be understood that the configuration of network 510 permits addition of new modules and subtraction of existing modules without requiring manual reconfiguration of the existing modules. When a new module is added, network 510 recognizes the module and facilitates communications between the added module and the existing modules automatically. Additionally, it should be noted that network 510 is implemented to operate as a masterless system, wherein each module 512, 514, 516, 518, 520, 522, 524 operates substantially autonomously. One feature of network 510 is the periodic transmission of each module 512, 514, 516, 518, 520, 522, 524 of a "heartbeat" message or status message to the bus for receipt by each of the remaining modules. In this manner, control system 44 periodically verifies the functionality of each module 512, 514, 516, 518, 520, 522, 524 in system 44, and is able to identify a non-operational module by the absence of the module's "heartbeat" message. As further described herein, communications by and among modules 512, 514, 516, 518, 520, 522, 524 are initiated by the individual modules on an event-driven basis.

Power for control system 44 is supplied through power supply module 514. More specifically, AC plug 45 of a power cord (not shown) secured to frame 12 is inserted into a conventional wall outlet supplying 100 VAC, 120 VAC, or 230 VAC power. Power conditioning circuitry 556 converts the AC input power to DC levels for use by the various electronic components of control system 44. Power supply module 514 further facilitates limited functionality of patient support 10 via battery 46 when AC plug 45 is not connected to a wall outlet. Battery 46 is automatically charged by battery charger 552, which provides a status signal to power supply module 514 to indicate the condition of the charge of battery 46. In one embodiment, battery charger 552 permits use of battery 46 as a back-up power source that allows logic module 512 to perform (for 24 hours after AC power has been disconnected) a single operation of high-low up/down, head up/down, tilt/reverse tilt, foot retract/extend, Trendelenburg, and chair out. When AC power is applied to patient support 10, a light emitting diode (LED) 737 (FIG. 31) indicates the status of battery 46. For example, the LED remains lit when battery 46 has sufficient power, blinks when battery 46 power is low, or is off when battery 46 has lost all power or is disconnected. As indicated, power supply module 514 controls the operation of pneumatic pump 64 (or a blower or other type of inflating means), which supplies air to mattress 14 (as described in greater detail below).

Power supply module 514 also receives the signal provided by obstacle detection device 58 as described herein. Power supply module outputs a message on network 510 when obstacle detection device 58 outputs a signal indicating the presence of an obstacle so that appropriate action can be taken to prevent injury or damage.

Power supply module 514 also controls night light 548. Specifically, night light 548, which illustratively is mounted to patient support 10 at a location to illuminate the ingress/egress area of patient support 10, is always active or on when AC power is provided to power supply module 514. Night light 548 may be disabled or shut off during battery powered operation. As further described herein, the illumination element (not shown) of night light 548 is enclosed by a housing, which also includes circuitry (not shown) to prevent flicker.

As further described herein, each foot pedal 1724, 1726, 1728, 1730 of foot pedal controls 56 provides a signal when depressed. Power supply module 514 uses these signals to generate messages for transmission on network 510 indicating the status of pedals 1724, 1726, 1728, 1730. Logic module 512 processes such messages to determine whether foot pedal controls 56 are enabled, and to control the operation of DC motors 604 of linear actuators 48, as further described herein. Of course, operation of DC motors 604 is conditioned upon the actual positions of the various components of patient support 10, and upon the status of various lockout signals generated by a caregiver using siderail controllers 52, 54.

Finally, power supply module 514 functions as an input location via a connector (not shown) for test device 558. Test device 558 is configured to operate as an additional module on network 510 for performing diagnostic operations on the various functions of patient support 10 as is further described herein.

Scale/ppm module 516 converts the signals from load cells 220, 222, 224, 226, described above, into actual weight measured on weigh frame 32. This information is outputted for display on a scale display (not shown) and possible transmission to a hospital information network via sidecomm module 524 and remote network interface 572. Scale/ppm module 516 further receives input from bed exit sensor 562, which determines, based on the weight measured on weigh frame 32, whether a patient has exited patient support 10.

Dynamic surface module 518 controls the dynamic air surface or mattress 14. It processes messages initiated by either of siderail controllers 52, 54 to operate solenoids 564 (part of valve assemblies 2406), which in turn adjust the level of inflation of mattress 14 during, for example, a turn assist procedure as further described herein. Additionally, dynamic surface module 518 receives feedback from pressure transducers 566 in the form of electrical signals that indicate pressure measurements of the various bladders of mattress 14. Dynamic surface module 518 operates solenoids 564 in response to the feedback signals from pressure transducers 566 to achieve the desired adjustments to mattress 14.

Sidecomm module 524 functions essentially as an environmental and communications interface. The nurse call, lighting, and entertainment functions are controlled by sidecomm module 524 based on inputs from siderail controllers 50, 52, 54. Sidecomm module 524 outputs signals to control these functions, and communicates with the facility's communication systems via remote network interface 572. Patient support 10 includes a connector 575 (FIG. 30) that is configured to interface with the facility's communication system and entertainment system. Another connector (not shown) is provided to interface with the nurse call control 570 and lighting controls 568. As such, sidecomm module 524 controls room lights, reading lights, television, radio, and communicates with the facility's nurse call network in response to activation of a nurse call switch or button mounted to patient support 10. Through remote network interface 572, sidecomm module 524 can provide information to the facility's information network regarding the operation of patient support 10. For example, hours of use may be reported for billing or maintenance purposes. Moreover, sidecomm module 524 can function as an interactive data link between a remote location and patient support 10. For example, the facility information network may request weight information on the patient occupying patient support 10. Sidecomm module 524 can send a message on the bus identified as a weight request. The message may be processed by scale/ppm module 516, which provides a message containing the requested weight information. Sidecomm module 524 processes the message and provides the weight information to the facility's information network via remote network interface 572. Additionally, brake-not-set sensor 576 provides an input to sidecomm module 524 to indicate that the brake preventing movement of patient support 10 is not in a set position.

Logic module 512 controls movement of patient support 10 and is the entry point for nearly all of the position sensors for the various components of patient support 10. As shown, logic module 512 controls the plurality of motors 604 of linear actuators 48 connected to the moveable components (e.g., the articulating deck sections 38, 40, 42, etc.) of patient support 10, as is described in detail herein. When a DC drive motor 604 is activated, a motor sensor 546 associated with the drive motor 604 provides a feedback signal to logic module from which logic module 512 can determine when to deactivate the drive motor 604. When logic module 512 processes a message requesting movement of a particular component of patient support 10, logic module 512 first reads the position of the component (via the appropriate sensor 546). If movement of the component is necessary, then logic module 512 determines whether a lockout signal has been generated from either of the first or second pair of permanent siderail controllers 52, 54. If no lockout is set, logic module 512 controls the appropriate DC drive motor 604, while monitoring the appropriate motor sensor 546, to move the component to the desired position.

Controller Area Network

In one illustrative embodiment, CAN specification 2.0B as specified in ISO 11898 is used for network 510. Network 510 involves three of the seven network layers defined in the ISO model: the physical layer, the data link layer and the application layer. The physical layer includes the actual cabling or wires connecting modules 512, 514, 516, 518, 520, 522, 524. The physical layer further includes the hardware present on each of modules 512, 514, 516, 518, 520, 522, 524 for enabling operation according to the CAN specifications. As indicated above, the hardware includes a transceiver for communicating with the bus and a microcontroller with a built-in CAN controller. A suitable transceiver is a TJA1054 CAN transceiver manufactured by Philips Electronics. A suitable microcontroller is a T89C51CC01 microcontroller manufactured by Amtel. The microcontroller is connected to a crystal oscillator, such as a 20 MHz crystal.

The data layer generates and receives the messages used for communications between modules 512, 514, 516, 518, 520, 522, 524 via the CAN protocol (described below).

The application layer complies with the CANopen specification as further described below. CANopen is an open standard based on a model including communication interface and protocol software, an object dictionary, and an application program interface. The communication interface and protocol software provides a means by which a CANopen device can transmit and receive messages over network 510. The object dictionary is a collection of all of the system variable information communicated over network 510. Finally, the application program interface controls how the application software interacts with the various network parameters.

The communication interface and protocol software includes a variety of services and protocols. One protocol that handles real-time transfer of data between modules is the Process Data Objects (PDO) protocol. Two PDO services are provided: receive (RPDO) and transmit (TPDO). RPDOs are used to obtain updated information for the object dictionary entries of a module 512, 514, 516, 518, 520, 522, 524. TPDOs, on the other hand, are used to transmit updated information to object dictionary entries of another module 512, 514, 516, 518, 520, 522, 524. According to one embodiment of the invention, eight PDOs can be used for each module 512, 514, 516, 518, 520, 522, 524 (four configured as RPDOs and four configured as TPDOs). Each PDO can transfer up to eight bytes of information. While both PDO services share the same basic structure, TPDOs are essentially broadcast messages (any module 512, 514, 516, 518, 520, 522, 524 could receive a TPDO), and RPDOs must be unique for each module 512, 514, 516, 518, 520, 522, 524 that transmits. For example, power supply module 514 may send battery status information to all other modules 512, 516, 518, 520, 522, 524 using a single TPDO. Each module 512, 516, 518, 520, 522, 524 that needs to use the information must have a corresponding RPDO to receive the information from power supply module 514. Moreover, each module 512, 514, 516, 518, 520, 522, 524 that needs information from any other module 512, 514, 516, 518, 520, 522, 524 must have a separate RPDO for the other module 512, 514, 516, 518, 520, 522, 524. In other words, RPDOs can only receive a message from a single module.

PDOs are constructed from object dictionary entries in the manner depicted in FIG. 35. As shown, PDO 578 is capable of including eight bytes 580 of information. In this example, PDO 578 includes only five bytes 580 of information. The eight bytes 580 of information can come from any of a variety of different object dictionary entries (such as object dictionary entries 582 and 584) associated with different modules, and the entire data type for the object dictionary entry does not have to be used. Where the entire data type is not used, then the number of bits specified (starting with the LSB) are used as shown in FIG. 35.

PDOs of control system 44 are event driven. When an object dictionary entry changes, for example, because a system variable changed, the corresponding PDO is automatically transmitted, and the object dictionary entry is automatically updated when a message is received. As explained herein, modules 512, 514, 516, 518, 520, 522, 524 determine which messages to process by analyzing an identifier included in the message. The identifier includes three digits in the form of x8y where x is the TPDO of the transmitting module 512, 514, 516, 518, 520, 522, 524 and y is the module ID of the transmitting module 512, 514, 516, 518, 520, 522, 524. Thus, if a module 512, 514, 516, 518, 520, 522, 524 maps one of its RPDOs with the CAN identifier 584, it correlates to TPDO2 from module 4.

Another protocol is the Service Data Objects (SDO) protocol, which is administered only by a master module. As indicated herein, control system 44 includes a master only when test device 558 is coupled to power supply module 514. In that case, SDOs allow test device 558 access to any object dictionary entry present in the other modules 512, 514, 516, 518, 520, 522, 524.

The object dictionary defines data types, communication objects, and application objects used on network 510. The object dictionary is essentially a group of objects that are accessible via network 510 in a predefined, ordered fashion, using either SDOs or PDOs. All entries in a object dictionary use a "wxyz" format where w is 2 if used by a PDO, 3 if used by an SDO, x is the module identifier for the transmitting module 512, 514, 516, 518, 520, 522, 524, y is 0 if the entry includes error information, 1 if it includes status information, and 8 if it includes control information, and z is a unique value for multiple wxy entries. For example, an object dictionary entry of 2110 indicates that the information is communicated between modules 512, 514, 516, 518, 520, 522, 524 during normal operation (i.e., using a PDO as opposed to an SDO used only during testing and diagnostics), that module number 1 is the transmitter of the information (e.g., scale/ppm module 516), and that it includes status information. The 0 indicates the unique value for multiple wxy entries.

Although in a typical CANopen implementation nodes only have object dictionary entries to information generated or received by the node, in control system 44, all PDO object dictionary entries (2xyz) are implemented in every module 512, 514, 516, 518, 520, 522, 524 to minimize the variance in software among modules 512, 514, 516, 518, 520, 522, 524. SDO entries (3xyz), however, are unique for each module 512, 514, 516, 518, 520, 522, 524 as a result of the application specific nature of built in self test (BIST) data objects.

Figure 36:
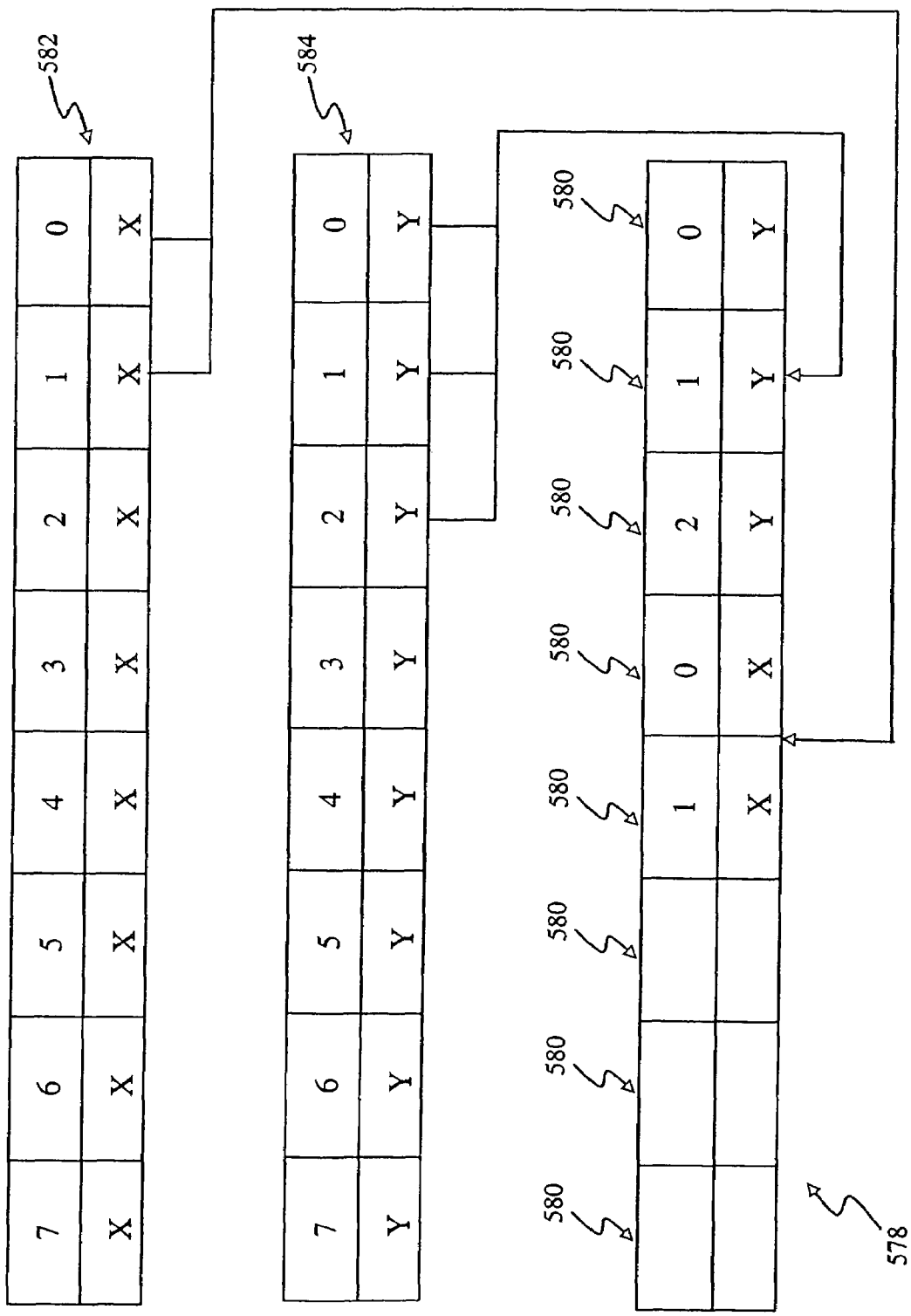
FIG. 36 is a schematic diagram illustrating a plurality of object dictionary entries of a Process Data Objects (PDO) protocol for use in connection with a controller area network (CAN) of an illustrative embodiment patient support of the present invention.
Figure 37:
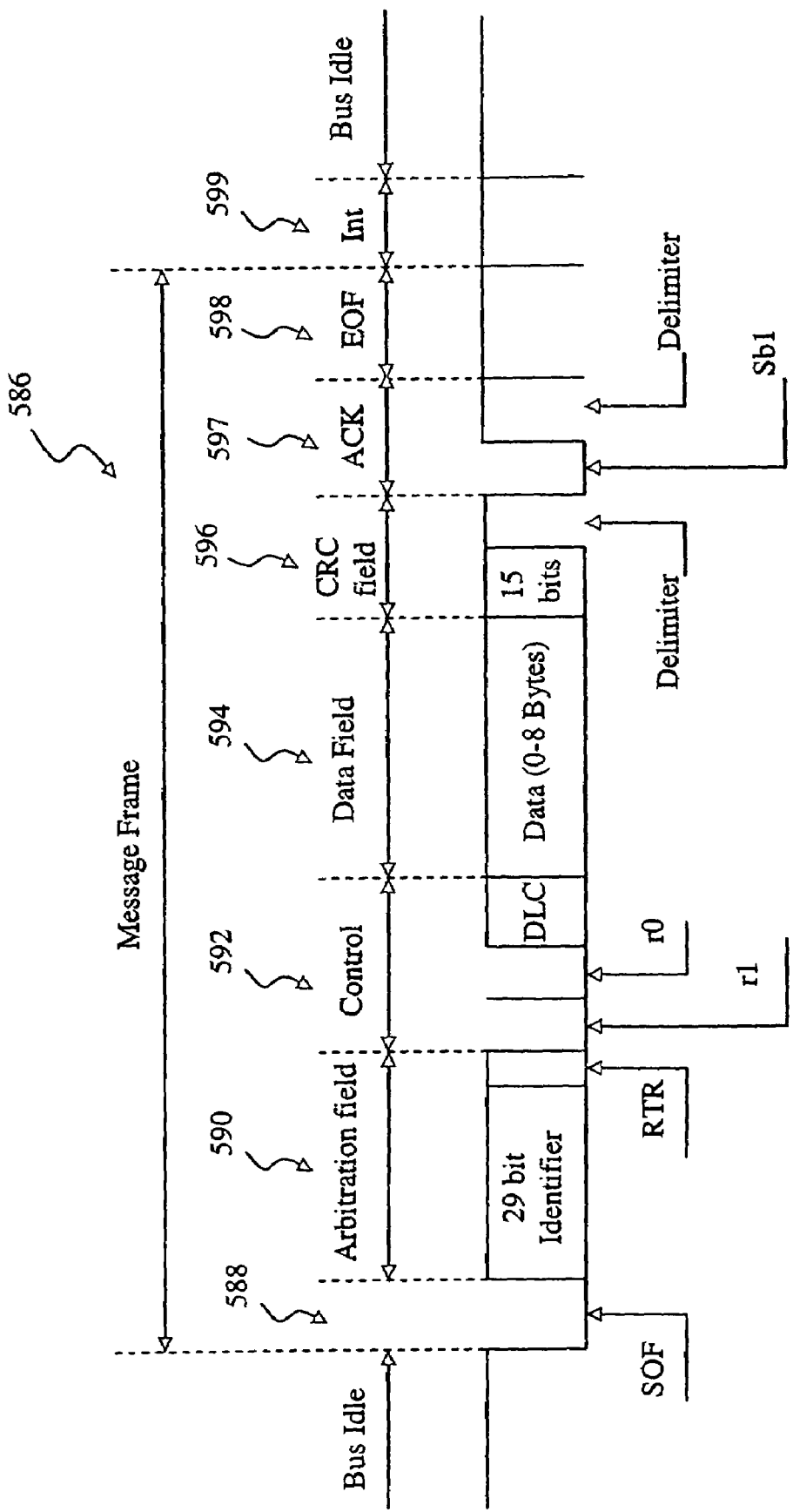
FIG. 37 is a waveform diagram of a message frame according to a communications protocol for use in connection with a controller area network (CAN) of an illustrative embodiment patient support of the present invention.

Messages of the type mentioned above are transmitted and received using message frames, such as the message frame 586 shown in FIG. 37. The structure of the message frames is a function of software executed by each module and configured for operation with various 8-bit 8051 family microprocessors. As already indicated, in one embodiment the software conforms to CANopen protocol for the application layer of network 510. As shown in FIG. 36, frame 586 includes seven different bit fields including start of frame (SOF) field 588, arbitration field 590, control field 592, data field 594, CRC field 596, acknowledge field 597, and end of frame (EOF) field 598. SOF field 588 indicates the beginning of message frame 586. Arbitration field 590 includes an 11-bit base identifier, and an 18-bit identifier extension. Together, these identifiers provide the message identifier introduced above. The identifier also determines the priority of the message for use in resolving bus access competition between or among modules 512, 514, 516, 518, 520, 522, 524 according to a non-destructive, contention-based arbitration scheme. This scheme, as is well-known in the art, ensures that messages are sent in order of priority, and that the content of each message is preserved. Arbitration field 590 further includes a substitute remote request bit that is transmitted as a recessive bit and used to resolve priority conflicts between different frame formats. Control field 592 includes six bits: two reserved bits (r0 and r1) and a four bit data length code (DLC) indicating the number of bytes in data field 594 that follows.

Data field 594 may contain up to eight bytes of data. CRC field 596 includes a 15-bit cyclical redundancy check code and a recessive delimiter bit. Acknowledge field 597 includes two bits: a slot bit which is transmitted as recessive but is subsequently over written by dominant bits transmitted from any module 512, 514, 516, 518, 520, 522, 524 that receives the transmitted message, and a recessive delimiter bit. Finally, EOF field 598 consists of seven recessive bits. After each message frame 586, an intermission field 599 is provided that includes three recessive bits. Thereafter, the bus is considered idle.

Linear actuators driven by DC brush motors are commonly used to perform raising and lowering movements (e.g., head, foot, hi/lo, knee, leg) of deck sections on hospital beds. For example, see U.S. Pat. Nos. 5,918,505; 5,939,803; and 6,158,295, all of which are assigned to Linak A/S of Denmark. In the hospital room environment, product safety is an important concern. DC motors used in hospital beds are configured to operate safely in the medical environment.

As discussed above, control system 44 includes logic module 512. In addition to other functions, logic module 512 includes a drive control system 601 which controls the DC motors 604 of linear actuators 48 used to articulate deck sections 38, 40, 42 of patient support 10.

Drive Control System

Figure 38:
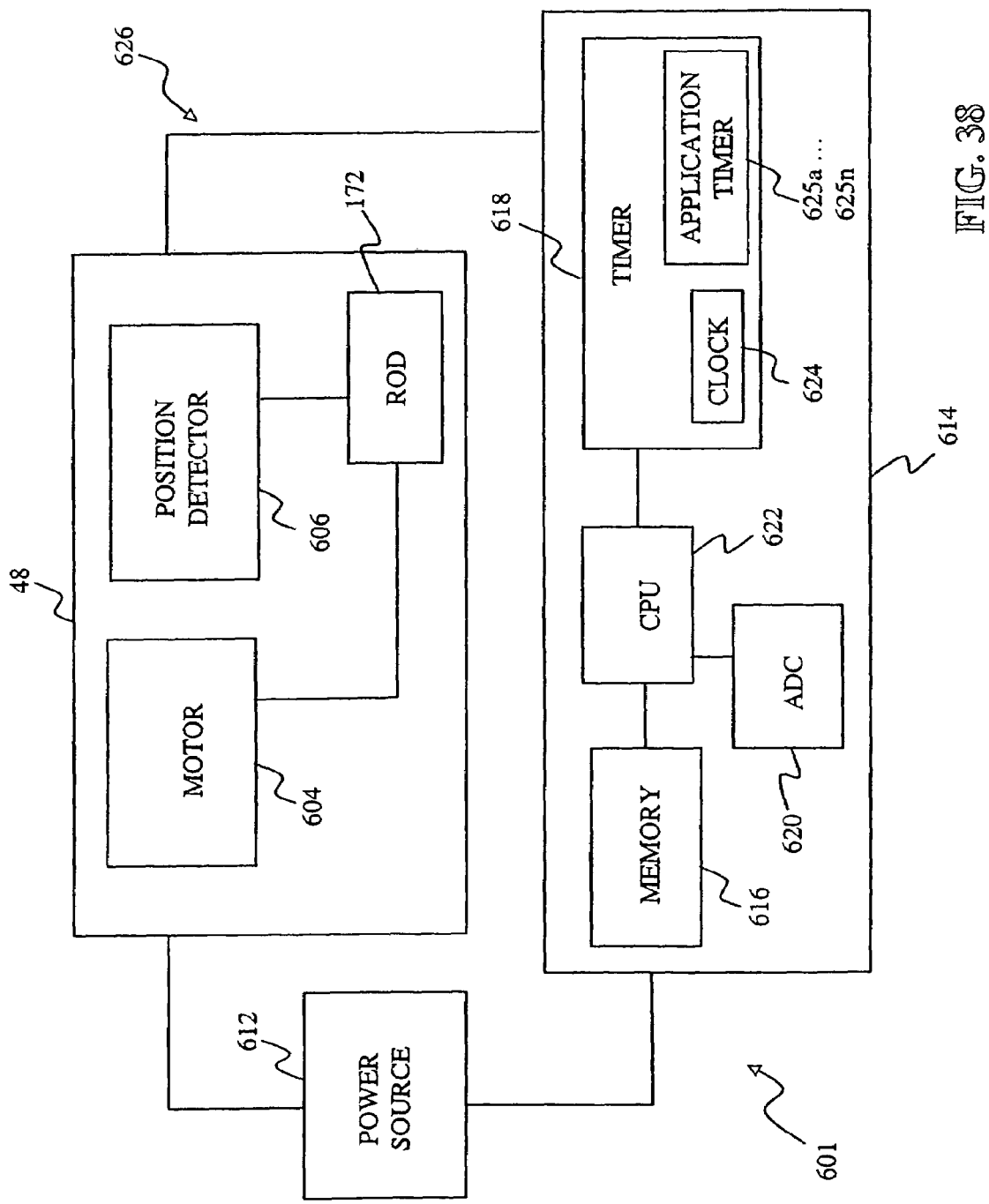
FIG. 38 is block diagram of an illustrative embodiment drive control system in accordance with the present invention.
Figure 39:
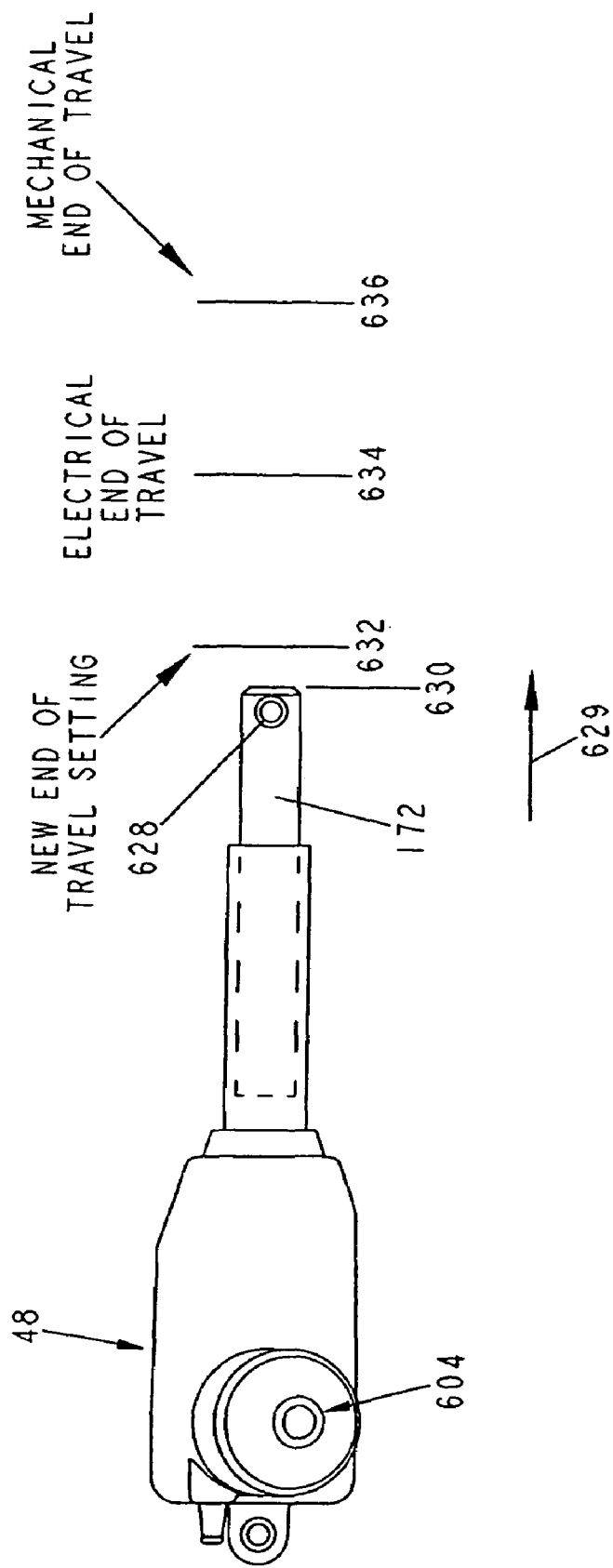
FIG. 39 is a side elevational view, in partial schematic, of an illustrative embodiment end of travel control system in accordance with the present invention.

FIG. 38 illustrates an embodiment of drive control system 601. As illustrated, each actuator 48 includes a drive motor 604 and a position detector 606. Actuator 48 is electronically coupled to a power source 612, such as a primary power source coupled to AC plug connection 45 or backup power source or battery 46, and a microcontroller 614.

Microcontroller 614 includes memory 616, timer 618, analog-to-digital converter 620 and central processing unit (CPU) 622. Illustratively, timer 618 may include a single system clock 624 coupled to the CPU 622 and/or a plurality of application timers 625a, 625b, . . . , 625n, as needed to execute the various features of drive control system 601. In general, application timers 625a, . . . 625n are incremented at a rate which is a function of the system clock 624 of CPU 622, as is well known.

The above-mentioned components of drive control system 601, e.g., actuators 48, power source 612, and microcontroller 614 are well-known and one of ordinary skill in the art would readily be able to select the appropriate models and/or types of such components as needed to operate the articulation functions of patient support 10. For example, memory 616 includes volatile (e.g., flash memory, RAM) and non-volatile (e.g., on-chip EEPROM) memory for storing computer programming code and data required by control system 601. In the illustrated embodiment, on-chip EEPROM memory is used for long term data storage while flash based memory is used for storage of computer programming code and RAM memory is used for short term data storage, however, it is understood that other suitable memory configurations would work equally as well.

Embodiments of drive control system 601 include one or more of the features described below.

End of Travel Control System

In an illustrative embodiment, linear actuators 48 including DC drive motors 604 are used to drive the movement of head, seat, and leg sections 38, 40, 42 of patient support surface 10. In general, actuators 48 are activated by activation by a caregiver or patient of one or more of the control buttons illustratively located on controllers 50, 52, 54 (e.g., buttons 1520, 1522 on detachable siderail controller 50; buttons 1550, 1551, 1564, 1566, 1574 on first siderail controllers 52; buttons 1628, 1624, 1626 on controllers 54) or one or more of the pedals of the foot pedal controls 56. As common with most linear actuators, failure of any of actuators 48 may occur if a drive or rod reaches its mechanical end of travel, for example, due to a heavy load on the actuator.

It is known to provide an actuator with an electrical end of travel that is defined to occur earlier than the mechanical end of travel to prevent the actuator from reaching its mechanical end of travel. Using the electrical end of travel, a loss of current occurs when the driving component, such as a piston rod moves past the electrical end of travel. Many existing drives operate until the electrical end of travel is reached. However, in patient support surfaces such as hospital beds, reaching even the electrical end of travel may cause the drive to bounce back and forth due to hysteresis of the drive mechanism. Such oscillatory motion or bouncing may present a safety concern, particularly in drives used to raise and lower the head section of the patient support surface and in drives that power the hi/lo mechanism.

To prevent the above-described oscillatory motion or bouncing in patient support 10, some or all of linear actuators 48 are coupled to a closed loop end of travel control system 626, which establishes a new end of travel setting and thus prevents the actuator from reaching either the electrical or mechanical end of travel during articulation of a section of patient support 10. In the illustrated embodiment, at least head section actuator 48c and deck actuators 48a, 48b are coupled to control system 626.

Another application of end of travel control system 626 relates to the CPR function of the illustrative embodiment patient support 10. As described above, when CPR handle 352 is activated by a caregiver or operator of patient support 10, head section 38 is mechanically lowered. Also, the actuator 48d for seat section 40 is automatically activated as needed to lower seat section 40 and the actuator 48e for leg section 42 is automatically activated as needed to raise leg section 42, to put patient support 10 into the horizontal position shown in FIG. 3. End of travel control system 626 operates to detect when head section 38, seat section 40 and leg section 42 have reached their respective bottom or zero positions, shown in FIG. 3. Upon detection of the bottom position of head, seat and leg sections 38, 40, 42, a timer is started. If the caregiver/operator continues to keep CPR handle 352 activated for a predefined period of time, patient support 10 is automatically moved into the emergency Trendelenburg position shown in FIG. 9. If CPR handle 352 is released before the predefined wait period expires, patient support 10 does not continue into the emergency Trendelenburg position. In this way, a "single action" CPR handle for moving patient support 10 into the CPR and emergency Trendelenburg positions is provided.

Closed loop end of travel control system 626 of the illustrative embodiment is provided in addition to any other electrical and mechanical end of travel systems. However, it is understood that in other embodiments, closed loop end of travel control system 626 may be provided in lieu of traditional end of travel systems.

Linear actuators 48a, 48b, 48c, 48d, 48e, 48f are shown, for example, in FIGS. 7 and 18. Each actuator 48 includes DC drive motor 604 that powers linear movement of respective piston rod 172, as is well known in the art. In FIG. 38, it is shown that as drive motor 604 moves piston rod 172 including load connector 628 in the direction of arrow 629, it approaches a mechanical end of travel. The closed loop end of travel control system 626 includes a built-in feedback mechanism that continuously monitors the actual position 630 of piston rod 172 and compares the actual position 630 to a new predetermined end of travel limit 632. The new end of travel limit 632 is set to occur earlier than either the electrical end of travel 634 or the mechanical end of travel 636 of the actuator 48, so that it will be reached before either the electrical or mechanical end of travel 634, 636. Movement of the rod 172 is limited to the predetermined end of travel limit setting 632 to prevent oscillating or bouncing and to prevent rod 172 from reaching mechanical end of travel 636.

In the illustrated embodiment, position detector 606 is a potentiometer located inside the housing of drive motor 604, however, it is understood that other means for detecting position, such as a tachometer, may be used. For actuators 48 that are provided with end of travel control system 626, potentiometer 606 has a predetermined setting approximately equal to new end of travel limit 632. Calculation of new end of travel limit 632 is discussed below. Position detector 606 measures the current position 630 of rod 172 and compares it to new end of travel limit 632. If the actual position 630 reaches new end of travel limit 632, an error message or message indicating that the limit has been reached is sent to microcontroller 614, and subsequent actions are taken as described below.

In certain embodiments of end of travel control system 626, timer 618 includes an application timer 625a that is programmed by software to time the operation of drive motor 604, e.g., to track the time of occurrence of each measured position 630, as described below. Each time drive motor 604 starts, whether to perform an up or down/forward or backward motion, timer 625a is started. When drive motor 604 stops, timer 625a stops. Position information 630, 632, 634, 636 and time of occurrence information are stored in memory 616.

Figure 40:
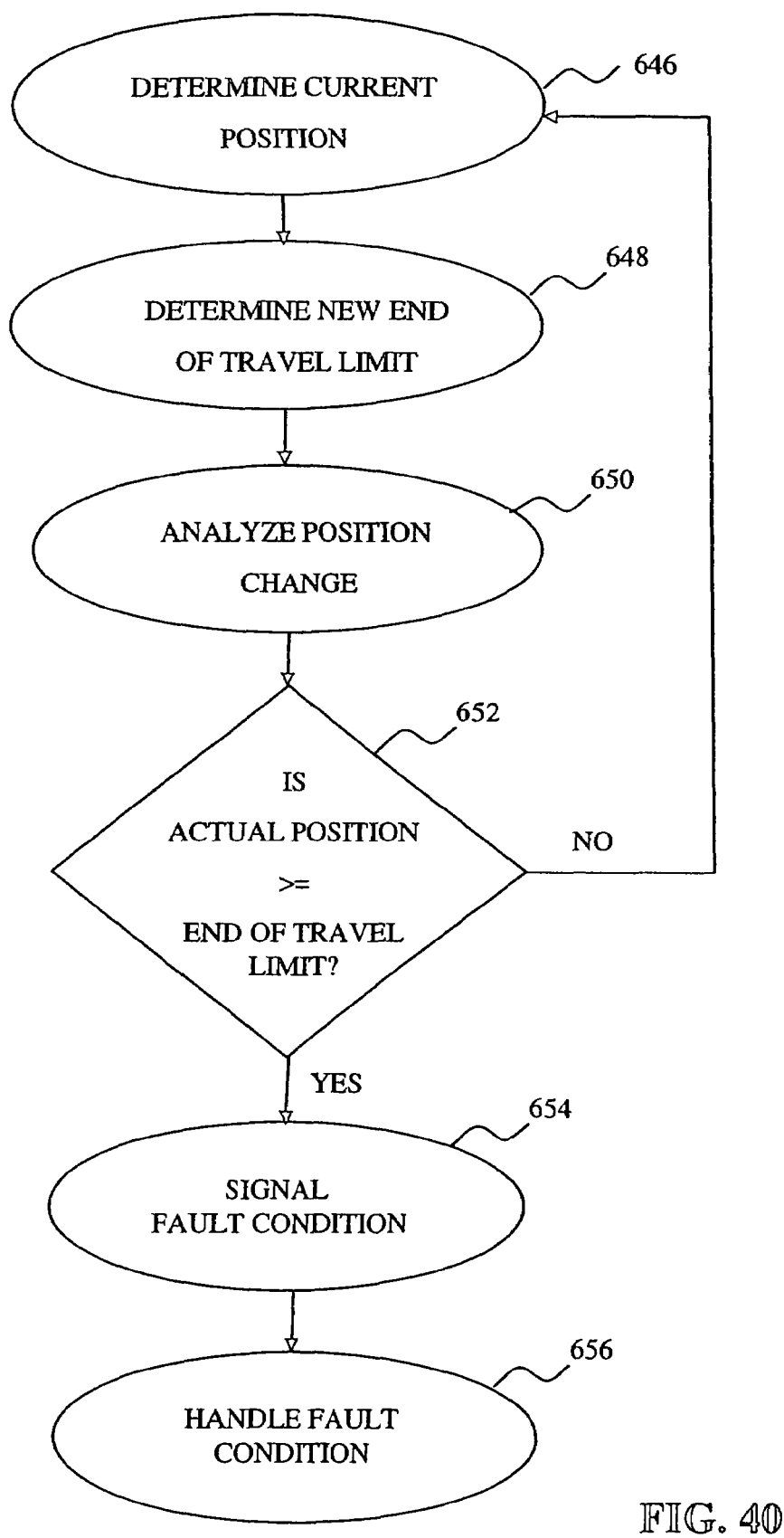
FIG. 40 is a flow diagram of an illustrative embodiment process for monitoring end of travel in accordance with the present invention.
Figure 41:
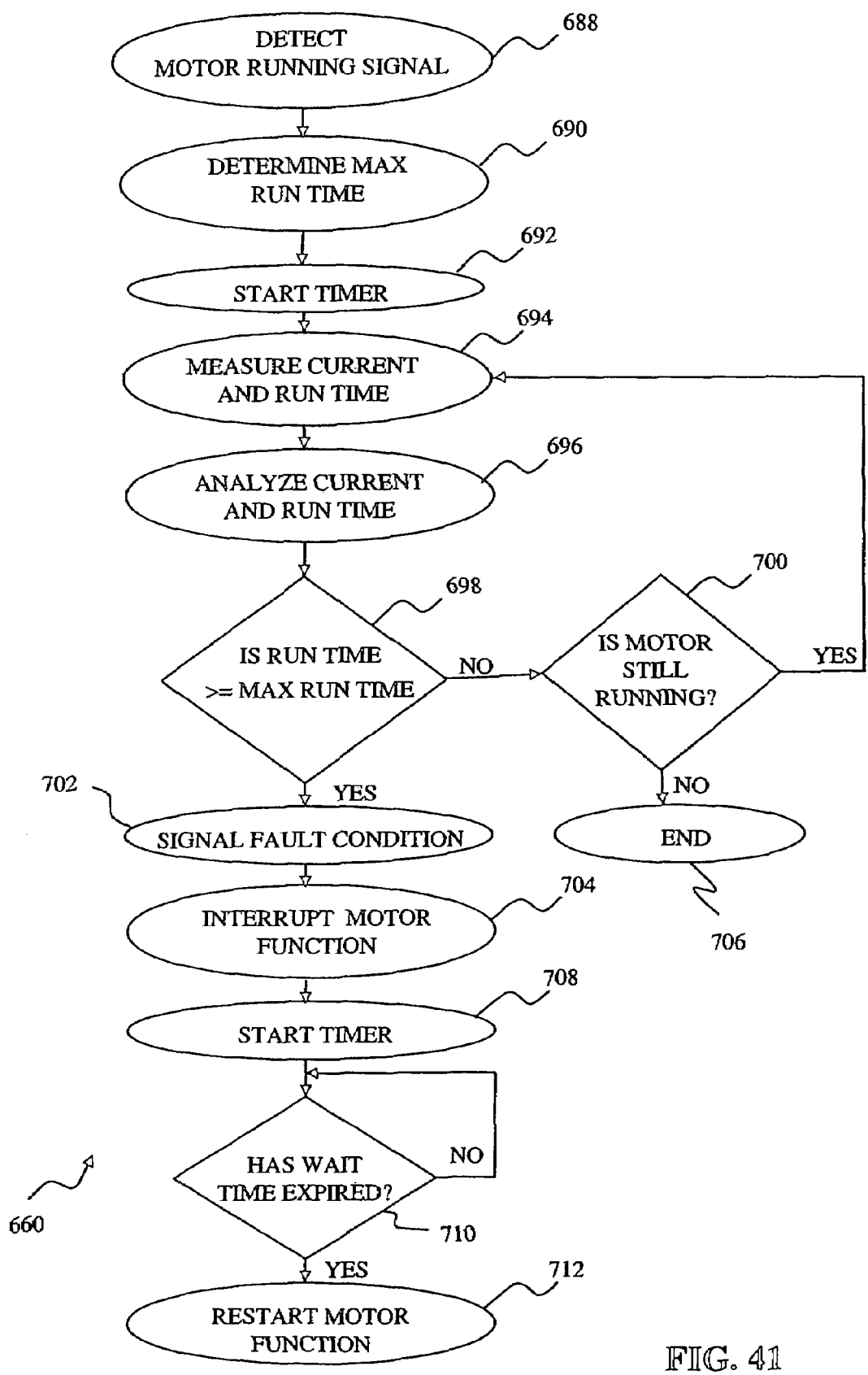
FIG. 41 is a flow diagram of an illustrative embodiment duty cycle protection process in accordance with the present invention.

FIG. 40 shows steps performed in the method of operation of end of travel control system 626 when a drive motor 604 is operating. Beginning at step 646, a current position 630 of the drive rod 172 during its operation is determined. For each actuator 48, the process associated with control system 626 identifies a known "initial" position of the drive rod 172. In the illustrated embodiment, the initial position of the drive rod 172 is the unextended position, but it is understood that any drive position could be designated as the initial position. The initial position may be different for each drive actuator 48. The initial position for each actuator 48 is obtained by measuring the voltage across potentiometer 606 in a voltage divider circuit and converting the measured value to digital form using A/D converter 620. The potentiometer 606 reading is representative of the movement of the drive shaft or rod 172 of drive motor 604.

Based on the potentiometer 606 reading at the initial position of each drive rod 172 and the total stroke length of the drive rod 172 (typically provided by the drive manufacturer), a correlation can be made between the potentiometer 606 reading and the stroke length (e.g., with stroke length illustratively measured in millimeters). In this way, current position 630 of drive rod 172 during its travel is determined by comparing the current potentiometer 606 reading to a table of known potentiometer readings and the corresponding stroke length for drive rod 172.

Typically, actual position 630 is measured on a recurring basis over predefined time intervals, such as every 20 milliseconds, as counted by timer 625a. In other embodiments, the time that position 630 is measured is also captured. In the illustrative embodiment, if rod 172 is traveling upward, the last position captured before current position 630 is kept in memory and used as detailed below. It is understood that the last position could be tracked during upward, downward, forward, and/or backward movement as needed. The last position, and current position 630, along with sample times associated with each of the last position and current position 630, are converted to digital form by A/D converter 620 and stored in memory 616.

At step 648, new end of travel limit 632 is determined in the manner described above, e.g., based on the potentiometer 606 value when the rod 172 is in the extended position. For example, in one embodiment, a look-up table stored in memory 616 is used. In another embodiment, limit 632 is calculated based on the anticipated amount of hysteresis of actuator 48. The anticipated amount of hysteresis can be estimated as a percentage of the total stroke length of drive rod 172. In the illustrative embodiment, the amount of hysteresis is estimated as about 1% or less of the total stroke length, however, it is understood that other suitable methods for calculating anticipated hysteresis may be used, depending on the particular type or model of drive actuator 48 being used and/or its particular application. New limit 632 is determined, for example, by adjusting electrical end of travel limit 634 by the anticipated amount of hysteresis, so that new limit 632 occurs earlier than electrical limit 634. New limit 632 may also be based on the height of patient support 10 and/or the angle of head section 38 and/or system level noise. For example, in the illustrated embodiment, new limit 632 is calculated assuming a bed height of approximately 36 centimeters and 65-75 degrees of head angle. It is understood that the values obtained for limits 632 and 634, stroke length, and estimated amount of hysteresis are stored in memory 616 as needed to perform the above-described calculations.

At step 650, the change in position of rod 172 is analyzed. Current position 630 is compared to limit 632 using computer programming logic. In additional embodiments, a rate of change of position of rod 172, is determined by comparing the time of measurement of current position 630 to the previously measured current position and its time of measurement.

It is understood by those skilled in the art that the rate of change of position of rod 172 is determined based on the position readings of potentiometer 606 and is also affected by the drive's spindle pitch. Speed and pitch data for the drive are generally provided by the manufacturer.

The rate of change of position is monitored, for example, to determine whether the drive is overloaded or whether something is interfering with the portion of the bed being moved by the drive. For instance, if a patient is attempting to raise the head end of the bed, but does not realize that the frame is caught on something, such as a window sill, the rate of change of position analysis will indicate that though the drive is running, the position has not changed as normal. As a result, an error code is generated and the motor shuts down to avoid further damage to the system or harm to the patient.

At decision step 652, actual position 630 is compared to limit 632. Additionally, the rate of change of position is compared to a predetermined rate of change position limit 653 stored in memory 616. If the actual position 630 of rod 172 has not reached limit 632, or if the actual rate of change of position has not reached the rate of change of position limit 663, then the process returns to step 646.

The illustrated embodiments are particularly concerned with monitoring upper position and rate of change of position limits, however, it is understood that in alternative or addition, lower limits may also be defined and controlled in similar fashion.

If actual position 630 has reached or exceeded limit 632, or if the actual rate of change of position has reached or exceeded the rate of change of position limit 653, then at step 664 potentiometer 606 sends a fault condition or "limit reached" signal to microcontroller 614.

At step 656, microcontroller 614 handles the fault or limit reached condition. In certain embodiments, if position limit 632 is reached or exceeded, or if the rate of change of position limit 661 is reached or exceeded, microcontroller 614 recovers from the error condition by initiating application code, e.g., via a software process or internal or external reset, which resets position 632 to a zero or home position and requests actuator 48 to begin motion in the opposite direction. For instance, if limit 632 is reached during downward travel, position 632 is reset to zero and a signal to begin travel in the upward direction is issued. The process would occur in reverse, if the actuator 48 was moving in the opposite direction.

In other embodiments, at step 656, if position limit 632 is reached or exceeded, or if the rate of change of position limit 663 is reached or exceeded, microcontroller 614 places patient support 10 in a safe/error state that minimizes hazards to patients, caregivers, associated individuals, equipment, and/or data. For instance, microcontroller 614 may initiate a reset or signal power source 612 to interrupt, disengage, or reduce current supplied to actuator 48.

At step 656, microcontroller 614 may also set a flag to indicate to an operator that service is necessary on the affected actuator 48 or on the entire drive system. Such indication may be communicated to an operator by illuminating, blinking or flashing one or more LEDs located on one of controllers 50, 52, 54, or other suitable location on patient support 10. Different colored LEDs may be used to signal different types of errors. In the illustrated embodiment, red, green, and amber colored LEDs are used. For example, if the position 630 of actuator 48c of head section 38 has exceeded limit 634, red and green LEDs may be set to blinking while an amber LED remains off. However, it is understood that any suitable combination of colors and LED activity may be used to indicate the various possible error types. Further, other conventional alarm devices may be utilized such as audible buzzers or bells.

As discussed above, the rate of change of position is monitored to detect whether the drive actuator 48 is overloaded or when an interference condition exists, for example, if drive motor 604 is powered on to raise a deck section 38, 40, 42, but something, such as a window sill, piece of equipment, or utility cart, interferes with its movement or there is excessive weight on the deck section. The rate of change of position is determined using a potentiometer 660 or by other suitable means known in the art. In the illustrated embodiment, potentiometer 606 is used to determine the rate of change of position by measuring the rate of change of the position of drive rod 172 over time. If the rate of position change is too high or too low, an overload or interference condition is detected. In the illustrated embodiment, "too high" or "too low" means that the rate of position change is at least approximately 200% above or below the normal operating rate of change of position of drive 48 when actuated by a user (i.e., the normal rate when an "up" or "down" button is pressed to raise or lower a bed section). If an overload or interference condition is detected, based on comparison of rate of change of position to rate of change of position limit 653, an error code will be generated at step 654 and the error condition will be handled at step 656 as described above.

Duty Cycle Protection

For safety and warranty reasons, linear actuator drive manufacturers typically set a maximum run time for their actuators. Typically, the maximum run time is specified in terms of minutes per hour, e.g., 6 minutes per hour. In view of the safety concerns of the medical environment, a reliable mechanism is needed to detect in a preventative way when an actuator's run time is approaching the predefined run time limit to prevent thermal overload of the actuators, protect against overuse of the actuators, and prolong the life of the actuators. Thus, in certain illustrative embodiments of the present invention, logic module 512 of control system 44 includes a closed loop control circuit 660 that monitors both current and drive run time. Duty cycle protection circuit 660 measures the actual run time of an actuator 48 and then prevents drive operation if a maximum run time 662 is exceeded, as described below. Circuit 660 is designed to prevent thermal protection circuit 670 (described below) from experiencing a fault condition.

FIG. 40 shows an illustrative embodiment method of operation of duty cycle protection circuit 660. At step 688, system 660 detects whether one or more actuator motors 604 are running, e.g., by detecting a signal from a motor sensor 546 or detecting that a signal to start one or more of actuators 48 has been received. In the illustrated embodiment, this occurs when any of the articulation control buttons (e.g., head up buttons 1551, 1520, head down buttons 1550, 1522, tilt button 1564, reverse tilt button 1566, etc.) of controllers 50, 52, 54 are activated (i.e., pressed by a patient or caregiver). Also, in the illustrated embodiment, articulation of a bed section will typically occur in response to activation of a control button for as long as the control button remains activated (until the travel limit is reached). If the patient or caregiver releases pressure from the control button, articulation will stop until the same button is pressed again, or another articulation button is activated. In alternative embodiments, a single press of an articulation button activates the articulation function, and a second press deactivates the articulation function.

If an articulation signal has been received, process 660 proceeds to step 690. At step 690, microcontroller 614 determines which actuators 48a, 48b, 48c, 48d, 48e, 48f have been activated, e.g., by reference to the correspondingly activated control button and the associated articulation function. For example, if head up button 1551 is activated, then head section actuator 48c is actuated. The maximum run time 662 is determined for the activated actuators 48 and stored in memory 616. The maximum run time may 662 vary depending on the particular actuator model used and/or its particular application. As mentioned above, the maximum run time 662 is typically defined by the manufacturer of the actuator. For example, for linear actuator model LA28, made by Linak A/S, the maximum run time is currently stated as 10% or 6 minutes per hour at continuous use. In the illustrative embodiment, the duty cycles of actuators 48 range from 20% to 80%, however, it is understood that the duty cycle for a suitable actuator may fall outside this range. Further, it is understood that other methods of determining maximum run time may be used, for example, depending upon the particular function to which actuator 48 is assigned.

At step 692, an application timer 625b for circuit 660 is started, in order to keep track of how long motor(s) 604 of activated actuator(s) 48 are running. At step 694, the actual current 668 is measured using an ammeter or other suitable means known in the art. Run time 666 is tracked by timer 625b.

At step 696, measured current 668 and run time 666 are analyzed by microcontroller 614. In the illustrated embodiment, run time 666 is evaluated by using an analysis of the rate of heat transfer in drive motor 604. It is known that as current increases, temperature increases, and that the rate of heat transfer is a function of conductivity and temperature gradient. Thus, the rate of heat transfer can be assessed based on the change in current 668 over time.

Before drive motor 604 has started running, e.g., when patient support 10 is first plugged in, run time 666 (e.g., the count of timer 625b) is initialized or set to zero. While drive motor 604 is running, timer 625b is incremented by a predefined amount which is based on the measured current 668. If current 668 is high, timer 625b will be incremented by a greater amount, and if current 668 is low, timer 625b will be incremented by a lesser amount. In the illustrated embodiment, different time increments are specified for four different ranges of current, e.g., timer 625b is incremented by 12, 14, 16 or 18 counts based on the amount of current 668 being drawn by drive motor 604.

If drive motor 604 stops running, timer 625b is decremented by a value "L" representative of the rate of heat transfer based on the known thermodynamics equation, $q=-K)T$, where q is the rate of heat transfer per unit area, $)T$ is the temperature gradient, and K is conductivity. The higher the level of the value of timer 625b, the greater the value "L" will be. In the illustrated embodiment, L is 1, 2, or 4 depending on how high timer 625b has been incremented.

If drive motor 604 is disconnected from power source 612, run time 666 (e.g., the count of timer 625b) is stored in memory 616. In this way, system 660 accounts for the fact that drive motor 604 may not have been disconnected from power for a significant time.

At decision step 698, if the drive run time 666 reaches or exceeds the predetermined run time threshold 662, the process proceeds to step 702. In the illustrated embodiment, this is determined by comparing the count of timer 625b (i.e., run time 666) to maximum run time 662.

At step 702, a fault condition is signaled and, at step 704, the current motor function (e.g., chair head up, head down, etc.) is deactivated or turned off. Also at step 702, logic may be used to allow certain emergency functions, such as CPR, to be activated prior to turning off the current motor function. For example, in the illustrated embodiment, CPR mode can still be activated at least one time after system 660 detects a duty cycle overrun. In response to a fault condition, microcontroller 614 may place patient support 10 in a "safe state" that minimizes hazards to patients, caregivers, associated individuals, equipment, and data, e.g., by signaling power source 612 to interrupt, disengage, or reduce current supplied to drive motor 604 of the activated actuator 48. Microcontroller 614 may also activate an audible or visual indicator to alert an operator that service is necessary on the affected drive or on the entire system. Such indication may be communicated to an operator by, for example, illuminating, blinking or flashing one or more LEDs located on one of controllers 50, 52, 54, or other suitable location on patient support 10.

At step 708, a timer 625c is started, which counts off a predefined wait period after which it is safe to restart the previously operating motor function. The wait period may be determined based on the value of run time 666 or maximum run time 662, or other criteria. For example, the wait period may be set equal to the maximum run time 662. In the illustrated embodiment, the wait period is set equal to half of the maximum run time 662.

At decision step 710, microcontroller 614 determines whether the wait period has expired. Step 710 is repeated until the wait period has expired. In the illustrated embodiment, when the wait period has expired, the motor function is restarted at step 712. However, it is understood that in other illustrative embodiments, it may not be necessary or desirable to restart the motor function and thus step 712 may be eliminated in those embodiments.

Returning to step 698, if run time 666 has not reached or exceeded maximum run time 662, the process proceeds to decision step 700. At step 700, system 660 determines whether drive motor 604 of the activated actuator 48 is still operating, e.g., by detecting a signal from a motor sensor 546 or by checking to see if one of the corresponding control buttons is activated. If the activated actuator 48 is still running, the process returns to step 694 to measure current 668 and run time 666. If actuator 48 is not still running, the process ends at step 706.

Thermal Protection

Figure 42:
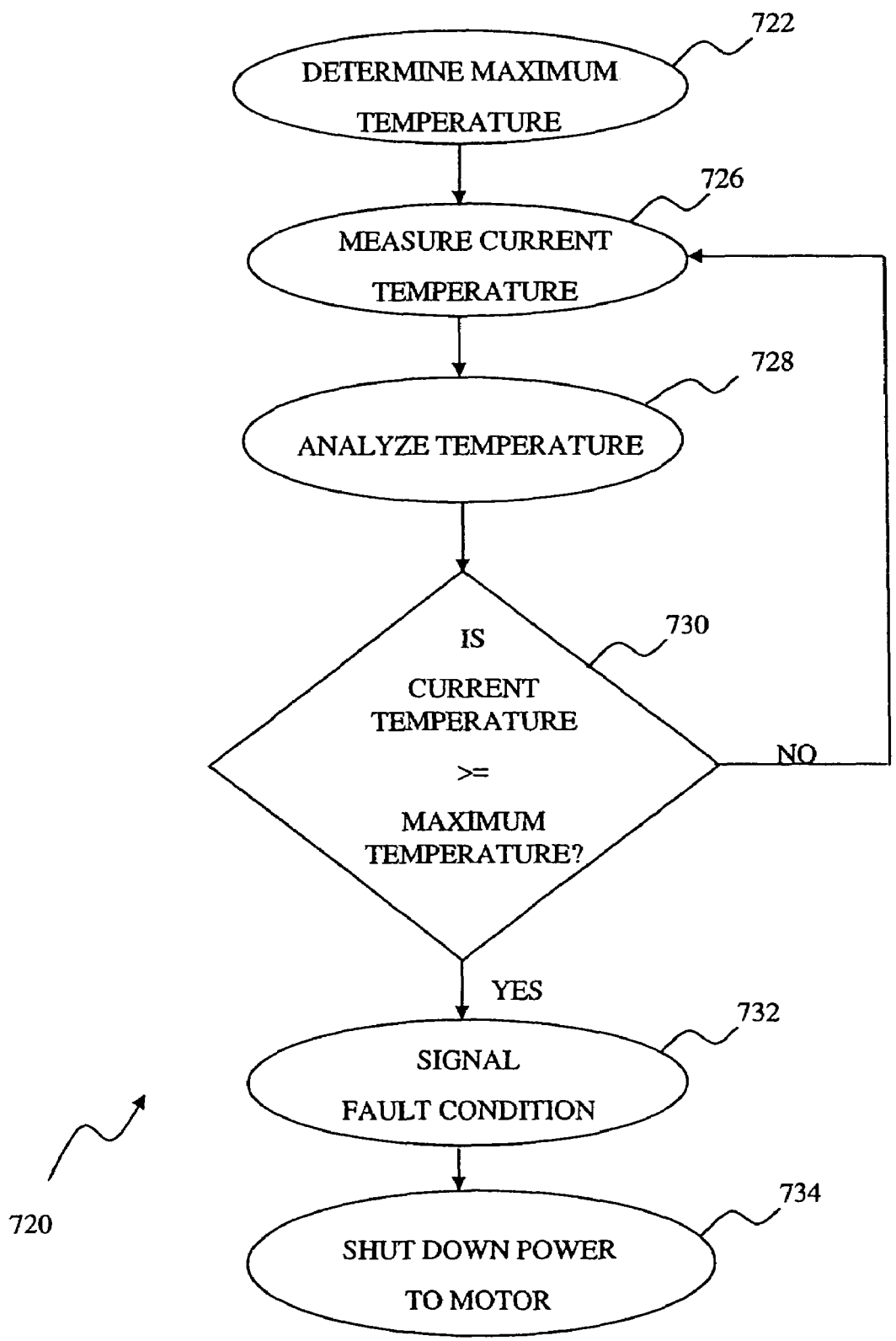
FIG. 42 is a flow diagram of an illustrative embodiment thermal protection process in accordance with the present invention.

To protect DC drive motors 604 from thermal overload during use in a hospital room environment, a method 720 for detecting thermal failure of the drive motors 604 is provided. A thermal overload condition can occur if, for example, failure of the current overload, interference/obstruction detection, or duty cycle protection mechanisms described above occurs. The presently described method 720 is adapted to the specific safety risks of a medical environment. An embodiment of the method is shown in FIG. 42.

At step 722, a maximum temperature 723 is determined for a drive motor 604 of a selected actuator 48. Maximum temperature 723 is typically determined by reference to the manufacturer's specifications for the particular actuator 48. However, it is understood that other means for determining maximum temperature 723, including experimentation, for example, under particular environmental conditions, may be used. Maximum temperature 723 is stored in memory 616.

Typically, activation of a selected actuator 48 occurs when a patient or caregiver selects the corresponding actuator control button on controller 50, 52, or 54, as described above. During operation of the selected actuator 48, a current temperature 724 of the drive 604 is measured inside the housing of drive motor 604, at step 726. Any suitable thermal sensing element, such as a conventional thermocouple, may be used to measure temperature 724. An application timer 625d is used to periodically sample temperature 724 during operation of actuator 48 as long as the drive is in operation and maximum temperature 723 has not been exceeded. Temperature 724 is converted to digital form by A/D converter 620 and is stored in memory 616.

At step 728, the temperature of drive motor 604 is analyzed. Current temperature 724 is compared to maximum temperature 723. At decision step 730, microcontroller 614 determines whether operation of actuator 48 should continue in view of current temperature 724. If current temperature 724 reaches or exceeds maximum temperature 723, the process 720 continues to step 732, where an error signal is generated. If current temperature 724 is less than maximum temperature 723, the process 720 returns to step 726.

At step 732, a fault condition is signaled and, at step 734, microcontroller 614 places patient support 10 in a safe state that minimizes hazards to patients, caregivers, associated individuals, equipment, and data, e.g., by signaling power source 612 to interrupt, disengage, or reduce current supplied to drive motor 604 of the activated actuator 48. Microcontroller 614 may also set a flag to indicate to an operator that service is necessary on the affected drive or on the entire system. Such indication may be communicated to an operator by illuminating, blinking or flashing one or more LEDs located on one of controllers 50, 52, 54, or other suitable location on patient support 10. In the illustrated embodiment, if measured temperature 724 exceeds maximum temperature 723, thermal failure is assumed and the drive 604 is automatically shut down. Typically, a bimetallic thermal switch located inside the motor housing opens to interrupt the current supply to drive 604.

Patient support surfaces, such as hospital beds, often include many features that are electrically powered. Such features include bed articulation controls that allow the various deck sections of the bed to be raised or lowered so that the bed can support patients in a number of different positions. There is a need for at least some of these bed controls to remain available when the bed's primary source of power is lost, i.e., due to a power outage, or while a patient is being transported from one hospital room to another.

Battery Backup System

As a result of government regulations that, for example, require hospital beds to be able to assume the emergency Trendelenburg position whether or not AC power is available, and for other reasons, existing hospital beds may include a battery backup system that powers the bed functions when AC power is not available. However, because hospital beds often require a substantial amount of power to operate the various features, a method to conserve battery power while maintaining compliance with existing regulations is desired.

As best shown in FIG. 31, frame 12 supports a battery enable switch 736. Battery enable switch 736 is a normally open contact, momentary function switch. In the illustrated embodiment, battery enable switch 736 is located on the portion of base frame 28 that is substantially underneath head section 38 of deck 26, however, it is understood that battery enable switch 706 could be located anywhere on base frame 28 or other area of patient support 10 as necessary or convenient. Battery enable switch 736 is electrically coupled to a battery 46, shown in FIGS. 2 and 31.

Battery enable switch 736 allows a person, such as a health care provider, to operate electrically-controlled bed functions (such as bed articulation functions) of patient support 10 using a backup power source (in the illustrated embodiment, battery system 46) when the primary power source 738 (e.g., AC power coupled to bed 10 by plug connection 45) is not available. Such instances may occur, for example, when a power outage occurs or when a bed 10 is being moved from one area of a hospital to another.

As shown in FIG. 31, battery enable switch 736 is a momentary switch, such as a push button. Switch 736 includes a light-emitting diode (LED) 737 or other suitable illuminating means known in the art, enclosed in or covered by a translucent or transparent housing made of plastic or other suitable material. The LED 737 is illuminated when either primary power source 738 is coupled to bed 10 through plug connection 45, or backup power or battery 46 is charged and supplying power to bed functions of patient support 10. When patient support 10 is disconnected from primary power source 738, or if backup power source 46 is discharged, the LED 737 is not illuminated. If primary power source 738 is disconnected and backup power source 46 is in need of power or is recharging, the LED 737 blinks or flashes intermittently on and off.

Figure 43:
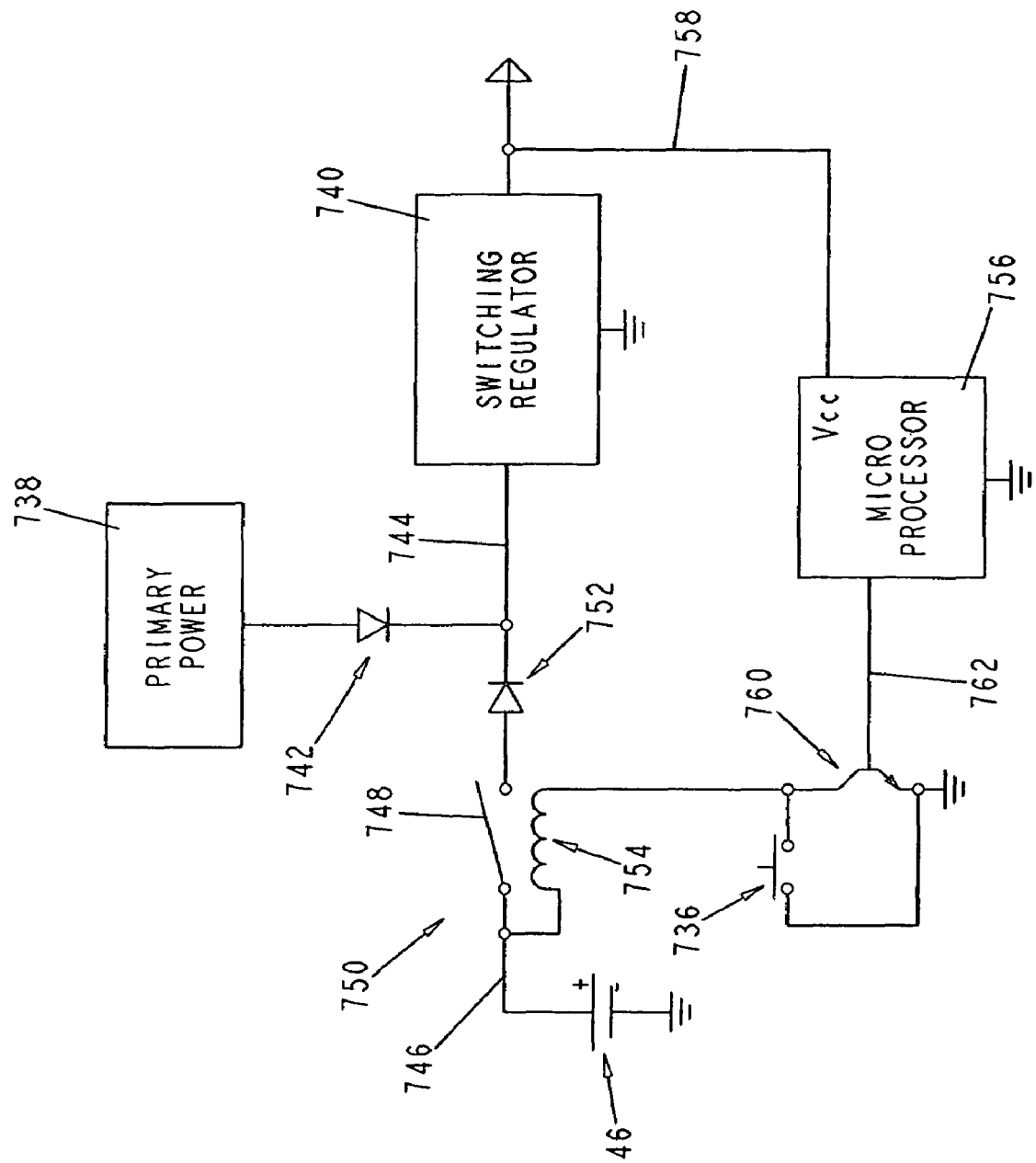
FIG. 43 is a block diagram of an illustrative embodiment battery enable switch apparatus in accordance with the present invention.

Circuitry for controlling the activation of backup power source 46 is included in control system 44. As illustrated in FIG. 43, primary power source 738 is connected to switching regulator 740 through diode 742 and connection 744. Backup power source 46 is connected to switching regulator 740 via connection 746, contact 748 of relay 750, diode 752 and connection 744. Switching regulator 740 provides power to at least the electrically-controlled bed functions that are required or desired to operate under backup power, such as bed articulation functions.

Relay 750 includes contact 748 and coil 754. When primary power source 738 is operating, voltage is applied to switching regulator 740 through connection 744 and to microprocessor 756 through connection 758. When voltage is not present on connection 758, microprocessor 756 senses the lack of primary power and closes contact 748 of relay 750 by energizing coil 754. Closing relay contact 748 provides sufficient backup power to the bed for a predetermined amount of time to allow an orderly shutdown of the bed functions. After the predetermined period of time expires, microprocessor 756 opens relay contact 748 to remove logic power from the bed functions and put patient support 10 into sleep mode.

When patient support 10 is in sleep mode, activation of battery enable switch 736, e.g., by momentarily pressing switch 736, causes patient support 10 to switch out of sleep mode. Activating switch 736 while primary power source 738 is operating has no effect.

In the illustrated embodiment, battery enable switch 736 is activated by the application of pressure on the housing, i.e., by depressing switch 736 with one's finger. In other embodiments, activating any one of the bed function control buttons located on controllers 50, 52, 54 while patient support 736 is in sleep mode will also switch it out of sleep mode.

When switch 736 is activated, sufficient power is provided from backup power source 46 so that at least certain required electrically operational functions of patient support 10, such as articulation of patient support 10, can be performed. In the illustrated embodiment, activation of switch 736 selectively powers certain bed functions, including the bed articulation functions, while other features, such as scale/ppm module 516 and dynamic surface module 518, are not powered by backup power source 46 in order to conserve power. Also, power is always provided to nurse call control 570, even when backup source 46 is in sleep mode. It is understood however, that control system 44 may be configured so that any particular combination of electrically-controlled features of patient support surface 10 (including scale/ppm module 516 and/or dynamic surface module 518) may be powered by backup power source 46.

When microprocessor 756 detects that no power is being supplied by primary power source 738, pressing switch 736 causes microprocessor 714 to apply voltage from backup power source 46 to energize relay coil 754 and close relay contact 748. Closing relay contact 748 again provides logic power to bed functions via switching regulator 740 and Vcc power to microprocessor 756. When microprocessor 756 receives power Vcc, it activates a transistor 760 through connection 762. Microprocessor 756 includes a timer and holds transistor 760 in an on or activated state for a predetermined period of time, as further explained below. When the predetermined period of time expires, microprocessor 756 turns off or deactivates transistor 760. Turning off transistor 760 shuts off logic power to the bed electronics, thus saving battery power.

Figure 44:
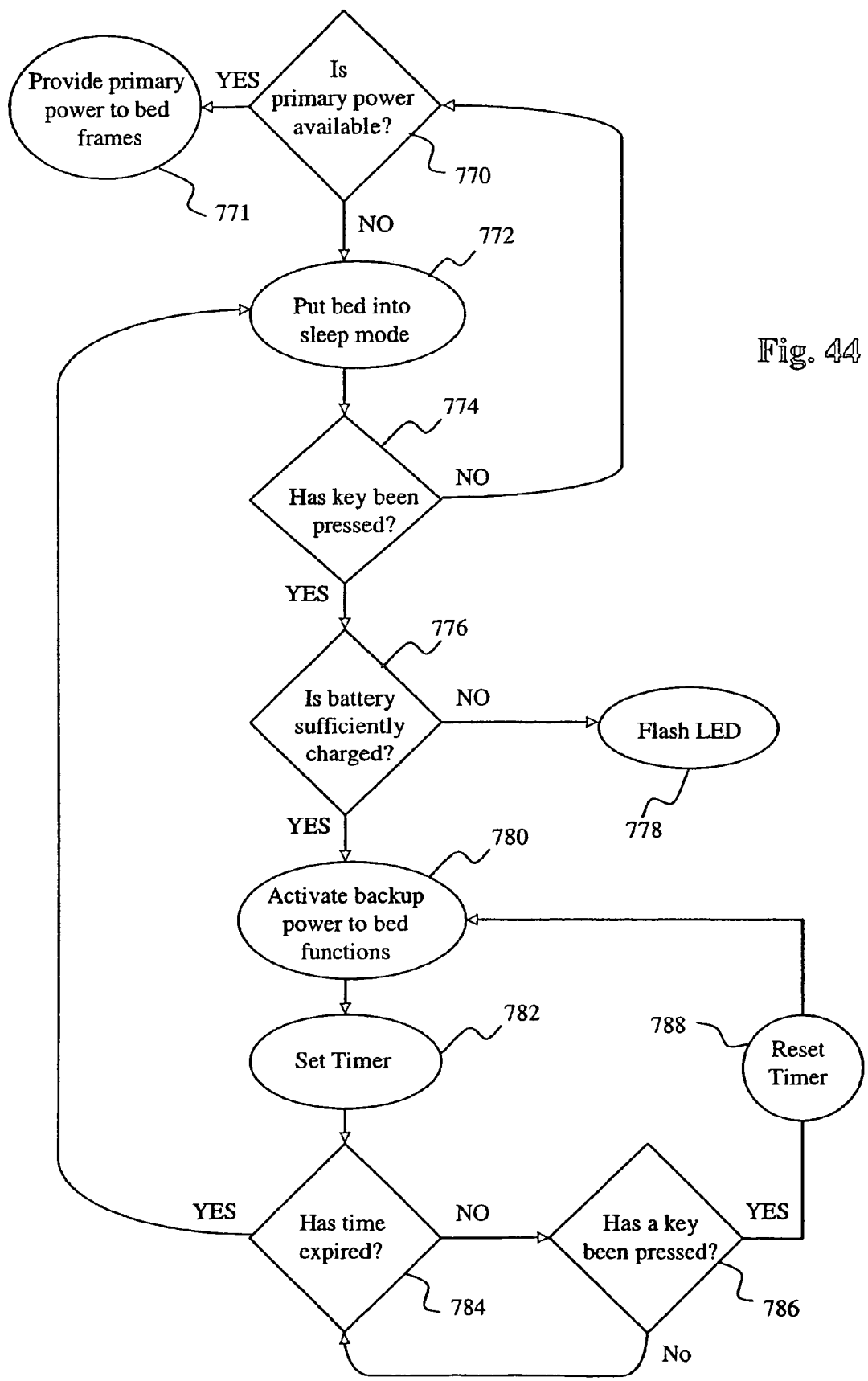
FIG. 44 is a flow diagram of a battery enable process.

FIG. 44 shows a flow diagram of an embodiment of the logic process encoded in microprocessor 756. At decision step 770, microprocessor 756 determines whether primary power source 738 is available. If primary power source 738 is operating, then normal power continues to be provided to the bed functions via primary power source 738, at step 771. Also, while primary power source 738 is operating, backup power source 46 is continuously charging as necessary.

If microprocessor 756 senses that primary power source 738 is not operating, electrically-controlled functions of patient support 10 are put into sleep mode as described above, at step 772.

At step 774, microprocessor 756 monitors the system to detect whether a bed function is activated or whether battery enable switch 736 is activated, e.g., by pressing a control button, key or switch. If no such function has been activated, microprocessor 756 returns to step 770, checks to see if primary power source 738 is available yet, and thereafter continues to either step 771 or 772 as described above.

If a key has been pressed, microprocessor 756 determines if backup power source 46 is sufficiently charged to provide power to the bed functions, at step 776. If backup power source 46 is in need of recharging, the LED 737 of battery enable switch 736 will begin flashing as described above, at step 778. If backup power source 46 is sufficiently charged, relay 750 is closed so that bed functions can be activated using backup power source 46, as described above, at step 780.

As mentioned above, microprocessor 756 includes a timer. At step 782, when backup power 46 is activated, microprocessor 756 sets the timer to count until one of the following occurs: a bed function control button is depressed, battery enable switch 736 is depressed, or a predetermined amount of time (e.g., 5 minutes) elapses. It is understood that in different embodiments, less than all of these conditions may be tested. For example, in one embodiment, pressing battery enable switch 736 may not interrupt the timer.

At step 784, microprocessor 756 determines whether the preset amount of time has elapsed. If the predefined time period has elapsed, the process returns to step 772, where the bed functions are put into sleep mode. If the time period has not elapsed, microprocessor 756 checks to see if another key (e.g., a bed function-activating key or the battery enable switch) has been pressed, at step 786. If no key has been pressed, the timer continues counting until the predetermined time period expires, at step 784.

If another key has been pressed, as determined at step 786, then the timer is reset at step 788. The process then returns to step 780 and backup power source 46 is reactivated or awakened out of sleep mode.

In this manner, backup power is conserved and, in embodiments where a battery 46 is used to support backup power system, a smaller battery can be used. At the same time, battery enable switch 736 permits patient support 10 to meet the above-mentioned regulatory requirements by enabling at least a portion of the bed's articulation features to be operable on backup power when needed.

Siderails and Headboard

Figure 45:
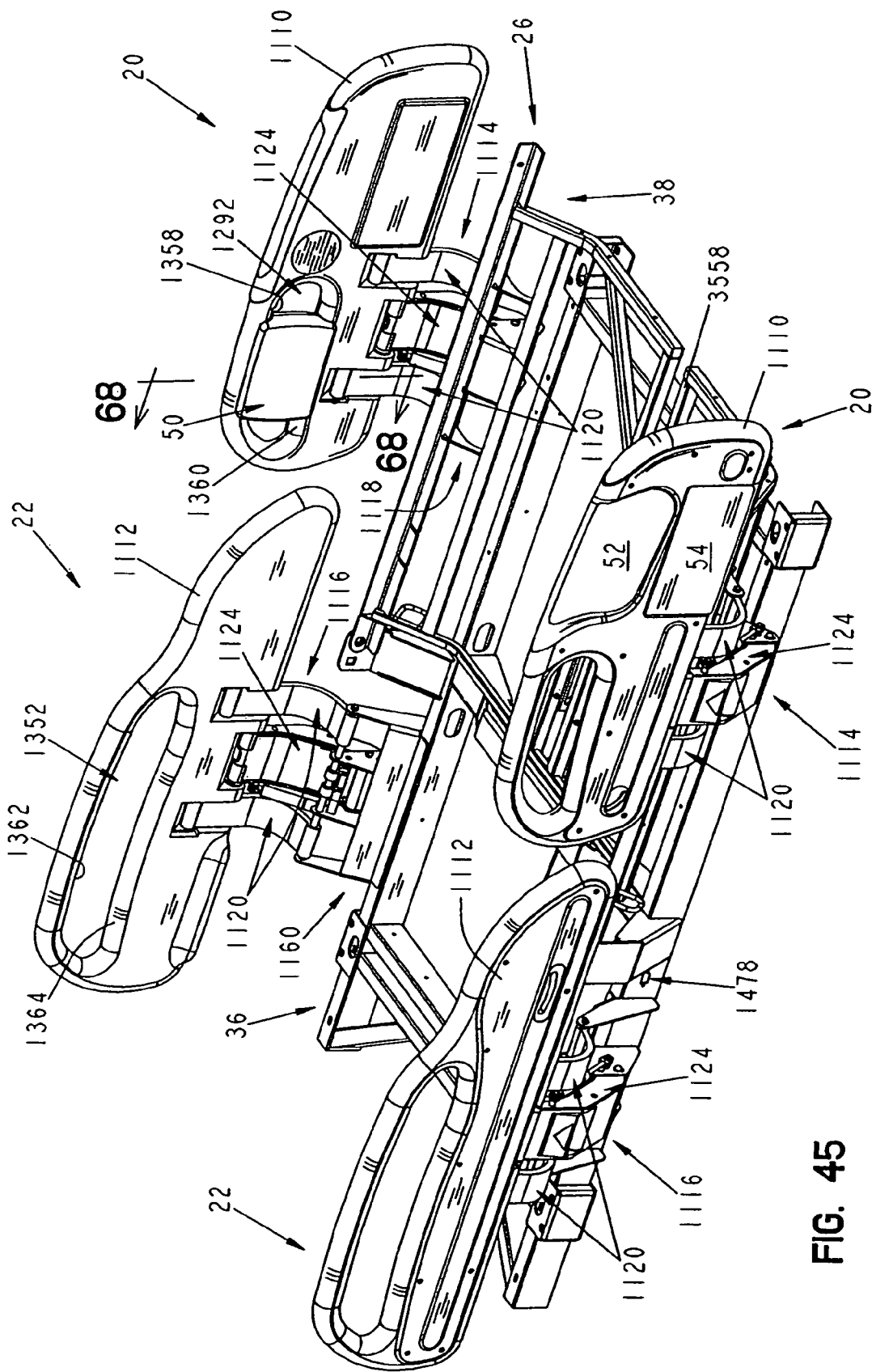
FIG. 45 is a perspective view of the weigh frame and portions of the deck of the patient support of FIG. 1, showing the illustrative head and foot end siderails in raised positions.
Figure 46:
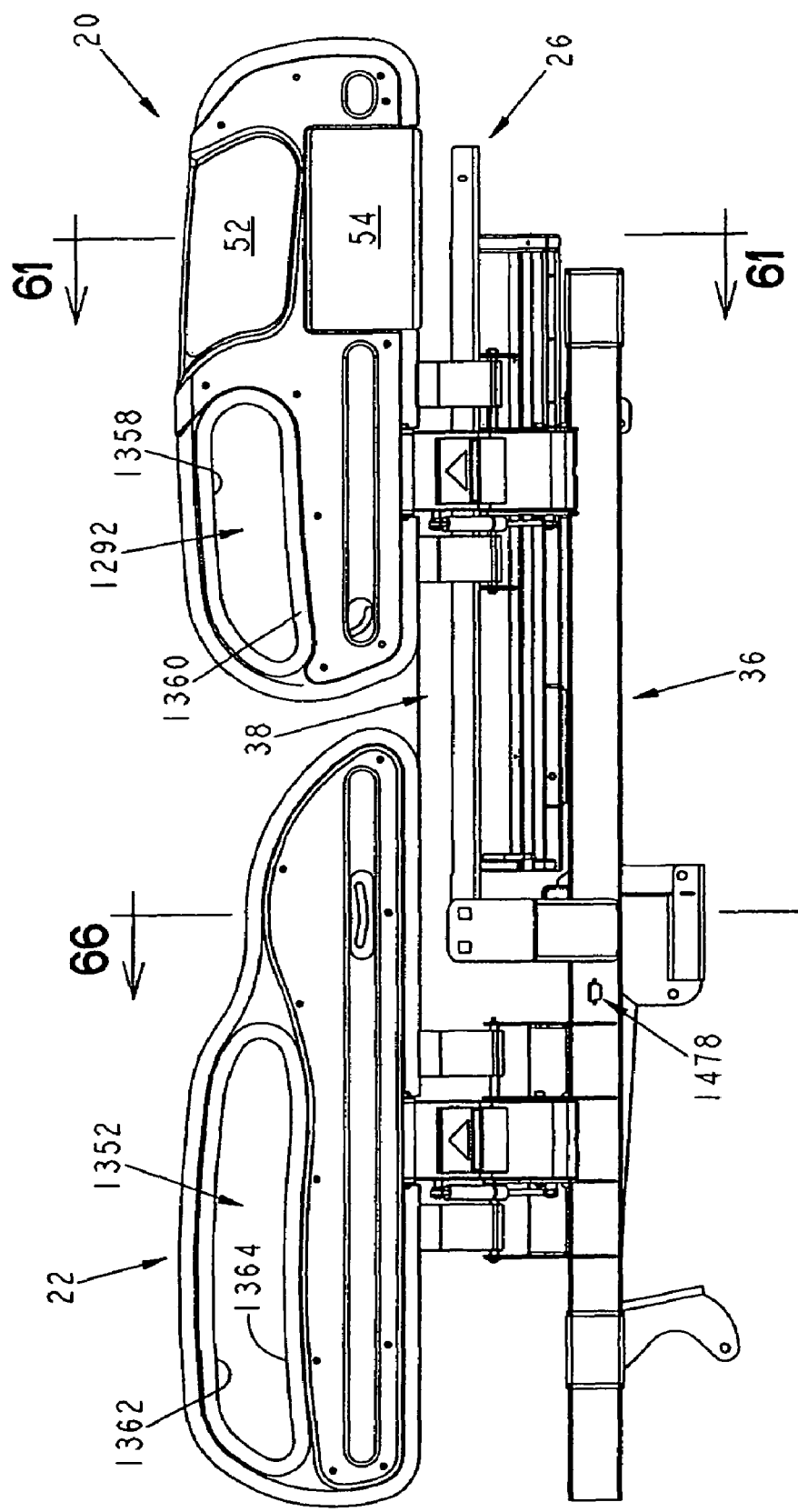
FIG. 46 is a side elevational view of the weigh frame and portions of the deck of FIG. 45, showing the head and foot end siderails in the raised positions.
Figure 47:
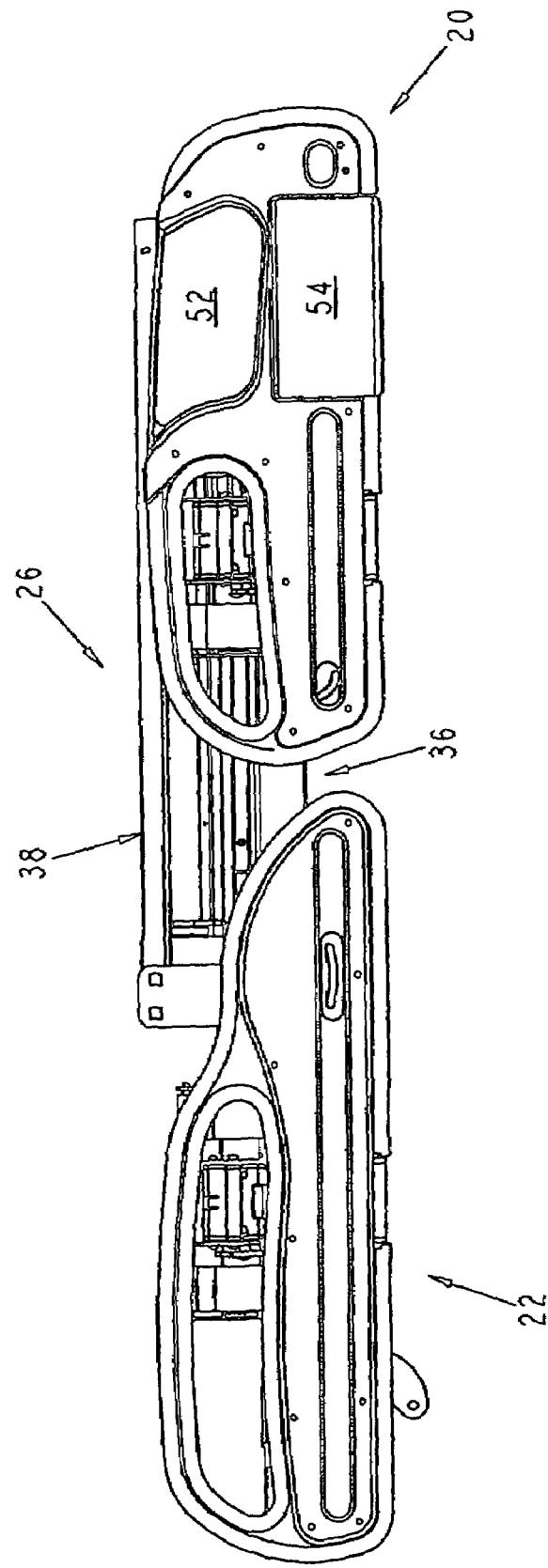
FIG. 47 is a view similar to FIG. 46, showing the head and foot end siderail in lowered positions.

Head and foot end siderails 20, 22 are configured to move between upper positions, as shown in FIGS. 1, 45, and 46, and lower positions, as shown in FIG. 47, to permit entry and egress of patients into and out of patient support 10. Head end siderails 20 are coupled to head section 38 and may be moved between raised and lowered positions. Foot end siderails 22 are coupled to weigh frame 36 and may also be moved between raised and lowered positions.

As head section 38 of deck 26 rotates relative to weigh frame 36, head end siderail 20 also rotates relative to weigh frame 36. However, regardless of the movement of sections 38, 40, 42, foot end siderails 22 do not move relative to weigh frame 36.

Siderails 20 include rail members 1110 and linkage assemblies 1114 coupled between rail members 1110 and head section 38 of deck 26 that permits rail members 1110 to be moved between upper and lower positions. Siderails 22 include rail members 1112 and linkage assemblies 1116 coupled between respective rail members 1112 and weigh frame 36 that permits rail members 1112 to be moved between upper and lower positions.

Figure 48:
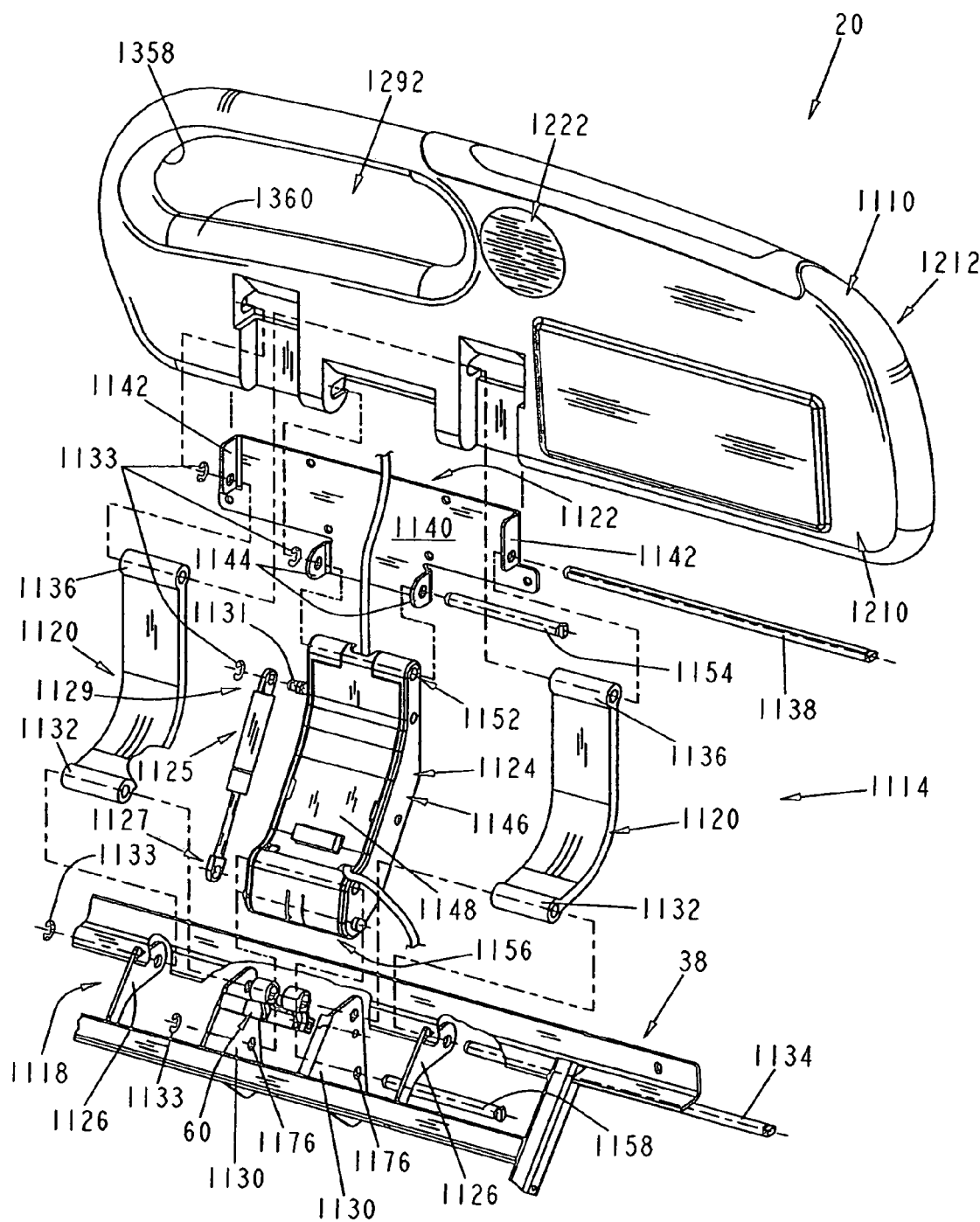
FIG. 48 is an exploded perspective view of the illustrative embodiment head end siderail of the patient support of FIG. 1.

As shown in FIGS. 45 and 48, linkage assembly 1114 of head end siderail 20 includes a first link 1118 rigidly coupled to head section 38, a pair of curved second links 1120 pivotably coupled to first link 1118, a third link 1122 pivotably coupled to second links 1120, and a curved fourth link 1124 pivotably coupled to third and first links 1122 and 1118. First link 1118 includes a pair of first flanges 1126 welded to head section 38 and a pair of second flanges 1130 welded to head section 38. Each second link 1120 includes a looped first end 1132 pivotably coupled to flanges 1126, 1130 by a rod 1134 and a looped second end 1136 pivotably coupled to third link 1122 by a rod 1138, as shown in FIG. 48.

Third link 1122 includes a base plate 1140, a first pair of inwardly extending flanges 1142 coupled to base plate 1140, and a second pair of inwardly extending flanges 1144 also coupled to base plate 1140, as shown in FIG. 48. Rod 1138 extends between flanges 1142 and through second ends 1136 of second link 1120 to provide the pivotable connection therebetween.

Figure 49:
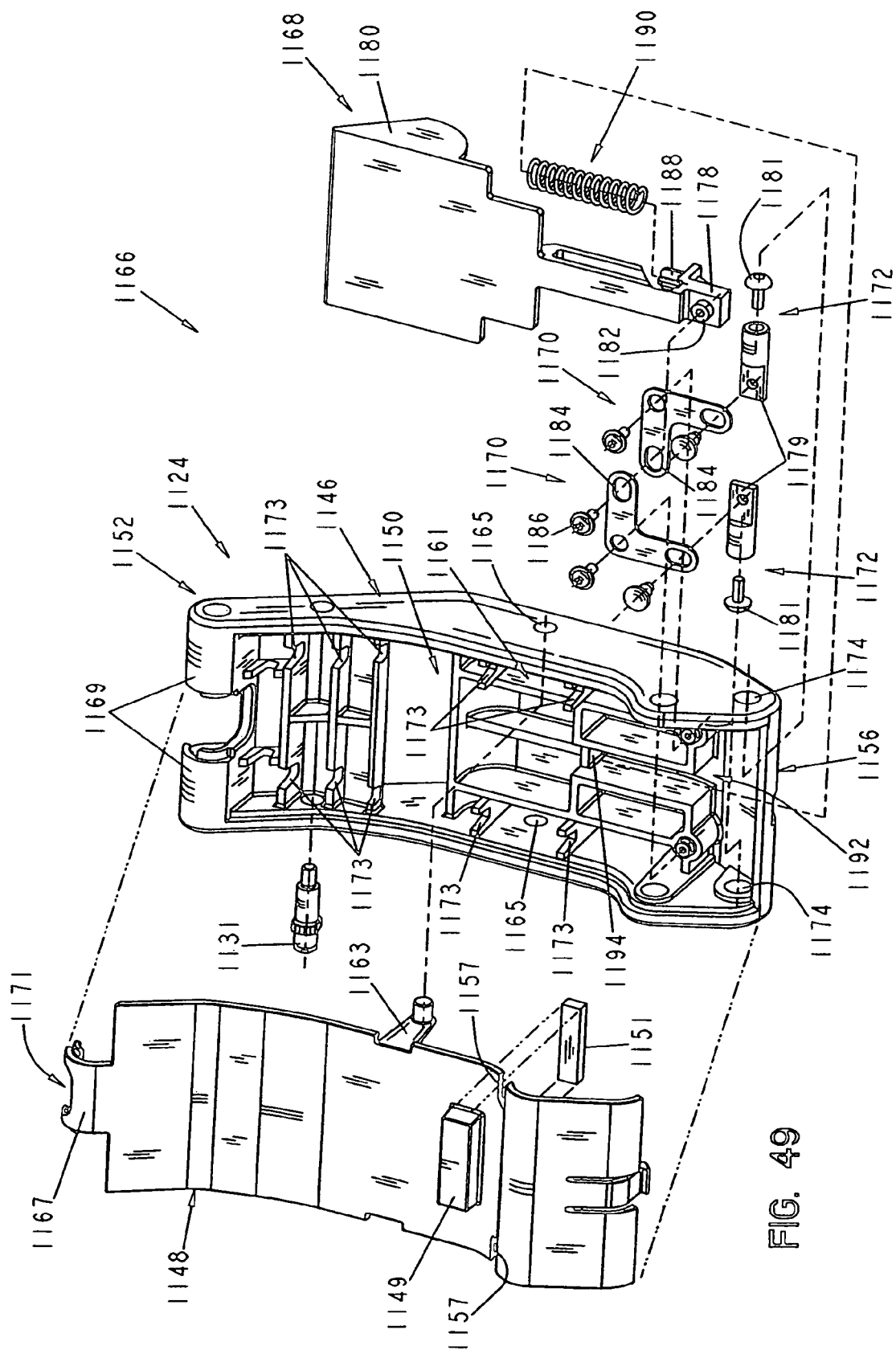
FIG. 49 is an exploded perspective view of a link of the head end siderail and a retainer or latch.

Referring to FIG. 49, fourth link 1124 includes a base 1146 and a cover 1148 that together define a latch-receiving void 1150. A first end 1152 of base 1146 is pivotably coupled to second pair of flanges 1144 of third link 1122 by a rod 1154. Similarly, a second end 1156 of base 1146 is pivotably coupled to the lower ends of flanges 1130 of first link 1118 by a rod 1158. Axial movement of each rod 1134, 1138, 1154, and 1158 is prevented by a C-shaped or open retaining ring 1133 of the type known in the art. Thus, linkage assembly 1114 provides a four bar linkage permitting head end siderail 20 to swing between the upper and lower positions.

A biasing device 1125, illustratively a conventional gas spring, may extend intermediate the first link 1118 and the fourth link 1124 in order to assist in the raising and lowering of the siderail 20. A first end 1127 of the biasing device 1125 is pivotably coupled to the rod 1134, while a second end 1129 of the biasing device 1125 is pivotably coupled to a connector 1131. The connector 1131 is illustratively coupled to the first end 1152 of the base 1146 of the fourth link 1124. The biasing device 1125 illustratively provides an upwardly acting force to control the rate of descent of the siderail 20 and to assist the caregiver 56 in raising the siderail 20.

Cover 1148 includes a pocket 1149 sized to receive a rectangular magnet 1151 therein. Magnet 1151 is coupled to cover 1148 and rotates with fourth link 1124 during raising and lowering of head end side rail 20. Hall effect sensor 60 is coupled to flanges 1130 of first link 1118 and rod 1134 to detect the position of magnet 1151. Based on this position, control system 44 knows when head end rail 20 is in the raised position and the lowered position.

Figure 50:
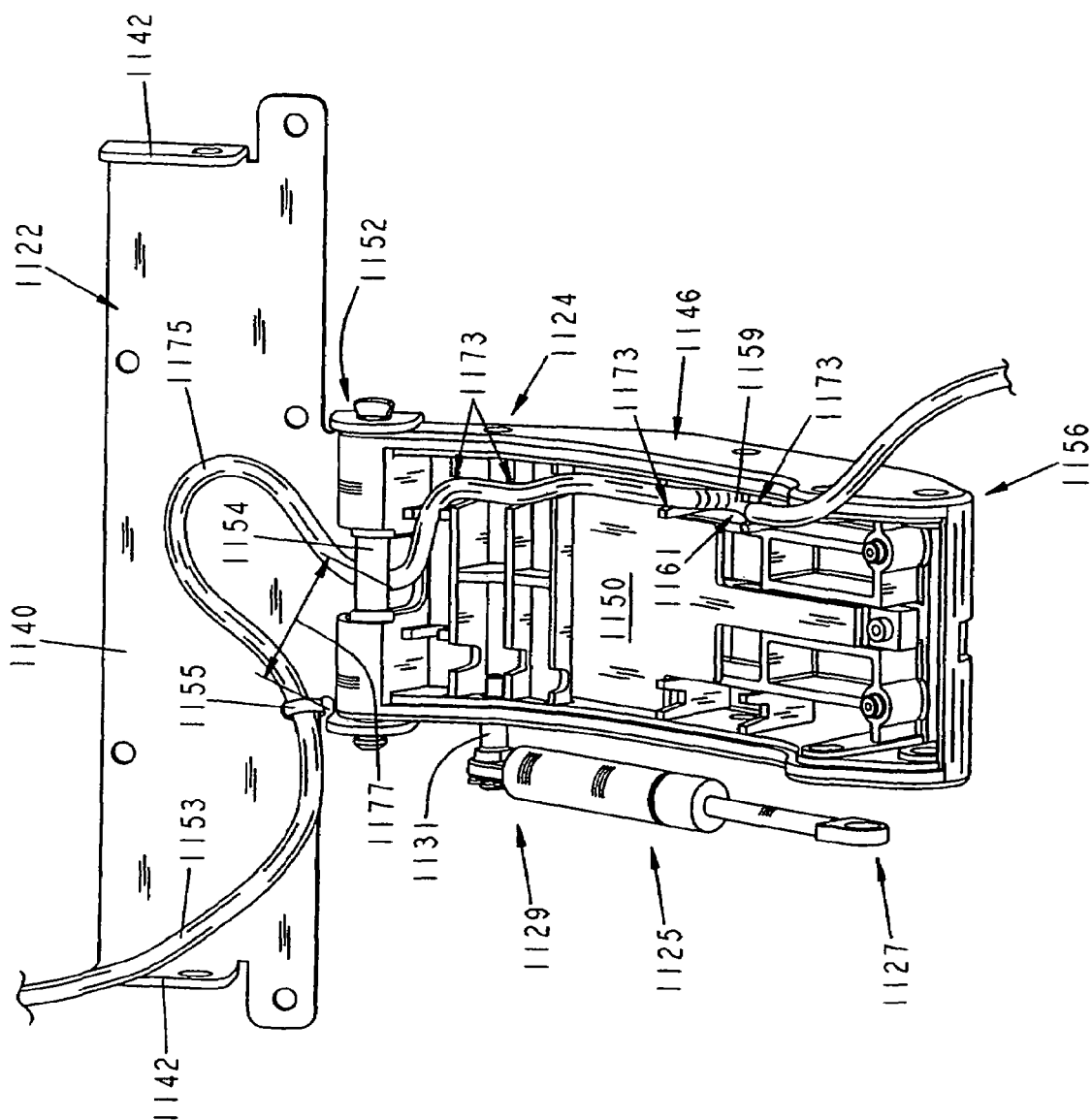
FIG. 50 is a perspective view of the link of FIG. 49, with the cover removed, illustrating a cord extending therethrough.

With reference to FIGS. 48-50, an electrical communication cord 1153 extends into latch-receiving void 1150 under rod 1154 and is coupled to third link 1122 by a cable tie 1155. Cover 1148 includes slits 1157 configured to receive cord 1153 which extends into void 1150. A portion 1159 of cord 1153 extends down into a pocket portion 1161 of void 1150 to provide clearance for tabs 1163 of cover 1148 that snap into apertures 1165 of base 1146.

As shown in FIGS. 49-50, cover 1148 includes a pin-receiving portion 1167 positioned between pin-receiving portions 1169 of base 1146. Pin-receiving portion 1167 includes a notch or slit 1171 through which cord 1153 extends from void 1150. As shown in FIGS. 49 and 50, base 1146 further includes a plurality of notches 1173 having a width slightly smaller than the diameter of cord 1153. Cord 1153 is positioned in these notches 1173 to limit movement of cord 1153 in void 1150.

Cord 1153 includes a portion or loop 1175 extending from notch 1171 to cable tie 1155. Portion 1175 is about three times as long as a distance 1177 from cable tie 1155 to notch 1171. This additional length provides stress relief by reducing the amount of tension on cord 1153 and chaffing of cord 1153 during raising and lowering of siderail 20.

Figure 51:
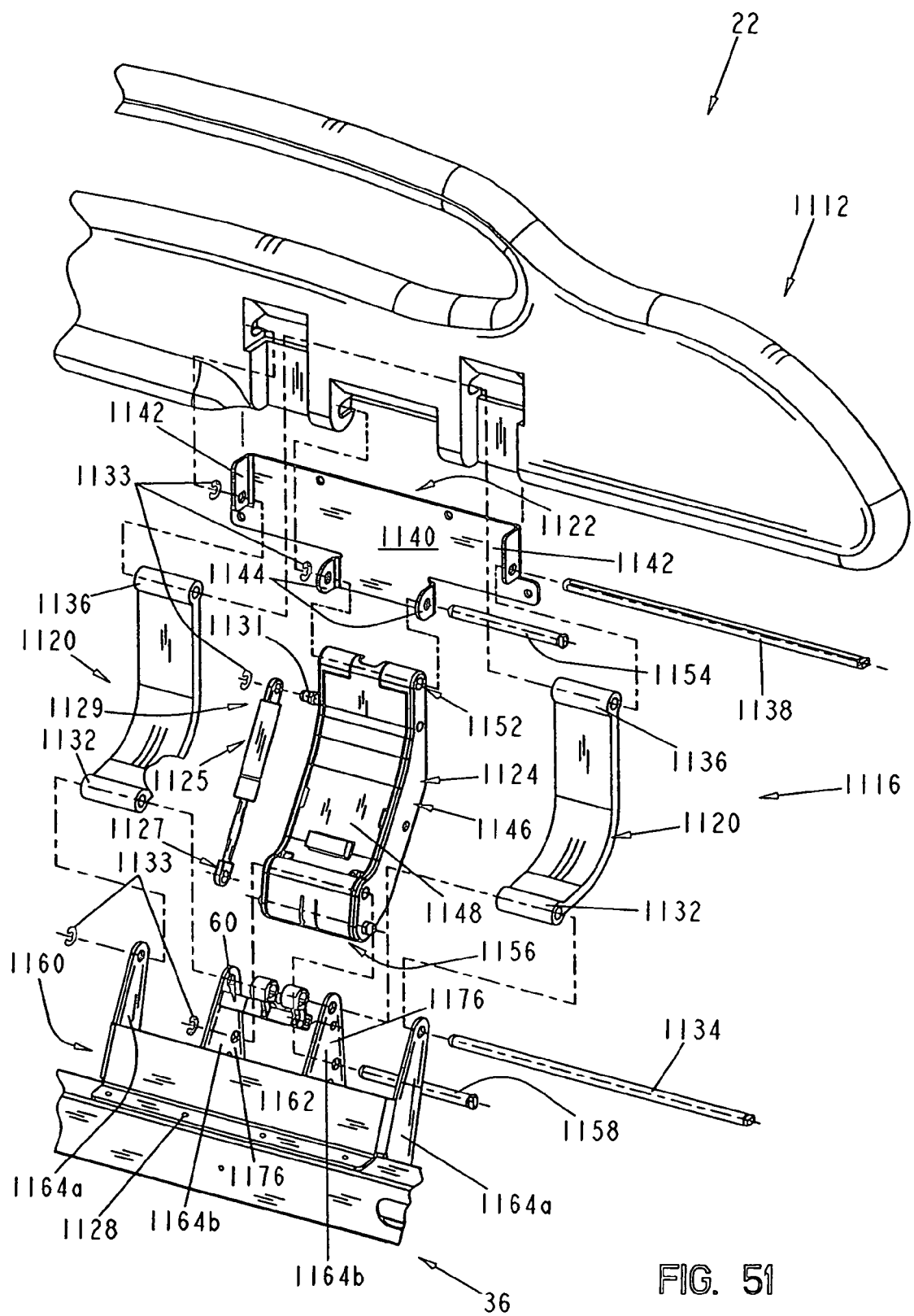
FIG. 51 is an exploded perspective view of the illustrative embodiment foot end siderail of the patient support of FIG. 1.

Referring to FIGS. 45 and 51, linkage assembly 1116 of foot end siderail 22 is substantially similar to linkage assembly 1114 of head end siderail 20. Linkage assembly 1116 includes a first link 1160 rigidly coupled to weigh frame 36, pair of curved second links 1120 pivotably coupled to first link 1160, third link 1122 pivotably coupled to second links 1120, and curved fourth link 1124 pivotably coupled to third and first links 1122, 1160 as shown in FIG. 51.

First link 1160 includes a base 1162 coupled to weigh frame 36 by fasteners 1128 and having outer and inner pairs of upwardly extending flanges 1164a, 1164b rigidly coupled to base 1162. Each second link 1120 has its looped first end 1132 pivotably coupled to flanges 1164a, 1164b of first link 1162 by rod 1134 and has its looped second end 1136 pivotably coupled to flanges 1142 of third link 1122 by rod 1138. First end 1152 of base 1146 of fourth link 1124 is pivotably coupled to flanges 1144 of third link 1122 by rod 1154. Second end 1156 of base 1146 is pivotably coupled to the lower ends of inner flanges 1164b of first link 1160 by rod 1158. The base plate 1140 of the third link 1122 is coupled to the body of the rail member 1112. Axial movement of each rod 1134, 1138, 1154 and 1158 is prevented by a C-shaped or open retaining ring 1133 of the type known in the art. Thus, linkage assembly 1116 provides a four bar linkage permitting foot end siderail 22 to swing between the upper and lower positions.

Figure 53:
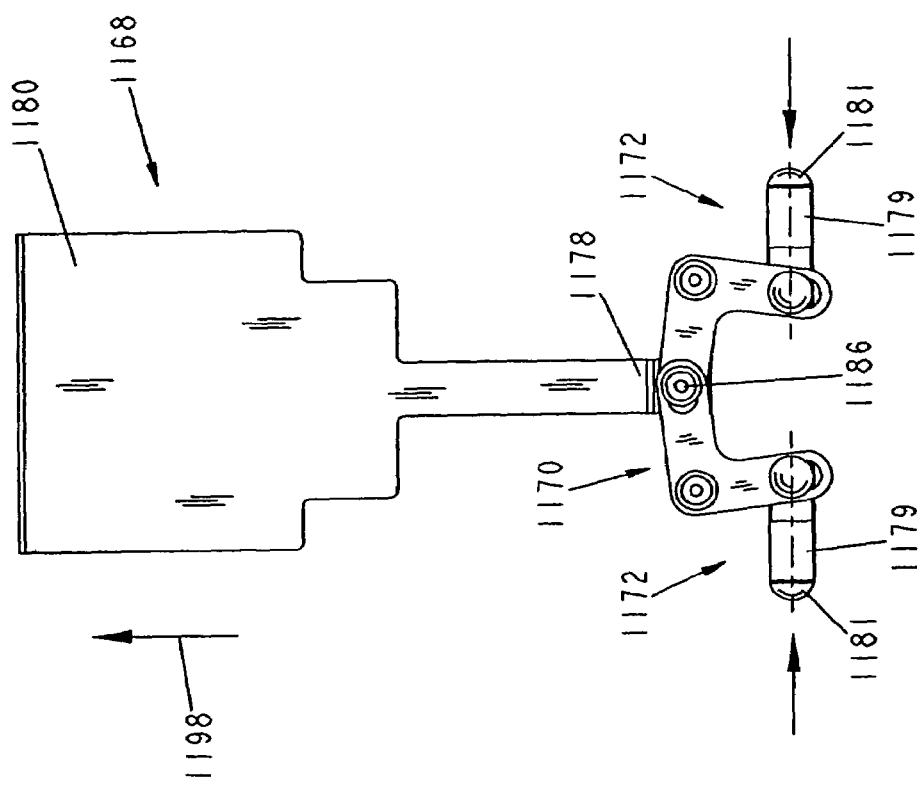
FIG. 53 is a view similar to FIG. 52, showing the latch in an unlatched position.
Figure 52:
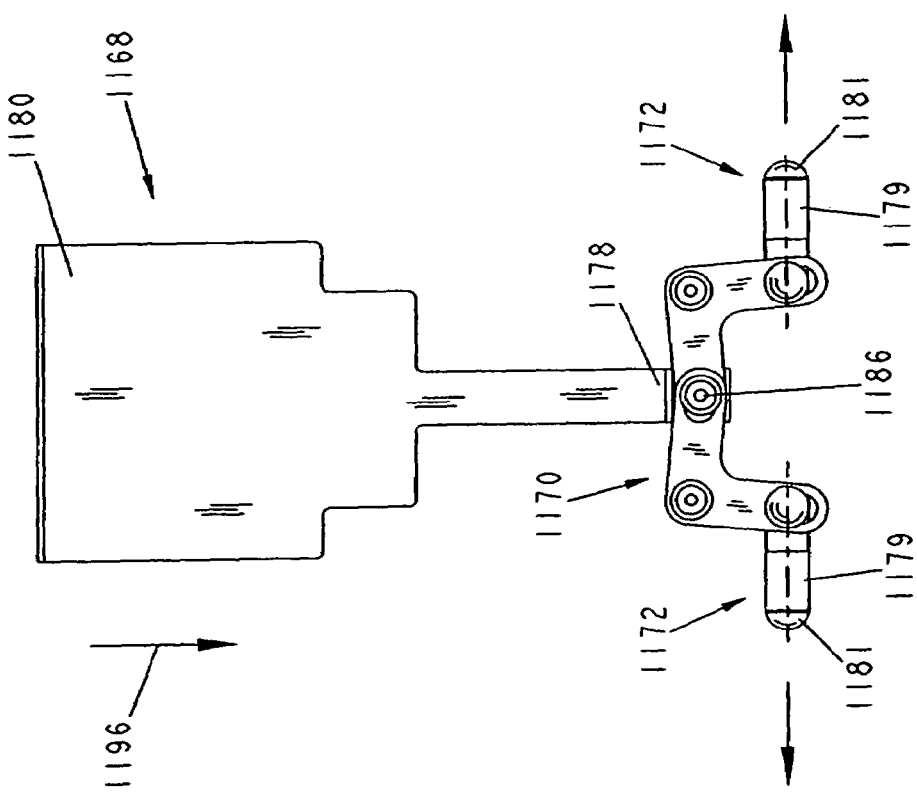
FIG. 52 is a top plan view of the latch in a latched position.

Each siderail 20, 22 further includes a retainer 1166 configured to "bind" the four bar linkage to prevent siderails 20, 22 from moving from the upper position to the lower position. As shown in FIG. 49, retainer 1166 includes a slide or handle member 1168 positioned in void 1150 to slide relative to base 1146 and cover 1148 of fourth link 1124 to move between a latched position, as shown in FIG. 52, and an unlatched position, as shown in FIG. 53, a pair of L-shaped rocker arms or members 1170 pivotably coupled to base 1146, and a pair of latch members or pins 1172 pivotably coupled to respective rocker arms 1170. Pins 1172 extend through apertures 1174 in base 1146 into apertures 1176 in respective flanges 1130, 1164 of respective first links 1118, 1160. Pins 1172 include body members 1179 and head members 1181 inserted into body members 1179.

Handle member 1168 includes a first end 1178 pivotably coupled to rocker arms 1170 and a second end or handle portion 1180 accessible from an handle opening 1183 in base 1146 as shown in FIGS. 54 and 55. First end 1178 includes a boss or lug 1182 positioned in slots 1184 defined in rocker arms 1170. A shoulder screw 1186 is provided to retain rocker arms 1170 on boss 1182. First end 1178 further includes a spring seat or mount 1188.

A spring 1190 is positioned in a spring-receiving channel 1192 defined by base 1146. Spring 1190 is positioned between spring seat 1188 and a wall 1194 of base 1146 to bias handle member 1168 downwardly in direction 1196 (FIGS. 52 and 54). Because slide member 1168 is biased in direction 1196, pins 1172 are biased outwardly into apertures 1176 in respective flanges 1130, 1164 of respective first links 1118, 1160. When pins 1172 are positioned in apertures 1176 of respective first links 1118, 1160, respective fourth links 1124 are coupled together at two axially spaced apart locations. This prevents rotation of respective linkage assemblies 1114, 1116 to prevent siderails 20, 22 from swinging to the lower position.

To unbind linkage respective assemblies 1114, 1116 and permit respective siderails 20, 22 to swing to the down position, pins 1172 must be moved from the latched position (FIGS. 52 and 54) to the unlatched position (FIGS. 53 and 55). A caregiver can unlatch pins 1172 by pulling upwardly on handle portion 1180 of slide member 1168 in direction 1198. This movement causes rocker arms 1170 to rotate about boss 1182 and pulls pins 1172 inwardly out of apertures 1176 of respective first links 1118, 1160 of linkage assemblies 1114, 1116 so that pins 1172 no longer binds respective first links 1118, 1160 and respective fourth links 1124.

Because respective first links 1118, 1160 and respective fourth links 1124 are free to pivot relative to one another, respective linkage assemblies 1114, 1116 are also unbound and free to permit siderails 20, 22 to swing between the upper and lower positions. According to alternative embodiments of the present disclosure, other retainers are provided to hold the siderails in the upper position such as clasps, catches, locks, other latches, clamps, pins, bolts, bars, hasp, hooks, or other retainers known to those of ordinary skill in the art.

Figure 56:
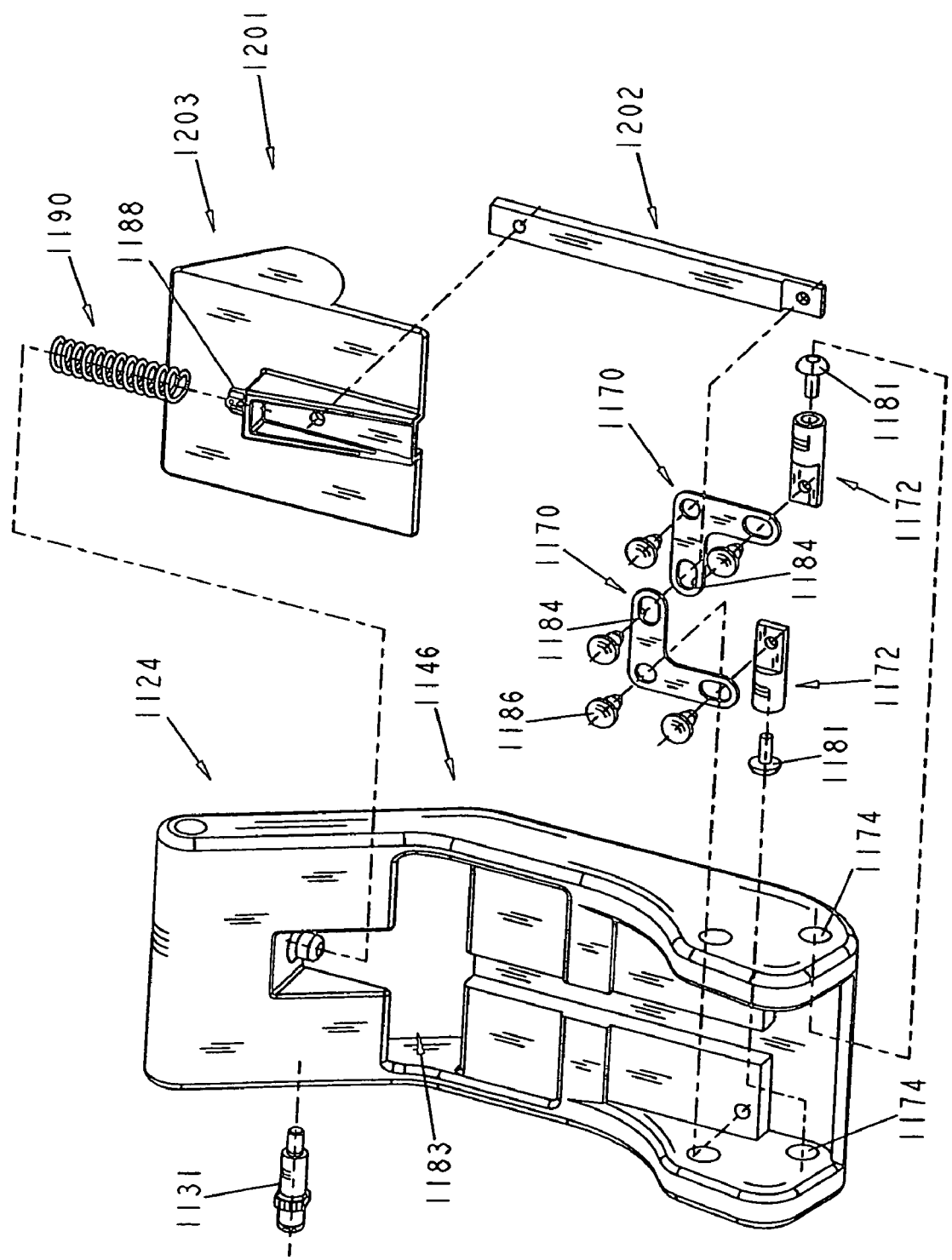
FIG. 56 is an exploded perspective similar to FIG. 49, illustrating an alternative embodiment latch.

An alternative embodiment slide or handle member 1201 is shown in FIG. 56. Handle member 1201 includes a bar member 1202 pivotably coupled to rocker arms 1170 and a second end or handle portion 1203 coupled to bar member 1202 and accessible from handle opening 1183 in base 1146. Shoulder screw 1186 is positioned in slots 1184 defined in rocker arms 1170 and is coupled to bar member 1202.

As shown in FIG. 1, when siderails 20, 22 are in upper position, rail members 1110, 1112 block a patient's egress from patient support 10. As shown in FIG. 19, siderail 22 and a lip or upper deck portion 263 of deck 26 cooperate to define a gap 1185 therebetween. According to an illustrative embodiment, gap 1185 is defined to be less than 60 millimeters. Similarly, the gap between siderail 22 and deck 26 is defined to be less than 60 millimeters.

FIG. 57 illustrates a patient support 109 including alternative embodiment siderails 209, 229 which are configured to move between upper positions and lower positions to permit entry and egress of patients into and out of patient support 109 in a manner similar to siderails 20, 22. As such, siderails 209, 229 are substantially similar to siderails 20, 22 and like reference numbers are used to identify like components.

Head end siderails 209 are coupled to head section 389 and may be moved between raised and lowered positions. Head board 169 extends between head end siderails 209. Foot end siderails 229 are coupled to weigh frame 36 and may also be moved between raised and lowered positions.

Siderails 209 include rail members 11109 and linkage assemblies 1114 coupled between rail members 11109 and head section 389 of deck 269 that permits rail members 11109 to be moved between upper and lower positions. Siderails 229 include rail members 11129 and linkage assemblies 1116 coupled between respective rail members 11129 and weigh frame 36 that permits rail members 11129 to be moved between upper and lower positions.

Figure 58:
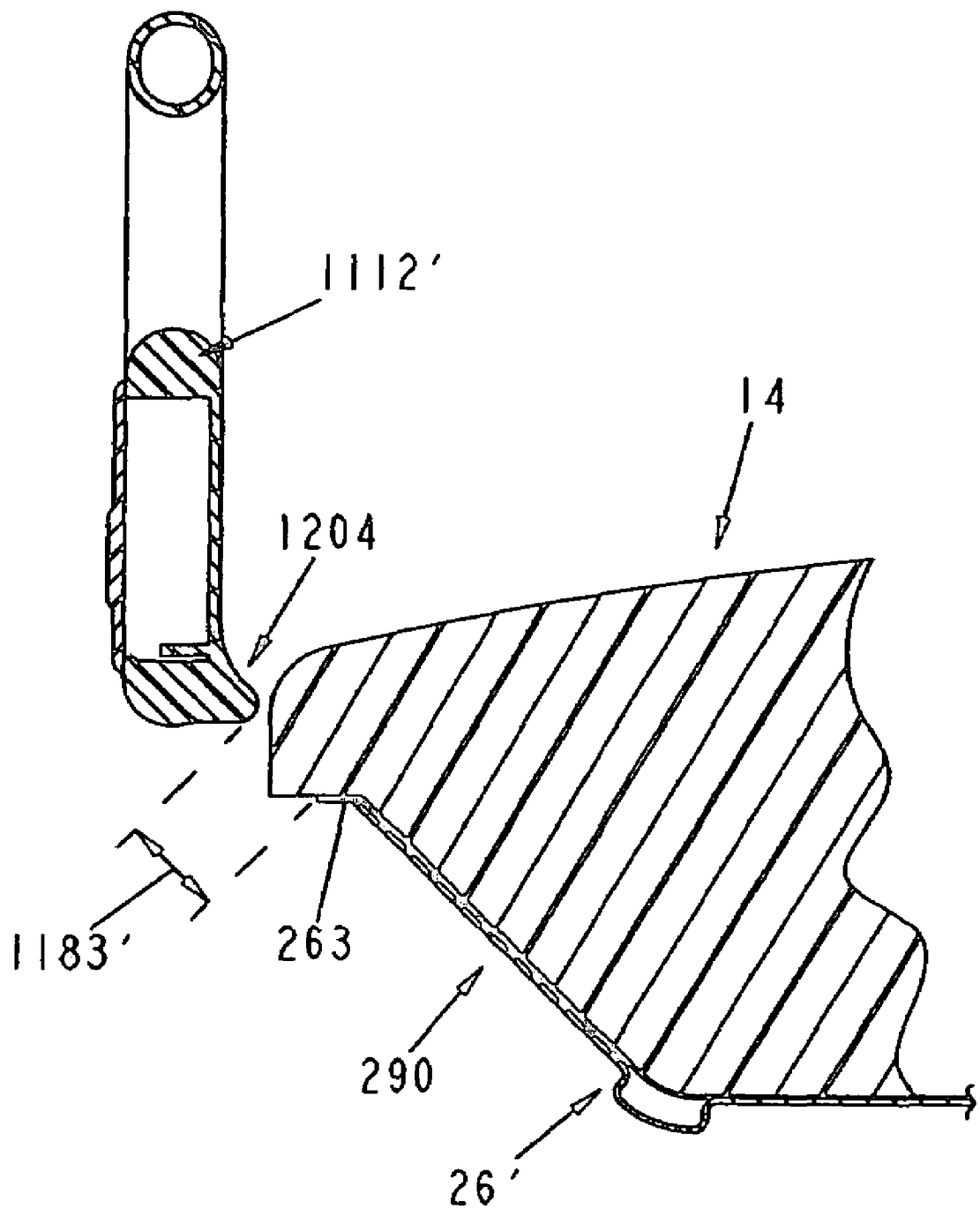
FIG. 58 is a cross-sectional view taken along lines 58-58 in FIG. 57 showing a gap defined between the deck and one of the foot end siderails and the foot end siderail including a bump to narrow the gap.

As shown in FIG. 57, when siderails 209, 229 are in upper position, rail members 11109, 11129 block a patient's egress from patient support 109. As shown in FIG. 58, foot end rail 229 includes a ridge or bump 1204 coupled to rail member 11129. Bump 1204 and a lip or upper deck portion 263 of first leg section member 290 of leg section 42 of deck 269 cooperate to define a gap 11839 therebetween. Bump 1204 reduces the width of gap 11839. According to the present disclosure, gap 11839 is less than 60 millimeters. Without bump 1204, gap 11839 between first leg section member 290 and rail 11129 would be wider than the gap between second leg section member 292 and rail 11129 because first leg section member 290 is not as wide as second leg section member 292 as shown in FIG. 21. The gap between rail 11129 and second leg section member 292 is also less than 60 millimeters. The gap between rail 11109 and deck 269 is also less than 60 millimeter.

Figure 59:
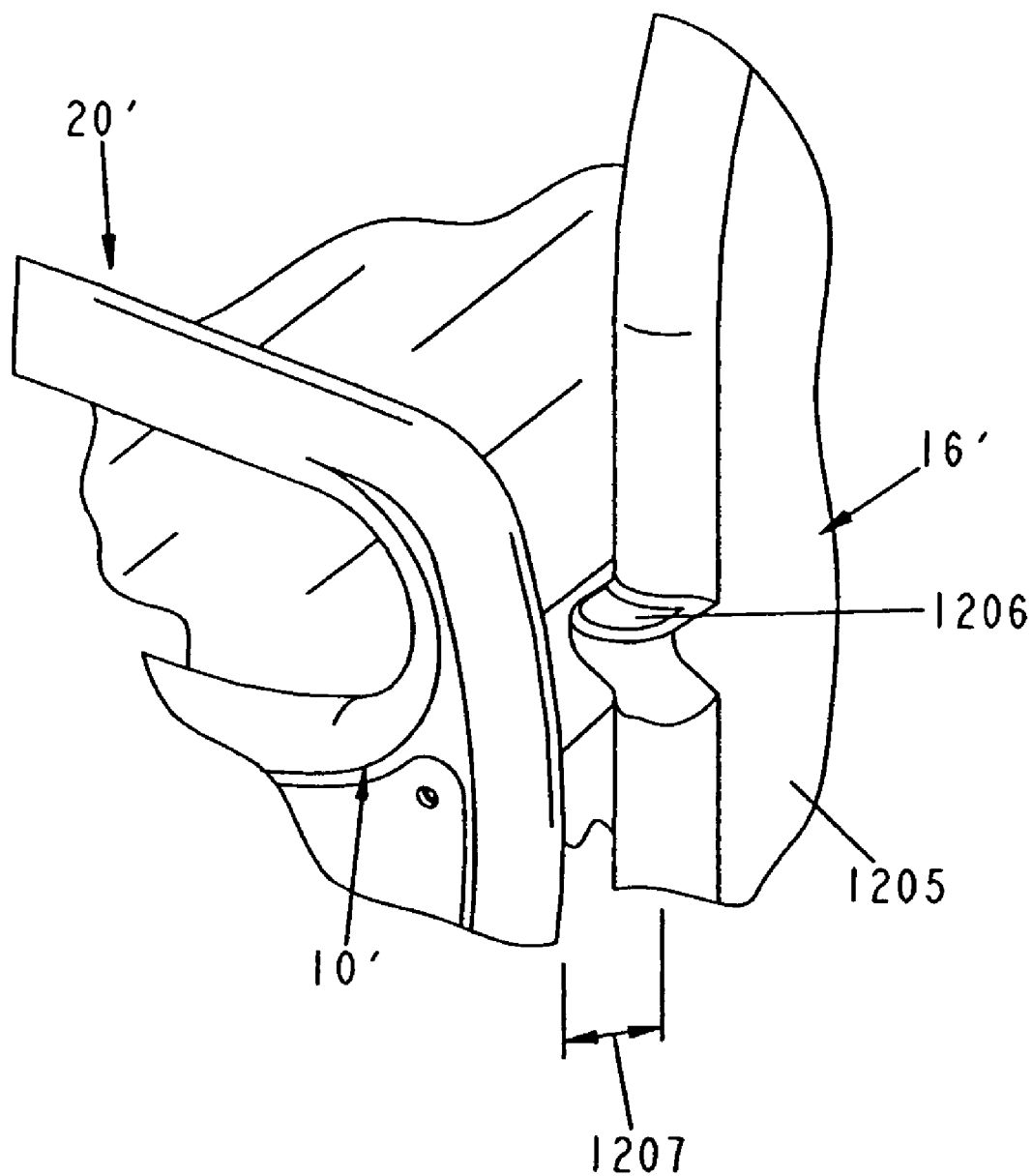
FIG. 59 is an enlarged view of a portion of FIG. 57 showing the headboard and one of the head end siderails cooperating to define a gap therebetween and the headboard including a bump to narrow the gap near the top portion of the head end siderail.

As shown in FIG. 59, headboard 169 includes a main body 1205 and a shelf or bump 1206 on each end of main body 1205. Headboard 169 and head end siderail 209 cooperate to define a gap 1207 therebetween at each end of main body 1205. Each shelf 1206 narrow gaps 1207 near the top of head end siderails 209 when siderails 209 are positioned adjacent headboard 169. According to an alternative embodiment of the present disclosure, a bump is provided on the footboard 18. According to another alternative embodiment of the present disclosure, no bump is provided on the headboard 169.

Figure 60:
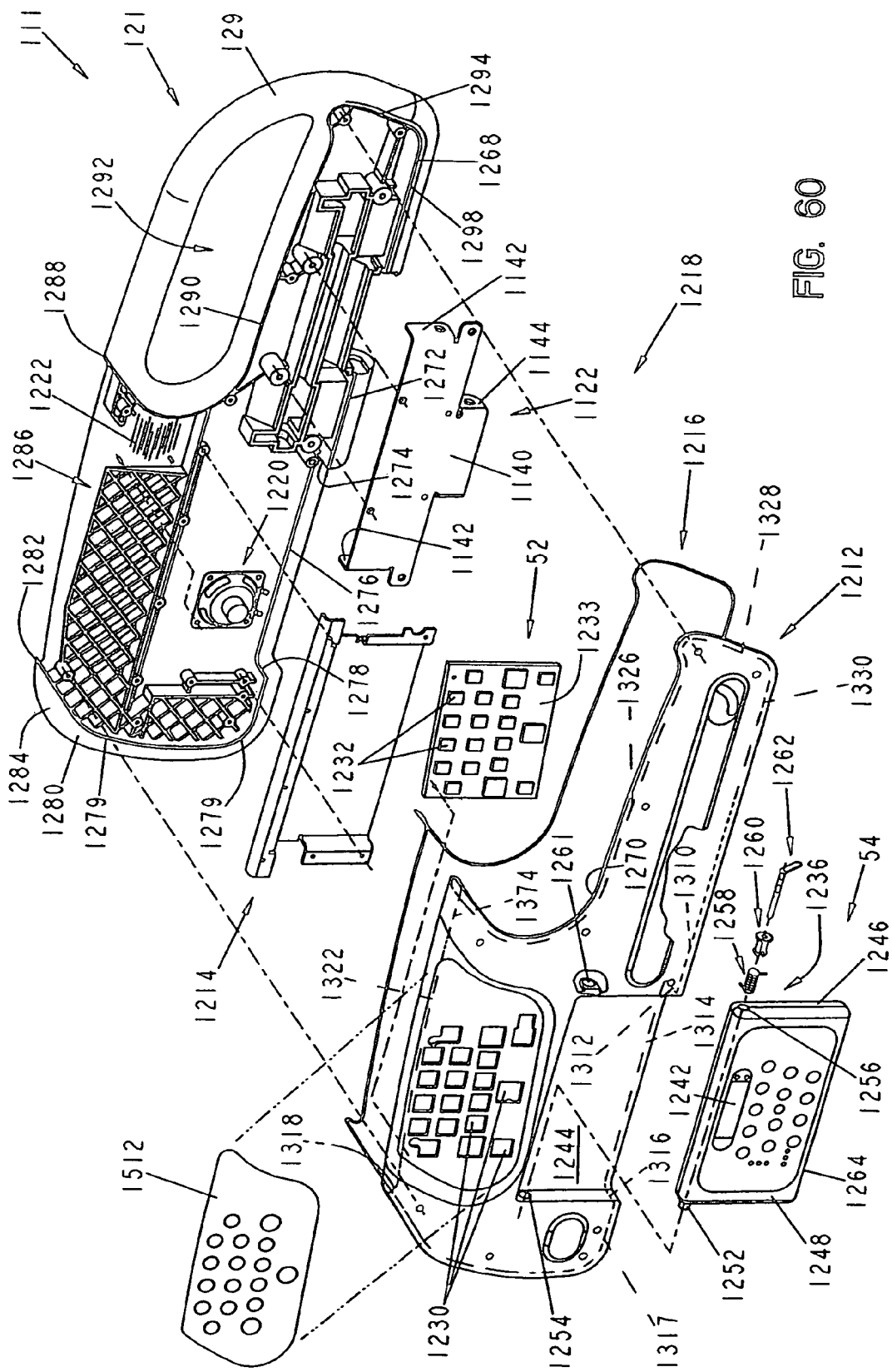
FIG. 60 is an exploded perspective view of an illustrative embodiment rail member of the head end siderail.

Returning now to the illustrative embodiment siderails 20, 22 of FIGS. 45-55, rail member 1110 of head end siderail 20 includes a main body 1210, a cover 1212, and a brace 1214 (FIGS. 48 and 60). An O-ring seal 1216 is provided between main body 1210 and cover 1212 to prevent liquids from entering an interior region 1218 defined between main body 1210 and cover 1212 as shown in FIGS. 60-62. Head end siderail 20 further includes a water-proof speaker 1220 coupled to main body 1210 that transmits sound through a plurality of slots 1222 defined in main body 1210.

Controllers

As discussed above, control system 44 is coupled to a first pair of controllers or control panel 52 rigidly coupled to main body 1210, a second controller or control panel 54 pivotably coupled to main body 1210, and third detachable controller 50 that is removably received by head and foot end siderails 20, 22 so that it can be removed from one of foot end siderails 20, 22 and coupled to the other foot end siderail 22 or head end siderails 20 to control various functions of patient support 10. As described below, controllers 52, 54, 50 control various functions of patient support 10 and are also configured to receive information from a caregiver related to a patient and to send and receive patient or bed-related data to a central computer for storage, tracking, and analysis.

Additional details of suitable electronics and other features of controllers are provided in U.S. Pat. No. 5,715,548, titled "Chair Bed," filed Aug. 4, 1995; U.S. Pat. No. 6,008,598, titled "Hand-Held Controller For Bed and Mattress Assembly," filed Apr. 22, 1998; U.S. Pat. No. 6,131,868, titled "Hospital Bed Communication and Control Device," filed Jan. 1, 1997; and U.S. Provisional Application Ser. No. 60/202,284, titled "Remote Control for a Hospital Bed," filed May 5, 2000, the disclosures of which are expressly incorporated by reference herein.

Cover 1212 includes a plurality of apertures 1230 that match with control buttons or switches 1232 of a circuit board 1233 of first controller 52 that is coupled to cover 1212. The functions controlled by switches 1232 will be described in greater detail below.

Second controller 54 includes a housing 1236 and a circuit board 1238 including a plurality of control buttons or switches 1240 and an LED display 1242. Cover 1212 includes a pocket 1244 configured to receive controller 54 as shown in FIGS. 60 and 61. According to alternative embodiments of the present disclosure, the display is an LCD, plasma, or other display known to those of ordinary skill in the art. The functions of switches 1240 will be described in greater detail below.

Housing 1236 includes first and second housing shells 1246, 1248 that cooperate to define a interior region 1250 sized to receive circuit board 1238. Shells 1246, 1248 cooperate to define a boss or post 1252 that is pivotably received in an aperture 1254 defined in cover 1212. Shells 1246, 1248 also cooperate to define an aperture 1256 sized to receive a torsion spring 1258, a bushing 1260, and a pin 1262. To couple second controller 54 to cover 1212, post 1252 is inserted into aperture 1254, and aperture 1256 is aligned with a corresponding aperture 1261 in cover 1212. Pin 1262 is then inserted into aperture 1261 and aperture 1256 to pivotably couple second controller 54 to cover 1212. When coupled, spring 1258 biases second controller 54 into pocket 1244.

This coupling allows the tilting of a lower edge 1264 of housing 1236 upward thereby permitting a user to better see control buttons 1240. According to alternative embodiments of the present disclosure, other configurations of couplers between the housing and the controller mount are provided. For example, hooks, hook-and-loop type fasteners, snaps, a detachable hinge, or other devices known to those of ordinary skill in the art are provided to pivotably or otherwise couple the controller to the siderail.

Figure 63:
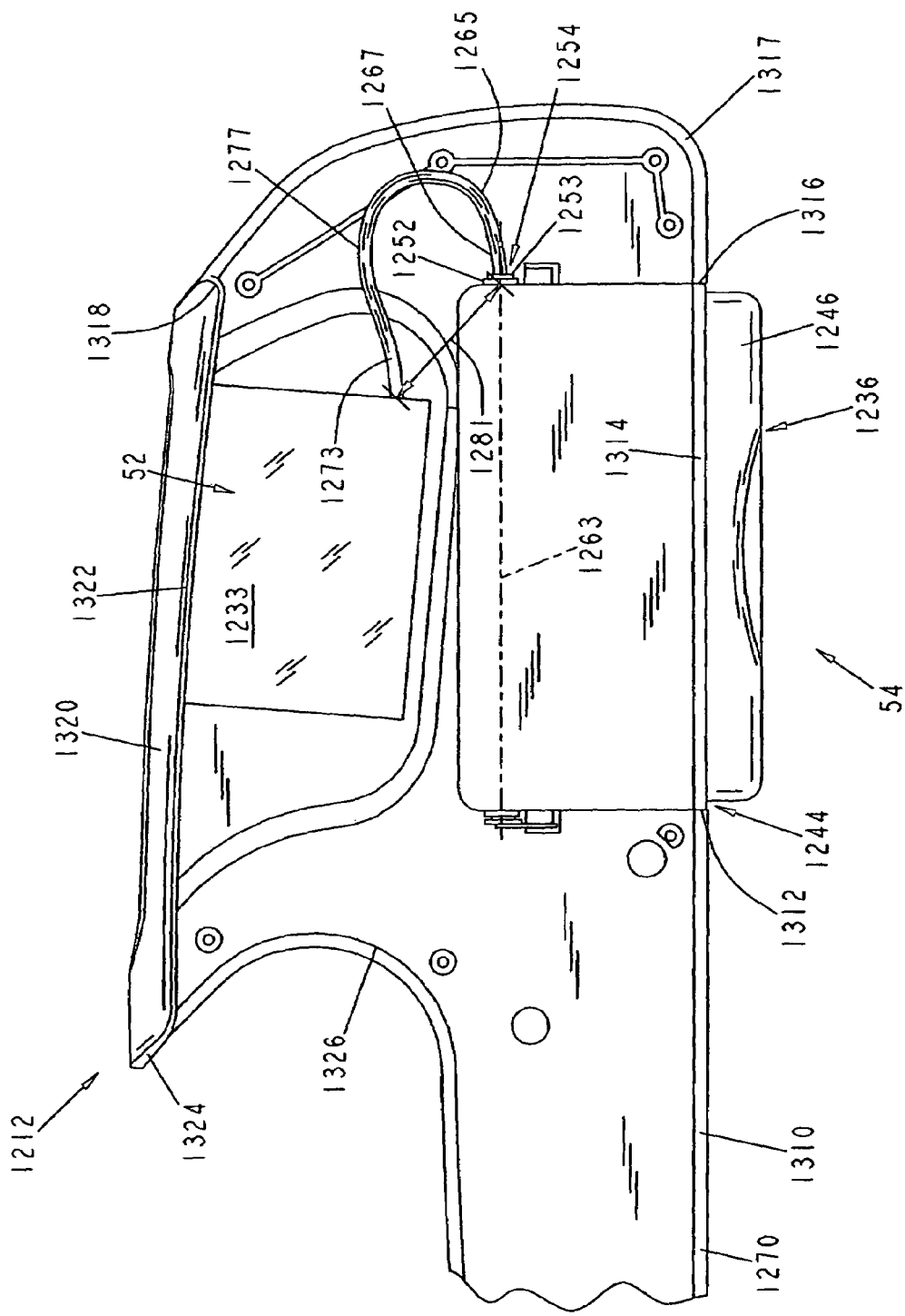
FIG. 63 is a partial side elevational view of an inner side of a cover of the rail member of the head end siderail of FIG. 60, showing a circuit board coupled to the cover and a cord extending from a controller to the circuit board.

An electrical communication cord 1265 of controller 54 is coupled to circuit board 1238 and extends from interior region 1250 defined by shells 1246, 1248 as shown in FIGS. 61 and 63. Post 1252 includes a channel or aperture 1253 through which cord 1265 extends. The channel is centered on an axis of rotation 1263 of controller 54. During rotation of controller 54, a first end 1267 of cord 1265 rotates with controller 54. However, a second end 1273 of cord 1265 coupled to circuit board 1238 does not rotate. A portion 1277 of cord 1275 between first and second ends 1267, 1273 twists during rotation of controller 54 to compensate for second end 1273 not twisting. Because cord 1265 extends through post 1252, no portion of cord 1265 is positioned outside of the interior regions 1218, 1250 of rail member 1110 and housing 1236.

Portion 1277 of cord 1265 extends from post 1252 to circuit board 1233 and has a length that is about three times as long as a distance 1281 from post 1252 to where it coupled to circuit board 1238. This additional length reduces the amount of tension on cord 1265 and chaffing of cord 1265 during the pivoting of controller 54 about axis of rotation 1263.

According to an alternative embodiment of the present disclosure, a rubber grommet is provided in the channel 1253 to provide a liquid proof seal between cord 1265 and housing 1236. According to another alternative embodiment, a rubber grommet is provided between post 1252 and cover 1212 to provide a liquid proof seal therebetween.

Figure 64:
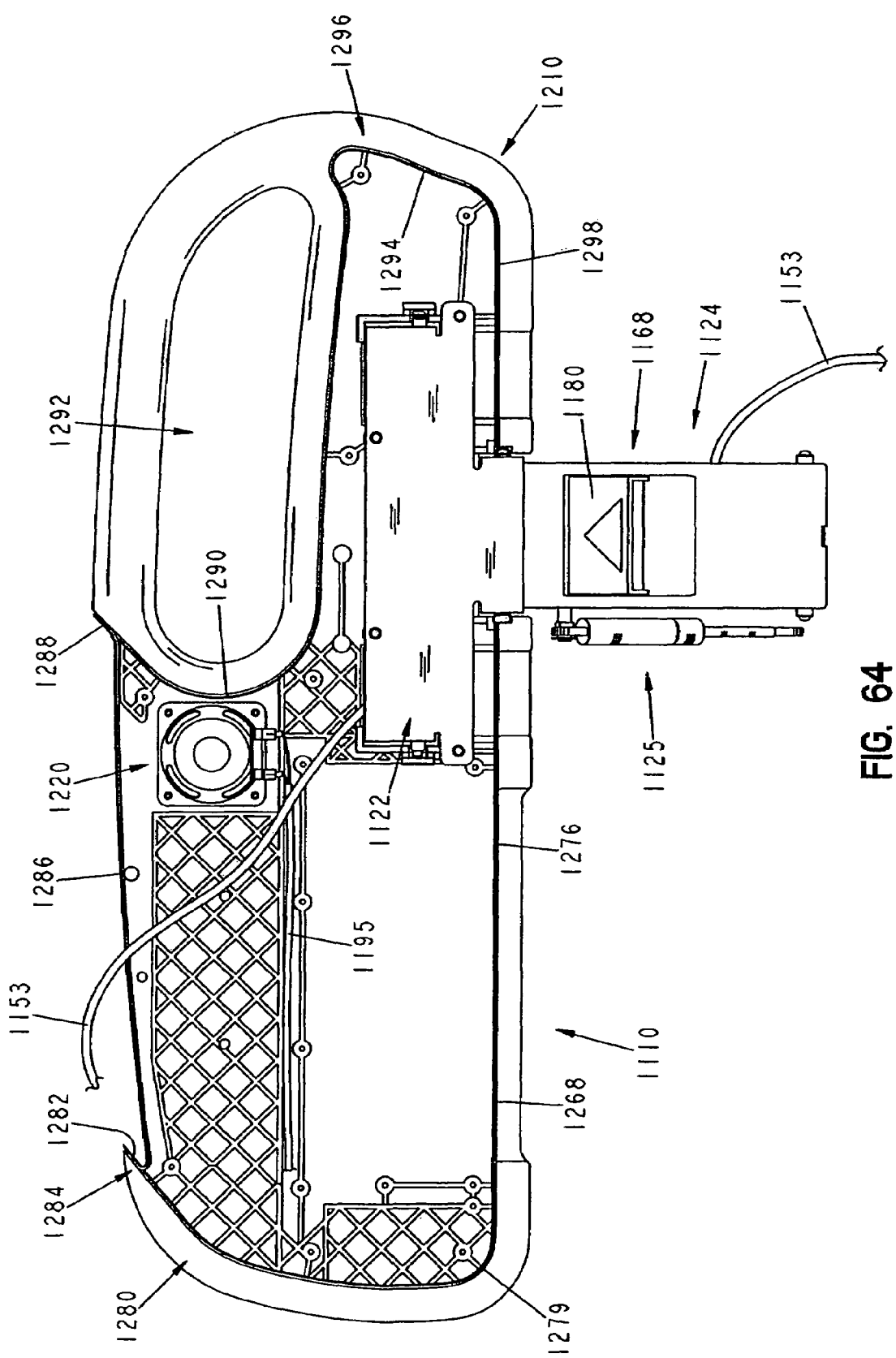
FIG. 64 is a side elevational view of an inner side of a main body of the rail member of the head end siderail of FIG. 60, showing the link of FIG. 49 positioned adjacent the head end siderail and showing a cord extending through the link and head end siderail.

Referring now to FIG. 64, cord 1153 passes through fourth link 1124 to third link 1122 in the manner detailed above. From behind third link 1122, cord 1153 extends to and is coupled to circuit board 1233 of controller 52. A cord 1271 extends from speaker 1220 of head end siderail 20 and is also coupled to circuit board 1233 of controller 52.

Fluid Sealing

As described above, main body 1210 and cover 1212 of head end siderail 20 are sealed together to prevent fluids from entering an interior region 1218 defined between main body 1210 and cover 1212. Main body 1210 and cover 1212 include sealing edges 1268 and 1270, respectively that face each other when cover 1212 is coupled to main body 1210 (FIG. 62).

With reference to FIGS. 60 and 64, sealing edge 1268 includes a first portion 1272 that extends longitudinally and faces outwardly, a second portion 1274 that extends laterally and faces toward a head end of patient support 10, a third portion 1276 that extends longitudinally and faces outwardly, a fourth portion 1278 that extends laterally and faces toward a foot end of patient support 10, a fifth portion 1279 that substantially vertically following a curved profile of a head end 1280 of main body 1210 and faces outwardly, a sixth portion 1282 that extends over a top end 1284 of main body 1210, a seventh portion 1286 that extends longitudinally and faces inwardly, an eighth portion 1288 that extends back over top end 1284 of main body 1210, a ninth portion 1290 that follows a curved profile of a handle aperture 1292 defined in main body 1210 and faces outwardly, a tenth portion 1294 that extends substantially vertically following a curved profile of a foot end 1296 of main body 1210 and faces outwardly, and an eleventh portion 1298 that extends longitudinally and faces outwardly. Similarly, with reference to FIGS. 60 and 63, sealing edge 1270 includes a first portion 1310 that extends longitudinally and faces inwardly, a second portion 1312 that extends laterally and faces toward a foot end of patient support 10, a third portion 1314 that extends longitudinally and faces inwardly, a fourth portion 1316 that extends laterally and faces toward a head end of patient support 10, a fifth portion 1317 that extends substantially vertically following the curved profile of head end 1280 of main body 1210 and faces inwardly, a sixth portion 1318 that extends under a hooked or channel portion 1320 of cover 1212, a seventh portion 1322 that extends longitudinally and faces outwardly, an eighth portion 1324 that extends back under hooked portion 1320 of cover 1212, a ninth portion 1326 that follows the curved profile of handle aperture 1292 and faces inwardly, a tenth portion 1328 that extends substantially vertically following a curved profile of foot end 1296 of main body 1210 and faces inwardly, and an eleventh portion 1330 that extends longitudinally and faces inwardly. The respective portions 1272, 1274, 1276, 1278, 1279, 1282, 1286, 1288, 1290, 1294, 1298 of sealing edge 1268 of main body 1210 face the respective portions 1310, 1312, 1314, 1316, 1317, 1318, 1322, 1324, 1326, 1328, 1330 of sealing edge 1270 of cover 1212.

Sealing edge 1268 includes a channel 1332 that extends along portions 1272, 1274, 1276, 1278, 1279, 1282, 1286, 1290, 1294, 1296 of main body 1210. See, for example, FIGS. 61 and 62, showing third portion 1276 and sixth portion 1286 having channel 1332 extending therethrough. O-ring seal 1216, made of rubber or other suitable material, is positioned in channel 1332. When cover 1212 is positioned over main body 1210 of head end siderail 20, sealing edge 1270 presses against seal 1216 to provide a seal between sealing edges 1268 and 1270 of main body 1210 and cover 1212.

According to an alternative embodiment of the present disclosure, the sealing edges disclosed herein that press against the O-ring, such as sealing edge 1270, are provided with a ridge that "bites" into the O-ring, such as O-ring 1216, along the length of the O-ring to increase the compression of the O-ring and the contact pressure between the sealing surface and the O-ring. According to an alternative embodiment of the present disclosure, sealing edges and an O-ring are provided around the opening in main body 1210 that receives third link 1122 of linkages 1114 to seal around this opening. Similar sealing edges and O-ring may also provided for foot end rail 22. According to another embodiment, these additional sealing edges extend down to the existing sealing edges.

Shells 1246, 1248 of housing 1236 of second controller 54 are sealed together to prevent fluids from entering interior region 1250 defined between shells 1246, 1248 as shown in FIG. 61. Similar to main body 1210 and cover 1212 of head end siderail 20, shells 1246, 1248 include sealing edges 1336, 1338 that face each other when shells 1246, 1248 are coupled together. Similar to sealing edge 1268 of main body 1210, sealing edge 1338 of shell 1248 includes a channel 1340 extending from one side of post 1252, around the perimeter of shell 1248, to the opposite side of post 1252. An O-ring seal 1342 made of rubber or other suitable material is positioned in channel 1340. When shell 1246 is positioned on shell 1248, sealing edge 1336 presses against seal 1342 to provide a seal between sealing edges 1336 and 1338 of shells 1246 and 1248, respectively.

Figure 65:
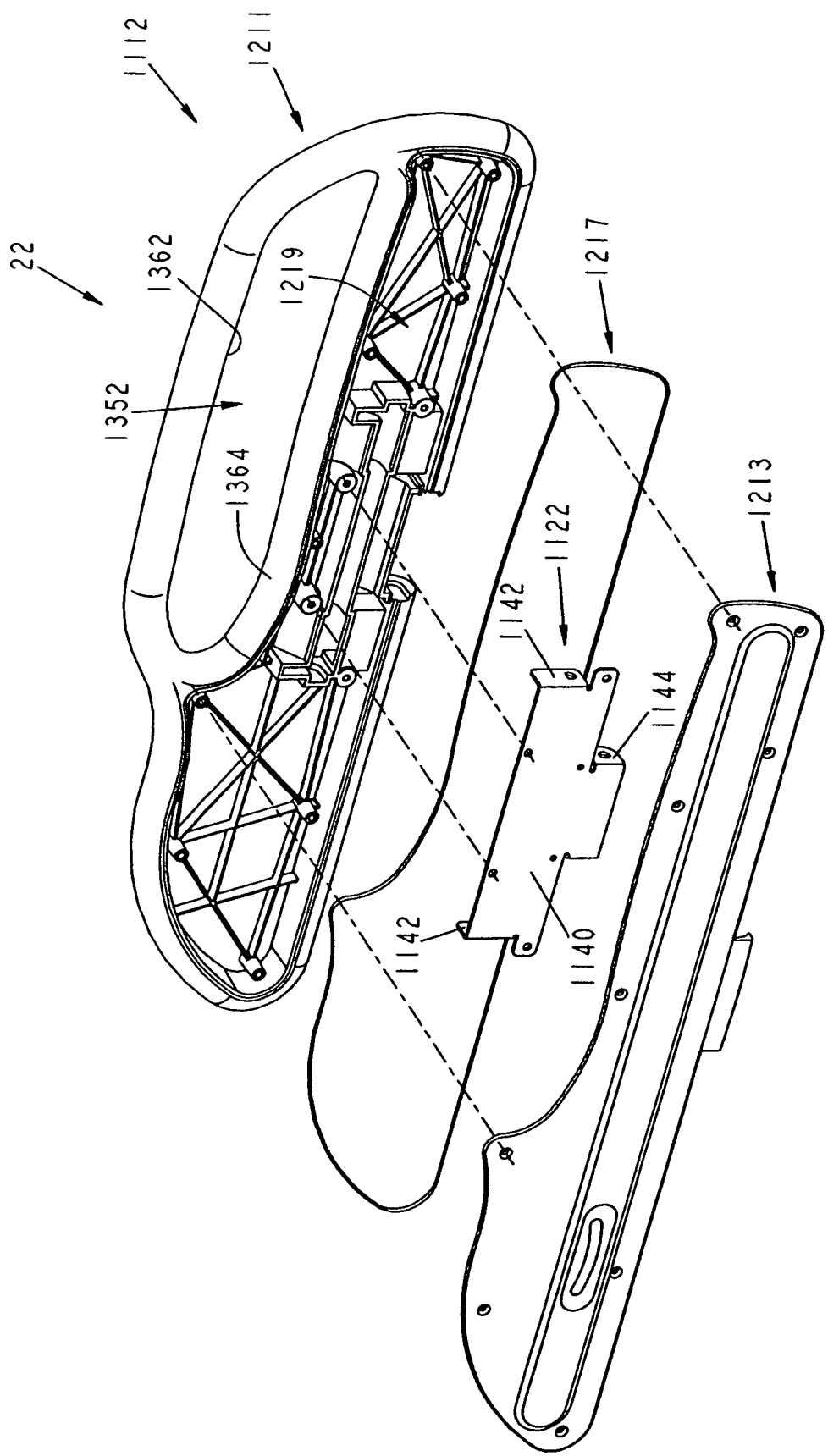
FIG. 65 is an exploded perspective view of a rail member of the foot end siderail.
Figure 67:
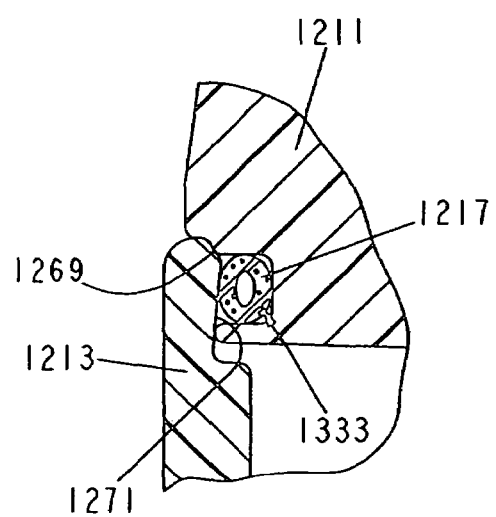
FIG. 67 is an enlarged view of a portion of FIG. 66, showing an O-ring seal positioned between a main body of foot end siderail and a cover of foot end siderail.
Figure 66:
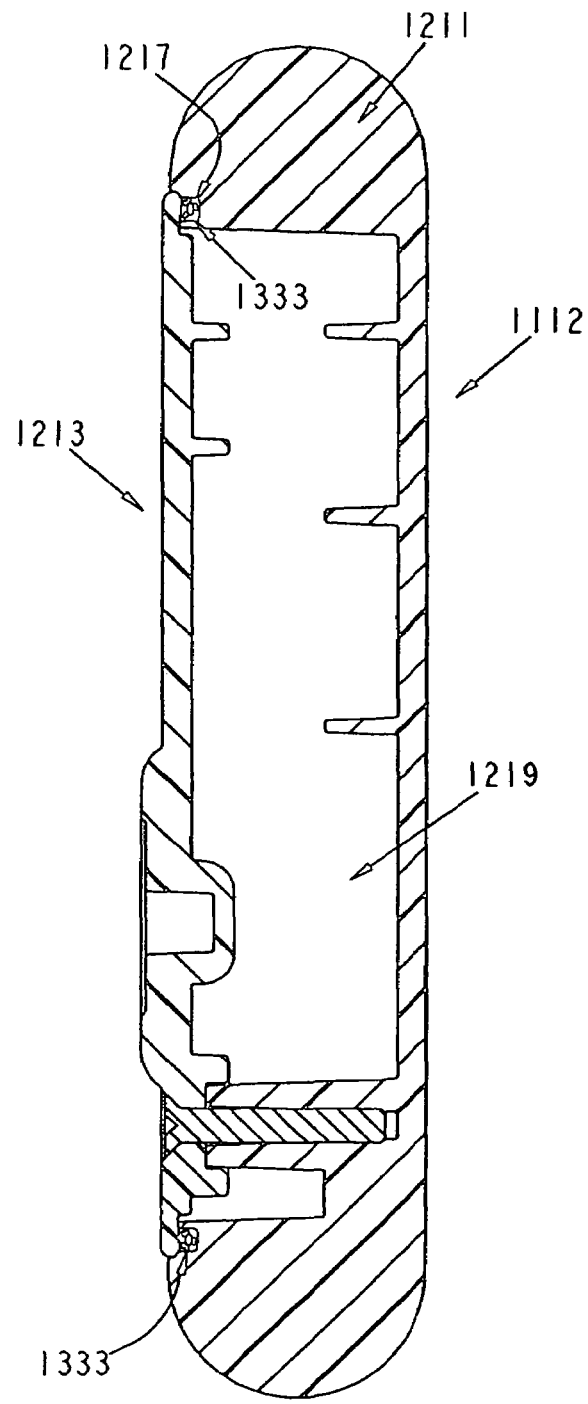
FIG. 66 is a cross sectional view taken along taken along line 66-66 of FIG. 46.

Similar to rail member 1110 of head end siderail 20, rail member 1112 of foot end siderail 22 includes a main body 1211 and a cover 1213 as shown in FIG. 65. An O-ring seal 1217 is provided between main body 1211 and cover 1213 to prevent liquids from an interior region 1219 defined between main body 1211 and cover 1213 as shown in FIGS. 66 and 67. Main body 1211 and cover 1213 include sealing edges 1269, 1271 that face each other when cover 1213 is coupled to main body 1211.

Sealing edge 1269 includes a channel 1333 as shown in FIGS. 66 and 67. O-ring seal 1217, made of rubber or other suitable material, is positioned in channel 1333. When cover 1213 is positioned on main body 1211 of foot end siderail 22, sealing edge 1271 presses against seal 1217 to provide a seal between sealing edges 1269, 1271 of main body 1211 and cover 1213.

Detachable Siderail Controller

Figure 68:
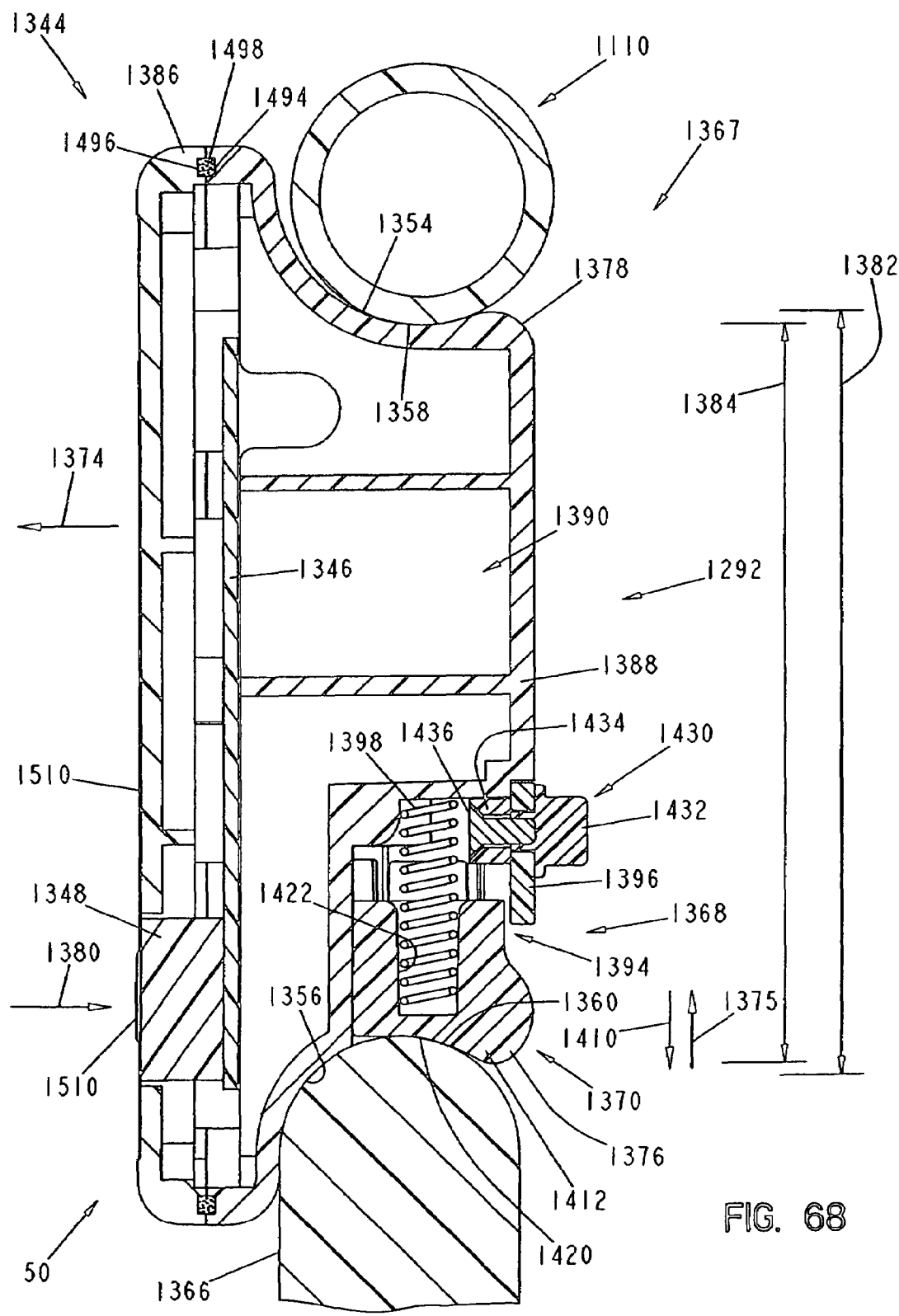
FIG. 68 is a cross-sectional view taken along line 68-68 of FIG. 45, showing a controller coupled to the head end siderail.
Figure 69:
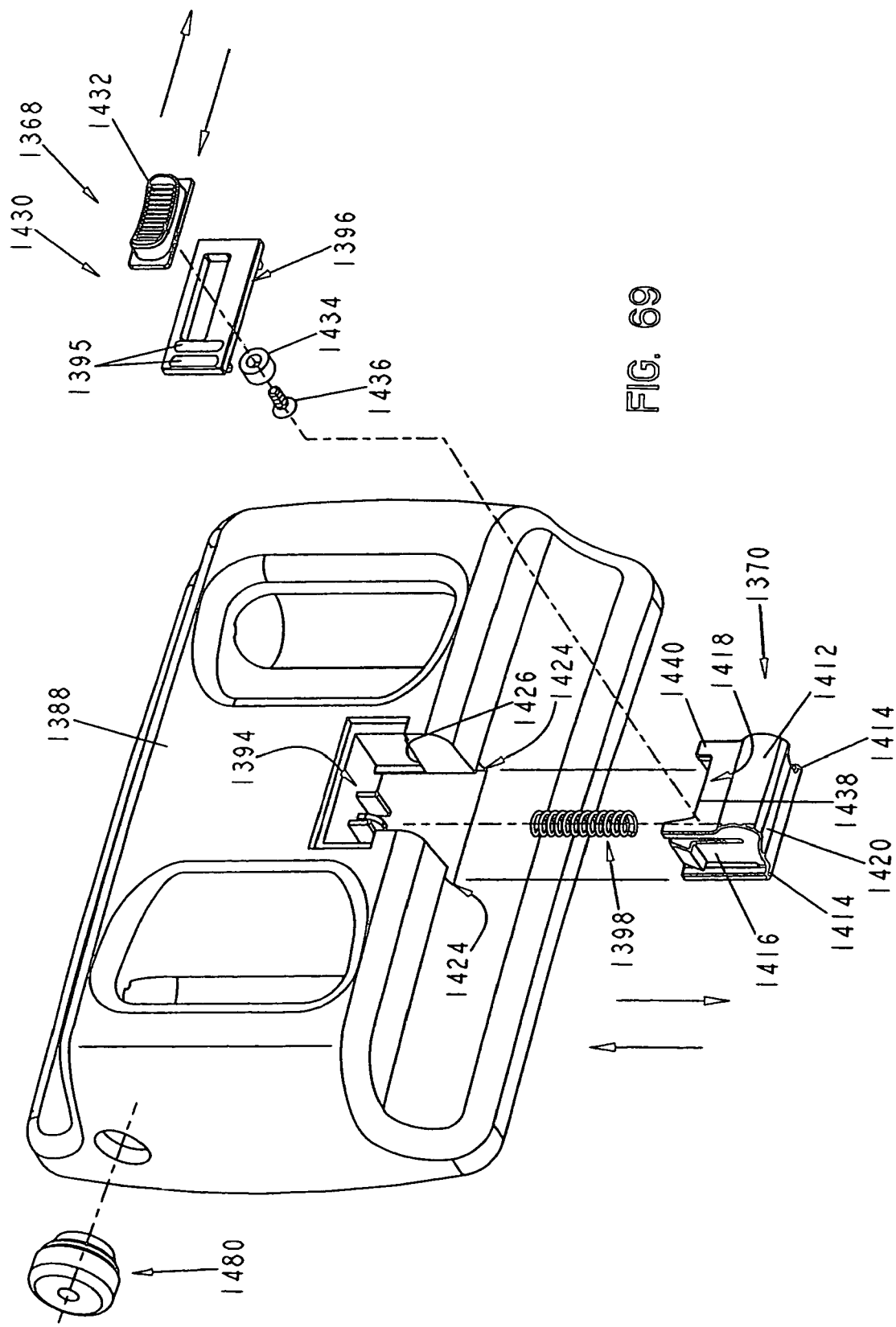
FIG. 69 is an exploded perspective view of the controller of FIG. 68.

As shown in FIG. 45 control system 44 is further coupled to detachable siderail controller 50 that may be a corded pendant configured to removably and slidably couple to head and foot end siderails 20, 22. As shown in FIG. 68 controller 50 includes a housing 1344, a circuit board 1346 including a plurality of control buttons or switches 1348, and a cord 1350 coupled to circuit board 1346 and extending from housing 1344 as shown in FIG. 69 The functions controlled by switches 1348 will be described in greater detail below.

Controller 50 is configured to slide in either handle opening 1292 of head end siderails 20 or handle opening 1352 of foot end siderails 22 between an infinite number of positions (FIG. 45). Because patients vary in size, one patient may find it more convenient to position controller 50 in one of the many available positions on either head or foot end siderails 20, 22 than another patient. Thus, various patients can position controller 50 in any of the infinite number of positions on any of head or foot end siderails 20, 22 depending on the preference of particular patient positioned on patient support 10. Furthermore, a patient may decide to adjust the position of controller 50 if the configuration of deck 26 is changed. For example, if head section 38 of deck 26 is raised, a patient may desire to reposition controller 50 along the particular siderail 20, 22 or remove controller 50 and place it on another siderail 20, 22.

As shown in FIGS. 45 and 68, housing 1344 of controller 50 includes an upper or first concave surface 1354 and a lower or second concave surface 1356 that complement convex surfaces 1358 and 1360, respectively, of rail member 1110 of head end siderail 20. Also as shown in FIG. 45, rail member 1112 of foot end siderail 22 includes convex surfaces 1362 and 1364 that are complemented by concave surfaces 1354 and 1356, respectively. As shown in FIG. 68, a substantial portion of controller 50 is positioned within rail member 1110 so that controller 50 maintains a relatively low profile compared to an inner surface 1366 of rail member 1110 when positioned in rail member 1110 to avoid interference with other components of patient support 10 or other pieces of medical equipment. According to alternative embodiments of the present disclosure, the controller 50 is positioned further in the opening formed in the rail member 1110, so that little or none of the controller extends beyond an inner surface of the rail member.

The respective pairs of convex surfaces 1358, 1360, 1362, 1364 of siderails 20, 22 cooperate to define a top rail and a bottom rail that define a guide 1367 operably coupled to the controller 50. Concave surfaces 1354 and 1356 and a retainer 1368 coupled to housing 1344 cooperate to define a complementary formation configured to ride along the top and bottom rails/guide. According to alternative embodiments of the present disclosure, other configurations of rails and guides and complementary formations are provided such as raised rails, channels, slots, or other configurations of guides and complementary formations known to those of ordinary skill in the art.

Retainer 1368 is configured to retain controller 50 in either opening 1292, 1352 to permit sliding of controller 50 along siderails 20, 22 and to permit removal of controller 50 from openings 1292, 1352, respectively. When controller 50 is positioned in opening 1352 of foot end siderail 22, retainer 1368 is positioned adjacent to concave surface 1356 of housing 1344.

As illustrated in FIG. 68, retainer 1368 includes a spring-biased retainer or latch member 1370. When a patient pulls on controller 50 in direction 1374, retainer member 1370 is pushed inwardly in direction 1375 so that a curved distal end 1376 of retainer member 1370 rides over the inner most portion of convex surface 1360, 1364. As such, retainer 1368 no longer retains controller 50 in the respective siderail 20, 22.

To reposition controller 50 back in one of siderails 20, 22, the patient positions second concave surface 1354 adjacent to convex surface 1358, 1362 of rail member 1110, 1112 of siderail 20, 22, respectively so that a peaked tip 1378 of housing 1344 captures rail member 1110, 1112. The lower end of controller 50 is pushed in direction 1380 so that retainer member 1370 rides back over respective convex surface 1360, 1364. Peaked tip 1378 and retainer member 1370 then define a width 1382 that is greater than a width 1384 of opening 1292, 1352 so that controller 50 is retained in respective siderail 20, 22. Identical procedures are followed for placing and removing controller 50 from opening 1352 in foot end siderails 22 and for placing and removing controller 50 from opening 1292 in head end siderails 20. Furthermore, controller 50 may also be coupled to rail members 1110, 1112 through the opposite side of respective opening 1292, 1352. According to an alternative embodiment of the present disclosure, the openings in the head and foot end siderails do not extend completely through the siderails.

As shown in FIG. 68, housing 1344 includes inner and outer shells 1386 and 1388 that cooperate to define an interior region 1390 configured to receive circuit board 1346. Outer shell 1388 defines a retainer-receiving void 1394 sized to receive portions of retainer 1368. Housing 1344 further includes a retainer cover 1396 that cooperates with outer shell 1388 to define void 1394. Retainer 1368 further includes a biasing member or spring 1398 positioned in void 1394 between outer shell 1388 and retainer member 1370. Spring 1398 biases retainer member 1370 in direction 1410 toward convex surface 1360 as shown in FIG. 68. According to alternative embodiments of the present disclosure, other biasing members are provided, such as torsion springs, the retainer member being cantilevered and flexible, or other configurations of biasing members known to those of ordinary skill in the art.

Figure 70:
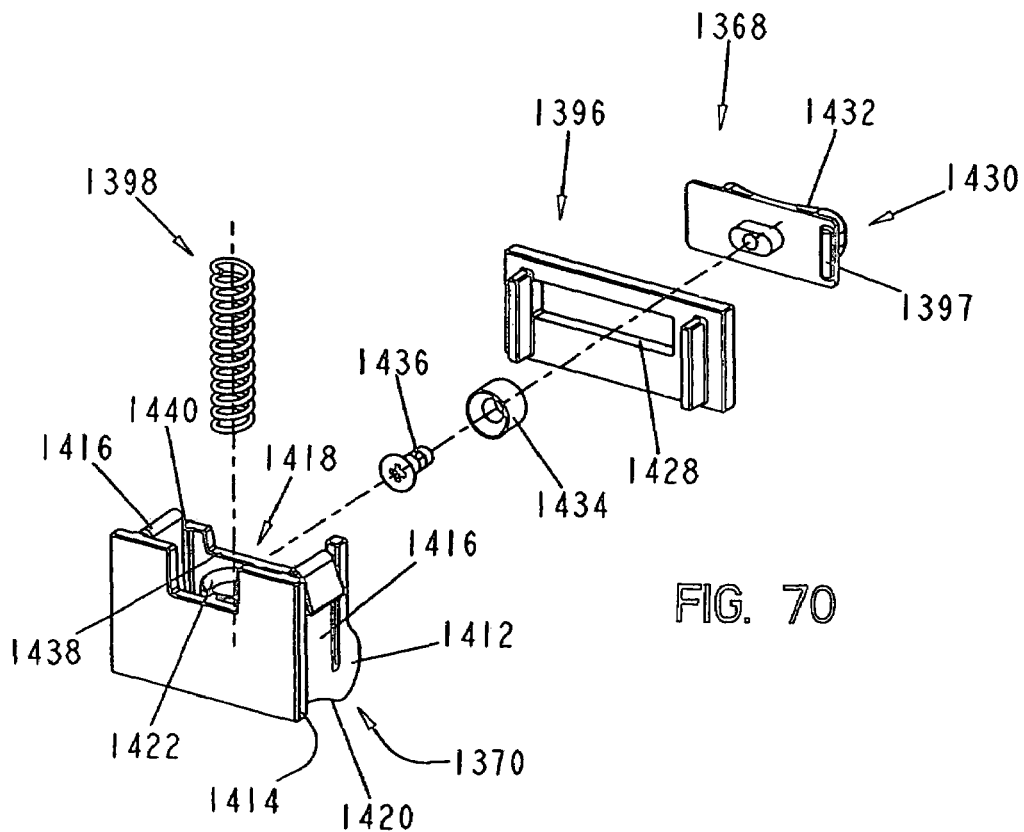
FIG. 70 is an exploded perspective view of a retainer or latch of the controller of FIG. 68.

As shown in FIGS. 69 and 70, retainer member 1370 includes a latch portion 1412, a pair of ribs 1414, a pair of locking tabs 1416, and a notched rib 1418. Latch portion 1412 includes a downwardly facing surface 1420 that matches the contour of upwardly facing surface 1360, 1364 of siderails 20, 22, respectively as shown in FIGS. 45 and 68. Latch portion 1412 further includes a spring-receiving aperture 1422 sized to receive an end of spring 1398.

Ribs 1414 slide in channel portions 1424 of void 1394 so that retainer member 1370 can move up and down. Housing 1344 includes a pair of lips 1426 on which locking tabs 1416 are caught preventing removal of retainer member 1370 from void 1394 after retainer member 1370 is slidably moved up and locking tabs 1416 snap into place over lips 1426.

Retainer 1368 further includes a lock or blocker 1430 configured to slide on retainer cover 1396 and block or permit movement of retainer member 1370. As shown in FIGS. 68-70, lock 1430 includes a slider button 1432 and a blocker or lug 1434 coupled to button 1432 by a screw 1436 so that retainer cover 1396 is positioned between lug 1434 and button 1432. Retainer cover 1396 with slider button 1432 and blocker 1434 coupled thereto, is coupled to housing 1344 so that blocker 1434 is positioned above notched rib 1418 as shown in FIG. 68. A portion of slider button 1432 passes through a lock guide or opening 1428 configured to guide lock 1430 in movement.

Depending on the position of button 1432 and blocker 1434 relative to lock guide 1428, blocker 1434 will prevent or permit movement of retainer member 1370 relative to housing 1344. If button 1432 is centered over a middle or lower portion 1438 of notched rib 1418, clearance exists between lower portion 1438 and blocker 1434 and retainer member 1370 is permitted to move further up in direction 1375 into void 1394 (FIG. 68). As mentioned above, this movement permits removal of controller 50 from respective head and foot end siderails 20, 22. However, if button 1432 is slidably moved so that blocker 1434 is positioned over a raised portion 1440 of notched rib 1418, there is little or no clearance between raised portion 1440 and blocker 1434 and retainer member 1370 is blocked from sliding further up in direction 1375 into void 1394 (FIG. 68). Cover 1396 includes a pair of ridges 1395 that restrain a ridge 1397 on button 1432 to resist movement of button 1432 between the locked position and the unlocked position.

Figure 71:
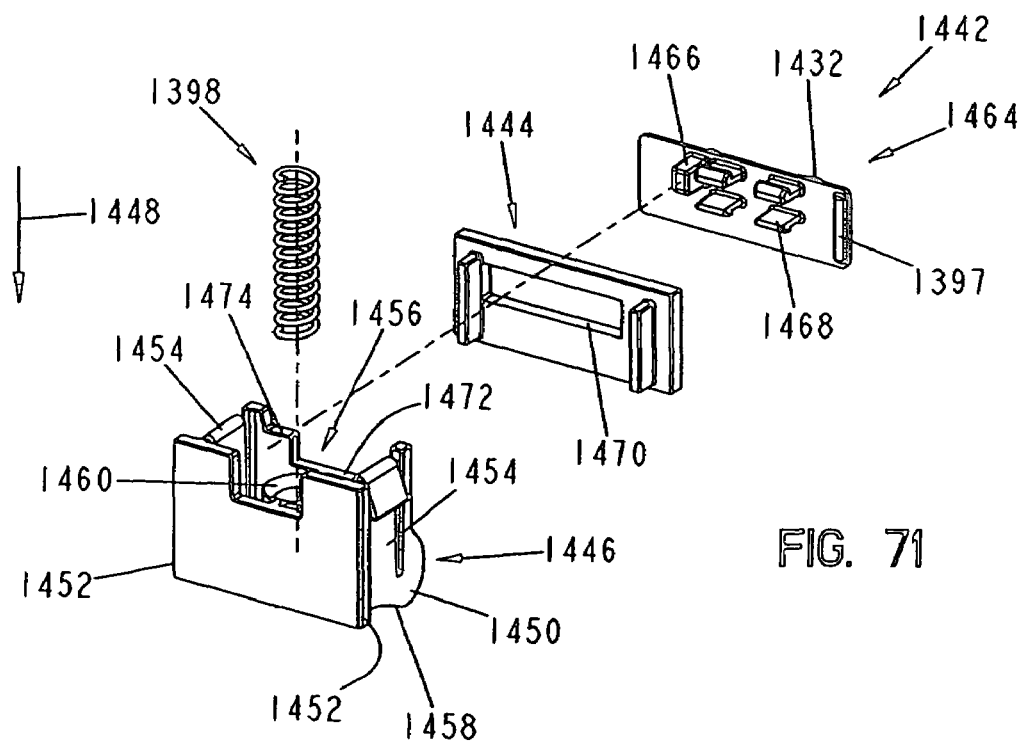
FIG. 71 in exploded perspective view of an alternative embodiment retainer or latch for the controller of FIG. 68.

An alternative embodiment retainer 1442 and retainer cover 1444 similar to retainer 1368 and retainer cover 1396 are shown in FIG. 71. Retainer cover 1444 cooperates with outer shell 1388 to define a void sized to receive portions of retainer 1442. Retainer 1442 includes a retainer member 1446 and spring 1398 positioned in the void between outer shell 1388 and retainer member 1446. Spring 1398 biases retainer member 1446 in direction 1448 toward convex surface 1360, 1364 of respective siderail 20, 22.

Retainer member 1446 includes a latch portion 1450, a pair of ribs 1452, a pair of locking tabs 1454, and a notched rib 1456. Latch portion 1450 includes a downwardly facing surface 1458 that matches the contour of upwardly facing surface 1360, 1364 of siderails 20, 22, respectively. Latch portion 1450 further includes a spring-receiving aperture 1460 sized to receive an end of spring 1398.

Ribs 1452 slide in channel portions 1424 of void 1394 so that retainer member 1446 can move up and down. Locking tabs 1454 are caught on lips 1426 of housing 1344 to prevent removal of retainer member 1446 from void 1394 after retainer member 1446 is slidably moved up and locking tabs 1454 snap into place over lips 1426.

Retainer 1442 further includes a lock or blocker 1464 configured to slide on retainer cover 1444 and block or permit movement of retainer member 1446. Lock 1464 includes slider button 1432 and a blocker or lug 1466 coupled integrally with button 1432. Lock 1464 includes a plurality of fingers 1468 that snap into an opening 1470 in cover 1444 so that lug 1466 extends through opening 1470. Cover 1444 with lock 1464 coupled thereto, is coupled to housing 1344 so that blocker 1466 is positioned above notched rib 1456.

Depending on the position of button 1432 and blocker 1466 relative to cover 1444, blocker 1466 will prevent or permit movement of retainer member 1446 relative to housing 1344. If button 1432 is centered over a middle or lower portion 1472 of notched rib 1456, clearance exists between lower portion 1438 and blocker 1466 and retainer member 1446 is permitted to move further up into void 1394. This movement permits removal of the controller 50 from respective head and foot end siderails 20, 22. However, if button 1432 is slidably moved so that blocker 1466 is positioned over a raised portion 1474 of notched rib 1456, there is little or no clearance between raised portion 1474 and blocker 1466 and retainer member 1446 is blocked from sliding further up into the void.

According to other alternative embodiments of the disclosure, other retainers known to those of ordinary skill in the art are provided to retain the controller in the siderails such as tabs, clasps, catches, locks, other latches, clamps, pins, bolts, bars, hasp, hooks, or other retainers known to those of ordinary skill in the art.

Figure 72:
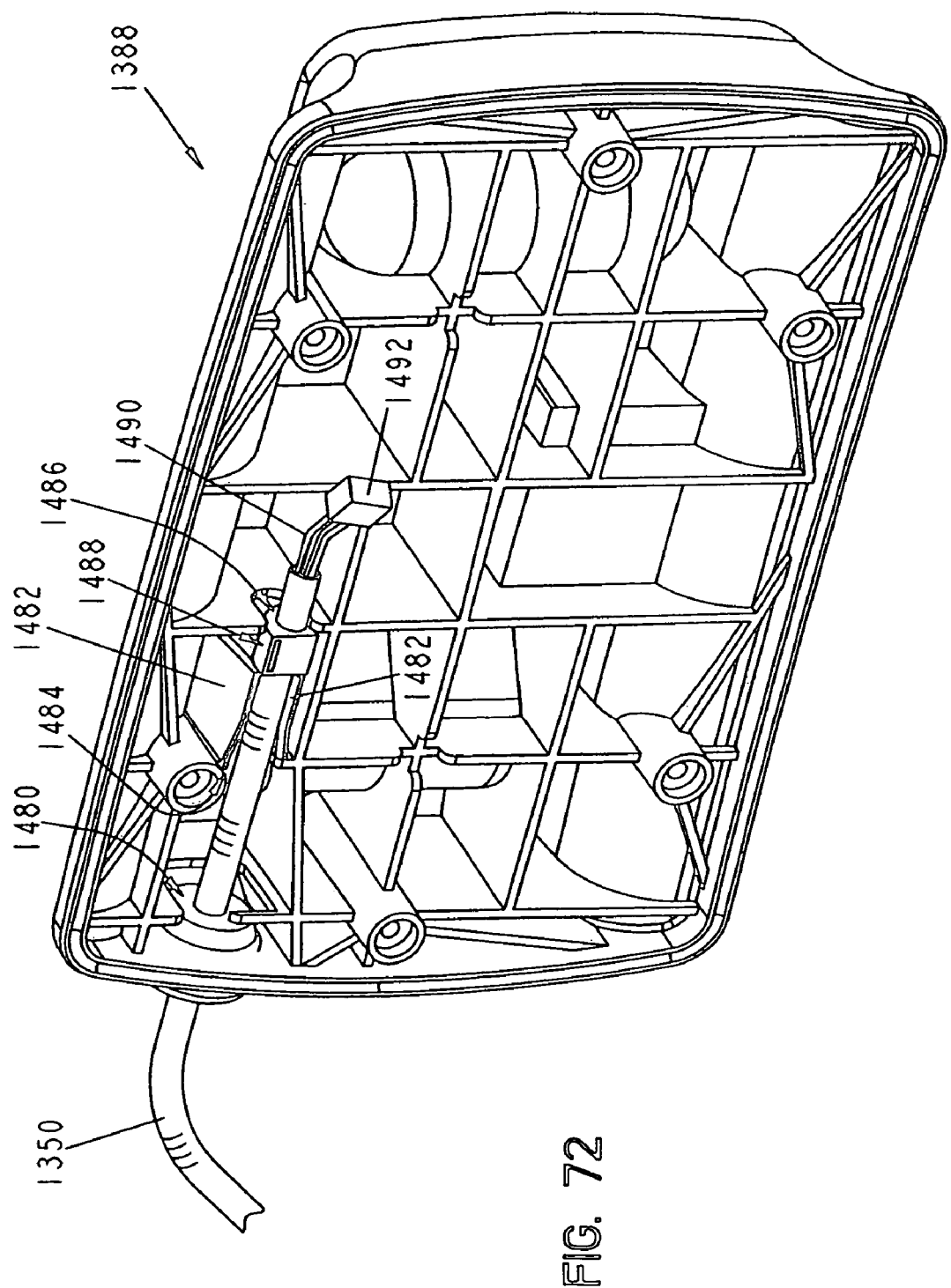
FIG. 72 is a perspective view of a shell of the controller of FIG. 68, showing a cord extending into the shell.

As shown in FIG. 72, cord 1350 communicates electric signals to and from controller 50. Cord 1350 includes a connector (not shown) that couples to either of two connectors 1478 shown in FIG. 45 on weigh frame 36. According to the illustrative embodiment of the disclosure, one of connectors 1478 is coupled to a first side of patient support 10 and the other connector 1478 is coupled to an opposite second side of patient support 10. A plurality of wires (not shown) are coupled to each connector 1478, and are configured to communicate with the various electrically controlled devices of patient support 10.

Because two connectors 1478 are provided on opposite sides of patient support 10, controller 50 may be plugged into either side of patient support 10. Thus, if a patient or caregiver finds it more convenient to position controller 50 on the pair of head and foot end siderails 20, 22 on the first side of patient support 10, controller 50 can be plugged into connector 1478 without cord 1350 having to be strung over the mattress 14. Similarly, if a patient or caregiver finds it more convenient to position controller 50 on the pair of head and foot end siderails 20, 22 on the second side of patient support 10, controller 50 can be plugged into connector without cord 1350 having to be strung over the mattress 14. Thus, a corded controller 50 is provided that can be removably coupled to either side of the patient support 10 without having to string the cord 1350 of the controller 50 over the mattress 14 of the patient support 10.

Controller 50 further includes a rubber grommet 1480 that is positioned in a aperture 1482 in outer shell 1386 as shown in FIGS. 69 and 72. Cord 1350 extends through grommet 1480. Grommet 1480 provide a water-tight seal between shell 1388 and cord 1350.

Outer shell 1388 further includes a pair of symmetric ribs or ramps 1482 that define a tapered channel 1484 configured to receive cord 1350. A stop 1486 is coupled to cord 1350. Stop 1486 is larger than a narrow opening 1488 defined between ramps 1482 so that cord 1350 cannot be pulled axially out of outer shell 1386. This prevents wires 1490 of cord 1350 and connector 1492 that couples to circuit board 1346 from being stressed if force is applied to cord 1350. Because channel 1484 is tapered, an assembler can initially place cord 1350 in the wider portion of channel 1484 and then press down to position cord 1350 in opening 1488. When cord 1350 is pressed down on, ramps 1482 guide cord 1350 toward narrow opening 1488 so that the assembler does not have to be as accurate with the initial placement of cord 1350 in channel 1484. According to the presently preferred embodiment, the stop 1486 is a cable tie that has had any extra length removed.

According to alternative embodiments of the present disclosure, other stops are provided. For example, according to one alternative embodiment, a staple or other clip is provided.

As shown in FIG. 68, inner and outer shells 1386, 1388 includes perimeter channels 1494, 1496. During the manufacture of inner shell 1394, a seal 1498 is formed in channel 1494. Preferably, shells 1386, 1388 are made of rigid plastic materials and seal 1498 is made of a rubber-like material that forms a liquid-proof seal between outer shells 1386, 1388.

Controller Interface Panels

Figure 73:
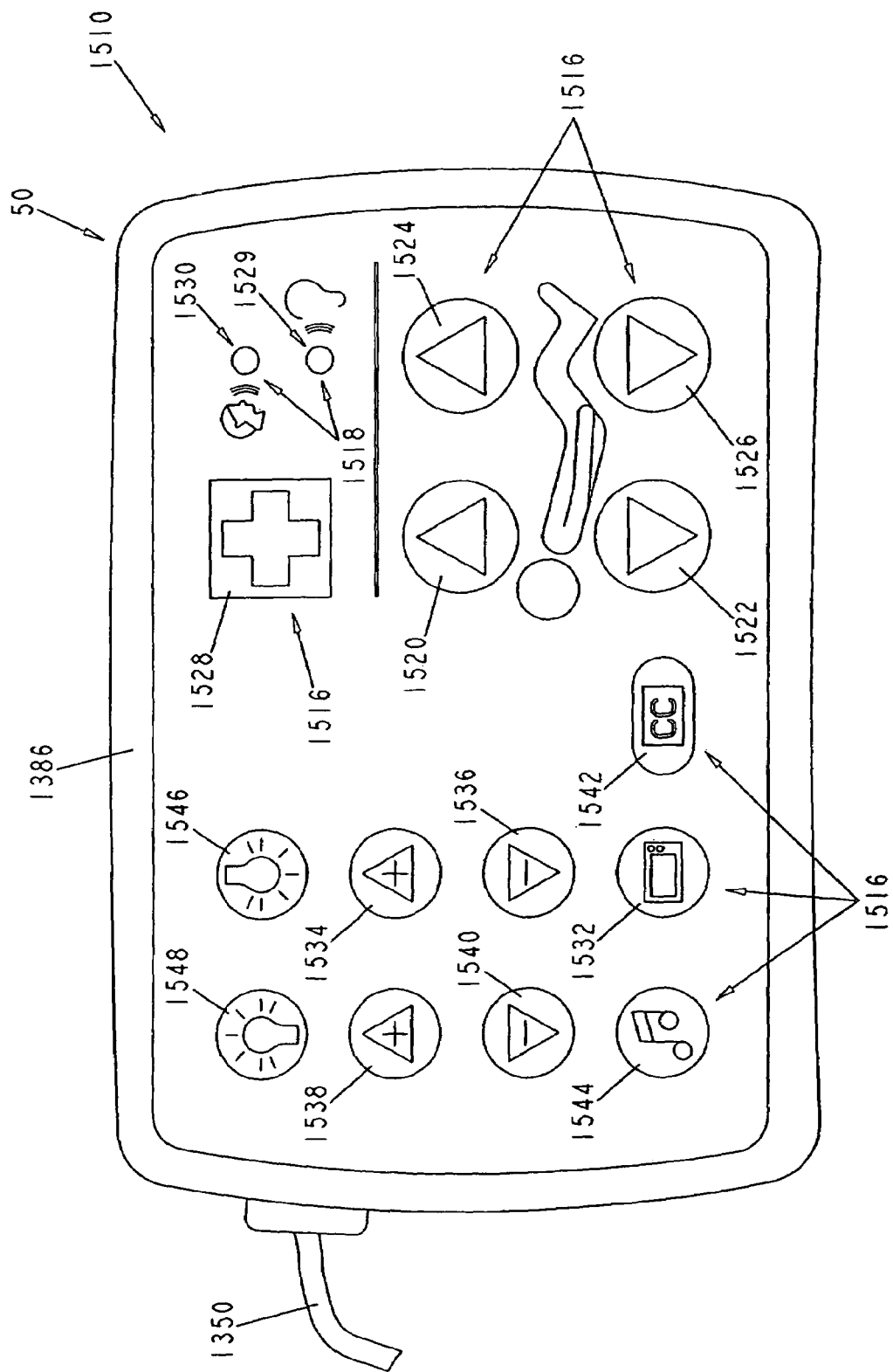
FIG. 73 is a side elevational view of a first interface panel.
Figure 74:
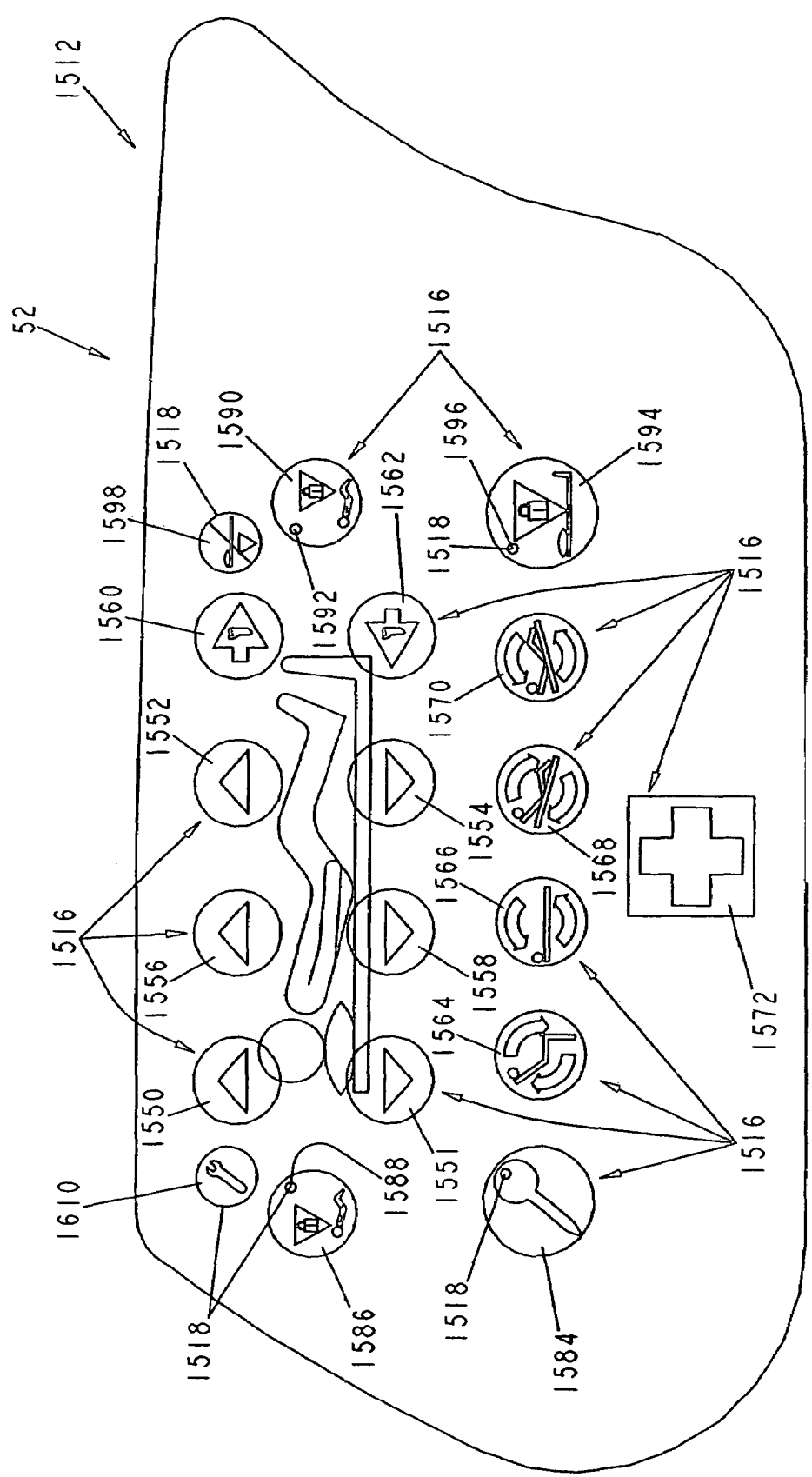
FIG. 74 is a side elevational view of a second interface panel.
Figure 75:
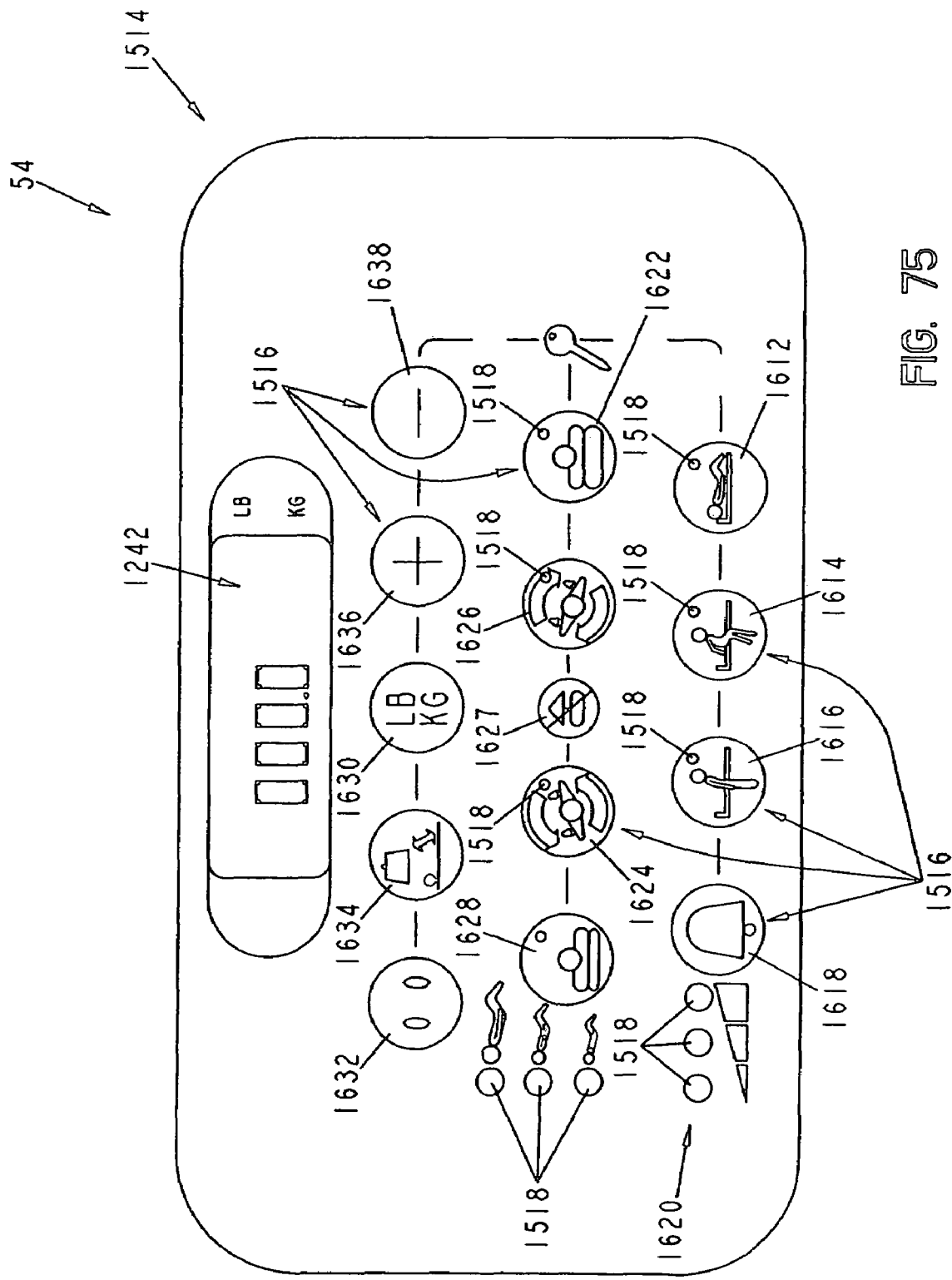
FIG. 75 is a side elevational view of a third interface panel.

Controllers 50, 52, 54 each include respective interface panels 1510, 1512, 1514, illustrated in FIGS. 73-75. Preferably, each panel 1510, 1512, 1514 is made of a flexible membrane. Panel 1510 couples to inner shell 1386 of controller 50 to provide a liquid-proof seal therebetween. Similarly, panel 1512 couples to cover 1212 of head end siderail 20 to provide a water-proof seal therebetween, and panel 1512 couples to outer housing 1248 of controller 54 to provide a water-proof seal therebetween.

Each interface panel 1510, 1512, 1514 includes a plurality status indicators and raised button covers having indicia. When a user presses on the button covers, they also press on one of respective switches or buttons 1348, 1232, 1240 positioned behind the button cover and initiate a function of patient support 10.

As shown in FIG. 73 interface panel 1510 includes a plurality of membrane input control buttons or raised button covers 1516 and a plurality of status indicators 1518 which are electrically coupled to circuit board 1346 of controller 50, allowing controller 50 to be used by persons in or out of patient support 10 to control the operation of various features of patient support 10, including articulation of deck 26, sending a nurse call signal, controlling entertainment devices, such as television, radio, or the like. In a preferred embodiment, status indicators 1518 are light emitting diodes (LEDs) electrically coupled to circuit board 1346. According to alternative embodiments of the present disclosure, other functions of the patient support 10 or remote equipment are controlled by the controller 50.

Head up button 1520 and head down button 1522 are provided to control adjustment of the position of head section 38 of deck 26 between the raised and lowered positions. Knee up button 1524 and knee down button 1526 are provided to control adjustment of the position of leg and seat sections 42 and 40.

When a nurse call button 1528 is pressed, a signal is sent to a nurse station or directly to predetermined caregivers that indicates that the patient needs attention. Speak indicator 1529 and listen indicator 1530 are provided to indicate the direction of communication between a patient in patient support 10 and nurse or other caregiver located at a nurse call station or other location. The caregiver at the nurse call station or elsewhere controls which way the communication travels. If neither indicator 1529, 1530 is illuminated, the communication lines are closed. When speak indicator 1529 is illuminated, the patient may speak to the caregiver. The patient speaks into a microphone (not shown) coupled to head end siderail 20. When listen indicator 1530 is illuminated, the caregiver may speak to the patient in patient support 10 from speakers 1220. A graphic of a listening ear is positioned adjacent to speak indicator 1529 to indicate that a nurse or other caregiver is listening to the patient when lit. A graphic of a speaking person is positioned adjacent to listen indicator 1530 to indicate the patient is to listen to a nurse or other caregiver when illuminated.

Controller 50 is also configured to control functions of other devices located within a patient's room such as a TV or lighting of a room (not shown) as further described above with reference to FIG. 35. TV button 1532 controls turning on and off a TV (not shown) located in a room. When TV button 1532 is pressed, the TV is turned on. When TV button 1532 is pressed again, the TV is turned off. To change the channel of the TV, channel up and channel down buttons 1534, 1536 are pressed. To change the TV volume up or down, volume up and volume down buttons 1538, 1540 are pressed. To turn closed captioning of the TV on and off, a closed caption button 1542 is pressed. Radio button 1544 controls turning on and off a radio (not shown) broadcasting from speakers 1220 or elsewhere in the patient's room. When only the radio is on, channel up and down buttons 1534, 1536 and volume up and down buttons 1538, 1540 operate the channels and volume of the radio. If both the radio and TV are on, channel up and down buttons 1534, 1536 and volume up and down buttons 1538, 1540 operate the TV only.

To turn on the direct lighting in a room, such a ceiling light or other lighting that shines down, a direct light button 1546 is provided that is pressed to turn the light(s) on and off. Similarly, to turn on indirect lightly, such as a light on a headwall unit that shines up on the ceiling or down on the floor from a low level, an indirect light button 1548 is provided that is pressed to turn the light(s) on and off.

As shown in FIG. 74 interface panel 1512 includes a plurality of membrane input control buttons or raised button covers 1516 and a plurality of status indicators 1518 which are electrically coupled to circuit board 1233 of controller 52, allowing controller 52 to be used by persons out of patient support 10 to control the operation of various features of patient support 10, including extension, tilting, and articulation of deck 26, sending a nurse call signal, and enablement of the other functions of patient support 10. In a preferred embodiment, status indicators 1518 are LED's electrically coupled to circuit board 1233. According to alternative embodiments of the present disclosure, other functions of the patient support or remote equipment are controlled by the controller.

Head up button 1550 and head down button 1551 are provided to control adjustment of the position of head section 38 of deck 26 between the raised and lowered positions. Knee up button 1552 and knee down button 1554 are provided to control adjustment of the position of leg and seat sections 42 and 40. High button 1556 and low button 1558 are provided to control raising and lowering intermediate frame 32 relative to base frame 28.

Foot extend button 1560 and foot retract button 1562 cause leg section 42 to extend and retract which permits the position of footboard 18 of patient support 10 to be adjusted relative to the position of the patient's foot. To extend leg section 42, extend button 1560 is pressed until the desired position of footboard 18 is reached. To retract foot section 42, retract button 1562 is pressed until the desired position is reached.

Chair bed button 1564 and flat bed button 1566 are provided to control adjustment of the position of deck 26 between the chair and bed positions. To move patient support 10 toward the chair position, chair button 1564 is pressed until the degree of the chair position is achieved of until patient support 10 reaches the full chair position. To move patient support 10 toward the bed position, flat bed button 1566 is pressed until the desired degree of the chair position is removed or until patient support 10 reaches the flat bed position.

Tilt (Reverse Trendelenburg) button 1568 and reverse tilt (Trendelenburg) button 1570 are provided to control adjustment of the position of deck 26 between head raised (Reverse Trendelenburg) and head lowered (Trendelenburg) positions. To move patient support 10 to the head raised position, tilt button 1568 is pressed until the degree of the incline of intermediate frame 32 is achieved. To move patient support 10 toward the head lowered position, reverse tilt button 1570 is pressed until the desired degree of incline of intermediate frame 32 is achieved. When a nurse call button 1572 is pressed, a signal is sent to a nurse station or directly to predetermined caregivers that indicates that the patient needs attention.

According to the illustrative embodiment of the present disclosure, most of the buttons are only operable after a key or enable button 1584 is first pressed. This helps prevent the accidental activation and deactivation of certain functions of patient support 10. According to the preferred embodiment of the present disclosure, enable button 1584 must first be pressed before the functions controlled by the other buttons on panels 1512 and 1514 will initiate. However, the nurse call feature controlled by nurse call button 1572 will initiate without the need to first press enable button 1584.

To enable the other buttons, enable button 1584 must be pressed for at least or about 0.5 seconds. By requiring that the button be depressed for a predetermined amount of time, an accidental momentary depression of enable button 1584, such as when panel 1512 is wiped during cleaning, will not enable the other buttons.

Once enabled, the user has about a twenty second window to press the other buttons to initiate a function. Once the twenty second window passes without one of the other buttons being pressed, the other buttons are disabled and enable button 1584 must be pressed again to operate the functions. However, if one of the other buttons is pressed during the initial twenty second window, the window is reset so that the user has another twenty second window to press another button. Once twenty seconds passes without any button being pressed, the twenty second window expires and enable button 1584 must be pressed again.

According to alternative embodiments of the present disclosure, other times required to press the enable button are provided. For example, according to one embodiment, one second is required. According to another embodiment, no time is required so that the other buttons are enabled whenever the enable button is pressed. According to other alternative embodiments of the present disclosure, other windows of time are provided during which the other buttons are enabled. For example, according to some embodiments, the window is 5, 10, 15, 25, 30 or more seconds. According to another alternative embodiment, no enable button 1584 is provided.

Patient control 52 also enables and disables (locks out) specific features of patient support 10. By pressing head lock-out button 1586, the function of head up buttons 1520, 1551 and head down buttons 1522, 1550 of respective controllers 50, 52 are disabled so that head section 38 of deck 26 cannot be raised or lowered. When disabled, an indicator 1588 on button 1586 lights up. When head lock-out button 1586 is pressed again, head section 38 may be raised and lowered again and indicator 1588 goes off. A similar knee lock-out button 1590 and indicator 1592 are provided to enable and disable the function of knee up buttons 1524, 1552 and knee down buttons 1526, 1554 of respective controllers 50, 52.

A similar all actuator lock-out button 1594 and indicator 1596 are provided that disable the function or initiate movement of linear actuators 48 operated by controllers 50, 52. When pressed, all functions controlled by controllers 50, 52 that change the configuration of deck 26 or raise, lower, or tilt intermediate frame 32 are disabled and indicator 1596 lights up. When pressed again, the functions are enabled and indicator 1596 turns off. By disabling certain functions of controllers 50, 52, a caregiver can prevent accidentally articulation or other movement of patient support 10 when such articulation may be undesirable. According to alternative embodiments of the present disclosure, the other functions of controllers 50, 52, 54 are also disabled and enabled by one or more lock-out buttons.

Other indicators which relate to various patient support status functions are also included on interface panel 1512. A bed position indicator 1598 is illuminated when intermediate frame 32 is not in the lowermost position. When intermediate frame 32 is in the lowermost position, this indicator 1598 is off. A service indicator 1610 is lit when patient support 10 detects that a component needs serviced. If patient support 10 does not detect that a component needs serviced, this indicator 1610 is off.

With reference to FIG. 75, interface panel 1514 includes a plurality of membrane input control buttons or raised button covers 1516 and a plurality of status indicators 1518 which are electrically coupled to circuit board 1238 of controller 54, allowing controller 54 to be used by persons out of patient support 10 to control the operation of various features of patient support 10, including detecting the position of a patient, the patient's weight, and operation of mattress 14. In a preferred embodiment, status indicators 1518 are LED's electrically coupled to circuit board 1238. According to alternative embodiments of the present disclosure, other functions of the patient support or remote equipment are controlled by the controller.

As shown in FIG. 75, patient position monitor buttons 1612, 1614, 1616 are provided to control activation of a patient position monitoring system, which notifies a caregiver when the patient changes position relative to patient support 10. When one of buttons 1612, 1614, 1616 is selected, the other respective buttons 1612, 1614, 1616 are automatically deselected. Status indicators 1518 are provided with each button 1612, 1614, 1616 indicating which of the monitoring modes is on. Patient position sensors 5004, 5008, 5010 are positioned on deck 26 underneath mattress 14. Details of suitable patient position detection systems are provided in U.S. Pat. No. 6,208,250, to Dixon et al.; U.S. Pat. No. 6,067,019, to Scott; and U.S. Pat. No. 5,808,552, to Wiley et al., the disclosures of which are expressly incorporated by reference herein.

Button 1616 controls activation of the position monitoring system to detect an "exit" condition when the patient has exited patient support 10. When button 1616 is pressed to activate monitoring of the exit condition, the respective indicator 1518 on button 1616 lights up. Otherwise the respective indicator 1518 on button 1616 is off. If the exit condition is detected by bed exit sensor 562, visual and audible alarms will activate notifying the caregiver that the patient has exited patient support 10.

Button 1614 controls activation of the position monitoring system to detect a "pre-exit" condition when the patient is bearing weight primarily on an edge of patient support 10, such as when the patient is sitting on the edge of patient support 10. When button 1614 is pressed to activate monitoring of the pre-exit condition, the respective indicator 1518 on button 1614 lights up. Otherwise the respective indicator 1518 on button 1614 is off. If the pre-exit condition is detected, the visual and audible alarms will activate notifying the caregiver that the patient has moved to the edge of patient support 10. Furthermore, the alarms will also activate if the exit condition is detected.

Button 1612 controls activation of the position monitoring system to detect a "patient up" condition when the patient's torso moves beyond a predetermined position relative to deck 26. When button 1612 is pressed to activate monitoring of the patient up condition, the respective indicator 1518 on button 1612 lights up. Otherwise the respective indicator 1518 on button 1612 is off. If the patient up condition is detected, the visual and audible alarms will activate notifying the caregiver that the patient has moved to the up position.

Alarm control button 1618 and volume indicator 1620 are provided to a caregiver to control the volume of the audible alarm that sounds when the patient monitoring system detects one of the above-mentioned conditions. Alarm button 1618 controls the volume of the alarm. Volume indicator 1620 comprises a plurality of LED's that are lit according to the selected volume level, i.e., the higher the volume selected, the more LED's that are lit. If a user wants to turn the volume up, alarm button 1618 is pressed repeatedly until the desired volume is reached. To lower the volume, alarm button 1618 is pressed repeatedly until the peak volume is reached. After the peak volume is reached, continued pressing on alarm button 1618 will gradually reduce the volume of the alarm until the lowest volume is reached. After the lowest volume is reached, continued pressing on alarm button 1618 will gradually increase the volume. If no LED's are lit, the alarm is deactivated.

Inflation system buttons 1622, 1624, 1626, 1628 are provided that control the function of the air pressure inflation system of mattress 14. Maximum inflation button 1622 inflates the mattress zones to a predefined air pressure level and may be used to facilitate administration of CPR. A corresponding indicator 1518 on button 1622 lights up when the maximum inflation function is activated. When pressed again, the mattress zones return to normal operating pressure and the corresponding indicator 1518 turns off.

First turn assist button 1624 controls the turning of a patient toward one side of patient support 10. Second turn assist button 1626 controls the turning of the patient toward the other side of patient support 10. When either of these buttons 1624, 1626 are pressed, they begin the turn assist function and the associated indicator 1518 lights up. When the respective turn assist function is complete, the associated indicators 1518 turn off. A rail down indicator 1627 is illuminated when any of siderails 20, 22 are not in the raised position. Patient size button 1628 button permits a caregiver to set the size of the patient positioned on mattress 14. Three graphics representing different sized patients are positioned next to corresponding indicators 1518. When patient size button 1628 is pressed, a different sized patient is selected and the corresponding indicator 1518 lights up. In an illustrative embodiment, depending on which size patient is selected, different air pressures are provided to mattress 14.

Interface panel 1514 further includes a plurality of buttons and LED display 1242 which permit a caregiver to weigh the patient using the patient weighing function. A unit selection button 1630 enables the caregiver to choose between pounds and kilograms as the unit of weight measurement. LED display 1242 displays the patient's weight and selected unit of measurement.

Calibration button 1632, change item button 1634, add item button 1636, and subtract item button 1638 are provided to the caregiver to calibrate the system for weighing a patient. For example, before a patient is placed on patient support 10, calibration button 1632 is pressed to set the weight reading to 000.0 lbs/kg so that the initial weight of mattress 14, deck 26, and any other patient support component or piece of medical equipment is negated from the weight reading. Thus, only the weight of the patient is indicated when the patient is on patient support 10.

If a patient support component or piece of medical equipment is added to or removed from patient support 10 that may affect the weight reading, change item button 1634, add item button 1636, and subtract item button 1638 are illustratively used to take the additional or subtracted weight into account. For example, if a piece of medical equipment, such as an IV pole, is added to patient support 10, change item button 1634 and add item button 1636 are pressed while the piece of medical equipment is added and the additional weight detected by the weigh system is subtracted from the measured weight so that the additional weight of the IV pole is negated from the weight displayed on display 1242. Similarly, if a piece of medical equipment is removed from patient support 10, change item button 1634 and subtract item button 1638 are pressed while the piece of medical equipment is removed and the removed weight detected by the weigh system is added to the measured weight so that the loss of weight of the removed pieced of medical equipment is negated from the weight displayed on display 1242.

Foot Pedal Controls and Nightlight

As shown in FIG. 1, foot pedal controls 56 are coupled to base frame 28. Foot pedal controls 56 are provided to control raising and lowering of deck 26 relative to base frame 28 and to control raising and lowering head section 38 of deck 26 relative to weigh frame 36.

Figure 76:
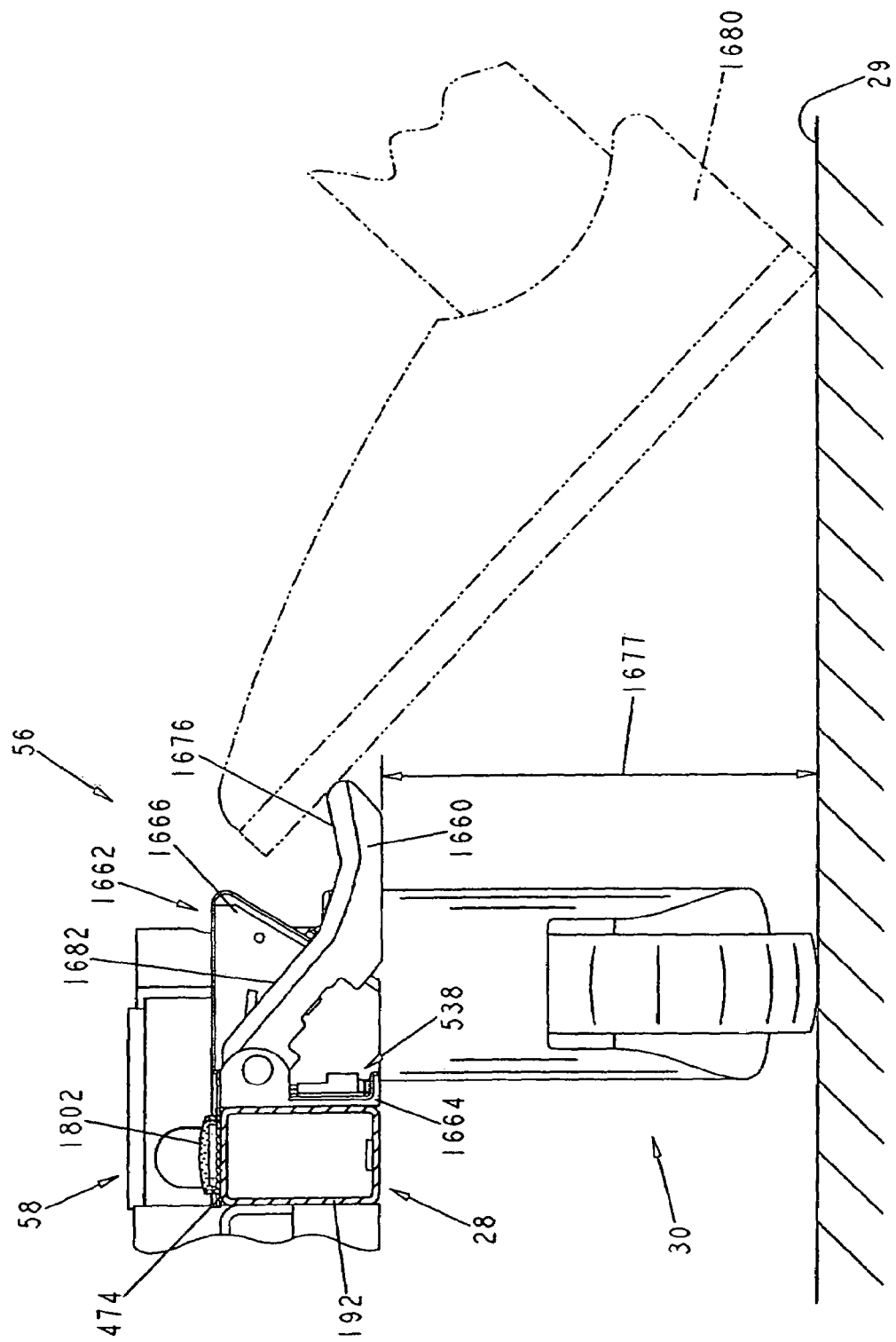
FIG. 76 is a side elevational view of an illustrative embodiment foot pedal control of the present invention, showing the foot of a caregiver (in phantom) positioned to step on the foot pedal control.

Each foot pedal control 56 is associated with one of the above-mentioned functions and includes a pedal or control member 1660 appropriately labeled for the respective function. By stepping on any of pedals 1660 with the tip of one's foot as shown in FIG. 76, one of these functions of patient support 10 is activated. When pedals 1660 are released, they are automatically biased back to the neutral position and the function terminates.

With reference to FIGS. 76-79, pedals 1660 are pivotably coupled to a pedal housing 1662 that is fixedly coupled to base frame 28 in a spaced-apart relationship with the floor 29. Pedal housing 1662 includes an L-shaped body portion 1664 that couples to base frame 28 and a housing portion 1666 that defines an enclosed space 1668.

Because housing portion 1666 is centrally located and raised relative to foot pedals 1660, it acts as a locator for pedals 1660. For example, a caregiver who is familiar with patient support 10 will be able to sweep their foot over pedals 1660 until striking either side of housing portion 1666. Because of their familiarity with patient support 10, they will recognize which pedal 1660 is located beneath their foot. If this pedal 1660 performs the desired function, the need only step down without looking down at the respective pedal 1660 for an decal or indicator that indicates the specific function of that respective pedal 1660. If the desired pedal 1660 is not the one located under their foot, they will recognize that they need to back away from housing portion 1666 to the next adjacent foot pedal 1660 that does perform the desired function. Preferably, the caregiver will initially sweep toward the correct side of housing portion 1666 on which the desired foot pedal 1660 is located.

Figure 77:
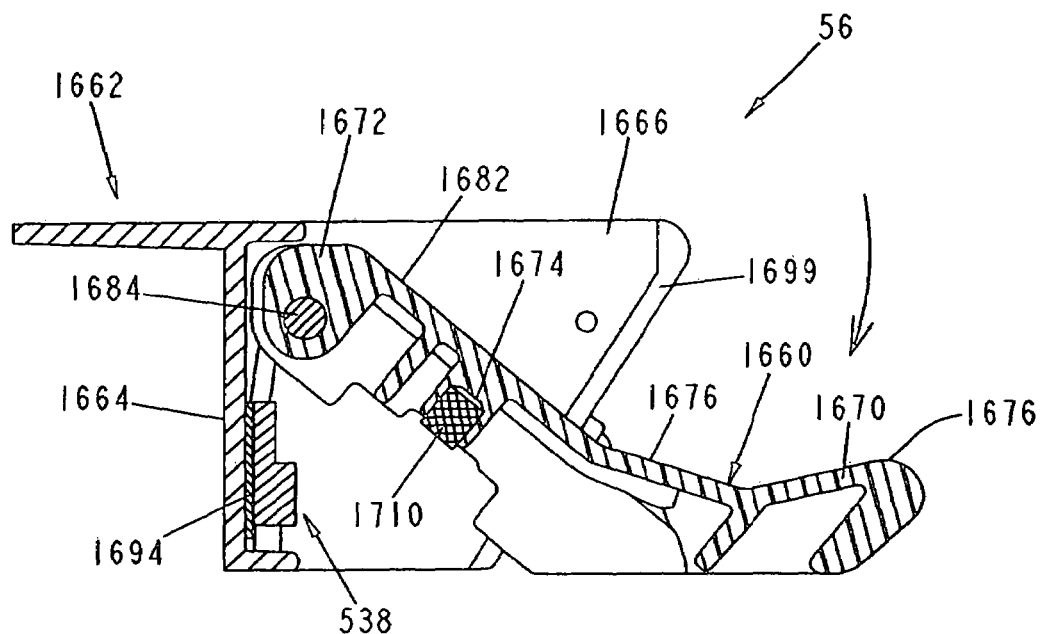
FIG. 77 is a cross sectional view taken along line 77-77 of FIG. 80, showing the foot pedal control in a raised position.
Figure 78:
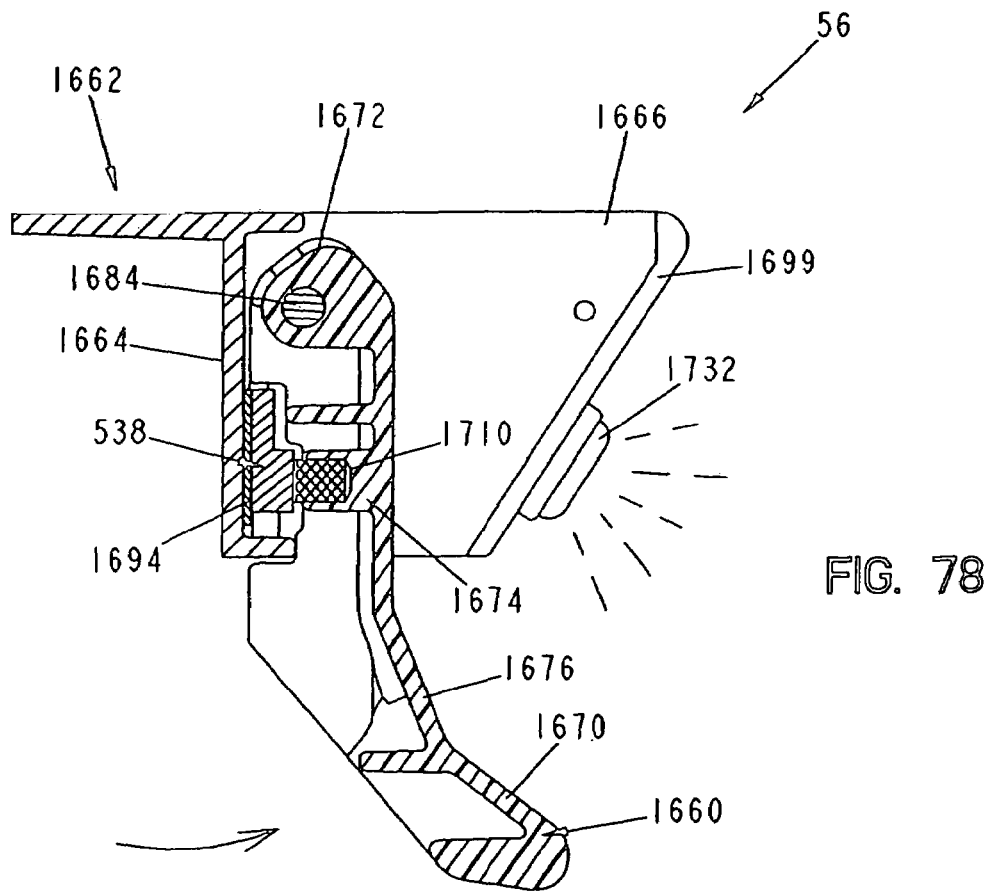
FIG. 78 is a view similar to FIG. 77, showing the foot pedal control in a lowered position.

As shown in FIGS. 77 and 78, each pedal 1660 is pivotable between a first or up position and a second or down position. Each pedal 1660 has a stepped profile and includes a pedal portion 1670, a pivot portion 1672, and a sensor portion 1674. Pedal portion 1670 extends beyond pedal housing 1662 to permit a caregiver to press down on pedal portion 1670 as shown in FIG. 76. When in the first raised position, a top surface 1676 of pedal portion 1670 is about 6 inches above the floor 29 so that 5.5 inches of clearance 1677 exists under pedal portion 1670. Furthermore, this spacing permits a caregiver or other person to operate pedals 1660 while his or her heal 1680 rests on floor 29. Because the caregiver's heal 1680 is on the ground 29 during the movement of patient support 10, his or her foot is further away from the moving components of the patient support. Preferably, decals or indicators (not shown) are provided on inward portions 1682 of top surface 1676 that is at an angle of 45 degrees from horizontal to help a caregiver's line of sight in viewing the decal or indicator that indicates what function of patient support 10 is controlled by the particular pedal 1660.

Figure 79:
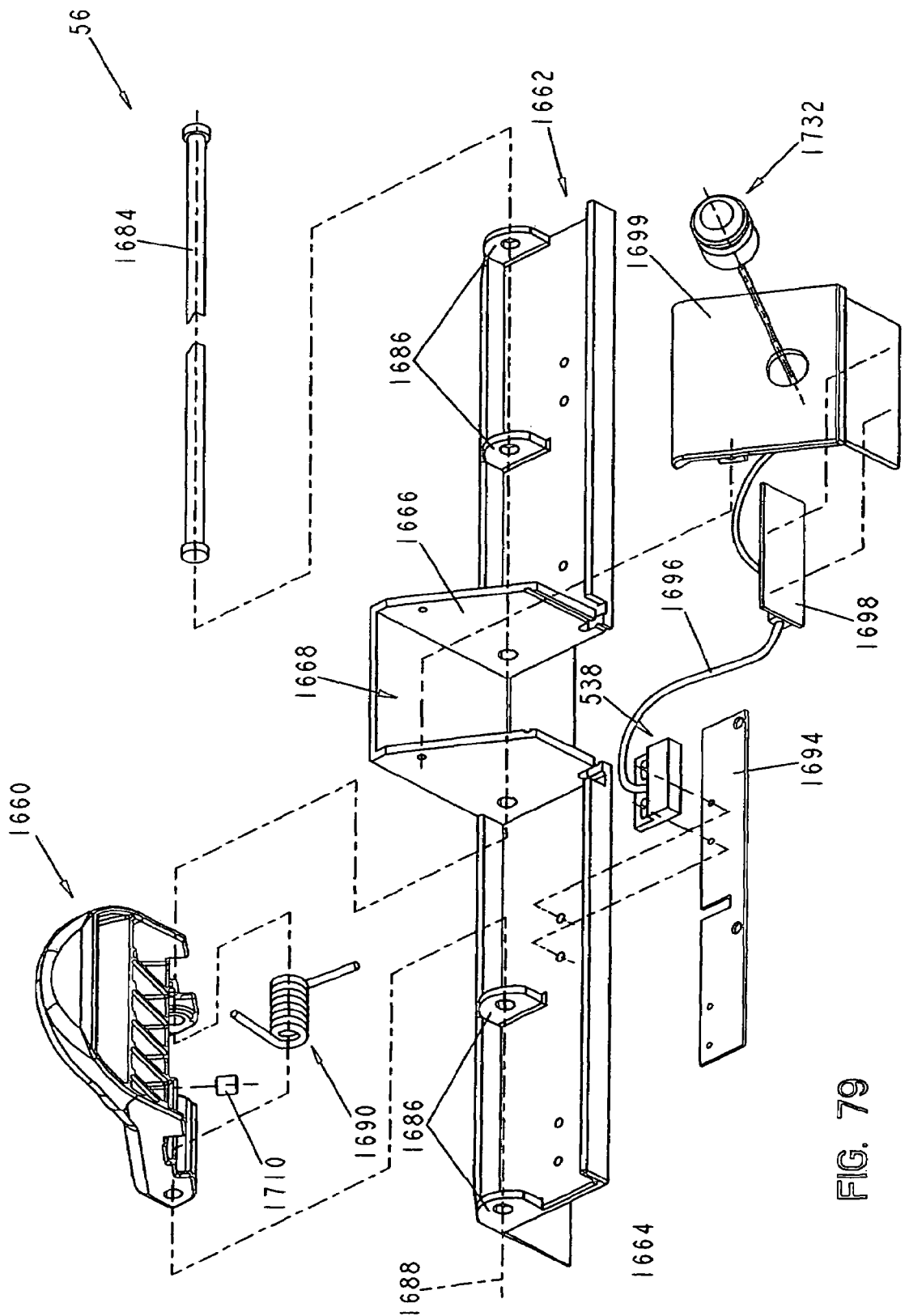
FIG. 79 is an exploded perspective view of the foot pedal control of FIG. 76.

As shown in FIG. 79, a pin 1684 is provided that extends through pivot flanges 1686 and to define a pivot axis 1688 about which pedals 1660 pivot on housing 1662. Each foot pedal control 1660 includes a biaser or spring 1690 through which pin 1684 extends that biases pedal 1660 up toward the first raised position.

The position of each pedal 1660 is detected by a sensor 538. If sensor 538 detects that any one of pedals 1660 is moved and held in the second lowered position for about one second and then returned to the first raised position, pedals 1660 are enabled to operate the respective functions of patient support 10 for twenty seconds. To activate any of these functions, a respective pedal 1660 must be moved to the second lowered position within the twenty second enabled window.

If a pedal 1660 is not moved back down to the second lowered position within the twenty second enabled widow, pedals 1660 are disabled and must be enabled again as described above by holding one of pedals 1660 in the second lowered position for about one second. If any of pedals 1660 are lowered within the twenty second window, the function is performed and the window is reset for another twenty seconds. If twenty seconds go by without any of the pedals 1660 being moved back down to the second lowered position, pedals 1660 are again disabled. If two pedals 1660 are simultaneously moved to the second lowered position, neither function is performed. Preferably, pedals 1660 travel through an angle of 50 degrees from the first raised position to the second lowered position.

Figure 80:
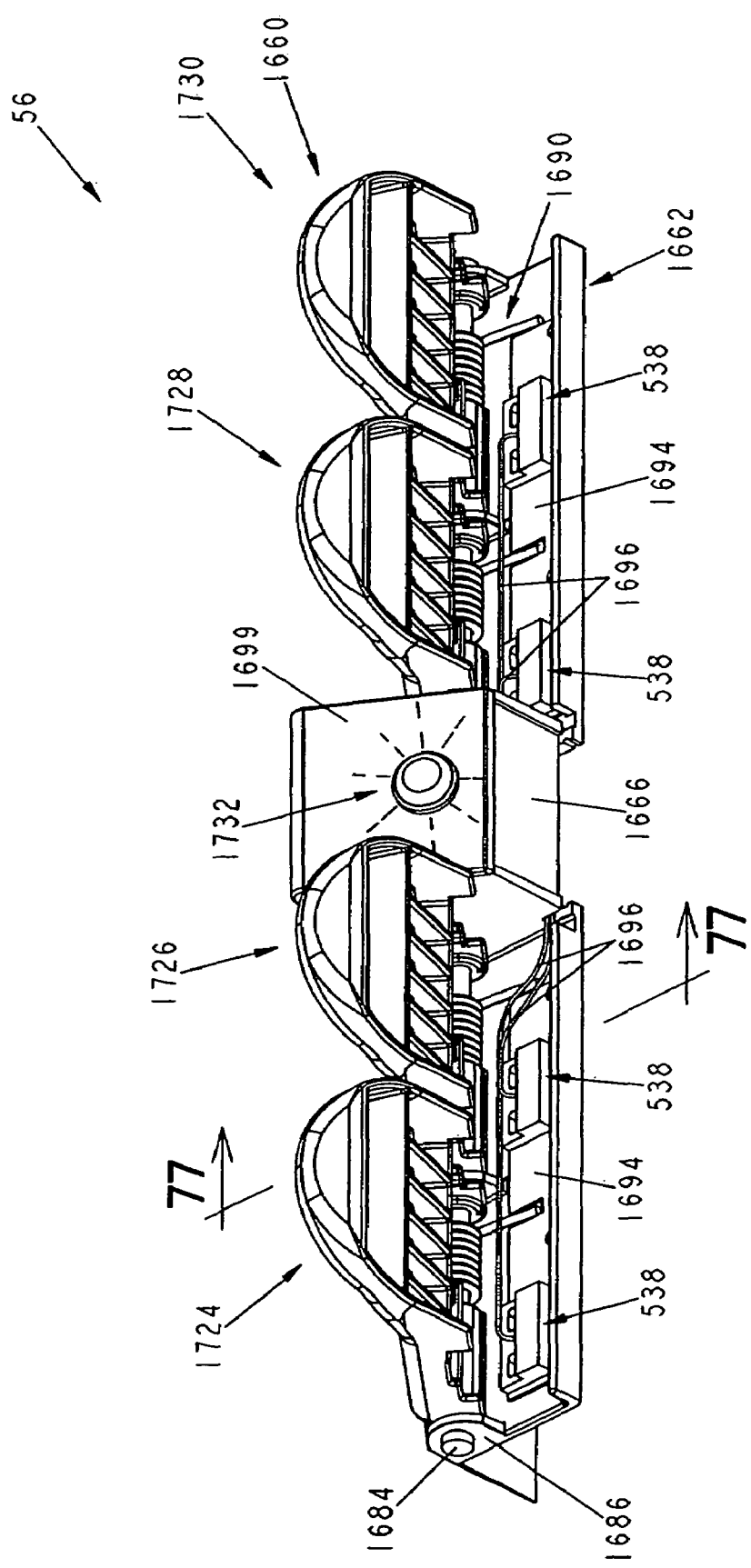
FIG. 80 is a perspective view of the foot pedal control of FIG. 76.

Each of the four sensors 538 is preferably mounted to one of a pair of mounting strips 1694 as shown in FIGS. 79 and 80 (only one is shown in FIG. 79) mounted to housing 1662. A cable 1696 is coupled to each sensor 538 (only one is shown in FIG. 79) to send signals indicative of the position of pedal 1660 detected by sensor 538. Cables 1696 extend into enclosed space 1668. Each cable 1696 is coupled to a circuit board 1698 positioned in enclosed space 1668 and a single cable is coupled to control system 44 to control respective linear actuators 48. A cover 1699 is also provided that encloses interior space 1668.

According to the preferred embodiment of the present disclosure, sensor 538 is a Hall effect field sensor that detects change in the characteristics of a magnetic field generated by pedal 1660. A magnet 1710 is positioned on sensor portion 1674 of each pedal 1660 in a position spaced apart from sensor 538. Sensor 538 detects the change in position of magnet 1710 during movement of the respective pedal 1660 by detecting the change in magnetic field. Based on this change in magnetic field, sensor 538 sends a signal indicative of the first raised and second lowered positions of the respective pedal 1660 to the control system 44. Control system 44 then initiates the application of power to actuators 48 to control and power the function of the respective components of patient support 10.

Figure 81:
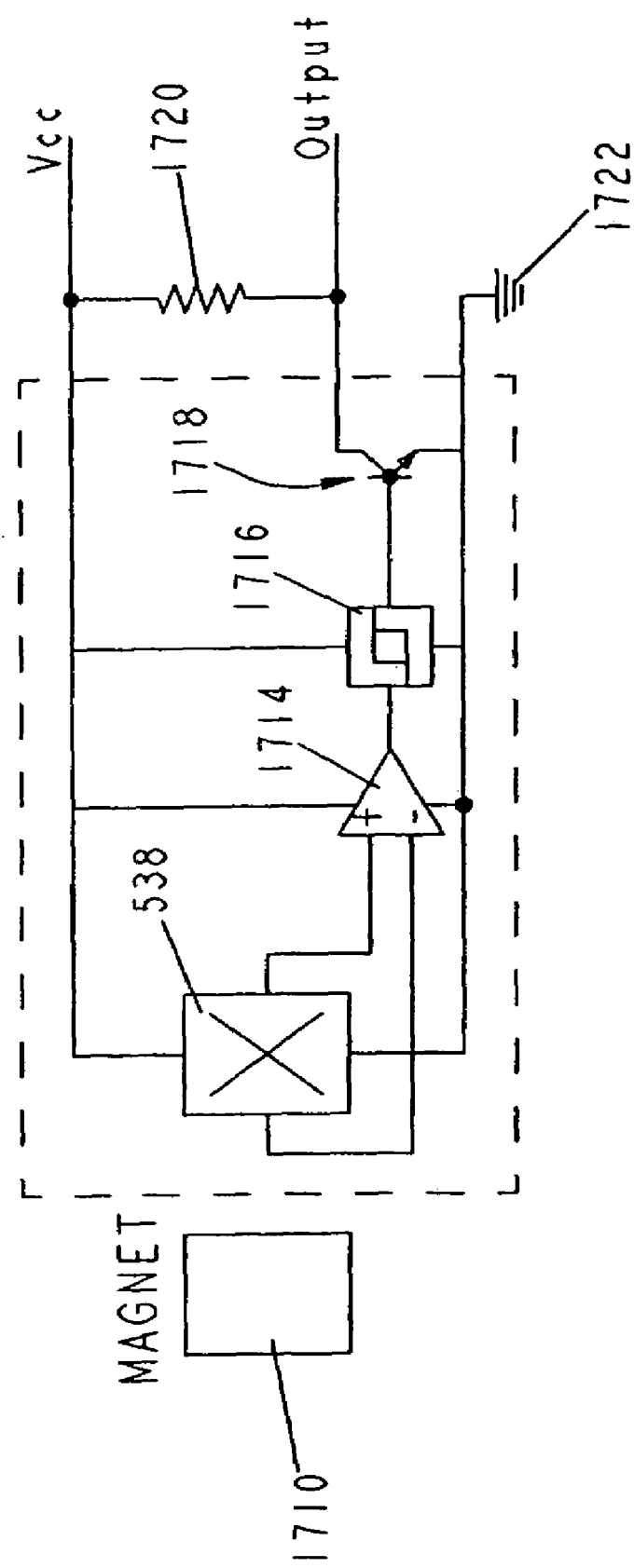
FIG. 81 is an electrical schematic diagram of a sensor and associated circuitry for the foot pedal control of FIG. 76.

An illustrative circuitry associated with sensor 538 is shown in FIG. 81. The circuitry includes an op-amp 1714 coupled to sensor 538, an open collector 1716, a transistor 1718, and a resistor 1720. Sensor 538, op-amp 1714, open collector 1716, and transistor 1718 are coupled to ground 1722. Sensor 538, op-amp 1714, open collector 1716, and resistor 1720 are coupled to a 5 volt source. Transistor 1718 and resistor 1720 are coupled to the output of the circuit. Illustratively, resistor 1720 is 470 ohms and sensor 538 is a Cherry MP1013 snap fit proximity sensor sold by The Cherry Corporation, 3600 Sunset Avenue, Waukegan, Ill. that detects magnetic fields.

As shown in FIG. 80, four pedals 1660 are provided to control various functions of patient support 10 when pushed down. For example, a first pedal 1724 is provided that when pivoted down, raises head section 38 of deck 26. A second pedal 1726 is provided for lowering head section 38 relative to weigh frame 36 when pivoted down. Series of pedals 1660 also includes a third pedal 1728 for raising intermediate frame 32 relative to base frame 28 when pivoted down, and a fourth pedal 1730 is provided for lowering intermediate frame 32 when pivoted down. According to an alternative embodiment, the plurality of pedals 1660 also includes a pedal for extending and retracting leg section 42 of the patient support 10 or for activating any other feature of the patient support 10.

As shown in FIGS. 79 and 80, a light 1732 is provided on cover 1699. Light 1732 illustratively includes four LED's (not shown) and is coupled to circuit board 1698. Preferably, light 1732 shines on floor 1678 so that a silhouette of pedals 1660 is provided in a semi-dark or dark room. Therefore, enough light is provided that a caregiver can locate foot pedals 1660 without producing enough light that would disturb a resting patient.

Figure 82:
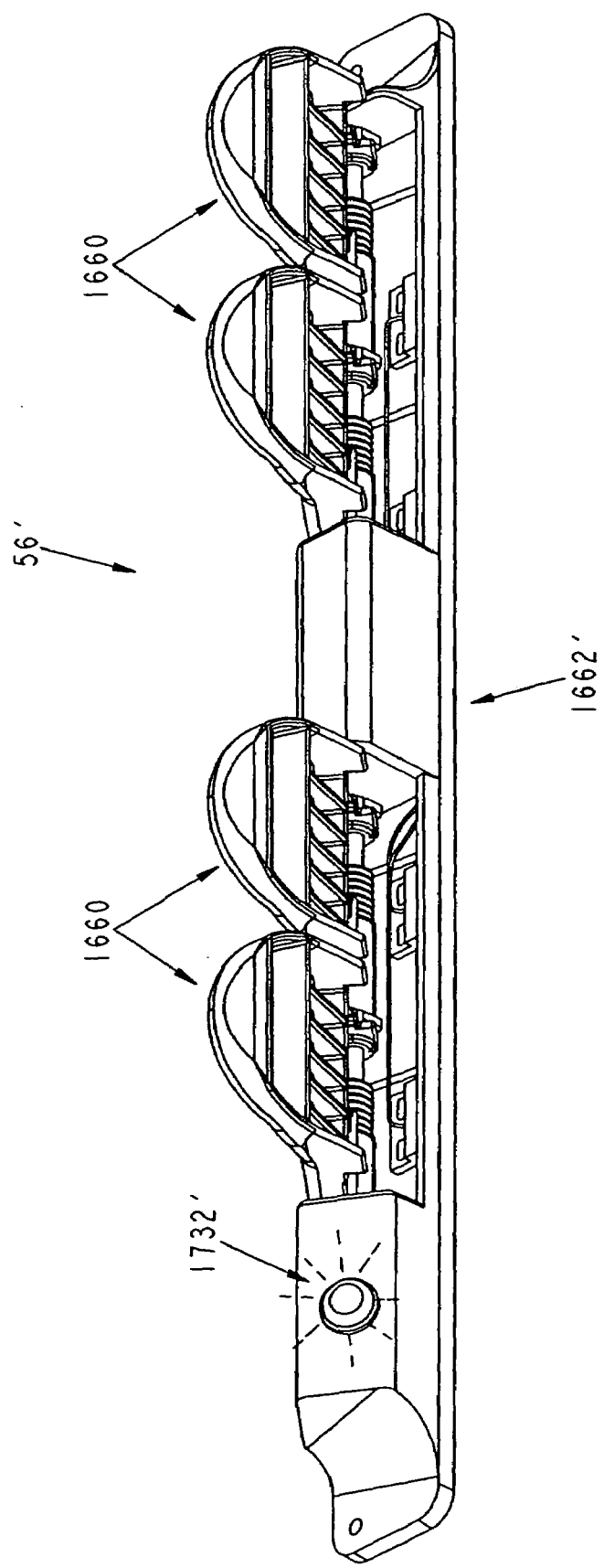
FIG. 82 is a perspective view of an alternative embodiment foot pedal control of the present invention.

An alternative embodiment foot pedal control 569 is illustrated in FIG. 82. Foot pedal control 569 is substantially similar to foot pedal control 56, such that like reference numbers are used to identify like components.

As shown in FIGS. 57 and 82, foot control pedal 569 includes light 17329 which is provided on pedal housing 16629. Light 17329 includes four LED's (not shown) and is coupled to circuit board 1698. According to the illustrative embodiment of FIG. 57, light 17329 is positioned at the end of pedal housing 16629 positioned nearest the longitudinal center of patient support 109.

According to alternative embodiments of the present disclosure, light 1732 is placed elsewhere on the patient support 10 to shine directly on foot pedals 1660. For example, according to one alternative embodiment, light 1732 is provided on the sides of housing portion 1666 (see FIGS. 1 and 58) of pedal housing 1662 so that light 1732 shines directly on pedals 1660. According to another alternative embodiment, a light 1732 is provided above pedals 1660. For example, according to one embodiment, light 1732 is mounted on the outwardly facing surface of the body portion 1664 of pedal housing 1662. In other alternative embodiments, light 1732 is mounted on the bed frame or other components of patient support 10, such as siderails 20, 22 or deck 26, to shine directly down on pedals 1660. As shown in FIG. 8, a set of foot pedal controls 56 are supported on base frame 28 on the opposite side of patient support 10. Pedal controls 56 on opposite sides of patient support 10 are mirror images of each other.

According to alternative embodiments of the present disclosure, other sensors are provided to detect the position of the pedals 1660 and to control the respective functions of the patient support 10, such as other proximity switches, a three-position mechanical switch, other mechanical switches, other electrical switches, other field sensors that detect changes in an electric field due to changes in capacitance or inductance, other field sensors known to those of ordinary skill in the art, or any other sensor known to those of ordinary skill in the art.

Figure 83:
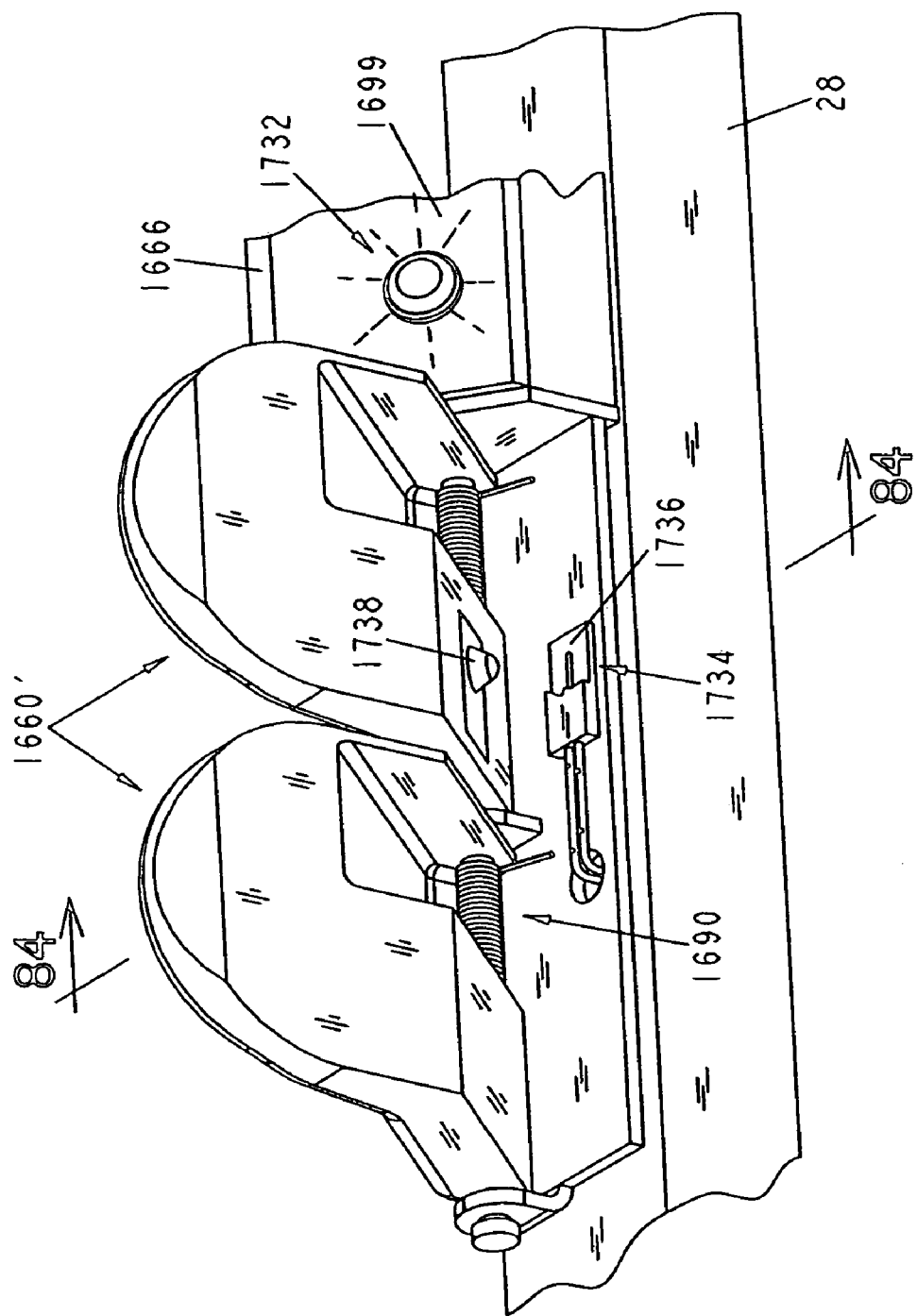
FIG. 83 is a partial perspective view of a further alternative embodiment foot pedal control of the present invention.
Figure 84:
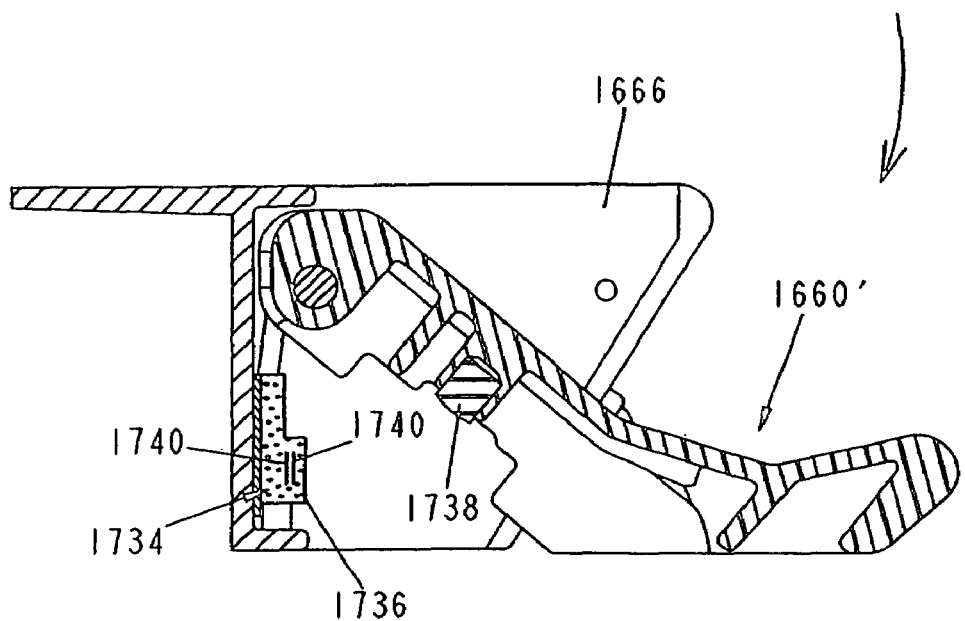
FIG. 84 is a cross-sectional view taken along line 84-84 of FIG. 83, showing the foot pedal of FIG. 83 in a raised position.
Figure 85:
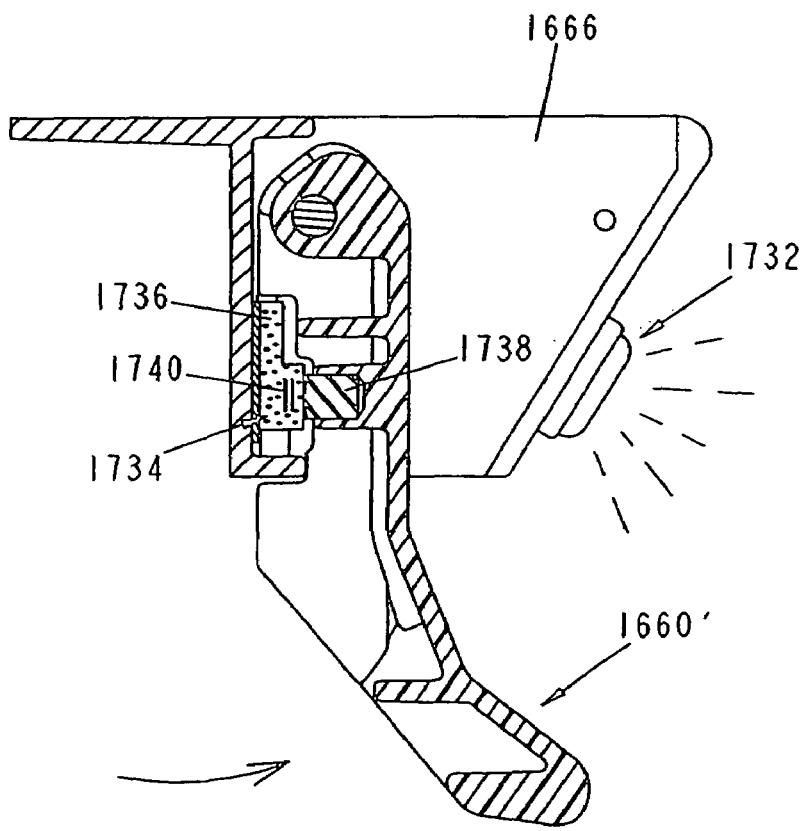
FIG. 85 is a view similar to FIG. 84, showing the foot pedal of FIG. 83 in a lowered position.

One such alternative embodiment sensor 1734 is shown in FIGS. 83-85. Sensor 1734 is preferably a tape sensor embedded in a resilient material 1736, such as potting material, that provides a water proof cover to sensor 1734. Pedals 16609 are provided with a rubber plunger 1738 that presses down on resilient material 1736 and moves contact strips 1740 of sensor 1734 to close a circuit. When the circuit is closed, control system 44 detects that the respective pedal 1660 is in the second lowered position. When the respective pedal 16609 is released, contact strips 1740 separate and the circuit is open. Control system 44 detects the open circuit and recognizes that the respective pedal 16609 has moved away from the second lowered position. Additional detail of a tape switch are provided in U.S. Pat. No. 4,539,560, to Fleck et al, the disclosure of which is expressly incorporated by reference herein.

Figure 86:
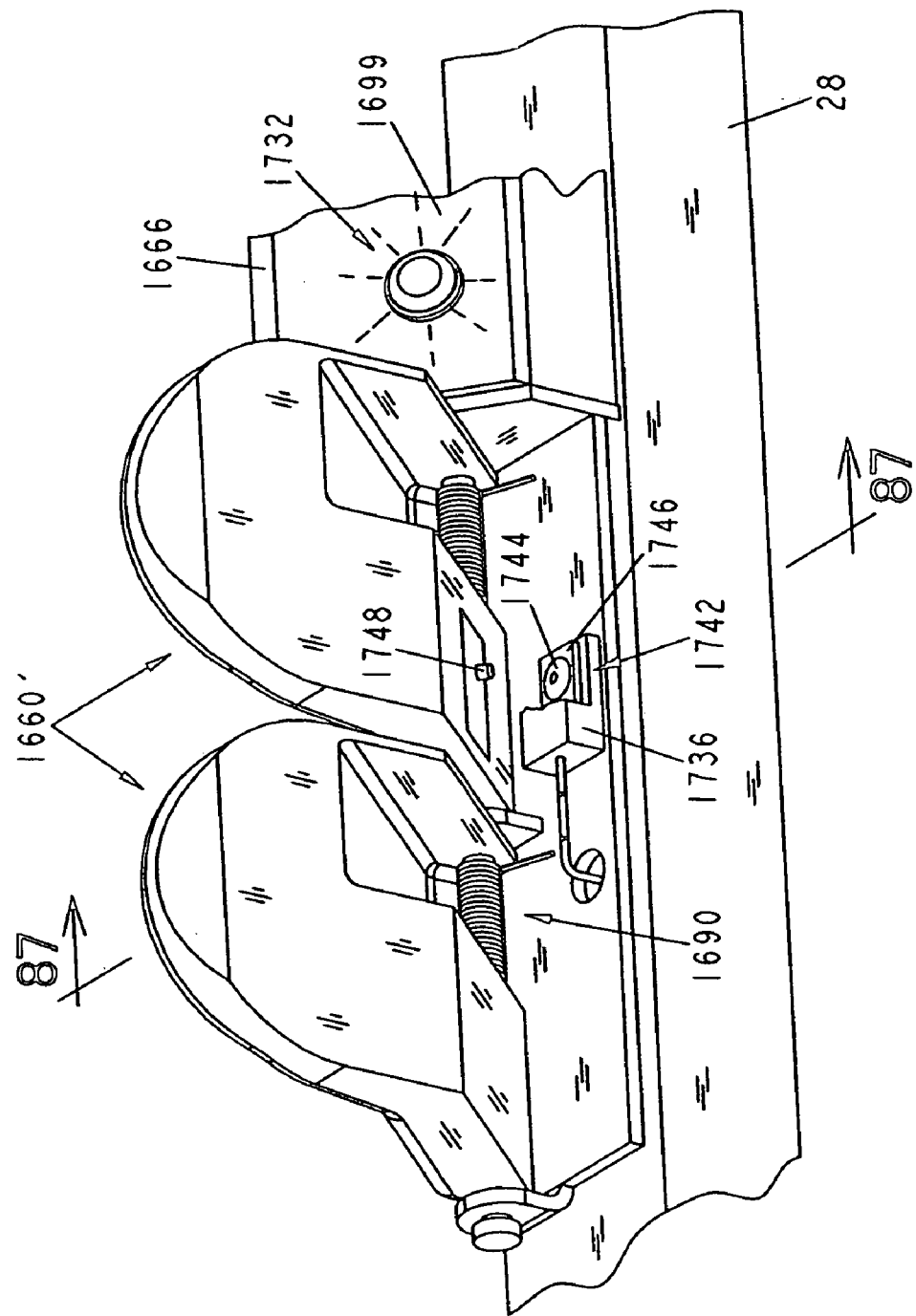
FIG. 86 is a perspective view of another alternative embodiment foot pedal control of the present invention.
Figure 87:
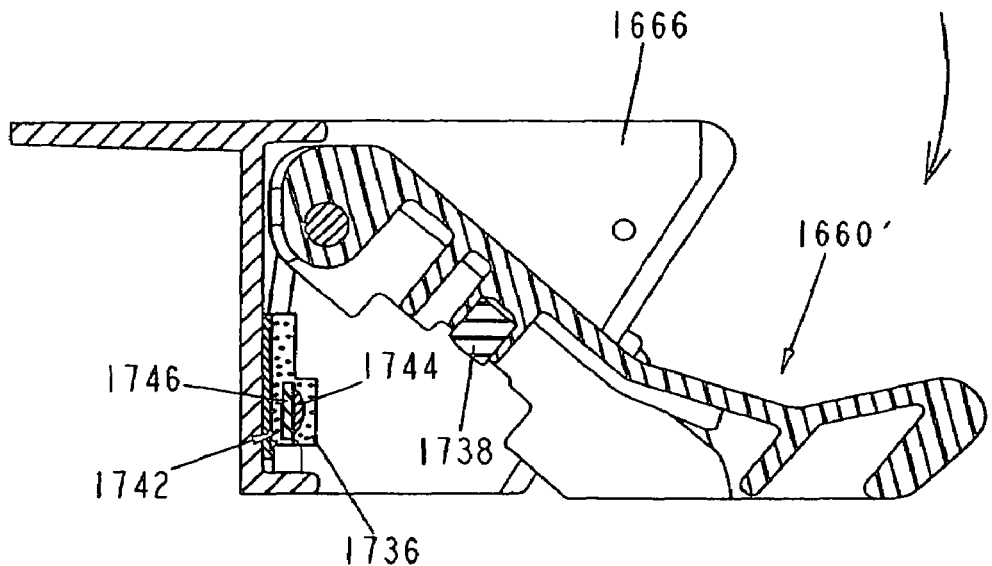
FIG. 87 is a cross-sectional view taken along line 87-87 of FIG. 86, showing the foot pedal of FIG. 86 in a raised position.
Figure 88:
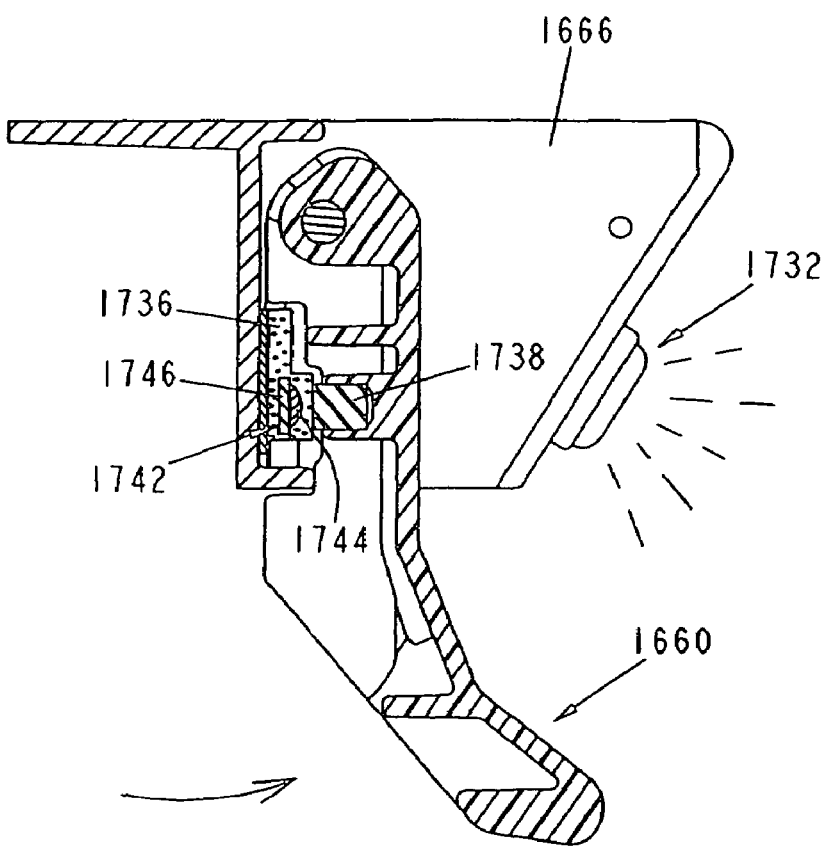
FIG. 88 is a view similar to FIG. 87, showing the foot pedal of FIG. 86 in a lowered position.

Another such alternative embodiment sensor 1742 is shown in FIGS. 86-88. Sensor 1742 is preferably a dome switch sensor embedded in a resilient material 1736, such as potting material, that provides a water proof cover to sensor 1742. Pedals 16609 are provided with rubber plunger 1738 that presses down on resilient material 1736 and moves dome 1744 of sensor 1734 that is mounted to a circuit board 1746 to close a circuit. An alternative plunger or actuator 1748 is shown in FIG. 86 that has a diameter of 0.118 inches. When the circuit is closed, control system 44 detects that the respective pedal 16609 is in the second lowered position. When the respective pedal 16609 is released, dome 1744 returns to its normal position and the circuit is open. Control system 44 detects the open circuit and recognizes that the respective pedal 16609 has moved away from the second lowered position. The preferred embodiment dome switch sensor is a Cannon SD 350 Dome Switch that requires 2.25 N operating forces and is sold by Cannon, ITT Industries.

Figure 89:
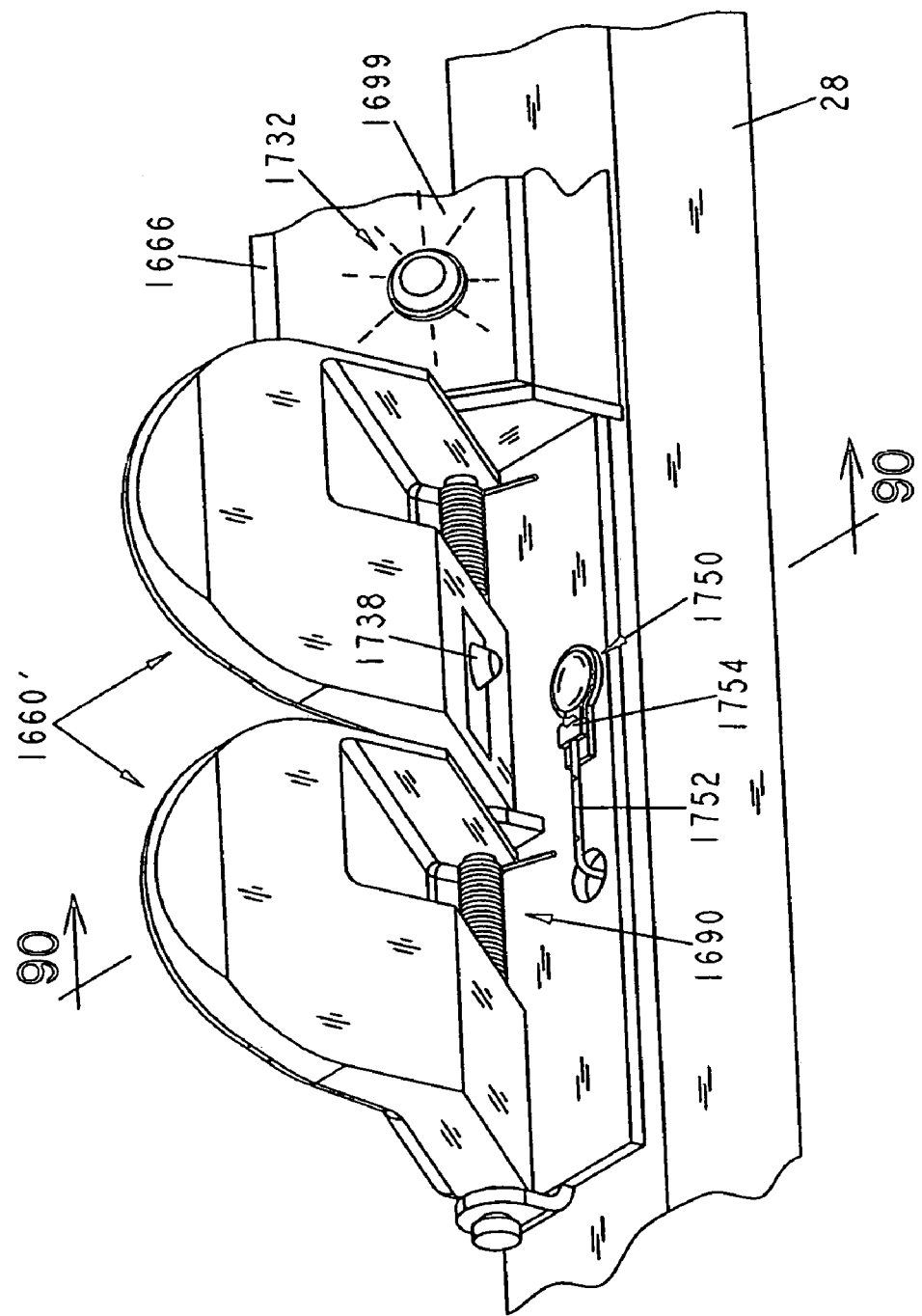
FIG. 89 is a perspective view of another alternative embodiment foot pedal control of the present invention.
Figure 90:
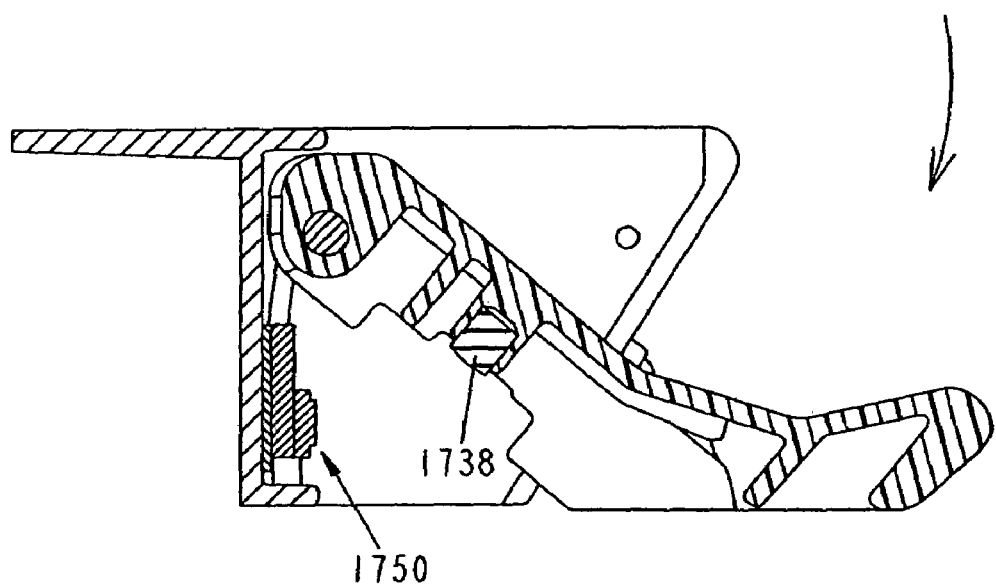
FIG. 90 is a cross-sectional view taken along line 90-90 of FIG. 89, showing the foot pedal of FIG. 89 in a raised position.
Figure 91:
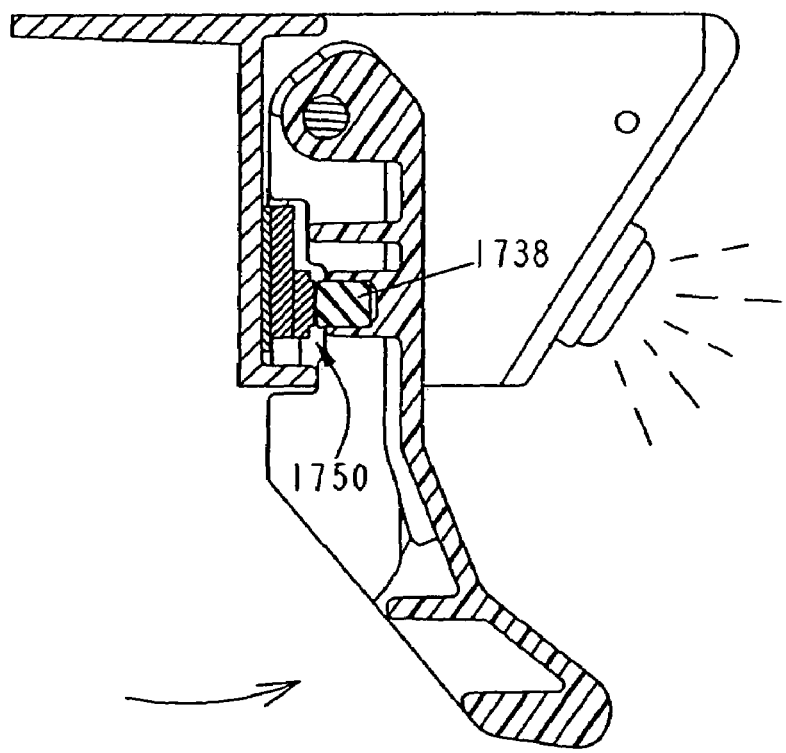
FIG. 91 is a view similar to FIG. 90, showing the foot pedal of FIG. 89 in a lowered position.

Another such alternative embodiment sensor 1750 is shown in FIGS. 89-91. Sensor 1750 is preferably a force sensing resistor having its contacts with a cable 1752 embedded in a resilient material 1754, such as potting material, that provides a water proof cover to the contact. Pedals 16609 are provided with rubber plunger 1738 that presses down on sensor 1750 and creates force on sensor 1750. When force is applied to sensor 1750, the overall electrical resistance of sensor 1750 changes. This change is resistance is monitored by the control system 44. When the resistance reaches a predetermined value, control system 44 detects that the respective pedal 16609 is in the second lowered position. When the respective pedal 16609 is released, the resistance returns to its normal value and control system 44 recognizes that the respective pedal 16609 has moved away from the second lowered position. Preferably, enough force is required that accidental lowering of the respective foot pedal 16609 will not change the resistance to the predetermined value. Furthermore, this force will preferably be greater that what a typical child can generate to avoid activation by children. According to an alternative embodiment, once the predetermined resistance is reached, the speed at which the function operates is controlled by the amount of force applied to the pedal 16609 which controls the amount of resistance of the sensor 1750 above the predetermined value. For example, if the force applied creates a resistance just above or at the predetermined value, the function, such as lowering the patient support 10, will occur slowly. However, if more force is applied and the resistance is increased above the predetermined value, the speed of the patient support lowering will increase proportionally with the amount of force applied to the pedal 16609. Thus, if a smaller force is applied, the patient support 10 will lower slowly. If a greater force is applied, the patient support 10 will lower faster. If an even greater force is applied, the patient support 10 will lower even faster. Preferably, the function will have a maximum speed that cannot be exceeded regardless of the amount of force applied.

Obstacle Detection Device

Referring now to FIGS. 1, 2, and 57, the obstacle or interference detection device 58 is shown as coupled to the base frame 28 of the patient support 10. The obstacle detection device 58 illustratively includes first and second sensors 1802 and 1804 which are coupled to top surfaces 474 and 476 of the longitudinally extending first and second side members 192 and 194 of the base frame 28, respectively. While in the following description, first and second sensors 1802 and 1804 are illustrated as being associated with the side members 192 and 194 of the patient support 10, it should be appreciated that additional sensors could be positioned adjacent the head end 25 and the foot end 27 of the patient support 10.

Each sensor 1802 and 1804 is configured to provide an obstacle detection signal to control system 44 in the event that it detects an obstacle or determines that a fault condition exists. More particularly, each sensor 1802 and 1804 is configured to provide the obstacle detection signal to control system 44 upon detecting that an object, such as an individual's foot, is supported on one of the upper surfaces 474 and 476 of the base frame 28.

In response to the obstacle detection signal from either of sensors 1802 or 1804, control system 44 will prevent the lowering of the intermediate frame 32 relative to the base frame 28. Moreover, the obstacle detection signal indicates that either an obstacle is supported on the base frame 28 or that at least one of the sensors 1802 or 1804 is not operating properly and is in a fault condition. As such, in order to avoid potential damaging impact with the detected obstacle, control system 44 prevents actuators 48a and 48b from operating to lower the intermediate frame 32. In an illustrative embodiment, control system 44 permits continued operation of the actuators 48a and 48b to raise the intermediate frame 32. Further, upon receiving the obstacle detection signal, control system 44 may instruct the actuators 48a and 48b to raise the intermediate frame 32 for a predetermined time period, illustratively 2 seconds, while preventing operation of the actuators 48a and 48b to lower the intermediate frame 32. Raising the intermediate frame 32 for a time period after an obstacle has been detected, provides for the immediate and automatic movement of the frame 32 in a direction away from the detected obstacle.

While the sensors 1802 and 1804 of the obstacle detection device 58 are illustratively positioned on the base frame 28, it should be appreciated that the sensors 1802 and 1804 could likewise be positioned on a lower surface of the intermediate frame 32. Further, the obstacle detection device 58 may be utilized to detect obstacles between any two portions of a patient support 10 which move relative to each other. For example, the obstacle detection device 58 may be used between the head end and foot end siderails 20 and 22, between the head end siderails 20 and the headboard 16, and between the foot end siderails 22 and the footboard 18.

Additional details of suitable obstacle detection devices are provided in U.S. Provisional Patent Application Ser. No. 60/373,819, title "Hospital Bed Obstacle Detection Device and Method", filed Apr. 19, 2002, and PCT International Patent Application No. PCT/US03/12166, titled "Hospital Bed Obstacle Detection Device and Method", filed Apr. 21, 2003, the disclosures of which are expressly incorporated by reference herein.

First Illustrative Embodiment Mattress Assembly

Figure 92:
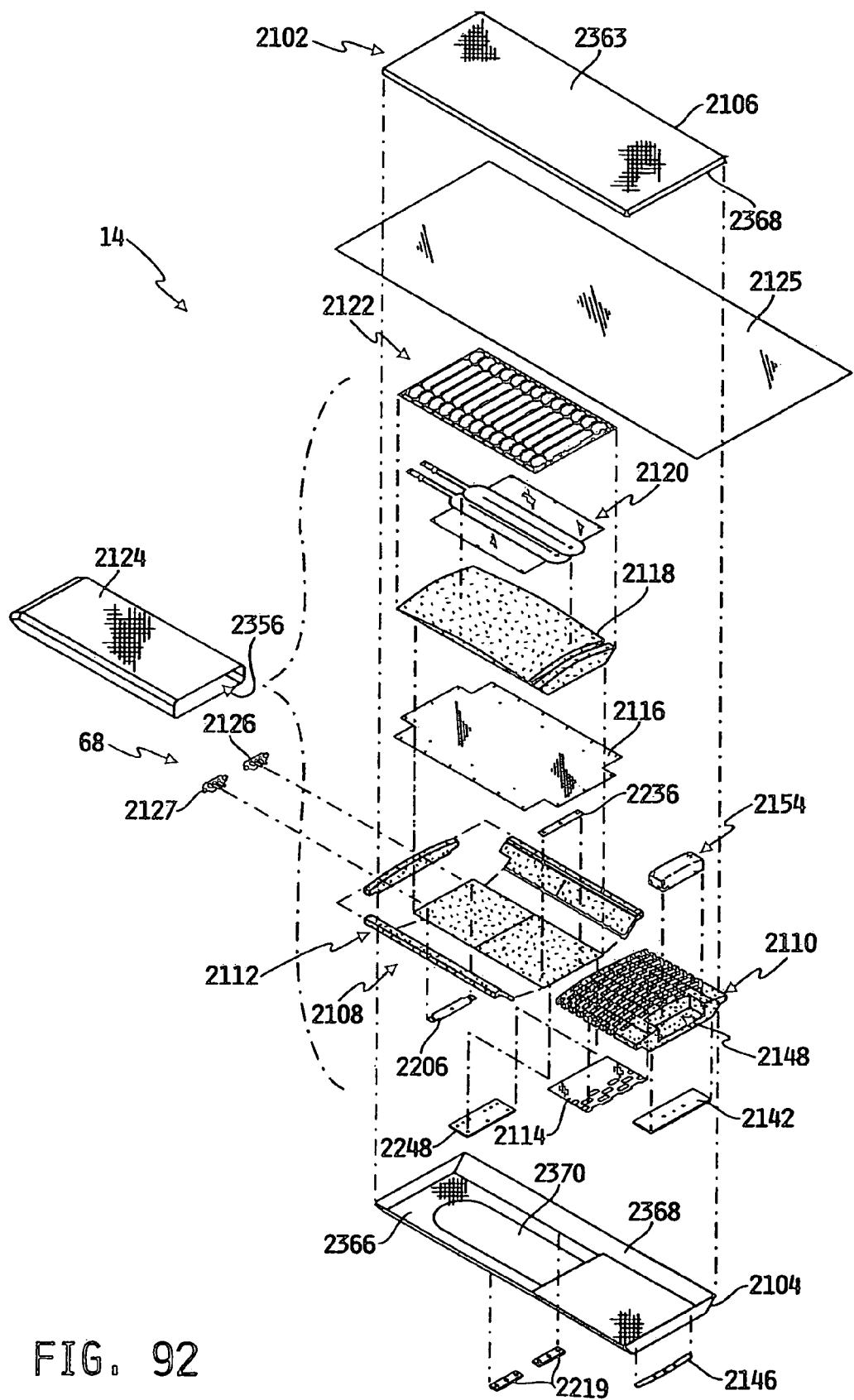
FIG. 92 is an exploded perspective view of an illustrative embodiment of the modular mattress assembly of the present invention.

Referring now to the FIG. 92, the modular mattress 14 according to an illustrative embodiment of the present invention includes an outer cover 2102 having a bottom cover portion 2104 and a top cover portion 2106 configured to encapsulate a plurality of internal components including a foam receiving base 2108. The receiving base 2108 includes a foot section 2110 and a body section 2112 coupled to the foot section 2110 by a foot section securing substrate 2114. A component mounting substrate 2116 is coupled to the body section 2112 of the base 2108. A foam crowning core 2118 is supported above the mounting substrate 2116 and is received within the base 2108. A turn assist bladder assembly 2120 is received above the foam core 2118 and is coupled to the mounting substrate 2116. An upper bladder assembly 2122 is received above the turn assist bladder assembly 2120 and is likewise coupled to the mounting substrate 2116. A fire sock or barrier 2124 is configured to surround the receiving base 2108, including the foot section 2110 and the body section 2112, the mounting substrate 2116, the foam core 2118, the turn assist bladder assembly 2120, and the upper bladder assembly 2122. A shear cover 2125 is configured to be received over the fire barrier 2124. The top cover portion 2106 provides a patient rest surface and is configured to be coupled to the bottom cover portion 2104 to define the outer cover 2102 and receive the other mattress components. Connectors 68 include a pair of mattress fluid connectors 2126 and 2127 coupled to the bottom cover portion 2104 and provide fluid communication between the manifold assembly 62, which is coupled to the pump 64, and the mattress 14.

Mattress Foot Section Assembly

Figure 93:
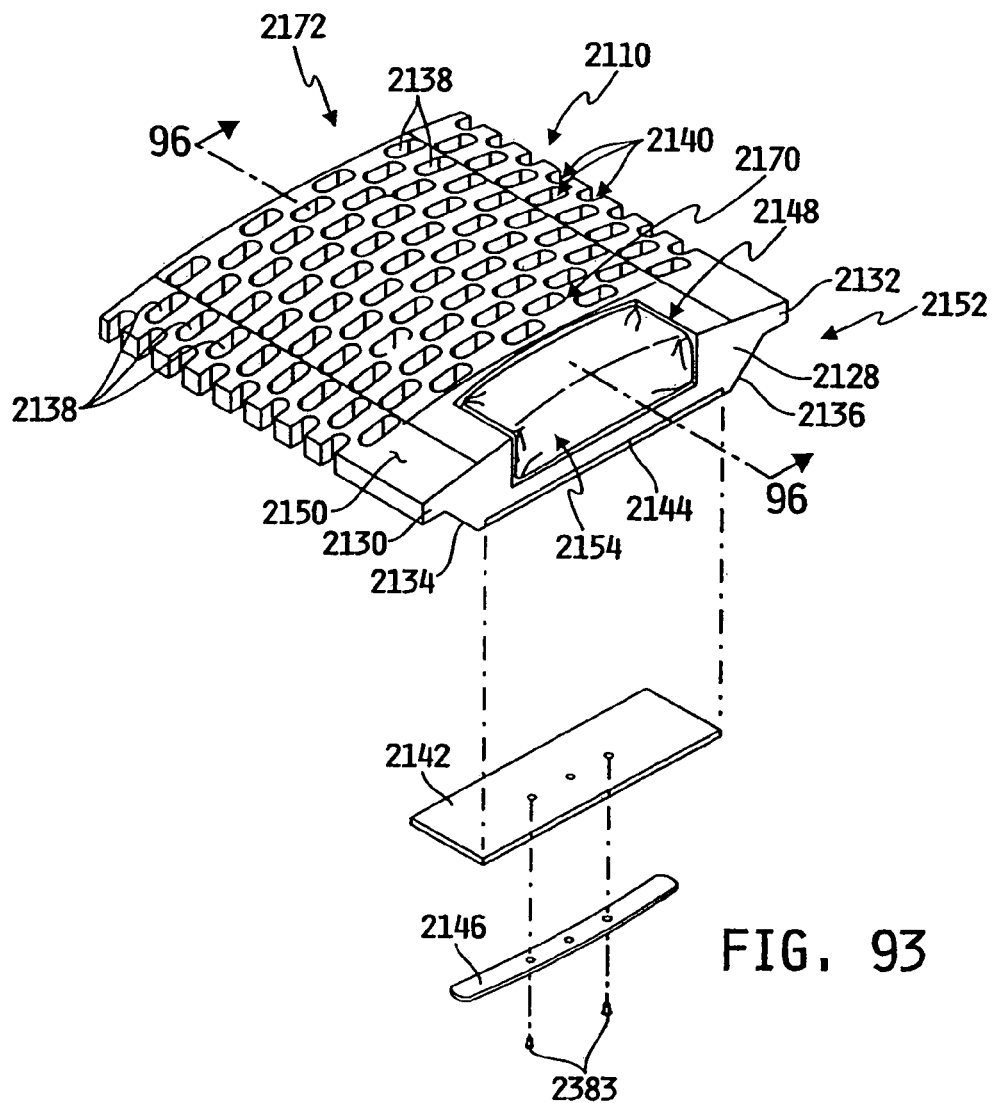
FIG. 93 is a perspective view of a foot section of the mattress of FIG. 92, illustrating a heel pressure relief sleeve received within a heel zone cavity, and with the outer cover, the shear liner, and the fire barrier removed for clarity.
Figure 96:
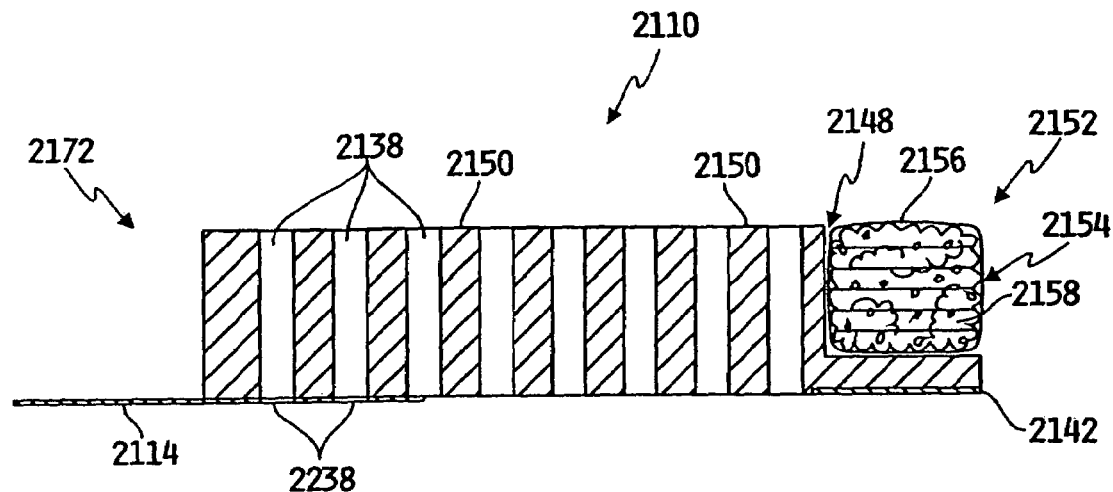
FIG. 96 is a cross-sectional view taken along line 96-96 of FIG. 93 illustrating the foot section in an extended position.
Figure 97:
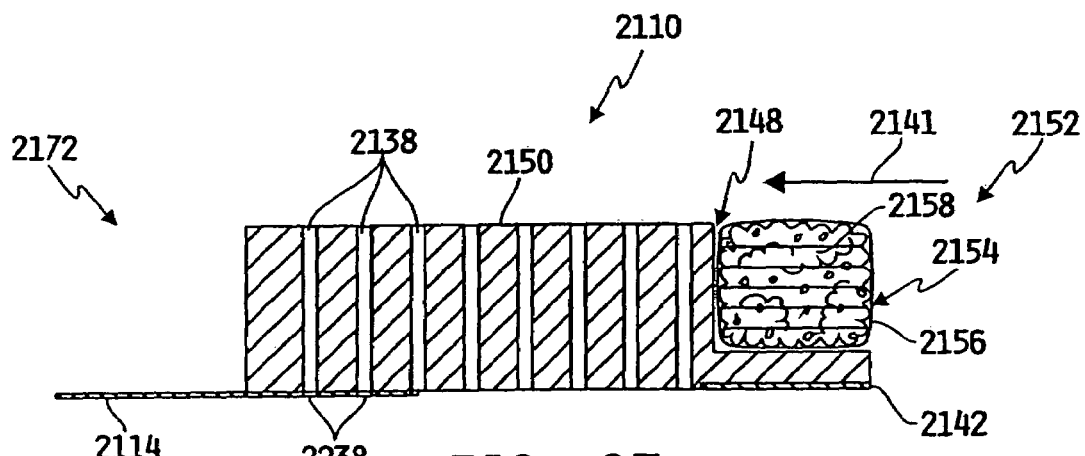
FIG. 97 is a cross-sectional view similar to that of FIG. 96 illustrating the foot section in a retracted position.

As detailed above, the leg section 42 of the deck 26 is extendable and retractable. FIGS. 93, 96, and 97 further illustrate the foot section 2110 of the mattress 14 which is configured to extend and retract with the movement of the adjustable length leg section 42 of the articulating deck 26. The foot section 2110 includes a base portion 2128 and a pair of opposing flange portions 2130 and 2132 supported above the base portion 2128. The base portion 2128 includes angled side walls 2134 and 2136 which are configured to conform to the angled side walls 291a, 300a and 291b, 300b of the deck 26. The flange portions 2130 and 2132 are configured to extend out beyond the angled side walls 291a, 300a and 291b, 300b of the deck 42. Illustratively, the foot section 2110 is made of a resilient polyurethane foam.

The foot section 2110 is perforated to facilitate its longitudinal extension and retraction. More particularly, the foot section 2110 is formed to include a plurality of apertures, illustratively transversely extending slots 2138 extending in a generally vertical direction through the base and flange portions 2130 and 2132, to facilitate compressibility of the foot section 2110 in response to the retraction of the leg section 42 of the deck 26. More particularly, the plurality of slots 2138 are arranged in a plurality of laterally extending rows 2140 wherein the individual slots 2138 of each row are laterally offset from those slots 2138 of longitudinally adjacent rows 2140. FIG. 96 illustrates the foot section 2110 when the leg section 42 of the deck 26 is in an extended position, wherein each slot 2138 widens to accommodate the extension. As illustrated in FIG. 97, as the leg section 42 of the deck 26 is retracted in the direction of arrow 2141, the foot section 2110 likewise retracts and the slots 2138 narrow.

While in the illustrative embodiment, a plurality of discrete laterally and longitudinally spaced transverse slots 2138 are illustrated to facilitate retraction and extension of the foot section 2110, it should be appreciated that other structures may be readily substituted therefor. More particularly, the foot section 2110 may be formed to include serpentine channels or other forms of openings, such as a plurality of slots extending substantially the full width of the foot section 2110 between opposing side edges of the flange portions 2130 and 2132.

A foot section mounting plate 2142 is secured to a lower surface 2144 of the foot section 2110, illustratively through an adhesive bond. As described in greater detail below, the foot section mounting plate 2142 provides a securing platform for a foot section anchor 2146 which couples the foot section to the leg section 42 of the deck 26 to facilitate movement in cooperation therewith.

Heel Pressure Relief Member

Figure 94:
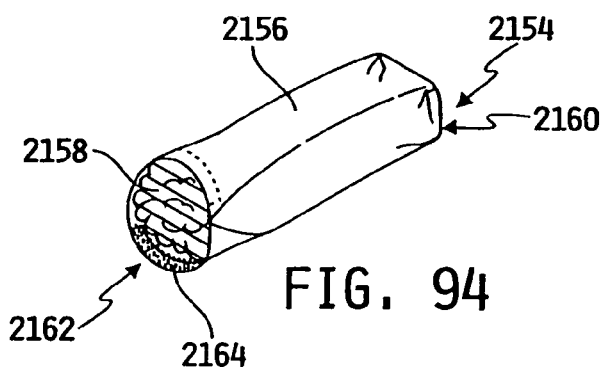
FIG. 94 is a perspective view of the heel pressure relief sleeve of the present invention.

The foot section 2110 includes a receiving recess 2148 extending downwardly from an upper surface 2150 of the base portion 2128 at a foot end 2152 thereof. A heel pressure relief member 2154 is configured to be received within the recess 2148. As illustrated in FIGS. 94-97, the heel pressure relief member 2154 includes a sleeve or case 2156 and a fiber fill 2158 received within the sleeve 2156. With further reference to FIG. 94, the sleeve 2156 includes a closed first end 2160 and an opposing releasably closable second end 2162. More particularly, a releasable fastener 2164, such as a hook and loop fastener, may be utilized to secure the second end 2162 of the sleeve 2156. Illustratively, the sleeve 2156 is formed from a substantially air impermeable material, such as a urethane coated twill. The fiber fill 2158 illustratively comprises a material having high loft properties, such as a layered polyfill material. In operation, air enters the sleeve 2156 through the hook and loop fastener 2164, thereby supplying the sleeve 2156 with air and providing air pressure for supporting the heels of a patient. The air pressure within the pressure relief member 2154 is self-regulating as changes in force applied by the patient's heels will cause air to enter or exit the sleeve 2156 through the releasable fastener 2164.

Figure 95:
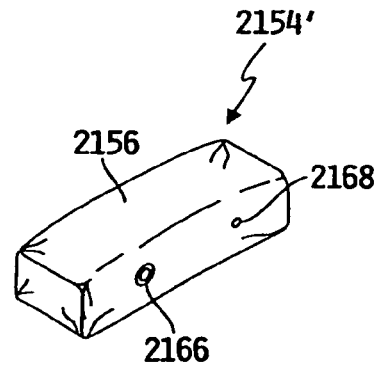
FIG. 95 is a perspective view of an alternative embodiment heel pressure relief sleeve of the present invention.

An alternative embodiment heel pressure relief member 2154' is illustrated in FIG. 95. In the alternative embodiment, a check valve 2166 and a bleed orifice 2168 are received within the sleeve 2156. The remainder of the member 2154' is substantially air impermeable. Rapid inflation of the sleeve 2156 is provided by air passing through the check valve 2166. However, the check valve 2166 prevents the passage of air therethrough from inside the sleeve 2156 to atmosphere. The bleed orifice 2168 permits for the slow passage of air from within the sleeve 2156 to atmosphere, such that pressure within the pressure relief member 2154' may be optimized and self-regulated for each individual patient.

The heel pressure relief member 2154 is configured to reduce the level of raised pressure between the patient's foot and the mattress. More particularly, the pressure relief member 2154 provides for a region of reduced pressure below the patient's heels. The foot section 2110 includes a calf portion 2170 (FIG. 93) which supports the portion of the patient's weight that would otherwise be supported by the patient's heel and thus reduces the overall interface pressure between the patient's heel and the mattress 14. It is envisioned that the calf portion 2170 of the mattress 14 may include a transition zone where the material stiffness of the foot section 2110 decreases in a longitudinal direction extending from a head end 2172 to the foot end 2152.

Mattress Body Section Assembly

Figure 98:
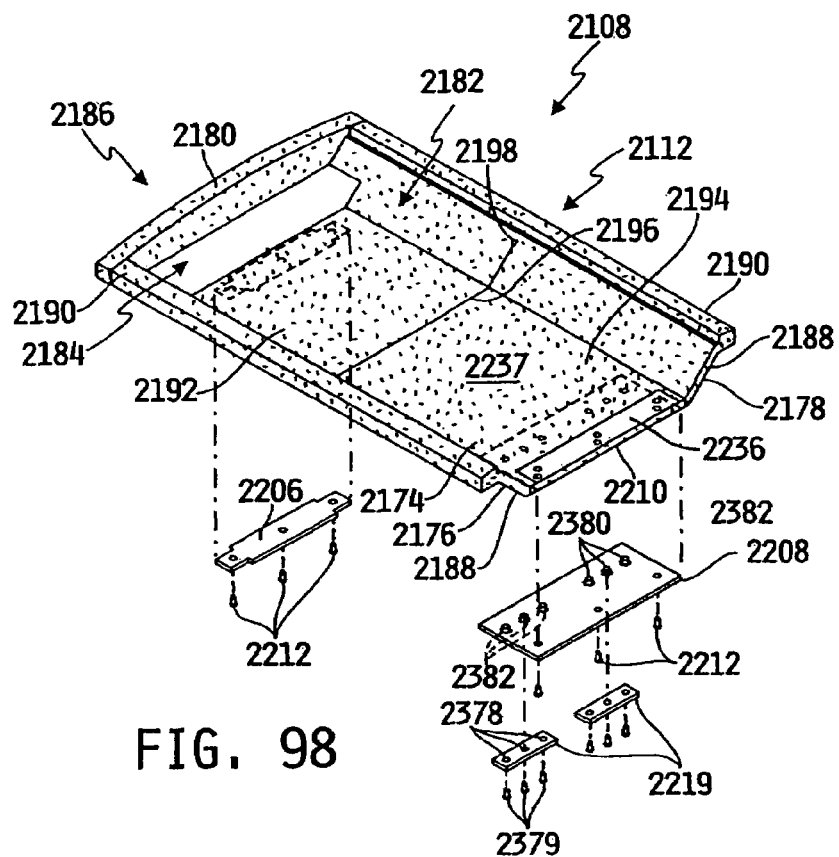
FIG. 98 is a perspective view of the receiving base of the mattress assembly of FIG. 92.

The body section 2112 of the receiving base 2108 is further illustrated in FIG. 98 as including a bottom layer 2174 secured to longitudinally extending first and second sidewalls or bolsters 2176 and 2178. Likewise, an end wall or bolster 2180 is coupled to the first and second sidewalls 2176 and 2178. As such, the body section 2112 defines a longitudinally extending channel or bucket 2182 configured to receive various components of the mattress 14. As described in greater detail below, a fluid connector recess 2184 is formed near the head end 2186 of the body section 2112 and is configured to receive the mattress fluid connectors 2126 and 2127.

The sidewalls 2176 and 2178 each include an angled or inclined portion 2188 coupled to a flange portion 2190. The angled portions 2188 are configured to conform to the angled sidewalls 260 and 262 of the deck 26, while the flange portions 2190 are configured to extend above and out beyond the sidewalls 260 and 262 of the deck 26. The body section 2112 of the receiving base 2108 includes a head portion 2192 and a seat portion 2194 separated by a laterally extending slit 2196. Opposing ends of the slit 2196 include stress relief apertures 2198 formed within the sidewalls 2176 and 2178. As described in greater detail below, the slit 2196 facilitates relative movement of the head and seat portions 2192 and 2194 of the body section 2112 during articulation of the head and seat sections 38 and 40 of the deck 26.

Mattress Mounting Substrate

Figure 99:
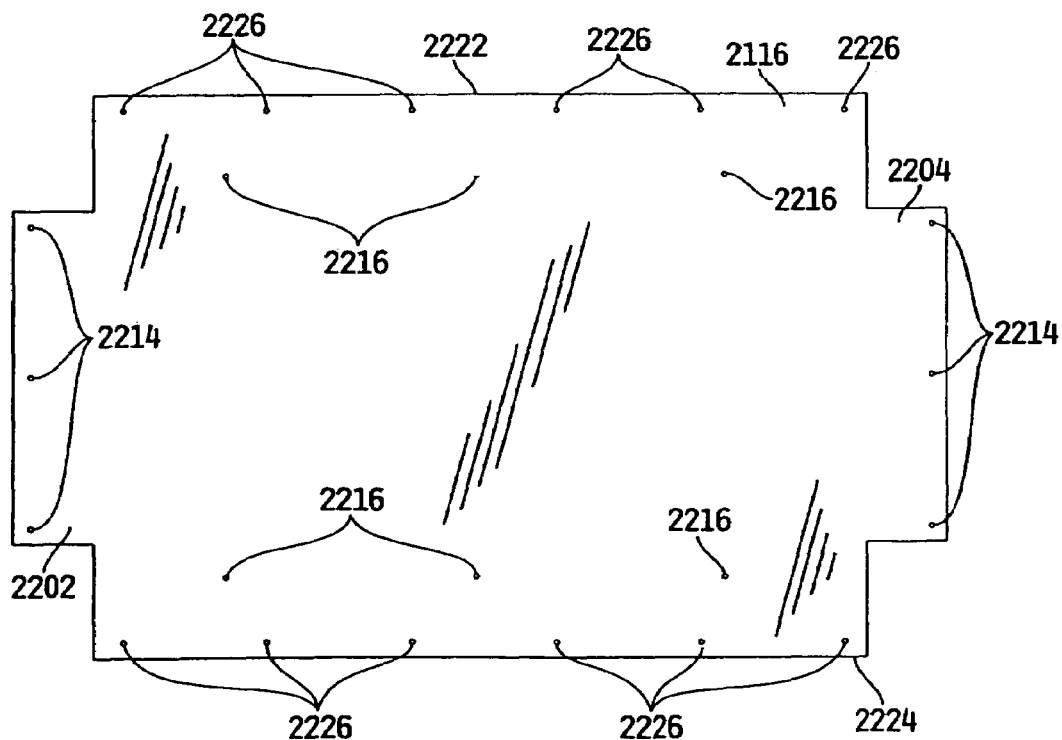
FIG. 99 is a top plan view of the mounting substrate of the mattress assembly of FIG. 92.

Turning now to FIGS. 99-101, the mounting substrate 2116 is received within channel 2182 defined by the body section 2112 of the receiving base 2108. Opposing first and second end portions 2202 and 2204 of the mounting substrate 2116 are secured to first and second lower mounting plates 2206 and 2208 (FIG. 98). The lower mounting plates 2206 and 2208 are secured to a lower surface 2210 of the receiving base 2108. More particularly, a plurality of fasteners, illustratively buttons 2212 are secured to the lower mounting plates 2206 and 2208. The buttons 2212 are releasably received within a plurality of substrate securing apertures 2214 formed within the mounting substrate 2116, thereby connecting the mounting substrate 2116 to the receiving base 2108 through the lower mounting plates 2206 and 2208. As detailed below, the lower mounting plate 2208 further provides a coupling platform for seat section anchors 2219 which secure the seat portion 2194 of the receiving base 2108 to the seat section 40 of the deck 26.

Figure 103:
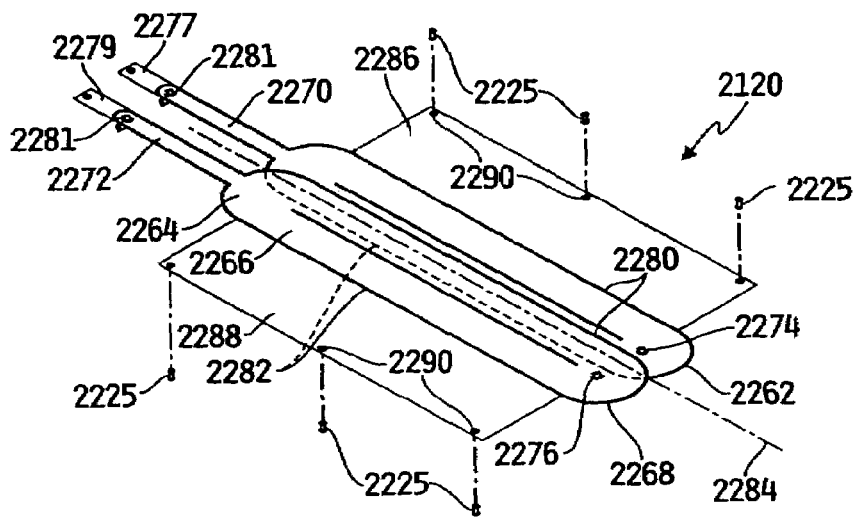
FIG. 103 is a perspective view of the turn assist bladder assembly of the mattress assembly of FIG. 92, illustrating the bladders in an inactive, deflated mode of operation.
Figure 114:
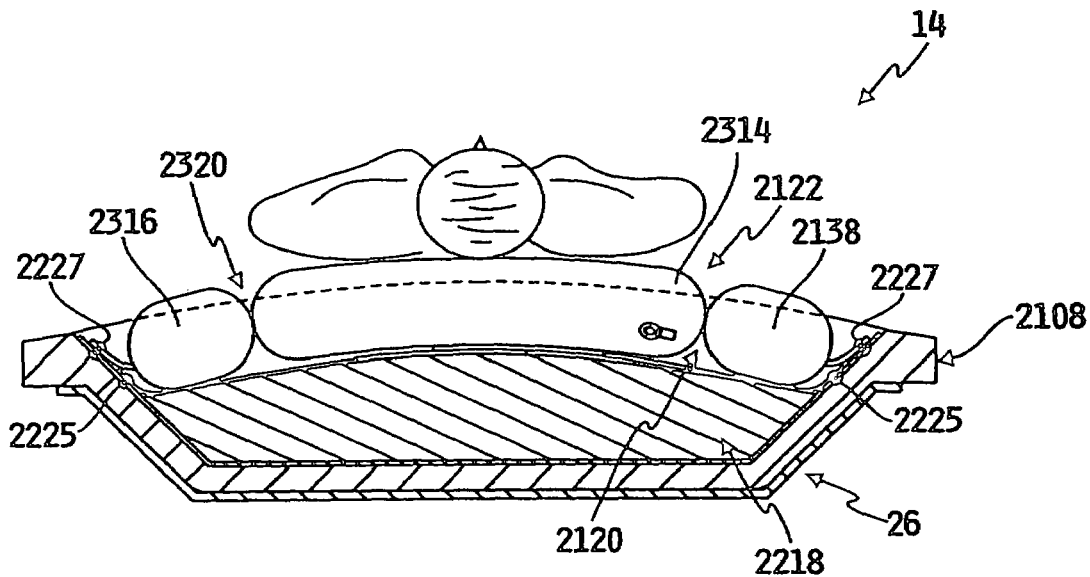
FIG. 114 is an end elevational view illustrating the upper bladder assembly in an active, inflated mode of operation.
Figure 115:
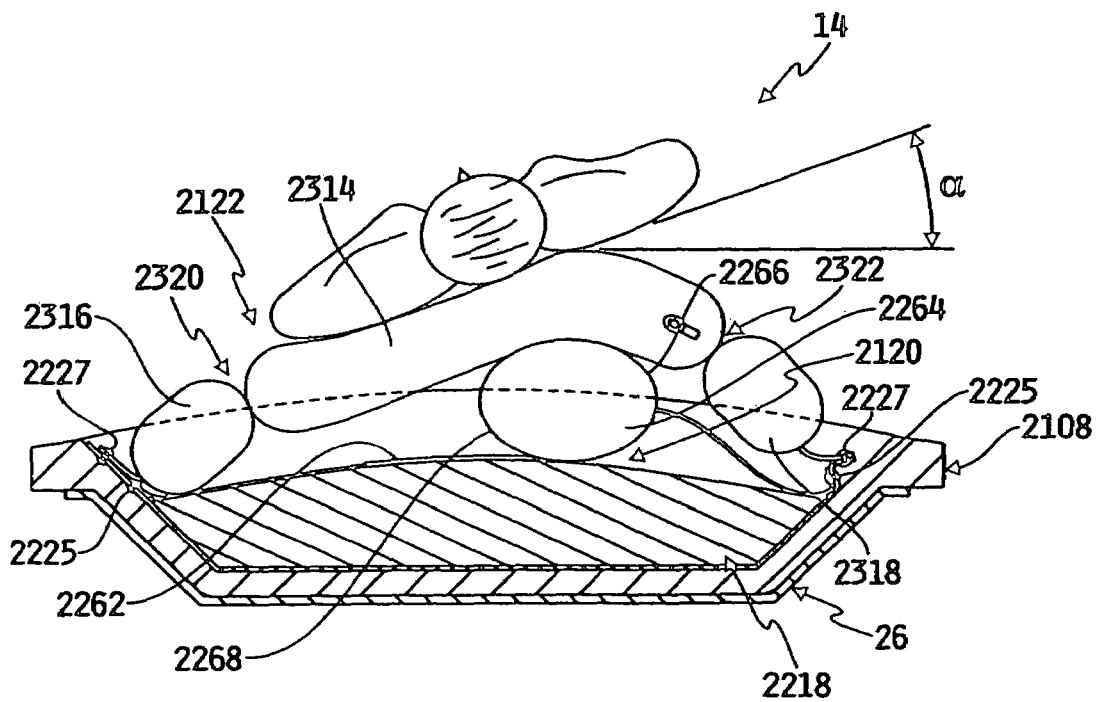

A plurality of turn assist bladder securing slots or apertures 2216 are formed proximate opposing longitudinally extending side edges 2222 and 2224 of the mounting substrate 2116. As detailed below, the apertures 2216 are configured to receive fasteners, such as buttons 2225 for securing the turn assist bladder assembly 2120 to the mounting substrate 2116 (FIGS. 103, 114, and 115). Likewise, a plurality of upper bladder assembly securing slots or apertures 2226 are formed within the mounting substrate 2116 and are laterally spaced outside of the apertures 2216. Again, as detailed below, the apertures 2226 are configured to receive fasteners, such as buttons 2227 for securing the upper bladder assembly 2122 to the mounting substrate 2116 (FIGS. 103, 114, and 115).

Foot Section Securing Substrate

With reference now to FIGS. 100 and 101, the foot section securing substrate 2114 includes a first portion 2228 secured to the seat portion 2194 of the receiving base 2108 above the upper surface 2229 of the mounting substrate 2116, and a second portion 2230 secured to the lower surface 2144 of the foot section 2110. More particularly, the first portion 2228 of the foot section securing substrate 2114 includes a plurality of mounting apertures 2232 configured to receive fasteners, such as buttons 2234. The buttons 2234 are secured to an upper mounting plate 2236 which is coupled to the upper surface 2237 of the receiving base 2108, illustratively through an adhesive. The second portion 2230 of the securing substrate 2114 is directly coupled to the lower surface 2144 of the foot section 2110, illustratively through an adhesive. The second portion 2230 includes a plurality of transverse slots 2238 configured to be received in parallel disposition with the transverse slots 2138 formed within the foot section 2110.

Illustratively, the foot section securing substrate 2114 is formed from a flexible sheet material, such as pack cloth or urethane coated twill. As a flexible sheet material, the foot section securing substrate 2114 may follow a serpentine path generally from a horizontal first plane of the upper surface 2229 of the mounting substrate 2116, vertically down around a foot end edge 2240 of the receiving base 2108, and back along a horizontal plane of the lower surface 2144 of the foot section 2110.

Foam Crowning Core

Figure 102:
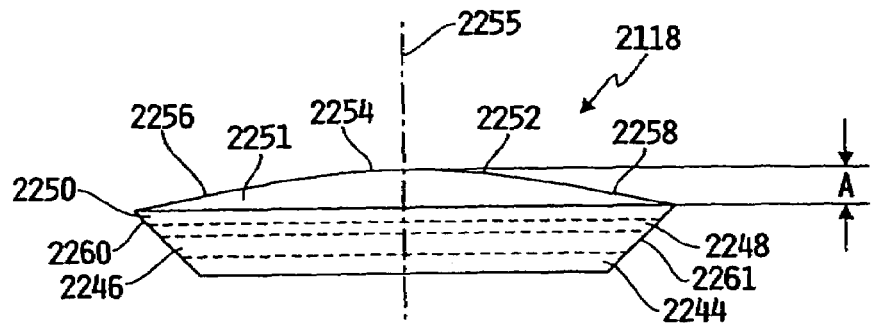
FIG. 102 is an end elevational view of the foam core of the mattress assembly of FIG. 92.

The foam crowning core 2118 is received within the channel 2182 defined by the sidewalls 2176 and 2178 of the body section of the receiving base 2108. As shown in FIG. 102, the core 2118 may be composed of a plurality of substantially planar layers 2244, 2246, 2248, 2250 of foam which are affixed together using conventional means, such as an adhesive. Similarly, an upper crown layer 2251 is affixed to the upper surface of layer 2250. Illustratively, the core 2118 is made of polyurethane foam having an indention force deflection (IFD) of between approximately 23 to approximately 29. The crowning core 2118 defines a crowned upper surface 2252 as illustrated in FIG. 102. Illustratively, a center portion 2254 of the upper surface 2252 proximate the longitudinal center axis 2255 of the core 2118 is positioned vertically above the side portions 2256 and 2258 of the crowned surface 2252 proximate opposing side walls 2260 and 2261 of the core 2118. More particularly, the vertical distance of the crowned surface 2252 between the center axis 2255 and the side walls 2260 and 2261 is represented by the reference letter A as shown in FIG. 102. Illustratively, the distance A is defined to be approximately 2 inches. In an alternative embodiment the distance A is defined to be approximately 3 inches. The upper surface 2252 is arcuate as it extends from the side walls 2260 and 2261 toward the longitudinal center axis 2255. The side walls 2260 and 2261 are angled to conform with the angled walls 2176 and 2178 of the receiving base 2108.

The crowned surface 2252 is configured to facilitate lateral patient transfer from the bed 10 to another patient support device positioned adjacent to the bed 10 by creating an inclined surface which provides a slight amount of gravity assistance when the caregiver is moving the patient toward the side of the mattress 14. Additionally, since the surface 2252 at the side walls 2260 and 2261 is lower than the center portion 2254 of the mattress 14, the siderails 20 and 22 may have a lower profile and still fulfill minimum height requirements. More particularly, the distance from the top cover portion 2106 of the mattress 14 above the side walls 2260 and 2261 of the crowning core 2118 to the top of the siderails 20 and 22 is configured to be at least approximately 9 inches.

Turn Assist Bladder Assembly

Figure 104:
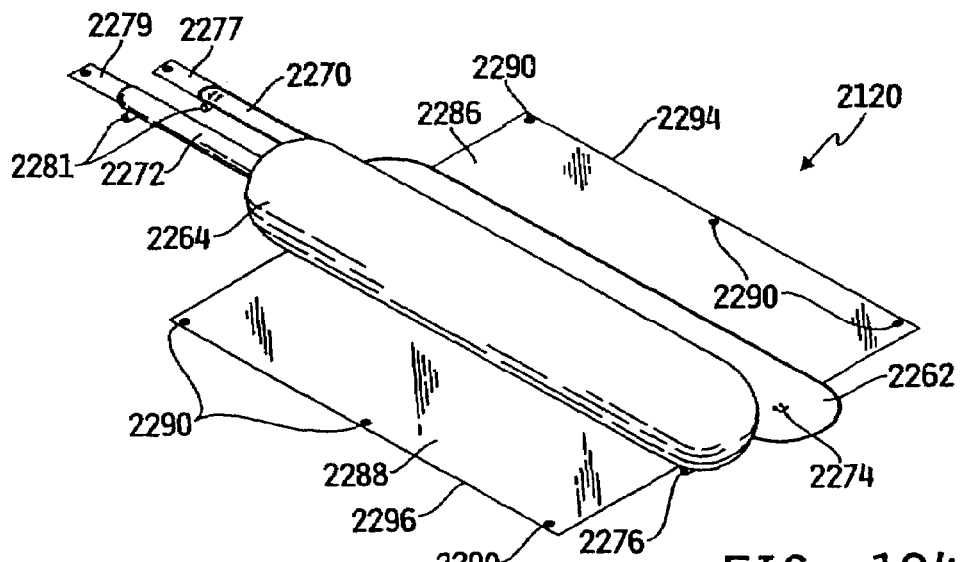
FIG. 104 is a perspective view similar to that of FIG. 103 illustrating the left turn assist bladder in an active, inflated mode of operation, and the right turn assist bladder in an inactive, deflated mode of operation.
Figure 105:
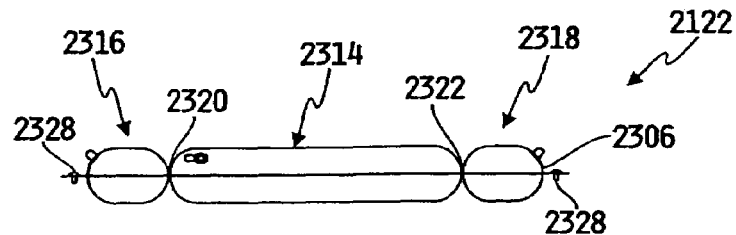
FIG. 105 is an end elevation view of the upper bladder assembly of the mattress assembly of FIG. 92.
Figure 106:
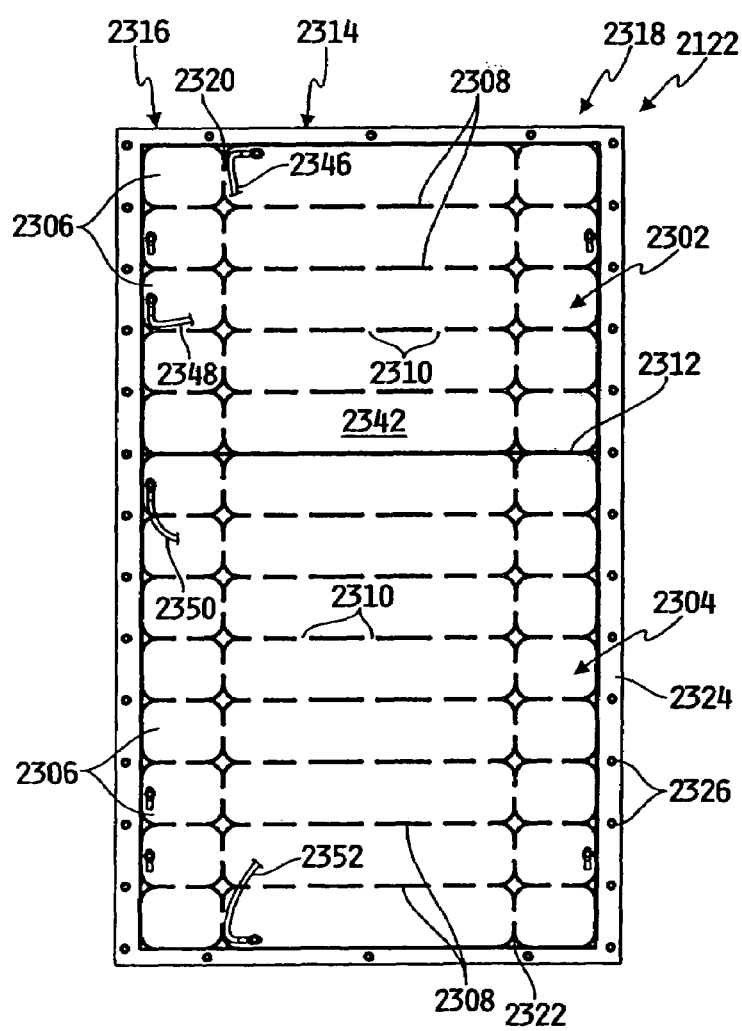
FIG. 106 is a top plan view of the upper bladder assembly of FIG. 105.
Figure 107:
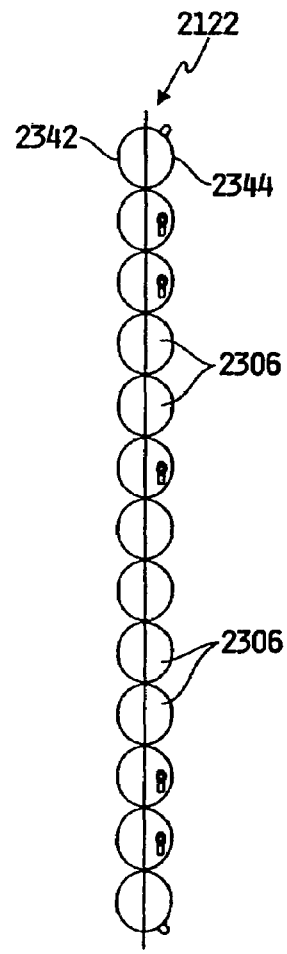
FIG. 107 is a side elevational view of the upper bladder assembly of FIG. 105.

With reference to FIGS. 92, 103, and 104, the turn assist bladder assembly 2120 is positioned above the crowning foam core 2118 and includes partially overlapping first, or right and second, or left inflatable turn assist bladders 2262 and 2264. As described in greater detail herein, each of the right and left turn assist bladders 2262 and 2264 are selectively and individually inflatable to assist in the turning of a patient supported on the mattress 14. FIG. 103 illustrates both the right and left turn assist bladders 2262 and 2264 in deflated positions, while FIG. 104 illustrates the right turn assist bladder 2262 in a deflated position and the left turn assist bladder 2264 in an inflated position.

Each of the turn assist bladders 2262 and 2264 include an upper layer 2266 and a lower layer 2268 coupled to the upper layer 2266. Inlet tubes 2270 and 2272 are coupled to the manifold assembly 62 which, in turn, is coupled to the pump 64 that provides pressurized air to inflate the chamber defined between the upper and lower layers 2266 and 2268. Sensing ports 2274 and 2276 are also provided in fluid communication with the chamber defined between the upper and lower layers 2266 and 2268 of the turn assist bladders 2262 and 2264. The sensing ports 2274 and 2276 are likewise in fluid communication with the manifold assembly 62 which, in turn, is in fluid communication with a pressure sensor or transducer 566 for detecting the pressure of air within the bladders 2262 and 2264. The fill tubes 2270 and 2272 extend in a longitudinal direction toward the head end 2186 of the receiving base 2108. Mounting tabs 2277 and 2279 are coupled to the fill tubes 2270 and 2272 and extend through the end wall 2180 of the receiving base 2108. Conventional fill ports or connectors 2281 are provided in fluid communication with the fill tubes 2270 and 2272. As illustrated in FIG. 103, the fill tubes 2270, 2272 and the sensing ports 2274, 2276 are positioned at opposing ends of the bladders 2262, 2264 in order for the pressure sensor 566 to receive a pressure reading from a location remote from the fill tubes 2270, 2272, thereby facilitating adequate pressure throughout the bladders 2262, 2264.

As illustrated in FIG. 103, each turn assist bladder 2262 and 2264 includes opposing longitudinally extending first, or right and second, or left side edges 2280 and 2282. The side edges 2280 and 2282 define a point where the upper layer 2266 is coupled to the respective lower layer 2268. The right side edge 2280 of the left bladder 2264 overlaps the left side edge 2282 of the right bladder 2262. In other words, each of the bladders 2262 and 2264 have a portion extending over the longitudinal center axis 2284 of the turn assist bladder assembly 2120.

Right and left mounting flanges 2286 and 2288 are coupled to opposing edges of the right and left turn assist bladders 2262 and 2264, respectively. Illustratively the mounting flanges 2286 and 2288 are secured to the lower layers 2268 of the bladders 2262 and 2264 through radio frequency (RF) welding. The mounting flanges 2286 and 2288 include a plurality of mounting apertures 2290 proximate their outside side edges 2294 and 2296. Releasable fasteners, such as the buttons 2225 identified above, are received within the apertures 2290 of the mounting flanges 2286 and 2288, and likewise are received within the apertures 2216 of the mounting substrate 2116. As such, the turn assist bladder assembly 2120 is secured to the mounting substrate 2116. The turn assist bladder assembly 2120 may be made from a polyurethane film.

Upper Bladder Assembly

With reference to FIGS. 92 and 105-108, the upper bladder assembly 2122 is positioned above the turn assist bladder assembly 2120, such that the turn assist bladder assembly 2120 is sandwiched between the foam crowning core 2118 and the upper bladder assembly 2122 (FIG. 115). The upper bladder assembly 2122 includes a head section or air zone 2302 and a seat section or air zone 2304, wherein each zone 2302 and 2304 includes a plurality of laterally extending bladders 2306. A plurality of baffles or walls 2308 separate the individual bladders 2306 in each zone 2302 and 2304.

Fluid passageways or ports 2310 are provided within the walls 2308 to provide for fluid communication between the bladders 2306 within each zone 2302 and 2304. A solid wall or divider 2312 seals the bladders 2306 of the head zone 2302 from the bladders 2306 of the seat zone 2304.

The upper bladder assembly 2122 includes a longitudinally extending center portion 2314 positioned intermediate longitudinally extending first and second side portions 2316 and 2318. First and second longitudinally extending hinges 2320 and 2322 connect the center portion 2314 to the first and second side portions 2316 and 2318, respectively. The hinges 2320 and 2322 provide increased flexibility to the inflated upper bladder assembly 2122, thereby allowing the individual bladders 2306 to generally follow the arcuate contour of the crowning core 2118. Further, the hinges 2320 and 2322 allow the inflated upper assembly 2122 to conform to the general contour defined by the turn assist bladder assembly 2120 when it is inflated (FIGS. 114 and 115).

The upper bladder assembly 2122 further includes a peripheral mounting flange 2324 including a plurality of securing apertures 2326 for receiving fasteners, such as buttons 2227. More particularly, the buttons 2227 pass through the apertures 2218 formed in the mounting substrate 2116 and through the apertures 2326 formed in the mounting flange 2324, thereby securing the upper bladder assembly 2122 to the mounting substrate 2116 (FIGS. 108 and 115). A pair of securing straps 2330 and 2332 secure the head end of the upper bladder assembly 2122 to the end wall 2180 of the receiving base 2108. More particularly, as shown in FIG. 109, a first end 2334 of each strap 2330 and 2332 is coupled to the head end of the mounting flange 2324 through conventional fasteners, such as buttons 2336. A second end 2338 of each strap 2230 and 2232 is coupled to one of the mounting tabs 2277 and 2279 of the fill tubes 2270 and 2272 of the turn assist bladder assembly 2120, again through conventional fasteners, such as buttons 2340.

The upper bladder assembly 2122 may be formed by an upper sheet 2342 and a lower sheet 2344 coupled together at various locations by seals, such as RF welds. More particularly, the welds may define the walls 2308 of the bladders 2306, the wall 2312 separating the head zone 2302 and the foot zone 2304, and the mounting flange 2324.

The head zone 2302 is in fluid communication with a supply tube 2346 that delivers pressurized air to the bladders 2306 and alternatively exhausts pressurized air from the bladders 2306. A sensing line 2348 is also provided in fluid communication with the head zone 2302 and provides pressurized air to the pressure sensor 566 as detailed herein. Likewise, the seat zone 2304 is in fluid communication with a supply tube 2350 that delivers pressurized air to the bladders 2306 and alternatively exhausts pressurized air from the bladders 2306. A sensing line 2352 is also provided in fluid communication with the seat zone 2304 and provides pressurized air to the pressure sensor 566.

Fire Barrier

Referring further to FIG. 92, the fire barrier 2124 receives the receiving base 2108, the mounting substrate 2116, the crowning core 2118, the turn assist bladder assembly 2120, and the upper bladder assembly 2122. The fire barrier 2124 includes an open end 2356 configured to permit the fire barrier 2124 to slide over the other mattress components. Upon assembly, the open end 2356 of the fire barrier 2124 is closed utilizing conventional means, such as fasteners. The fire barrier 2124 may be made from a conventional fire-resistant mesh material, such as a fiberglass knit.

Shear Cover

With reference to FIGS. 92 and 110, the shear cover 2125 is configured to fit over the above-identified mattress components as received within the fire barrier 2124. The shear cover 2125 is substantially planar, but folded during assembly to form a top surface 2360, a sidewall 2362, and bottom inwardly extending flaps 2364. RF welded seams are utilized to form the four corners of the shear cover 2125 about the mattress components. A belly band (not shown) may be wrapped laterally around the outer surface of the shear cover 2125 to assist in securing a mid-portion thereof. The shear cover 2125 is configured to be located between the internal components and the top cover portion 2106 to permit the top cover portion 2106 to slide easily over the mattress components and reduce shear forces between the patient's body and the mattress 14 and reduce the likelihood of sacral breakdown.

The shear cover 2125 is formed from a material having a low coefficient of friction so that the mattress outer cover 2102 can slide relative to the other mattress components. As the mattress 14 is articulated or as the patient moves, the shear cover 2125 minimizes shear forces acting between the mattress top cover portion 2106 and the patient's body. The shear cover 2125 may be made from a woven nylon or parachute material. Illustratively, the shear cover 2125 is made from a polyurethane material such as Deerfield urethane PT611OS having a thickness of approximately 0.002 inches. The polyurethane material provides an inexpensive shear material which reduces shear forces applied to the patient's body situated on the mattress 14.

Outer Cover

Referring now to FIGS. 92 and 111, the top cover portion 2106 of the outer cover 2102 includes a top wall 2363 and a sidewall 2365. The top cover portion 2106 is illustratively formed from a ticking material, such as a stretchable polyurethane material which is resistant to fluids and chemical stains.

The bottom cover portion 2104 includes a bottom wall 2366 and a sidewall 2368. The sidewall 2368 is illustratively formed from a ticking material similar to the sidewall 2365 of the top cover portion 2106. The sidewall 2368 of the bottom cover portion 2104 is coupled to the sidewall 2365 of the top cover portion 2106, illustratively through RF welding. Illustratively, the bottom wall 2366 of the bottom cover portion 2104 is formed from a polyurethane coated twill material for enhanced wear resistance and to protect other components of the mattress 14 from contamination. The bottom wall 2366 includes an access panel 2370 defined by a zipper 2372. The access panel 2370 is utilized during assembly of the mattress 14 and further facilitates removal of the replacement of the modular components of the mattress 14. Illustratively, the zipper 2372 is RF welded to the bottom wall 2366. In an alternative embodiment of the invention, the zipper 2372 may be utilized to couple the sidewall 2368 of the bottom cover portion 2104 to the sidewall 2365 of the top cover portion 2106.

With further reference to FIGS. 111-113, the bottom cover portion 2104 includes a stress relief zone 2374 of extra material, which is illustratively pleated, to accommodate movement of the head section 38 of the deck 26 relative to the seat section 40 of the deck 26. More particularly, as the head section 38 is elevated relative to the seat section 40, the head portion 2192 of the receiving base 2108 moves relative to the seat portion 2194 of the receiving base 2108. The slit 2196 and stress relief apertures 2198 and 2200 reduce the stress applied to the receiving base 2108 during this movement.

Likewise, the stress relief zone 2374 of the bottom cover portion 2104 reduces stress within the outer cover 2102 of the mattress 14. As the mattress 14 bends to follow the contour of the deck 26, the extra material within the stress relief zone 2374 accounts for the increased distance between the head portion 2192 and the seat portion 2194 proximate the bottom cover portion 2104 as illustrated in FIGS. 112 and 113.

Mattress Anchors

Referring now to FIGS. 98 and 111, the seat section anchors 2219 are positioned below the bottom cover portion 2104 of the mattress 14 and are coupled to the mounting plate 2208 fixed to the receiving base 2108. Illustratively, the anchors 2219 comprise laterally extending magnets received within recesses 2376 formed in the seat section 40 of the deck 26. As such, the anchors 2219 are attracted to the metal deck 26 and essentially "stick" thereto. Each anchor 2219 includes a plurality of mounting apertures 2378 for receiving conventional fasteners, such as screws 2379, which are threadably received within mounting apertures 2380 formed in the mounting plate 2208. The mounting apertures 2380 are illustratively concentrically formed within locating protuberances or cones 2382 (FIG. 96). The locating cones 2382 facilitate proper placement of the anchors 2119 during assembly.

With reference to FIGS. 93 and 111, the foot section anchor 2146 is secured to the foot section 2110 of the mattress 14 below the bottom cover portion 2104 through conventional fasteners, such as screws 2383. The foot section anchor 2146 illustratively comprises a resilient tab having opposing ends 2384 and 2386 which may be flexed away from the mattress 14 and placed under retaining arms 2387 formed within the leg section 42 of the deck 26.

Manifold Assembly and Mattress Connectors

The pair of mattress fluid connectors 2126 and 2127 are secured to the bottom cover portion 2104 and are received within the connector recess 2184 formed within the receiving base 2108. Each connector 2126 and 2127 includes a plurality of barbed fittings 2388 which are sealingly received within flexible tubing 2390 illustratively connected to one of the right turn assist bladder 2262, the left turn assist bladder 2264, the head zone 2302 of the upper bladder assembly 2122, and the seat zone 2304 of the upper bladder assembly 2122. Additional details regarding the mattress fluid connectors 2126 and 2127 are provided below in connection with the manifold assembly 62.

FIGS. 114 and 115 illustrate operation of the mattress 14 including the upper bladder assembly 2122 and the turn assist bladder assembly 2120. More particularly, FIG. 114 illustrates a normal mode of operation with the head zone 2302 of the upper bladder assembly 2122 inflated, and the turn assist bladders 2262 and 2264 deflated. FIG. 115 illustrates a left turn assist mode of operation wherein the left turn assist bladder 2264 is inflated. Since the left turn assist bladder 2264 is laterally offset from the longitudinal center axis 2284 of the mattress 14, inflation of the bladder 2264 causes one side of the upper bladder assembly 2122 to raise above the other side. The hinges 2320 and 2322 between the side portions 2316 and 2318 and the center portion 2314 of the bladders 2306 of the upper bladder assembly 2122 permit the mattress 14 to substantially conform to the shape resulting from the inflation of the left turn assist bladder 2264. In an illustrative embodiment, upon inflation of one of the turn assist bladders 2262 and 2264, a patient supported on the mattress 14 is rotated by an angle $\alpha$ of approximately 20 degrees from horizontal. Upon completion of the turn assist, the control system 44 causes the inflated turn assist bladder 2262, 2264 to vent to atmosphere. Simultaneously, the upper bladder assembly 2122 is instructed by the central system 44 to inflate to a maximum pressure. Since the turn assist bladder assembly 2120 is sandwiched intermediate the upper bladder assembly 2122 and the crowning core 2218, inflation of the upper bladder assembly 2122 facilitates the rapid venting of air within the turn assist bladders 2262 and 2264 to atmosphere.

Referring now to FIGS. 116-119, an illustrative embodiment manifold assembly 62 for use in connection with the mattress 14 is shown. The manifold assembly 62 is configured to provide fluid communication between the pump 64 and the air mattress 14. The manifold assembly 62 includes first and second manifolds 2402 and 2404 configured to control the supply of air to and the exhaust of air from the controlled air zones of the mattress 14. Air is supplied to the manifolds 2402 and 2404 by the pump 64, while air is exhausted to atmosphere 2405 through the manifolds 2402 and 2404. More particularly, the manifolds control air pressure within the right turn assist bladder 2262, the left turn assist bladder 2264, the head zone 2302 of the upper bladder assembly 2122, and the seat zone 2304 of the upper bladder assembly 2122. While in FIGS. 116-119, first and second manifolds 2402 and 2404 are positioned in spaced relation, it should be appreciated that in other embodiments, such as described herein, a single manifold may be utilized.

Figure 116:
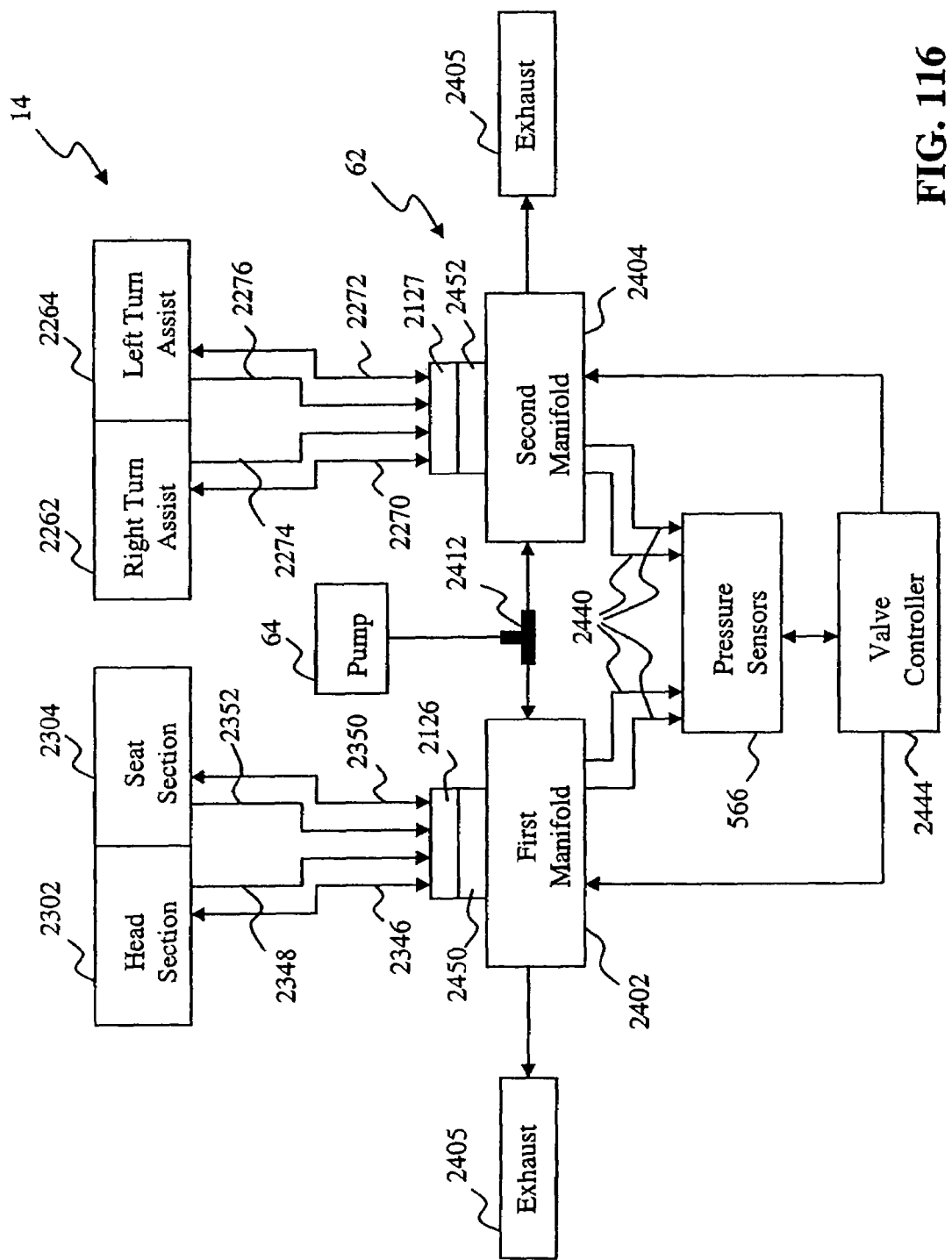
Figure 117:
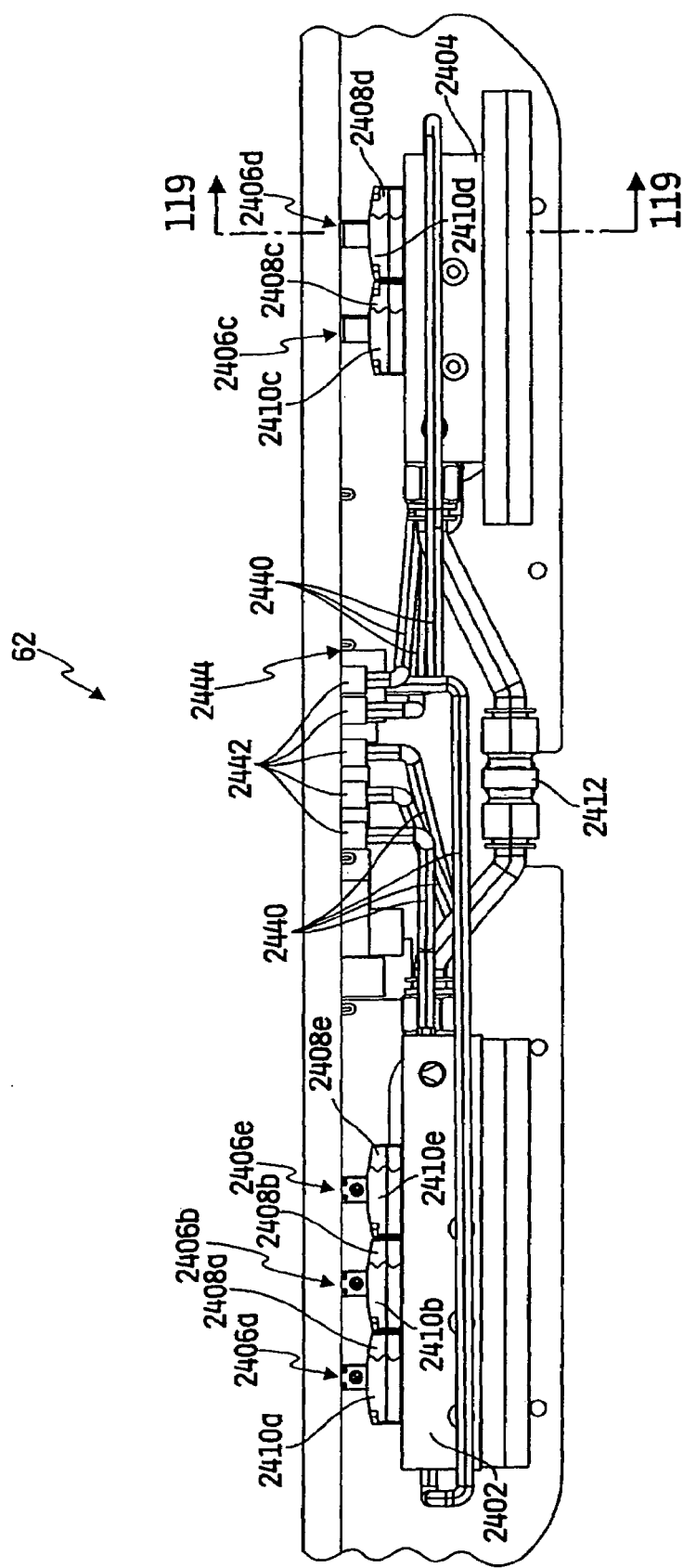

With further reference to FIGS. 116 and 117, a separate valve assembly 2406, comprising first and second solenoid actuated pilot valves 2408 and 2410, are provided for each controlled air zone 2262, 2264, 2302, and 2304 of the mattress 14. The valve assembly 2406*a* for controlling the head zone 2302 of the upper bladder assembly 2122 is coupled to the first manifold 2402 and includes a normally closed pilot valve 2408*a* for controlling the air intake and a normally closed pilot valve 2410*a* for controlling the air exhaust. The valve assembly 2406*b* for controlling the seat zone 2304 of the upper bladder assembly 2122 is likewise coupled to the first manifold 2402 and includes a normally closed pilot valve 2408*b* for controlling the air intake and a normally closed pilot valve 2410*b* for controlling the air exhaust.

The valve assembly 2406*c* for controlling the right turn assist bladder 2262 is coupled to the second manifold 2404 and includes a normally closed pilot valve 2408*c* for controlling air intake and a normally open pilot valve 2410*c* for controlling the air exhaust. Likewise, the valve assembly 2406*d* for controlling the left turn assist bladder 2264 is coupled to the second manifold 2404 and includes a normally closed pilot valve 2408*d* for controlling air intake and a normally open pilot valve 2410*d* for controlling the air exhaust. An optional valve assembly 2406*e* is illustrated as coupled to the first manifold 2402 and may include pilot valves 2408*e* and 2410*e*, as desired, to control optional additional air zones within the mattress 14.

In an illustrative embodiment, the normally closed pilot valves comprise SY series piloted valves, Model No. SY114-5GZ available from SMC Corporation of Indianapolis, Ind. Likewise, in an illustrative embodiment of the invention, the normally open pilot valves comprise SY Series piloted valves, Model No. SY124-5GZ available from SMC Corporation of Indianapolis, Ind.

With further reference now to FIGS. 116-119, air supplied from the pump 64 passes through a conventional fluid T-connector 2412 which separates the air flow to the first and second manifolds 2402 and 2404 through first and second supply tubes 2414 and 2416. Once entering each manifold 2402 and 2404, the supplied air is routed through to the various valve assemblies 2406.

Figure 119:
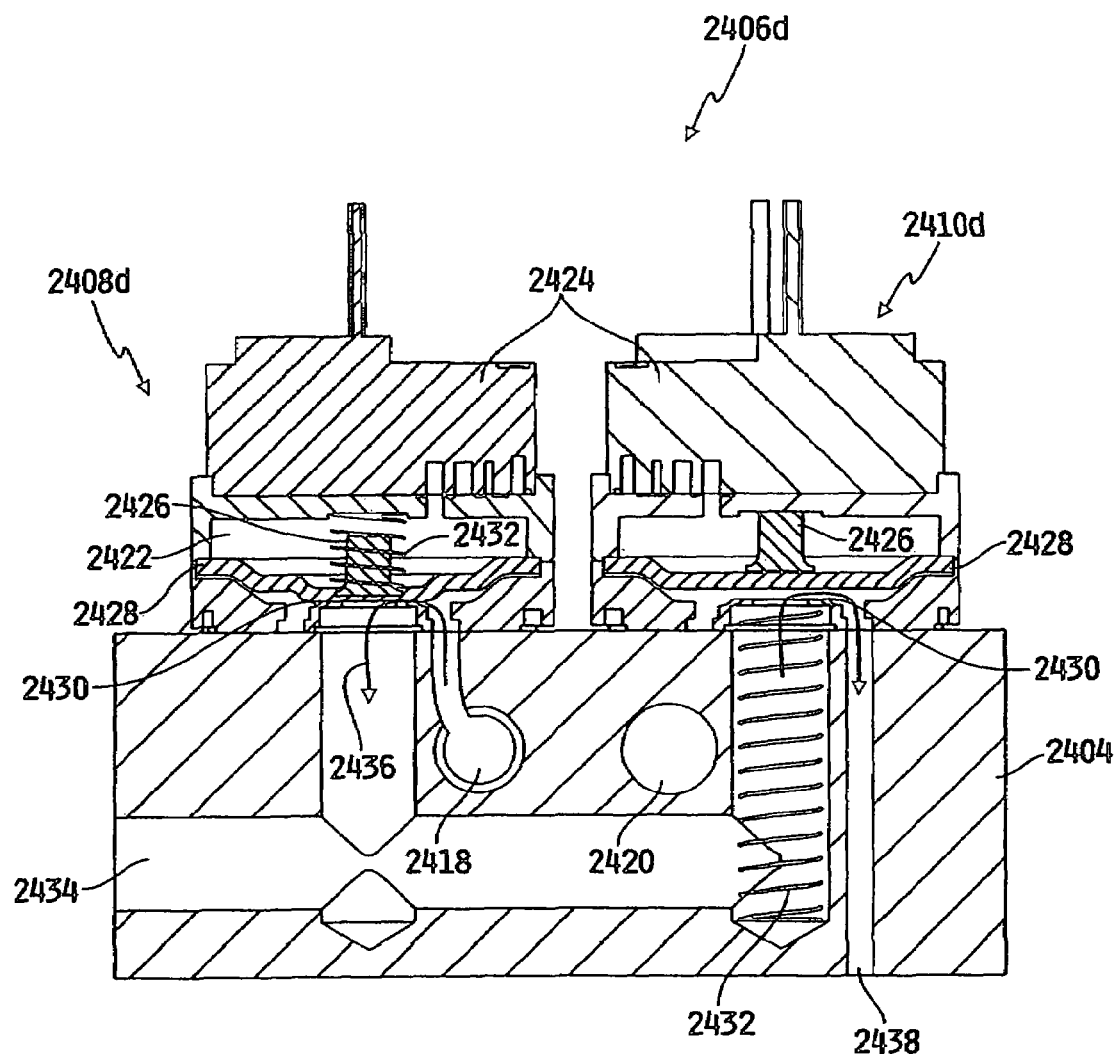

Details of the valve assembly 2406*c* for controlling air pressure within the right turn assist bladder 2262 is illustrated in FIG. 119. It should be appreciated that the valve assembly 2406d for use with the left turn assist bladder 2264 is identical. Further, the valve assemblies 2406a and 2406b for use with the head zone 2302 and the seat zone 2304 of the upper bladder assembly 2122 are substantially the same except for the substitution of a second normally closed pilot valve for the normally open pilot valve 2410c of the valve assembly 2406c.

With reference to FIG. 119, air is supplied to the valve assembly 2406c by a fill port 2418 which is in communication with the pump 64. The fill port 2418 is in fluid communication with an accumulator port 2420 through a check valve (not shown). The check valve provides for air flow from the fill port 2418 to the accumulator port 2420 but prevents air flow in the reverse direction. The check valve therefore helps maintain pressure within the accumulator port 2420 should pressure be lost in the fill port 2418, for example, if the pump 64 would stop operating. The accumulator port 2420, in turn, is in fluid communication with the upper pilot pressure chamber 2422 of the first pilot valve 2408c.

Each pilot valve 2408c and 2410c includes a conventional solenoid (not shown) received within a body portion 2424 and configured to move a pin 2426. The first pilot valve 2408c is normally closed, such that a diaphragm 2428 coupled to the pin 2426 sealingly engages a valve seat 2430. The normally closed valve 2408c includes a spring 2432 concentrically disposed around the pin 2426 and biasing the diaphragm 2428 downwardly into sealing engagement with the valve seat 2430. As such, air from the fill port 2418 may not pass to a supply port 2434 connected to the right turn assist bladder 2262 of the mattress 14. However, upon activation, the solenoid is energized such that the pin 2426 is pulled upwardly and the diaphragm 2428 moves away from the valve seat 2430. As such, a passageway represented by arrow 2436 is defined such that air may pass through the fill port 2418 over the valve seat 2430 and through the supply port 2434 to the right turn assist bladder 2262.

At the same time that the normally closed valve 2408c is activated, the normally open valve 2410c is likewise activated such that the solenoid is energized to push its pin 2426 downwardly thereby causing the diaphragm 2418 to sealingly engage the valve seat 2430. As such, the supply port 2434 is sealed off from an exhaust port 2438 in fluid communication with atmosphere. In the normally open valve 2410, the spring 2432 is concentrically received within a portion of the supply port 2434 and is configured to bias against the diaphragm 2428 to push the diaphragm 2428 away from the valve seat 2430 such that the supply port 2434 is in fluid communication with the exhaust port 2438.

The sensing ports or lines 2274, 2276, 2348, and 2352 from the controlled air zones 2262, 2264, 2302, and 2304 of the mattress 14 are coupled in fluid communication with the first and second manifolds 2402 and 2404 as shown in FIG. 116. Each sensing line 2274, 2276, 2348, and 2352 supplies air which illustratively passes through fluid sensing ports 2439 formed within the first and second manifolds 2402 and 2404 and then exits through pressure sensing tubes 2440. Each tube 2440 is coupled to a pressure sensor or transducer 566 supported on a valve controller circuit board 2444. The circuit board 2444 is illustratively positioned intermediate the first and second manifolds 2402 and 2404. The circuit board 2444 is in communication with the control system 44 and, as such, provides signals to the control system 44 indicative of pressure within the various controlled air zones 2262, 2264, 2302, and 2304 of the mattress 14. Additional details regarding the control of the valve assemblies 2406 in response to pressure within the various controlled air zones of the mattress 14 is provided herein.

Figure 120:
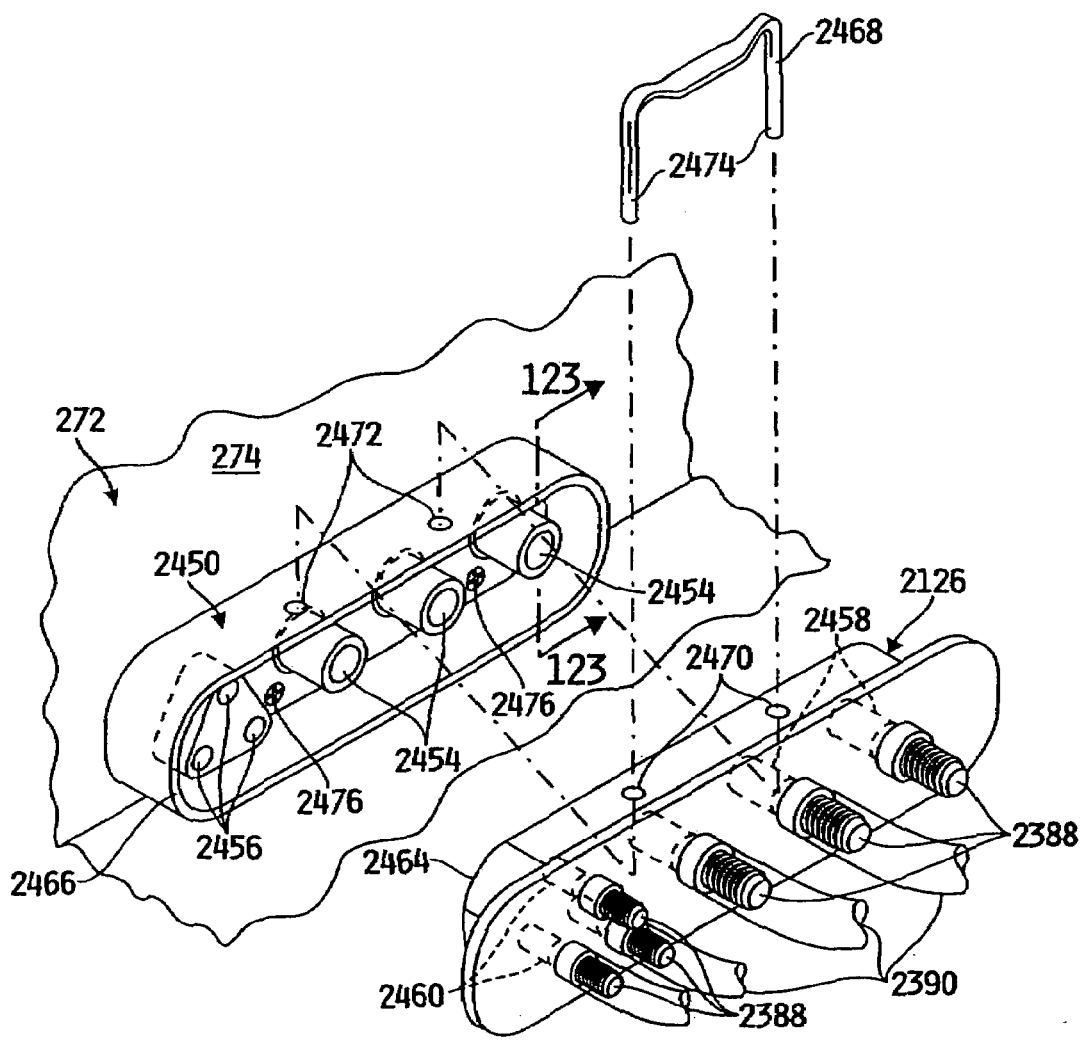
Figure 121:
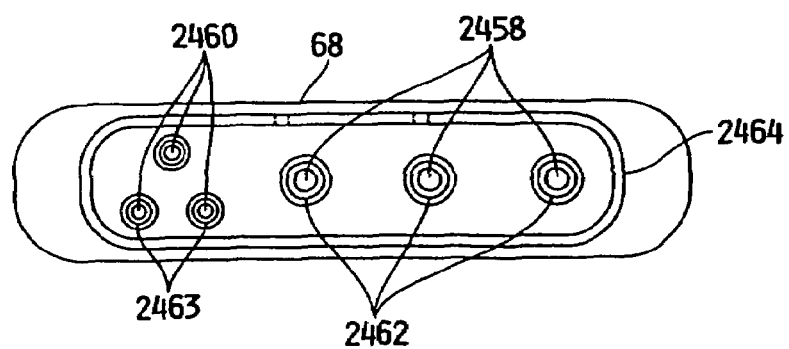

With reference to FIGS. 16, 118, 120, and 121, connectors 70 include first and second manifold or receiving connectors 2450 and 2452 coupled to the first and second manifolds 2402 and 2404. The partition wall 274 coupled to the deck 26 is positioned intermediate the manifold connectors 2450 and 2452 and the manifolds 2402 and 2404. The manifold connectors 2450 and 2452 are configured to sealingly mate with the mattress connectors 2126 and 2127, respectively. Each manifold connector 2450 and 2452 includes a plurality of outlets 2454 and 2456 configured to sealingly receive plugs 2458 and 2460, respectively, of the mating mattress connector 2126 and 2127. While FIG. 120 illustrates manifold connector 2450 and mattress connector 2126, it should be noted that manifold connector 2452 and mattress connector 2127 are substantially identical to manifold connector 2450 and mattress connector 2126.

The outlets 2454 are in fluid communication with the supply ports 2434 of the valve assemblies 2406, while the plugs 2458 are in fluid communication with the intake ports 2270, 2272, 2346, and 2350 of the various controlled air zones 2262, 2264, 2302 and 2304 of the mattress 14 in the manner detailed herein. The outlets 2456 are in fluid communication with the pressure sensing tubes 2440 through the manifolds 2402 and 2404, while the plugs 2460 are in fluid communication with the sensing lines 2274, 2276, 2348, and 2352 of the controlled air zones of the mattress 14. In an alternative embodiment of the invention, the sensing lines 2274, 2276, 2348, and 2352 may bypass the manifolds 2402 and 2404 and be directly connected to the pressure sensors 2442.

Each of the plugs 2458 and 2460 illustratively includes an O-ring gasket 2462 and 2463 to promote sealing with a mating outlet 2454 and 2456, respectively. The mattress connectors 2126 and 2127 each include a peripheral inner flange 2464 which is configured to be received within a peripheral outer flange 2466 of a respective manifold receiving connector 2450 and 2452. A fastener, illustratively a u-shaped staple 2468 locks the peripheral flanges 2464 and 2466 together. More particularly, the inner flange 2464 includes apertures 2470 and the outer flange 2466 includes apertures 2472 which are coaxially aligned with the apertures 2470 when the mattress connector 2126, 2127 is properly seated within the mating manifold receiving connector 2450, 2452. The staple 2468 includes a pair of legs 2474 which are received within the aligned apertures 2470 and 2472 to lock the connectors. While a staple 2468 is illustrated, it should be appreciated that other fasteners, such as latches, may be readily substituted therefor.

As described above, the manifold receiving connectors 2450 and 2452 are coupled to the manifolds 2402 and 2404, respectively, through the partition wall 272. Conventional fasteners, such as screws 2476, may be utilized to secure the manifold receiving connectors 2450 and 2452 and the first and second manifolds 2402 and 2404 relative to the partition wall 272. In one illustrative embodiment, cylindrical gaskets may be positioned intermediate each outlet 2454 of the receiving connectors 2450 and 2452 and the manifold 2402 and 2404 in order to effect sealing therebetween.

Figure 122:
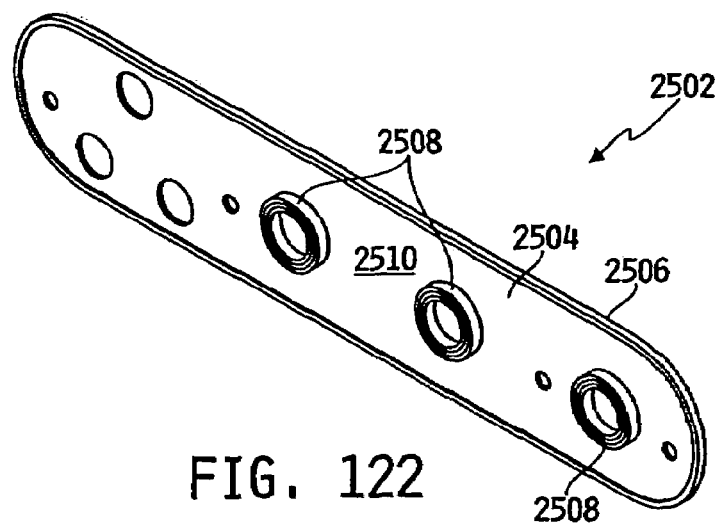
Figure 123:
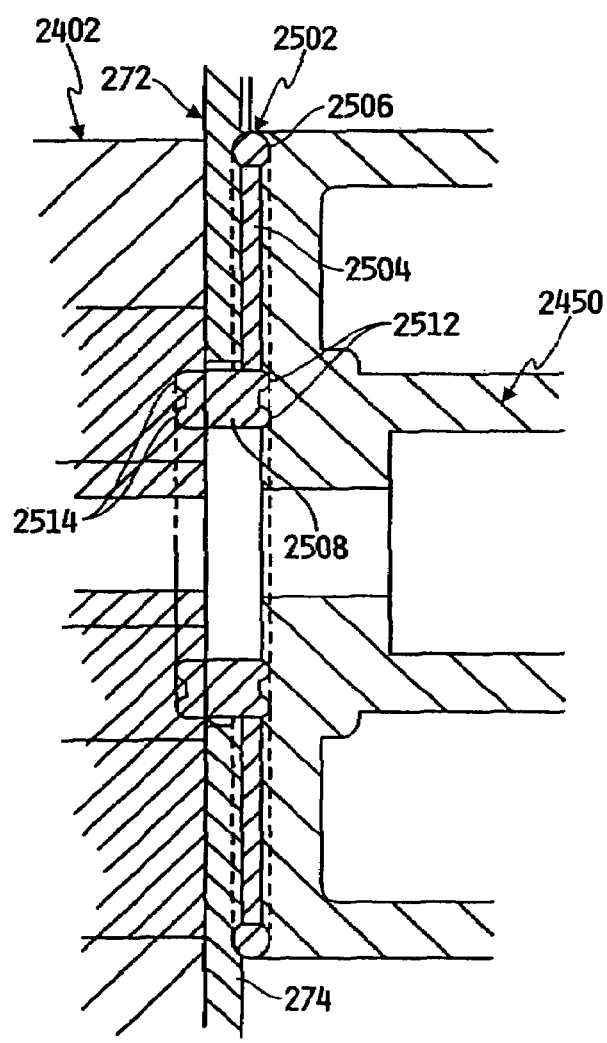

In a further illustrative embodiment, a gasket 2502 such as that shown in FIGS. 122 and 123 may be positioned intermediate the manifold connectors 2450 and 2452 and the vertical wall 274 of partition 272. The gasket 2502 includes a rigid substrate 2504 supporting a perimeter seal 2506. Likewise, the substrate 2504 supports a plurality of outlet seals 2508. The outlet seals 2508 extend outwardly from a first surface 2510 of the substrate 2504. Illustratively, the substrate 2504 is molded as a single piece of vulcanized fiber paper. Further illustratively, the perimeter seal 2506 and the outlet seals 2508 are formed from a neoprene material of approximately 25 durometer.

The outlet seals 2508 pass through apertures formed within the vertical wall 274 of partition 272 and are compressed between the manifold connectors 2450 and 2452 and the manifolds 2402 and 2404. Each outlet seal 2508 includes first and second pairs of annular sealing rings 2512 and 2514 which extend in opposite directions (FIG. 123). More particularly, the first pair of sealing rings 2512 is configured to be compressed against the respective manifold connector 2450 and 2452, while the second pair of sealing rings 2514 is configured to be compressed against the respective manifold 2402 and 2404. FIG. 123 illustrates an outlet seal 2508 in an uncompressed state in order to illustrate the expected amount of compression by the manifold 2402 and the manifold connector 2450.

The gasket assembly 2502 provides for a rigid substrate 2504 which does not compress during assembly and thereby provides for a definite torque specification or tightening of the receiving connectors 2450 and 2452 against the respective manifolds 2402 and 2404. Likewise, the rigid substrate 2504 provides for a positive seal and accounts for variations or discrepancy in material dimensions. The individual cylindrical outlet seals 2508 provide for zone controlled sealing and prevent cross-communication between the various outlets 2454. Finally, the perimeter seal 2506 provides secondary sealing and prevents contamination within the receiving connectors 2450 and 2452 by dirt or other contaminants.

Pressure Control System

Figure 124:
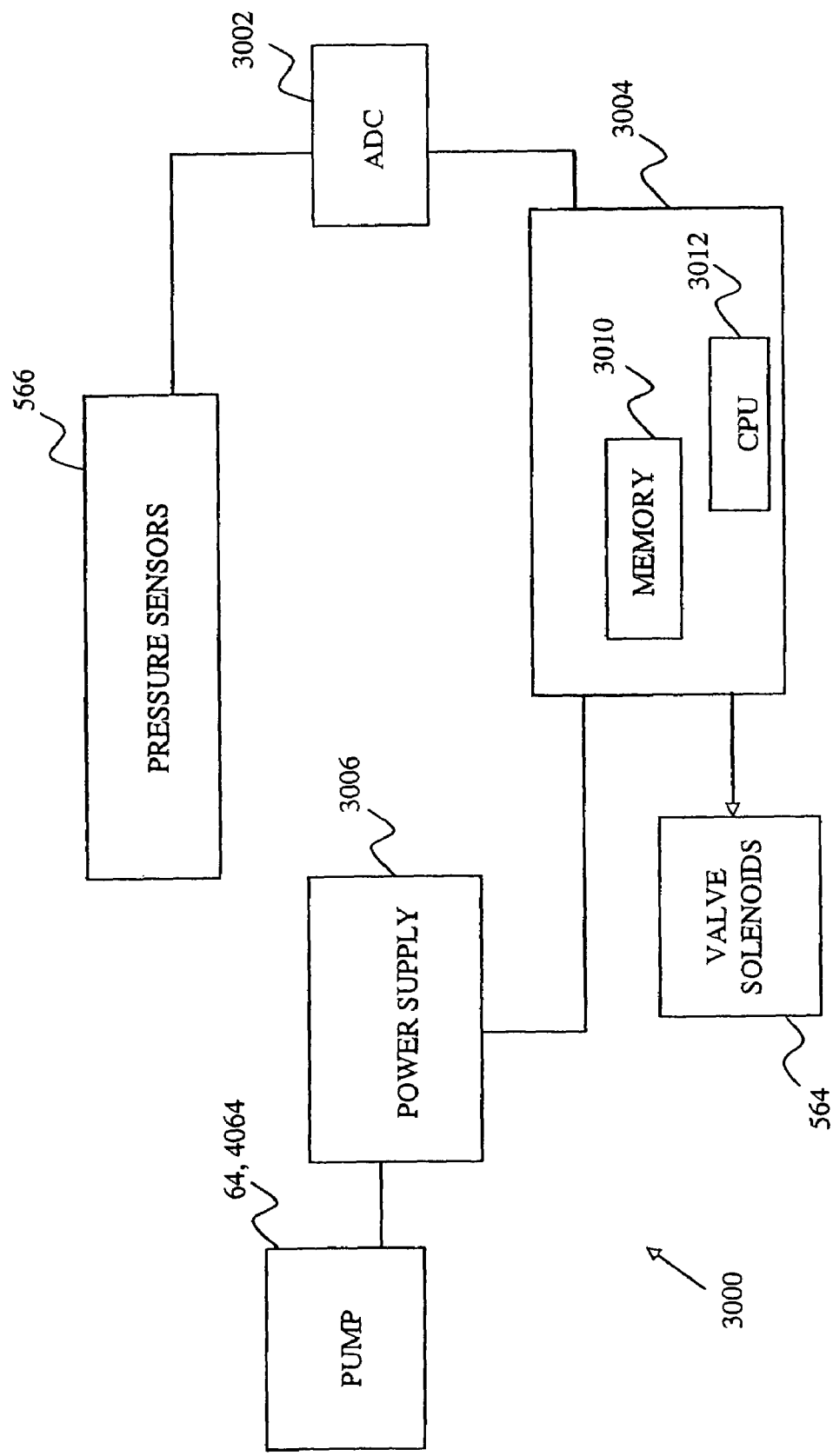

As mentioned elsewhere in this disclosure, control system 44 includes dynamic surface module 518. In addition to other functions, dynamic surface module 518 includes a pressure control system 3000. As shown in FIG. 124, pressure control system 3000 includes a plurality valve solenoids 564, a plurality of pressure sensors or transducers 566, an analog to digital converter 3002, a microcontroller 3004, a power supply 3006 and pump 64. Microcontroller 3004 includes memory 3010 and central processing unit 3012.

Pressure sensors, illustratively transducers 566, periodically sense the pressure in one or more of controlled air zones 2262, 2264, 2302, 2304 of mattress 14 and output a voltage proportional to the amount of pressure that is sensed. Analog-to-digital converter 3002 converts the voltage to digital form and feeds the digital value to microcontroller 3004. Microcontroller 3004 analyzes the current pressure and determines whether the current pressure in controlled air zones 2262, 2264, 2302, 2304 is correct, too high, or too low in comparison to a desired pressure. Memory 3010 stores data, e.g. in the form of look-up tables, which is used in this analysis. For example, the desired pressure of an air zone 2262, 2264, 2302, 2304 may depend upon the particular operating mode of the system 3000 (e.g., pressure relief, max-inflate, CPR, right turn assist, or left turn assist), whether head section 38 is elevated and the degree of elevation, and/or the size of the patient. Tables 1, 2, and 3 show examples of desired pressures for controlled air zones 2262, 2264, 2302, 2304 based on the air system operating mode, patient size, and, for seat section 42, head section elevation.

TABLE 1

HEAD SECTION
(Pressure measured in inches H₂O)

| MODE | PT. SIZE | | |
|---|---|---|---|
| | SM | MED | LG |
| Pressure Relief* | 5-7 | 7-9 | 11-13 |
| Max Inflate | | 26.5-27.5 | |
| CPR | | 20-30 | |
| Right-Left Turn Assist* | 5-7 | 7-9 | 11-13 |
| Post-Turn Assist | | 20-22 | |

*May vary according to head angle.

TABLE 2

SEAT SECTION**
(Pressure measured in inches H₂O)

| MODE | PT. SIZE | | |
|---|---|---|---|
| | SM | MED | LG |
| Pressure Relief | 7-21 | 9-25 | 13-31 |
| Max Inflate | | 25-29 | |
| CPR | | 20-30 | |
| Right-Left Turn Assist | 7-21 | 9-25 | 13-31 |
| Post-Turn Assist | | 20-22 | |
| Seat Boost | 23-25 | 27-29 | 33-35 |

**Pressure also varies with head elevation - see Table 4.

TABLE 3

TURN ASSIST BLADDERS
(Pressure measured in inches H₂O)

| MODE | PT. SIZE | | |
|---|---|---|---|
| | SM | MED | LG |
| Pressure Relief | — | — | — |
| Max Inflate | — | — | — |
| CPR | — | — | — |
| Right-Left Turn Assist | 18-24 | 22-28 | 27-33 |

If the pressure of an air zone 2262, 2264, 2302, 2304 is too high, microcontroller 3004 actuates the appropriate valve assembly 2406 to allow air to escape from the air zone 2262, 2264, 2302, 2304. If the pressure is too low, microcontroller 3004 sends a message over network 510 to power supply module 514 of patient support 10 (parts of which are generally depicted in FIG. 124 as power supply 3006), and power supply 3006 activates pump 64. When microcontroller 3004 detects that pump 64 is turned on, it actuates the appropriate valve assembly 2406 to allow air to enter the appropriate controlled air zone 2262, 2264, 2302, 2304.

Among other things, embodiments of pressure control system 3000 illustratively include one or more of the following features: a process 3030 for controlling the inflation of controlled air zones 2262, 2264, 2302, 2304 according to the size of a patient, a process 3032 for controlling inflation of turn assist bladders 2262, 2264, and/or a process 3070 for controlling inflation of seat section 40 in response to elevation of head section 38.

Mattress Pressure Determination

In certain embodiments of pressure control system 3000 of dynamic surface module 518, a process 3030 for controlling the inflation of controlled air zones 2262, 2264, 2302, 2304 according to the size of a patient disposed on patient support 10 is provided. One embodiment of process 3030 is shown in FIG. 125 and described below.

Figure 125:
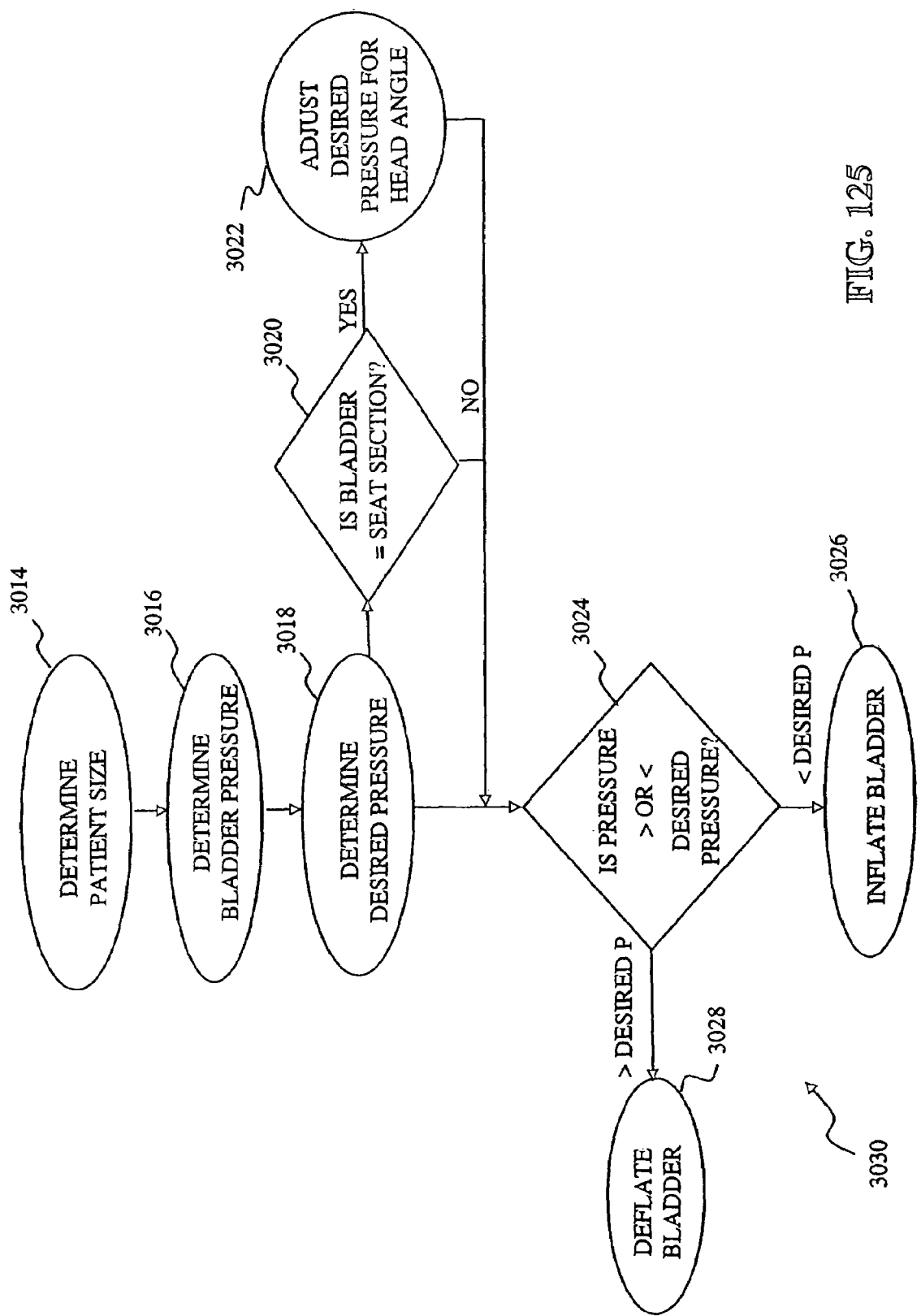

Process 3030 begins at step 3014 of FIG. 125, where the microcontroller 3004 detects whether it has been activated to determine patient size. In one illustrative embodiment, patient size button 1628 of siderail controllers 52, 54 is optional. In other embodiments, button 1628 is not optional and the operator or caregiver is required to select an appropriate patient size. In still other illustrative embodiments, button 1628 automatically selects a default setting, e.g., the "medium" size, if a patient size is not selected by the operator or caregiver.

In the illustrative embodiment of FIG. 125, there are three possible patient sizes that can be selected by using button 1628: "small," "medium," and "large." In general, the determination of whether a patient is of small, medium, or large size is made by the caregiver. However, it is understood that there are any number of different ways to indicate a patient's size. For example, in lieu of button 1628, pressure control system 3000 may provide the ability to automatically determine the patient's size based on the patient's weight, which may be determined by weigh frame 36 and/or by a force sensor located in seat section 40 in the manner detailed herein. Another alternative is to provide a user interface on siderail controllers 52,54 whereby the caregiver may enter the patient's height, and system 3000 determines the patient's size based on the entered height value and the patient's weight.

At step 3016, the controlled air zone(s) 2262, 2264, 2302, 2304 being monitored is determined. All of head section air zone 2302, seat section air zone 2304, and turn assist bladders 2262, 2264 may be inflated to varying pressures based on patient size. However, it is understood that in alternative embodiments not all of air zones 2262, 2264, 2302, 2304 may be inflated based on patient size.

At step 3018, process 3030 determines the desired inflation pressure for the respective air zone(s) 2262, 2264, 2302, 2304 being monitored based on the patient size. In the illustrated embodiment, microcontroller 3004 obtains the desired pressure for the air zone(s) 2262, 2264, 2302, 2304 from at least one look-up table stored in memory 3010. The desired pressure may be a discrete value or a range of permissible values. Also, the desired pressure may be different for each air zone 2262, 2264, 2302, 2304. Further, various other factors, including environmental factors such as temperature and/or altitude, may affect the desired pressure values and be reflected in data in the look-up table. As an example, in one embodiment, under normal hospital room conditions, for a patient considered "small," the appropriate pressure is about 4-7 inches in water for head section air zone 2302, about 7 to 21 inches in water for seat section air zone 2304, and about 18-24 inches in water for turn assist bladders 2262, 2264. Tables 1, 2, and 3 show examples of desired pressure values based upon patient size.

As indicated by decision step 3020, in the illustrative embodiment of FIG. 125, the appropriate pressure for seat section air zone 2304 also depends on the elevation of head section 38. If process 3030 causes inflation of seat section air zone 2304, then at step 3022 the pressure of seat section air zone 2304 is adjusted based on the angle of head section 38. This adjustment is discussed in connection with FIG. 128 below. Thus, for seat section air zone 2304, the appropriate pressure is determined by reference to both patient size and head angle. However, adjusting the pressure of seat section air zone 2304 based on only one of these criteria is also within the scope of the present invention.

At decision step 3024, microcontroller 3004 measures the current pressure as described above and determines whether the current pressure is less than, equal to, or greater than the desired pressure determined as described above. If the current pressure is less than the desired pressure at step 3026, microcontroller 3004 commands power supply 3006 to activate pump 64 to inflate air zone 2304 to the desired pressure as described above. If the current pressure is greater than the desired pressure, then at step 3028, air zone 2304 are deflated as described above.

Patient Turn Assist

Figure 126:
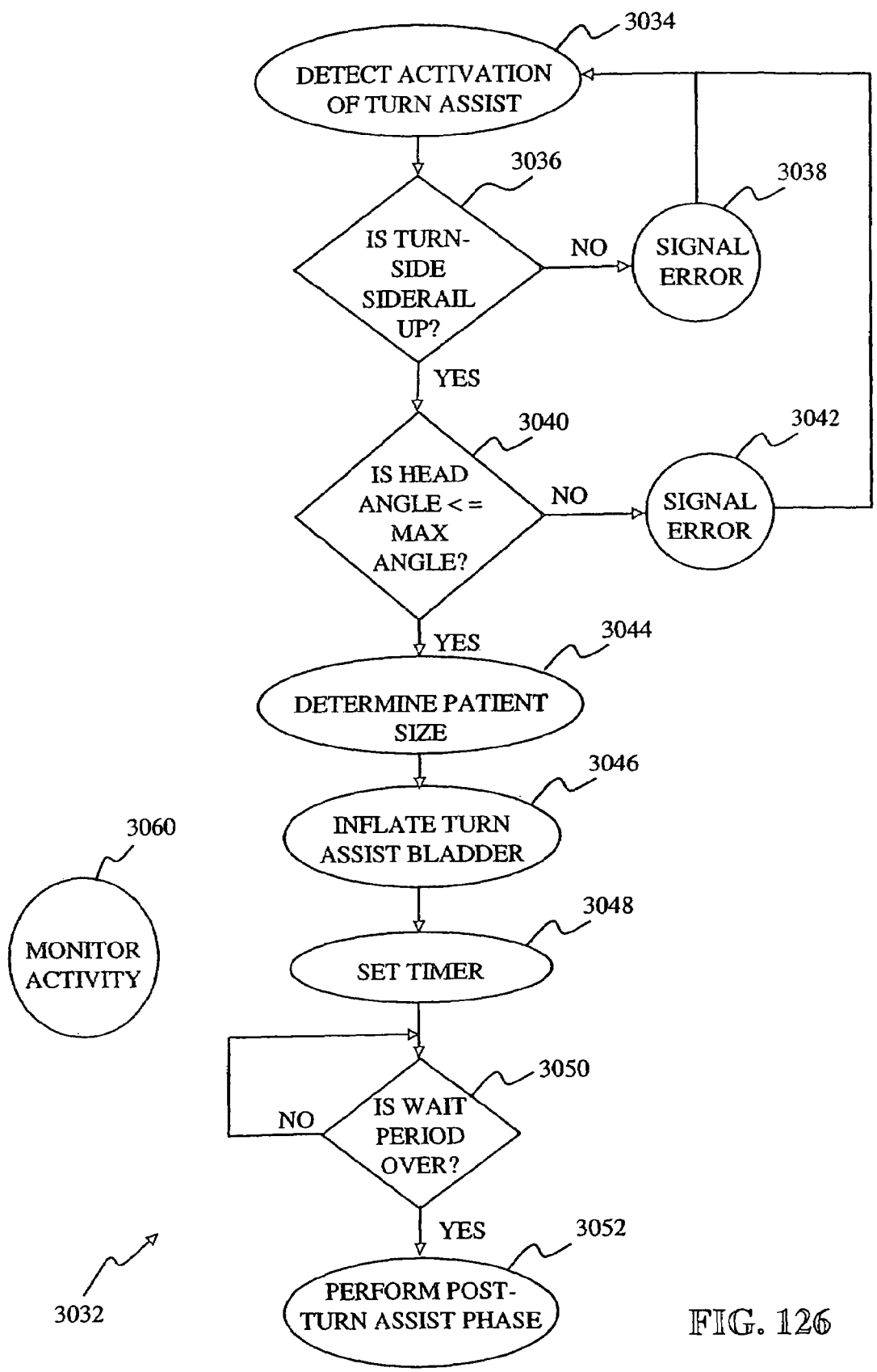

In addition to other functions discussed above and elsewhere in this disclosure, pressure control system 3000 of dynamic surface module 518 controls the operation of turn assist bladders 2262, 2264. Turn assist bladders 2262, 2264 illustratively are bladders of mattress 14 that selectively inflate to assist a caregiver in turning or rotating a patient, e.g., for therapy or treatment reasons. One embodiment of a process 3032 for controlling operation of turn assist bladders 2262, 2264 is shown in FIGS. 126 and 127 as described below. Process 3032 is implemented using application software stored in memory 3010 of microcontroller 3004. The structure of illustrative turn assist bladders 2262, 2264 is described above.

Process 3032 begins at step 3034 of FIG. 126, where microcontroller 3004 detects whether a request has been received to activate one of turn assist bladders 2262, 2264. In the illustrated embodiment, such a request is initiated by an operator or caregiver activating one of turn assist buttons 1624, 1626 located on siderail controllers 52, 54. However, it is understood that other means for activating the turn assist may be used. For example, control system 44 may be programmed to automatically activate one or more of turn assist buttons 1624, 1626 at scheduled times during the day or night.

At decision step 3036, prior to initiating the turn assist function, process 3032 checks to make sure that the siderail(s) 20, 22 toward which the patient is being turned is in the up or raised position, based on signals provided by siderail position detector(s) 60. If one or more of siderails 20, 22 toward which the patient is being turned is not in the up position (i.e. in down or lowered position), an error signal is generated at step 3038 and process 3032 returns to step 3034 without activating the turn assist bladders 2262, 2264. In the illustrative embodiment, an audible or visual signal is generated for a brief period or until the siderail or siderails 20, 22 are brought to the up position. Thus, in the illustrative embodiment, the siderails 20, 22 toward which the patient is being turned must be in the up position in order for the turn assist process to initiate. It is possible, however, that in other embodiments, a caregiver or operator may override this restriction, or that this restriction may be made optional, for example, depending on the circumstances of a particular patient.

At decision step 3040, microcontroller 3004 checks to see if the angle of head section 38 (head angle) is less than, equal to, or greater than a predetermined maximum angle. In the illustrated embodiment, the maximum head angle is about 40°. The head angle determination is made by logic module 512 and is discussed in connection with FIG. 128 below. Logic module 512 reports the head angle to dynamic surface module 518 for use in process 3032, via network 510. If the head angle is less than or equal to 40°, then the turn assist process continues to step 3044. However, if the head angle is greater than about 40°, an error signal is generated at step 3042, and the turn assist process returns to block 3034 without activating the turn assist bladders 2262, 2264.

At step 3044, the size of the patient being supported by patient support 10 (e.g., small-medium-large) is determined as described above so that a desired pressure based on patient size is applied to the selected turn assist bladder 2262, 2264.

At step 3046, if first turn assist button 1624 is activated, first turn assist bladder 2262 inflates to rotate a person in patient support 10 upwardly in a counter-clockwise from the perspective of a person standing behind head section 38. If second turn assist button 1626 is activated, second turn assist bladder 2264 inflates to rotate the person upwardly in the opposite direction as rotated in response to activation of first turn assist button 1624. Inflation of the selected turn assist bladder 2262, 2264 raises one side of the patient to a predetermined angle. In the illustrated embodiment, the selected turn assist bladder 2262, 2264 inflates to rotate the patient onto his or her side at about a 20 degree angle with respect to mattress 14, in approximately 20-50 seconds, depending on the size of the patient. It is understood that the predetermined angle and speed of inflation may be changed or modified as needed based on a variety of factors, including the purpose for rotating the patient.

A timer, illustratively part of the central processing unit 3012, is set at step 3048 when the selected turn assist bladder 2262, 2264 is inflated. The selected turn assist bladder 2262, 2264 remains inflated for a predetermined period of time, for example 5-30 seconds. In the illustrated embodiment, the duration of turn assist inflation is about 5 seconds. At step 3050 the timer counts out this wait period. After the wait period is complete (e.g., after 5 seconds), an audible or visual signal is generated to indicate to the patient and caregiver that the selected turn assist bladder is about to enter a "post-turn assist" phase. Process 3032 then begins deflating the selected turn assist bladder 2262, 2264 at step 3052. In the illustrated embodiment, deflation is expedited by quickly "hyperinflating" bladders 2302, 2304 to a firm, "post-turn assist" inflation pressure (see, e.g., Table 1 and Table 2). Inflation of bladders 2302, 2304 exerts pressure on turn assist bladders 2262, 2264, causing turn assist bladders 2262, 2264 to expel air more rapidly. Alternatively, a vacuum mechanism may be coupled to turn assist bladders 2262, 2264 to accelerate deflation.

The post-turn assist inflation and deflation processes may be interrupted under certain circumstances. For example, when a patient's bed 10 needs a linen change, it may be desirable for first and second turn assist bladders 2262, 2264 to be activated in more rapid succession than would be possible if the full post-turn assist process were performed. In such instances, if one of turn assist buttons 1624, 1626 is activated, and then the other turn assist button 1624, 1626 is activated before the previous turn assist process is complete, the previous process is interrupted and, as long as the turned-to-side siderails 20, 22 are in the up position as described above, and head section 38 is positioned at an angle less than or equal to 40°, the new turn assist mode is started.

For example, assume a caregiver presses first turn assist button 1624. If the caregiver then presses second turn assist button 1626 while first turn assist bladder 2262 is inflating, then process 3032 will interrupt the inflation, bypass the post-turn assist phase (i.e., head and seat bladders 2302, 2304 will not be inflated), and begin inflating second turn assist bladder 2264 as long as siderails 20, 22 are up on the side of the bed the patient is being turned to, and the head angle is less than or equal to the maximum head angle. If the caregiver presses second turn assist button 1626 while first turn assist bladder 2262 is in post-turn assist mode, post-turn assist mode is interrupted and second turn assist bladder 2264 begins inflating as discussed above.

Monitor activity step 3060 is a step that is periodically executed during the turn assist operation. The monitor activity process 3060 is shown in more detail in FIG. 127. This process 3060 detects whether a patient or caregiver attempts to utilize other bed features while either turn assist bladder 2262, 2264 is in operation. For example, at step 3062, process 3032 checks to see if siderail 20, 22 on the side to which the patient is being turned is raised or lowered. In the illustrated embodiment, if siderails 20, 22 are in the raised position at the beginning of turn assist, but one or more of them are lowered during turn assist, an audible signal or alarm is generated for a brief period at step 3064, or until the siderail 20, 22 is returned to the raised position, but the turn assist process 3032 is not interrupted. In alternative embodiments, however, upon detecting a lowering of siderail 20, 22, the turn assist process 3032 may be suspended for a brief period or stopped until or unless the lowered siderail 20, 22 is returned to the raised position.

At step 3066, process 3060 detects whether a patient or caregiver has selected another mode, e.g., turn assist for the other side of the patient, max inflate, or pressure relief. During the turn assist operation, the selection of another mode causes process 3060 to begin exiting the turn assist mode at block 3067. If the other turn assist mode is selected, the current turn assist bladder 2262, 2264 is deflated and the other turn assist mode is entered substantially immediately. If the pressure relief mode or the max-inflate mode is selected, process 3060 immediately enters the post-turn assist operation and enters the newly selected mode upon completion of the post-turn assist phase. However, if the CPR function is activated, process 3060 immediately deflates turn assist bladder 2262, 2264 and enters the CPR mode substantially immediately. If no mode is selected during turn assist, process 3060 will exit as described previously and enter the pressure relief mode upon completion of the post-turn assist phase.

At step 3068, process 3060 detects whether the angle of head section 38 has been increased above the maximum head angle as described above. If the head angle increases above the maximum head angle, an error message, e.g., in the form of an audible or visual signal, is generated at step 3069. In the illustrated embodiment, the turn assist process 3032 is interrupted if the head angle exceeds the maximum angle. In alternative embodiments, the turn assist process 3032 is not interrupted.

Head Section Elevation

In addition to other functions discussed above and elsewhere in this disclosure, pressure control system 3000 may include another process 3070 for controlling the inflation of seat section air zone 2304 according to the position of head section 38. One embodiment of such method is shown in FIG. 128 and described below.

When head section 38 is elevated, a portion of the patient's weight naturally shifts from head section 38 to seat section 40. To anticipate this weight shift and prevent "bottoming out," the inflation pressure of seat section air zone 2304 is adjusted in response to changes in the position of head section 38. Table 4 below shows pressure ranges for seat section air zone 2304 depending on both patient size and angle of elevation of head section 38.

TABLE 4

| SEAT SECTION PRESSURE RANGES BY HEAD ANGLE | | | |
|---|---|---|---|
| HEAD | PT. SIZE | | |
| ANGLE (E) | SM | MED | LG |
| 0-10 | 7-9 | 9-11 | 13-15 |
| 6-20 | 9-11 | 11-13 | 15-17 |

TABLE 4-continued

SEAT SECTION PRESSURE RANGES
BY HEAD ANGLE

| HEAD | PT. SIZE | | |
| --- | --- | --- | --- |
| ANGLE (E) | SM | MED | LG |
| 16-30 | 11-13 | 13-15 | 17-19 |
| 26-40 | 13-15 | 15-17 | 19-21 |
| 36-50 | 15-17 | 17-19 | 21-23 |
| 46-60 | 17-19 | 19-21 | 25-27 |
| 56-65+ | 19-21 | 23-25 | 29-31 |

At step 3072 of FIG. 128, the position of head section 38, or head angle, is determined by position detector 606. In the illustrative embodiment, a potentiometer reading corresponding to the head angle is determined by logic module 512 and reported to dynamic surface module 518 via network 510 for use in process 3070. In the illustrated embodiment the potentiometer reading is a value ranging from 0 to 255. A change of 10 counts has been determined to indicate a change of approximately 3 degrees of head angle in the illustrated embodiment. The potentiometer 624 in the motor housing of actuator 48c, which operates to raise and lower head section 38 varies proportionally with movement of the motor drive shaft 172c while actuator 48c is operating. The logic module 512 measures a change in voltage across potentiometer 624 in a voltage divider circuit and converts it to a digital value using A/D converter 620. The corresponding head angle is determined in process 3070 by reference to a look-up table stored in memory 3010. Table 5 below shows examples of the head angle values and their corresponding potentiometer readings. While a potentiometer 624 is used in the illustrated embodiment, it is understood that a tachometer or other means for determining head angle are equally suitable.

TABLE 5

HEAD ANGLE VALUES

| REGION | POT. VALUE | HEAD ANGLE ° |
| --- | --- | --- |
| 0 | 0-51 | 0-10 |
| 1 | 41-76 | 6-20 |
| 2 | 60-100 | 16-30 |
| 3 | 90-122 | 26-40 |
| 4 | 112-142 | 36-50 |
| 5 | 132-157 | 46-60 |
| 6 | 147-255 | 56-65+ |

At decision step 3074, process 3070 evaluates the input received from logic module 512 and determines whether head section 38 has experienced at least a 3 degree change in position by comparing the current head angle to the previous head angle. If the head angle has changed at least approximately 3 degrees, the process 3070 continues to step 3076. If no change or less than approximately 3 degrees change in either direction has occurred, process 3070 returns to step 3072. It is understood that 3 degrees is an exemplary value and that a change in the head angle may be indicated by a greater or lesser value as appropriate. Of course, during this time, pressure control system 3000 continues to periodically measure the pressure of seat section air zone 2304 to make sure that it is within the desired ranges.

At decision step 3076, it is determined whether the change in position of head section 38 occurred in the upward or downward direction. This determination is derived from the comparison of the current head angle to the previous head angle. As shown in Table 5, the ranges of values indicating a change in head elevation overlap, in order to take into consideration hysteresis in the head angle evaluation.

For example, head section 38 will be considered to have moved from region zero to region 1 if a potentiometer value of about 52 is received by process 3070 (corresponding to a head angle of 1-10 degrees). However, once head section 38 is in region 1, it will not be considered to have moved back to region zero unless a potentiometer reading outside the specified range for region 1, e.g., approximately 40 or less, is received.

If a change in position occurs in the downward direction, i.e., head section 38 is lowered, then at step 3078 the inflation pressure of seat section air zone 2304 is decreased according to the size of the patient and the current head angle. The desired pressure range is determined by reference to a look-up table stored in memory 3010. Table 4 above is an example of such a table.

If a change in position occurs in the upward direction, i.e., head section 38 is elevated, then at step 3080 the inflation pressure of seat section air zone 2304 is increased. First, a "seat boost" is applied to seat section air zone 2304, meaning that seat section air zone 2304 is initially over-inflated for a brief period of time to compensate for the above-mentioned weight shift. Examples of the initial "seat boost" pressures are shown in Table 2 above. In the illustrated embodiment, the period of time for the seat boost is about 15 seconds. After the seat boost period expires, process 3070 adjusts the pressure of seat section bladders 2304 to the desired level based on patient size and head angle, as determined by the look-up table mentioned above.

Second Illustrative Embodiment Mattress Assembly

A second illustrative embodiment modular mattress assembly 4014 of the present invention is configured to be supported by deck 269, as shown in FIG. 129, of the illustrative patient support 109 of FIG. 57. Referring now to FIGS. 130 and 131, the mattress assembly 4014 includes first and second sides 4017a and 4017b extending substantially parallel to a longitudinal center axis 4019 between head and foot ends 4018a and 4018b. The modular mattress assembly 4014 includes an outer cover 2102 having a bottom cover portion 2104 and a top cover portion 2106 (FIG. 146) configured to encapsulate a plurality of internal components including a foam receiving base 4208. The receiving base 4208 includes a foam foot section 4210 and a foam body section 4212 coupled to the foot section 4210 illustratively by a foot section securing substrate 4340 (FIG. 138). Component mounting substrates 4214, 4216 are coupled to the foot section 4210 and the body section 4212, respectively, of the base 4208. A foot or heel bladder assembly 4215 is coupled to the mounting substrate 4214. A foam filler or panel 4218 is supported above the mounting substrate 4216 and is received within the base 4208. A turn assist bladder assembly 4220 is received above the foam filler 4218 and is coupled to the mounting substrate 4216. An upper bladder assembly 4222 is received above the turn assist bladder assembly 4220 and is likewise coupled to the mounting substrate 4216. A fire sock or barrier 2124 is configured to surround the receiving base 4208, including the foot section 4210 and the body section 4212, the mounting substrates 4214 and 4216, the heel bladder assembly 4215, the foam filler 4218, the turn assist bladder assembly 4220, and the upper bladder assembly 4222. A shear cover 2125 is configured to be received over the fire barrier 2124. The top cover portion 2106 is configured to be coupled to the bottom cover portion 2104 to receive the other mattress components and to define the outer cover 2102. A mattress fluid connector 4068 is coupled to the bottom cover portion 2104 and is configured to provide fluid communication between a manifold 4063, which is coupled to a pump 4064, and the mattress 4014.

Mattress Foot Section Assembly

As detailed above with respect to leg section 42 of deck 26, the leg section 429 of the deck 269 is likewise extendable and retractable. FIGS. 132 and 133 further illustrate the foot section 4210 of the mattress 4014 which is configured to extend and retract with the movement of the adjustable leg section 429 of the articulating deck 269. The foot section 4210 includes a base portion 4228 and a pair of opposing flange portions 4230 and 4232 supported above the base portion 4228. The base portion 4228 includes angled sidewalls 4234 and 4236 which are configured to conform to the angled sidewalls 291, 300 of the deck 269. The flange portions 4230 and 4232 are configured to extend out beyond the angled sidewalls 291, 300 of the deck 269. Illustratively, the foot section 4210 is made of a resilient polyurethane foam.

The foot section 4210 is perforated to facilitate its longitudinal extension and retraction. More particularly, the foot section 4210 is formed to include a plurality of apertures, illustratively transversely extending slots 4238 extending in a generally vertical direction through the base portion 4228 and the flange portions 4230 and 4232, to facilitate compressibility of the foot section 4210 in response to the retraction of the leg section 429 of the deck 269. More particularly, the plurality of slots 4238 are arranged in a plurality of laterally extending rows 4240 wherein the individual slots 4238 of each row 4240 are laterally offset from those slots 4238 of longitudinally adjacent rows 4240. It may be readily appreciated, each slot 4238 widens to accommodate the extension of the leg section 429 and narrows to accommodate the retraction of the leg section 429 of the deck 269.

While in the illustrative embodiment a plurality of discrete laterally and longitudinally spaced transverse slots 4238 are illustrated to facilitate retraction and extension of the foot section 4210, it should be appreciated that other structures may be readily substituted therefor. More particularly, the foot section 4210 may be formed to include serpentine channels or a plurality of slots extending substantially the full width of the foot section 4210 between opposing side edges of the flange portions 4230 and 4232.

A foot section mounting plate 4242 is secured to a lower surface 4244 of the foot section 4210, illustratively through an adhesive tape 4245. As described in greater detail below, the foot section mounting plate 4242 provides a securing platform for a foot section anchor 4246 which couples the foot section 4210 to the leg section 429 of the deck 269 to facilitate movement in cooperation therewith.

The foot section 4210 further includes a receiving recess 4248 extending downwardly from an upper surface 4250 of the base portion 4228 at a foot end 4252 thereof. The heel bladder assembly 4215 defines a heel pressure relief zone 4254 and is coupled to the foot mounting substrate 4214 and is received within the recess 4248. Opposing first and second ends of the foot mounting substrate 4214 are coupled to a pair of foot attachment straps 4256. The attachment straps 4256 each have a center mounting aperture 4257 coupled to the foot section mounting member 4242 through a conventional fastener, such as a button 4258. Similarly, opposing ends of the foot attachment straps 4256 including mounting apertures 4259 which are secured to the opposing ends of the foot mounting substrate 4214 through conventional fasteners, such as buttons 4258 (FIGS. 133 and 136).

Heel Bladder Assembly

As noted above, the heel bladder assembly 4215 is supported within the recess 4248 and is coupled to the foot mounting substrate 4214. As illustrated in FIGS. 132, 134 and 135, the heel bladder assembly 4215 includes a total of four laterally extending air bladders 4264. However, it should be appreciated that any number of bladders 4264 may be provided in the foot section 4210 depending upon the area required for the heel pressure relief zone 4254. Each bladder 4264 includes a fluid chamber illustratively defined by a sheet 4265 which is generally folded in half to form a tubular member, wherein the open side edges and bottom edges are sealed through conventional means, such as radio-frequency (RF) welding, to form the fluid chamber. The bladders 4264 are illustratively formed of a polymer material, such as a polyolefin. The plurality of air bladders 4264 are fluidly connected. More particularly, the first bladder 4264a is fluidly connected to the second air bladder 4264b through a conventional U-shaped fluid connector 4266a, the second bladder 4264b is fluidly connected to the third bladder 4264c through a conventional U-shaped fluid connector 4266b, and the third bladder 4264c is fluidly connected to the fourth bladder 4264d through a conventional U-shaped fluid connector 4266c (FIGS. 130 and 134).

Referring further to FIGS. 130 and 133-135, a plurality of outer and inner fasteners 4268 and 4270, illustratively snaps, are secured to the foot mounting substrate 4214 proximate opposing side edges thereof. The foot mounting substrate 4214 is formed from a flexible sheet material, such as polyurethane coated twill. Opposing ends of each bladder 4264 include an upper fastener 4272 and a lower fastener 4274, illustratively snaps, which cooperate with the outer fastener 4268 and the inner fastener 4270 of the foot mounting substrate 4255.

A foot fill tube 4276 is fluidly connected to the first bladder 4264a while a foot sensor tube 4278 is fluidly connected to the fourth fluid bladder 4264d. As illustrated in FIGS. 134 and 135, the foot fill tube 4276 and the foot sensor tube 4278 extend from the heel bladder assembly 4215 toward the body section 4212 of the receiving base 4208 and from proximate the first side 4017a of the mattress 4014 to proximate the second side 4017b of the mattress 4014. In other words, respective portions of the tubes 4276 and 4278 extend diagonally below the lower surface 4244 of the foot section 4210 of the base 4208 in order to accommodate extension and retraction thereof without kinking or pulling. The tubes 4276 and 4278 next extend toward the head end 4018a of the mattress 4014 by passing between the mounting substrate 4216 and the body section 4212 of base 4208 proximate second side 4017b of the mattress 4014. The tubes 4276 and 4278 pass through a slit 4275 formed in the mounting substrate 4216 and pass between the mounting substrate 4216 and the turn assist bladder assembly 4220 to the mattress connector 4068.

The tubes 4276 and 4278 may be coupled to the foot section mounting member 4242 through a conventional cable tie (not shown). Further retention of the tubes 4276 and 4278 to the mounting substrate 4216 may be provided by a securing loop 4338 coupled to the mounting substrate 4216.

The heel bladder assembly 4215 is configured to provide heel pressure relief by reducing the level of raised pressure between the patient's foot and the mattress. More particularly, the heel bladder assembly 4215 provides for a region of reduced pressure below the patient's heels. The foot section 4210 includes a calf portion 4279 which supports the portion of the patient's weight that would otherwise be supported by the patient's heel and thus reduces the overall interface pressure between the patient's heel and the mattress 4014. It is envisioned that the calf portion 4279 of the mattress 4014 may include a transition zone where the material stiffness of the foot section 4210 decreases in a longitudinal direction extending generally from head end 4018a to the foot end 4018b of mattress 4014.

Mattress Body Section Assembly

The body section 4212 of the receiving base 4208 is further illustrated in FIGS. 138 and 140 as including a bottom layer 4280 secured to longitudinally extending first and second sidewalls or bolsters 4281 and 4282. Likewise, an end wall or bolster 4283 is coupled to the first and second sidewalls 4281 and 4282 and the bottom layer 4280. As such, the body section 4212 defines a longitudinally extending channel or bucket 4284 configured to receive various components of the mattress 4014. As described in greater detail below, a fluid connector recess 4285 is formed near the head end 4286 of the body section 4212 and is configured to receive the mattress fluid connector 4068.

The sidewalls 4281 and 4282 each include an angled or inclined portion 4288 coupled to a flange portion 4290. The angled portions 4288 are configured to conform to the angled sidewalls 260 and 262 of the deck 269, while the flange portions 4290 are configured to extend above and out beyond the sidewalls 260 and 262 of the deck 269. The body section 4212 of the receiving base 4208 includes a head portion 4292 and a seat portion 4294 separated by a laterally extending slit 4296 (FIG. 130). Opposing ends of the slit 4296 include stress relief apertures (not shown) formed within the sidewalls 4281 and 4282. As described in greater detail below, the slit 4296 facilitates relative movement of the head and seat portions 4292 and 4294 of the body section 4212 during articulation of the head and seat sections 4038 and 4040 of the deck 269.

Mattress Mounting Substrate

With reference to FIGS. 130, 137 and 138, the mounting substrate 4216 is received within channel 4284 defined by the body section 4212 of the receiving base 4208. Opposing first and second end portions 4302 and 4304 of the mounting substrate 4216 are coupled to first and second upper mounting plates 4306 and 4308. In turn, the upper mounting plates 4306 and 4308 are secured to an upper surface of the receiving base 4208, illustratively through double sided adhesive tape 4307 and 4309, respectively. A plurality of fasteners, illustratively buttons 4312 are secured to the upper mounting plates 4306 and 4308. The buttons 4312 are releasably received within a plurality of substrate securing apertures 4314 formed within the mounting substrate 4216, thereby connecting the mounting substrate 4216 to the receiving base 4208 through the upper mounting plates 4306 and 4308. A head section mounting plate 4316 is secured to a lower surface of the receiving base 4208, illustratively through means of a double sided adhesive tape 4318. As detailed below, the head section mounting plate 4316 provides a coupling platform for a head anchor strip 4320 which secures the body section 4212 of the receiving base 4208 to the head section 4038 of the deck 269.

The mounting substrate 4216 includes a base portion 4322 and first and second mounting portions 4324 and 4326 extending along opposing longitudinal side edges of the base portion 4322. Each mounting portion 4324 and 4326 includes a outer mounting member 4328 and an inner mounting member 4330 hingedly connected to the outer mounting member 4328 through a hinge 4329. The mounting members 4328 and 4330 include a plurality of longitudinally spaced outer and inner fasteners 4332 and 4334, illustratively snaps, configured to couple to corresponding fasteners of the upper bladder assembly 4222 as detailed below. A plurality of turn assist bladder assembly securing apertures 4336 are formed proximate opposing longitudinally extending side edges of the mounting substrate 4216. As detailed below, the apertures 4336 are configured to receive fasteners, such as buttons 4337 for securing the turn assist bladder assembly 4220 to the mounting substrate 4216. First and second securing loops 4338 and 4339 are coupled to the base portion 4322 and are configured to receive various fluid tubes for retention therein.

Foot Section Securing Substrate

With further reference to FIG. 138, the foot section 4210 may be secured to the receiving base 4208 through the use of a foot section securing substrate 4340. The foot section securing substrate 4340 includes a first portion 4342 secured to the upper mounting plate 4308 of the seat portion of the receiving base 4208 and a second portion 4344 secured to lower surface 4277 of the foot section 4210. More particularly, the first portion 4342 of the foot section securing substrate 4340 includes a plurality of mounting apertures configured to receive fasteners, such as buttons 4312. The buttons 4312 are secured to the upper mounting plate 4308, which is coupled to the upper surface of receiving base 4208 as detailed above. The second portion 4344 of the securing substrate 4340 is directly coupled to a lower surface of the foot section 4210, illustratively through an adhesive. The second portion 4344 includes a plurality of transverse slots 4350 configured to be received in parallel disposition with the transverse slots 4238 formed within the foot section 4210.

Illustratively, the foot section securing substrate 4340 is formed from a flexible sheet material, such as pack cloth urethane coated twill. As a flexible sheet material, the foot section securing substrate 4340 may follow a serpentine path from a horizontal first plane of the bottom layer 4280 of the receiving base 4208 and vertically down around a foot end edge 4352 of the receiving base 4208, and back along a horizontal plane of the lower surface 4277 of the foot section 4210.

Foam Filler

The foam filler or panel 4218 is received within the channel 4284 defined by the sidewalls 4281 and 4282 of the body section 4212 of the receiving base 4208. Illustratively, the filler 4218 is made of polyurethane foam having an indention force deflection (IFD) of between approximately 23 pounds to approximately 29 pounds. IFD is commonly defined in the art as the amount of force necessary to indent an 8 inch disc plate 25 percent into the foam of a 4 inch thick sample 15 inches by 15 inches square. Further illustratively, the filler 4218 includes sidewalls 4354 and 4355 which are angled to conform with the angled walls 4281 and 4282 of the receiving base 4208. A fastener, illustratively a loop portion 4356 of a conventional hook and loop fastener, is secured to a lower surface of the foam filler 4218 and is configured to couple with a mating hook portion 4357 secured to an upper surface of the receiving base 4208. A clearance opening 4359 is formed within the mounting substrate 4216 to allow for coupling of the fastener portions 4356 and 4357.

Turn Assist Bladder Assembly

Referring to FIGS. 130 and 139-141, the turn assist bladder assembly 4220 is positioned above the foam filler 4218 and includes a first, or right, inflatable turn assist bladder 4358 and a second, or left, inflatable turn assist bladder 4360. As described in greater detail herein, each of the right and left turn assist bladders 4358 and 4360 are selectively and individually inflatable to assist in the turning of a patient supported on the mattress 4014. FIG. 140 illustrates both the right and left turn assist bladders 4358 and 4360 in deflated positions, while FIG. 141 illustrates the left turn assist bladder 4360 in a deflated position and the right turn assist bladder 4358 in an inflated position.

Each of the turn assist bladders 4358 and 4360 include an upper layer 4362 and a lower layer 4364 coupled to the upper layer 4362. Right and left turn assist fill tubes 4366 and 4368 are configured to be coupled to the manifold assembly 4063 which, in turn, is coupled to the pump 4064 that provides pressurized air to inflate the chamber defined between the upper and lower layers 4362 and 4364 of the turn assist bladders 4358 and 4360, respectively. Right and left turn assist sensor tubes 4370 and 4372 are also provided in fluid communication with the chamber defined between the upper and lower layers 4362 and 4364 of the turn assist bladders 4358 and 4360, respectively. The sensor tubes 4370 and 4372 are likewise configured to be placed in fluid communication with the manifold assembly 4063 which, in turn, is in fluid communication with a pressure sensor 566 for detecting the pressure of air within the bladders 4358 and 4360. The fill tubes 4366 and 4368 extend generally in a longitudinal direction from proximate the head end of the respective bladders 4358 and 4360 to the mattress connector 4068 proximate the head end of the receiving base 4208. The sensor tubes 4370 and 4372 extend from a foot end of the respective bladders 4358 and 4360 laterally to proximate first side 4017*a* of the mattress 4014 and intermediate the turn assist bladder assembly 4220 and the mounting substrate 4216. The sensor tubes 4370 and 4372 continue through securing loop 4339 and are coupled to mattress connector 4068.

Right and left mounting flanges 4376 and 4378 extend in directions outwardly from opposing edges of the right and left turn assist bladders 4358 and 4360, respectively. Illustratively the mounting flanges 4376 and 4378 are secured to the lower layers 4364 of the bladders 4358 and 4360 through radio frequency (RF) welding. The mounting flanges 4376 and 4378 include a plurality of mounting apertures 4380 proximate their respective side edges 4382 and 4384. Releasable fasteners, such as the buttons 4337, are received within the apertures 4380 of the mounting flanges 4376 and 4378, and likewise are received within the apertures 4336 of the mounting substrate 4216. As such, the turn assist bladder assembly 4220 is secured to the mounting substrate 4216. The turn assist bladder assembly 4220 may be made from polyurethane film.

Upper Bladder Assembly

The upper bladder assembly 4222 is positioned above the turn assist bladder assembly 4220, such that the turn assist bladder assembly 4220 is sandwiched between the foam filler 4218 and the upper bladder assembly 4222 (FIGS. 130, 140 and 141). Referring to FIGS. 142 and 143, the upper bladder assembly 4222 defines a head section or air zone 4390 and a seat section or air zone 4392, wherein each zone 4390 and 4392 includes a respective bladder assembly 4394 and 4396. Both bladder assemblies 4394 and 4396 include a plurality of laterally extending bladders 4398 and 4400, respectively. Each bladder 4398, 4400 is movable independently from every other bladder 4398, 4400 and is separately coupled to the mounting substrate 4216. In the illustrated embodiment, a total of nine (9) bladders 4398*a*-4398*i* define the head section 4390, while a total of six (6) bladders 4400*a*-4400*f* define the seat section 4392. However, it should be appreciated that any number of bladders 4398, 4400 may be included within the various sections or zones 4390, 4392 of the mattress 4014.

Each bladder 4398, 4400 is substantially identical to the bladders 4264 of the heel bladder assembly 4215. As such, similar or identical reference numbers are utilized to indicate similar or identical components in bladders 4264, 4398 and 4400. Bladders 4398, 4400 each includes upper and lower inflatable center portions 4402 and 4404 and opposing upper inflatable end portions 4406 and 4408. The upper inflatable center portion 4404 is separated from the end portions 4406 and 4408 by hinge portions 4403 and 4405. The end portions 4406 and 4408 define first and second notches or spaces 4407 and 4409 which are configured to provide clearance for movement of the bladder 4398 about the hinge portions 4403 and 4405. Webs 4415 and 4417 are located in the notches 4407 and 4409 and connect the lower center portion 4404 to the end portions 4406 and 4408, respectively.

The bladders 4398, 4400 each include an upper fastener 4272 and a lower fastener 4274, illustratively snaps, configured to cooperate with the outer and inner fasteners 4332 and 4334 of the mounting substrate 4216. As illustrated in FIGS. 17 and 18, the inner mounting member 4330 is configured to move vertically relative to the outer mounting member 4328 through hinge 4329, thereby facilitating movement of the end portions 4406 and 4408 of the bladders 4398 relative to the center portions 4402 and 4404 of the bladders 4398. More particularly, the inner mounting member 4330 is configured to pivot relative to the outer mounting member 4328 about the hinge 4329. This coupling structure permits the end portions 4406 and 4408 of the bladders 4398 to hinge during operation of the turn assist bladder assembly 4220 and prevent undesirable raising of the end portions 4406 and 4408 or uncoupling from the mounting substrate 4216.

Further, the couplings between the bladders 4398 of the upper bladder assembly 4220 and the mounting substrate 4216 define an upper crowning surface 4410. More particularly, the upper surface 4410 of the bladder assembly 4220 proximate the longitudinal center axis 4019 of the assembly 4220 is positioned vertically above the upper surface 4410 proximate the opposing longitudinal side edges 4412, 4413 of the bladder assembly 4220. Illustratively, the vertical distance of the crowning upper surface 4410 from the center axis 4019 to the respective side edges 4412, 4413, as represented by reference letter "d" in FIG. 140, is approximately 2 inches. The upper surface 4019 is arcuate as it extends from the center axis 4410 to the side edges 4412, 4413.

The crowning surface 4410 is configured to facilitate lateral patient transfer from the bed 4010 to another patient support device positioned adjacent to the bed 4010 by creating an inclined surface which provides a slight amount of gravity assistance when the caregiver is moving the patient toward the side of the mattress 4014. Additionally, since the surface 4410 at the side edges 4412 and 4413 is lower than proximate the center axis 4411, the siderails 4020 and 4022 may have a lower profile and still fulfill minimum height requirements.

FIG. 141 illustrates a right turn assist mode of operation wherein the right turn assist bladder 4358 is inflated. Since the right turn assist bladder 4358 is laterally offset from the longitudinal center axis 4019 of the mattress 4014, inflation of the bladder 4358 causes side edge 4413 of the upper bladder assembly 4222 to raise above the opposing side edge 4412. The hinge portions 4403 and 4405 between the end portions 4406 and 4408 and the center portion 4407 of the bladders 4398, 4400 of the upper bladder assembly 4222 permit the mattress 4014 to substantially conform to the shape resulting from the inflation of either turn assist bladder 4358, 4360. In an illustrative embodiment, upon inflation of one of the turn assist bladders 4358 and 4360, a patient supported on the mattress 4014 is rotated by an angle of approximately 20 degrees from horizontal. Upon completion of the turn assist, the control system 44 causes the inflated turn assist bladder 4358, 4360 to vent to atmosphere. Simultaneously, the upper bladder assembly 4222 is instructed by the central system 44 to inflate to a maximum pressure, also known as a max inflate mode of operation. Since the turn assist bladder assembly 4220 is sandwiched intermediate the upper bladder assembly 4222 and the filler 4218, inflation of the upper bladder assembly 4222 facilitates the rapid venting of air within the turn assist bladders 4358 and 4360 to atmosphere.

A pair of seat attachment straps 4425 are configured to couple together selected air bladders 4440 of the seat bladder assembly 4396, illustratively bladders 4400a-4400c. The straps 4425 illustratively wrap around the bladders 4440a-4440c and have ends coupled together with conventional fasteners, such as buttons 4427.

Fluid Tube Routing

A head section fill tube 4414 and a head section sensor tube 4416 are coupled to the head section 4390. More particularly, the fill tube 4414 is fluidly coupled to the air bladder 4398e proximate the longitudinal center of the head section 4390, and the sensor tube 4416 is fluidly coupled to the air bladder 4398i proximate the seat section 4392. Both the fill tube 4414 and the sensor tube 4416 travel from respective bladders 4398e and 4398i in a generally longitudinal direction, to the mattress connector 4068 at the head end of the receiving base 4208, intermediate the bladders 4398 and the turn assist bladder assembly 4220. Both tubes 4414 and 4416 are received within securing loop 4338. A head section connection assembly 4418 fluidly connects each of the bladders 4398 and illustratively comprises a plurality of conventional T-shaped fluid connectors 4420 and L-shaped fluid connectors 4422.

A seat section fill tube 4424 and a seat section sensor tube 4426 are coupled to the seat section 4392. More particularly, the fill tube 4424 is fluidly coupled to a seat section connection assembly 4428 which, in turn, is fluidly coupled to each air bladder 4400 of the seat bladder assembly 4396. The seat section connection assembly 4428 illustratively comprises a plurality of T-shaped fluid connectors 4420 and an L-shaped fluid connector 4422. The sensor tube 4426 is fluidly coupled to air bladder 4400d located proximate the longitudinal center of the seat section 4392. Both the fill tube 4424 and the sensor tube 4426 travel from the seat bladder assembly 4396 in a generally longitudinal direction to the mattress connector 4068 at the head end of the receiving base 4208. The fill tube 4424 travels along sidewall 4282 of the receiving base 4208 intermediate the upper bladder assembly 4222 and the turn assist bladder assembly 4220, and is received within securing loop 4339 of the mounting substrate 4216. Similarly, the sensor tube 4426 travels along sidewall 4281 of the receiving base 4208 intermediate the upper bladder assembly 4222 and the turn assist bladder assembly 4220, and is received within securing loop 4338 of the mounting substrate 4216.

Fire Barrier

Referring again to FIG. 130, the fire barrier 2124 receives the internal mattress components including the receiving base 4208, the mounting substrates 4214 and 4216, the foam filler 4218, the turn assist bladder assembly 4220, the upper bladder assembly 4222, and the heel bladder assembly 4215. The fire barrier 2124 includes an open end 2356 configured to permit the fire barrier 2124 to slide over the other mattress components. Upon assembly, the open end 2356 of the fire barrier 2124 is closed utilizing conventional means, such as fasteners. The fire barrier 2124 may be made from a conventional fire-resistant mesh material, such as a fiberglass knit.

Shear Cover

The shear cover 2125 is configured to fit over the above-identified mattress components as received within the fire barrier 2124. The shear cover 2125 is configured to be located between the fire barrier 2124 and the outer cover 2102 to permit the top cover portion 2106 to slide easily over the fire barrier 2124 and move relative to the other internal mattress components, thereby reducing shear forces between the patient's body and the mattress 4014 and reducing the likelihood of sacral breakdown.

The shear cover 2125 is formed from a material having a low coefficient of friction so that the mattress outer cover 2102 can slide relative to the other mattress components. As the mattress 4014 is articulated or as the patient moves, the shear cover 2125 minimizes shear forces acting between the mattress top cover portion 2106 and the patient's body. The shear cover 2125 may be made from a woven nylon or parachute material. Illustratively, the shear cover 2125 is made from a polyurethane material such as Deerfield urethane PT6110S having a thickness of approximately 0.002 inches. The polyurethane material provides an inexpensive shear material which reduces shear forces applied to the patient's body situated on the mattress 4014.

Additional details of the shear cover 2125 and the top cover portion 2106 are described above.

Outer Cover

Referring now to FIGS. 57 and 146, the bottom cover portion 2104 includes a bottom wall 2366 and a sidewall 2368. The sidewall 2368 is illustratively formed from a ticking material and is coupled to the sidewall 2364 of the top cover portion 2106, illustratively through RF welding. Illustratively, the bottom wall 2366 of the bottom cover portion 2104 is formed from a polyurethane coated twill material for enhanced wear resistance and to protect other components of the mattress 4014 from contamination. The bottom wall 2366 includes an access panel 2370 defined by a zipper 2372. The access panel 2370 is utilized during assembly of the mattress 4014 and further facilitates removal of the replacement of the modular components of the mattress 4014. Illustratively, the zipper 2372 is RF welded to the bottom wall 2366. In an alternative embodiment of the invention, the zipper 2372 may be utilized to couple the sidewall 2368 of the bottom cover portion 2104 to the sidewall 2364 of the top cover portion 2106.

With further reference to FIG. 146, the bottom cover portion 2104 includes a stress relief zone 2374 of extra material, which is illustratively pleated, to accommodate movement of the head section 4038 of the deck 269 relative to the seat section 4040 of the deck 269. More particularly, as the head section 4038 is elevated relative to the seat section 4040, the head portion 4292 of the receiving base 4208 moves relative to the seat portion 4294 of the receiving base 4208. The slit 4296, and connected stress relief apertures, reduce the stress applied to the receiving base 4208 during this movement. Likewise, the stress relief zone 2374 of the bottom cover portion 2104 reduces stress within the outer cover 2102 of the mattress 4014. As the mattress 4014 bends to follow the contour of the deck 269, the extra material within the stress relief zone 2374 accounts for the increased distance between the head portion 4292 and the seat portion 4294 proximate the bottom cover portion 2104.

Mattress Anchors

With further reference to FIGS. 7130, 132, 133, and 146, the foot section anchor 4246 is coupled to the foot section 4210 of the receiving base 4208 below the bottom cover portion 2104, illustratively through fasteners 4247 threadably received within the foot section mounting plate 4242. Likewise, the head section anchor 4320 is secured to the head portion 4292 of the receiving base 4208 below the bottom cover portion 2104, illustratively through fasteners 4247 threadably received within the head section mounting plate 4316. The foot section anchor 4246 and the head section anchor 4320, each illustratively comprises a resilient tab or strip 4429 having opposing first and second ends 4430 and 4431 which may be flexed away from the bottom cover portion 2104 of the mattress 4014, and placed under the respective retaining brackets 4082 and 4080 formed within the leg section 429 and the head section 389 of the deck 269, respectively, as illustrated in FIG. 129.

Manifold Assembly and Mattress Connectors

Referring now to FIGS. 130, 138 and 148-150, the mattress fluid connector 4068 is secured to the bottom cover portion 2104 and is received within the connector recess 4285 formed within the receiving base 4208. The mattress connector 4068 includes a plurality of barbed fittings 4432 and 4434, each of which is sealingly received within flexible tubing illustratively connected to one of the heel bladder assembly 4215, the right turn assist bladder 4358, the left turn assist bladder 4360, the head section 4390 of the upper bladder assembly 4222, and the seat section 4392 of the upper bladder assembly 4222. More particularly, fitting 4432a is fluidly coupled to right turn assist fill tube 4366, fitting 4432b is fluidly coupled to left turn assist fill tube 4368, fitting 4432c is fluidly coupled to foot section fill tube 4276, fitting 4432d is fluidly coupled to seat section fill tube 4424, and fitting 4432e is fluidly coupled to head section fill tube 4414. In a similar fashion, fitting 4434a is fluidly coupled to the foot section sensor tube 4278, fitting 4434b is fluidly coupled to the head section sensor tube 4416, fitting 4434c is fluidly coupled to the seat section sensor tube 4426, fitting 4434d is fluidly coupled to the left turn assist sensor tube 4372, and fitting 4434e is fluidly coupled to the right turn assist sensor tube 4370.

The pneumatic connections to the manifold assembly 4063 of the present invention is further illustrated in FIG. 147. The manifold assembly 4063 is configured to provide fluid communication between the pump 4064 and the air mattress 4014. The manifold assembly 4063 is configured to control the supply of air to and the exhaust of air from the controlled air zones of the mattress 4014. Air is supplied to the manifold 4063 by the pump 4064, while air is exhausted to atmosphere 2405 through the manifold 4063. More particularly, the manifold 4063 controls air pressure within the right turn assist bladder 4358, the left turn assist bladder 4360, the head zone of the upper bladder assembly 4222 and the seat zone of the upper bladder assembly 4222. While in the following description, a single manifold 4063 is utilized, it should be appreciated that in other embodiments multiple manifolds may be substituted therefore.

With further reference now to FIG. 147, air supplied from the pump 4064 passes to the manifold 4063 though a supply tube. Once entering the manifold 4063, the supplied air is routed through to various valve assemblies in the manner detailed above with respect to valve assemblies 2406.

The sensing lines 4278, 4370, 4372, 4416, and 4426 from the controlled air zones of the mattress 4014 are coupled in fluid communication with the manifold 4063. In the illustrative embodiment, each sensing line 4278, 4370, 4372, 4416, and 4426 supplies air to the mattress connector 4068 which, in turn, provides air to the manifold connector 4070. The air exits the manifold connector 4070 through pressure sensing tubes 2440. Each tube 2440 is coupled to a pressure sensor 566 supported on a valve controller circuit board 2444. The circuit board 2444 is in communication with the control system 44 and as such, provides signals to the control system 44 indicative of pressure within the various controlled air zones of the mattress 4014. In an alternative embodiment, each sensing line 4278, 4370, 4372, 4416, and 4426 supplies air which passes through fluid sensing ports (not shown) formed within the manifold 4063 and then exits through pressure sensing tubes 2440.

The mattress connector 4068 is configured to couple to the manifold connector 4070 which is in fluid communication with the manifold 4063. The partition wall 272 coupled to the deck 269 is positioned intermediate the manifold connector 4070 and the manifold 4063. The manifold connector 4070 is configured to sealingly mate with the mattress connector 4068. The manifold connector 4070 includes a plurality of outlets 4436, 4438 configured to sealingly receive plugs 4440, 4442, respectively, of the mating mattress connector 4068. The outlets 4436 of the manifold connector 4070 are in fluid communication with the valve assemblies of the manifold 4063, while the plugs 4440a, 4440b, 4440c, 4440d, and 4440e are in fluid communication with the controlled air zones 4358, 4360, 4254, 4392, and 4390 of the mattress 4014 through respective fittings 4432 and fill tubes 4366, 4368, 4276, 4424, and 4414 in the manner detailed above. The outlets 4438 of the manifold connector are in fluid communication with the pressure sensors 566 through the manifold 4063, while the plugs 4442a, 4442b, 4442c, 4442d, and 4442e are in fluid communication with the controlled air zones 4358, 4360, 4254, 4392, and 4390 of the mattress 4014 through fittings 4434 and sensor tubes 4278, 4416, 4426, 4372, and 4370. As may be readily appreciated, in alternative embodiments, the sensor tubes may bypass the manifold 4063 and be directly connected to the respective pressure sensors 566.

Each of the plugs 4440 and 4442 illustratively includes a conventional O-ring gasket 4444 to promote sealing with a mating outlet 4436 and 4438. The mattress connector 4068 includes a peripheral inner flange 4446 which is configured to be received within a peripheral outer flange 4448 of the manifold connector 4070. Illustratively, a plurality of fasteners 4450 lock the peripheral flanges 4446 and 4448 together. Illustratively, each fastener 4450 comprises a spring-biased U-shaped tab 4452 extending outwardly from the mattress connector 4068 and including an opening 4454 configured to be received over a locking tab 4456 supported by the manifold connector 4070. A U-shaped retaining member 4457 is supported by the manifold connector 4070 in spaced relation to the locking tab 4456 such that the tab 4452 of the mattress connector 4068 may be received therebetween. In the illustrative embodiment of FIG. 148, the locking tab 4456 in an upper fastener 4450 is removed to assist in the uncoupling and removal of the connectors 4068 and 4070. It should be appreciated that other conventional fasteners, such as hook and loop fasteners, clamps or staples may be readily substituted therefor.

As described above, the manifold connector 4070 is coupled to the manifold 4063, respectively, through the partition wall 272. Conventional fasteners, such as screws 4058, may be utilized to secure the manifold connector 4070 and the manifold 4063 relative to the partition wall 272. In one illustrative embodiment, cylindrical gaskets may be positioned intermediate each outlet 4436, 4438 of the manifold receiving connector 4070 and the manifold 4063 in order to effect sealing therebetween. In a further illustrative embodiment, a gasket 25029 (FIG. 151) may be positioned intermediate the manifold connector 4070 and the partition 272. Gasket 25029 may be of a design substantially similar to gasket 2502 as shown in FIGS. 122 and 123.

Mattress Sensor

With reference to FIGS. 35A, 150, and 151, the connection between the mattress connector 4068 and the manifold connector 4070 is detected by a mattress sensor 4462. If the sensor 4462 does not detect that a mattress 4014 has been connected to the control system 44 by the coupling of the mattress connector 4068 to the manifold connector 4070, then the control system 44 does not permit operation of the air mattress functions.

According to an illustrative embodiment, the sensor 4462 comprises a Hall effect field sensor 4464 that detects the characteristics of a dynamic field generated by the mattress connector 4068. More particularly, a magnet 4466 is positioned within a receiving boss 4468 of the mattress connector 4068 (FIG. 151). The manifold connector 4070 includes an opening 4470 configured to receive the boss 4468, and the magnet 4466 received therein, when the mattress connector 4068 is fluidly coupled with the manifold connector 4070. As such, the Hall effect sensor 4464 detects the magnetic field generated by the magnet 4466. Based upon the detection of the predetermined magnetic field, the sensor 4464 sends a signal indicative of the respective mattress 4014 to the control system 44. The control system 44 then permits operation of the air mattress functions.

An illustrative circuitry associated with the sensor 4464 is shown in FIG. 152. The circuitry includes an op-amp 4474 coupled to the sensor 4464, an open collector 4476, a transistor 4478, and a resistor 4480. The sensor 4464, the op-amp 4474, the open collector 4476, and the transistor 4478 are coupled to ground 4482. The sensor 4464, the op-amp 4474, the open collector 4476, and the resistor 4480 are illustratively coupled to a five volt source. The transistor 4478 and the resistor 4480 are coupled to the output of the circuit. Illustratively, the resistor 4480 has a value of 470 ohms, and the sensor 4464 is a Cherry MP1013 Snap Fit Proximity Sensor that detects magnetic fields and is sold by the Cherry Corporation, 3600 Sunset Avenue, Waukegan, Ill. It should be appreciated that based upon the desired control characteristics, the value of the resistor 4480 and the proximity sensor 4464 may be varied.

Further, the type and functionality of an air mattress 4014 connected to the manifold connector 4070 may be associated with a predetermined sensitivity of Hall effect sensor 4464 or strength of magnet 4466. Alternatively, multiple magnets 4466 and associated Hall effect sensors 4464 may be used to distinguish between different types of mattresses 4014. Upon sensing a particular type of mattress 4014, the control system 44 may deactivate and/or activate selected functions. For example, should the control system 44 receive a signal from the mattress sensor 4462 indicating that the mattress 4014 has no turn assist bladder assembly 4220, then the left and right turn assist functionality may be deactivated.

In a further illustrative embodiment, the presence of the fluid connector 4068 of the mattress 4014 may be detected by the pressure sensors, illustratively pressure transducers 566, which are in communication with the control system 44. More particularly, the control system 44 can initiate a diagnostic routine or process at predetermined intervals by supplying pressure to the outlets 4436 in the manifold connector 4070. Should no mattress 4014 be connected to the manifold connector 4070, then the pressure transducers 566 connected to the sensor outlets 4438 will measure atmospheric pressure (i.e., no back pressure). However, if a mattress 4014 is connected, then the sensor outlets 4438, upon the application of fluid through the fill outlets 4436, will measure a certain amount of back pressure. As such, through this diagnostic routine, the control system 44 can determine if a mattress 4014 is connected to the manifold 4063, and also which outlets 4436 are connected to respective air zones 4254, 4358, 4360, 4390 and 4392. Again, if the control system 44, through operation of the pressure sensors 566, determines that only certain air zones 4254, 4358, 4360, 4390, and 4392 are coupled to the manifold 4063, then certain functions may be activated and others deactivated.

It should be further noted that other mattress detection devices or sensors may be readily substituted for those detailed herein. For example, mechanical switches, conducting pins, and other proximity sensors may be readily substituted therefor.

Pressure Control System

As detailed above with respect to FIG. 124, control system 44 includes dynamic surface module 518. In addition to other functions, dynamic surface module 518 includes a pressure control system 3000. As shown in FIG. 124, pressure control system 3000 includes a plurality of valve solenoids 564, a plurality of pressure sensors or transducers 566, an analog to digital converter 3002, a microcontroller 3004, a power supply 3006 and pump 4064. Microcontroller 3004 includes memory 3010 and central processing unit 3012.

Pressure sensors, illustratively transducers 566, periodically sense the pressure in one or more of controlled air zones 4254, 4358, 4360, 4390, and 4392 of mattress 4014 and output a voltage proportional to the amount of pressure that is sensed. Analog-to-digital converter 3002 converts the voltage to digital form and feeds the digital value to microcontroller 3004. Microcontroller 3004 analyzes the current pressure and determines whether the current pressure in controlled air zones 4254, 4358, 4360, 4390, and 4392 is correct, too high, or too low in comparison to a desired pressure. Memory 3010 stores data, illustratively in the form of look-up tables or algorithms, which is used in this analysis. For example, the desired pressure of air zones 4254, 4358, 4360, 4390, and 4392 may depend on the particular operating mode of the system 3000 (e.g., pressure relief, max-inflate, CPR, turn assist, and post-turn assist), whether head section 4038 is elevated and the degree of elevation, and/or the size or weight of the patient. The microcontroller 3004 operates valve solenoids 564 in response to the feedback signals from pressure transducers 566 to achieve the desired adjustments to mattress 4014. The valve solenoids 564 control the flow of air to and resulting pressure within the mattress 4014. Additional details regarding the valve solenoids 564 are provided above.

Valve Sensor

With reference now to FIG. 153, a valve sensor 4484 is operably coupled to the valve solenoids 564 to determine the type of pneumatic valve 2406 application or technology. More particularly, the valve sensor 4484 determines the presence of either (1) a direct acting solenoid valve or (2) a pilot operated, or pilot assisted, solenoid valve. The operational requirements for these two types of valves differ. The direct acting solenoid valve pulls more current from a solenoid voltage source 4486, and therefore pulse modulation of the current is employed. The pilot operated solenoid valve requires the application and maintenance of a pilot air pressure.

The determination of the particular type of valve 2406 is achieved by energizing each connected solenoid 564 individually. When a valve 2406 is actuated by the closing of a valve control relay 4488, the current pulled by the respective solenoid 564 is measured by a current transducer 4490. This measurement is supplied to an analog to digital converter 4492 which, in turn, supplies the measurement to a microcontroller, illustratively the microcontroller 3004 of the pressure control system 3000. Alternatively, the microcontroller may be independent of the microcontroller 3004. The microcontroller 3004 compares the measurement to known operating current values which are representative of the direct acting solenoid valve and the pilot operated solenoid valve. This comparison is the basis for deciding the type of valve 2406 (i.e. direct acting solenoid valve or pilot operated solenoid valve).

If the microcontroller 3004 determines that the number and types of valves 2406 equal a predetermined configuration, then the valves 2406 are driven by the microcontroller 3004 as appropriate for those types. If the microcontroller 3004 determines that the number and types of valves 2406 does not equal the predetermined configuration, then an error is reported by the microcontroller 3004. In one illustrative embodiment, the predetermined configuration is defined such that all of the valves 2406 coupled to the manifold 4063 are pilot operated solenoid valves. As such, the microcontroller 3004 queries whether all of the valves 2406 are pilot operated solenoid valves. If so, then the valves 2406 are driven by the microcontroller 3004 as appropriate for pilot operated solenoid valves. If the valves 2406 collectively are determined not to be of the predetermined configuration, in this illustrative embodiment meaning that all of the valves 2406 are not pilot operated solenoid valves, then the microcontroller 3004 reports an error. It should be appreciated that the predetermined configuration may comprise all direct acting solenoid valves, all pilot operated solenoid valves, or any combination thereof.

As further illustrated in FIG. 153, a supervisor relay 4496 may be positioned intermediate the solenoid voltage source 4486 and the current transducer 4490. Further, the solenoid 564 is coupled to ground 4498 through the valve control relay 4488.

The valve sensor 4484 permits the utilization of different predetermined configurations of valves 2406 in different patient supports. More particularly, the configuration of valves 2406 may be varied for different types or model years of patient supports in order to facilitate cost effectiveness and to take advantage of technological developments in valve design. For example, in a first patient support, all pilot operated valves may be utilized and the predetermined configuration stored in the microcontroller 3004 reflects this situation. However, in a later second patient support, all direct acting solenoid valves may be utilized. As such, the microcontroller 3004 may be modified or re-programmed to detect this new predetermined configuration.

Mattress Pressure Determination

As detailed herein, the various modes of operation include a pressure relief mode, which is a standard operating mode of the respective air zones for providing pressure relief to the body of the patient. The max inflate mode of operation is the operating mode for providing maximum inflation of the respective air zones. The CPR mode of operation is the operating mode for providing a firm pressure in the respective air zones for assisting in the delivery of CPR to the patient. The turn assist mode of operation is the operating mode for providing pressure in the respective air zones for assisting in the left or right turning or rotation of the patient. Finally, the post-turn assist mode of operation is the operating mode for providing pressure in the respective air zones for assisting in the deflation of the turn assist bladders.

Tables 6-9 illustrating examples of desired pressures of air zones 4254, 4358, 4360, 4390, and 4392 based on the air system operating mode, patient weight, and, for seat air zone 4392, head section elevation, are provided as follows:

TABLE 6 *

HEAD SECTION

| MODE | Head Section Pressure (in $H_2O$) (Pressure_Head range) |
|---|---|
| Pressure Relief | $\left[\left(\frac{Patient\_Weight}{100} + 1\right) \times 3\right] \pm 1$ |
| Max Inflate | 25.0–29.0 |
| CPR | 20.0–30.0 |
| Turn Assist | $\left[\left(\frac{Patient\_Weight}{100} + 1\right) \times 3\right] \pm 1$ |
| Post-Turn Assist | 25.0–29.0 |

* Minimum Calculated: 65 lbs.; Maximum Calculated: 350 lbs.; Weight used for greater than 350 lbs.; 400 lbs.; Default Weight incase of error condition: 200 lbs.

TABLE 7

SEAT SECTION

| MODE | Seat Section Pressure (in $H_2O$) (Pressure_Seat range) |
|---|---|
| Pressure Relief | $\left[\left(\frac{Patient\_Weight}{50} + 4\right) \times \left(\frac{Head\_Elevation}{60} + 1\right)\right] \pm 1$ |
| Max Inflate | 25.0–29.0 |
| CPR | 20.0–30.0 |
| Turn Assist | $\left[\left(\frac{Patient\_Weight}{50} + 4\right) \times \left(\frac{Head\_Elevation}{60} + 1\right)\right] \pm 1$ |
| Post-Turn Assist | 25.0–29.0 |

TABLE 8

TURN ASSIST BLADDER ASSEMBLY

| MODE | Turn Assist Pressure (in $H_2O$) (Pressure_TA range) |
|---|---|
| Pressure Relief | 0–2.0 |
| Max Inflate | 0–2.0 |
| CPR | 0–2.0 |
| Turn Assist (Inactive Bladder) | 0–2.0 |
| Turn Assist (Active Bladder) | $\left(\frac{Patient\_Weight}{25} + 10\right) \pm 5$ |
| Post-Turn Assist | 0–2.0 |

TABLE 9

HEEL PRESSURE RELIEF MEMBER

| MODE | Heel Pressure (in H$_2$O) (Pressure_Heel range) |
|---|---|
| Pressure Relief | $\left(\dfrac{\text{Patient\_Weight}}{200} + 1\right) \pm 0.5$ |
| Max Inflate | $\left(\dfrac{\text{Patient\_Weight}}{200} + 1\right) \pm 0.5$ |
| CPR | — |
| Turn Assist | — |
| Post Turn Assist | — |

With reference now to FIG. 154, an illustrative process 4710 of operation of the dynamic surface module 518 incorporating the mattress sensor 4462 begins at block 4712 with the operator or caregiver depressing appropriate keys or buttons on the one of the controllers 50, 52, 54 to deactivate or turn off the air pressure control system 3000. For example, in one embodiment, the operator simultaneously depresses the "Pressure Relief" button 1628 and the "Max Inflate" button 1622 on the controller 54 for a minimum of five (5) seconds in order to cause the pressure control system 3000 to deactivate or enter into an OFF mode. By deactivating the pressure control system 3000, continuous alarms or error messages for alerting the operator of the absence of an air mattress 4014 coupling are eliminated. In other words, if the pressure control system 3000 is active or in an ON mode when the air mattress 4014 is uncoupled from the control system 44 of the bed 4010, then the mattress sensor 4462 detects the absence of the air mattress 4014 and controller 3004 causes an error code to display on panel 1242 of the controller 54 and causes the activation of an audible alarm for a preset time period.

Next, as indicated at block 4714, the pressures in the head, seat, right turn assist and left turn assist zones 4390, 4392, 4360 and 4362 are not regulated by the pressure control system 3000. Further, all air mode indicators 1518 on the controller 54 are deactivated or off. At block 4716, the controller 3004 queries whether a mode button 1622, 1624, 1626, 1628 for operation of the pressure control system 3000, has been selected on the controller 54. If not, then the process returns to block 4714. If a mode button 1622, 1624, 1626, 1628 has been selected, then the process continues to decision block 4718, where the controller 3004 determines if the mattress sensor 4462 detects a mattress 4014.

If at block 4718, the mattress sensor 4462 does not detect a coupled mattress 4014, then the controller 3004 at block 4720 flashes selected mode indicators 1518 on the controller 54 and also sounds an audible alarm for a selected time period. The process then returns to block 4714. If at block 4718, the mattress sensor 4462 detects a coupled mattress 4014, then the process continues to block 4722 when the pressure controller 3000 enters or initiates the selected mode of operation.

As such, it may be appreciated that the mattress sensor 4462 of the present invention provides the operator with the flexibility of utilizing the bed 109 with a dynamic air mattress 4014 or some other support surface, such as a static foam mattress. If the bed 109 is to be used with a static foam mattress, for example, then the mattress sensor 4462 signals the controller 3004 which, in turn, cannot be activated by the operator. The pressure control system 3000 remains in an inactive or OFF mode, thereby locking out an operator from activating or turning ON the pressure control system 3000 and attempting to use the system on a foam mattress.

The controller 3004 of pressure control system 3000 regulates pressure within the air mattress 4014. If the pressure of an air zone 4254, 4358, 4360, 4390, and 4392 is too high, controller 3004 actuates the appropriate valve assembly actuator 564 to allow air to escape from the air zone 4254, 4358, 4360, 4390, and 4392. If the pressure is too low, microcontroller 3004 sends a message over network 510 to power supply module 514 of patient support 4010 (parts of which are generally depicted in FIG. 124 as power supply 3006), and power supply 3006 activates pump 4064. When microcontroller 3004 detects that pump 4064 is turned on, it actuates the appropriate valve assembly actuator 564 to allow air to enter the respective air zone 4254, 4358, 4360, 4390, 4392.

Among other things, embodiments of pressure control system 3000 include one or more of the following functionalities: a process 3030 for controlling the inflation of air zones 4254, 4358, 4360, 4390, and 4392 according to the size or weight of a patient, a process 3032 for controlling inflation of turn assist bladders 4358, 4360, a process 3070 for controlling inflation of seat section 4392 of mattress 4014 in response to elevation of the head section 4038 of the deck 269 and/or a process for controlling inflation of seat section 4392 of mattress 4014 in response to the patient sitting up on the bed 4014 with little or no support by the head section 4038 of the deck 269.

Mattress Pressure Dependency on Patient Weight

In certain illustrative embodiments of pressure control system 3000 of dynamic surface module 518, a process 4730 for controlling the inflation of air zones 4254, 4358, 4360, 4390, and 4392 according to the size or weight of a patient disposed on patient support 4010 is provided. One illustrative embodiment of process 4730 is shown in FIG. 155 and described below.

In certain illustrative embodiments as detailed above, an operator or caregiver is required to select an appropriate patient weight. In still other embodiments, the controller 3004 automatically selects a default setting, e.g., the "medium" size, if a patient weight is not selected by the operator or caregiver.

In yet another illustrative embodiment, pressure control system 3000 automatically determines the patient's weight through measurements by weigh frame 36 and/or by a force sensor supported by seat section 409. More particularly, and with reference to FIGS. 129 and 156, the patient's weight is derived from an algorithm whose inputs include force sensing resistors (FSRs) 5002, 5004, 5006, 5008, and 5010 supported on the deck 269 below the mattress 4014, and the four load cells 220, 222, 224, and 226 forming a portion of the in-bed scale weighing system. The load cells 220, 222, 224, 226 are coupled to the scale controller 5012, which is configured to perform diagnostic evaluations of the load cells to determine if they are working properly. In the illustrative embodiment, there are a total of five FSRs, including three FSRs 5002, 5004, and 5006 supported by the head section 389 of the bed deck 269, and two FSRs 5008 and 5010 supported by the seat section 409 of the bed deck 269. The two FSRs 5008 and 5010 in the seat section 409 and one of the FSRs 5004 in the head section 389 are connected to a scale controller 5012. These FSRs 5004, 5008, and 5010 are used for a patient position monitoring (PPM) system operated by the scale controller 5012 and which is configured to notify a caregiver when the patient changes position relative to the patient support 109. The two additional FSRs 5002 and 5006 in the head section 389 are connected to the air controller 3004. These two additional FSRs 5002 and 5006 provide additional detection coverage in the head section 4038, and also provide a diagnostic function in order to allow the air controller 3004 to determine when these FSRs 5002 and 5006 are disconnected or malfunctioning.

The FSRs are of conventional design and have resistance values which change depending upon the amount of force applied thereto. FSRs generally comprise polymer thick film (PTF) devices which exhibit a decrease in resistance with an increase in the force applied to an active surface. More particularly, the resistance of the FSRs drop below a predetermined value when a certain force is applied. While force sensing resistors (FSRs) are utilized in the illustrated embodiment, it should be appreciated that other sensors for detecting the presence of a patient supported on the head section 4390 and the seat section 4392 of the mattress 4014 may be substituted therefore. Illustratively, the FSRs are available from Interlink Electronics of Camarillo, Calif. as part number 408.

Patient Weight Determination

As noted above, four load cells 220, 222, 224, and 226 are attached to the four corners of the weigh frame 36 of the bed 109. The summation of these four load cells 220, 222, 224, and 226, when their output is converted to a weight, provide the total weight supported by the weigh frame 36. The weight of weigh frame 36 and anything supported by weigh frame 36, such as deck 269, mattress 4014, any other bed components supported on weigh frame 36, and a patient, is transmitted to load cells 220, 222, 224, 226. This weight deflects or otherwise changes a characteristic of load cells 220, 222, 224, 226 that is detected to determine the total weight supported thereby. By subtracting a known weight of weigh frame 36, deck 269, mattress 4014 and any other bed components supported on weigh frame 36, the weight of the patient positioned on patient support 10 can be determined. Additional description of load cells and methods for determining a patient's weight, position in the bed, and other indications provided by load cells is provided in U.S. patent application Ser. No. 09/669,707, filed Sep. 26, 2000, titled Load Cell Apparatus, to Mobley et al., and PCT international patent application Ser. No. PCT/US/08189, titled Hospital Bed Control Apparatus, to Dixon et al., the disclosures of which are expressly incorporated by reference herein. In one illustrative embodiment, the load cells are available from HBM, Inc. of Marlborough, Mass. According to alternative embodiments of the present disclosure, other configurations and methods of using load cells or other devices to determine a patient's weight or other information related to the patient known to those of ordinary skill in the art are provided.

Information from the scale controller 5012 is transmitted to the air controller 3004 through the controller area network (CAN) 510. The information is parsed into seven data sets (four load cells 220, 222, 224, 226, three FSRs 5004, 5008, 5010) with each transmission being spaced apart by approximately 100 milliseconds. Along with each data set is an error byte that contains diagnostic information pertaining to the load cells 220, 222, 224, 226.

Referring further to the flow chart of FIG. 155, the illustrative process begins upon appropriate activation of the controller 3004 and with the initialization of all variables. Next, the process continues at block 4734, where the scale controller 5012 determines the weight of the patient, as represented by the variable Patient_Weight. In the illustrative process 4730, the value of Patient_Weight is determined by the sub-process 5020 illustrated in FIGS. 157 and 158.

Process 5020 begins at block 5022 with the initialization of all variables. As detailed below, the variable Load_Beam_Offset is set to equal a value from the most recent operation of the controller 3004. At decision block 5024, the controller 3004 queries whether it is ready for processing data. More particularly, the controller 3004 determines whether a complete set of data from the FSRs 5002, 5004, 5006, 5008, 5010 and load cells 220, 222, 224, 226 is available for utilization. As noted above, a complete set of updated data is received every 700 milliseconds. More particularly, seven packages of data are received from the scale controller 5012 at the rate of one package every 100 milliseconds. Two additional packages of information are received from the first and third head section FSRs 5002 and 5006, one every 350 milliseconds. If a complete new set of data from the FSRs 5002, 5004, 5006, 5008, 501.0 and the load cells 220, 222, 224, 226 is not available, then the process returns at block 5026 to start block 5022. If decision block 5024 is answered in the affirmative, then the process continues to decision block 5028 where the controller 3004 processes data from the FSRs 5002 and 5006 and the scale controller 5012. More particularly, the processor 3004 determines the value of the variable Load_Beam_Total to be equal to the sum of the four inputs from the load cells 220, 222, 224, 226. The controller 3004 further analyzes the values from the FSRs 5002, 5004, 5006, 5008, 5010. If any of the FSRs 5002, 5004, 5006, 5008, 5010 have a resistance indicating the presence of a patient, then the controller 3004 sets the flag Patient_Present to TRUE.

The process 5020 next continues to block 5030 where the controller 3004 queries whether the data from both the FSRs 5002, 5004, 5006, 5008, 5010 and the scale controller 5012 are stable. More particularly, the controller 3004 queries whether the patient has been consistently detected as being present or not present for a minimum predetermined amount of time. In the illustrative embodiment, if (1) the patient has been detected for at least approximately 3.5 seconds as indicated by the flag Patient_Present being set to TRUE, or (2) the patient has not been detected for at least approximately 3.5 seconds as indicated by the flag Patient_Present being set to FALSE, then the FSR data is considered stable. Similarly, if the Load_Beam_Total variable has not changed by more than five pounds for at least approximately 3.5 seconds, then the scale data is considered stable. If the controller 3004 determines that the data is not stable at block 5030, then the process proceeds to block 5026. If the data is considered stable, then the process 5020 then continues to process block 5032.

In one illustrative embodiment, the FSRs 5002, 5004, 5006, 5008, 5010 are grouped into two sets, with the first group comprising all of the FSRs 5002, 5004, 5006, 5008, 5010, and the second group comprising the head section FSRs 5002, 5004, 5006. In order for the FSR data to be considered stable by the controller 3004, then (1) all of the FSRs in either the first group or the second group must not detect a patient for at least approximately 3.5 seconds, or (2) any of the FSRs in either the first group or the second group must detect a patient for at least approximately 3.5 seconds.

At block 5032, the controller 3004 recalculates the variable Load_Beam_Adj. More particularly, the controller sets Load_Beam_Adj to be equal to the variable Load_Beam_Total minus the variable Load_Beam_Offset. As mentioned above, the variable Load_Beam_Offset is saved from the prior operation of the controller 3004. The Load_Beam_Offset is defined as the weight measured by the scale controller 5012 prior to a patient getting on the bed 109 and being supported by the weigh frame 36, and following the addition of the mattress 4014, footboard 18 and any other equipment supported by the weigh frame 36. The Load_Beam_Offset takes into consideration the factory calibration, typically the zeroing or initializing of the weight measured by the scale controller 5012 without the mattress 4014, footboard 18, or other equipment supported by the weigh frame 36. In summary, the Load_Beam_Offset is equal to a load applied to the weigh frame 36 in excess of that when the bed 109 is calibrated during manufacture and without the patient supported by the weigh frame 36.

The process 5020 then continues to decision block 5034, where the controller 3004 queries whether the conditions have been satisfied to "zero" the bed 109. In other words, the controller 3004 determines whether conditions are satisfied for recalculating the offset (Load_Beam_Offset) for the bed 109. More particularly, the controller 3004 queries whether (1) the variable Load_Beam_Adj is less than zero or (2) the variable Load_Beam_Adj is less than a maximum detected offset value and the flag Patient_Present is FALSE. The first instance, where the Load_Beam_Adj is negative, could occur where equipment has been removed from the weigh frame 36 since the last operation of the controller 3004. As such, the value of the variable Load_Beam_Total could be less than the value of the variable Load_Beam_Offset as saved from the prior operation. The second instance, where the variable Load_Beam_Adj is less than a maximum detected offset value and the Patient_Present flag is FALSE could occur where equipment has been added to the bed 4010 and is supported by the weigh frame 36 since the last operation of the controller 3004, and no patient is detected as being supported by the deck 269. If at block 5034, the controller 3004 determines that the conditions are right to zero the bed 109 then the process 5020 continues to block 5036. Illustratively, the maximum detected offset value is defined as approximately 50 pounds.

At process block 5036, the controller 3004 calculates a new offset and clears the flag New_Offset_Pending. More particularly, the controller 3004 equates the variable Load_Beam_Offset to the variable Load_Beam_Total, and sets the New_Offset_Pending flag to FALSE. As such, the controller 3004 resets the Load_Beam_Offset to be equal to the value of the Load_Beam_Total. The process then continues at block 5038 where the controller 3004 recalculates the variable Load_Beam_Adj. More particularly, the controller 3004 equates the variable Load_Beam_Adj to be equal to the variable Load_Beam_Total minus the variable Load_Beam_Offset.

The process 5020 then continues to block 5040 where the controller 3004 applies output filter and weight limits. More particularly, the controller 3004 updates the variable Patient_Weight only if (1) the variable Load_Beam_Adj is greater than the variable Patient_Weight plus a minimum patient weight change or (2) the variable Load_Beam_Adj is less than the variable Patient_Weight minus the minimum patient weight change. Illustratively, the minimum patient weight change is defined as approximately ten pounds. If the variable Load_Beam_Adj is greater than a maximum patient weight, then the controller 3004 sets Patient_Weight to be equal to a default maximum patient weight. Illustratively, the maximum patient weight is defined as approximately 350 pounds, while the default maximum patient weight is defined as approximately 400 pounds. If the variable Load_Beam_Adj is less than a minimum patient weight, then the variable Patient_Weight is set to be equal to a default minimum patient weight. Illustratively, the minimum patient weight and the default minimum patient weight are both set to be equal to approximately 65 pounds. The process 5020 then continues to return block 5026 and subsequently to decision block 5024.

Referring again to decision block 5034 of FIG. 157, if the conditions are not proper for resetting the bed 4010 as detailed above, then the process 5020 continues to decision block 5042. At decision block 5042, the controller 3004 queries whether there is a possible large offset to record. More particularly, the controller 3004 determines whether (1) the variable Load_Beam_Adj is greater than or equal to the maximum detected offset value and (2) the flag Patient_Present is FALSE. In other words, the controller 3004 determines whether a large load has been measured by the weigh frame 36 and no patient is detected on the deck 269. As noted above, the maximum detected offset value is illustratively defined as approximately 50 pounds. If decision block 5042 is answered in the affirmative, then the process 5020 continues to process block 5044.

At block 5044, the controller 3004 stores the pending offset and sets the New_Offset_Pending flag. More particularly, the variable Pending_Offset is set equal to the Load_Beam_Total and the flag New_Offset_Pending is set to TRUE. The process 5020 then continues to process block 5040 and continues to operate as detailed herein as if a patient is present on the deck 269.

Figure 34:
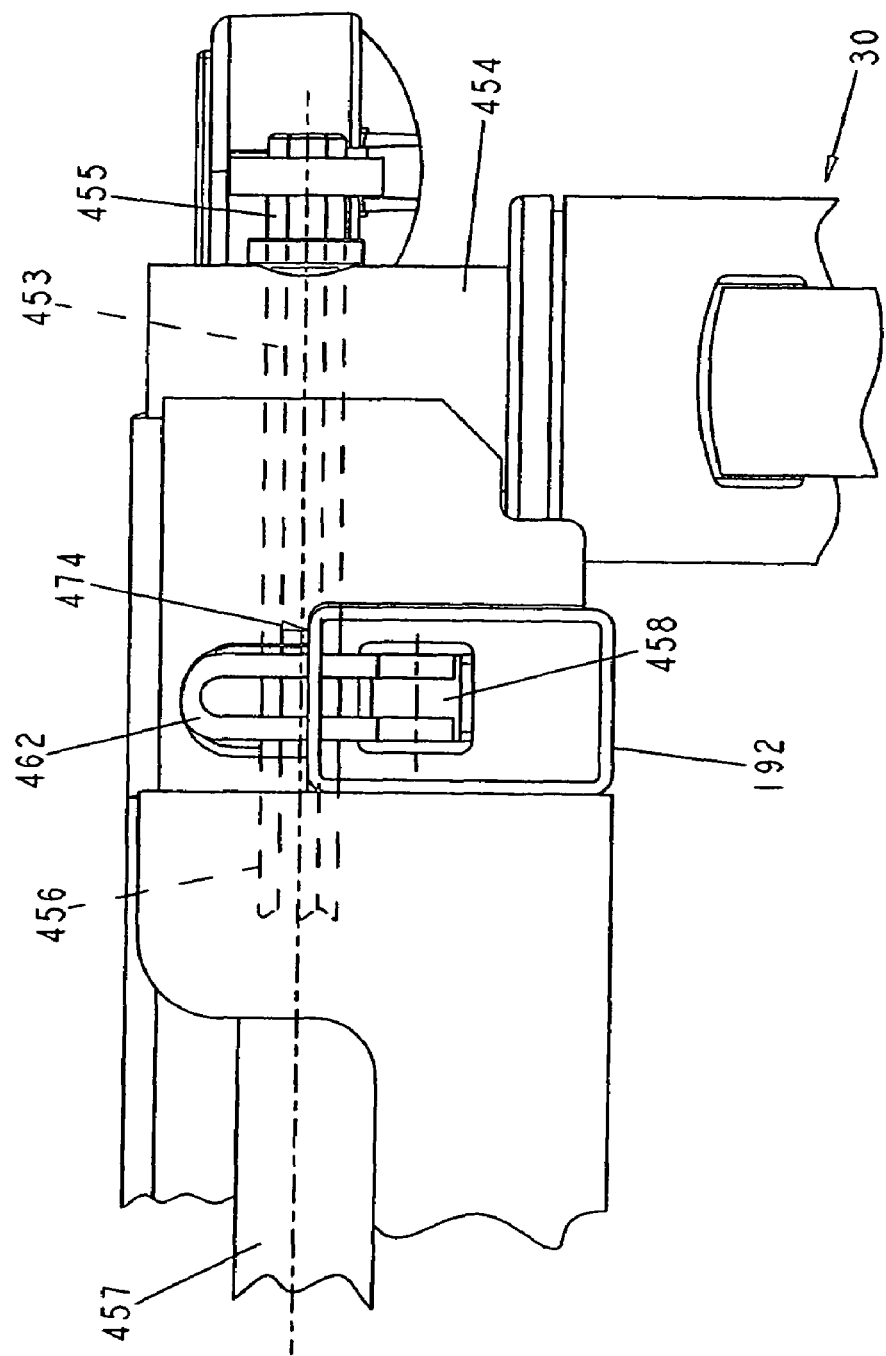
FIG. 34 is an end view of one of the caster devices shown in FIG. 32 and showing the interconnection between the caster device, a hexagonal rod, a bracket configured to couple the hexagonal rod to the first brake link and a transverse rod coupled to the hexagonal rod.

Referring again to decision block 5042, if there is no possible large offset to record, then the process continues to decision block 5046 (FIG. 158). At decision block 5046, the controller 3004 queries whether there is an existing pending offset. More particularly, the controller 3004 queries whether the flag New_Offset_Pending is set to TRUE. If decision block 5046 is answered in the negative, then the process 5020 continues to process block 5040 (FIG. 34). If decision block 5046 is answered in the affirmative, then the process 5020 continues to decision block 5048.

At decision block 5048 of FIG. 158, the controller 3004 queries whether the variable Load_Beam_Adj is much greater than the pending offset. More particularly, the controller 3004 determines whether the variable Load_Beam_Adj is greater than the variable Pending_Offset plus a minimum new patient weight. Illustratively, the value of the minimum new patient weight is defined as approximately 90 pounds. If decision block 5048 is answered in the negative, then the process 5020 continues to process block 5050 where the New_Offset_Pending flag is cleared or set to FALSE. The process 5020 then continues to process block 5040 (FIG. 157). If the decision block 5048 is answered in the affirmative, then the process continues to block 5052.

At block 5052, the controller 3004 updates the offset with the pending offset. More particularly, the controller 3004 sets a variable Load_Beam_Offset to be equal to the variable Pending_Offset. The situation could occur where a patient is now present on the deck 269 and the prior pending offset value was equipment supported by the weigh frame 36. The process then continues to process block 5054. At process block 5054, the controller 3004 recalculates the variable Load_Beam_Adj. Again, Load_Beam_Adj is equal to the variable Load_Beam_Total minus the variable Load_Beam_Offset. The process 5020 then continues to block 5050 where the New_Offset_Pending flag is cleared or set to FALSE. The process 5020 then continues to process block 5040 (FIG. 157) where the controller 3004 applies output filter and weight limits and updates the patient weight if appropriate. The process 5020 then continues to the return block 5026 and subsequently to decision block 5024.

Once the value of the variable Patient_Weight has been determined, for example by the above detailed process 5020, the process 4730 of FIG. 155 continues at block 4736. At step 4736, the air zone(s) 4254, 4358, 4360, 4390, and 4392 being monitored is determined. The bladders in the heel pressure relief member 4254, the head section 4390, the seat section 4392, and the turn assist bladders 4358, 4360 may be inflated to varying pressures based on patient weight, as represented by the variable Patient_Weight. However, it is understood that in alternative embodiments not all of the air zones 4254, 4358, 4360, 4390, and 4392 may be inflated based on patient weight.

At step 4736, process 4730 determines the desired inflation pressure for the air zone(s) 4254, 4358, 4360, 4390, and 4392 being monitored based on the patient weight. In the illustrated embodiment, microcontroller 3004 obtains the desired pressure for the air zone(s) 4254, 4358, 4360, 4390, and 4392 from data, such as one or more look-up tables, stored in memory 3010. The desired pressure may be a discrete value, a range of permissible values, or calculated from an equation or algorithm as a function of patient weight. Also, the desired pressure may be different for each air zone 4254, 4358, 4360, 4390, and 4392. Further, various other factors, including environmental factors such as temperature and/or altitude, may affect the desired pressure values and be reflected in data in the look-up table.

As detailed in Table 7, in the illustrated embodiment the appropriate pressures for the seat section 4392, in pressure relief and turn assist modes of operation, also depends on the elevation of head section 389, as represented by the variable Head_Elevation. Thus, for seat section 4392, the appropriate pressure is determined by reference to both patient weight and head angle. However, adjusting the pressure of seat section 4392 based on only one of these criteria, regardless of the mode of operation, is also within the scope of the present invention.

Mattress Seat Section Boost

As may be appreciated, when the head section 389 is elevated, a portion of the patient's weight naturally shifts from being supported by the head section 4390 of the mattress 4014 to the seat section 4392 of the mattress 4014. To compensate for this weight shift, the inflation pressure of the seat section 4392 is adjusted in response to changes in the position of the head section 4038. In the illustrated embodiment, and as shown in Table 7, the pressure in the seat section 4392 is dependent upon the elevation of the head section 4390 only during the pressure relief and turn assist modes of operation. In other words, the pressure in the seat section 4392 is not varied in response to changes in elevation of the head section 4390 in the max inflate, CPR, or post-turn assist modes of operation.

Illustratively, the position of head section 389, or head angle, is determined by position detector 606. In the illustrated embodiment, a potentiometer reading corresponding to the head angle is determined by logic module 512 and reported to dynamic surface module 518 via network 510 for use in process 4730. Additional details regarding operation of the potentiometer for determining head angle is detailed above.

In determining the pressure for the seat section 4392 at block 4738, the microcontroller 3004 compares the angle as determined by the position detector 606 to data stored in memory 3010, such as those values contained in Table 10 below. The ranges of values for adjacent angular regions indicating a change in head elevation in Table 10 overlap, in order to take into consideration hysteresis (dependence of the state of a system on its previous history, generally in the form of a lagging of a physical effect behind its cause) in the head angle evaluation.

TABLE 10

HEAD ELEVATION ANGLE
Head Elevation Angle Regions

| Angular Region | Minimum Angle | Maximum Angle | Tolerance | Angle Used in Calculations for Head_Elevation |
|---|---|---|---|---|
| 0 | 0° | 30° | +/−3° | 30° |
| 1 | 26° | 40° | +/−3° | 40° |
| 2 | 36° | 50° | +/−3° | 50° |
| 3 | 46° | 60° | +/−3° | 60° |
| 4 | 56° | 65° | +/−3° | 65° |

For example, head section 389 will be considered to have moved from region 0 (zero) to region 1 (one) if the position detector 606 measures a head angle of between approximately 30 and 40 degrees. However, once head section 389 is in region 1 (one), it will not be considered to have moved back to region 0 (zero) unless the position detector 606 measures a head angle below region 1 (one), e.g., approximately 26 degrees or less, is received. Further, as indicated in Table 10, the variable Head_Elevation for use in pressure calculations is set to a predetermined value for each region of measured head elevation. For example, in region 1 (one), the variable Head_Elevation is set to 40 degrees, while in region 2 (two), the variable Head_Elevation is set to 50 degrees.

If a change in position occurs in the downward direction, from one angular region to a different angular region, i.e., head section 4038 is lowered from region 2 (two) to region 1 (one) in Table 10, then at step 4738 the desired pressure of seat section 4392 is decreased according to the weight of the patient, represented by Patient_Weight, and the current head angle set as Head_Elevation. The desired pressure range (Pressure_Seat range) is determined by reference to a look-up table stored in memory 3010. Table 7 is an example of such a table.

If a change in position occurs in the upward direction, from one angular region to a different angular region, i.e., head section 389 is elevated from region 0 (zero) to region 1 (one) in Table 10, then at step 4738 the desired pressure of seat section 4392 is increased according to the weight of the patient, represented by the variable Patient_Weight, and the current head angle set as Head_Elevation. In addition, a "seat boost" may be applied to seat section, as detailed below, meaning that seat section 4392 is initially over-inflated for a brief period of time to compensate for the above-mentioned weight shift.

At step 4740, microcontroller 3004 measures the current pressure as described above and determines whether the current pressure is less than, equal to, or greater than the desired pressure determined as described above. At block 4742, the microcontroller 3004 queries whether the actual pressure is greater than the desired pressure determined at step 4738 above. If so, then at step 4744, the zone is deflated to the desired pressure. At block 4746, the microcontroller 3004 queries whether the current pressure is less than the desired pressure. If so, the microcontroller 3004 commands power supply 3006 to activate pump 4064 to inflate bladders 2304 to the desired pressure as described above, at step 4738.

After the pressure is decreased or increased at blocks 4744 and 4748, respectively, the process 4730 continues to block 4750. At block 4750, the controller 3004 determines if the seat section 4392 requires a pressure "boost."

In addition to other functions discussed above and elsewhere in this disclosure, pressure control system 3000 may perform additional processes 4800, 4900 for increasing or "boosting" the inflation of seat section according to the elevation of head section 4038. One embodiment of such method is shown in FIG. 160 and described below.

As noted above, when head section 389 is elevated, a portion of the patient's weight naturally shifts from head section 4390 of the mattress 4014 to seat section 4392 of the mattress 4014. A similar weight shift occurs when the patient sits up in the bed 109 such that the patient's weight is supported mostly or entirely by the seat section 4392. To anticipate this weight shift and prevent "bottoming out," the inflation pressure of seat section 4392 is boosted in response to changes in the position of head section 389. Table 11 shows boost pressure ranges for seat section depending on ranges of patient weight.

TABLE 11

SEAT BOOST PRESSURE (in H₂O)

| | Patient_Weight | | |
|---|---|---|---|
| MODE | >0, [140 | >140, [260 | >260 |
| Head Angle Increase* | 10.0-20.0 | 15.0-21.0 | 19.0-29.0 |
| Sitting-Up | 10.0-20.0 | 15.0-21.0 | 19.0-29.0 |

*Duration of Head Angle Increase Boost: 15 seconds 6 5 seconds; Head Angle Change Required for Boost: +3° 6 1.5°

Process 4800 begins at block 4802 with the determination of the elevation of the head section (Head_Elevation), in the manner detailed above. At decision step 4804, process 4800 evaluates the input received from logic module 512 and determines whether head section 389 has experienced at least a 3 degree increase in position by comparing the current head angle to the previous head angle. If the head angle has increased by at least approximately 3 degrees, the process 4800 continues to step 4806. If the head section 389 has not been elevated by at least approximately 3 degrees, then process 4800 returns to step 4802. It is understood that 3 degrees is an exemplary value and that a change in the head angle may be indicated by a greater or lesser value as appropriate. Of course, during this time, pressure control system 3000 continues to periodically measure the pressure of the seat section 4392 to make sure that it is within the desired ranges.

It should be appreciated that if a change in position occurs in the downward direction, i.e., head section 389 is lowered, then at step 4804 no pressure increase in the seat section 4392 is triggered. If a change in position occurs in the upward direction by at least 3 degrees, i.e., head section 389 is elevated, then at step 4806 the inflation pressure of seat section is increased. In other words, a "seat boost" is applied to seat section 4392, meaning that seat section 4392 is initially over-inflated for a brief period of time to compensate for the above-mentioned weight shift. At block 4808, a timing decision is executed by the controller 3004 to determine if the pressure boost exceeds a predetermined time, illustratively between 1 second and 30 seconds. In one illustrative embodiment, the predetermined time is set at approximately 15 seconds. If the pressure boost does not exceed the predetermined time, then the pressure boost continues at block 4806. If the predetermined time has passed, then the process 4800 continues to block 4810, where the pressure boost is terminated.

Examples of the initial "seat boost" pressures are shown in Table 11. After the seat boost period expires, process 4800 adjusts the pressure of seat section 4392 to the desired level based on patient weight and head angle, as determined by the look-up Table 7 as detailed above.

Referring now to FIG. 161, process 4900 for providing a sudden elevation or "boost" of pressure in the seat section 4392 likewise is triggered when the patient sits up in the bed 109 such that the patient's weight is supported mostly or entirely by the seat section 4392. Process 4900 begins at block 4902 with the controller 3004 monitoring the patient sensors or FSRs 5002, 5004, 5006, 5008, 5010. At decision block 4904, the controller 3004 queries whether the head section patient sensors or FSRs 5002, 5004, 5006 detect the presence of a patient in the head section 389. If block 4904 is answered in the affirmative, then the process returns to block 4902 and the controller 3004 continues monitoring the FSRs 5002, 5004, 5006, 5008, 5010. If at block 4904 the head section FSRs 5002, 5004, 5006 do not detect a patient, then the process continues to block 4906.

At decision block 4906, the controller 3004 queries whether the patient weight (Patient_Weight) is greater than a predetermined amount. In the illustrative embodiment, the predetermined amount is approximately 100 pounds. If the value of Patient_Weight is not greater than approximately 100 pounds, then the process returns to block 4902. In other words, the no pressure boost will occur in the seat section 4392 if the determined patient weight is not greater than approximately 100 pounds. If the value of Patient_Weight is greater than approximately 100 pounds, then the process 4900 continues to block 4908 where the inflation pressure of seat section 4392 is increased. In other words, a "seat boost" is applied to seat section 4392, meaning that seat section 4392 is initially over-inflated for a brief period of time to compensate for the above-mentioned weight shift. The seat boost continues indefinitely as long as the decision blocks 4904 and 4906 are answered affirmatively. Of course, during this time, pressure control system 3000 continues to periodically measure the pressure of the seat section 4392 to make sure that it is within the desired ranges.

Examples of the initial "seat boost" pressures are shown in Table 11. After the seat boost period expires, process 4900 adjusts the pressure of seat section 4392 to the desired level based on patient weight and head angle, as determined by the look-up Table 7 as detailed above.

Patient Turn Assist

In addition to other functions discussed above and elsewhere in this disclosure, pressure control system 3000 of dynamic surface module 518 controls the operation of turn assist bladder assembly 4220 during the turn assist mode of operation. Turn assist bladders 4358, 4360 are configured to be selectively inflated to assist a caregiver in turning or rotating a patient, e.g., for therapy or treatment reasons. One embodiment of a process 3032 for controlling operation of turn assist bladders 4358, 4360 is shown in FIG. 159 described below. Process 3032 is implemented using application software stored in memory 3010 of microcontroller 3004. The structure of turn assist bladders 4358, 4360 is described elsewhere in this application.

At step 3034 of FIG. 159, process 3032 detects whether a request has been received to activate one of turn assist bladders 2262, 2264. In the illustrated embodiment, such a request is initiated by an operator or caregiver activating one of the turn assist buttons 1624, 1626 (FIG. 75) located on siderail controllers 52, 54. However, it is understood that other means for activating the turn assist may be used. For example, control system 44 may be programmed to automatically activate one or more of the turn assist buttons 1624, 1626 at scheduled times during the day or night.

At decision step 3036, prior to initiating the turn assist function, process 3032 checks to make sure that the siderails 4020, 4022 located on the side of patient support 109 that the patient is being turned toward are in the up position, based on signals provided by siderail position detectors 60. If one or more of siderails 4020, 4022 on the side of patient support 109 toward which the patient is being turned is not in the up position, an error signal is generated at step 3038 and process 3032 ends. In the illustrated embodiment, an audible or visual signal is generated for a brief period or until the siderail or siderails 4020, 4022 are brought to the up position. Thus, in the illustrated embodiment, the siderails 4020, 4022 toward which the patient is being turned must be in the up position in order for the turn assist process to initiate. It is possible, however, that in other embodiments, a caregiver or operator may override this restriction, or that this restriction may be made optional, for example, depending on the circumstances of a particular patient.

At step 3040, process 3032 checks to see if the angle of head section 389 (Head_Elevation) is less than, equal to, or greater than a predetermined maximum angle. In the illustrated embodiment, the maximum head angle is about 25°. In one embodiment, signals are provided by the position detector 606 directly to the dynamic surface module 518, which determines the head angle. Alternatively, the head angle determination is made by logic module 512 which reports the head angle to dynamic surface module 518 for use in process 3032, via CAN network 510. If the head angle is less than or equal to 25°, then the turn assist process continues to step 3044. However, if the head angle is greater than about 25°, an error signal is generated at step 3042, and the turn assist process is not permitted to continue.

At step 3044, the weight of the patient (Patient_Weight) being supported by patient support 109 is determined as described above so that a desired pressure based on patient weight is applied to the selected turn assist bladder 4358, 4360.

At step 3046, if first turn assist button 1624 is activated, first turn assist bladder 4358 inflates to rotate a person in patient support 109 upwardly in a counter-clockwise from the perspective of a person standing behind head section 389. If second turn assist button 1626 is activated, second turn assist bladder 4360 inflates to rotate the person upwardly in the opposite direction as rotated in response to activation of first turn assist button 1624. Inflation of the selected turn assist bladder 4358, 4360 raises one side of the patient to a predetermined angle. In the illustrated embodiment, the selected turn assist bladder 4358, 4360 inflates to rotate the patient onto his or her side at about a 20 degree angle with respect to mattress 4014, in approximately 20-50 seconds, depending on the weight or size of the patient. It is understood that the predetermined angle and speed of inflation may be changed or modified as needed based on a variety of factors, including the purpose for rotating the patient.

A timer is set at step 3048 when the selected turn assist bladder 4358, 4360 is inflated. The selected turn assist bladder 4358, 4360 remains inflated for a predetermined period of time and is then automatically "reset" or deflated. The predetermined time is empirically determined by the needs and desires of the patient and caregiver in an operating environment and illustratively is a time within a range of approximately 5 seconds to approximately 5 minutes. In the illustrative embodiment, the duration of turn assist inflation is about 10 seconds. At step 3050 the timer counts out this wait period. After the wait period is complete (e.g., after 10 seconds), an audible or visual signal is generated to indicate to the patient and caregiver that the selected turn assist bladder 4358, 4360 is about to enter a "post-turn assist" mode or phase.

In the post-turn assist mode, process 3032 begins deflating the selected turn assist bladder 4358, 4360 at step 3052. In the illustrated embodiment, deflation is expedited by quickly "hyperinflating" bladders of the head and seat sections 4390 and 4392 to a firm, "post-turn assist" inflation pressure (see, e.g., Table 6 and Table 7). Inflation of head and seat sections 4390 and 4392 exerts pressure on turn assist bladders 4358, 4360 causing turn assist bladders 4358, 4360 to expel air more rapidly. Alternatively, a vacuum mechanism may be coupled to turn assist bladders 4358, 4360 to accelerate deflation.

Monitor activity step 3060 is a step that is periodically executed during the turn assist operation. This process detects whether a patient or caregiver attempts to utilize other bed features while the turn assist is in operation. Additional details regarding the operation of the dynamic surface module are provided above.

CPR Configuration

Patient support 109 may be placed in the preferred CPR configuration by providing an indication to control system 44 which in turn controls actuators 48c, 48d, 48e to place head, seat, and leg sections in a generally linear relationship, controls pump 4064, to inflate upper bladder assembly 4222 to the desired pressures, and controls deck support 24 to lower a head end relative to a foot end. In the illustrative embodiment, the control system 44 inflates the bladder assembly 4394 of the head section 4390 to its desired CPR pressure before it inflates the bladder assembly 4396 of the seat section 4392 to its desired CPR pressure. As such, the head section 4390 reaches its desired firmness prior to the seat section 4392. This functionality is desirable since CPR procedures typically require pressure to be applied to the upper torso or chest of a patient.

Mattress Air Pump

Pump 64 is configured to provide pressurized air to manifold 62 and the pneumatic devices of mattresses 14, 4014. As shown in the illustrative embodiment of FIGS. 162 and 163, pump 64 includes a support bracket 5440 coupled to a strut 211 of weigh frame 36, a pump cover support plate or bracket 5444 supported by support bracket 5440, a pump cover 5446 supported by housing support bracket 5444, a pump unit support bracket 5448 also supported by housing support bracket 5444, a pump unit 5450 supported by pump unit support bracket 5448, and a filter and muffler unit 5452 supported on the outside of pump cover 5446.

Many pump units, such as pump unit 5450, create noise and vibration during operation. Several of the components of pump 64 are configured to reduce the transmission of the noise and vibration generated by pump unit 5450.

As shown in FIGS. 113 and 162-164, support bracket 5440 includes a pair of saddle-shaped portions 5454 that hook or loop over strut 211 and four arms 5456 that extend down from saddle-shaped portions 5454. U-shaped rubber or elastic members 5458 (only one is shown in FIG. 163) are positioned between saddle-shaped portions 5454 and strut 211 as shown in FIG. 164 to reduce the vibration transmitted from pump 64 to strut 211.

Saddle-shape portions 5454 includes apertures 5460 sized to receive fasteners 5462 that couple bracket 5440 to strut 211. Similarly, strut 211 includes apertures 5464 sized to receive fasteners 5462. However apertures 5464 are large enough that strut 211 does not come into contact with fasteners 5462 to avoid a direct, rigid coupling between bracket 5440 and strut 211 (FIG. 164). Rather coupling occurs through U-shaped rubber members 5458.

Pump cover support bracket 5444 includes four arms 5466 that include fastener-receiving notches 5468. Rubber or elastic grommets 5470 (only one is shown in FIG. 163) are provided that are received in each of notches 5468. Each grommet 5470 includes two head portions 5472, an annular groove 5474 defined between head portions 5472, and a fastener-receiving aperture (not shown) sized to receive fasteners 5476 therethrough.

Grommets 5470 are positioned in notches 5468 so that head portions 5472 overlaps portions of arms 5466 and portions of arms 5466 are positioned in grooves 5474. As shown in FIG. 162, lower head portions 5472 of grommets 5470 are positioned on top of arms 5456 of support bracket 5440 so that lower head portions 5472 are positioned between support bracket 5440 and pump cover support bracket 5444. Fasteners 5476 extends through grommets 5470 so that upper head portions 5472 are positioned between head portions of fasteners 5476 and arms 5466 and a nut (not shown) coupled to lower thread portions of fasteners 5476 abut the undersides of arms 5456. Because portions of grommets 5470 are positioned between fasteners 5476 and arms 5466, 5456, no rigid, direct coupling is provided between pump cover support bracket 5444 and support bracket 5440.

Pump cover 5446 is coupled to pump cover support bracket 5444 by a plurality of fasteners 5478. A foam gasket 5480 is compressed between pump cover bracket 5444 and pump cover 5446 to reduce the transmission of noise and vibration. Similarly, a foam lining 5482 is provided on the interior surfaces of pump cover 5446. According to an alternative embodiment of the present disclosure a foam lining is also provided on the underside of pump cover support bracket 5444.

Pump unit support bracket 5448 is welded or otherwise rigidly coupled to the underside of pump cover support bracket 5444 so that pump unit support bracket 5448 is suspended within an interior region 5484 defined by foam lining 5482. Preferably, no portion of pump unit support bracket 5448 or pump unit 5450 touch foam lining 5482.

Pump unit 5450 is supported on pump unit support bracket 5448 by at least four resilient feet 5486 (only one such foot is shown in FIG. 163) made of a rubber material. As shown in FIG. 166, each foot 5486 includes four annular head portions 5488 that define annular grooves 5490 therebetween, a support portion 5492 positioned between head portions 5488, and two pull portions 5494 positioned at opposite ends. As shown in FIGS. 163 and 166, pump unit 5450 illustratively includes a plurality of apertures 5496 and pump unit support bracket 5448 includes a plurality of apertures 5498 sized to receive feet 5486. To install feet 5486, an assembler inserts pull portions 5494 through respective apertures 5496, 5498 and pulls on pull portions 5494 until the upper-most and lower most head portions 5488 are pulled through respective apertures 5496, 5498. After assembly, portions of pump unit support bracket 5448 and pump unit 5450 are positioned in annular grooves 5490 as shown in FIG. 166.

An alterative embodiment resilient foot 5510 is shown in FIG. 167 coupled to pump unit 5450 and pump unit support bracket 5448. Resilient foot 5510 includes a body portion 5512 made of a rubber or elastic material, a nut 5514, and a threaded stud 5516. Body portion 5512 is molded around nut 5514 and threaded stud 5516. To couple foot 5510 to pump unit 5450 and pump unit support bracket 5448, a bolt 5518 is threaded into nut 512 and a nut 5520 is threaded onto stud 5516. Preferably, portions of body portion 5512 are positioned between nut 5514 and pump unit 5450 and between stud 5516 and pump unit support bracket 5448 to provide increased frictional contact therebetween.

As shown in FIG. 162, a lower end of filter and muffler unit 5452 is positioned in an inverted cover or pan 5522 of pump cover 5446. Pan 5522 includes three side walls 5524, 5526, 5528 and a bottom wall 5530. Side walls 5524, 5526, 5528 cooperate to form a pair of slits or inlets 5532 therebetween and side wall 5526 includes a pair of apertures 5534. As shown in FIG. 165, lower end of filter and muffler unit 5452 is spaced apart from bottom wall 5530 by a distance 5531 so that a downwardly facing inlet 5536 of filter and muffler unit 5452 is spaced apart and facing bottom wall 5530. A cable tie 5538 is provided that wraps around filter and muffler unit 5452 and extends through apertures 5534 to couple filter and muffler unit 5452 to side wall 5526.

If liquid is sprayed into or otherwise enters pan 5522, it will drain out of slits 5532. Furthermore, because inlet 5536 is facing and relative close to bottom wall 5530, liquid cannot be sprayed into inlet 5536 through slits 5532 from outside of pan 5522 because the path between slits 5532 and inlet 5536 is non-linear. Thus, pan 5522 blocks any direct spray path into inlet 5536 so that it is difficult for liquid to inter filter and muffler unit 5452.

Preferably, filter and muffler unit 5452 is configured to filter out many impurities in the air so that these impurities are not introduced to pump unit 5450, manifold 62, or mattress 14. With further reference to FIGS. 163 and 165, air from filter and muffler unit 5452 is communicated to pump unit 5450 through tube 5540 coupled to an outlet 5542 of filter and muffler unit 5452. Tube 5540 extends through a tube-receiving notch 5544 in pump cover support bracket 5444 shown in FIG. 103 and couples to an inlet fitting 5546 of pump unit 5450.

During operation, pump unit 5450 generates noise that can travel through tube 5540. Filter and muffler unit 5452 is configured to attenuate this noise so that it is not introduced into the patient environment.

Figure 118:
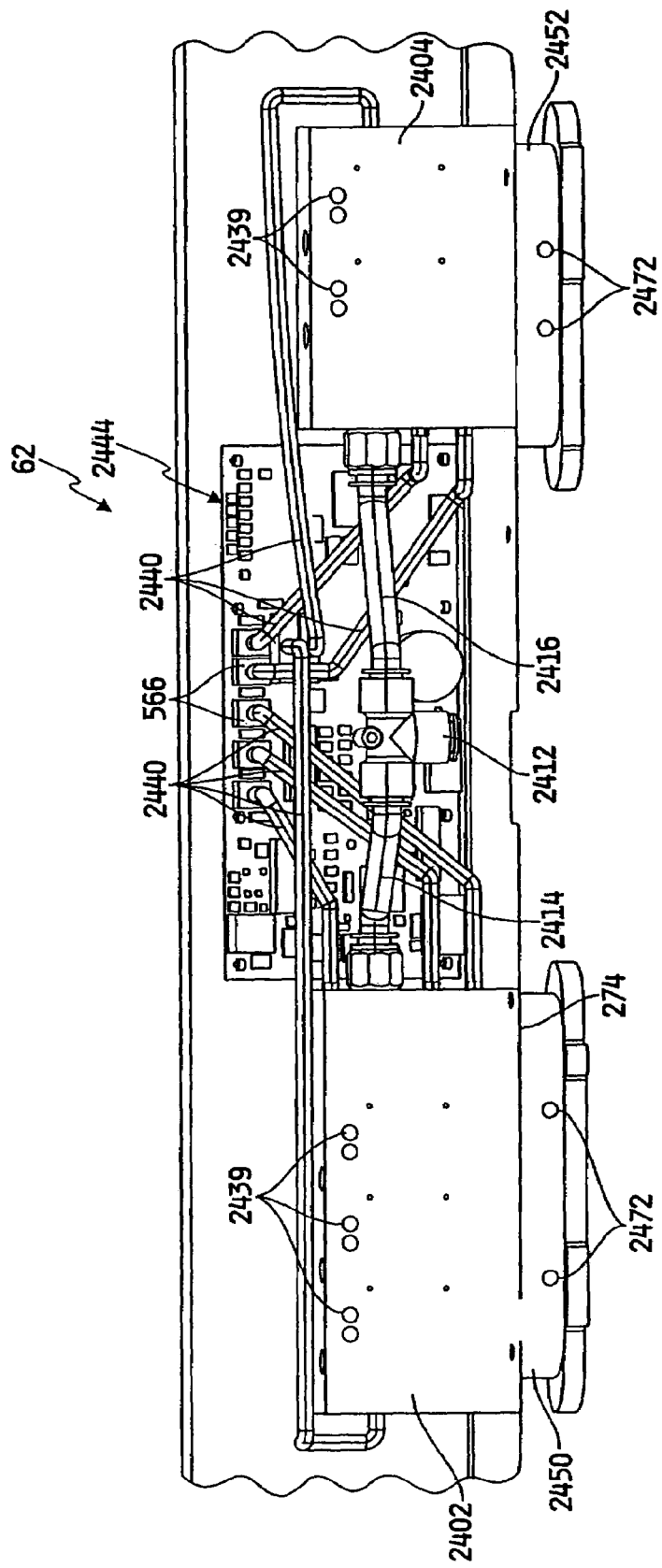

Another tube 5548 is coupled to an outlet fitting 5550 of pump unit 5450 that supplies pressurized air to manifold 62. Tube 5548 extends through another tube-receiving notch 5552 in pump cover support bracket 5444. Tube 5548 extends along strut 211 of weight frame 36 as shown in FIG. 18 until it reaches longitudinally extending member 198 of weigh frame 36. As shown in phantom in FIG. 18, tube 5548 extends toward foot end of patient support 10 along an inner side of longitudinally extending member 198 until it reaches a middle portion thereof. Then, tube 5548 turns inward toward the center of patient support 10. As shown in FIG. 13, tube 5548 extends through an aperture 5556 and extends up head section 38 of deck 26 between two strut members 5558 (shown best in FIG. 45) of head section 38 until it reaches T-connector 2412 of manifold 62 as shown in FIGS. 117 and 118.

A further illustrative embodiment mattress air pump 4064, as shown in FIGS. 168 and 170, includes a support bracket 5640 coupled to strut 211 of weigh frame 36, a pump cover support plate or bracket 5644 supported by support bracket 5640, a pump cover 5646 supported by housing support bracket 5644, a pump unit support bracket 5648 also supported by housing support bracket 5644, a pump unit 5650 supported by pump unit support bracket 5648, and a filter and muffler unit 5652 supported inside pump cover 5646. Pump unit 5650 draws air through filter and muffler unit 5652 from outside of pump 4064 and provides the air to manifold 62.

As shown in FIGS. 169 and 170, support bracket 5640 includes a saddle member 5654 that hangs from strut 211 and a support member 5657 having four arms 5656 that extend away from saddle member 5654. A pair of rubber or elastic grommets 5658 are positioned between respective tab sets 5659 of saddle member 5654 and strut 211 as shown in FIG. 170 to reduce the vibration transmitted from pump 4064 to strut 211. Steel sleeves 5661 (only one is shown in FIG. 169) are welded in place within strut 211 to receive grommets 5658.

Tab sets 5659 includes apertures 5660 sized to receive fasteners 5662 that couple bracket 5654 to strut 211. Similarly, strut 211 includes apertures 5664 sized to receive steel sleeve 5661. When positioned in apertures 5664, portions of steel sleeves 5661 extend below the bottom of strut 211 as shown in FIG. 170. Steel sleeves 5661 are welded to strut 211 along two lines 5665 (as shown in FIG. 169) defined between the bottom of strut 211 and sleeve 5661.

Steel sleeves 5663 (only one is shown in FIG. 169) are positioned in respective grommets 5658 to receive fasteners 5662. Grommets 5658 are sandwiched or positioned between strut 211 and bracket 5654 and strut 211 and fasteners 5662 to avoid a direct, rigid coupling between bracket 5654 and strut 211. Rather, the coupling occurs through grommets 5658.

Pump cover support bracket 5644 includes four arms 5666 that include fastener-receiving notches 5668. Resilient bushings 5670 and provided that are received in each of notches 5668. Bushings 5670 are positioned in notches 5668 so that upper head portions 5671 of bushings 5670 overlap portions of arms 5666 and a shank portions 5673 are positioned in notches 5668 as shown in FIG. 173. Resilient washers 5675 are positioned on top of arms 5656 of support bracket 5640 so that the lower head portions are positioned between support bracket 5640 and pump cover support bracket 5644. Fasteners 5676, such as machine screws, extend through metal washers 5677 and bushings 5670 so that washers 5677 and upper head portions 5671 of bushings 5670 are positioned between head portions of fasteners 5676 and arms 5666. Fasteners 5676 are screwed into arms 5656. Because portions of bushings 5670 and washers 5675 are positioned between fasteners 5676 and arms 5666, 5656, no rigid, direct coupling is provided between pump cover support bracket 5644 and support bracket 5640.

Bushings 5670 and wasters 5675 are preferable made of thermoset, polyether-based, polyurethane material sold under the name SORBOTHANE by Sorbothane, Inc. of Kent, Ohio. SORBOTHANE-brand material is a visco-elastic material. According to alternative embodiments, other resilient or elastic materials such as rubber are used for the bushings and washers.

Pump cover 5646 is coupled to pump cover support bracket 5644 by a plurality of fasteners 5678. As shown in FIG. 171, a foam lining 5680 is provided in an interior region 5684 defined by pump cover 5646 and pump cover support bracket 5644 to reduce the transmission of noise and vibration. Foam lining 5680 includes a foam top 5682 adhered to pump cover support bracket 5644, a foam wall 5683 adhered to the walls of pump cover 5646, and a foam bottom 5685 adhered to the bottom of pump cover 5646. Foam top 5644 provides a seal between pump cover 5646 and pump cover support bracket 5644. Foam lining 5680 is made of acoustic damping material to attenuate noise introduced inside pump cover 5646.

Pump unit support bracket 5648 is welded or otherwise rigidly coupled to the underside of pump cover support bracket 5644 so that pump unit support bracket 5648 is suspended within an interior region 5684 defined by foam lining 5680. As shown in phantom in FIG. 171, pump unit 5650 extends into and compresses portions of foam lining 5680.

Pump unit 5650 is supported on pump unit support bracket 5648 by at least four resilient feet 5686 (only two such feet are shown in FIG. 169) made of a rubber or elastic material. Additional description of suitable resilient feet 5686 is provided above.

As shown in FIG. 171, filter and muffler unit 5652 is held in interior region 5684 by a flange 5688 welded to a sidewall 5690 of pump cover 5646. Before assembly, flange 5688 toward the center of pump cover 5646. During assembly, filter and muffler unit 5652 is positioned adjacent flange 5688. Flange 5688 is then bent toward sidewall 5690 to the position shown in FIG. 169 to press filter and muffler unit 5652 into foam lining 5680 as shown in FIG. 171.

As shown in FIG. 171, an inlet 5710 of filter and muffler unit 5652 is coupled to a tube or hose 5712 that extends through an aperture or inlet 5714 in pump cover 5646. A grommet 5716 is positioned in aperture 5714 to provide a seal between tube 5712 and pump cover 5646. A tube cover 5718 is welded to pump cover 5646 that cover an end 5713 of tube 5712 extending out of pump cover 5646. Tube cover 5718 includes three sidewalls 5720, 5722, 5724 and a top wall 5726. Sidewalls 5720, 5722, 5724 cooperate with pump cover 5646 to form an aperture or inlet 5728.

If liquid is sprayed into or otherwise enters cover 5646, it will drain out of aperture 5728. Furthermore, because end 5713 of tube 5712 is facing and relative close to wall 5722 of cover 5718, liquid cannot be directly sprayed into inlet end 5713 of tube 5712 through aperture 5728 from outside of pan cover 5718 because the path between aperture 5714 and aperture 5728 is non-linear. Thus, cover 5718 blocks any direct spray path into end 5713 of tube 5712 so that it is difficult for liquid to enter filter and muffler unit 4652.

Interior components (not shown) of filter and muffler unit 5652 filter out many impurities in the air so that these impurities are not introduced to pump unit 5650, manifold 62, or mattress 4014. Air from filter and muffler unit 5652 is communicated to pump unit 5650 through interior region 5684 from an outlet 5642 of filter and muffler unit 5652. During operation of pump unit 5650, air from interior region 5684 is drawn into an inlet 5730 of pump unit 5650 that is spaced apart from filter and muffler unit 5652. This creates negative pressure within interior region 5684. Because of the pressure difference between interior region 5684 and the environment outside of pump 5660, air is drawn into interior region 5684 through filter and muffler unit 5652. This air enters interior region 5684 defined by foam lining 5680 before entering into inlet 5730 of pump unit 5650. Thus, foam lining 5680 defines a portion of the path of travel of the air through pump unit 5650.

Because inlet 5730 of pump unit 5650 is not directly coupled to filter and muffler unit 5652, noise exiting pump unit 5650 is not directly transmitted to filter and muffler unit 5652. This noise exits pump unit 5650 into interior region 5684 and is attenuated by foam lining 5680. Any noise that enters outlet 5642 of filter and muffler unit 5652 from interior region 5684 is attenuated further by filter and muffler unit 5652. Furthermore, because pump unit 5650 is not directly coupled to filter and muffler unit 5652, most vibration generated by pump unit 5650 is not transmitted outside of pump 4064 by tube 5712.

Another tube 5732 is coupled to an outlet fitting 5734 of pump unit 5650 that supplies pressurized air to manifold 62. Tube 5732 extends through an aperture 5736 in pump cover support bracket 5644. A grommet 5738 is positioned in aperture 5736 to provide a seal between tube 5732 and pump cover support bracket 5644. As shown in FIG. 172, support member 5657 includes a notch 5739 that provides clearance for tube 5732 to extend through support member 5657. Pump unit 5650 also includes a power cord 5740 that extends through a cord-receiving notch 5742 in pump cover support bracket 5644 and couples to the power supply.

Although the invention has been described in detail with reference to certain preferred embodiments, variations and modifications exist within the spirit and scope of the invention as described and defined in the following claims.

The invention claimed is:

1. A patient support comprising:
   a frame;
   a deck supported by the frame, the deck including a head section and a foot section;
   a controller area network including a plurality of control modules, none of the control modules operating as a master controller for the network, and
   a logic module coupled to the controller area network and coupled to the foot section, the logic module operable to control extension and retraction of the foot section to correspond to a position of the head section; and
   a mattress supported by the deck, the mattress having a head portion positioned over the head section of the deck and a foot portion positioned over the foot section of the deck.

2. The patient support of claim 1, wherein the logic module processes a signal from a sensor configured to detect the position of the head section relative to the frame.

3. The patient support of claim 1, wherein the length of the foot portion of the mattress decreases with the lowering of the head section.

4. The patient support of claim 1, wherein the length of the foot portion of the mattress increases as the head section lowers and decreases as the head section raises.

5. A patient support comprising:
   a frame;
   a controller area network including a plurality of control modules, none of the control modules operating as a master controller for the network;
   a deck supported by the frame, the deck including a head section, a seat section, and a foot section, the head section movable relative to the seat section between a first generally horizontal position and a first chair position, the foot section movable relative to the seat section between a second generally horizontal position and a second chair position;
   a logic module coupled to the controller area network, the logic module operable to coordinate movement of the head and foot sections between the generally horizontal positions and chair positions;
   a dynamic surface module coupled to the controller area network; and
   an adjustable mattress supported by the deck, the mattress coupled to the dynamic surface module such that the dynamic surface module is operable to control at least one operating parameter of the mattress.

6. The patient support of claim 5, wherein the mattress includes a foam portion including a plurality of transversely extending members.

7. The patient support of claim 5, wherein the patient support further comprises a scale/ppm module coupled to the controller area network, and a user interface coupled to the controller area network, the user interface configured to display a weight of a patient as determined by the scale/ppm module and to allow a user to adjust an operational parameter of the mattress.

8. The patient support of claim 7, wherein the user interface is configured to allow a user to adjust a position of a patient on the patient-support apparatus.

9. The patient support of claim 5, wherein the patient support further comprises a scale/ppm module coupled to the controller area network, and a user interface coupled to the controller area network, the user interface configured to display a weight of a patient as determined by the scale/ppm module and a status of a bed parameter, and wherein a visual alarm is activated if the bed parameter deviates from an acceptable condition.

10. The patient support of claim 5, wherein the frame comprises linkage means for supporting the deck. Image Page 8

11. The patient support of claim 10, wherein the frame further comprises electrically powered lift system means for actuating the linkage means between a raised and a lowered position.

12. The patient support of claim 5, wherein the patient support further comprises movable siderail means for providing a baffler.

13. The patient-support apparatus of claim 12, wherein the patient support further comprises user interface means for operating at least one function of the patient support, the user interface means spaced apart from the siderail means.

14. A patient-support apparatus comprising
   a frame,
   a controller area network including a plurality of control modules, none of the control modules operating as a master controller for the network,
   a scale/ppm module coupled to the controller area network, and
   a user interface coupled to the controller area network, the user interface configured to display a weight of a patient as determined by the scale/ppm module and to allow a user to adjust an operational parameter of the patient-support apparatus.

15. The patient-support apparatus of claim 14, wherein the user interface is configured to allow a user to adjust a position of a patient on the patient-support apparatus.

16. The patient-support apparatus of claim 15, wherein the user interface is configured to display a status of a bed parameter.

17. The patient-support apparatus of claim 16, wherein the status is a patient position monitoring status.

18. The patient-support apparatus of claim 17, wherein a visual alarm is activated when a patient moves beyond a predetermined position.

19. The patient-support apparatus of claim 15, wherein the user interface is configured to simultaneously display a weight of a patient and to allow a user to adjust an operational parameter of the patient-support apparatus.

20. The patient-support apparatus of claim 19, wherein the user interface is configured to display a status of a bed parameter.

21. The patient-support apparatus of claim 20, wherein the status is a patient position monitoring status.

22. The patient-support apparatus of claim 21, wherein a visual alarm is activated when a patient moves beyond a predetermined position.

23. The patient-support apparatus of claim 22, wherein the patient-support apparatus further comprises a plurality of siderails and the user interface is not coupled to a siderail of the patient-support.

24. The patient-support apparatus of claim 15, wherein the patient-support apparatus further comprises a plurality of siderails and the user interface is not coupled to a siderail of the patient-support.

25. The patient-support apparatus of claim 14, wherein the patient-support apparatus further comprises adjustable mattress means for supporting a person thereon.

* * * * *

UNITED STATES PATENT AND TRADEMARK OFFICE
CERTIFICATE OF CORRECTION

| | | |
|---|---|---|
| PATENT NO. | : 7,520,006 B2 | Page 1 of 1 |
| APPLICATION NO. | : 11/393631 | |
| DATED | : April 21, 2009 | |
| INVENTOR(S) | : Menkedick et al. | |

It is certified that error appears in the above-identified patent and that said Letters Patent is hereby corrected as shown below:

In claim 10, at col. 116, lines 13 and 14, please delete "ImagePage8"

Signed and Sealed this
Third Day of May, 2011

David J. Kappos
*Director of the United States Patent and Trademark Office*